United States Patent
Sill et al.

(10) Patent No.: US 9,944,752 B2
(45) Date of Patent: *Apr. 17, 2018

(54) BLOCK COPOLYMERS FOR STABLE MICELLES

(71) Applicant: Intezyne Technologies, Inc., Tampa, FL (US)

(72) Inventors: Kevin Sill, Tampa, FL (US); Tomas Vojkovsky, Palm Beach Gardens, FL (US); Adam Carie, Ruskin, FL (US); Joseph Edward Semple, Tampa, FL (US); Hooshmand Sheshbaradaran, Tampa, FL (US)

(73) Assignee: Intezyne Technologies, Inc., Tampa, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/067,129

(22) Filed: Mar. 10, 2016

(65) Prior Publication Data

US 2016/0264732 A1    Sep. 15, 2016

Related U.S. Application Data

(63) Continuation-in-part of application No. 14/694,760, filed on Apr. 23, 2015, now Pat. No. 9,499,665, which is a continuation of application No. 13/840,133, filed on Mar. 15, 2013, now Pat. No. 9,078,930, application No. 15/067,129, which is a continuation-in-part of application No. 14/028,472, filed on Sep. 16, 2013, now abandoned, which is a continuation-in-part of application No. 13/839,715, filed on Mar. 15, 2013, now abandoned, application No. 15/067,129, which is a continuation-in-part of application No. 14/028,477, filed on Sep. 16, 2013, now abandoned, which is a continuation-in-part of application No. 13/839,715, filed on Mar. 15, 2013, now abandoned, application No. 15/067,129, which is a continuation-in-part of application No. 14/028,485, filed on Sep. 16, 2013, now abandoned, which is a
(Continued)

(51) Int. Cl.

| C08G 65/48 | (2006.01) |
| A61K 31/506 | (2006.01) |
| A61K 31/555 | (2006.01) |
| A61K 31/337 | (2006.01) |
| A61K 9/10 | (2006.01) |
| A61K 47/69 | (2017.01) |
| A61K 47/60 | (2017.01) |
| A61K 47/64 | (2017.01) |
| A61K 47/34 | (2017.01) |
| A61K 31/704 | (2006.01) |
| A61K 31/475 | (2006.01) |
| A61K 31/4745 | (2006.01) |
| A61K 31/427 | (2006.01) |
| A61K 9/107 | (2006.01) |
| A61K 47/48 | (2006.01) |
| C08F 283/06 | (2006.01) |
| C08G 69/10 | (2006.01) |
| C08G 69/40 | (2006.01) |

(52) U.S. Cl.
CPC ............ *C08G 65/48* (2013.01); *A61K 9/1075* (2013.01); *A61K 31/337* (2013.01); *A61K 31/427* (2013.01); *A61K 31/475* (2013.01); *A61K 31/4745* (2013.01); *A61K 31/506* (2013.01); *A61K 31/555* (2013.01); *A61K 31/704* (2013.01); *A61K 47/34* (2013.01); *A61K 47/488* (2013.01); *A61K 47/48215* (2013.01); *A61K 47/48315* (2013.01); *C08F 283/06* (2013.01); *C08G 69/10* (2013.01); *C08G 69/40* (2013.01)

(58) Field of Classification Search
CPC .. A61K 47/34; A61K 31/337; A61K 31/4745; A61K 31/475; A61K 31/704; A61K 31/506; A61K 31/427; A61K 31/555; A61K 9/1075; C08G 69/40; C08G 69/12; C08G 69/32; C08G 65/48
See application file for complete search history.

(56) References Cited

U.S. PATENT DOCUMENTS

| 7,601,796 B2 | 10/2009 | Breitenkamp et al. |
| 7,638,556 B2 * | 12/2009 | Takada ...................... A61K 9/19 514/535 |
| 7,638,558 B2 | 12/2009 | Breitenkamp et al. |

(Continued)

FOREIGN PATENT DOCUMENTS

| WO | WO-2006/107903 A2 | 10/2006 |
| WO | WO-2008/134731 A1 | 11/2008 |

(Continued)

OTHER PUBLICATIONS

Aiedeh, K. et al., Synthesis of iron-crosslinked chitosan succinate and iron-crosslinked hydroxamated chitosan succinate and their in vitro evaluation as potential matrix materials for oral theophyllne sustained-release beads, European Journal of Pharmaceutical Sciences, 13:159-168 (2001).

(Continued)

*Primary Examiner* — Blessing M Fubara
(74) *Attorney, Agent, or Firm* — Andrea L. C. Reid; Dechert LLP

(57) ABSTRACT

The present invention relates to the field of polymer chemistry and more particularly to multiblock copolymers and micelles comprising the same. Compositions herein are useful for drug-delivery applications.

4 Claims, 25 Drawing Sheets

Related U.S. Application Data continuation-in-part of application No. 13/839,715, filed on Mar. 15, 2013, now abandoned.

(60) Provisional application No. 61/622,755, filed on Apr. 11, 2012, provisional application No. 61/659,841, filed on Jun. 14, 2012.

(56) References Cited

U.S. PATENT DOCUMENTS

| | | | |
|---|---|---|---|
| 7,799,339 B2 | 9/2010 | Sill et al. | |
| 8,263,663 B2 | 9/2012 | Sill et al. | |
| 8,263,665 B2 * | 9/2012 | Sill | A61K 9/1075 514/772.1 |
| 8,299,128 B2 | 10/2012 | Sill et al. | |
| 8,426,477 B1 * | 4/2013 | Breitenkamp | A61K 9/1075 514/772.1 |
| 8,609,146 B2 * | 12/2013 | Sill | A61K 9/1075 423/594.1 |
| 8,779,008 B2 * | 7/2014 | Breitenkamp | A61K 9/1075 514/772.1 |
| 8,980,326 B2 | 3/2015 | Sill et al. | |
| 9,078,930 B2 * | 7/2015 | Sill | C08G 69/40 |
| 9,499,665 B2 * | 11/2016 | Sill | C08G 69/40 |
| 2008/0274173 A1 | 11/2008 | Sill et al. | |
| 2009/0036611 A1 | 2/2009 | Wilker et al. | |
| 2010/0278927 A1 | 11/2010 | Mirosevich et al. | |
| 2010/0278932 A1 | 11/2010 | Sill et al. | |
| 2010/0324259 A1 | 12/2010 | Sill et al. | |
| 2013/0280306 A1 | 10/2013 | Sill et al. | |
| 2013/0288991 A1 | 10/2013 | Sill et al. | |
| 2013/0296531 A1 | 11/2013 | Sill et al. | |
| 2014/0113879 A1 | 4/2014 | Carie et al. | |
| 2014/0114051 A1 | 4/2014 | Semple | |
| 2014/0127271 A1 | 5/2014 | Sill et al. | |
| 2015/0232616 A1 | 8/2015 | Sill et al. | |
| 2015/0368401 A1 | 12/2015 | Sill et al. | |
| 2017/0253699 A1 | 9/2017 | Sill et al. | |

FOREIGN PATENT DOCUMENTS

| | | |
|---|---|---|
| WO | WO-2010/129581 A1 | 11/2010 |
| WO | WO 2010129581 A1 * | 11/2010 |
| WO | WO-2013/154774 A1 | 10/2013 |

OTHER PUBLICATIONS

Aisen, P. et al., Stochiometric and site characteristics of the binding of iron to human transferrin, J. Bioi. Chem., 253(6): 1930-1937 (1978).

Ajith, S. and Rakshit, A.K., Effect of NaCl on a Nonionic Surfactant Microemulsion System, Langmuir, 11:1122-1126 (1995).

Andres, G.O. and Rossi, R.H., Mechanism of phthalate ester hydrolysis in water and in cyclodextrin mediated reactions, Arkivoa, 127-138 (2003).

Crowe, L.M. et al., Is trehalose special for preserving dry biomaterials?, Biophysical Journal, 71:2087-2093 (1996).

Eby, G.A., Zinc ion availability—the determinant of efficacy in zinc lozenge treatment of common colds, Journal of Antimicrobial Chemotherapy, 40:483-493 (1997).

Genbank Entry, AAN17825: For Human Serum Albumin, 1 (2013).

Giroux, E.L. and Henkin, R.I., Competition for Zinc Among Serum Albumin and Amino Acids, Biochimica et Biophysica Acta, 273:64-72 (1972).

Honzl, J. and Rudinger, J., Synthetic studies in the oxytocin field. II. The synthesis of some dertivatives of I-cysteinyl-I-tyrosyl-glycine,I-cysteinyl-I-leucine and I-cysteinyl-I-isoleucine, Collection of Czechoslovakian Chemical Communications, 1190-1198 (1955).

Hoshi, A. et al., Antitumor Activity of Berberrubine Derivatives, Gann, 67(2):321-325 (1976).

Hutcheson, R.M. et al., Voltammetric studies of zn and fe complexes of edta: evidence for the push mechanism, Biometals, 18: 43-51 (2005).

International Search Report for PCT/US2013/032409, 3 pages (dated Jun. 10, 2013).

Izutsu, K., Stabilization of Therapeutic Proteins by Chemical and Physical Methods, Methods in Molecular Biology, 308:287-292 (2005).

Janssen, S. et al., Screening a combinatorial peptide library to develop a human glandular kallikrein 2-activated prodrug as targeted therapy for prostate cancer, Molecular Cancer Therapy, 3(11):1439-1450 (2004).

Jolivet, J. et al., Iron Oxide Chemistry. From Molecular Clusters to Extended Solid Networks, Chemical Communications, 481-487 (2004).

Jurado, R.L., Iron, Infections, and Anemia of Inflammation, Clinical Infectious Diseases, 25:888-895 (1997).

Kakizawa, Y. et al., Environment-Sensitive Stabilization of Core-Shell Structures Polyion Complex Michelle by Reversible Cross-Linking of the Core through Disulfide Bond, Journal of Americal Chemical Society, 121:11247-11248.

Kozlowski, H. et al., The Influence of Aspartic or Glutmaic Acid Residues in Tetrapeptides on the Formation of Complexes with Nickel(II) and Zinc(II), Polyhedron, 14(2):211-218 (1995).

Li, J. and Sha, Y., A convenient synthesis of amino acid methyl esters, Molecules, 13: 1111-1119 (2008).

Li, Y. et al., pH-Responsive Shell Cross-Linked Nanoparticles with Hydrolytically Labile Cross-Links, Macromolecules, xx(x):1-3 (2008).

Li, Y. et al., Well-Defined, Reversible Boronate Crosslinked Nanocarriers for Targeted Drug Delivery in Response to Acidic pH Values and cis-Diols, Agnewandte Chemie International Edition, 51:1-7 (2012).

Liu, S. et al., Synthesis of Shell Cross-Linked Micelles with pH-Responsive Cores Using ABC Triblock Copolymers, Macromolecules, 35:6121-6131 (2002).

Lokitz, B.S. et al., Aqueous RAFT Synthesis of Micelle-Forming Amphiphilic Block Copolymers Containing N-Acryloylvaline. Dual Mode, Temperature/pH Responsiveness, and "Locking" of Micelle Structure through Interpolyelectrolyte Complexation, Macromolecules, 40(18):6473-6480 (2007).

Lu, J. et al., Stability of Self-Assembled Polymeric Micelles in Serum, Macromolecules, 44:6002-6008 (2011).

March, J., Advanced Organic Chemistry, Reactions, Mechanisms, and Structure, 4:421-424 (1992).

Miller, M.J., Syntheses and Therapeutic Potential of Hydroxamic Acid Based Siderophores and Analogues, Chemical Review, 89(7):1563-1579 (1989).

Miyata, K. et al., Block Cationer Polyplexes with Regulated Densities of Charge and Disulfide Cross-Linking Directed to Enhance Gene Expression, Journal of American Chemical Society, 126:2355-2361 (2004).

Neilands, J.B., Hydroxamic Acids in Nature, Science, 156(3781):1443-1447 (1967).

Nishiyama, N. et al., Preparation and Characterization of Self-Assembled Polymer-Metal Complex Michelle from cis-Dichlorodiammineplatinum (II) and Poly(ethylene glycol)-Poly($\alpha$,$\beta$-aspartic acid) Block Copolymer in an Aqueous Medium, Langmuir, 15(2):377-383 (1999).

Oikawa, A. et al., Chemical analysis of acetylated bovine growth hormone, a growth hormone inhibitor, Biochemistry Journal, 104:947-952 (1967).

Owen, W.F. et al., The Urea Reduction Ratio and Serum Albumin Concentration as Predictors of Mortality in Patients Undergoing Hemodialysis, The New England Journal of Medicine, 329(14):1001-1006 (1993).

Poupri, S.R. et al., Adsorptive removal of copper and nickel ions from water using chitsan coated pvc beads, Bioresource Tech., 100: 194-199 (2009).

Read, E.S. and Armes, S.P., Recent advances in shell cross-linked micelles, Chemical Communications, 3021-3035 (2007).

(56) References Cited

OTHER PUBLICATIONS

Rosthauser, J.W. and Winston, A., Cross-Linking of Hydroxamic Acid Copolymers through Iron Chelation, Macromolecules, 14:538-343 (1981).
Savic, R. et al., Assessment of the Integrity of Poly(caprolactone)-b-poly(ethylene oxide) Micelles under Biological Conditions: A Fluorogenic-Based Approach, Langmuir, 22(8):3570-8 (2006).
Schoenbach, E.B. et al., Observations on the Effects of the Folic Acid Antagonists, Aminopterin and Amethopterin, in Patients with Advanced Neoplasms, Cancer, 5(6):1201-1220 (1952).
The University of Wisconsin-Madison's chemical of the week for chelating agents, <http://scifun.chem.wisc.edu/chemweek!chelates/chelates.html> Available Online (Jul. 1998).
Weisberg, E. et al., Smac mimetics: implications for enhancement of targeted therapies in leukemia, Leukemia, 24: 2100-2109 (2010).
Winston, A. and Kirchner, D., Hydroxamic acid polymers: Effect of structure on the selective chelation of iron in water, Macromolecules, 11(3):597-603 (1978).
Response to Final Office Action filed in U.S. Appl. No. 13/839,994 dated Jan. 26, 2015.
Written Opinion for PCT/US2013/032409, 4 pages (dated Jun. 10, 2013).
Non-Final Rejection in U.S. Appl. No. 13/839,994 dated Oct. 29, 2013.
Non-Final Rejection in U.S. Appl. No. 14/028,485 dated Jul. 7, 2014.
Non-final office Action in U.S. Appl. No. 13/839,715 dated Jul. 15, 2014.
Response to non-final office Action filed in U.S. Appl. No. 13/839,715 dated Dec. 5, 2013.
Non-Final Rejection in U.S. Appl. No. 13/839,715 dated Oct. 10, 2013.
Final Rejection in U.S. Appl. No. 13/839,715 dated Jan. 6, 2014.
Response to non-final Office Action filed in U.S. Appl. No. 14/028,485 dated Jan. 7, 2015.
Declaration of Kevin Sill filed in U.S. Appl. No. 13/839,715 dated Jan. 15, 2015.
Response to non-final Office Action filed in U.S. Appl. No. 13/839,994 dated Feb. 27, 2014.
Declaration of Kevin Sill filed in U.S. Appl. No. 14/028,485 dated Jan. 7, 2015.
Response to Office Action filed in U.S. Appl. No. 13/839,715 dated Jun. 6, 2014.
Declaration of Kevin Sill filed in U.S. Appl. No. 13/839,994 dated Jan. 26, 2015.
Final Office Action in U.S. Appl. No. 13/839,994 dated Apr. 29, 2014.
Final Rejection in U.S. Appl. No. 14/028,485 dated Feb. 13, 2015.
Declaration of Kevin Sill filed in U.S. Appl. No. 13/839,715 dated Jun. 6, 2014.
Response to non-final Office Action filed in U.S. Appl. No. 13/839,715 dated Jan. 15, 2015.
Non-Final Office Action for U.S. Appl. No. 13/839,994, 28 pages dated Jun. 4, 2015.
Final Rejection in U.S. Appl. No. 13/839,715 dated Feb. 13, 2015.
Final Rejection in U.S. Appl. No. 14/028,472 dated Feb. 13, 2015.
Final Rejection in U.S. Appl. No. 14/028,477 dated Feb. 13, 2015.
Non Final Rejection in U.S. Appl. No. 14/028,472 dated Jul. 8, 2014.
Non Final Rejection in U.S. Appl. No. 14/028,477 dated Jul. 9, 2014.
Response to Non Final Rejection in U.S. Appl. No. 14/028,472 dated Jan. 8, 2015.
Response to Non Final Rejection in U.S. Appl. No. 14/028,477 dated Jan. 9, 2015.
Response to Restriction Requirement in U.S. Appl. No. 14/028,472 dated Mar. 28, 2014.
Response to Restriction Requirement in U.S. Appl. No. 14/028,477 dated Mar. 28, 2014.
Restriction Requirement in U.S. Appl. No. 14/028,472 dated Mar. 21, 2014.
Restriction Requirement in U.S. Appl. No. 14/028,477 dated Mar. 7, 2014.

\* cited by examiner

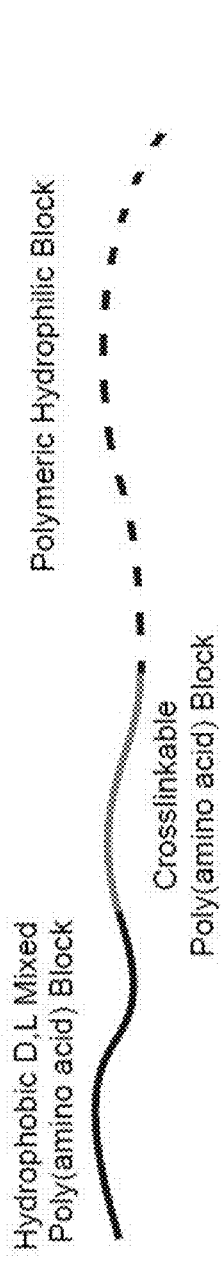
Figure 1A Triblock Copolymer
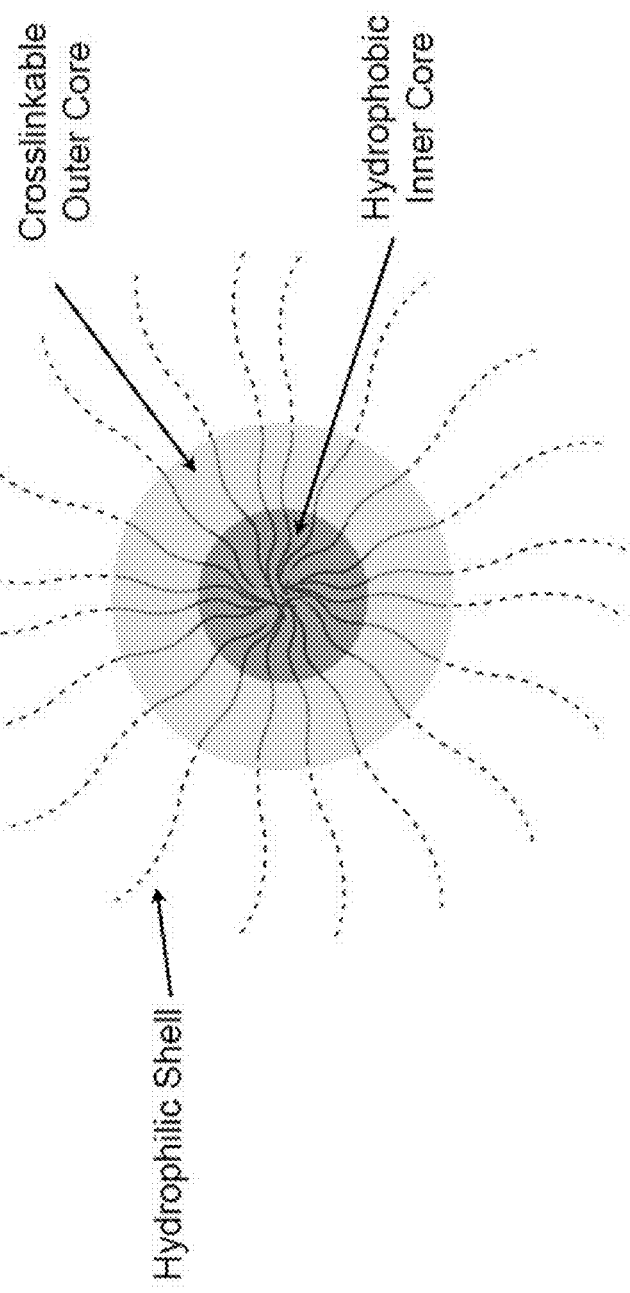
Figure 1B Polymer Micelle

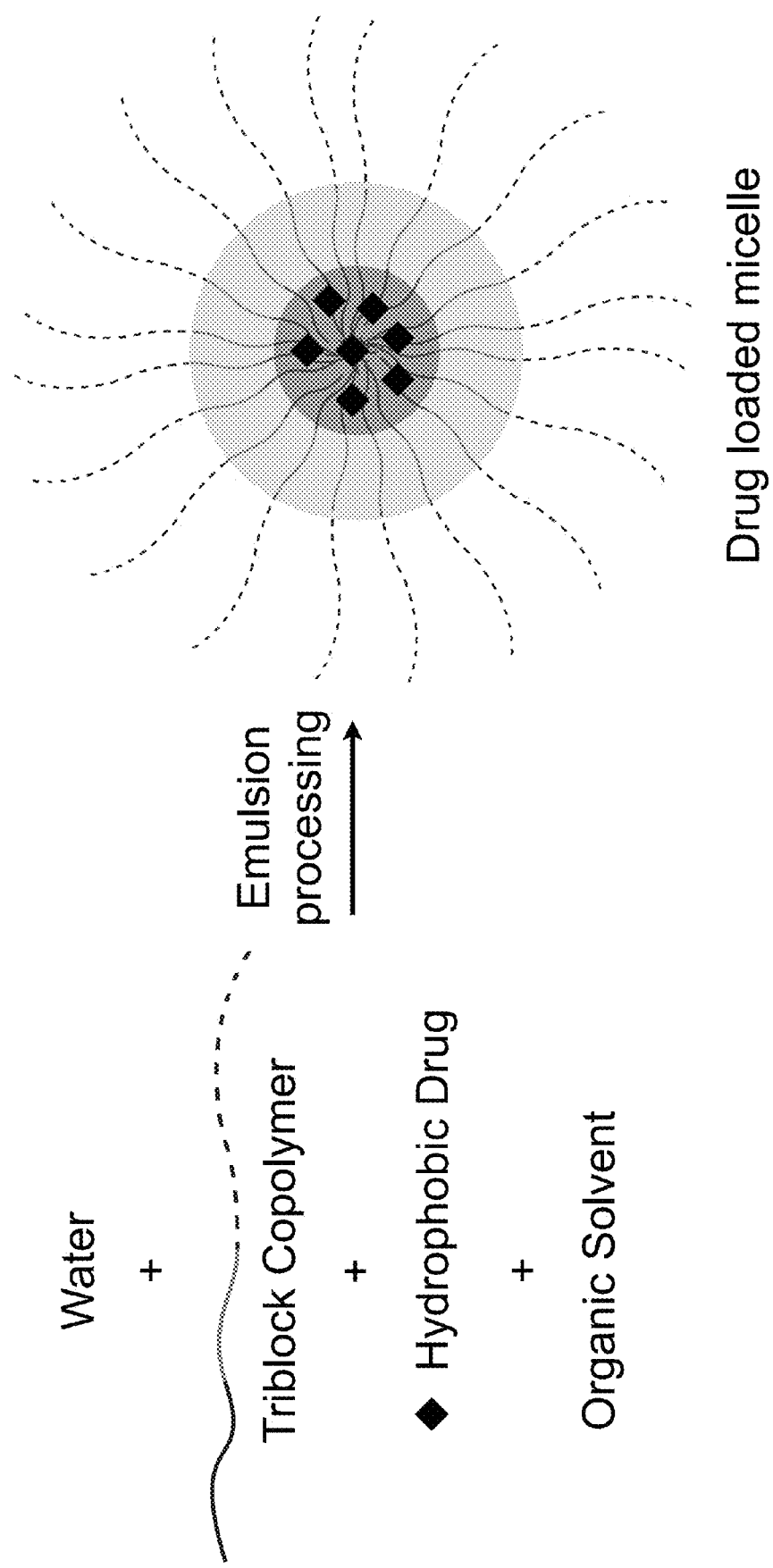
Figure 2. Drug Loaded Micelle Preparation

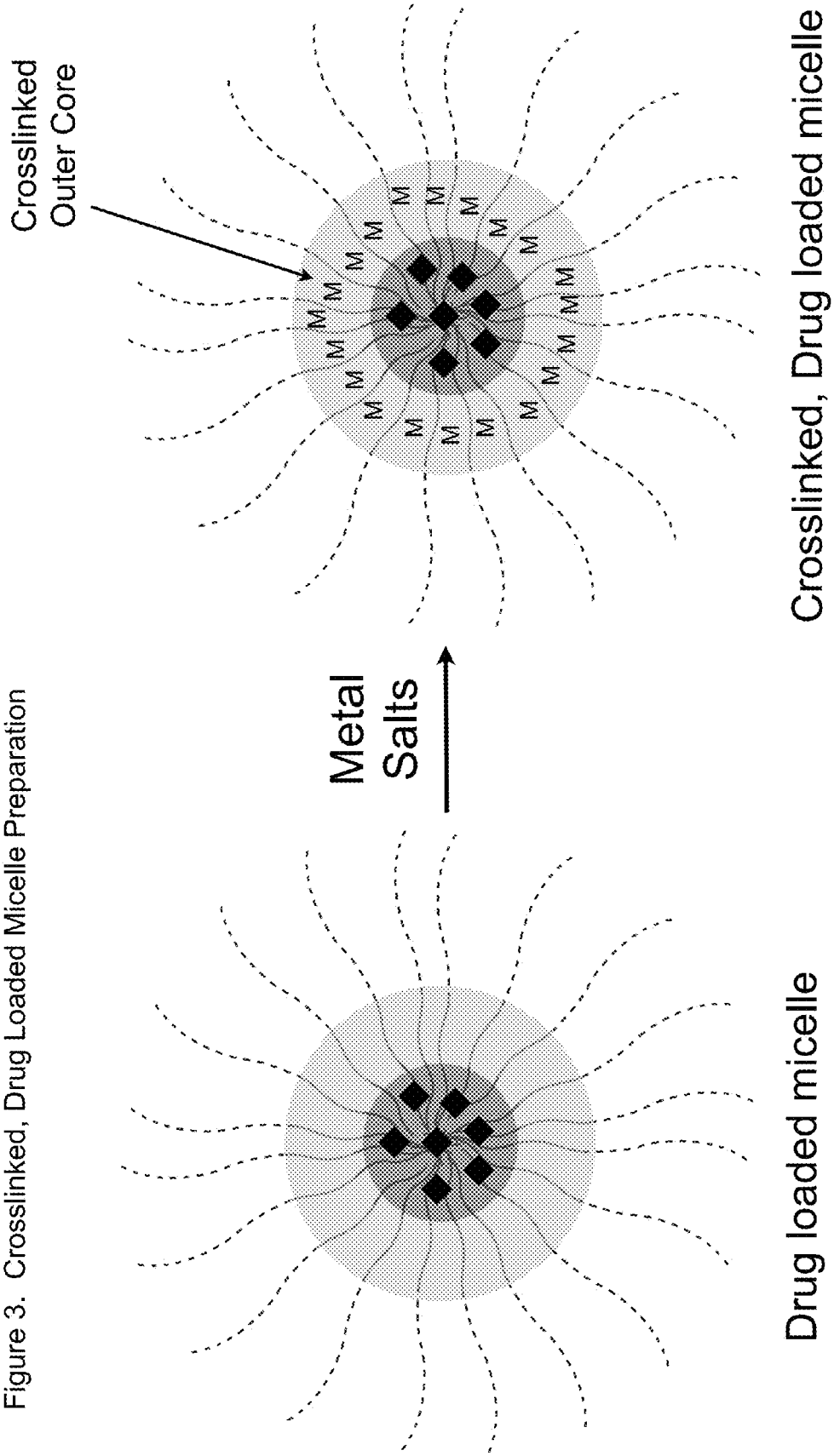
Figure 3. Crosslinked, Drug Loaded Micelle Preparation

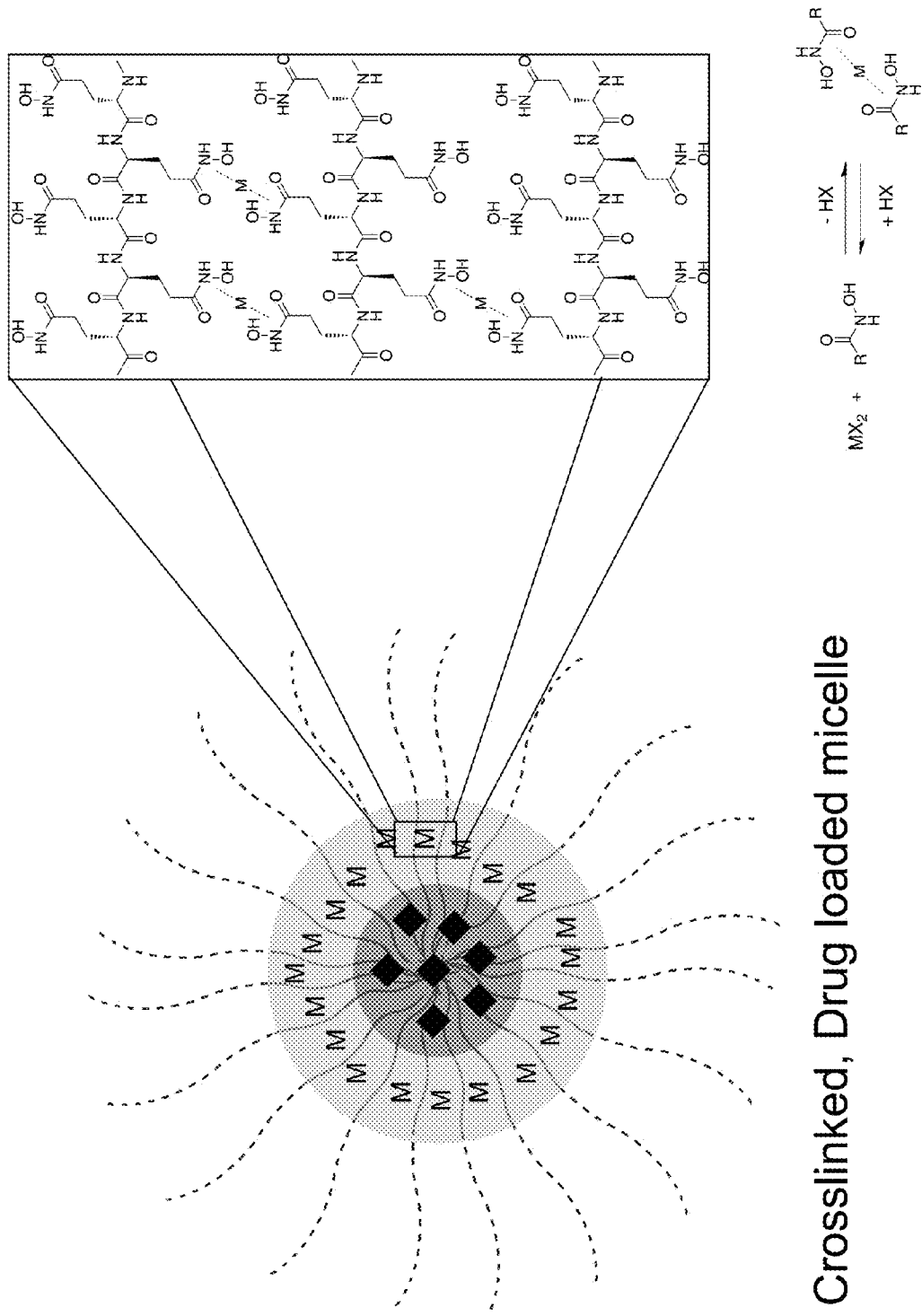
Figure 4. Crosslinked, Drug Loaded Micelle

```
                        SEQUENCE LISTING

<160> NUMBER OF SEQ ID NOS: 9

<210> SEQ ID NO 1
<211> LENGTH: 10
<212> TYPE: PRT
<213> ORGANISM: Human immunodeficiency virus

<400> SEQUENCE: 1

Gly Arg Lys Lys Arg Arg Gln Arg Arg Arg
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Arg Arg Arg Arg Arg Arg Arg Arg Arg
1               5

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 3

His His His His His
1               5

<210> SEQ ID NO 4
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Glu Glu Phe Phe Phe Phe Phe Phe Phe Phe Phe Phe Phe Phe Phe Phe
1               5                   10                  15

Phe Tyr Tyr Tyr Tyr Tyr Tyr Tyr Tyr Tyr Tyr Tyr Tyr Tyr Tyr Tyr
            20                  25                  30

Tyr Tyr Tyr Tyr Tyr Tyr Tyr Tyr Tyr Tyr
        35                  40

<210> SEQ ID NO 5
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Glu Glu Glu Glu Glu Glu Glu Phe Phe Phe Phe Phe Phe Phe Phe Phe
1               5                   10                  15

Phe Phe Phe Phe Phe Phe Tyr Tyr Tyr Tyr Tyr Tyr Tyr Tyr Tyr Tyr
            20                  25                  30

Tyr Tyr Tyr Tyr Tyr Tyr Tyr Tyr Tyr Tyr Tyr Tyr Tyr Tyr Tyr
        35                  40                  45

<210> SEQ ID NO 6
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Glu Glu Glu Glu Glu Glu Glu Glu Glu Phe Phe Phe Phe Phe Phe
1               5                   10                  15

Phe Phe Phe Phe Phe Phe Phe Phe Phe Tyr Tyr Tyr Tyr Tyr Tyr Tyr
            20                  25                  30

Tyr Tyr Tyr Tyr Tyr Tyr Tyr Tyr Tyr Tyr Tyr Tyr Tyr Tyr Tyr Tyr
        35                  40                  45

Tyr Tyr
    50

<210> SEQ ID NO 7
<211> LENGTH: 60
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7
```

Glu Glu Glu Glu Glu Glu Glu Glu Glu Glu Glu Glu Glu Glu Glu
1               5                   10                  15

Glu Glu Glu Glu Phe Phe Phe Phe Phe Phe Phe Phe Phe Phe Phe
            20                  25                  30

Phe Phe Phe Tyr Tyr Tyr Tyr Tyr Tyr Tyr Tyr Tyr Tyr Tyr Tyr
        35                  40                  45

Tyr Tyr Tyr Tyr Tyr Tyr Tyr Tyr Tyr Tyr Tyr
    50                  55                  60

<210> SEQ ID NO 8
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Asp Asp Asp Asp Asp Asp Asp Asp Asp Asp Leu Leu Leu Leu Leu
1               5                   10                  15

Leu Leu Leu Leu Leu Leu Leu Leu Leu Leu Leu Leu Leu Tyr Tyr
            20                  25                  30

Tyr Tyr Tyr Tyr Tyr Tyr Tyr Tyr Tyr Tyr Tyr Tyr Tyr Tyr Tyr
        35                  40                  45

Tyr Tyr
    50

<210> SEQ ID NO 9
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Glu Glu Glu Glu Glu Glu Glu Glu Glu Asp Asp Asp Asp Asp Leu
1               5                   10                  15

Leu Leu Leu Leu Leu Leu Leu Leu Leu Leu Leu Leu Leu Tyr Tyr
            20                  25                  30

Tyr Tyr Tyr Tyr Tyr Tyr Tyr Tyr Tyr Tyr Tyr Tyr Tyr Tyr Tyr
        35                  40                  45

Tyr Tyr
    50

BLOCK COPOLYMERS FOR STABLE MICELLES

CROSS REFERENCE TO RELATED APPLICATIONS

The present application is co-pending with and a continuation-in-part of U.S. patent application Ser. No. 14/694,760 filed on Apr. 23, 2015, and claims benefit of priority thereof under 35 U.S.C. § 120. U.S. patent application Ser. No. 14/694,760 was co-pending with and is a continuation of U.S. patent application Ser. No. 13/840,133 filed on Mar. 15, 2013, and claims benefit of priority thereof under 35 U.S.C. § 120; the present application also claims benefit of priority to U.S. patent application Ser. No. 13/840,133. U.S. patent application Ser. No. 13/840,133 was co-pending with and claims priority to U.S. provisional patent application Ser. No. 61/622,755, filed Apr. 11, 2012, and U.S. provisional patent application Ser. No. 61/659,841, filed Jun. 14, 2012, under 35 U.S.C. § 119; the present application also claims benefit of priority to each of U.S. provisional patent application Ser. No. 61/622,755 and U.S. provisional patent application Ser. No. 61/659,841.

The present application is co-pending with U.S. patent application Ser. No. 14/028,472 filed on Sep. 16, 2013, and claims benefit of priority thereof under 35 U.S.C. § 120. U.S. patent application Ser. No. 14/028,472 is co-pending with and is a continuation-in-part of U.S. patent application Ser. No. 13/839,715 filed on Mar. 15, 2013, and claims benefit of priority thereof under 35 U.S.C. § 120; the present application also claims benefit of priority to U.S. patent application Ser. No. 13/839,715. U.S. patent application Ser. No. 13/839,715 was co-pending with and claims benefit of priority to U.S. provisional patent application Ser. No. 61/622,755, filed Apr. 11, 2012, and U.S. provisional patent application Ser. No. 61/659,841, filed Jun. 14, 2012, under 35 U.S.C. § 119; as indicated above, the present application also claims benefit of priority to each of U.S. provisional patent application Ser. No. 61/622,755 and U.S. provisional patent application Ser. No. 61/659,841.

The present application is co-pending with U.S. patent application Ser. No. 14/028,477 filed on Sep. 16, 2013, and claims benefit of priority thereof under 35 U.S.C. § 120. U.S. patent application Ser. No. 14/028,477 is co-pending with and is a continuation-in-part of U.S. patent application Ser. No. 13/839,715 filed on Mar. 15, 2013, and claims benefit of priority thereof under 35 U.S.C. § 120; as indicated above, the present application also claims benefit of priority to U.S. patent application Ser. No. 13/839,715. U.S. patent application Ser. No. 13/839,715 was co-pending with and claims benefit of priority to U.S. provisional patent application Ser. No. 61/622,755, filed Apr. 11, 2012, and U.S. provisional patent application Ser. No. 61/659,841, filed Jun. 14, 2012, under 35 U.S.C. § 119; as indicated above, the present application also claims benefit of priority to each of U.S. provisional patent application Ser. No. 61/622,755 and U.S. provisional patent application Ser. No. 61/659,841.

The present application is co-pending with U.S. patent application Ser. No. 14/028,485 filed on Sep. 16, 2013, and claims benefit of priority thereof under 35 U.S.C. § 120. U.S. patent application Ser. No. 14/028,485 is co-pending with and is a continuation-in-part of U.S. patent application Ser. No. 13/839,715 filed on Mar. 15, 2013, and claims benefit of priority thereof under 35 U.S.C. § 120; as indicted above, the present application also claims benefit of priority to U.S. patent application Ser. No. 13/839,715. U.S. patent application Ser. No. 13/839,715 was co-pending with and claims benefit of priority to U.S. provisional patent application Ser. No. 61/622,755, filed Apr. 11, 2012, and U.S. provisional patent application Ser. No. 61/659,841, filed Jun. 14, 2012, under 35 U.S.C. § 119; as indicated above, the present application also claims benefit of priority to each of U.S. provisional patent application Ser. No. 61/622,755 and U.S. provisional patent application Ser. No. 61/659,841.

These applications are incorporated herein by reference in their entirety.

FIELD OF THE INVENTION

The present invention relates to the field of polymer chemistry and more particularly to multiblock copolymers and uses thereof.

SEQUENCE LISTING

The instant application contains a Sequence Listing which has been submitted electronically in ASCII format and is hereby incorporated by reference in its entirety. The ASCII copy, created on Mar. 11, 2015, is named "Sequence Listing.txt" and is 8 kilobytes in size.

BACKGROUND OF THE INVENTION

The development of new therapeutic agents has dramatically improved the quality of life and survival rate of patients suffering from a variety of disorders. However, drug delivery innovations are needed to improve the success rate of these treatments. Specifically, delivery systems are still needed which effectively minimize premature excretion and/or metabolism of therapeutic agents and deliver these agents specifically to diseased cells thereby reducing their toxicity to healthy cells.

Rationally-designed, nanoscopic drug carriers, or "nanovectors," offer a promising approach to achieving these goals due to their inherent ability to overcome many biological barriers. Moreover, their multi-functionality permits the incorporation of cell-targeting groups, diagnostic agents, and a multitude of drugs in a single delivery system. Polymer micelles, formed by the molecular assembly of functional, amphiphilic block copolymers, represent one notable type of multifunctional nanovector.

Polymer micelles are particularly attractive due to their ability to deliver large payloads of a variety of drugs (e.g. small molecule, proteins, and DNA/RNA therapeutics), their improved in vivo stability as compared to other colloidal carriers (e.g. liposomes), and their nanoscopic size which allows for passive accumulation in diseased tissues, such as solid tumors, by the enhanced permeation and retention (EPR) effect. Using appropriate surface functionality, polymer micelles are further decorated with cell-targeting groups and permeation enhancers that can actively target diseased cells and aid in cellular entry, resulting in improved cell-specific delivery.

While self assembly represents a convenient method for the bottom-up design of nanovectors, the forces that drive and sustain the assembly of polymer micelles are concentration dependent and inherently reversible. In clinical applications, where polymer micelles are rapidly diluted following administration, this reversibility, along with high concentrations of micelle-destabilizing blood components (e.g. proteins, lipids, and phospholipids), often leads to premature dissociation of the drug-loaded micelle before active or passive targeting is effectively achieved. For polymer micelles to fully reach their cell-targeting potential and exploit their envisioned multi-functionality, in vivo circulation time must be improved. Drug delivery vehicles are needed, which are infinitely stable to post-administration dilution, can avoid biological barriers (e.g. reticuloendothelial system (RES) uptake), and deliver drugs in response to the physiological environment encountered in diseased tissues, such as solid tumors.

BRIEF DESCRIPTION OF THE DRAWINGS

FIG. 1A and FIG. 1B. Schematic illustrations depicting the triblock copolymer (FIG. 1A) and polymer micelle (FIG. 1B) of the present invention.

FIG. 2. Schematic illustrations showing the preparation of drug loaded micelles.

FIG. 3. Schematic illustrations showing the crosslinking of a drug loaded micelle with metal ions.

FIG. 4. Schematic illustrations depicting the crosslinked, drug loaded micelle of the present invention.

DETAILED DESCRIPTION OF CERTAIN EMBODIMENTS OF THE INVENTION

1. General Description

Figure 5:
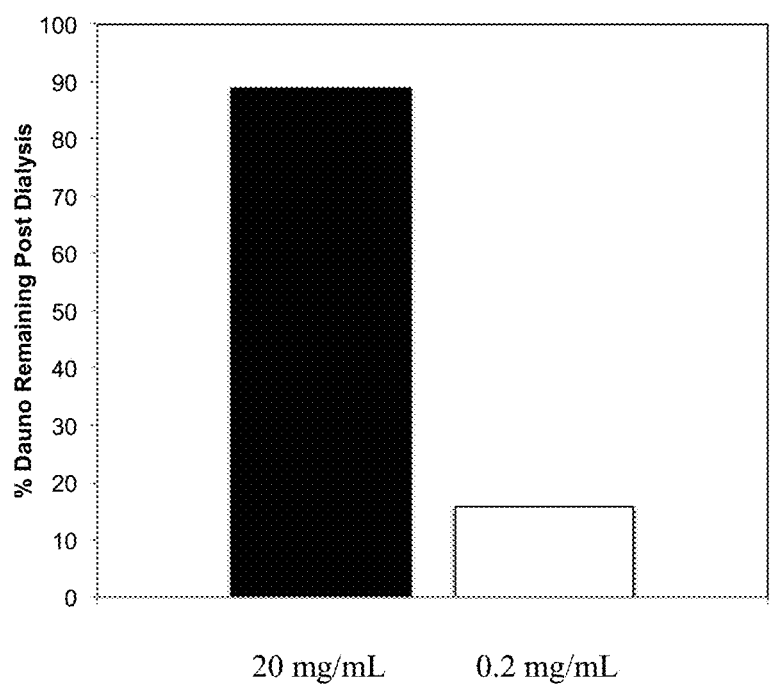
FIG. 5. Validation of encapsulation of daunorubicin by dialysis of the uncrosslinked formulation at 20 mg/ml (black bar) and 0.2 mg/mL (white bar) for 6 hours against phosphate buffer pH 8.

According to one embodiment, the present invention provides a micelle comprising a multiblock copolymer which comprises a polymeric hydrophilic block, optionally a crosslinkable or crosslinked poly(amino acid block), and a hydrophobic D,L-mixed poly(amino acid) block, characterized in that said micelle has an inner core, optionally a crosslinkable or crosslinked outer core, and a hydrophilic shell. It will be appreciated that the polymeric hydrophilic block corresponds to the hydrophilic shell, the optionally crosslinkable or crosslinked poly(amino acid block) corresponds to the optionally crosslinked outer core, and the hydrophobic D,L-mixed poly(amino acid) block corresponds to the inner core.

The "hydrophobic D,L-mixed poly(amino acid)" block, as described herein, consists of a mixture of D and L enantiomers to facilitate the encapsulation of hydrophobic moieties. It is well established that homopolymers and copolymers of amino acids, consisting of a single stereoisomer, may exhibit secondary structures such as the α-helix or β-sheet. See α-*Aminoacid-N-Caroboxy-Anhydrides and Related Heterocycles*, H. R. Kricheldorf, Springer-Verlag, 1987. For example, poly(L-benzyl glutamate) typically exhibits an α-helical conformation; however this secondary structure can be disrupted by a change of solvent or temperature (see *Advances in Protein Chemistry XVI*, P. Urnes and P. Doty, Academic Press, New York 1961). The secondary structure can also be disrupted by the incorporation of structurally dissimilar amino acids such as β-sheet forming amino acids (e.g. proline) or through the incorporation of amino acids with dissimilar stereochemistry (e.g. mixture of D and L stereoisomers), which results in poly(amino acids) with a random coil conformation. See Sakai, R.; Ikeda; S.; Isemura, T. *Bull Chem. Soc. Japan* 1969, 42, 1332-1336, Paolillo, L.; Temussi, P. A.; Bradbury, E. M.; Crane-Robinson, C. *Biopolymers* 1972, 11, 2043-2052, and Cho, I.; Kim, J. B.; Jung, H. J. *Polymer* 2003, 44, 5497-5500.

While the methods to influence secondary structure of poly(amino acids) have been known for some time, it has been surprisingly discovered that block copolymers possessing a random coil conformation are particularly useful for the encapsulation of hydrophobic molecules and nanoparticles when compared to similar block copolymers possessing a helical segment. See US Patent Application 2008-0274173. Without wishing to be bound to any particular theory, it is believed that provided block copolymers having a coil-coil conformation allow for efficient packing and loading of hydrophobic moieties within the micelle core, while the steric demands of a rod-coil conformation for a helix-containing block copolymer results in less effective encapsulation.

The hydrophobic forces that drive the aqueous assembly of colloidal drug carriers, such as polymer micelles and liposomes, are relatively weak, and these assembled structures dissociate below a finite concentration known as the critical micelle concentration (CMC). The CMC value of polymer micelles is of great importance in clinical applications because drug-loaded colloidal carriers are diluted in the bloodstream following administration and rapidly reach concentrations below the CMC (M or less). This dilution effect will lead to micelle dissociation and drug release outside the targeted area and any benefits associated with the micelle size (EPR effect) or active targeting will be lost. While a great deal of research throughout the 1990's focused on identifying polymer micelles with ultra-low CMC values (nM or less), Maysinger (Savic et. al., *Langmuir*, 2006, p 3570-3578) and Schiochet (Lu et. al., *Macromolecules*, 2011, p 6002-6008) have redefined the concept of a biologically relevant CMC by showing that the CMC values for polymer micelles shift by two orders of magnitude when the CMC values in saline are compared with and without serum.

In addition to their core-shell morphology, polymer micelles can be modified to enable passive and active cell-targeting to maximize the benefits of current and future therapeutic agents. Because drug-loaded micelles typically possess diameters greater than 20 nm, they exhibit dramatically increased circulation time when compared to stand-alone drugs due to minimized renal clearance. This unique feature of nanovectors and polymeric drugs leads to selective accumulation in diseased tissue, especially cancerous tissue due to the enhanced permeation and retention effect ("EPR"). The EPR effect is a consequence of the disorganized nature of the tumor vasculature, which results in increased permeability of polymer therapeutics and drug retention at the tumor site. In addition to passive cell targeting by the EPR effect, micelles are designed to actively target tumor cells through the chemical attachment of targeting groups to the micelle periphery. The incorporation of such groups is most often accomplished through end-group functionalization of the hydrophilic block using chemical conjugation techniques. Like viral particles, micelles functionalized with targeting groups utilize receptor-ligand interactions to control the spatial distribution of the micelles after administration, further enhancing cell-specific delivery of therapeutics. In cancer therapy, targeting groups are designed to interact with receptors that are over-expressed in cancerous tissue relative to normal tissue such as folic acid, oligopeptides, sugars, and monoclonal antibodies. See Pan, D.; Turner, J. L.; Wooley, K. L. *Chem. Commun.* 2003, 2400-2401; Gabizon, A.; Shmeeda, H.; Horowitz, A. T.; Zalipsky, S. *Adv. Drug Deliv. Rev.* 2004, 56, 1177-1202; Reynolds, P. N.; Dmitriev, I.; Curiel, D. T. *Vector. Gene Ther.* 1999, 6, 1336-1339; Derycke, A. S. L.; Kamuhabwa, A.; Gijsens, A.; Roskams, T.; De Vos, D.; Kasran, A.; Huwyler, J.; Missiaen, L.; de Witte, P. A. M. T *J. Nat. Cancer Inst.* 2004, 96, 1620-30; Nasongkla, N., Shuai, X., Ai, H.; Weinberg, B. D. P., J.; Boothman, D. A.; Gao, J. *Angew. Chem. Int. Ed.* 2004, 43, 6323-6327; Jule, E.; Nagasaki, Y.; Kataoka, K. *Bioconj. Chem.* 2003, 14, 177-186; Stubenrauch, K.; Gleiter, S.; Brinkmann, U.; Rudolph, R.; Lilie, H. *Biochem. J* 2001, 356, 867-873; Kurschus, F. C.; Kleinschmidt, M.; Fellows, E.; Dornmair, K.; Rudolph, R.; Lilie, H.; Jenne, D. E. *FEBS Lett.* 2004, 562, 87-92; and Jones, S. D.; Marasco, W. A. *Adv. Drug Del. Rev.* 1998, 31, 153-170.

Despite the large volume of work on micellar drug carriers, little effort has focused on improving their in vivo stability to dilution. One potential reason is that the true effects of micelle dilution in vivo are not fully realized until larger animal studies are utilized. Because a mouse's metabolism is much higher than larger animals, they can receive considerably higher doses of toxic drugs when compared to larger animals such as rats or dogs. Therefore, when drug loaded micelles are administered and completely diluted throughout the entire blood volume, the corresponding polymer concentration will always be highest in the mouse model. Therefore, it would be highly desirable to prepare a micelle that is stabilized (crosslinked) to dilution within biological media.

In the present invention, the optionally crosslinkable or crosslinked poly(amino acid block) is comprised of chemical functionality that strongly binds or coordinates with metal ions. One specific example is hydroxamic acids and iron (III). Another example is ortho-substituted dihydroxy benzene groups (catechols) with iron. Both hydroxamic acid and catechol moieties are common in siderophores, high-affinity iron chelating agents produced by microorganisms. Additionally, it has been reported that hydroxamic acid modified poly(acrylates) can form a crosslinked gel following treatment with iron (III) (Rosthauser and Winston, *Macromolecules*, 1981, p 538-543). Without wishing to be bound to any particular theory, it is believed that the incorporation of high affinity metal chelating group such as hydroxamic acids and catechols in the outer core of the micelle, following treatment with a metal ion will result in a micelle that is stable to dilution within biological media.

Previous work has utilized carboxylic acids to interact with metal ions in order to provide micelle stability. See US Patent Application 2006-0240092. It has been surprisingly discovered that the use of hydroxamic acid-modified polymers is effective at reversibly stabilizing the polymer micelle to dilution within biological media. This hydroxamic acid chemistry has been demonstrated to be particularly effective when encapsulating a drug that possesses one or more chemical functionalities known to bind iron (e.g. carboxylic acids). Without wishing to be bound to any particular theory, it is believed that the metal ions used to stabilize the micelle will preferentially bind to the high affinity metal chelating group such as hydroxamic acids and catechols, resulting in a stabilized micelle. Furthermore, the chelation reaction between iron (III) and hydroxamic acid moieties proceeds within seconds, allowing for a rapid crosslinking step.

2. Definitions

Compounds of this invention include those described generally above, and are further illustrated by the embodiments, sub-embodiments, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito:

1999, and "March's Advanced Organic Chemistry", 5$^{th}$ Ed., Ed.: Smith, M. B. and March, J., John Wiley & Sons, New York: 2001, the entire contents of which are hereby incorporated by reference.

As used herein, the term "sequential polymerization", and variations thereof, refers to the method wherein, after a first monomer (e.g. NCA, lactam, or imide) is incorporated into the polymer, thus forming an amino acid "block", a second monomer (e.g. NCA, lactam, or imide) is added to the reaction to form a second amino acid block, which process may be continued in a similar fashion to introduce additional amino acid blocks into the resulting multi-block copolymers.

As used herein, the term "multiblock copolymer" refers to a polymer comprising one synthetic polymer portion and two or more poly(amino acid) portions. Such multi-block copolymers include those having the format W—X—X', wherein W is a synthetic polymer portion and X and X' are poly(amino acid) chains or "amino acid blocks". In certain embodiments, the multiblock copolymers of the present invention are triblock copolymers. As described herein, one or more of the amino acid blocks may be "mixed blocks", meaning that these blocks can contain a mixture of amino acid monomers thereby creating multiblock copolymers of the present invention. In some embodiments, the multiblock copolymers of the present invention comprise a mixed amino acid block and are tetrablock copolymers.

One skilled in the art will recognize that a monomer repeat unit is defined by parentheses around the repeating monomer unit. The number (or letter representing a numerical range) on the lower right of the parentheses represents the number of monomer units that are present in the polymer chain. In the case where only one monomer represents the block (e.g. a homopolymer), the block will be denoted solely by the parentheses. In the case of a mixed block, multiple monomers comprise a single, continuous block. It will be understood that brackets will define a portion or block. For example, one block may consist of four individual monomers, each defined by their own individual set of parentheses and number of repeat units present. All four sets of parentheses will be enclosed by a set of brackets, denoting that all four of these monomers combine in random, or near random, order to comprise the mixed block. For clarity, the randomly mixed block of [BCADDCBADABCDABC] would be represented in shorthand by $[(A)_4(B)_4(C)_4(D)_4]$.

As used herein, the monomer repeat unit described above is a numerical value representing the average number of monomer units comprising the polymer chain. For example, a polymer represented by $(A)_{10}$ corresponds to a polymer consisting of ten "A" monomer units linked together. One of ordinary skill in the art will recognize that the number 10 in this case will represent a distribution of numbers with an average of 10. The breadth of this distribution is represented by the polydispersity index (PDI). A PDI of 1.0 represents a polymer wherein each chain length is exactly the same (e.g. a protein). A PDI of 2.0 represents a polymer wherein the chain lengths have a Gaussian distribution. Polymers of the present invention typically possess a PDI of less than 1.20.

As used herein, the term "triblock copolymer" refers to a polymer comprising one synthetic polymer portion and two poly(amino acid) portions.

As used herein, the term "tetrablock copolymer" refers to a polymer comprising one synthetic polymer portion and either two poly(amino acid) portions, wherein 1 poly(amino acid) portion is a mixed block or a polymer comprising one synthetic polymer portion and three poly(amino acid) portions.

As used herein, the term "inner core" as it applies to a micelle of the present invention refers to the center of the micelle formed by the hydrophobic D,L-mixed poly(amino acid) block. In accordance with the present invention, the inner core is not crosslinked. By way of illustration, in a triblock polymer of the format W—X'—X", as described above, the inner core corresponds to the X" block.

As used herein, the term "outer core" as it applies to a micelle of the present invention refers to the layer formed by the first poly(amino acid) block. The outer core lies between the inner core and the hydrophilic shell. In accordance with the present invention, the outer core is either crosslinkable or is cross-linked. By way of illustration, in a triblock polymer of the format W—X'—X", as described above, the outer core corresponds to the X' block. It is contemplated that the X' block can be a mixed block.

As used herein, the terms "drug-loaded" and "encapsulated", and derivatives thereof, are used interchangeably. In accordance with the present invention, a "drug-loaded" micelle refers to a micelle having a drug, or therapeutic agent, situated within the core of the micelle. In certain instances, the drug or therapeutic agent is situated at the interface between the core and the hydrophilic coronoa. This is also referred to as a drug, or therapeutic agent, being "encapsulated" within the micelle.

As used herein, the term "polymeric hydrophilic block" refers to a polymer that is not a poly(amino acid) and is hydrophilic in nature. Such hydrophilic polymers are well known in the art and include polyethyleneoxide (also referred to as polyethylene glycol or PEG), and derivatives thereof, poly(N-vinyl-2-pyrolidone), and derivatives thereof, poly(N-isopropylacrylamide), and derivatives thereof, poly(hydroxyethyl acrylate), and derivatives thereof, poly(hydroxylethyl methacrylate), and derivatives thereof, and polymers of N-(2-hydroxypropoyl)methacrylamide (HMPA) and derivatives thereof.

As used herein, the term "poly(amino acid)" or "amino acid block" refers to a covalently linked amino acid chain wherein each monomer is an amino acid unit. Such amino acid units include natural and unnatural amino acids. In certain embodiments, each amino acid unit of the optionally crosslinkable or crosslinked poly(amino acid block) is in the L-configuration. Such poly(amino acids) include those having suitably protected functional groups. For example, amino acid monomers may have hydroxyl or amino moieties, which are optionally protected by a hydroxyl protecting group or an amine protecting group, as appropriate. Such suitable hydroxyl protecting groups and amine protecting groups are described in more detail herein, infra. As used herein, an amino acid block comprises one or more monomers or a set of two or more monomers. In certain embodiments, an amino acid block comprises one or more monomers such that the overall block is hydrophilic. In still other embodiments, amino acid blocks of the present invention include random amino acid blocks, ie blocks comprising a mixture of amino acid residues.

As used herein, the term "D,L-mixed poly(amino acid) block" refers to a poly(amino acid) block wherein the poly(amino acid) consists of a mixture of amino acids in both the D- and L-configurations. In certain embodiments, the D,L-mixed poly(amino acid) block is hydrophobic. In other embodiments, the D,L-mixed poly(amino acid) block consists of a mixture of D-configured hydrophobic amino acids and L-configured hydrophilic amino acid side-chain groups such that the overall poly(amino acid) block comprising is hydrophobic.

Exemplary poly(amino acids) include poly(benzyl glutamate), poly(benzyl aspartate), poly(L-leucine-co-tyrosine), poly(D-leucine-co-tyrosine), poly(L-phenylalanine-co-tyrosine), poly(D-phenylalanine-co-tyrosine), poly(L-leucine-coaspartic acid), poly(D-leucine-co-aspartic acid), poly(L-phenylalanine-co-aspartic acid), poly(D-phenylalanine-co-aspartic acid).

As used herein, the phrase "natural amino acid side-chain group" refers to the side-chain group of any of the 20 amino acids naturally occurring in proteins. For clarity, the side chain group —$CH_3$ would represent the amino acid alanine. Such natural amino acids include the nonpolar, or hydrophobic amino acids, glycine, alanine, valine, leucine isoleucine, methionine, phenylalanine, tryptophan, and proline. Cysteine is sometimes classified as nonpolar or hydrophobic and other times as polar. Natural amino acids also include polar, or hydrophilic amino acids, such as tyrosine, serine, threonine, aspartic acid (also known as aspartate, when charged), glutamic acid (also known as glutamate, when charged), asparagine, and glutamine. Certain polar, or hydrophilic, amino acids have charged side-chains. Such charged amino acids include lysine, arginine, and histidine. One of ordinary skill in the art would recognize that protection of a polar or hydrophilic amino acid side-chain can render that amino acid nonpolar. For example, a suitably protected tyrosine hydroxyl group can render that tyroine nonpolar and hydrophobic by virtue of protecting the hydroxyl group.

As used herein, the phrase "unnatural amino acid side-chain group" refers to amino acids not included in the list of 20 amino acids naturally occurring in proteins, as described above. Such amino acids include the D-isomer of any of the 20 naturally occurring amino acids. Unnatural amino acids also include homoserine, ornithine, and thyroxine. Other unnatural amino acids side-chains are well know to one of ordinary skill in the art and include unnatural aliphatic side chains. Other unnatural amino acids include modified amino acids, including those that are N-alkylated, cyclized, phosphorylated, acetylated, amidated, azidylated, labelled, and the like.

As used herein, the term "tacticity" refers to the stereochemistry of the poly(amino acid) hydrophobic block. A poly(amino acid) block consisting of a single stereoisomer (e.g. all L isomer) is referred to as "isotactic". A poly(amino acid) consisting of a random incorporation of D and L amino acid monomers is referred to as an "atactic" polymer. A poly(amino acid) with alternating stereochemistry (e.g. . . . DLDLDL . . . ) is referred to as a "syndiotactic" polymer. Polymer tacticity is described in more detail in "Principles of Polymerization", 3rd Ed., G. Odian, John Wiley & Sons, New York: 1991, the entire contents of which are hereby incorporated by reference.

As used herein, the phrase "living polymer chain-end" refers to the terminus resulting from a polymerization reaction which maintains the ability to react further with additional monomer or with a polymerization terminator.

As used herein, the term "termination" refers to attaching a terminal group to a polymer chain-end by the reaction of a living polymer with an appropriate compound. Alternatively, the term "termination" may refer to attaching a terminal group to an amine or hydroxyl end, or derivative thereof, of the polymer chain.

As used herein, the term "polymerization terminator" is used interchangeably with the term "polymerization terminating agent" and refers to a compound that reacts with a living polymer chain-end to afford a polymer with a terminal group. Alternatively, the term "polymerization terminator" may refer to a compound that reacts with an amine or hydroxyl end, or derivative thereof, of the polymer chain, to afford a polymer with a terminal group.

As used herein, the term "polymerization initiator" refers to a compound, which reacts with, or whose anion or free base form reacts with, the desired monomer in a manner which results in polymerization of that monomer. In certain embodiments, the polymerization initiator is the compound that reacts with an alkylene oxide to afford a polyalkylene oxide block. In other embodiments, the polymerization initiator is an amine salt as described herein. In certain embodiments, the polymerization initiator is a trifluoroacetic acid amine salt.

The term "aliphatic" or "aliphatic group", as used herein, denotes a hydrocarbon moiety that may be straight-chain (i.e., unbranched), branched, or cyclic (including fused, bridging, and spiro-fused polycyclic) and may be completely saturated or may contain one or more units of unsaturation, but which is not aromatic. Unless otherwise specified, aliphatic groups contain 1-20 carbon atoms. In some embodiments, aliphatic groups contain 1-10 carbon atoms. In other embodiments, aliphatic groups contain 1-8 carbon atoms. In still other embodiments, aliphatic groups contain 1-6 carbon atoms, and in yet other embodiments aliphatic groups contain 1-4 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "heteroatom" means one or more of oxygen, sulfur, nitrogen, phosphorus, or silicon. This includes any oxidized form of nitrogen, sulfur, phosphorus, or silicon; the quaternized form of any basic nitrogen, or; a substitutable nitrogen of a heterocyclic ring including =N— as in 3,4-dihydro-2H-pyrrolyl, —NH— as in pyrrolidinyl, or =N(R⁺)— as in N-substituted pyrrolidinyl.

The term "unsaturated", as used herein, means that a moiety has one or more units of unsaturation.

As used herein, the term "bivalent, saturated or unsaturated, straight or branched $C_{1-12}$ hydrocarbon chain", refers to bivalent alkylene, alkenylene, and alkynylene chains that are straight or branched as defined herein.

The term "aryl" used alone or as part of a larger moiety as in "aralkyl", "aralkoxy", or "aryloxyalkyl", refers to monocyclic, bicyclic, and tricyclic ring systems having a total of five to fourteen ring members, wherein at least one ring in the system is aromatic and wherein each ring in the system contains three to seven ring members. The term "aryl" may be used interchangeably with the term "aryl ring".

As described herein, compounds of the invention may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position.

Combinations of substituents envisioned by this invention are preferably those that result in the formation of stable or chemically feasible compounds. The term "stable", as used herein, refers to compounds that are not substantially altered when subjected to conditions to allow for their production, detection, and, in certain embodiments, their recovery, purification, and use for one or more of the purposes disclosed herein.

Monovalent substituents on a substitutable carbon atom of an "optionally substituted" group are independently halogen; —$(CH_2)_{0-4}R°$; —$(CH_2)_{0-4}OR°$; —O—$(CH_2)_{0-4}C(O)OR°$; —$(CH_2)_{0-4}CH(OR°)_2$; —$(CH_2)_{0-4}SR°$; —$(CH_2)_{0-4}Ph$, which may be substituted with R°; —$(CH_2)_{0-4}O(CH_2)_{0-1}Ph$ which may be substituted with R°; —CH=CHPh, which may be substituted with R°; —$NO_2$; —CN; —$N_3$; —$(CH_2)_{0-4}N(R°)_2$; —$(CH_2)_{0-4}N(R°)C(O)R°$; —$N(R°)C(S)R°$; —$(CH_2)_{0-4}N(R°)C(O)NR°_2$; —$N(R°)C(S)NR°_2$; —$(CH_2)_{0-4}N(R°)C(O)OR°$; —$N(R°)N(R°)C(O)R°$; —$N(R°)N(R°)C(O)NR°_2$; —$N(R°)N(R°)C(O)OR°$; —$(CH_2)_{0-4}C(O)R°$; —$C(S)R°$; —$(CH_2)_{0-4}C(O)OR°$; —$(CH_2)_{0-4}C(O)SR°$; —$(CH_2)_{0-4}C(O)OSiR°_3$; —$(CH_2)_{0-4}OC(O)R°$; —$OC(O)(CH_2)_{0-4}SR—$, $SC(S)SR°$; —$(CH_2)_{0-4}SC(O)R°$; —$(CH_2)_{0-4}C(O)NR°_2$; —$C(S)NR°_2$; —$C(S)SR°$; —$SC(S)SR°$, —$(CH_2)_{0-4}OC(O)NR°_2$; —$C(O)N(OR°)R°$; —$C(O)C(O)R°$; —$C(O)CH_2C(O)R°$; —$C(NOR°)R°$; —$(CH_2)_{0-4}SSR°$; —$(CH_2)_{0-4}S(O)_2R°$; —$(CH_2)_{0-4}S(O)_2OR°$; —$(CH_2)_{0-4}OS(O)_2R°$; —$S(O)_2NR°_2$; —$(CH_2)_{0-4}S(O)R°$; —$N(R°)S(O)_2NR°_2$; —$N(R°)S(O)_2R$; —$N(OR°)R°$; —$C(NH)NR°_2$; —$P(O)_2R$; —$P(O)R°_2$; —$OP(O)R°_2$; —$OP(O)(OR°)_2$; $SiR°_3$; —$(C_{1-4}$ straight or branched alkylene)O—$N(R°)_2$; or —$(C_{1-4}$ straight or branched alkylene)C(O)O—$N(R°)_2$, wherein each R° may be substituted as defined below and is independently hydrogen, $C_{1-6}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Monovalent substituents on R° (or the ring formed by taking two independent occurrences of R° together with their intervening atoms), are independently halogen, —$(CH_2)_{0-2}R^•$, -(haloR$^•$), —$(CH_2)_{0-2}OH$, —$(CH_2)_{0-2}OR^•$, —$(CH_2)_{0-2}CH(OR^•)_2$; —O(haloR$^•$), —CN, —$N_3$, —$(CH_2)_{0-2}C(O)R^•$, —$(CH_2)_{0-2}C(O)OH$, —$(CH_2)_{0-2}C(O)OR^•$, —$(CH_2)_{0-2}SR^•$, —$(CH_2)_{0-2}SH$, —$(CH_2)_{0-2}NH_2$, —$(CH_2)_{0-2}NHR^•$, —$(CH_2)_{0-2}NR^•_2$, —$NO_2$, —$SiR^•_3$, —$OSiR^•_3$, —$C(O)SR^•$, —$(C_{1-4}$ straight or branched alkylene)C(O)OR$^•$, or —$SSR^•$ wherein each R$^•$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Such divalent substituents on a saturated carbon atom of R° include =O and =S.

Divalent substituents on a saturated carbon atom of an "optionally substituted" group include the following: =O, =S, =$NNR^*_2$, =$NNHC(O)R^*$, =$NNHC(O)OR^*$, =$NNHS(O)_2R^*$, =$NR^*$, =$NOR^*$, —$O(C(R^*_2))_{2-3}O—$, or —$S(C(R^*_2))_{2-3}S—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Divalent substituents that are bound to vicinal substitutable carbons of an "optionally substituted" group include: —$O(CR^*_2)_{2-3}O—$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. A tetravalent substituent that is bound to vicinal substitutable methylene carbons of an "optionally substituted" group is the dicobalt hexacarbonyl cluster represented by

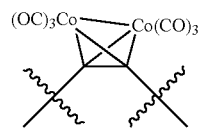

when depicted with the methylenes which bear it.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —$NH_2$, —NHR$^•$, —NR$^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^†$, —$NR^†_2$, —$C(O)R^†$, —$C(O)OR^†$, —$C(O)C(O)R^†$, —$C(O)CH_2C(O)R^†$, —$S(O)_2R^†$, —$S(O)_2NR^†_2$, —$C(S)NR^†_2$, —$C(NH)NR^†_2$, or —$N(R^†)S(O)_2R^†$; wherein each $R^†$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^†$ are independently halogen, —R$^•$, -(haloR$^•$), —OH, —OR$^•$, —O(haloR$^•$), —CN, —C(O)OH, —C(O)OR$^•$, —$NH_2$, —NHR$^•$, —NR$^•_2$, or —$NO_2$, wherein each R$^•$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Protected hydroxyl groups are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected hydroxyl groups further include, but are not limited to, esters, carbonates, sulfonates allyl ethers, ethers, silyl ethers, alkyl ethers, arylalkyl ethers, and alkoxyalkyl ethers. Examples of suitable esters include formates, acetates, proprionates, pentanoates, crotonates, and benzoates. Specific examples of suitable esters include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio) pentanoate, pivaloate (trimethylacetate), crotonate, 4-methoxy-crotonate, benzoate, p-benylbenzoate, 2,4,6-trimethylbenzoate. Examples of carbonates include 9-fluorenylmethyl, ethyl, 2,2,2-trichloroethyl, 2-(trimethylsilyl) ethyl, 2-(phenylsulfonyl)ethyl, vinyl, allyl, and p-nitrobenzyl carbonate. Examples of silyl ethers include trimethylsilyl, triethylsilyl, t-butyldimethylsilyl, t-butyldiphenylsilyl, triisopropylsilyl ether, and other trialkylsilyl ethers. Examples of alkyl ethers include methyl, benzyl, p-methoxybenzyl, 3,4-dimethoxybenzyl, trityl, t-butyl, and allyl ether, or derivatives thereof. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyran-2-yl ether. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

Protected amines are well known in the art and include those described in detail in Greene (1999). Mono-protected amines further include, but are not limited to, aralkylamines, carbamates, allyl amines, amides, and the like. Examples of mono-protected amino moieties include t-butyloxycarbonylamino (—NHBOC), ethyloxycarbonylamino, methyloxycarbonylamino, trichloroethyloxycarbonylamino, allyloxycarbonylamino (—NHAlloc), benzyloxocarbonylamino (—NHCBZ), allylamino, benzylamino (—NHBn), fluorenylmethylcarbonyl (—NHFmoc), formamido, acetamido, chloroacetamido, dichloroacetamido, trichloroacetamido, phenylacetamido, trifluoroacetamido, benzamido, t-butyldiphenylsilyl, and the like. Di-protected amines include amines that are substituted with two substituents independently selected from those described above as mono-protected amines, and further include cyclic imides, such as phthalimide, maleimide, succinimide, and the like. Di-protected amines also include pyrroles and the like, 2,2,5,5-tetramethyl-[1,2,5]azadisilolidine and the like, and azide.

Protected aldehydes are well known in the art and include those described in detail in Greene (1999). Protected aldehydes further include, but are not limited to, acyclic acetals, cyclic acetals, hydrazones, imines, and the like. Examples of such groups include dimethyl acetal, diethyl acetal, diisopropyl acetal, dibenzyl acetal, bis(2-nitrobenzyl) acetal, 1,3-dioxanes, 1,3-dioxolanes, semicarbazones, and derivatives thereof.

Protected carboxylic acids are well known in the art and include those described in detail in Greene (1999). Protected carboxylic acids further include, but are not limited to, optionally substituted $C_{1-6}$ aliphatic esters, optionally substituted aryl esters, silyl esters, activated esters, amides, hydrazides, and the like. Examples of such ester groups include methyl, ethyl, propyl, isopropyl, butyl, isobutyl, benzyl, and phenyl ester, wherein each group is optionally substituted. Additional protected carboxylic acids include oxazolines and ortho esters.

Protected thiols are well known in the art and include those described in detail in Greene (1999). Protected thiols further include, but are not limited to, disulfides, thioethers, silyl thioethers, thioesters, thiocarbonates, and thiocarbamates, and the like. Examples of such groups include, but are not limited to, alkyl thioethers, benzyl and substituted benzyl thioethers, triphenylmethyl thioethers, and trichloroethoxycarbonyl thioester, to name but a few.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as in neutron scattering experiments, as analytical tools or probes in biological assays.

As used herein, the term "detectable moiety" is used interchangeably with the term "label" and relates to any moiety capable of being detected (e.g., primary labels and secondary labels). A "detectable moiety" or "label" is the radical of a detectable compound.

"Primary" labels include radioisotope-containing moieties (e.g., moieties that contain $^{32}$P, $^{33}$P, $^{35}$S, or $^{14}$C), mass-tags, and fluorescent labels, and are signal-generating reporter groups which can be detected without further modifications.

Other primary labels include those useful for positron emission tomography including molecules containing radioisotopes (e.g. $^{18}$F) or ligands with bound radioactive metals (e.g. $^{62}$Cu). In other embodiments, primary labels are contrast agents for magnetic resonance imaging such as gadolinium, gadolinium chelates, or iron oxide (e.g $Fe_3O_4$ and $Fe_2O_3$) particles. Similarly, semiconducting nanoparticles (e.g. cadmium selenide, cadmium sulfide, cadmium telluride) are useful as fluorescent labels. Other metal nanoparticles (e.g colloidal gold) also serve as primary labels.

"Secondary" labels include moieties such as biotin, or protein antigens, that require the presence of a second compound to produce a detectable signal. For example, in the case of a biotin label, the second compound may include streptavidin-enzyme conjugates. In the case of an antigen label, the second compound may include an antibody-enzyme conjugate. Additionally, certain fluorescent groups can act as secondary labels by transferring energy to another compound or group in a process of nonradiative fluorescent resonance energy transfer (FRET), causing the second compound or group to then generate the signal that is detected.

Unless otherwise indicated, radioisotope-containing moieties are optionally substituted hydrocarbon groups that contain at least one radioisotope. Unless otherwise indicated, radioisotope-containing moieties contain from 1-40 carbon atoms and one radioisotope. In certain embodiments, radioisotope-containing moieties contain from 1-20 carbon atoms and one radioisotope.

The terms "fluorescent label", "fluorescent group", "fluorescent compound", "fluorescent dye", and "fluorophore", as used herein, refer to compounds or moieties that absorb light energy at a defined excitation wavelength and emit light energy at a different wavelength. Examples of fluorescent compounds include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethyl-rhodamine (TAMRA), Texas Red, Texas Red-X.

The term "substrate", as used herein refers to any material or macromolecular complex to which a functionalized end-group of a block copolymer can be attached. Examples of commonly used substrates include, but are not limited to, glass surfaces, silica surfaces, plastic surfaces, metal surfaces, surfaces containing a metallic or chemical coating, membranes (e.g., nylon, polysulfone, silica), micro-beads (e.g., latex, polystyrene, or other polymer), porous polymer matrices (e.g., polyacrylamide gel, polysaccharide, polymethacrylate), macromolecular complexes (e.g., protein, polysaccharide).

The term hydroxamic acid, as used herein, refers to a moiety containing a hydroxamic acid (—CO—NH—OH) functional group. The structured is represented by

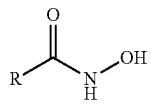

and may also be represented by

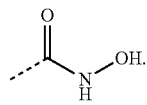

One skilled in the art would recognize that the dotted bond represents the attachment point to the rest of the molecule.

The term hydroxamate, as used herein, refers to a moiety containing either hydroxamic acid or an N-substituted hydroxamic acid. Due to the N-substitution, two separate locations exist for chemical attachment, as shown by the R and R' groups here

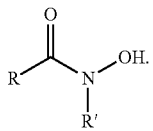

Hydroxamates may also be represented by

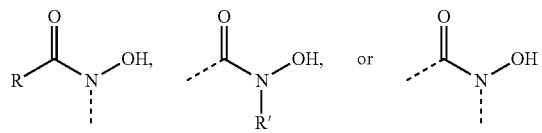

herein.

The term catechol, as used herein, refers to a substituted ortho-dihydroxybenezene derivative. Two different isomeric conformations are represented by

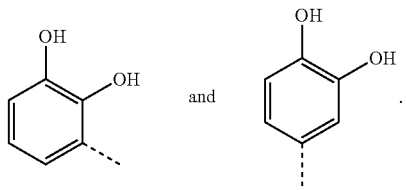

Catechol is also known as pyrocatechol and benzene-1,2-diol.

3. Description of Exemplary Embodiments

A. Multiblock Copolymers

In certain embodiments, the multiblock copolymer comprises a hydrophilic poly(ethylene glycol) block, a hydroxamic acid-containing poly(amino acid) block, and a hydrophobic poly(amino acid) block characterized in that the resulting micelle has an inner core, a hydroxamic acid-containing outer core, and a hydrophilic shell. It will be appreciated that the hydrophilic poly(ethylene glycol) block corresponds to the hydrophilic shell, stabilizing hydroxamic acid-containing poly(amino acid) block corresponds to the hydroxamic acid-containing outer core, and the hydrophobic poly(amino acid) block corresponds to the inner core.

In other embodiments, the multiblock copolymer comprises a hydrophilic poly(ethylene glycol) block, a catechol-containing poly(amino acid) block, and a hydrophobic poly(amino acid) block characterized in that the resulting micelle has an inner core, an catechol-containing outer core, and a hydrophilic shell. It will be appreciated that the hydrophilic poly(ethylene glycol) block corresponds to the hydrophilic shell, stabilizing catechol-containing poly(amino acid) block corresponds to the catechol-containing outer core, and the hydrophobic poly(amino acid) block corresponds to the inner core.

In certain embodiments, the multiblock copolymer comprises a hydrophilic poly(ethylene glycol) block, a hydroxamate-containing poly(amino acid) block, and a hydrophobic poly(amino acid) block characterized in that the resulting micelle has an inner core, a hydroxamate-containing outer core, and a hydrophilic shell. It will be appreciated that the hydrophilic poly(ethylene glycol) block corresponds to the hydrophilic shell, stabilizing hydroxamate-containing poly(amino acid) block corresponds to the hydroxamate-containing outer core, and the hydrophobic poly(amino acid) block corresponds to the inner core.

In certain embodiments, the multiblock copolymer comprises a hydrophilic poly(ethylene glycol) block, a hydroxamic acid-containing poly(amino acid) block, and a hydrophobic D,L mixed poly(amino acid) block characterized in that the resulting micelle has an inner core, a hydroxamic acid-containing outer core, and a hydrophilic shell. It will be appreciated that the hydrophilic poly(ethylene glycol) block corresponds to the hydrophilic shell, stabilizing hydroxamic acid-containing poly(amino acid) block corresponds to the hydroxamic acid-containing outer core, and the hydrophobic D,L mixed poly(amino acid) block corresponds to the inner core.

In other embodiments, the multiblock copolymer comprises a hydrophilic poly(ethylene glycol) block, a catechol-containing poly(amino acid) block, and a hydrophobic D,L mixed poly(amino acid) block characterized in that the resulting micelle has an inner core, an catechol-containing outer core, and a hydrophilic shell. It will be appreciated that the hydrophilic poly(ethylene glycol) block corresponds to the hydrophilic shell, stabilizing catechol-containing poly (amino acid) block corresponds to the catechol-containing outer core, and the hydrophobic D,L mixed poly(amino acid) block corresponds to the inner core.

In certain embodiments, the multiblock copolymer comprises a hydrophilic poly(ethylene glycol) block, a hydroxamate-containing poly(amino acid) block, and a hydrophobic D,L mixed poly(amino acid) block characterized in that the resulting micelle has an inner core, a hydroxamate-containing outer core, and a hydrophilic shell. It will be appreciated that the hydrophilic poly(ethylene glycol) block corresponds to the hydrophilic shell, stabilizing hydroxamate-containing poly(amino acid) block corresponds to the hydroxamate-containing outer core, and the hydrophobic D,L mixed poly(amino acid) block corresponds to the inner core.

In certain embodiments, the present invention provides a triblock copolymer of formula I:

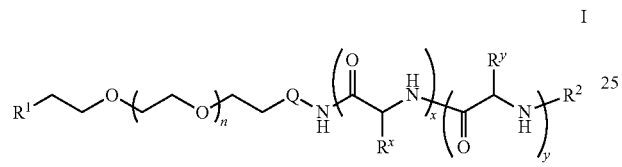

wherein:
n is 20-500;
x is 3 to 50;
y is 5 to 100;
$R^x$ is a hydroxamate or catechol containing moiety;
$R^y$ is selected from one or more natural or unnatural amino acid side chain groups such that the overall block is hydrophobic;
$R^1$ is $-Z(CH_2CH_2Y)_p(CH_2)_tR^3$, wherein:
  Z is —O—, —NH—, —S—, —C≡C—, or —CH$_2$—;
  each Y is independently —O— or —S—;
  p is 0-10;
  t is 0-10; and
  $R^3$ is hydrogen, —N$_3$, —CN, —NH$_2$, —CH$_3$,

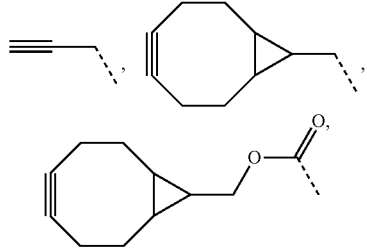

a strained cyclooctyne moiety, a mono-protected amine, a di-protected amine, an optionally protected aldehyde, an optionally protected hydroxyl, an optionally protected carboxylic acid, an optionally protected thiol, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

Q is a valence bond or a bivalent, saturated or unsaturated, straight or branched $C_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
  -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;
$R^2$ is a mono-protected amine, a di-protected amine, —N(R$^4$)$_2$, —NR$^4$C(O)R$^4$, —NR$^4$C(O)N(R$^4$)$_2$, —NR$^4$C(O)OR$^4$, or —NR$^4$SO$_2$R$^4$; and
each $R^4$ is independently hydrogen or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety, or:
  two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

According to another embodiment, the present invention provides compounds of formula I, as described above, wherein said compounds have a polydispersity index ("PDI") of 1.0 to 1.2. According to another embodiment, the present invention provides compounds of formula I, as described above, wherein said compound has a polydispersity index ("PDI") of 1.01 to 1.10. According to yet another embodiment, the present invention provides compounds of formula I, as described above, wherein said compound has a polydispersity index ("PDI") of 1.10 to 1.20. According to other embodiments, the present invention provides compounds of formula I having a PDI of less than 1.10.

As defined generally above, the n is 20 to 500. In certain embodiments, the present invention provides compounds wherein n is 225. In other embodiments, n is 40 to 60. In other embodiments, n is 60 to 90. In still other embodiments, n is 90 to 150. In other embodiments, n is 150 to 200. In some embodiments, n is 200 to 300, 300 to 400, or 400 to 500. In still other embodiments, n is 250 to 280. In other embodiments, n is 300 to 375. In other embodiments, n is 400 to 500. In certain embodiments, n is selected from 50±10. In other embodiments, n is selected from 80±10, 115±10, 180±10, 225±10, or 275±10.

In certain embodiments, the x is 3 to 50. In certain embodiments, the x is 10. In other embodiments, x is 20. According to yet another embodiment, x is 15. In other embodiments, x is 5. In other embodiments, x is selected from 5±3, 10±3, 10±5, 15±5, or 20±5.

In certain embodiments, y is 5 to 100. In certain embodiments, y is 10. In other embodiments, y is 20. According to yet another embodiment, y is 15. In other embodiments, y is 30. In other embodiments, y is selected from 10±3, 15±3, 17±3, 20±5, or 30±5.

In certain embodiments, the $R^3$ moiety of the $R^1$ group of formula I is —N$_3$.

In other embodiments, the $R^3$ moiety of the $R^1$ group of formula I is —$CH_3$.

In some embodiments, the $R^3$ moiety of the $R^1$ group of formula I is hydrogen.

In certain embodiments, the $R^3$ moiety of the $R^1$ group of formula I is an optionally substituted aliphatic group. Examples include methyl, t-butyl, 5-norbornene-2-yl, octane-5-yl, acetylenyl, trimethylsilylacetylenyl, triisopropylsilylacetylenyl, and t-butyldimethylsilylacetylenyl. In some embodiments, said $R^3$ moiety is an optionally substituted alkyl group. In other embodiments, said $R^3$ moiety is an optionally substituted alkynyl or alkenyl group. When said $R^3$ moiety is a substituted aliphatic group, substituents on $R^3$ include CN, $N_3$, trimethylsilyl, triisopropylsilyl, t-butyldimethylsilyl, N-methyl propiolamido, N-methyl-4-acetylenylanilino, N-methyl-4-acetylenylbenzoamido, bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, N-methyl-propargylamino, N-methyl-hex-5-ynyl-amino, N-methyl-pent-4-ynyl-amino, N-methyl-but-3-ynyl-amino, 2-hex-5-ynyldisulfanyl, 2-pent-4-ynyldisulfanyl, 2-but-3-ynyldisulfanyl, and 2-propargyldisulfanyl. In certain embodiments, the $R^1$ group is 2-(N-methyl-N-(ethynylcarbonyl)amino)ethoxy, 4-ethynylbenzyloxy, or 2-(4-ethynylphenoxy)ethoxy.

In certain embodiments, the $R^3$ moiety of the $R^1$ group of formula I is an optionally substituted aryl group. Examples include optionally substituted phenyl and optionally substituted pyridyl. When said $R^3$ moiety is a substituted aryl group, substituents on $R^3$ include CN, $N_3$, $NO_2$, —$CH_3$, —$CH_2N_3$, —CH=$CH_2$, —C≡CH, Br, I, F, bis-(4-ethynyl-benzyl)-amino, dipropargylamino, di-hex-5-ynyl-amino, di-pent-4-ynyl-amino, di-but-3-ynyl-amino, propargyloxy, hex-5-ynyloxy, pent-4-ynyloxy, di-but-3-ynyloxy, 2-hex-5-ynyloxy-ethyldisulfanyl, 2-pent-4-ynyloxy-ethyldisulfanyl, 2-but-3-ynyloxy-ethyldisulfanyl, 2-propargyloxy-ethyldisulfanyl, bis-benzyloxy-methyl, [1,3]dioxolan-2-yl, and [1,3]dioxan-2-yl.

In other embodiments, the $R^3$ moiety of the $R^1$ group of formula I is a protected aldehyde group. In certain embodiments the protected aldehydo moiety of $R^3$ is an acyclic acetal, a cyclic acetal, a hydrazone, or an imine. Exemplary $R^3$ groups include dimethyl acetal, diethyl acetal, diisopropyl acetal, dibenzyl acetal, bis(2-nitrobenzyl) acetal, 1,3-dioxane, 1,3-dioxolane, and semicarbazone. In certain embodiments, $R^3$ is an acyclic acetal or a cyclic acetal. In other embodiments, $R^3$ is a dibenzyl acetal.

In yet other embodiments, the $R^3$ moiety of the $R^1$ group of formula I is a protected carboxylic acid group. In certain embodiments, the protected carboxylic acid moiety of $R^3$ is an optionally substituted ester selected from $C_{1-6}$ aliphatic or aryl, or a silyl ester, an activated ester, an amide, or a hydrazide. Examples of such ester groups include methyl, ethyl, propyl, isopropyl, butyl, isobutyl, benzyl, and phenyl ester. In other embodiments, the protected carboxylic acid moiety of $R^3$ is an oxazoline or an ortho ester. Examples of such protected carboxylic acid moieties include oxazolin-2-yl and 2-methoxy-[1,3]dioxin-2-yl. In certain embodiments, the $R^1$ group is oxazolin-2-ylmethoxy or 2-oxazolin-2-yl-1-propoxy.

In still other embodiments, the $R^3$ moiety of the $R^1$ group of formula I is a detectable moiety. According to one aspect of the invention, the $R^3$ moiety of the $R^1$ group of formula I is a fluorescent moiety. Such fluorescent moieties are well known in the art and include coumarins, quinolones, benzoisoquinolones, hostasol, and Rhodamine dyes, to name but a few. Exemplary fluorescent moieties of the $R^3$ group of $R^1$ include anthracen-9-yl, pyren-4-yl, 9-H-carbazol-9-yl, the carboxylate of rhodamine B, and the carboxylate of coumarin 343. In certain embodiments, the $R^3$ moiety of the $R^1$ group of formula I is a detectable moiety selected from:

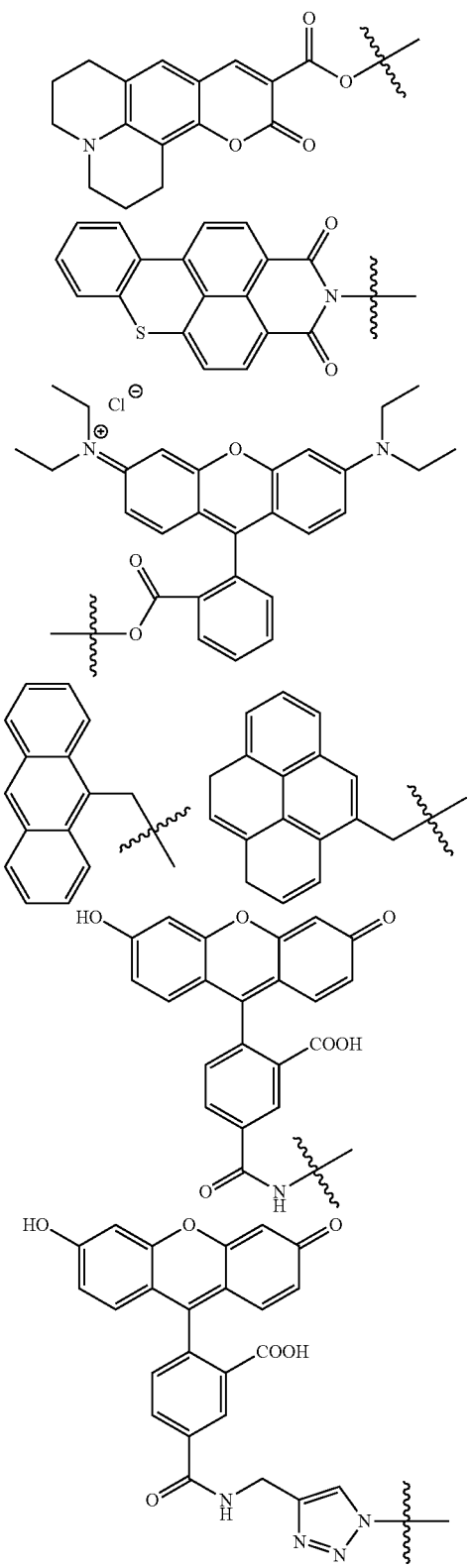

-continued

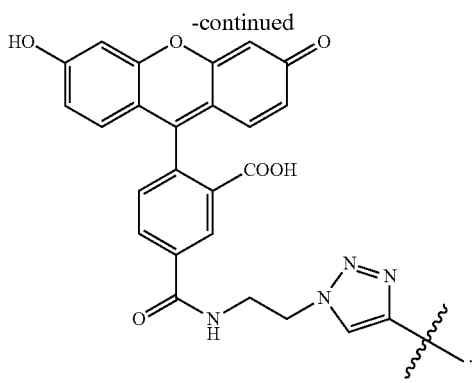

In certain embodiments, the $R^3$ moiety of the $R^1$ group of formula I is a group suitable for Click chemistry. Click reactions tend to involve high-energy ("spring-loaded") reagents with well-defined reaction coordinates, giving rise to selective bond-forming events of wide scope. Examples include the nucleophilic trapping of strained-ring electrophiles (epoxide, aziridines, aziridinium ions, episulfonium ions), certain forms of carbonyl reactivity (aldehydes and hydrazines or hydroxylamines, for example), and several types of cycloaddition reactions. The azide-alkyne 1,3-dipolar cycloaddition is one such reaction. Click chemistry is known in the art and one of ordinary skill in the art would recognize that certain $R^3$ moieties of the present invention are suitable for Click chemistry.

Compounds of formula I having $R^3$ moieties suitable for Click chemistry are useful for conjugating said compounds to biological systems or macromolecules such as proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule. Thus, another embodiment of the present invention provides a method of conjugating the $R^1$ groups of a compound of formula I to a macromolecule via Click chemistry. Yet another embodiment of the present invention provides a macromolecule conjugated to a compound of formula I via the $R^1$ group.

According to one embodiment, the $R^3$ moiety of the $R^1$ group of formula I is an azide-containing group. According to another embodiment, the $R^3$ moiety of the $R^1$ group of formula I is an alkyne-containing group. In certain embodiments, the $R^3$ moiety of the $R^1$ group of formula I has a terminal alkyne moiety. In other embodiments, $R^3$ moiety of the $R^1$ group of formula I is an alkyne moiety having an electron withdrawing group. Accordingly, in such embodiments, the $R^3$ moiety of the $R^1$ group of formula I is

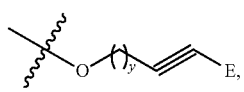

wherein E is an electron withdrawing group and y is 0-6. Such electron withdrawing groups are known to one of ordinary skill in the art. In certain embodiments, E is an ester. In other embodiments, the $R^3$ moiety of the $R^1$ group of formula I is

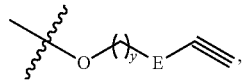

wherein E is an electron withdrawing group, such as a —C(O)O— group and y is 0-6.

Certain metal-free click moieties are known in the literature. Examples include 4-dibenzocyclooctynol (DIBO)

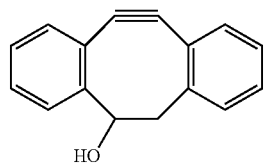 [SMILES: OC1Cc2ccccc2C#Cc2ccccc21]

(from Ning et. al; Angew Chem Int Ed, 2008, 47, 2253); difluorinated cyclooctynes (DIFO or DFO)

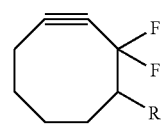

(from Codelli, et. al.; J. Am. Chem. Soc. 2008, 130, 11486-11493); biarylazacyclooctynone (BARAC)

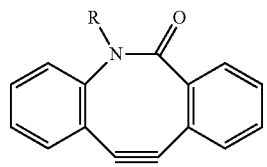

(from Jewett et. al.; J. Am. Chem. Soc. 2010, 132, 3688); or bicyclononyne (BCN)

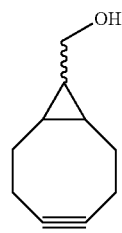 [SMILES: OCC1C2CCC#CCCC12]

(From Dommerholt, et. al.; *Angew Chem Int Ed*, 2010, 49, 9422-9425). The preparation of metal free click PEG derivatives is described in U.S. application Ser. No. 13/601,606, the entire contents of which are hereby incorporated by reference.

According to one embodiment, the $R^3$ moiety of the $R^1$ group of formula I is metal free click moiety. In another embodiment, the $R^3$ moiety of the $R^1$ group of formula I is an optionally substituted strained cyclooctyne moiety. In certain embodiments, the $R^3$ moiety of the $R^1$ group of formula I is a metal free click moiety selected from:

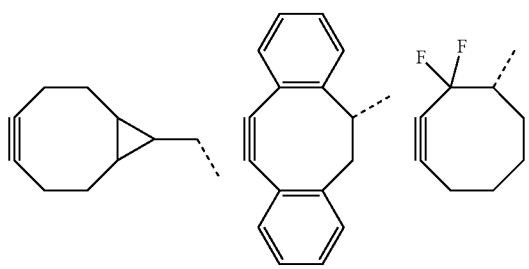

As defined generally above, Q is a valence bond or a bivalent, saturated or unsaturated, straight or branched $C_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur. In certain embodiments, Q is a valence bond. In other embodiments, Q is a bivalent, saturated $C_{1-12}$ alkylene chain, wherein 0-6 methylene units of Q are independently replaced by -Cy-, —O—, —NH—, —S—, —OC(O)—, —C(O)O—, or —C(O)—, wherein -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur.

In certain embodiments, Q is -Cy- (i.e. a $C_1$ alkylene chain wherein the methylene unit is replaced by -Cy-), wherein -Cy- is an optionally substituted 5-8 membered bivalent, saturated, partially unsaturated, or aryl ring having 0-4 heteroatoms independently selected from nitrogen, oxygen, or sulfur. According to one aspect of the present invention, -Cy- is an optionally substituted bivalent aryl group. According to another aspect of the present invention, -Cy- is an optionally substituted bivalent phenyl group. In other embodiments, -Cy- is an optionally substituted 5-8 membered bivalent, saturated carbocyclic ring. In still other embodiments, -Cy- is an optionally substituted 5-8 membered bivalent, saturated heterocyclic ring having 1-2 heteroatoms independently selected from nitrogen, oxygen, or sulfur. Exemplary -Cy- groups include bivalent rings selected from phenyl, pyridyl, pyrimidinyl, cyclohexyl, cyclopentyl, or cyclopropyl.

As defined above, $R^x$ is a hydoxamate or catechol containing moiety. In certain embodiments, $R^x$ is a hydroxamic acid containing moiety. In other embodiments, $R^x$ is a catechol containing moiety. In certain embodiments, $R^x$ is selected from

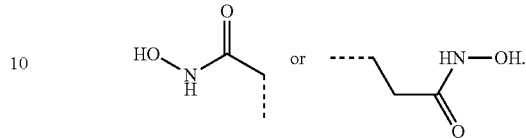

In certain embodiments, $R^x$ is selected from:

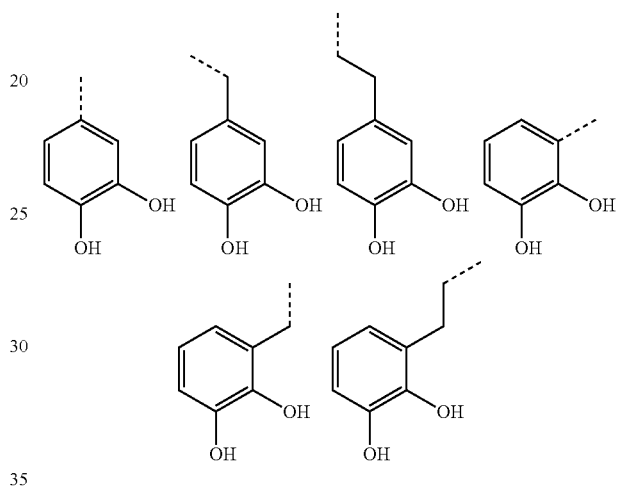

As defined above, $R^y$ is selected from one or more natural or unnatural amino acid side chain groups such that the overall block is hydrophobic. Such hydrophobic amino acid side-chain groups include an optionally protected tyrosine side-chain, an optionally protected serine side-chain, an optionally protected threonine side-chain, phenylalanine, alanine, valine, leucine, tryptophan, proline, benzyl and alkyl glutamates, or benzyl and alkyl aspartates or mixtures thereof. One of ordinary skill in the art would recognize that protection of a polar or hydrophilic amino acid side-chain can render that amino acid nonpolar. For example, a suitably protected tyrosine hydroxyl group can render that tyrosine nonpolar and hydrophobic by virtue of protecting the hydroxyl group. Protecting groups for the hydroxyl, amino, and thiol, and carboylate functional groups of $R^y$ are as described herein. Furthermore, one of ordinary skill in the art would recognize that hydrophilic and hydrophobic amino acid side chains can be combined such that the overall block is hydrophobic. For example, a majority of leucine side chain groups can be combined with a minority of aspartic acid side chain groups wherein the resulting block is net hydrophobic. Such mixtures of amino acid side-chain groups include tyrosine and leucine, tyrosine and phenylalanine, serine and phenylalanine, aspartic acid and phenylalanine, glutamic acid and phenylalanine, tyrosine and benzyl glutamate, serine and benzyl glutamate, aspartic acid and benzyl glutamate, glutamic acid and benzyl glutamate, aspartic acid and leucine, and glutamic acid and leucine.

In some embodiments, Ry consists of a mixture of three natural or unnatural amino acid side chain groups such that the overall block is hydrophobic. Such ternary mixtures of amino acid side-chain groups include, but are not limited to: leucine, tyrosine, and aspartic acid; leucine, tyrosine, and glutamic acid; phenylalanine, tyrosine, and aspartic acid; or phenylalanine, tyrosine, and glutamic acid.

In other embodiments, $R^y$ consists of a mixture of D-hydrophobic and L-hydrophilic amino acid side-chain groups such that the overall poly(amino acid) block comprising $R^y$ is hydrophobic and is a mixture of D- and L-configured amino acids. Such mixtures of amino acid side-chain groups include L-tyrosine and D-leucine, L-tyrosine and D-phenylalanine, L-serine and D-phenylalanine, L-aspartic acid and D-phenylalanine, L-glutamic acid and D-phenylalanine, L-tyrosine and D-benzyl glutamate, L-serine and D-benzyl glutamate, L-aspartic acid and D-benzyl glutamate, L-glutamic acid and D-benzyl glutamate, L-aspartic acid and D-leucine, and L-glutamic acid and D-leucine. Ratios (D-hydrophobic to L-hydrophilic) of such mixtures include any of 6:1, 5:1, 4:1, 3:1, 2:1, 1:1, 1:2, 1:3, 1:4; 1:5, and 1:6.

As used herein, $R^{ya}$ is selected from one or more natural or unnatural, hydrophobic amino acid side chain groups. Suitable examples of such hydrophobic side chain groups include, but are not limited to: leucine, phenylalanine, glycine, alanine, benzyl glutamate, benzyl asparate, methyl glutamate, methyl aspartate, ethyl glutamate, ethyl aspartate, norleucine, valine, or methionine.

As defined generally above, the $R^2$ group of formula I is a mono-protected amine, a di-protected amine, —$NHR^4$, —$N(R^4)_2$, —$NHC(O)R^4$, —$NR^4C(O)R^4$, $NHC(O)NHR^4$, —$NHC(O)N(R^4)_2$, —$NR^4C(O)NHR^4$, —$NR^4C(O)N(R^4)_2$, —$NHC(O)OR^4$, —$NR^4C(O)OR^4$, —$NHSO_2R^4$, or —$NR^4SO_2R^4$, wherein each $R^4$ is independently an optionally substituted group selected from aliphatic, a 5-8 membered saturated, partially unsaturated, or aryl ring having 0-4 heteroatoms independently selected from nitrogen, oxygen, or sulfur, an 8-10-membered saturated, partially unsaturated, or aryl bicyclic ring having 0-5 heteroatoms independently selected from nitrogen, oxygen, or sulfur, or a detectable moiety, or two $R^4$ on the same nitrogen atom are taken together with said nitrogen atom to form an optionally substituted 4-7 membered saturated, partially unsaturated, or aryl ring having 1-4 heteroatoms independently selected from nitrogen, oxygen, or sulfur.

In certain embodiments, the $R^2$ group of formula I is —$NHR^4$ or —$N(R^4)_2$ wherein each $R^4$ is an optionally substituted aliphatic group. One exemplary $R^4$ group is 5-norbornen-2-yl-methyl. According to yet another aspect of the present invention, the $R^{2a}$ group of formula I is —$NHR^4$ wherein $R^4$ is a $C_{1-6}$ aliphatic group substituted with $N_3$. Examples include —$CH_2N_3$. In some embodiments, $R^4$ is an optionally substituted $C_{1-6}$ alkyl group. Examples include methyl, ethyl, propyl, butyl, pentyl, hexyl, 2-(tetrahydropyran-2-yloxy)ethyl, pyridin-2-yldisulfanylmethyl, methyldisulfanylmethyl, (4-acetylenylphenyl)methyl, 3-(methoxycarbonyl)-prop-2-ynyl, methoxycarbonylmethyl, 2-(N-methyl-N-(4-acetylenylphenyl)carbonylamino)-ethyl, 2-phthalimidoethyl, 4-bromobenzyl, 4-chlorobenzyl, 4-fluorobenzyl, 4-iodobenzyl, 4-propargyloxybenzyl, 2-nitrobenzyl, 4-(bis-4-acetylenylbenzyl)aminomethyl-benzyl, 4-propargyloxy-benzyl, 4-dipropargylamino-benzyl, 4-(2-propargyloxy-ethyldisulfanyl)benzyl, 2-propargyloxy-ethyl, 2-propargyldisulfanyl-ethyl, 4-propargyloxy-butyl, 2-(N-methyl-N-propargylamino)ethyl, and 2-(2-dipropargylaminoethoxy)-ethyl. In other embodiments, $R^4$ is an optionally substituted $C_{2-6}$ alkenyl group. Examples include vinyl, allyl, crotyl, 2-propenyl, and but-3-enyl. When $R^4$ group is a substituted aliphatic group, substituents on $R^4$ include $N_3$, CN, and halogen. In certain embodiments, $R^4$ is —$CH_2CN$, —$CH_2CH_2CN$, —$CH_2CH(OCH_3)_2$, 4-(bisbenzyloxymethyl)phenylmethyl, and the like.

According to another aspect of the present invention, the $R^2$ group of formula I is —$NHR^4$ wherein $R^4$ is an optionally substituted $C_{2-6}$ alkynyl group. Examples include —$CC\equiv CH$, —$CH_2C\equiv CH$, —$CH_2C\equiv CCH_3$, and —$CH_2CH_2C\equiv CH$.

In certain embodiments, the $R^2$ group of formula I is —$NHR^4$ wherein $R^4$ is an optionally substituted 5-8-membered aryl ring. In certain embodiments, $R^4$ is optionally substituted phenyl or optionally substituted pyridyl. Examples include phenyl, 4-t-butoxycarbonylaminophenyl, 4-azidomethylphenyl, 4-propargyloxyphenyl, 2-pyridyl, 3-pyridyl, and 4-pyridyl. In certain embodiments, $R^{2a}$ is 4-t-butoxycarbonylaminophenylamino, 4-azidomethylphenamino, or 4-propargyloxyphenylamino.

In certain embodiments, the $R^{2a}$ group of formula I is —$NHR^4$ wherein $R^4$ is an optionally substituted phenyl ring. Substituents on the $R^4$ phenyl ring include halogen; —$(CH_2)_{0-4}R^\circ$; —$(CH_2)_{0-4}OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —$CH=CHPh$, which may be substituted with $R^\circ$; —$NO_2$; —$CN$; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$(CH_2)_{0-4}SC(O)R^\circ$; —$(CH_2)_{0-4}C(O)NR^\circ_2$; —$C(S)NR^\circ_2$; —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R$; —$N(OR^\circ)R^\circ$; —$C(NH)NR^\circ_2$; —$P(O)_2R$; —$P(O)R^\circ_2$; —$OP(O)R^\circ_2$; $SiR^\circ_3$; wherein each independent occurrence of $R^\circ$ is as defined herein supra. In other embodiments, the $R^{2a}$ group of formula I is —$NHR^4$ wherein $R^4$ is phenyl substituted with one or more optionally substituted $C_{1-6}$ aliphatic groups. In still other embodiments, $R^4$ is phenyl substituted with vinyl, allyl, acetylenyl, —$CH_2N_3$, —$CH_2CH_2N_3$, —$CH_2C\equiv CCH_3$, or —$CH_2C\equiv CH$.

In certain embodiments, the $R^2$ group of formula I is —$NHR^4$ wherein $R^4$ is phenyl substituted with $N_3$, $N(R^\circ)_2$, $CO_2R$, or $C(O)R^\circ$ wherein each $R^\circ$ is independently as defined herein supra.

In certain embodiments, the $R^2$ group of formula I is —$N(R^4)_2$ wherein each $R^4$ is independently an optionally substituted group selected from aliphatic, phenyl, naphthyl, a 5-6 membered aryl ring having 1-4 heteroatoms independently selected from nitrogen, oxygen, or sulfur, or a 8-10 membered bicyclic aryl ring having 1-5 heteroatoms independently selected from nitrogen, oxygen, or sulfur, or a detectable moiety.

In other embodiments, the $R^2$ group of formula I is —$N(R^4)_2$ wherein the two $R^4$ groups are taken together with said nitrogen atom to form an optionally substituted 4-7 membered saturated, partially unsaturated, or aryl ring having 1-4 heteroatoms independently selected from nitrogen, oxygen, or sulfur. According to another embodiment, the two $R^4$ groups are taken together to form a 5-6-membered saturated or partially unsaturated ring having one nitrogen wherein said ring is substituted with one or two oxo groups. Such $R^{2a}$ groups include, but are not limited to, phthalimide, maleimide and succinimide.

In certain embodiments, the $R^2$ group of formula I is a mono-protected or di-protected amino group. In certain embodiments $R^{2a}$ is a mono-protected amine. In certain embodiments $R^{2a}$ is a mono-protected amine selected from aralkylamines, carbamates, allyl amines, or amides. Exemplary mono-protected amino moieties include t-butyloxycarbonylamino, ethyloxycarbonylamino, methyloxycarbonylamino, trichloroethyloxy-carbonylamino, allyloxycarbonylamino, benzyloxocarbonylamino, allylamino, benzylamino, fluorenylmethylcarbonyl, formamido, acetamido, chloroacetamido, dichloroacetamido, trichloroacetamido, phenylacetamido, trifluoroacetamido, benzamido, and t-butyldiphenylsilylamino. In other embodiments $R^{2a}$ is a di-protected amine. Exemplary di-protected amino moieties include di-benzylamino, di-allylamino, phthalimide, maleimido, succinimido, pyrrolo, 2,2,5,5-tetramethyl-[1,2,5]azadisilolidino, and azido. In certain embodiments, the $R^{2a}$ moiety is phthalimido. In other embodiments, the $R^{2a}$ moiety is mono- or di-benzylamino or mono- or di-allylamino.

In certain embodiments, the present invention provides a triblock copolymer of formula II:

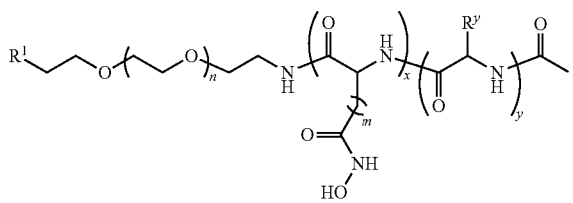

II wherein:
n is 20-500;
m is 0, 1, or 2;
x is 3 to 50;
y is 5 to 100;
$R^y$ is selected from one or more natural or unnatural amino acid side chain groups such that the overall block is hydrophobic;
$R^1$ is $-Z(CH_2CH_2Y)_p(CH_2)_tR^3$, wherein:
  Z is $-O-$, $-NH-$, $-S-$, $-C\equiv C-$, or $-CH_2-$;
  each Y is independently $-O-$ or $-S-$;
  p is 0-10;
  t is 0-10; and
$R^3$ is hydrogen, $-N_3$, $-CN$, $-NH_2$, $-CH_3$,

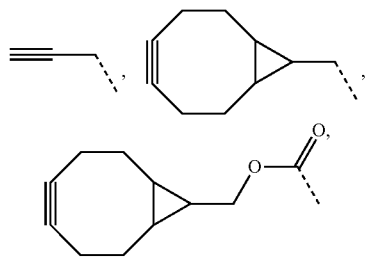

a strained cyclooctyne moiety, a mono-protected amine, a di-protected amine, an optionally protected aldehyde, an optionally protected hydroxyl, an optionally protected carboxylic acid, an optionally protected thiol, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety.

In certain embodiments, a triblock copolymer of Formula II is selected from the following exemplary compounds shown in Table 1,

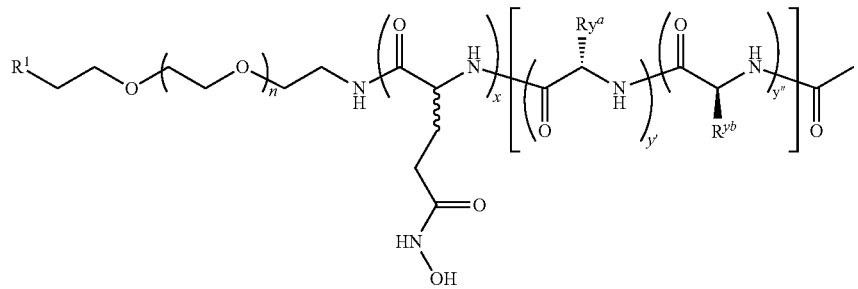

wherein n is 20 to 500, x is 3 to 50, y' is 3 to 50, and y" is 3 to 50.

TABLE 1

| Compound # | $R^1$ | $R^{ya}$ | $R^{yb}$ |
|---|---|---|---|
| 1 | CH₃O---- | isobutyl | 4-hydroxybenzyl |

TABLE 1-continued

| Compound # | R¹ | R^{ya} | R^{yb} |
|---|---|---|---|
| 2 | CH₃O---- | isobutyl | CH₂OH |
| 3 | CH₃O---- | isobutyl | CH₂COOH |
| 4 | CH₃O---- | isobutyl | CH₂CH₂COOH |
| 5 | CH₃O---- | benzyl | 4-hydroxybenzyl |
| 6 | CH₃O---- | benzyl | CH₂OH |
| 7 | CH₃O---- | benzyl | CH₂COOH |
| 8 | CH₃O---- | benzyl | CH₂CH₂COOH |
| 9 | CH₃O---- | CH₂C(O)O-benzyl | 4-hydroxybenzyl |
| 10 | CH₃O---- | CH₂C(O)O-benzyl | CH₂OH |
| 11 | CH₃O---- | CH₂C(O)O-benzyl | CH₂COOH |
| 12 | CH₃O---- | CH₂C(O)O-benzyl | CH₂CH₂COOH |
| 13 | CH₃O---- | CH₂CH₂C(O)O-benzyl | 4-hydroxybenzyl |

TABLE 1-continued
| Compound # | R¹ | R^{ya} | R^{yb} |
|---|---|---|---|
| 14 | CH₃O---- | 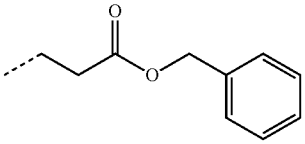 | 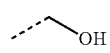 |
| 15 | CH₃O---- | 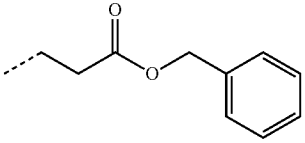 | 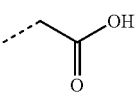 |
| 16 | CH₃O---- | 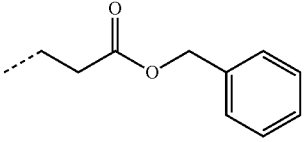 |  |
| 17 | 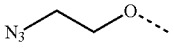 | 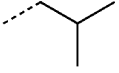 | 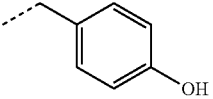 |
| 18 | 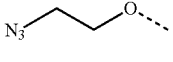 | 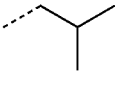 | 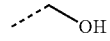 |
| 19 | 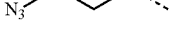 | 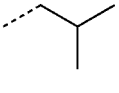 | 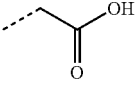 |
| 20 | 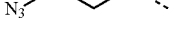 |  | 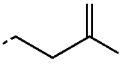 |
| 21 | 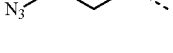 | 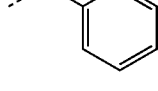 | 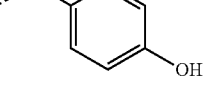 |
| 22 |  | 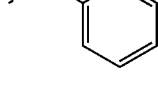 |  |
| 23 |  | 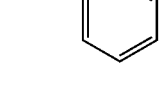 |  |
| 24 | 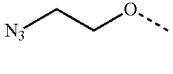 | 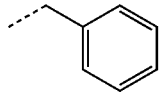 | 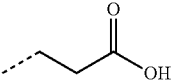 |
| 25 |  | 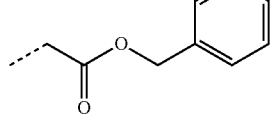 | 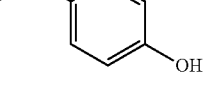 |

TABLE 1-continued

| Compound # | R¹ | R^ya | R^yb |
|---|---|---|---|
| 26 | N₃-CH₂CH₂-O- | -CH₂-C(=O)-O-CH₂-C₆H₅ | -CH₂-OH |
| 27 | N₃-CH₂CH₂-O- | -CH₂-C(=O)-O-CH₂-C₆H₅ | -CH₂-C(=O)OH |
| 28 | N₃-CH₂CH₂-O- | -CH₂-C(=O)-O-CH₂-C₆H₅ | -CH₂CH₂-C(=O)OH |
| 29 | N₃-CH₂CH₂-O- | -CH₂CH₂-C(=O)-O-CH₂-C₆H₅ | -CH₂-C₆H₄-OH (para) |
| 30 | N₃-CH₂CH₂-O- | -CH₂CH₂-C(=O)-O-CH₂-C₆H₅ | -CH₂-OH |
| 31 | N₃-CH₂CH₂-O- | -CH₂CH₂-C(=O)-O-CH₂-C₆H₅ | -CH₂-C(=O)OH |
| 32 | N₃-CH₂CH₂-O- | -CH₂CH₂-C(=O)-O-CH₂-C₆H₅ | -CH₂CH₂-C(=O)OH |
| 33 | HC≡C-CH₂-O- | -CH₂-CH(CH₃)₂ | -CH₂-C₆H₄-OH (para) |
| 34 | HC≡C-CH₂-O- | -CH₂-CH(CH₃)₂ | -CH₂-OH |
| 35 | HC≡C-CH₂-O- | -CH₂-CH(CH₃)₂ | -CH₂-C(=O)OH |
| 36 | HC≡C-CH₂-O- | -CH₂-CH(CH₃)₂ | -CH₂CH₂-C(=O)OH |

TABLE 1-continued
| Compound # | R¹ | R^{ya} | R^{yb} |
|---|---|---|---|
| 37 | 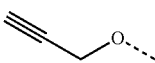 | 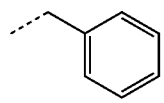 | 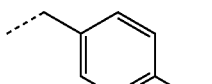 |
| 38 | 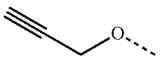 | 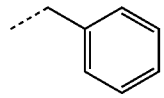 | 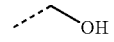 |
| 39 | 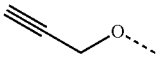 | 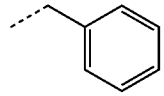 | 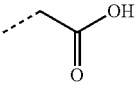 |
| 40 | 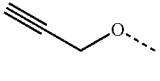 | 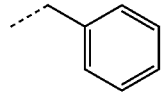 | 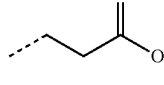 |
| 41 | 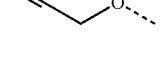 | 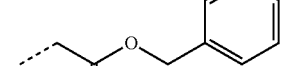 | 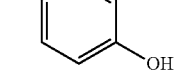 |
| 42 | 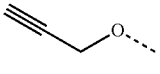 | 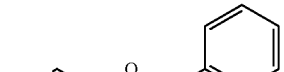 | 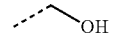 |
| 43 | 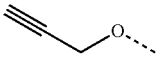 | 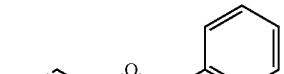 | 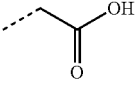 |
| 44 | 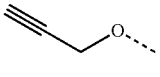 |  | 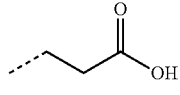 |
| 45 | 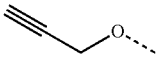 | 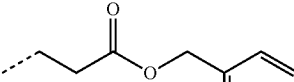 | 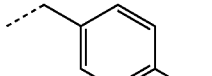 |
| 46 | 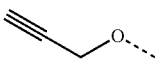 | 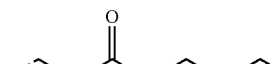 | 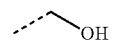 |
| 47 | 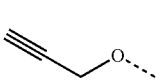 |  | 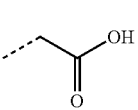 |

TABLE 1-continued

| Compound # | R¹ | R^{ya} | R^{yb} |
|---|---|---|---|
| 48 | propargyl-O- | -CH₂CH₂C(O)O-CH₂-phenyl | -CH₂CH₂C(O)OH |
| 49 | BCN-CH₂-O- | -CH₂CH(CH₃)₂ | -CH₂-C₆H₄-OH |
| 50 | BCN-CH₂-O- | -CH₂CH(CH₃)₂ | -CH₂OH |
| 51 | BCN-CH₂-O- | -CH₂CH(CH₃)₂ | -CH₂C(O)OH |
| 52 | BCN-CH₂-O- | -CH₂CH(CH₃)₂ | -CH₂CH₂C(O)OH |
| 53 | BCN-CH₂-O- | -CH₂-phenyl | -CH₂-C₆H₄-OH |
| 54 | BCN-CH₂-O- | -CH₂-phenyl | -CH₂OH |
| 55 | BCN-CH₂-O- | -CH₂-phenyl | -CH₂C(O)OH |
| 56 | BCN-CH₂-O- | -CH₂-phenyl | -CH₂CH₂C(O)OH |
| 57 | BCN-CH₂-O- | -CH₂C(O)O-CH₂-phenyl | -CH₂-C₆H₄-OH |
| 58 | BCN-CH₂-O- | -CH₂C(O)O-CH₂-phenyl | -CH₂OH |

TABLE 1-continued

| Compound # | R¹ | R^{ya} | R^{yb} |
|---|---|---|---|
| 59 | cyclooctyne-fused cyclopropane-CH2-O--- | -CH2-C(=O)-O-CH2-phenyl | -CH2-C(=O)-OH |
| 60 | cyclooctyne-fused cyclopropane-CH2-O--- | -CH2-C(=O)-O-CH2-phenyl | -CH2-CH2-C(=O)-OH |
| 61 | cyclooctyne-fused cyclopropane-CH2-O--- | -CH2-CH2-C(=O)-O-CH2-phenyl | -CH2-(4-hydroxyphenyl) |
| 62 | cyclooctyne-fused cyclopropane-CH2-O--- | -CH2-CH2-C(=O)-O-CH2-phenyl | -CH2-OH |
| 63 | cyclooctyne-fused cyclopropane-CH2-O--- | -CH2-CH2-C(=O)-O-CH2-phenyl | -CH2-C(=O)-OH |
| 64 | cyclooctyne-fused cyclopropane-CH2-O--- | -CH2-CH2-C(=O)-O-CH2-phenyl | -CH2-CH2-C(=O)-OH |
| 65 | DBCO-O--- | -CH2-CH(CH3)2 | -CH2-(4-hydroxyphenyl) |
| 66 | DBCO-O--- | -CH2-CH(CH3)2 | -CH2-OH |
| 67 | DBCO-O--- | -CH2-CH(CH3)2 | -CH2-C(=O)-OH |

TABLE 1-continued

| Compound # | R¹ | R^{ya} | R^{yb} |
|---|---|---|---|
| 68 | dibenzocyclooctyne-O- | isobutyl | -CH₂CH₂C(O)OH |
| 69 | dibenzocyclooctyne-O- | benzyl | -CH₂-C₆H₄-OH (para) |
| 70 | dibenzocyclooctyne-O- | benzyl | -CH₂OH |
| 71 | dibenzocyclooctyne-O- | benzyl | -CH₂C(O)OH |
| 72 | dibenzocyclooctyne-O- | benzyl | -CH₂CH₂C(O)OH |
| 73 | dibenzocyclooctyne-O- | -CH₂C(O)O-CH₂-C₆H₅ | -CH₂-C₆H₄-OH (para) |
| 74 | dibenzocyclooctyne-O- | -CH₂C(O)O-CH₂-C₆H₅ | -CH₂OH |

TABLE 1-continued

| Compound # | R¹ | R^{ya} | R^{yb} |
|---|---|---|---|
| 75 | dibenzocyclooctyne-O- | -CH2C(O)OCH2-phenyl | -CH2C(O)OH |
| 76 | dibenzocyclooctyne-O- | -CH2C(O)OCH2-phenyl | -CH2CH2C(O)OH |
| 77 | dibenzocyclooctyne-O- | -CH2CH2C(O)OCH2-phenyl | -CH2-(4-hydroxyphenyl) |
| 78 | dibenzocyclooctyne-O- | -CH2CH2C(O)OCH2-phenyl | -CH2OH |
| 79 | dibenzocyclooctyne-O- | -CH2CH2C(O)OCH2-phenyl | -CH2C(O)OH |
| 80 | dibenzocyclooctyne-O- | -CH2CH2C(O)OCH2-phenyl | -CH2CH2C(O)OH |

In certain embodiments, a triblock copolymer of Formula II is
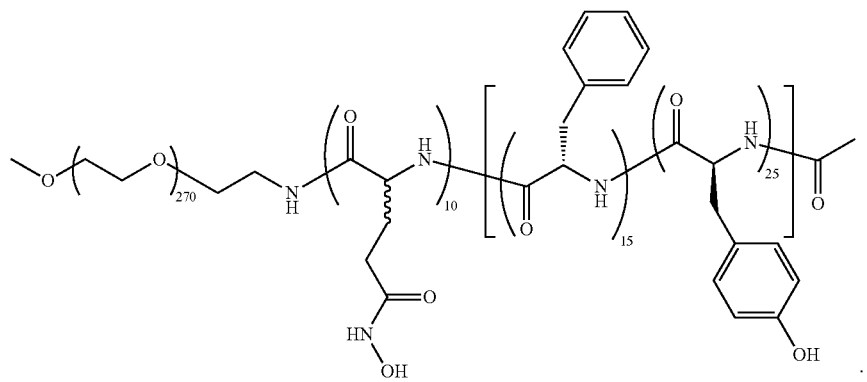
In certain embodiments, a triblock copolymer of Formula II is
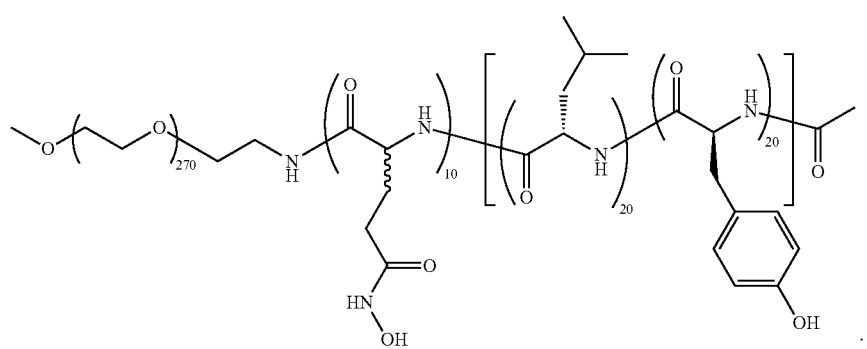
In certain embodiments, a triblock copolymer of Formula II is
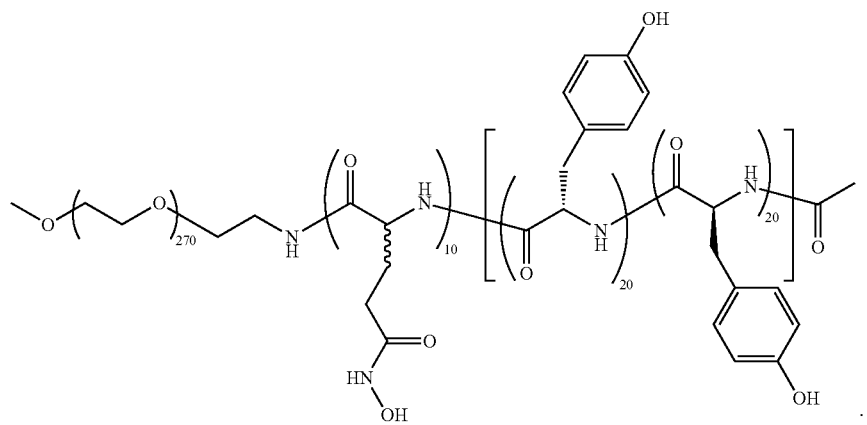
In certain embodiments, the present invention provides a triblock copolymer of formula III:

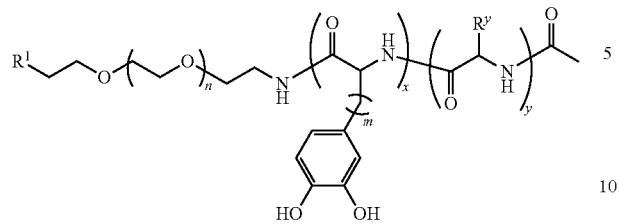

wherein:
- n is 20-500;
- m is 0, 1, or 2;
- x is 3 to 50;
- y is 5 to 100;
- $R^y$ is selected from one or more natural or unnatural amino acid side chain groups such that the overall block is hydrophobic;
- $R^1$ is $-Z(CH_2CH_2Y)_p(CH_2)_tR^3$, wherein:
  - Z is $-O-$, $-NH-$, $-S-$, $-C\equiv C-$, or $-CH_2-$;
  - each Y is independently $-O-$ or $-S-$;
  - p is 0-10;
  - t is 0-10; and
  - $R^3$ is hydrogen, $-N_3$, $-CN$, $-NH_2$, $-CH_3$, a strained cyclooctyne moiety, a mono-protected amine, a di-protected amine, an optionally protected aldehyde, an optionally protected hydroxyl, an optionally protected carboxylic acid, an optionally protected thiol, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety.

In certain embodiments, a triblock copolymer of Formula III is selected from the following exemplary compounds shown in Table 2,

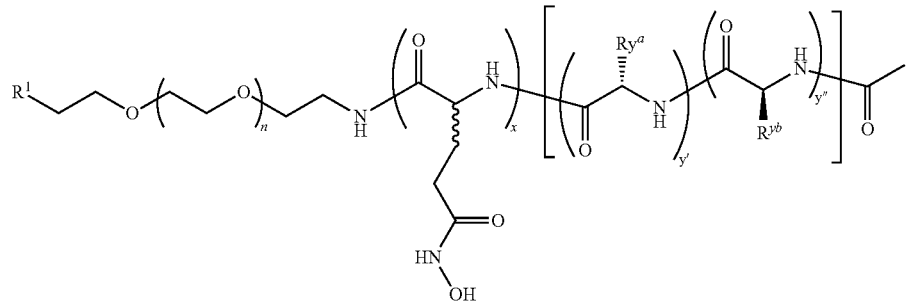

wherein n is 20 to 500, x is 3 to 50, y' is 3 to 50, and y" is 3 to 50.

TABLE 2

| # | $R^1$ | $R^{ya}$ | $R^{yb}$ |
|---|---|---|---|
| 81 | CH₃O---- | isopropyl | 4-hydroxybenzyl |
| 82 | CH₃O---- | isopropyl | hydroxymethyl |
| 83 | CH₃O---- | isopropyl | carboxymethyl |
| 84 | CH₃O---- | isopropyl | 2-carboxyethyl |
| 85 | CH₃O---- | benzyl | 4-hydroxybenzyl |

US 9,944,752 B2
49 50
TABLE 2-continued
| 86 | CH₃O---- | 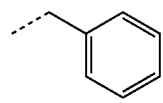 |  |
| 87 | CH₃O---- | 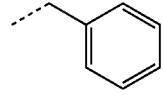 | 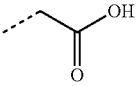 |
| 88 | CH₃O---- | 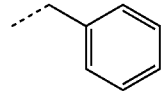 | 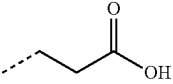 |
| 89 | CH₃O---- | 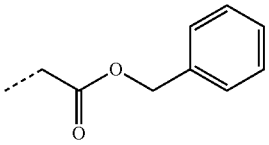 | 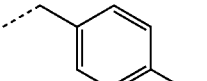 |
| 90 | CH₃O---- | 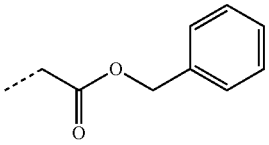 |  |
| 91 | CH₃O---- | 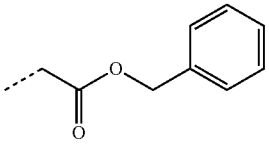 | 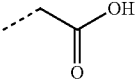 |
| 92 | CH₃O---- | 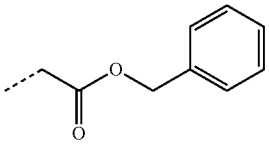 | 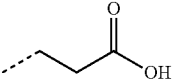 |
| 93 | CH₃O---- | 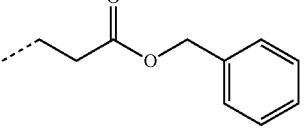 | 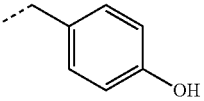 |
| 94 | CH₃O---- | 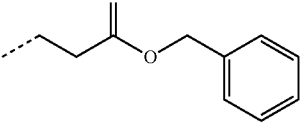 |  |
| 95 | CH₃O---- | 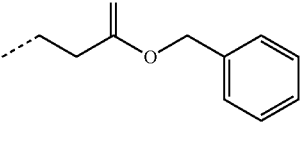 | 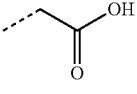 |
| 96 | CH₃O---- | 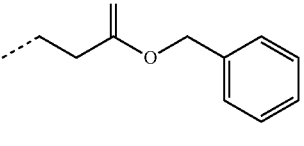 | 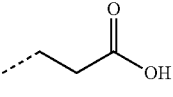 |

US 9,944,752 B2
51 52
TABLE 2-continued
| 97 | 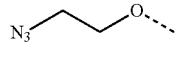 | 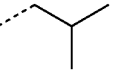 | 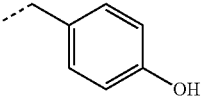 |
| 98 | 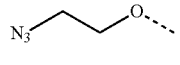 | 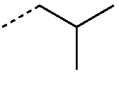 |  |
| 99 | 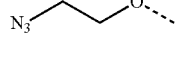 | 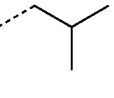 | 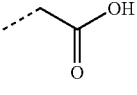 |
| 100 | 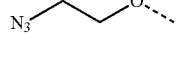 | 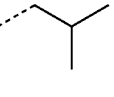 | 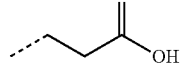 |
| 101 | 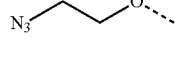 | 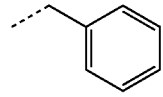 | 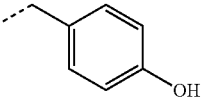 |
| 102 | 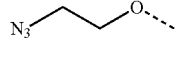 | 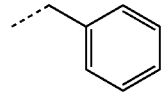 |  |
| 103 | 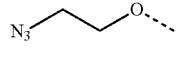 | 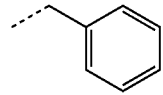 | 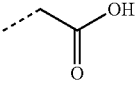 |
| 104 |  | 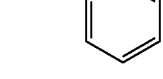 | 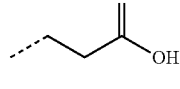 |
| 105 | 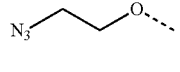 | 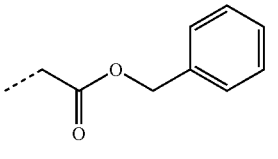 | 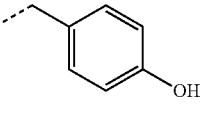 |
| 106 | 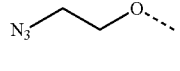 | 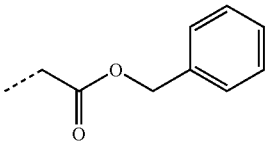 |  |
| 107 | 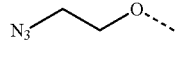 | 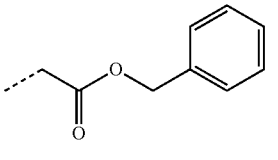 | 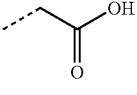 |
| 108 | 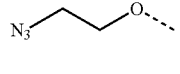 | 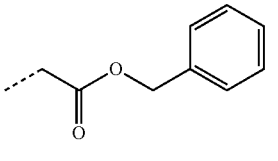 | 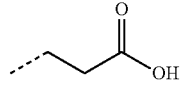 |
| 109 | 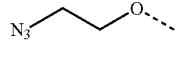 | 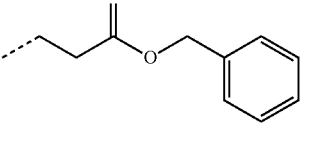 | 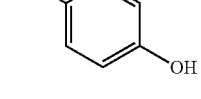 |

TABLE 2-continued
| | | | |
|---|---|---|---|
| 110 | 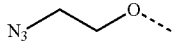 | 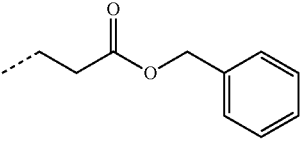 | 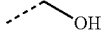 |
| 111 | 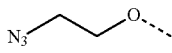 | 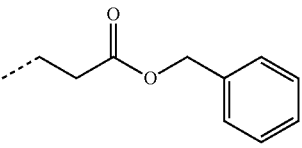 | 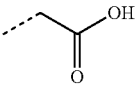 |
| 112 | 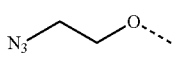 | 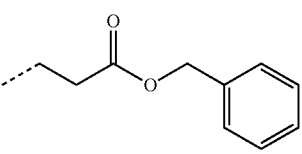 |  |
| 113 |  | 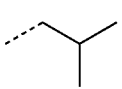 | 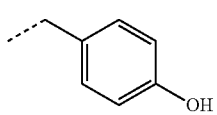 |
| 114 | 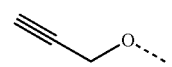 | 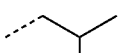 | 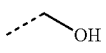 |
| 115 | 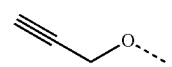 | 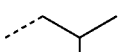 | 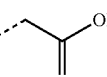 |
| 116 |  | 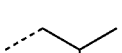 | 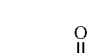 |
| 117 |  | 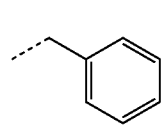 | 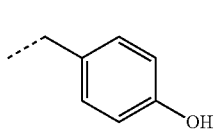 |
| 118 |  | 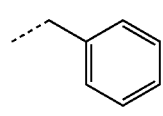 | 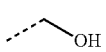 |
| 119 |  | 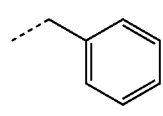 | 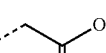 |
| 120 |  | 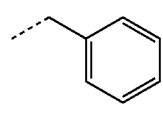 | 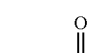 |
| 121 | 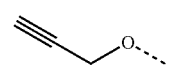 | 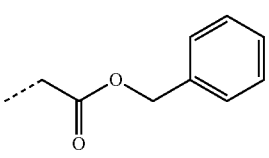 | 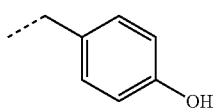 |

TABLE 2-continued
| | | | |
|---|---|---|---|
| 122 | 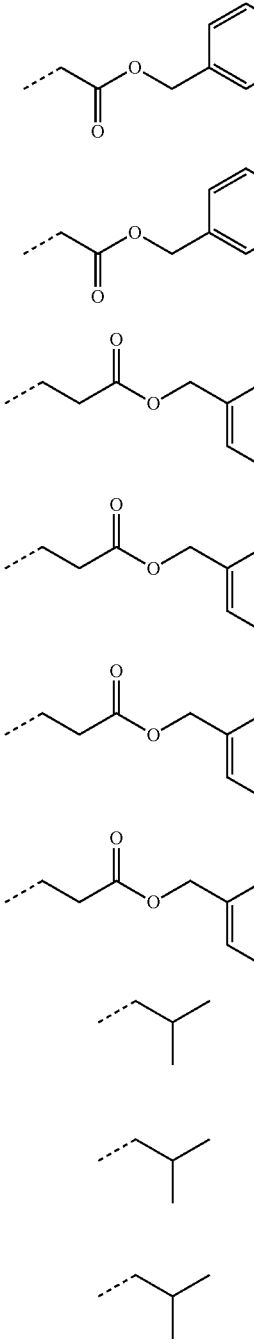 |  | 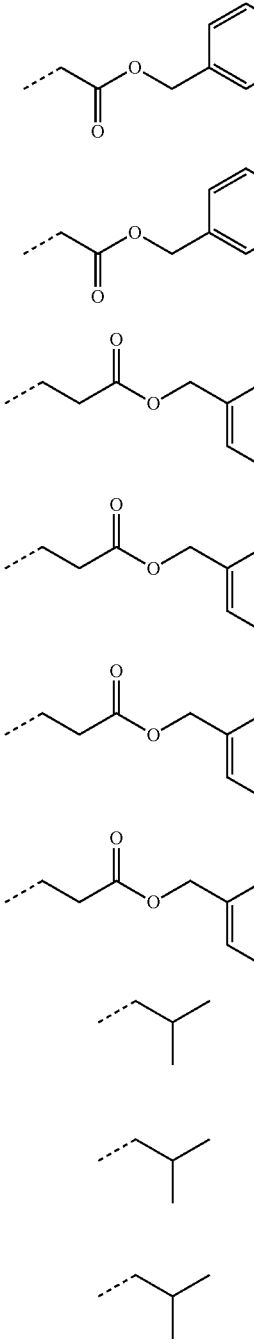 |
| 123 |  | 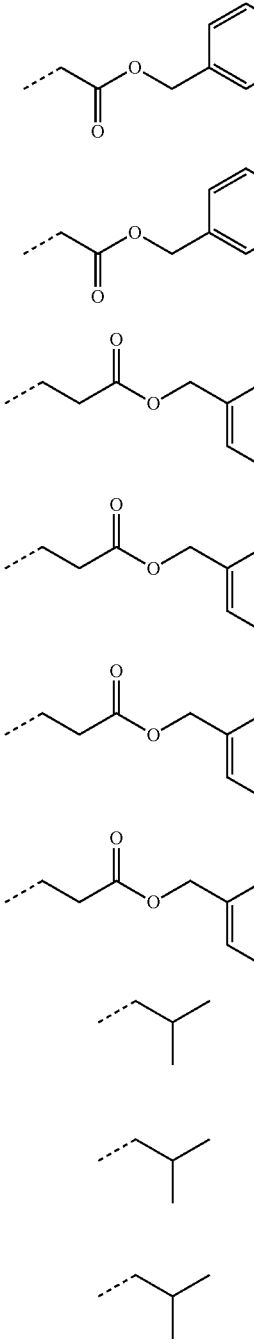 |  |
| 124 | 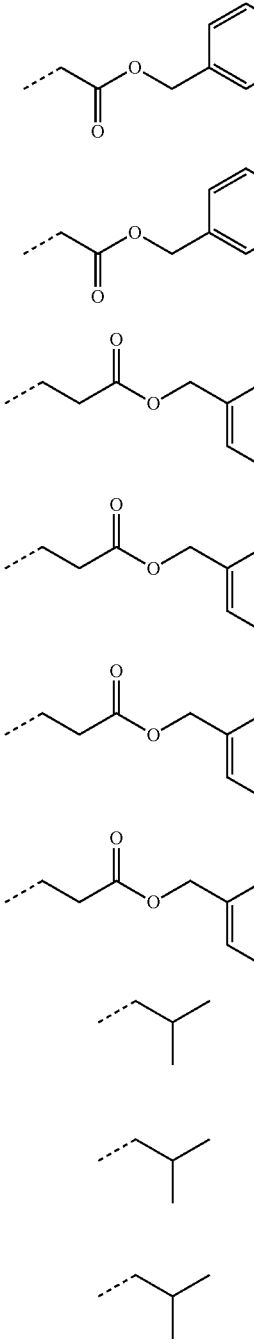 |  | 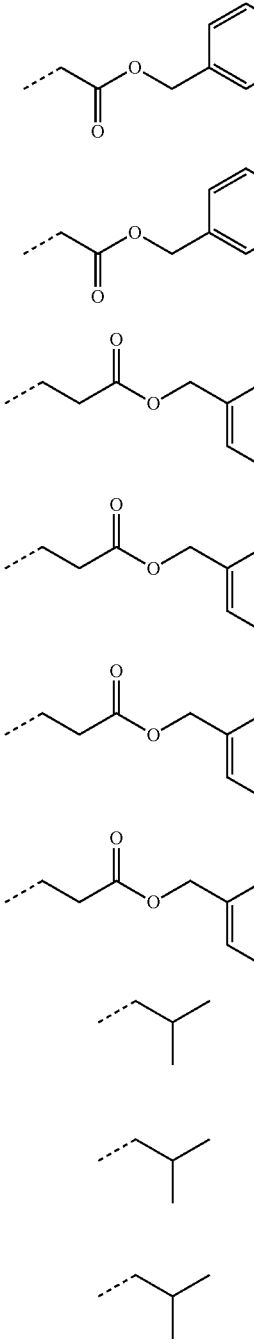 |
| 125 |  | 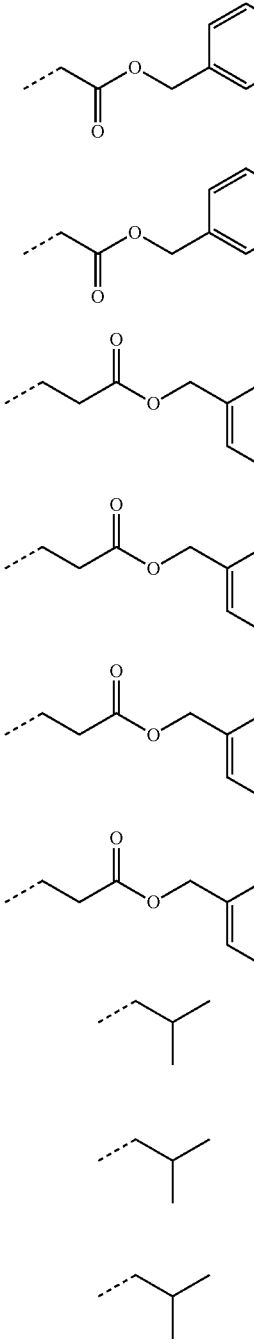 |  |
| 126 | 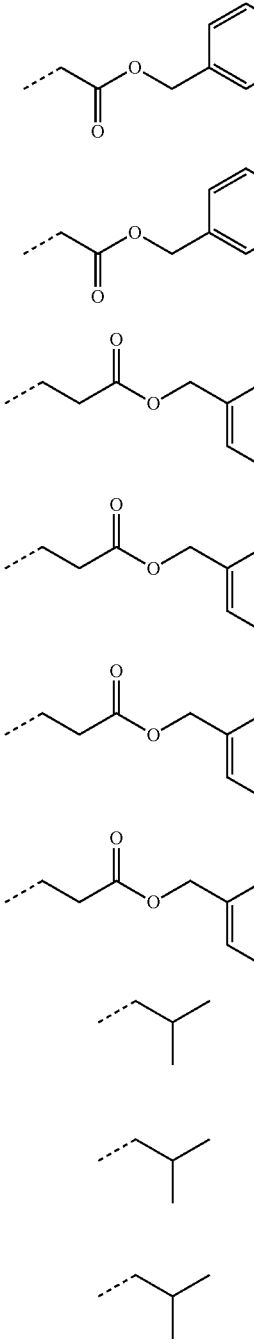 |  | 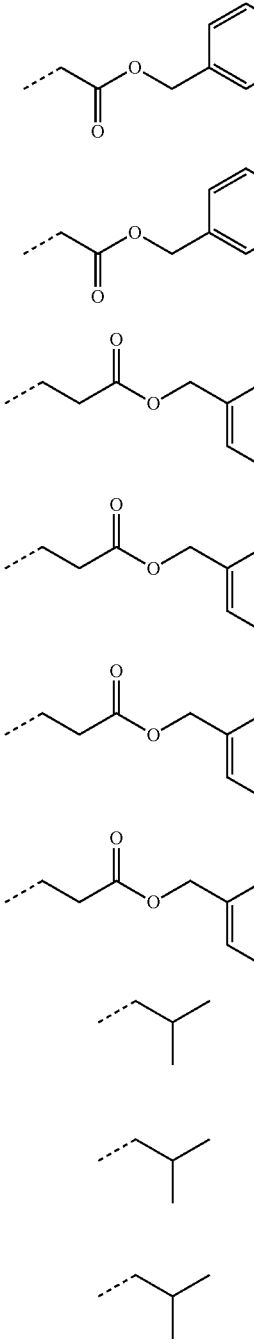 |
| 127 |  | 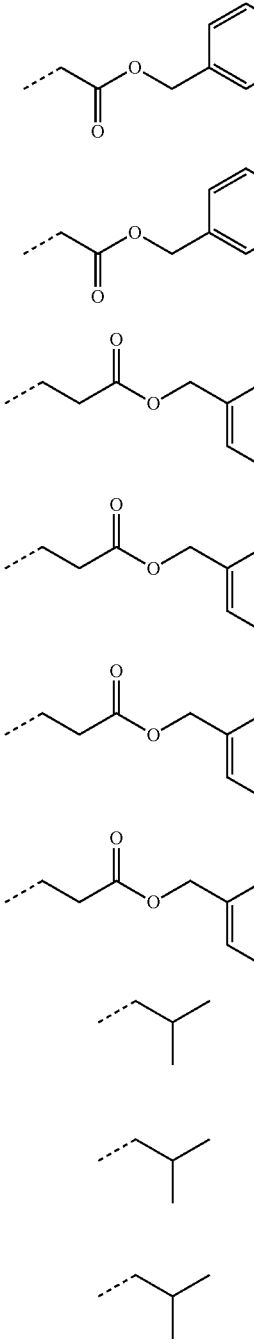 |  |
| 128 | 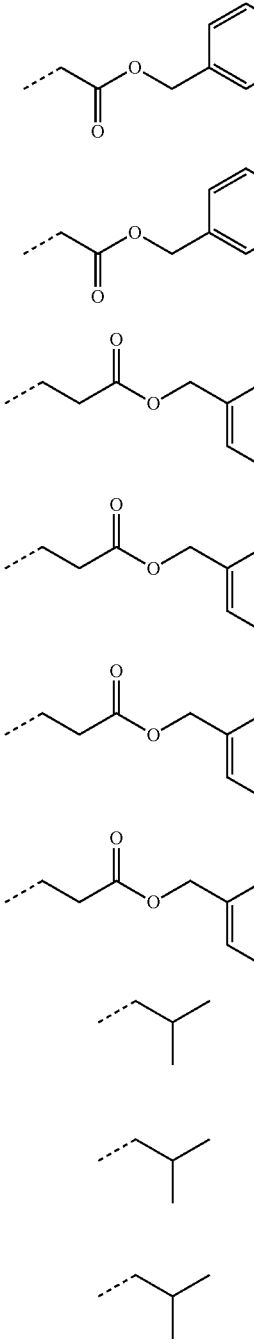 |  | 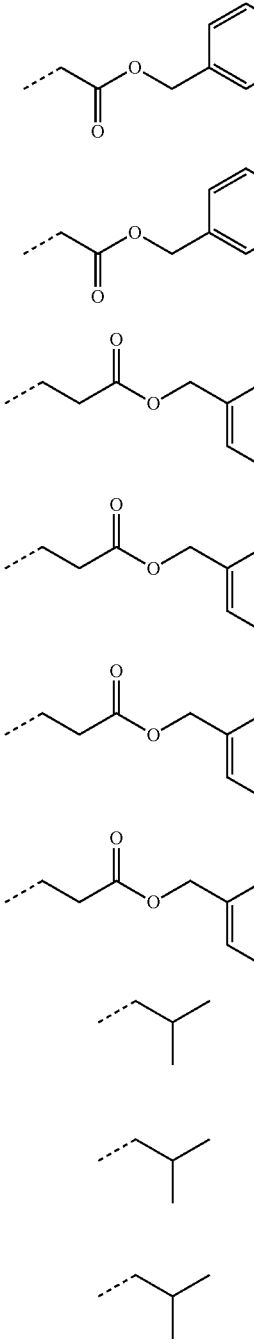 |
| 129 |  | | |
| 130 | | | |
| 131 | | | |
| 132 | | | |

TABLE 2-continued

| # | Structure 1 | Structure 2 | Structure 3 |
|---|---|---|---|
| 133 | BCN-CH2-O- | benzyl | 4-hydroxybenzyl |
| 134 | BCN-CH2-O- | benzyl | CH2OH |
| 135 | BCN-CH2-O- | benzyl | CH2COOH |
| 136 | BCN-CH2-O- | benzyl | CH2CH2COOH |
| 137 | BCN-CH2-O- | -CH2C(O)O-benzyl | 4-hydroxybenzyl |
| 138 | BCN-CH2-O- | -CH2C(O)O-benzyl | CH2OH |
| 139 | BCN-CH2-O- | -CH2C(O)O-benzyl | CH2COOH |
| 140 | BCN-CH2-O- | -CH2C(O)O-benzyl | CH2CH2COOH |
| 141 | BCN-CH2-O- | -CH2CH2C(O)O-benzyl | 4-hydroxybenzyl |
| 142 | BCN-CH2-O- | -CH2CH2C(O)O-benzyl | CH2OH |
| 143 | BCN-CH2-O- | -CH2CH2C(O)O-benzyl | CH2COOH |

TABLE 2-continued

| | | | |
|---|---|---|---|
| 144 | [bicyclononyne-CH2-O-] | [-CH2CH2C(=O)O-CH2-phenyl] | [-CH2CH2C(=O)OH] |
| 145 | [dibenzocyclooctyne-O-] | [-isobutyl] | [-CH2-C6H4-OH] |
| 146 | [dibenzocyclooctyne-O-] | [-isobutyl] | [-CH2-OH] |
| 147 | [dibenzocyclooctyne-O-] | [-isobutyl] | [-CH2C(=O)OH] |
| 148 | [dibenzocyclooctyne-O-] | [-isobutyl] | [-CH2CH2C(=O)OH] |
| 149 | [dibenzocyclooctyne-O-] | [-CH2-phenyl] | [-CH2-C6H4-OH] |
| 150 | [dibenzocyclooctyne-O-] | [-CH2-phenyl] | [-CH2-OH] |
| 151 | [dibenzocyclooctyne-O-] | [-CH2-phenyl] | [-CH2C(=O)OH] |

TABLE 2-continued
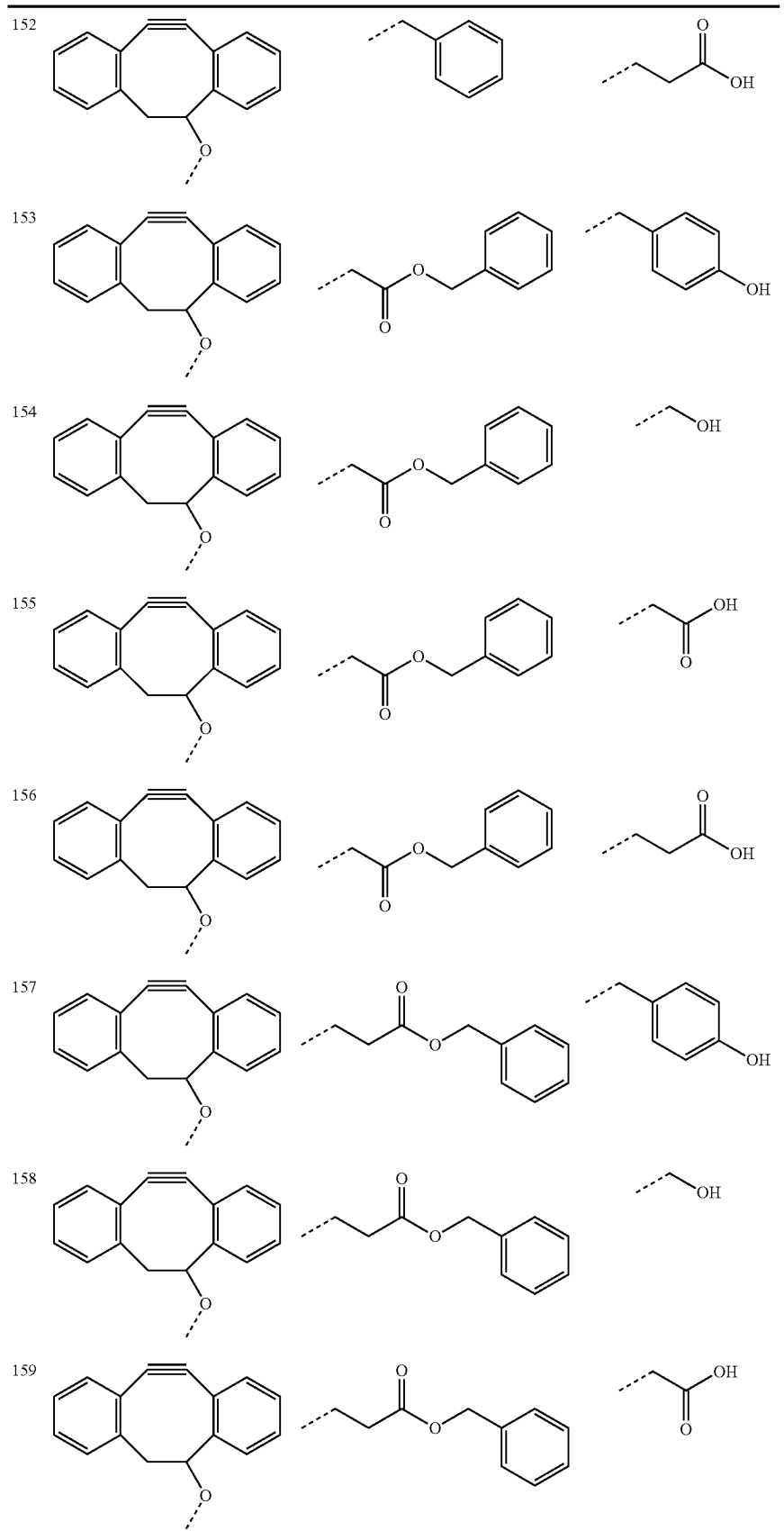

TABLE 2-continued

160 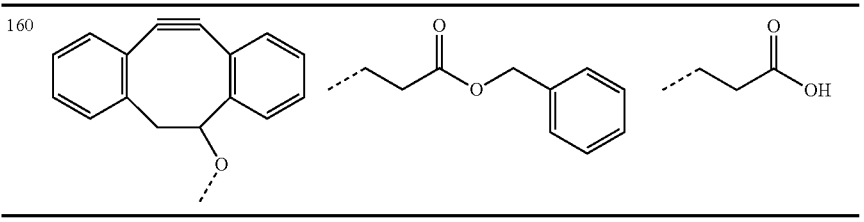

In certain embodiments, the present invention provides a triblock copolymer of formula IV:

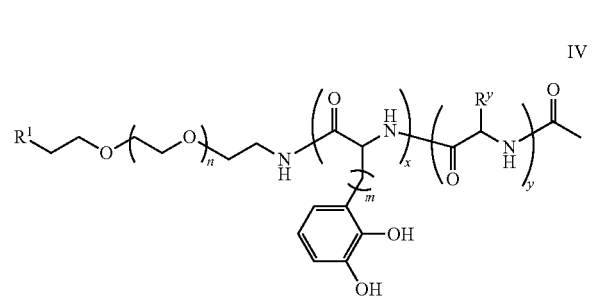

IV wherein:
n is 20-500;
m is 0, 1, or 2;
x is 3 to 50;
y is 5 to 100;
$R^y$ is selected from one or more natural or unnatural amino acid side chain groups such that the overall block is hydrophobic;
$R^1$ is —Z(CH$_2$CH$_2$Y)$_p$(CH$_2$)$_t$R$^3$, wherein:
  Z is —O—, —NH—, —S—, —C≡C—, or —CH$_2$—;
  each Y is independently —O— or —S—;
  p is 0-10;
  t is 0-10; and
$R^3$ is hydrogen, —N$_3$, —CN, —NH$_2$, —CH$_3$,

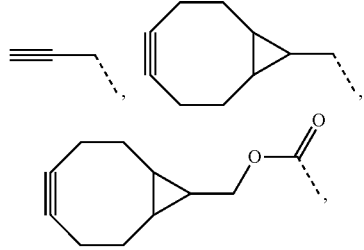

a strained cyclooctyne moiety, a mono-protected amine, a di-protected amine, an optionally protected aldehyde, an optionally protected hydroxyl, an optionally protected carboxylic acid, an optionally protected thiol, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety.

B. Targeting Group Attachment

Compounds of any of formulae I, II, III, and IV having $R^3$ moieties suitable for Click chemistry are useful for conjugating said compounds to biological systems or macromolecules such as peptides, proteins, viruses, and cells, to name but a few. The Click reaction is known to proceed quickly and selectively under physiological conditions. In contrast, most conjugation reactions are carried out using the primary amine functionality on proteins (e.g. lysine or protein end-group). Because most proteins contain a multitude of lysines and arginines, such conjugation occurs uncontrollably at multiple sites on the protein. This is particularly problematic when lysines or arginines are located around the active site of an enzyme or other biomolecule. Thus, another embodiment of the present invention provides a method of conjugating the $R^1$ groups of a compound of any of formulae I, II, III, and IV to a macromolecule via Click chemistry. Yet another embodiment of the present invention provides a macromolecule conjugated to a compound of any of any of formulae I, II, III, and IV via the $R^1$ group.

After incorporating the poly (amino acid) block portions into the multi-block coploymer of the present invention resulting in a multi-block copolymer of the form W—X—X', the other end-group functionality, corresponding to the $R^1$ moiety of any of formulae I, II, III, and IV can be used to attach targeting groups for cell specific delivery including, but not limited to, attach targeting groups for cell specific delivery including, but not limited to, proteins, oliogopeptides, antibodies, monosaccharides, oligosaccharides, vitamins, or other small biomolecules. Such targeting groups include, but are not limited to monoclonal and polyclonal antibodies (e.g. IgG, IgA, IgM, IgD, IgE antibodies), sugars (e.g. mannose, mannose-6-phosphate, galactose), proteins (e.g. Transferrin), oligopeptides (e.g. cyclic and acylic RGD-containing oligopedptides), and vitamins (e.g. folate). Alternatively, the $R^1$ moiety of any of formulae I, II, III, and IV is bonded to a biomolecule, drug, cell, or other substrate.

In other embodiments, the $R^1$ moiety of any of formulae I, II, III, and IV is bonded to biomolecules which promote cell entry and/or endosomal escape. Such biomolecules include, but are not limited to, oligopeptides containing protein transduction domains such as the HIV Tat peptide sequence (GRKKRRQRRR (SEQ ID NO: 1)) or oligoarginine (RRRRRRRRR (SEQ ID NO: 2)). Oligopeptides which undergo conformational changes in varying pH environments such oligohistidine (HHHHH (SEQ ID NO: 3)) also promote cell entry and endosomal escape.

In other embodiments, the $R^1$ moiety of any of formulae I, II, III, and IV is bonded to detectable moieties, such as fluorescent dyes or labels for positron emission tomography including molecules containing radioisotopes (e.g. $^{18}$F) or ligands with bound radioactive metals (e.g. $^{62}$Cu). In other embodiments, the $R^1$ moiety of any of formulae I, II, III, and IV is bonded to a contrast agents for magnetic resonance imaging such as gadolinium, gadolinium chelates, or iron oxide (e.g Fe$_3$O$_4$ and Fe$_2$O$_3$) particles. In other embodiments, the $R^1$ moiety of any of formulae I, II, III, and IV is bonded to a semiconducting nanoparticle such as cadmium selenide, cadmium sulfide, or cadmium telluride or bonded to other metal nanoparticles such as colloidal gold. In other embodiments, the $R^1$ moiety of any of formulae I, II, III, and IV is bonded to natural or synthetic surfaces, cells, viruses, dyes, drugs, chelating agents, or used for incorporation into hydrogels or other tissue scaffolds.

In one embodiment, the $R^1$ moiety of any of formulae I, II, III, and IV is an alkyne or a terminal alkyne derivative which is capable of undergoing [3+2]cycloaddition reactions with complementary azide-bearing molecules and biomolecules. In another embodiment, the $R^1$ moiety of any of formulae I, II, III, and IV is an azide or an azide derivative which is capable of undergoing [3+2]cycloaddition reactions with complementary alkyne-bearing molecules and biomolecules (i.e. click chemistry).

Click chemistry has become a popular method of bioconjugation due to its high reactivity and selectivity, even in biological media. See Kolb, H. C.; Finn, M. G.; Sharpless, K. B. *Angew. Chem. Int. Ed.* 2001, 40, 2004-2021; and Wang, Q.; Chan, T. R.; Hilgraf, R.; Fokin, V. V.; Sharpless, K. B.; Finn, M. G. *J. Am. Chem. Soc.* 2003, 125, 3192-3193. In addition, currently available recombinant techniques permit the introduction of azides and alkyne-bearing non-canonical amino acids into proteins, cells, viruses, bacteria, and other biological entities that consist of or display proteins. See Link, A. J.; Vink, M. K. S.; Tirrell, D. A. *J. Am. Chem. Soc.* 2004, 126, 10598-10602; Deiters, A.; Cropp, T. A.; Mukherji, M.; Chin, J. W.; Anderson, C.; Schultz, P. G. *J. Am. Chem. Soc.* 2003, 125, 11782-11783.

In another embodiment, the [3+2]cycloaddition reaction of azide or acetylene-bearing nanovectors and complimentary azide or acetylene-bearing biomolecules are transition metal catalyzed. Copper-containing molecules which catalyze the "click" reaction include, but are not limited to, copper bromide (CuBr), copper chloride (CuCl), copper sulfate ($CuSO_4$), copper iodide (CuI), $[Cu(MeCN)_4](OTf)$, and $[Cu(MeCN)_4](PF_6)$. Organic and inorganic metal-binding ligands can be used in conjunction with metal catalysts and include, but are not limited to, sodium ascorbate, tris(triazolyl)amine ligands, tris(carboxyethyl)phosphine (TCEP), and sulfonated bathophenanthroline ligands.

In another embodiment, the $R^1$ moiety of any of formulae I, II, III, and IV is an hydrazine or hydrazide derivative which is capable of undergoing reaction with biomolecules containing aldehydes or ketones to form hydrazone linkages. In another embodiment, the $R^1$ moiety of any of formulae I, II, III, and IV is an aldehyde or ketone derivative which is capable of undergoing reaction with biomolecules containing a hydrazine or hydrazide derivative to form hydrazone linkages.

In another embodiment, the $R^1$ moiety of any of formulae I, II, III, and IV is a hydroxylamine derivative which is capable of undergoing reaction with biomolecules containing aldehydes or ketones. In another embodiment, the $R^1$ moiety of any of formulae I, II, III, and IV is an aldehyde or ketone which is capable of undergoing reaction with biomolecules containing a hydroxylamine, or a hydroxylamine derivative.

In yet another embodiment, the $R^1$ moiety of any of formulae I, II, III, and IV is an aldehyde or ketone derivative which is capable of undergoing reaction with biomolecules containing primary or secondary amines to form imine linkages. In another embodiment, the $R^1$ moiety of any of formulae I, II, III, and IV is a primary or secondary amine which is capable of undergoing reaction with biomolecules containing an aldehyde or ketone functionality to form imine linkages. It will be appreciated that imine linkages can be further converted to stable amine linkages by treatment with a reducing agent (e.g. lithium aluminum hydride, sodium borohydride, sodium cyanoborohydride, etc.)

In yet another embodiment, the $R^1$ moiety of any of formulae I, II, III, and IV is an amine (primary or secondary) or alcohol which is capable of undergoing reaction with biomolecules containing activated esters (e.g. 4-nitrophenol ester, N-hydroxysuccinimide, pentafluorophenyl ester, ortho-pyridylthioester), to form amide or ester linkages. In still other embodiments, the $R^1$ moiety of any of formulae I, II, III, and IV is an activated ester which is capable of undergoing reaction with biomolecules possessing amine (primary or secondary) or alcohols to form amide or ester linkages.

In still other embodiments, the $R^1$ moiety of any of formulae I, II, III, and IV is an amine or alcohol which is bound to biomolecules with carboxylic acid functionality using a coupling agent. In still other embodiments, the $R^1$ moiety of any of formulae I, II, III, and IV is a carboxylic acid functionality which is bound to biomolecules containing amine or alcohol functionality using a coupling agent. Such coupling agents include, but are not limited to, carbodiimides (e.g. 1-ethyl-3-(3-dimethylaminopropyl)-carbodiimide (EDC), diisopropyl carbodiimide (DIC), dicyclohexyl carbodiimide (DCC)), aminium or phosphonium derivatives (e.g. PyBOP, PyAOP, TBTU, HATU, HBTU), or a combination of 1-hydroxybenzotriazole (HOBt) and a aminium or phosphonium derivative.

In another embodiment, the $R^1$ moiety of any of formulae I, II, III, and IV is an electrophile such as maleimide, a maleimide derivative, or a bromoacetamide derivative, which is capable of reaction with biomolecules containing thiols or amines. In another embodiment, the $R^1$ moiety of any of formulae I, II, III, and IV is a nucleophile such as an amine or thiol which is capable or reaction with biomolecules containing electrophilic functionality such as maleimide, a maleimide derivative, or a bromoacetamide derivative.

In still other embodiments, the $R^1$ moiety of any of formulae I, II, III, and IV is a ortho-pyridyl disulfide moiety which undergoes disulfide exchange with biomolecules containing thiol functionality. In still other embodiments, the $R^1$ moiety of any of formulae I, II, III, and IV is a thiol or thiol derivative which undergoes disulfide exchange with biomolecules containing ortho-pyridyl disulfide functionality. It will be appreciated that such exchange reactions result in a disulfide linkage, which is reversible in the presence of a reducing agent (e.g. glutathione, dithiothreitol (DTT), etc.).

In certain embodiments, micelles of the present invention are mixed micelles comprising one or more compounds of formulae I, II, III, and IV. It will be appreciated that mixed micelles having different $R^1$ groups, as described herein, can be conjugated to multiple other compounds and/or macromolecules. For example, a mixed micelle of the present invention can have one $R^1$ group suitable for Click chemistry and another $R^1$ group suitable for covalent attachment via a variety of coupling reactions. Such a mixed micelle can be conjugated to different compounds and/or macromolecules via these different $R^1$ groups. Such conjugation reactions are well known to one of ordinary skill in the art and include those described herein.

In certain embodiments, the present invention provides a triblock copolymer of formula V:

V

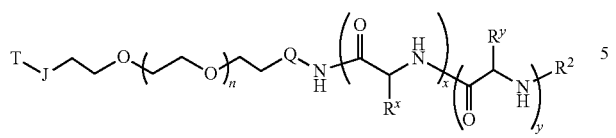

wherein each of Q, x, y, n, $R^x$, $R^y$ and $R^2$ is as defined above and as described in classes and subclasses herein, both singly and in combination;

J is independently a valence bond or a bivalent, saturated or unsaturated, straight or branched $C_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:

-Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

each T is independently a targeting group.

As generally described above, T is a targeting group. Such targeting groups are described in detail in United States patent application publication number 2009/0110662, published Apr. 30, 2009, the entirety of which is hereby incorporated by reference. Additional targeting groups are described in detail in U.S. patent application Ser. No. 13/415,910, filed Mar. 9, 2012, the entirety of which is hereby incorporated by reference.

In certain embodiments, the J group is a valence bond as described above. In certain embodiments, the J group is a methylene group. In other embodiments, the J group is a carbonyl group. In certain embodiments, the J group of Formula V is a valence bond. In other embodiments, the J group is represented by a moiety in Table 3.

TABLE 3

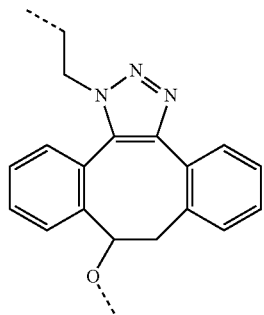
a

TABLE 3-continued

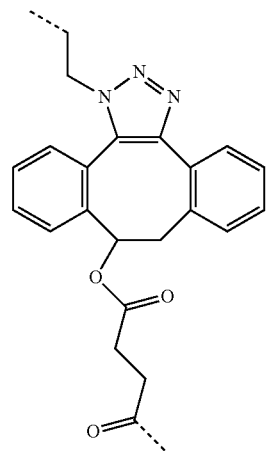
b

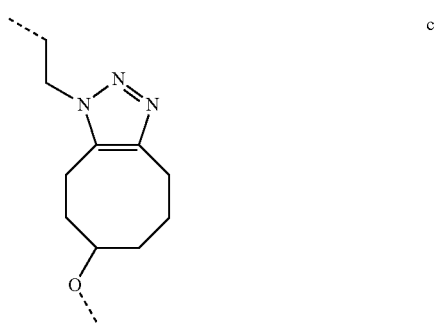
c

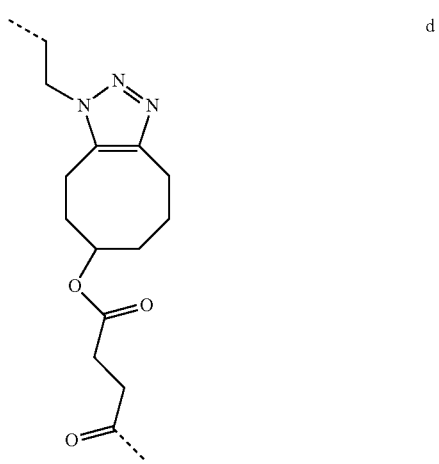
d

TABLE 3-continued

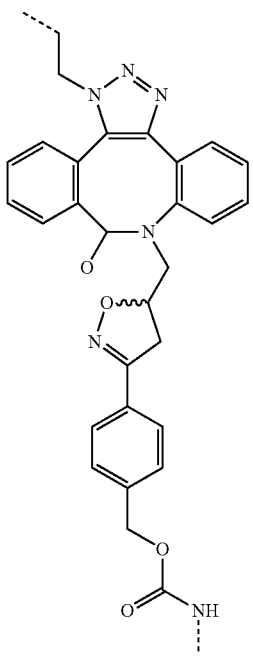
e

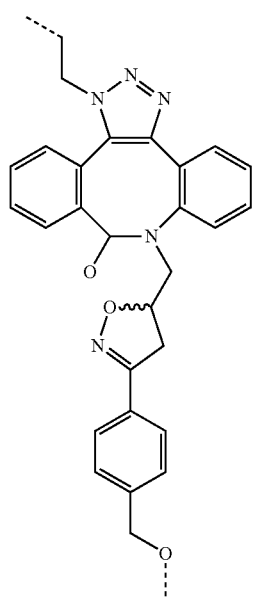
f

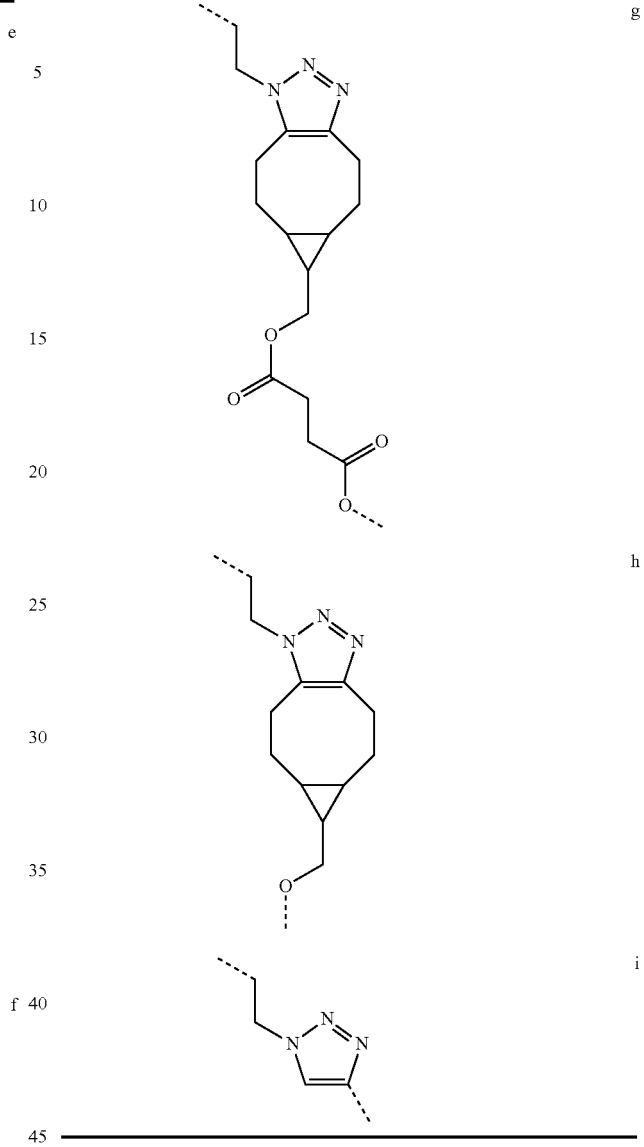

C. Micelle Formation

Amphiphilic multiblock copolymers, as described herein, can self-assemble in aqueous solution to form nano- and micron-sized structures. In water, these amphiphilic multiblock copolymers assemble by multi-molecular micellization when present in solution above the critical micelle concentration (CMC). Without wishing to be bound by any particular theory, it is believed that the hydrophobic poly (amino acid) portion or "block" of the copolymer collapses to form the micellar core, while the hydrophilic PEG block forms a peripheral corona and imparts water solubility. In certain embodiments, the multiblock copolymers in accordance with the present invention possess distinct hydrophobic and hydrophilic segments that form micelles. In addition, these multiblock polymers optionally comprise a poly (amino acid) block which contains functionality for crosslinking. It will be appreciated that this functionality is found on the corresponding amino acid side-chain.

D. Drug Loading

According to one embodiment, the present invention provides a micelle comprising a triblock copolymer which comprises a polymeric hydrophilic block, optionally a crosslinkable or crosslinked poly(amino acid block), and a hydrophobic D,L-mixed poly(amino acid) block, characterized in that said micelle has an inner core, optionally a crosslinkable or crosslinked outer core, and a hydrophilic shell. As described herein, micelles of the present invention are especially useful for encapsulating therapeutic agents. In certain embodiments the therapeutic agent is hydrophobic.

Without wishing to be bound by any particular theory, it is believed that the accommodation of structurally diverse therapeutic agents within a micelle of the present invention is effected by adjusting the hydrophobic D,L-mixed poly (amino acid) block, i.e., the block comprising $R^y$. As discussed above, the hydrophobic mixture of D and L stereoisomers affords a poly(amino acid) block with a random coil conformation thereby enhancing the encapsulation of hydrophobic drugs.

Hydrophobic small molecule drugs suitable for loading into micelles of the present invention are well known in the art. In certain embodiments, the present invention provides a drug-loaded micelle as described herein. In other embodiments, the present invention provides a drug-loaded micelle as described herein, wherein the drug is a hydrophobic drug selected from those described herein, infra.

As used herein, the terms hydrophobic small molecule drugs, small molecule drugs, therapeutic agent, and hydrophobic therapeutic agents are all interchangeable.

According to another embodiment, the present invention provides a drug-loaded micelle comprising a triblock copolymer of formula I and a therapeutic agent.

According to another embodiment, the present invention provides a drug-loaded micelle comprising a triblock copolymer of formula I and a hydrophobic therapeutic agent.

In other embodiments, the present invention provides a system comprising a triblock copolymer of formula I and a hydrophobic therapeutic agent. In another embodiment, the present invention provides a system comprising a triblock copolymer of any of formulae I, II, III, or IV, either singly or in combination, and a hydrophobic therapeutic agent. In yet another embodiment, the present invention provides a system comprising a triblock copolymer of formula II and a hydrophobic therapeutic agent.

In some embodiments, the present invention provides a micelle, having a suitable hydrophobic therapeutic agent encapsulated therein, comprising a multiblock copolymer of formula I and a multiblock copolymer of formula V, wherein each of formula I and formula V are as defined above and described herein, wherein the ratio of Formula I to Formula V is between 1000:1 and 1:1. In other embodiments, the ratio is 1000:1, 100:1, 50:1, 33:1, 25:1, 20:1, 10:1, 5:1, or 4:1. In yet other embodiments, the ratio is between 100:1 and 25:1.

In some embodiments, the present invention provides a micelle, having an hydrophobic therapeutic agent encapsulated therein, comprising a multiblock copolymer of formula II and a multiblock copolymer of formula V, wherein each of formula II and formula V are as defined above and described herein, wherein the ratio of Formula II to Formula V is between 1000:1 and 1:1. In other embodiments, the ratio is 1000:1, 100:1, 50:1, 33:1, 25:1, 20:1, 10:1, 5:1, or 4:1. In yet other embodiments, the ratio is between 100:1 and 25:1.

Embodiments with respect to each of the $R^1$, $R^{2a}$, Q, $R^x$, $R^y$, n, m, and m' groups of formula I, are as described in various classes and subclasses, both singly and in combination, herein.

In certain embodiments, the present invention provides a drug-loaded micelle, as described herein, wherein the drug is a taxane.

Taxanes are well known in the literature and are natural products produced by plants of the genus *Taxus*. The mechanism of action is microtubule stabilization, thus inhibiting mitosis. Many taxanes are poorly soluble or nearly completely insoluble in water. Exemplary epothilones are shown below.

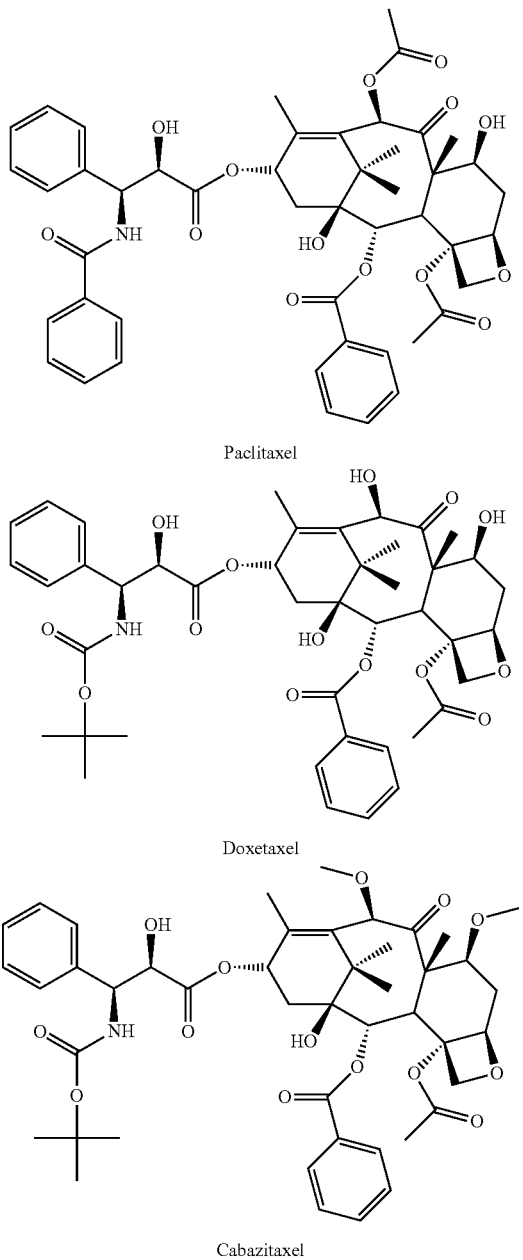

Paclitaxel

Doxetaxel

Cabazitaxel

Epothilones are a group of molecules that have been shown to be microtubule stabilizers, a mechanism similar to paclitaxel (Bollag D M et al. Cancer Res. 1995, 55, 2325-2333). Biochemical studies demonstrated that epothilones can displace paclitaxel from tubulin, suggesting that they compete for the same binding site (Kowalski R J, Giannakakou P, Hamel E. J Biol Chem. 1997, 272, 2534-2541). One advantage of the epothilones is that they exert much greater cytotoxic effect in PGP overexpressing cells compared to paclitaxel. Exemplary epothilones are shown below.

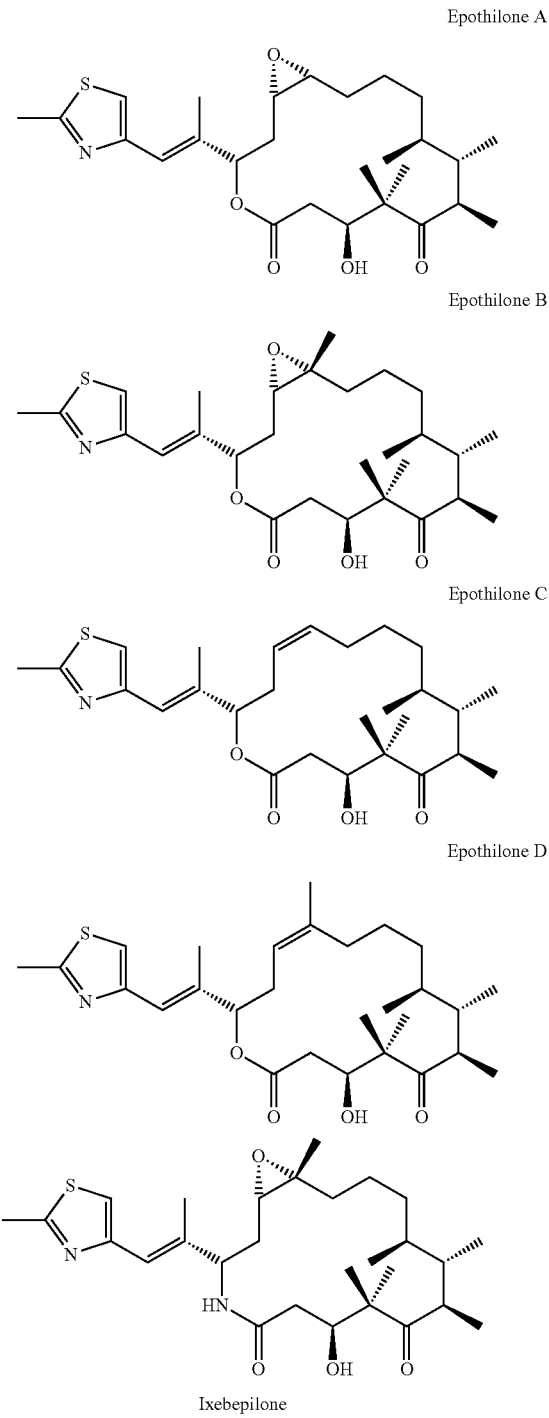

In certain embodiments, the present invention provides a drug-loaded micelle, as described herein, wherein the drug is paclitaxel.

In certain embodiments, the present invention provides a drug-loaded micelle, as described herein, wherein the drug is docetaxel.

In certain embodiments, the present invention provides a drug-loaded micelle, as described herein, wherein the drug is cabazitaxel.

In certain embodiments, the present invention provides a drug-loaded micelle, as described herein, wherein the drug is an epothilone.

In certain embodiments, the present invention provides a drug-loaded micelle, as described herein, wherein the drug is Epothilone B or Epothilone D.

In certain embodiments, the present invention provides a drug-loaded micelle, as described herein, wherein the drug is Epothilone A or Epothilone C.

Vinca alkaloids are well known in the literature and are a set of anti-mitotic agents. Vinca alkaloids include vinblastine, vincristine, vindesine, and vinorelbine, and act to prevent the formation of microtubules. Exemplary vinca alkaloids are shown below.

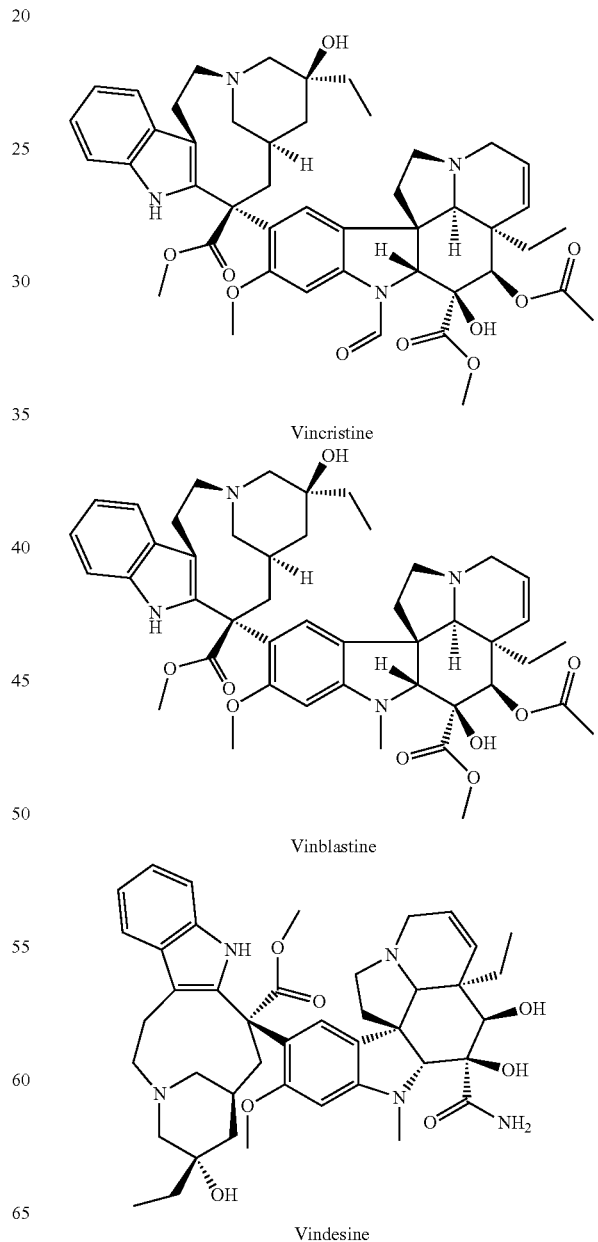

-continued

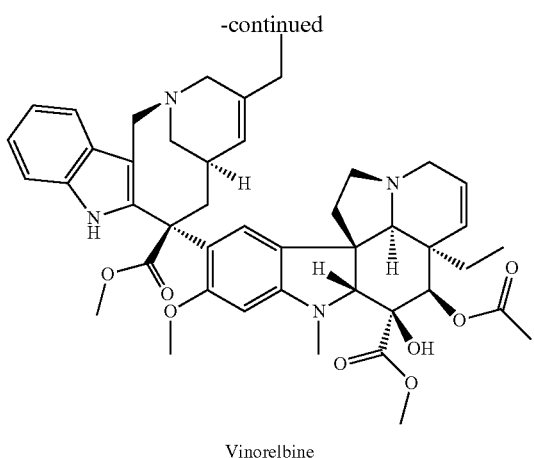

Vinorelbine

In certain embodiments, the present invention provides a drug-loaded micelle, as described herein, wherein the drug is a vinca alkaloid.

In certain embodiments, the present invention provides a drug-loaded micelle, as described herein, wherein the drug is vinorelbine.

Berberine is well known in the literature and shown pharmaceutical effects in a range of applications including antibacterial and oncology applications. The anti-tumor activity of berberine and associated derivatives are described in Hoshi, et. al. *Gann,* 1976, 67, 321-325. Specifically, berberrubine and ester derivatives of berberrubine are shown to have increased anti-tumor activity with respect to berberine. The structures of berberine and berberrubine are shown below.

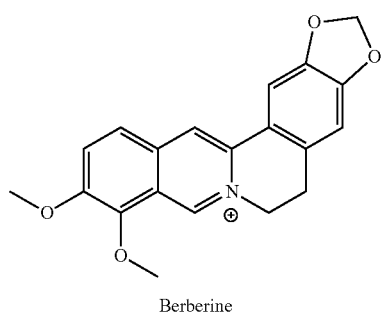

Berberine

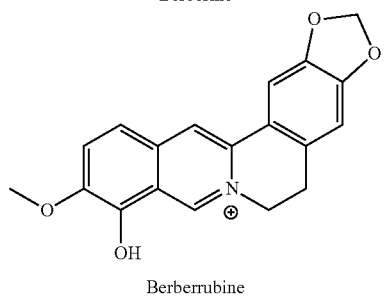

Berberrubine

In certain embodiments, the present invention provides a drug-loaded micelle, as described herein, wherein the drug is berberine.

In certain embodiments, the present invention provides a drug-loaded micelle, as described herein, wherein the drug is berberrubine.

The antitumor plant alkaloid camptothecin (CPT) is a broad-spectrum anticancer agent that targets DNA topoisomerase I. Although CPT has shown promising antitumor activity in vitro and in vivo, it has not been clinically used because of its low therapeutic efficacy and severe toxicity. Among CPT analogues, irinotecan hydrochloride (CPT-11) has recently been shown to be active against colorectal, lung, and ovarian cancer. CPT-11 itself is a prodrug and is converted to 7-ethyl-10-hydroxy-CPT (known as SN-38), a biologically active metabolite of CPT-11, by carboxylesterases in vivo. A number of camptothecin derivatives are in development, the structures of which are shown below.

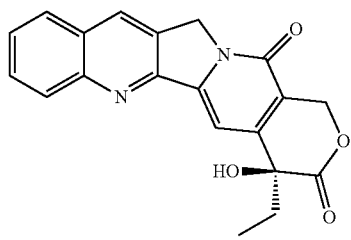

Camptothecin

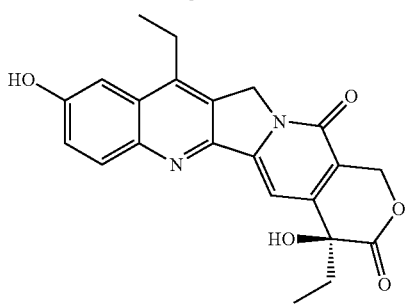

SN-38

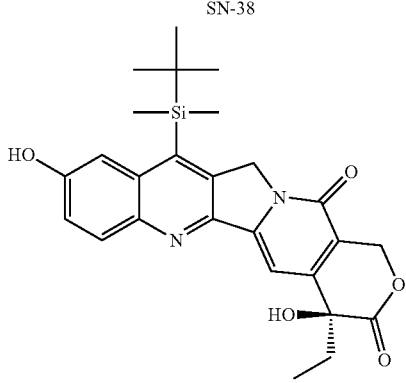

DB 67

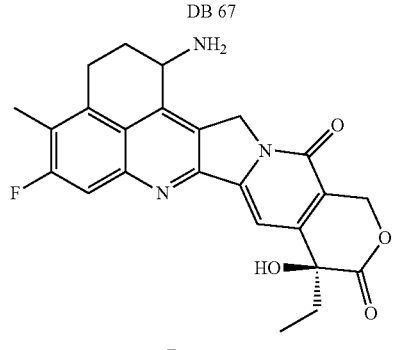

Exatecan

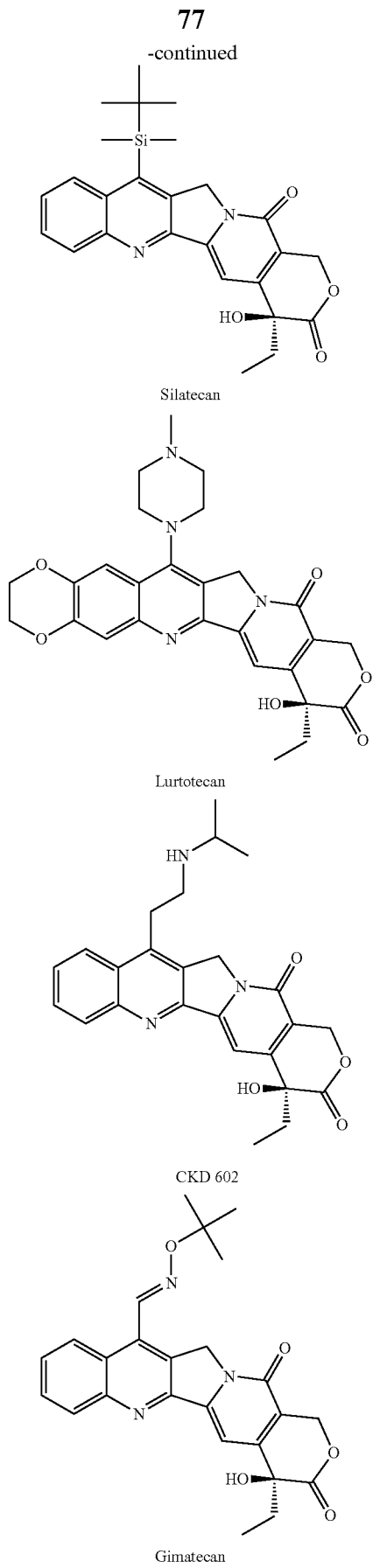

Silatecan

Lurtotecan

CKD 602

Gimatecan

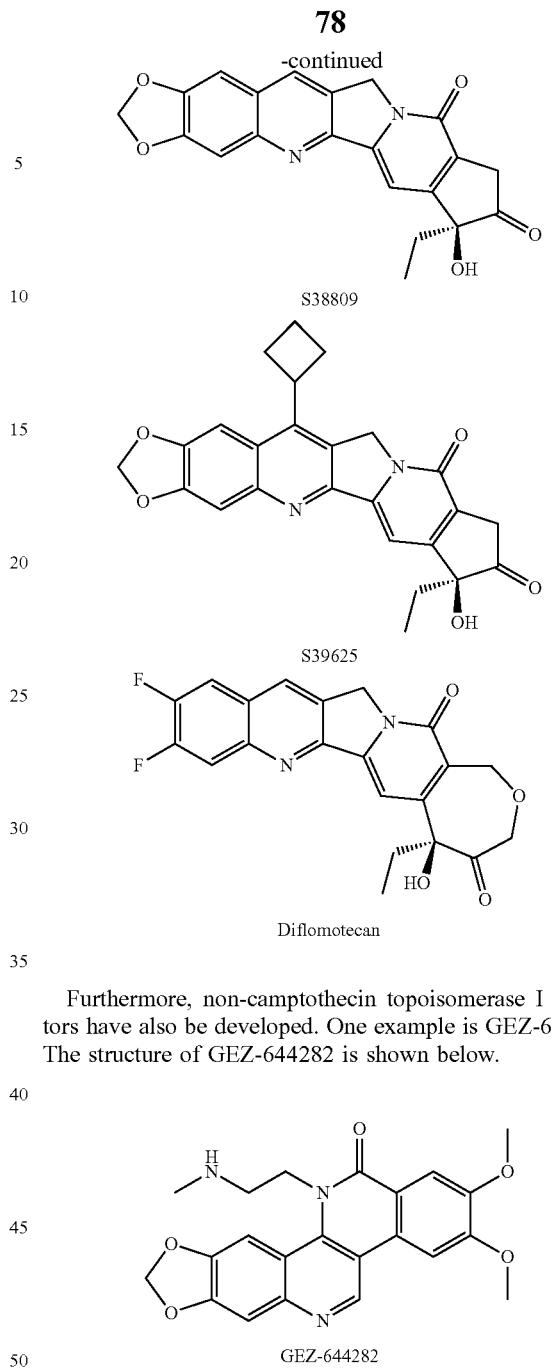

S38809

S39625

Diflomotecan

Furthermore, non-camptothecin topoisomerase I inhibitors have also be developed. One example is GEZ-644282. The structure of GEZ-644282 is shown below.

GEZ-644282

In certain embodiments, the present invention provides a drug-loaded micelle, as described herein, wherein the drug is a camptothecin.

In certain embodiments, the present invention provides a drug-loaded micelle, as described herein, wherein the drug is SN-38.

In certain embodiments, the present invention provides a drug-loaded micelle, as described herein, wherein the drug is S39625.

In certain embodiments, the present invention provides a drug-loaded micelle, as described herein, wherein the drug is GEZ-644282.

Several anthracycline derivates have been produced and have found use in the clinic for the treatment of leukemias, Hodgkin's lymphoma, as well as cancers of the bladder, breast, stomach, lung, ovaries, thyroid, and soft tissue sarcoma. Such anthracycline derivatives include daunorubicin (also known as Daunomycin or daunomycin cerubidine), doxorubicin (also known as DOX, hydroxydaunorubicin, or adriamycin), epirubicin (also known as Ellence or Pharmorubicin), idarubicin (also known as 4-demethoxydaunorubicin, Zavedos, or Idamycin), and valrubicin (also known as N-trifluoroacetyladriamycin-14-valerate or Valstar). Anthracyclines are typically prepared as an ammonium salt (e.g. hydrochloride salt) to improve water solubility and allow for ease of administration.

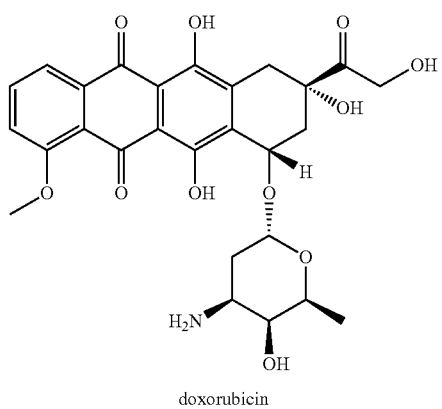

doxorubicin

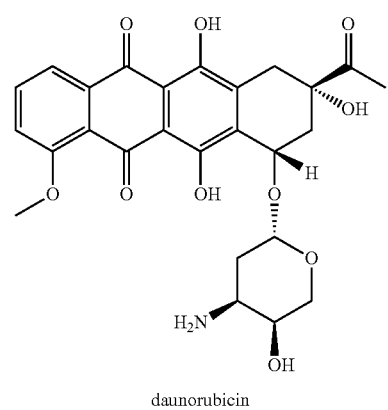

daunorubicin

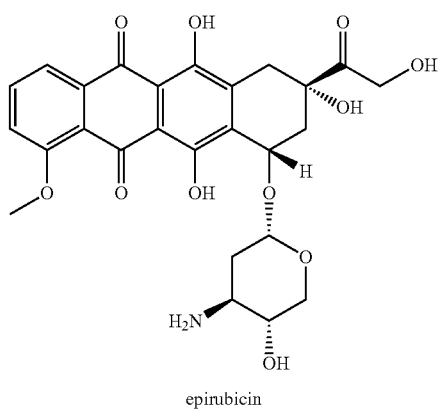

epirubicin

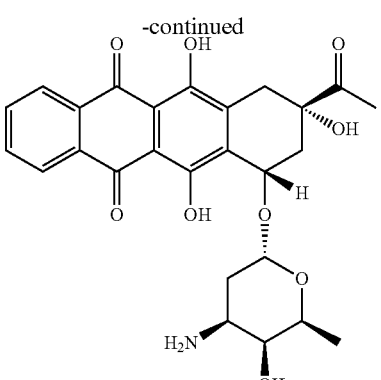

idarubicin

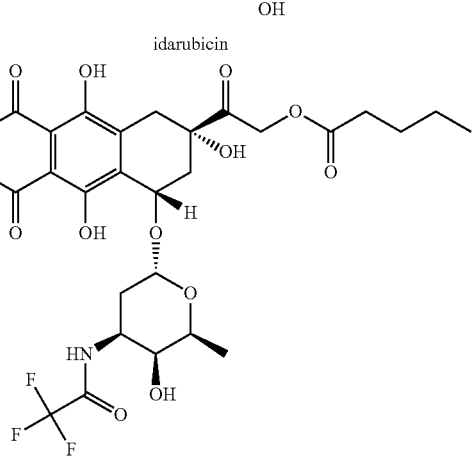

valrubicin

In certain embodiments, the present invention provides a drug-loaded micelle, as described herein, wherein the drug is daunorubicin.

In certain embodiments, the present invention provides a drug-loaded micelle, as described herein, wherein the drug is doxorubicin.

In certain embodiments, the present invention provides a drug-loaded micelle, as described herein, wherein the drug is an anthracyline.

Aminopterin is well known in the literature and is an analog of folic acid that is an antineoplastic agent. Aminopterin works as an enzyme inhibitor by competing for the folate binding sight of the enzyme dihydofolate reductase. The structure of aminopterin is shown below.

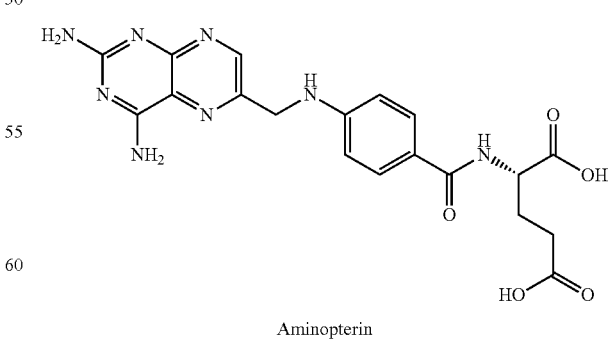

Aminopterin

In certain embodiments, the present invention provides a drug-loaded micelle, as described herein, wherein the drug is aminopterin.

Platinum based therapeutics are well known in the literature. Platinum therapeutics are widely used in oncology and act to crosslink DNA which results in cell death (apoptosis). Carboplatin, picoplatin, cisplatin, and oxaliplatin are exemplary platinum therapeutics and the structures are shown below.

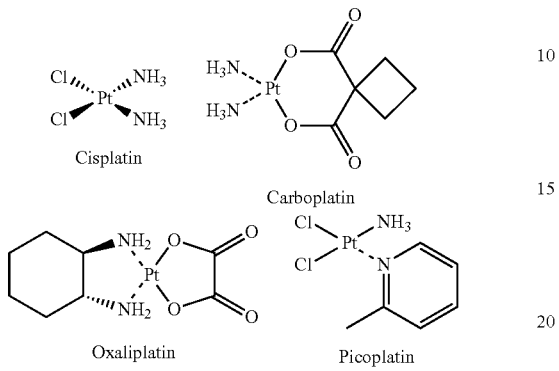

Cisplatin

Carboplatin

Oxaliplatin

Picoplatin

In certain embodiments, the present invention provides a drug-loaded micelle, as described herein, wherein the drug is picoplatin.

In certain embodiments, the present invention provides a drug-loaded micelle, as described herein, wherein the drug is a platinum therapeutic.

Molecularly targeted therapeutics are well known in the literature. Molecularly targeted therapies are widely used in oncology and act to inhibit specific enzyme activity or to block certain cellular receptors. Tyrosine kinase inhibitors are one subclass of molecularly targeted therapeutics. Other classes of molecularly targeted therapeutics include, but are not limited to, proteasome inhibitors, Janus kinase inhibitors, ALK inhibitors, Bcl-2 inhibitors, PARP inhibitors, PI3K inhibitors, Braf inhibitors, MEK inhibitors, SMAC mimetics, and CDK inhibitors. LY2835219, palociclib, selumetinib, MEK162, trametinib, alisertib, birinapant, LCL161, AT-406, BBI608, KP46, everolimus, and XL147 are exemplary molecularly targeted therapeutics and the structures are shown below.

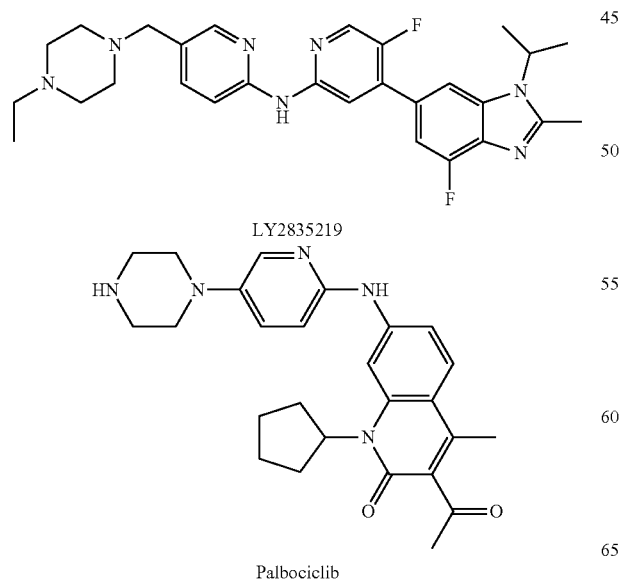

LY2835219

Palbociclib

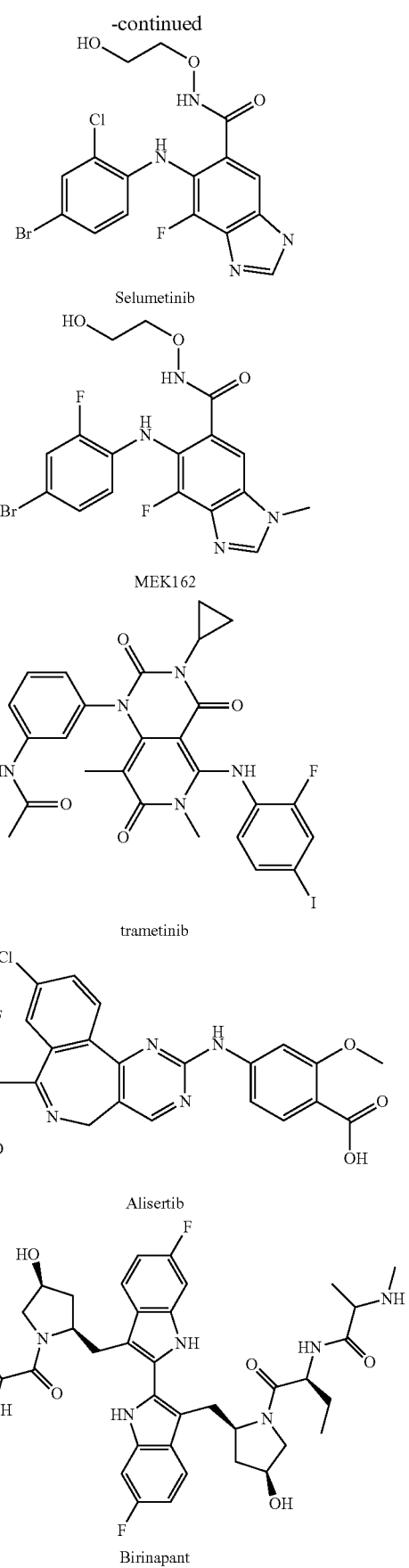

Selumetinib

MEK162 trametinib

Alisertib

Birinapant

-continued
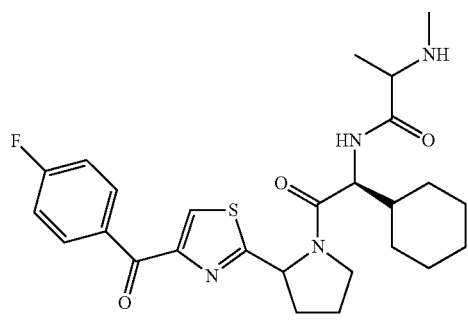
LCL161
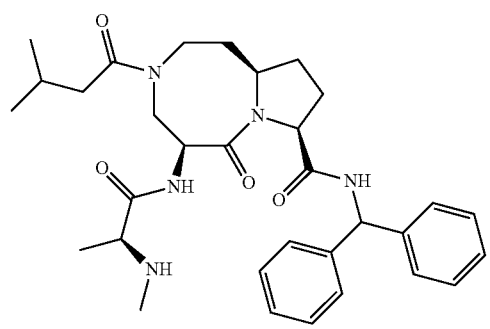
AT-406
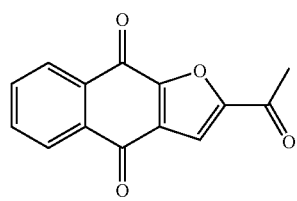
BB1608
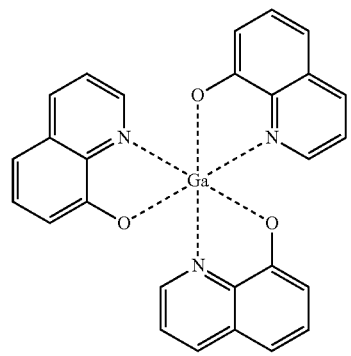
KP46
-continued
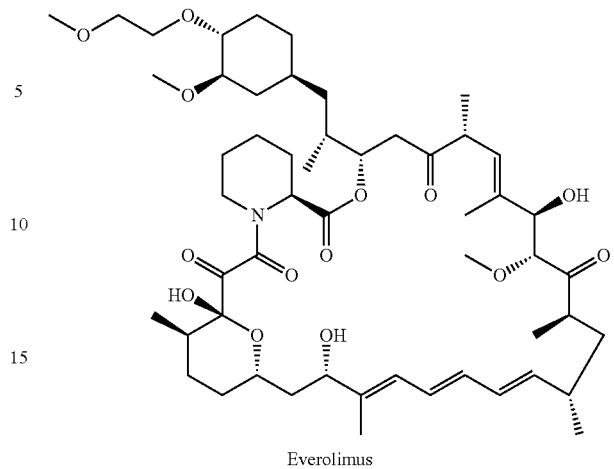
Everolimus
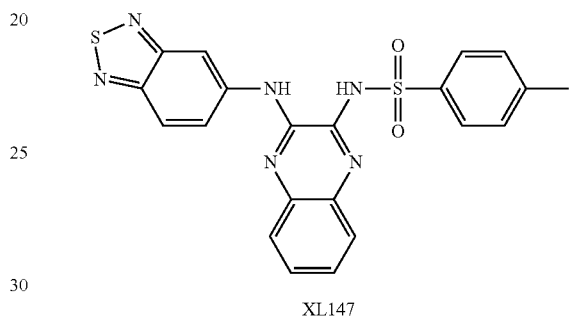
XL147
Additional molecularly targeted therapeutics are also in development. Examples include E7016, XL765, TG101348, E7820, eribulin, INK 128, TAK-385, MLN2480, TAK733, MLN-4924, motesanib, ixazomib, TAK-700, dacomitinib, and sunitinib. The structures of each are shown below.
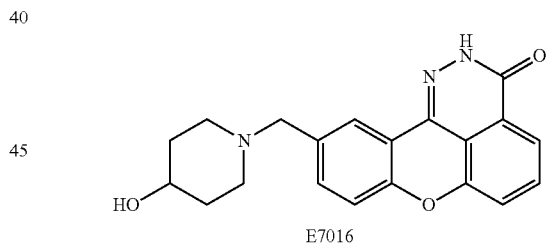
E7016
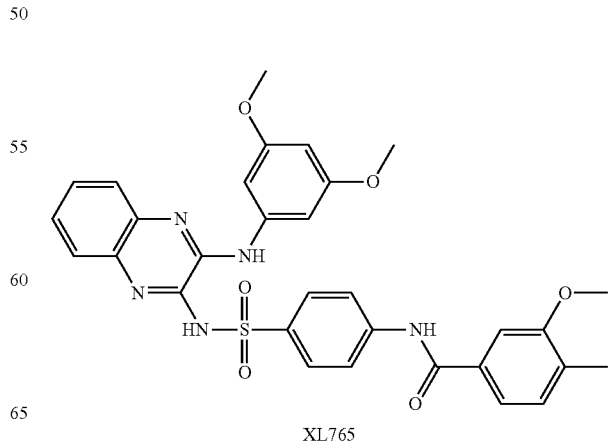
XL765

85
-continued
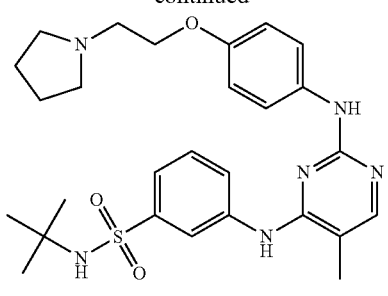
TG101348
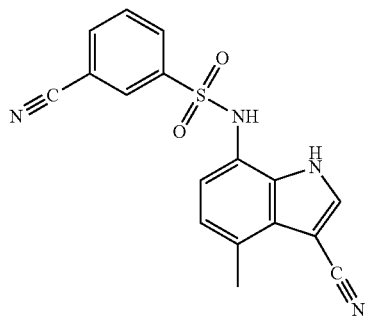
E7820
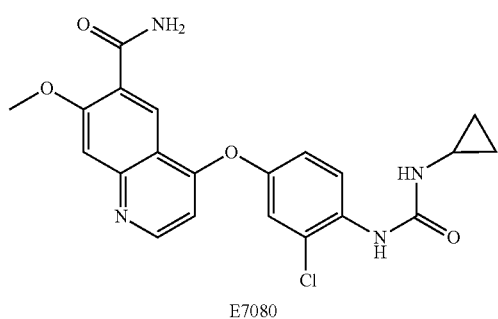
E7080
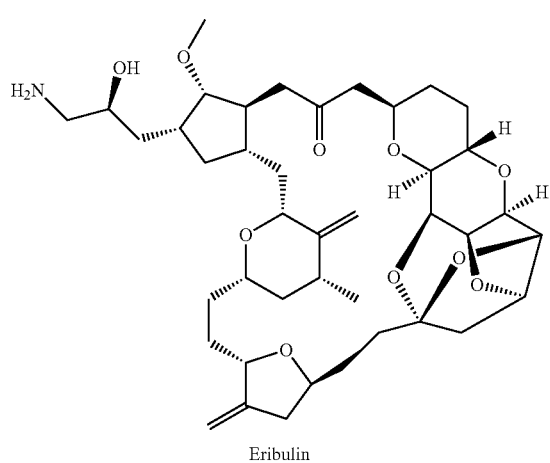
Eribulin
86
-continued
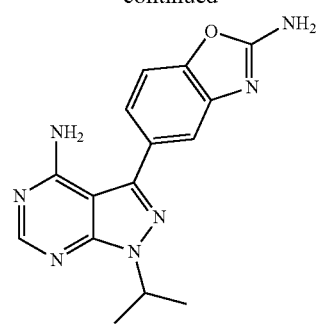
INK 128
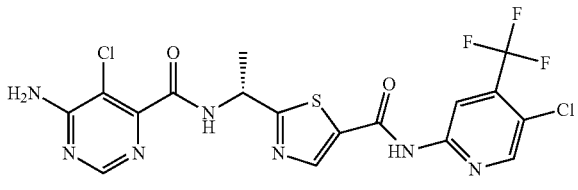
TAK-385
MLN2480
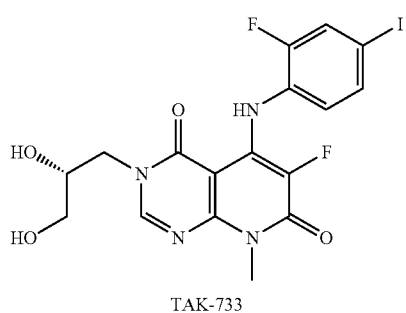
TAK-733
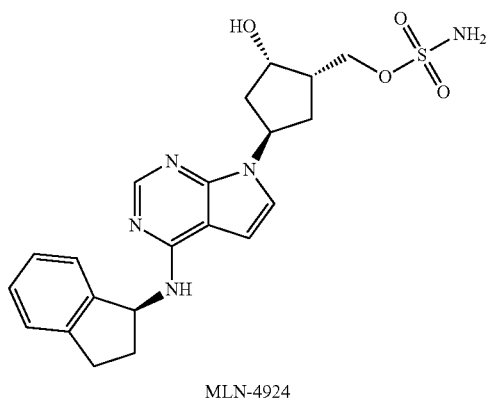
MLN-4924

87
-continued
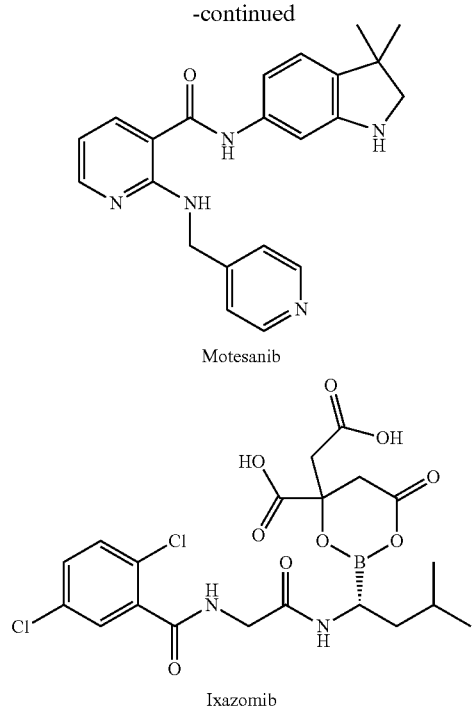
Motesanib
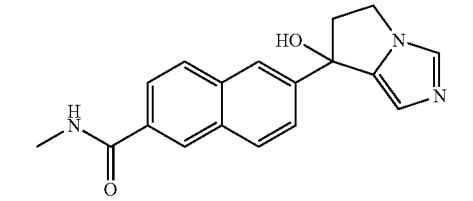
Ixazomib
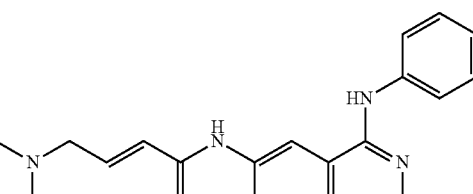
TAK-700
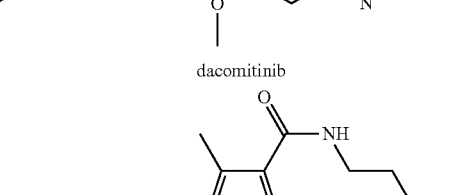
dacomitinib
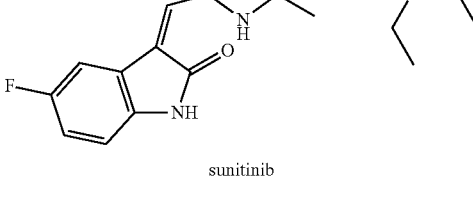
sunitinib
Further examples of molecularly targeted therapeutics include crizotinib, axitinib, PF 03084014, PD 0325901, PF 05212384, PF 04449913, ridaforlimus, MK-1775, MK-2206, GSK2636771, GSK525762, eltrombopag, dabrefenib, and foretinib. The structures of each are shown below.
88
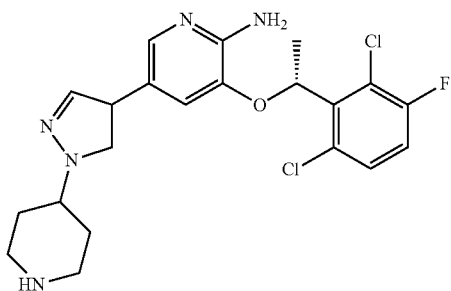
crizotinib
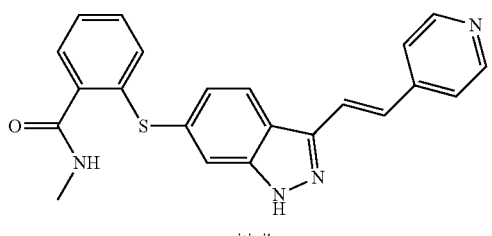
axitinib
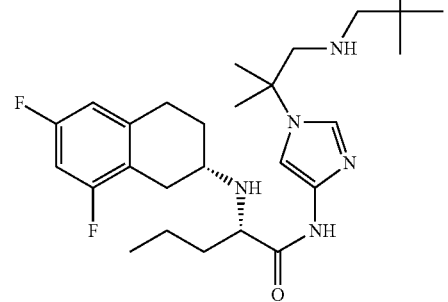
PF 03084014
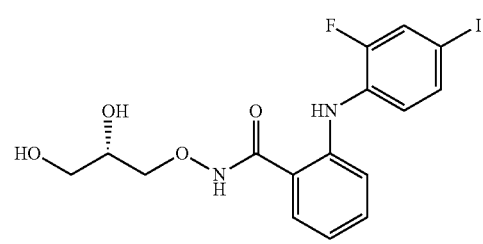
PD 0325901
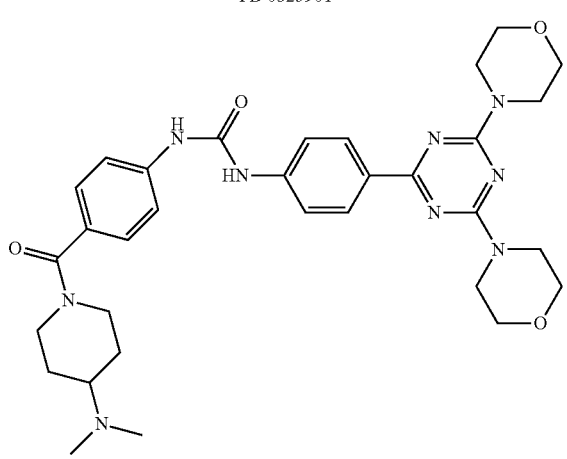
PF 05212384

89
-continued
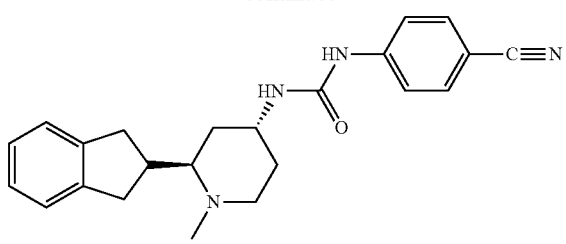
PF 04449913
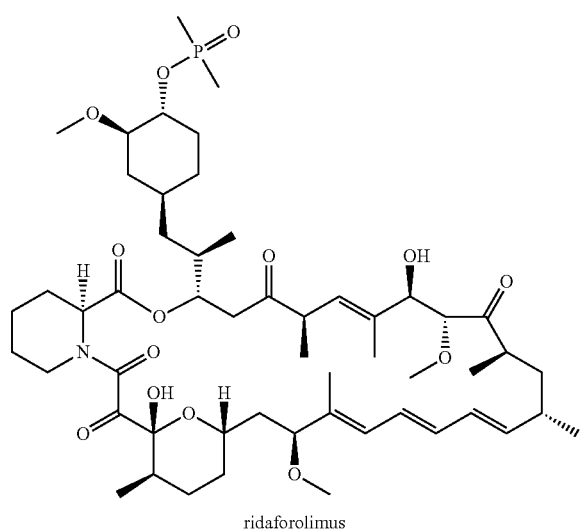
ridaforolimus
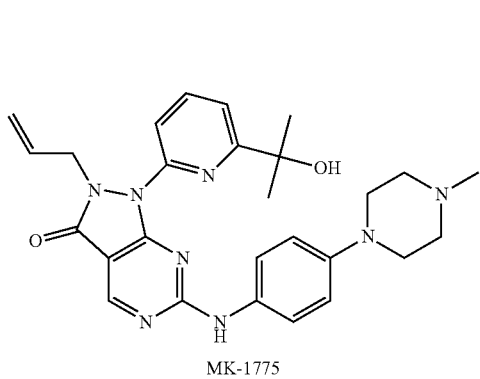
MK-1775
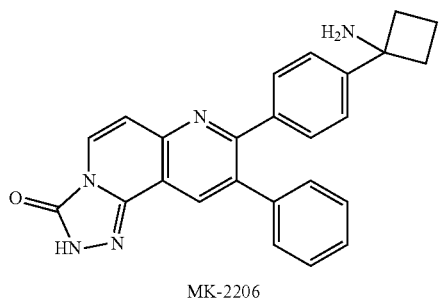
MK-2206
90
-continued
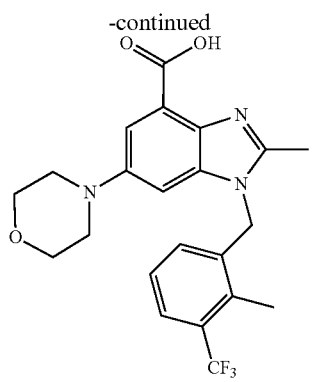
GSK2636771
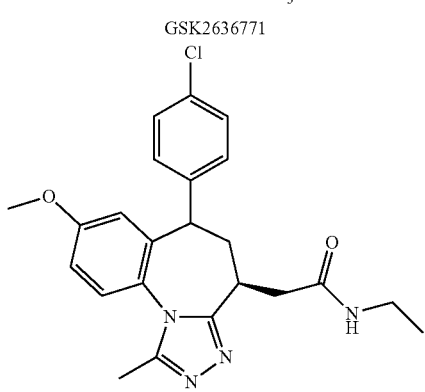
GSK525762
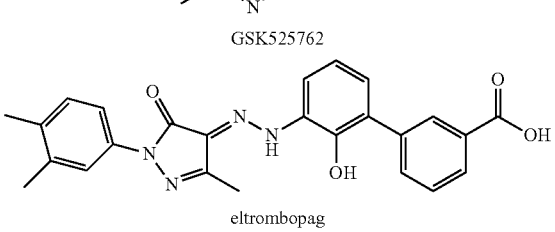
eltrombopag
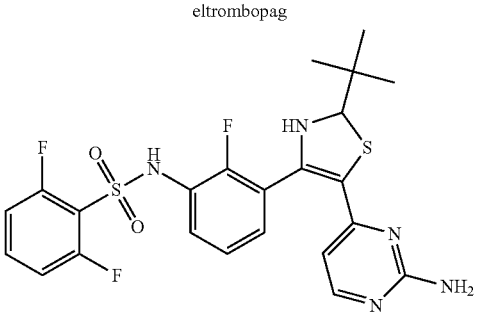
dabrafenib
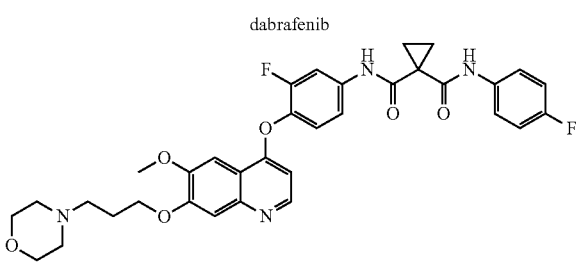
foretinib
Yet further examples of molecularly targeted therapeutics include lapatinib, pazopanib, CH5132799, RO4987655, RG7338, A0379, erlotinib, pictilisib, GDC-0032, venurafenib, GDC-0980, GDC-0068, arry-520, pasireotide, dovitinib, and cobmetinib. The structures of each are shown below.

91
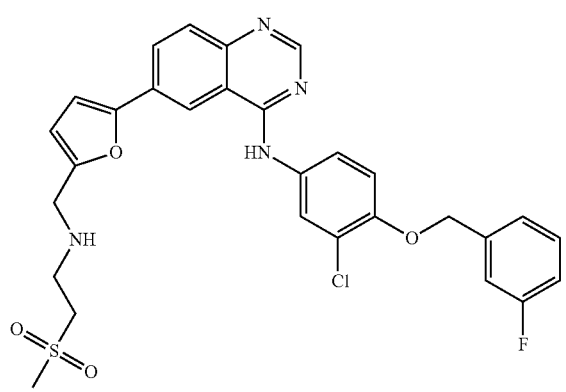
lapatinib
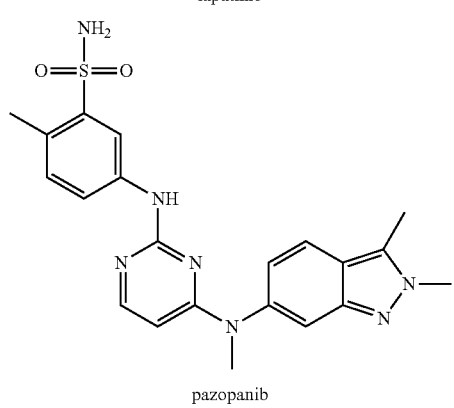
pazopanib
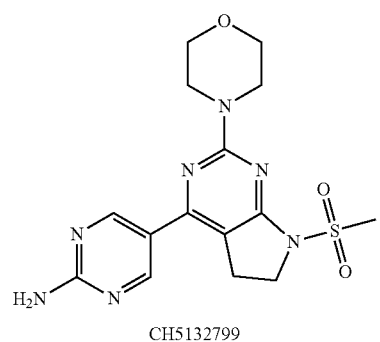
CH5132799
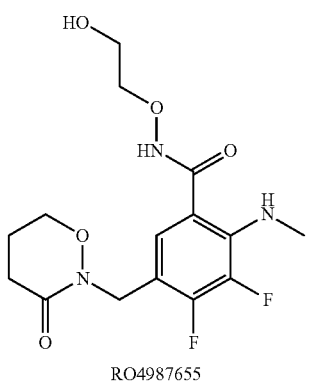
RO4987655
92
-continued
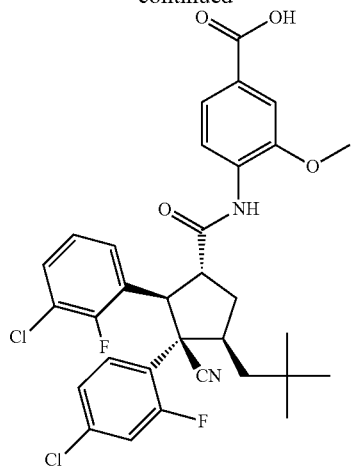
RG7388
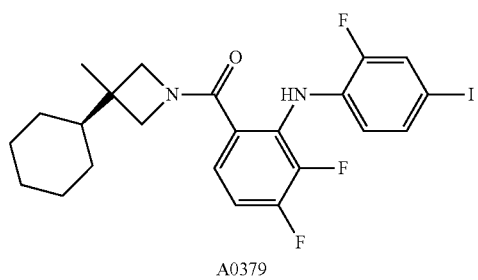
A0379
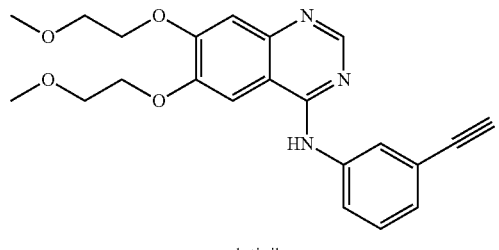
erlotinib
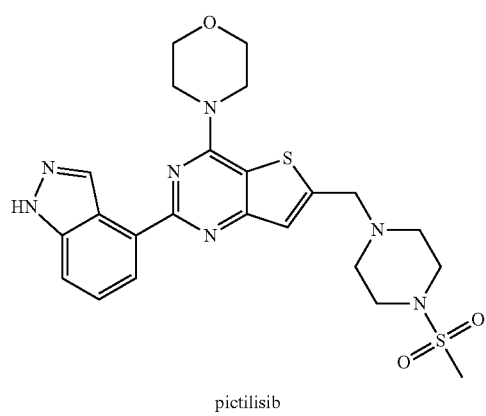
pictilisib -continued
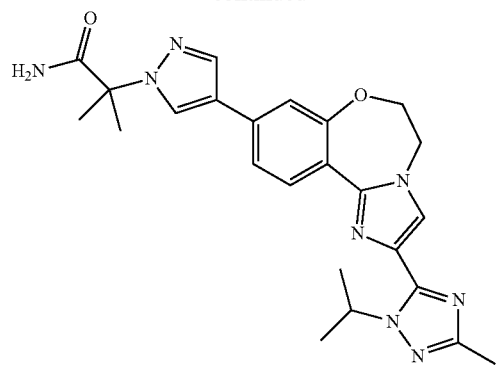
GDC-0032
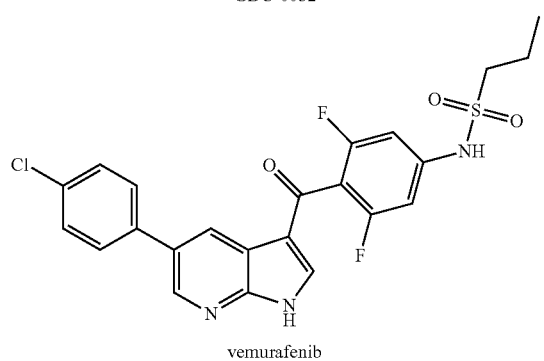
vemurafenib
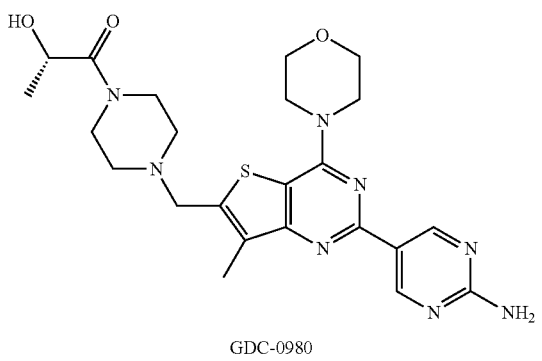
GDC-0980
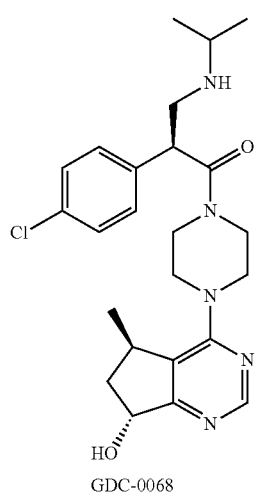
GDC-0068
-continued
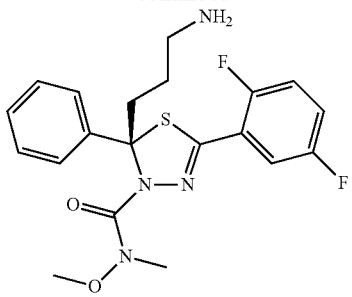
arry-520
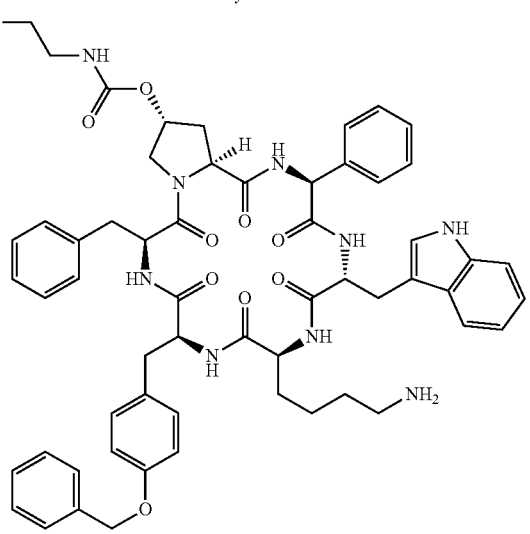
pasireotide
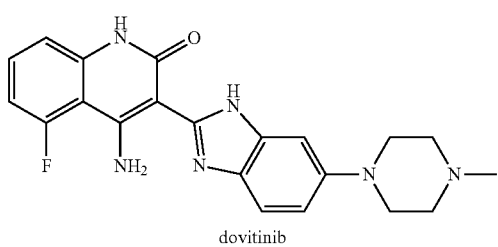
dovitinib
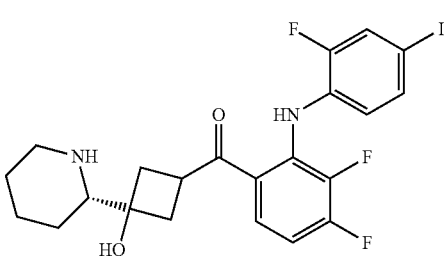
cobmetinib
Additional examples of molecularly targeted therapeutics include buparlisib, AVL-292, romidepsin, arry-797, lenalidomide, thalidomide, apremilast, AMG-900, AMG208, rucaparib, NVP-BEZ 235, AUY922, LDE225, and midostaurin. The structures of each are shown below.

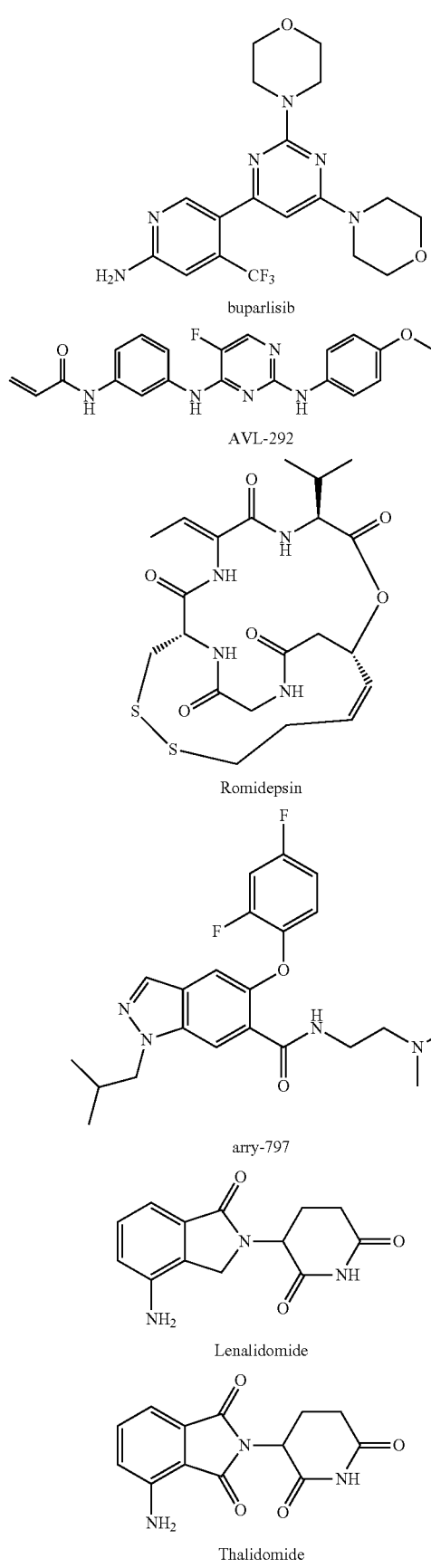
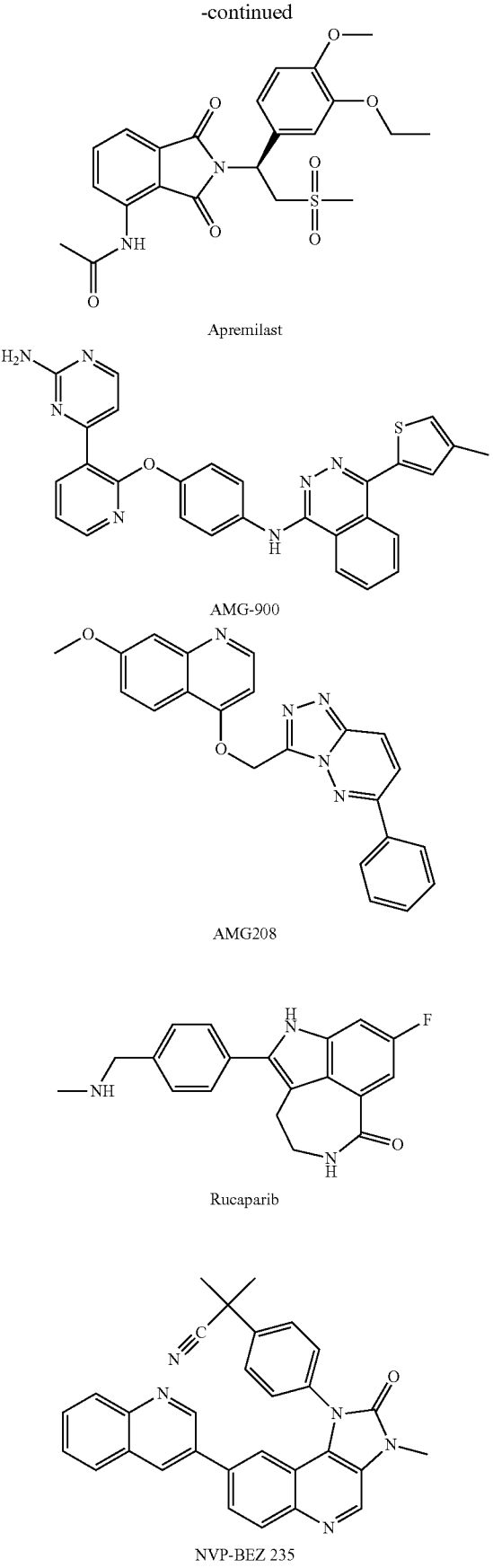

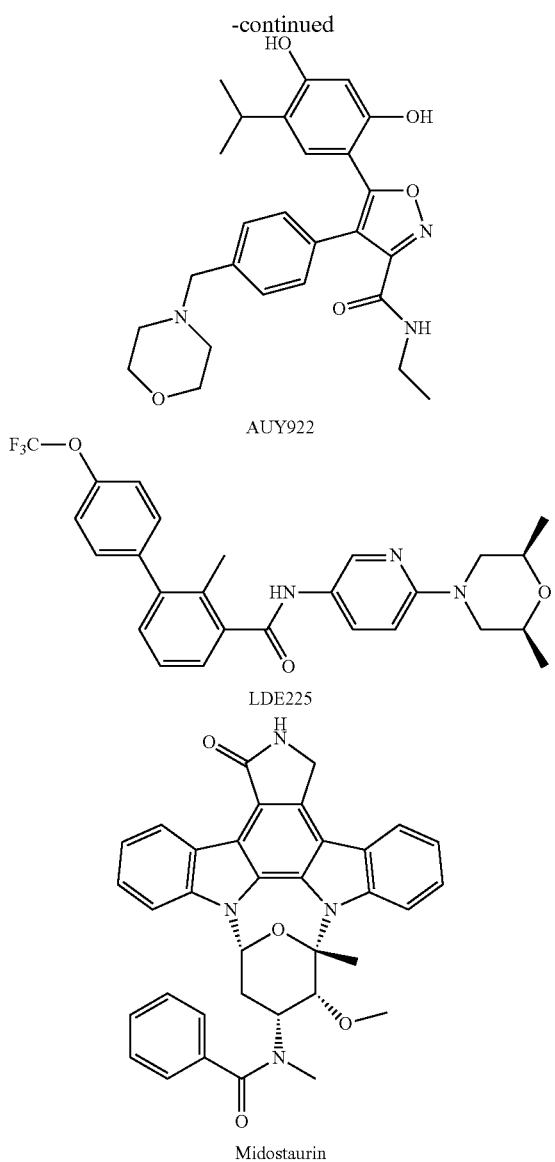

In certain embodiments, the present invention provides a drug-loaded micelle, as described herein, wherein the drug is a tyrosine kinase inhibitor.

In certain embodiments, the present invention provides a drug-loaded micelle, as described herein, wherein the drug is a molecularly targeted therapeutic.

In certain embodiments, the present invention provides a drug-loaded micelle, as described herein, wherein the drug is LY2835219.

In certain embodiments, the present invention provides a drug-loaded micelle, as described herein, wherein the drug is palbociclib.

In certain embodiments, the present invention provides a drug-loaded micelle, as described herein, wherein the drug is selumetinib.

In certain embodiments, the present invention provides a drug-loaded micelle, as described herein, wherein the drug is MEK162.

In certain embodiments, the present invention provides a drug-loaded micelle, as described herein, wherein the drug is trametinib.

In certain embodiments, the present invention provides a drug-loaded micelle, as described herein, wherein the drug is alisertib.

In certain embodiments, the present invention provides a drug-loaded micelle, as described herein, wherein the drug is birinapant.

In certain embodiments, the present invention provides a drug-loaded micelle, as described herein, wherein the drug is LCL161.

In certain embodiments, the present invention provides a drug-loaded micelle, as described herein, wherein the drug is AT-406.

In certain embodiments, the present invention provides a drug-loaded micelle, as described herein, wherein the drug is BBI608.

In certain embodiments, the present invention provides a drug-loaded micelle, as described herein, wherein the drug is KP46 [tris(8-quinolinolato)gallium(III)].

In certain embodiments, the present invention provides a drug-loaded micelle, as described herein, wherein the drug is everolimus.

In certain embodiments, the present invention provides a drug-loaded micelle, as described herein, wherein the drug is XL 147.

In certain embodiments, the present invention provides a drug-loaded micelle, as described herein, wherein the drug is E7016.

In certain embodiments, the present invention provides a drug-loaded micelle, as described herein, wherein the drug is XL765.

In certain embodiments, the present invention provides a drug-loaded micelle, as described herein, wherein the drug is TG101348.

In certain embodiments, the present invention provides a drug-loaded micelle, as described herein, wherein the drug is E7820.

In certain embodiments, the present invention provides a drug-loaded micelle, as described herein, wherein the drug is eribulin.

In certain embodiments, the present invention provides a drug-loaded micelle, as described herein, wherein the drug is INK 128.

In certain embodiments, the present invention provides a drug-loaded micelle, as described herein, wherein the drug is TAK-385.

In certain embodiments, the present invention provides a drug-loaded micelle, as described herein, wherein the drug is MLN2480.

In certain embodiments, the present invention provides a drug-loaded micelle, as described herein, wherein the drug is TAK733.

In certain embodiments, the present invention provides a drug-loaded micelle, as described herein, wherein the drug is MLN-4924.

In certain embodiments, the present invention provides a drug-loaded micelle, as described herein, wherein the drug is motesanib.

In certain embodiments, the present invention provides a drug-loaded micelle, as described herein, wherein the drug is ixazomib.

In certain embodiments, the present invention provides a drug-loaded micelle, as described herein, wherein the drug is TAK-700.

In certain embodiments, the present invention provides a drug-loaded micelle, as described herein, wherein the drug is dacomitinib.

In certain embodiments, the present invention provides a drug-loaded micelle, as described herein, wherein the drug is sunitinib.

In certain embodiments, the present invention provides a drug-loaded micelle, as described herein, wherein the drug is crizotinib.

In certain embodiments, the present invention provides a drug-loaded micelle, as described herein, wherein the drug is axitnib.

In certain embodiments, the present invention provides a drug-loaded micelle, as described herein, wherein the drug is PF 03084014.

In certain embodiments, the present invention provides a drug-loaded micelle, as described herein, wherein the drug is PD 0325901.

In certain embodiments, the present invention provides a drug-loaded micelle, as described herein, wherein the drug is PF05212384.

In certain embodiments, the present invention provides a drug-loaded micelle, as described herein, wherein the drug is PF 04449913.

In certain embodiments, the present invention provides a drug-loaded micelle, as described herein, wherein the drug is ridaforlimus.

In certain embodiments, the present invention provides a drug-loaded micelle, as described herein, wherein the drug is MK-1775.

In certain embodiments, the present invention provides a drug-loaded micelle, as described herein, wherein the drug is MK-2206.

In certain embodiments, the present invention provides a drug-loaded micelle, as described herein, wherein the drug is GSK2636771.

In certain embodiments, the present invention provides a drug-loaded micelle, as described herein, wherein the drug is GSK525762.

In certain embodiments, the present invention provides a drug-loaded micelle, as described herein, wherein the drug is eltrombopag.

In certain embodiments, the present invention provides a drug-loaded micelle, as described herein, wherein the drug is dabrefenib.

In certain embodiments, the present invention provides a drug-loaded micelle, as described herein, wherein the drug is foretinib.

In certain embodiments, the present invention provides a drug-loaded micelle, as described herein, wherein the drug is lapatinib.

In certain embodiments, the present invention provides a drug-loaded micelle, as described herein, wherein the drug is pazopanib.

In certain embodiments, the present invention provides a drug-loaded micelle, as described herein, wherein the drug is CH5132799.

In certain embodiments, the present invention provides a drug-loaded micelle, as described herein, wherein the drug is RO4987655.

In certain embodiments, the present invention provides a drug-loaded micelle, as described herein, wherein the drug is RG7338.

In certain embodiments, the present invention provides a drug-loaded micelle, as described herein, wherein the drug is A0379.

In certain embodiments, the present invention provides a drug-loaded micelle, as described herein, wherein the drug is erlotinib.

In certain embodiments, the present invention provides a drug-loaded micelle, as described herein, wherein the drug is pictilisib.

In certain embodiments, the present invention provides a drug-loaded micelle, as described herein, wherein the drug is GDC-0032.

In certain embodiments, the present invention provides a drug-loaded micelle, as described herein, wherein the drug is venurafenib.

In certain embodiments, the present invention provides a drug-loaded micelle, as described herein, wherein the drug is GDC-0980.

In certain embodiments, the present invention provides a drug-loaded micelle, as described herein, wherein the drug is GDC-0068.

In certain embodiments, the present invention provides a drug-loaded micelle, as described herein, wherein the drug is arry-520.

In certain embodiments, the present invention provides a drug-loaded micelle, as described herein, wherein the drug is pasireotide.

In certain embodiments, the present invention provides a drug-loaded micelle, as described herein, wherein the drug is dovitinib.

In certain embodiments, the present invention provides a drug-loaded micelle, as described herein, wherein the drug is cobmetinib.

In certain embodiments, the present invention provides a drug-loaded micelle, as described herein, wherein the drug is buparlisib.

In certain embodiments, the present invention provides a drug-loaded micelle, as described herein, wherein the drug is AVL-292.

In certain embodiments, the present invention provides a drug-loaded micelle, as described herein, wherein the drug is romidepsin.

In certain embodiments, the present invention provides a drug-loaded micelle, as described herein, wherein the drug is arry-797.

In certain embodiments, the present invention provides a drug-loaded micelle, as described herein, wherein the drug is lenalidomide.

In certain embodiments, the present invention provides a drug-loaded micelle, as described herein, wherein the drug is thalidomide.

In certain embodiments, the present invention provides a drug-loaded micelle, as described herein, wherein the drug is apremilast.

In certain embodiments, the present invention provides a drug-loaded micelle, as described herein, wherein the drug is AMG-900.

In certain embodiments, the present invention provides a drug-loaded micelle, as described herein, wherein the drug is AMG208.

In certain embodiments, the present invention provides a drug-loaded micelle, as described herein, wherein the drug is rucaparib.

In certain embodiments, the present invention provides a drug-loaded micelle, as described herein, wherein the drug is NVP-BEZ 235.

In certain embodiments, the present invention provides a drug-loaded micelle, as described herein, wherein the drug is AUY922.

In certain embodiments, the present invention provides a drug-loaded micelle, as described herein, wherein the drug is LDE225.

In certain embodiments, the present invention provides a drug-loaded micelle, as described herein, wherein the drug is midostaurin.

Small molecule drugs suitable for loading into micelles of the present invention are well known in the art. In certain embodiments, the present invention provides a drug-loaded micelle as described herein, wherein the drug is a hydrophobic drug selected from analgesics, anti-inflammatory agents, HDAC inhibitors, mitotic inhibitors, microtubule stabilizers, DNA intercalators, topoisomerase inhibitors, antihelminthics, anti-arrhythmic agents, anti-bacterial agents, anti-viral agents, anti-coagulants, anti-depressants, anti-diabetics, anti-epileptics, anti-fungal agents, anti-gout agents, anti-hypertensive agents, anti-malarials, anti-migraine agents, anti-muscarinic agents, anti-neoplastic agents, erectile dysfunction improvement agents, immunosuppressants, anti-protozoal agents, anti-thyroid agents, anxiolytic agents, sedatives, hypnotics, neuroleptics, β-blockers, cardiac inotropic agents, corticosteroids, diuretics, anti-parkinsonian agents, gastro-intestinal agents, histamine receptor antagonists, keratolyptics, lipid regulating agents, anti-anginal agents, Cox-2 inhibitors, leukotriene inhibitors, macrolides, muscle relaxants, nutritional agents, opiod analgesics, protease inhibitors, sex hormones, stimulants, muscle relaxants, anti-osteoporosis agents, anti-obesity agents, cognition enhancers, anti-urinary incontinence agents, anti-benign prostate hypertrophy agents, essential fatty acids, non-essential fatty acids, and mixtures thereof.

In other embodiments, the hydrophobic drug is selected from one or more analgesics, anti-bacterial agents, anti-viral agents, anti-inflammatory agents, anti-depressants, anti-diabetics, anti-epileptics, anti-hypertensive agents, anti-migraine agents, immunosuppressants, anxiolytic agents, sedatives, hypnotics, neuroleptics, β-blockers, gastro-intestinal agents, lipid regulating agents, anti-anginal agents, Cox-2 inhibitors, leukotriene inhibitors, macrolides, muscle relaxants, opioid analgesics, protease inhibitors, sex hormones, cognition enhancers, anti-urinary incontinence agents, and mixtures thereof.

According to one aspect, the present invention provides a micelle, as described herein, loaded with a hydrophobic drug selected from any one or more of a Exemestance (aromasin), Camptosar (irinotecan), Ellence (epirubicin), Femara (Letrozole), Gleevac (imatinib mesylate), Lentaron (formestane), Cytadren/Orimeten (aminoglutethimide), Temodar, Proscar (finasteride), Viadur (leuprolide), Nexavar (Sorafenib), Kytril (Granisetron), Taxotere (Docetaxel), Taxol (paclitaxel), Kytril (Granisetron), Vesanoid (tretinoin) (retin A), XELODA (Capecitabine), Arimidex (Anastrozole), Casodex/Cosudex (Bicalutamide), Faslodex (Fulvestrant), Iressa (Gefitinib), Nolvadex, Istubal, Valodex (tamoxifen citrate), Tomudex (Raltitrexed), Zoladex (goserelin acetate), Leustatin (Cladribine), Velcade (bortezomib), Mylotarg (gemtuzumab ozogamicin), Alimta (pemetrexed), Gemzar (gemcitabine hydrochloride), Rituxan (rituximab), Revlimid (lenalidomide), Thalomid (thalidomide), Alkeran (melphalan), and derivatives thereof.

E. Crosslinking Chemistries

In certain embodiments, the present invention provides crosslinked micelles which effectively encapsulate hydrophobic or ionic therapeutic agents at pH 7.4 (blood) but dissociate and release the drug at targeted, acidic pH values ranging from 5.0 (endosomal pH) to 6.8 (extracellular tumor pH). In yet other embodiments, the pH value can be adjusted between 4.0 and 7.4. These pH-targeted nanovectors will dramatically improve the cancer-specific delivery of chemotherapeutic agents and minimize the harmful side effects commonly encountered with potent chemotherapy drugs. In addition, the utilization of chemistries which can be tailored to dissociate across a range of pH values make these drug-loaded micelles applicable in treating solid tumors and malignancies that have become drug resistant.

In certain embodiments, the present invention provides a drug loaded micelle comprising a triblock copolymer, wherein said micelle has a drug-loaded inner core, a crosslinked outer core, and a hydrophilic shell, wherein the triblock copolymer is of formula VI:

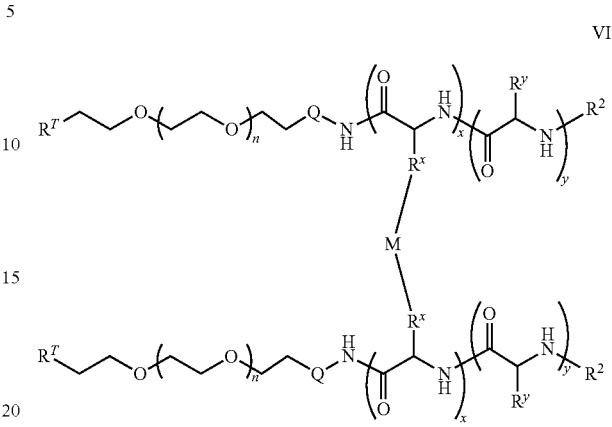

wherein each of Q, J, T, x, y, n, $R^x$, $R^y$ and $R^2$ is as defined above and as described in classes and subclasses herein, both singly and in combination;

M is a metal ion;

Each $R^T$ independently selected from either -J-T or —Z(CH$_2$CH$_2$Y)$_p$(CH$_2$)$_t$R$^3$, wherein:
  Z is —O—, —S—, —C≡C—, or —CH$_2$—;
  each Y is independently —O— or —S—;
  p is 0-10;
  t is 0-10; and $R^3$ is —N$_3$, —CN, a mono-protected amine, a di-protected amine, a protected aldehyde, a protected hydroxyl, a protected carboxylic acid, a protected thiol, a 9-30 membered crown ether, or an optionally substituted group selected from aliphatic, a 5-8 membered saturated, partially unsaturated, or aryl ring having 0-4 heteroatoms independently selected from nitrogen, oxygen, or sulfur, an 8-10 membered saturated, partially unsaturated, or aryl bicyclic ring having 0-5 heteroatoms independently selected from nitrogen, oxygen, or sulfur, or a detectable moiety;

Q is a valence bond or a bivalent, saturated or unsaturated, straight or branched C$_{1-12}$ hydrocarbon chain, wherein 0-6 methylene units of Q are independently replaced by -Cy-, —O—, —NH—, —S—, —OC(O)—, —C(O)O—, —C(O)—, —SO—, —SO$_2$—, —NHSO$_2$—, —SO$_2$NH—, —NHC(O)—, —C(O)NH—, —OC(O)NH—, or —NHC(O)O—, wherein:
  -Cy- is an optionally substituted 5-8 membered bivalent, saturated, partially unsaturated, or aryl ring having 0-4 heteroatoms independently selected from nitrogen, oxygen, or sulfur, or an optionally substituted 8-10 membered bivalent saturated, partially unsaturated, or aryl bicyclic ring having 0-5 heteroatoms independently selected from nitrogen, oxygen, or sulfur;

In certain embodiments, M is iron. In other embodiments, M is zinc. In another embodiment, M is nickel, cobalt, copper, or platinum. In other embodiments, M is calcium or aluminum. In yet other embodiments, M is strontium, manganese, platinum, palladium, silver, gold, cadmium, chromium, indium, or lead.

In certain embodiments, the present invention provides a drug loaded micelle comprising a triblock copolymer, wherein said micelle has a drug-loaded inner core, a crosslinked outer core, and a hydrophilic shell, wherein the triblock copolymer is of formula VII:

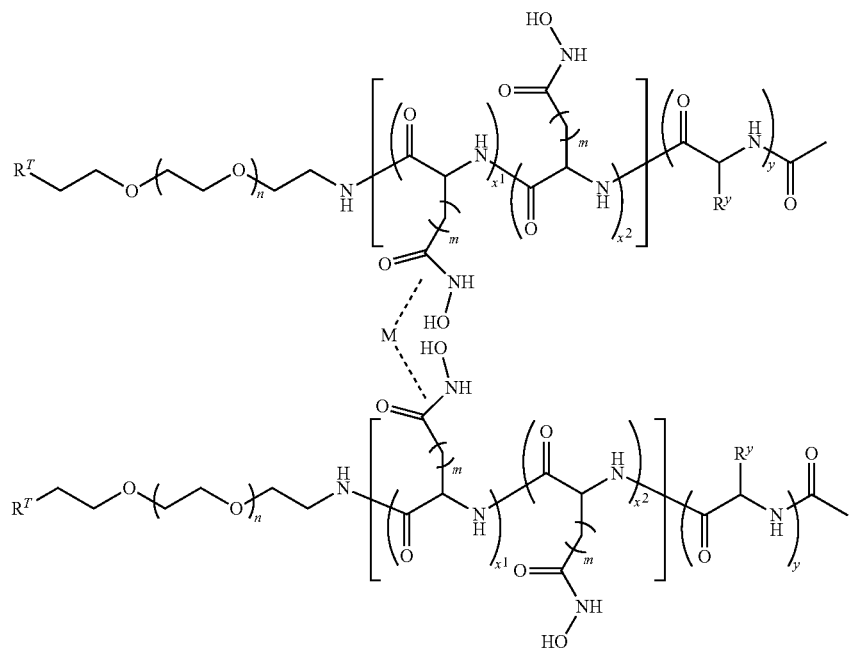

VII wherein each of Q, J, T, M, m, y, n, $R^y$ and $R^T$ is as defined above and as described in classes and subclasses herein, both singly and in combination;
$x^1$ is 1-20 and;
$x^2$ is 0-20.

In certain embodiments, the present invention provides a drug loaded micelle comprising a triblock copolymer, wherein said micelle has a drug-loaded inner core, a cross-linked outer core, and a hydrophilic shell, wherein the triblock copolymer is of formula VIII:

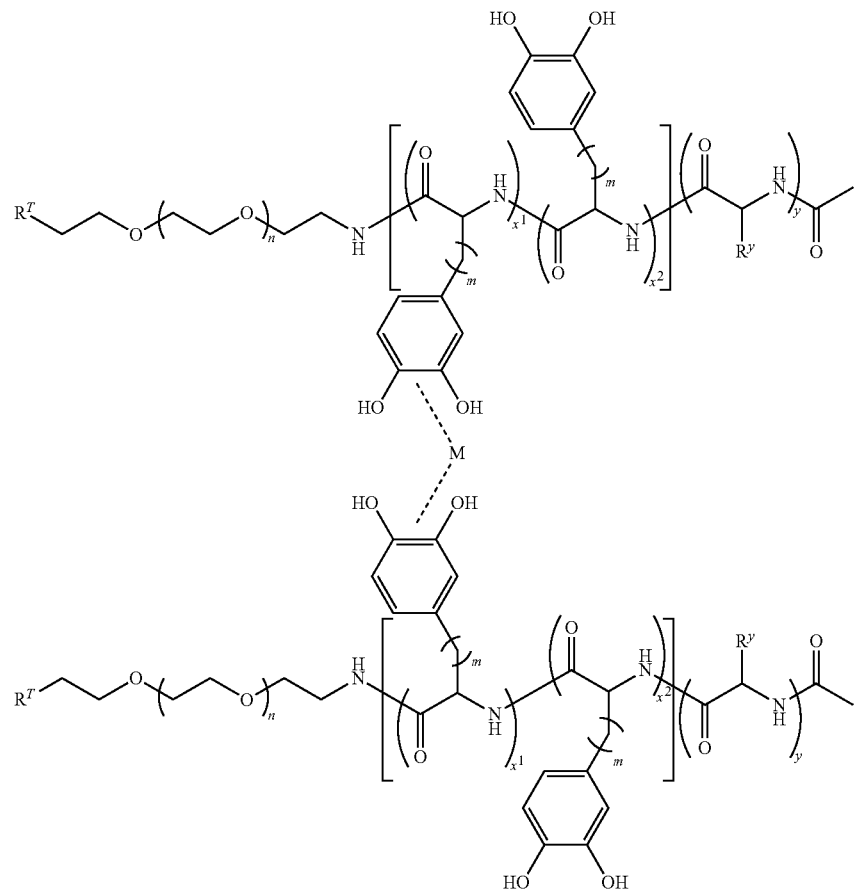

VIII wherein each of Q, J, T, M, m, y, $x^1$, $x^2$, n, $R^y$ and $R^T$ is as defined above and as described in classes and subclasses herein, both singly and in combination.

In certain embodiments, the present invention provides a drug loaded micelle comprising a triblock copolymer, wherein said micelle has a drug-loaded inner core, a cross-linked outer core, and a hydrophilic shell, wherein the triblock copolymer is of formula IX:

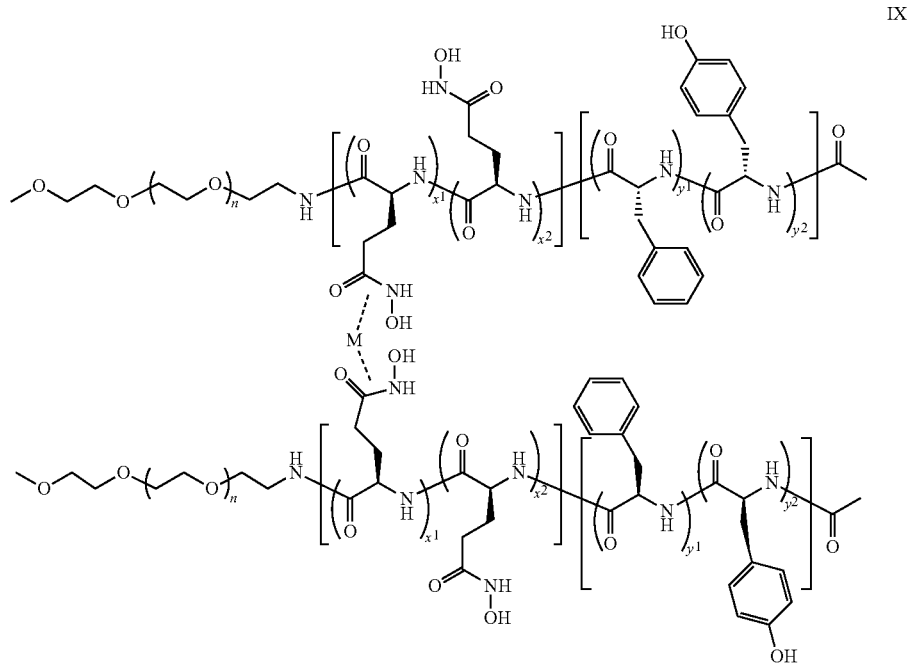

IX wherein each of M, $x^1$, $x^2$, and n is as defined above and as described in classes and subclasses herein, both singly and in combination;
$y^1$ is 5-30 and;
$y^2$ is 10-40.

It will be obvious to one skilled in the art that the drug loaded, crosslinked micelle of the present invention is comprised of tens to hundreds of polymer chains. Despite the fact that only two polymer chains linked by a metal ion is depicted in any of Formula VI, VII, VIII, or IX, it will be understood that the polymer micelle is comprised of many more polymer chains that are not depicted for ease of presentation.

In other embodiments, the present invention provides a system comprising a triblock copolymer of formula I, a hydrophobic therapeutic agent, and a metal ion. In another embodiment, the present invention provides a system comprising a triblock copolymer of any of formulae I, II, III, and IV, either singly or in combination, a hydrophobic therapeutic agent, and a metal ion. In yet another embodiment, the present invention provides a system comprising a triblock copolymer of formula II, a hydrophobic therapeutic agent, and a metal ion.

In other embodiments, the present invention provides a system comprising a triblock copolymer of formula VI and a hydrophobic therapeutic agent. In another embodiment, the present invention provides a system comprising a triblock copolymer of any of formulae VI, VII, VIII, and IX, either singly or in combination, and a hydrophobic therapeutic agent. In yet another embodiment, the present invention provides a system comprising a triblock copolymer of formula VII and a hydrophobic therapeutic agent. In some embodiments, the present invention provides a system comprising a triblock copolymer of formula XI and a hydrophobic therapeutic agent.

The ultimate goal of metal-mediated crosslinking is to ensure micelle stability when diluted in the blood (pH 7.4) followed by rapid dissolution and drug release in response to a finite pH change such as those found in a tumor environment.

In one aspect of the invention, a drug-loaded micelle is crosslinked via a hydroxamic acid moiety. Hydroxamic acids as described above chelate certain metals as described in Rosthauser et. al. *Macromolecules* 1981, 14, 538-543 and in Miller *Chemical Reviews* 1989, 89, 1563-1579 (hereinafter "Miller"). This chelation chemistry is shown in Scheme 1.

Scheme 1.

Divalent Metal

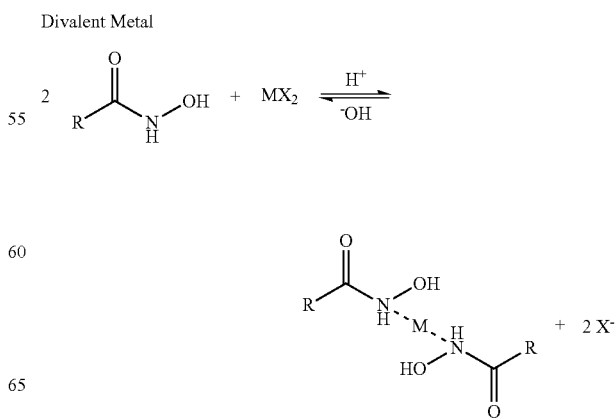

Trivalent Metal

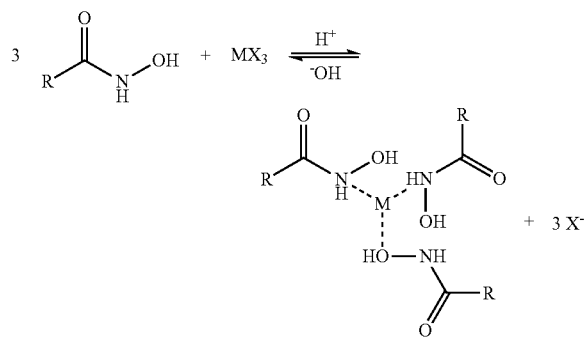

Accordingly, the addition of a metal ion to a drug loaded micelle of the present invention would result in the chelation of the metal ions by the hydroxamic acid, affording a crosslinked, drug loaded micelle. Metal ions are selected from, but not limited to: iron, nickel, cobalt, zinc, calcium, copper, strontium, platinum, palladium, vanadium, manganese, and titanium.

One skilled in the art will recognize that the M group of Formula VI, VII, or VIII may be either a divalent or trivalent metal ion. It is also recognized that the structures of Formula VI, VII, or VIII, for clarity, are represented using a divalent metal ion. In the case of a trivalent metal ion as described in Scheme 1, it is understood that there may be three hydroxamic acid or catechol groups bound to a single metal ion.

In one aspect of the invention, a drug-loaded micelle is crosslinked via a catechol moiety. Catechols, as described above, complex metal ions as represented in Scheme 2. The chelation of catechols with metal ions is also described in Miller. Accordingly, the addition of a metal ion to a drug loaded micelle of the present invention would result in the chelation of the metal ions by the hydroxamic acid, affording a crosslinked, drug loaded micelle. Metal ions are selected from, but not limited to: iron, nickel, cobalt, zinc, calcium, copper, strontium, vanadium, manganese, and titanium.

Scheme 2.

Divalent Metal

Trivalent Metal

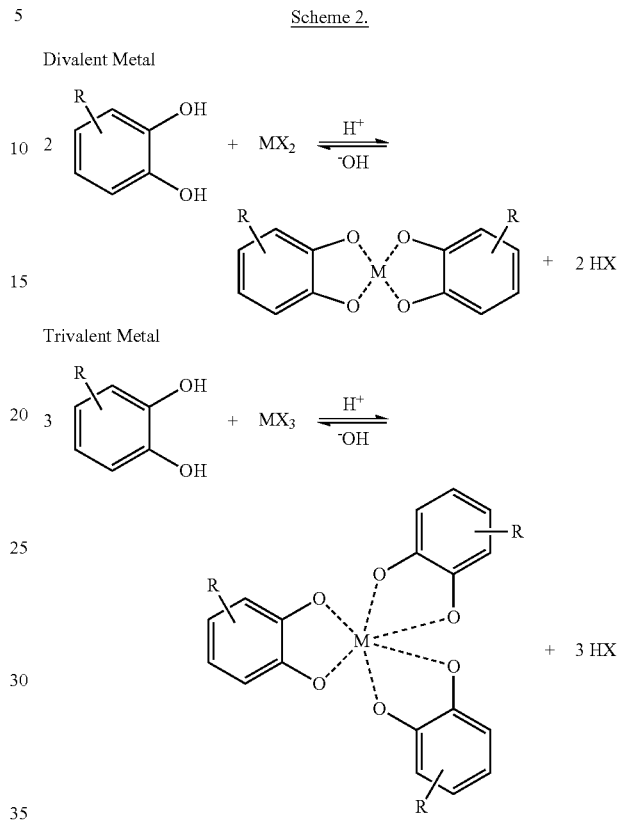

In certain embodiments, the present invention provides a crosslinked, drug-loaded micelle, as described herein, wherein the polymer is

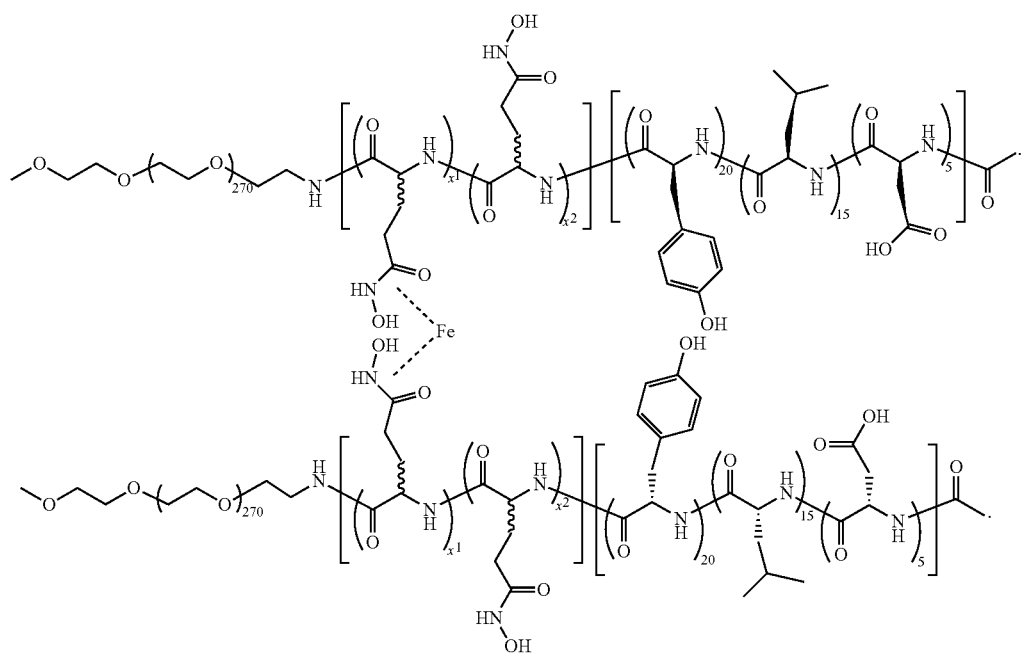

In certain embodiments, the present invention provides a crosslinked, drug-loaded micelle, as described herein, wherein the polymer is In certain embodiments, the present invention provides a crosslinked, drug-loaded micelle, as described herein, wherein the drug is paclitaxel.

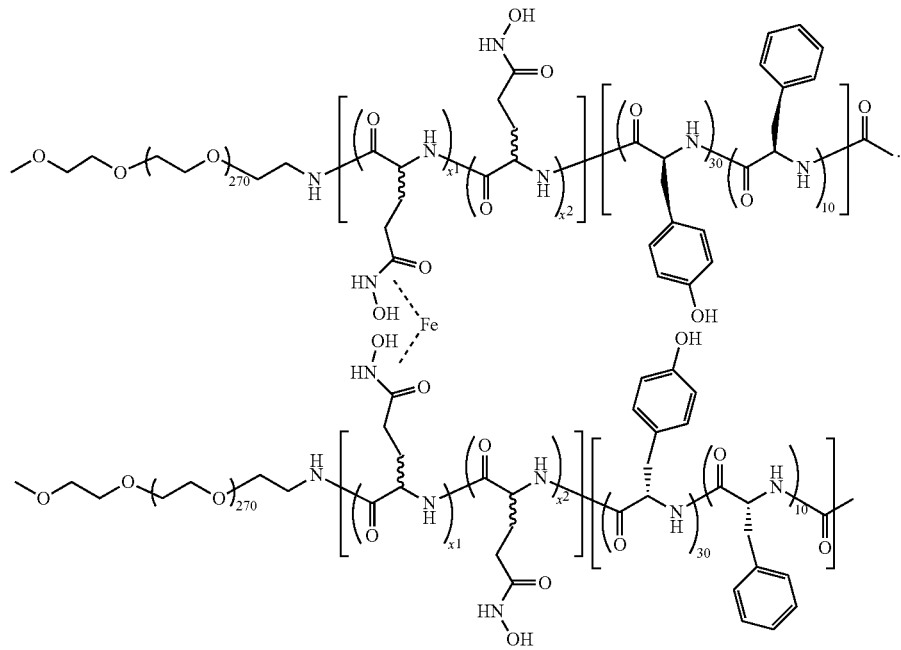

In certain embodiments, the present invention provides a crosslinked, drug-loaded micelle, as described herein, wherein the polymer is In certain embodiments, the present invention provides a crosslinked, drug-loaded micelle, as described herein, wherein the drug is docetaxel.

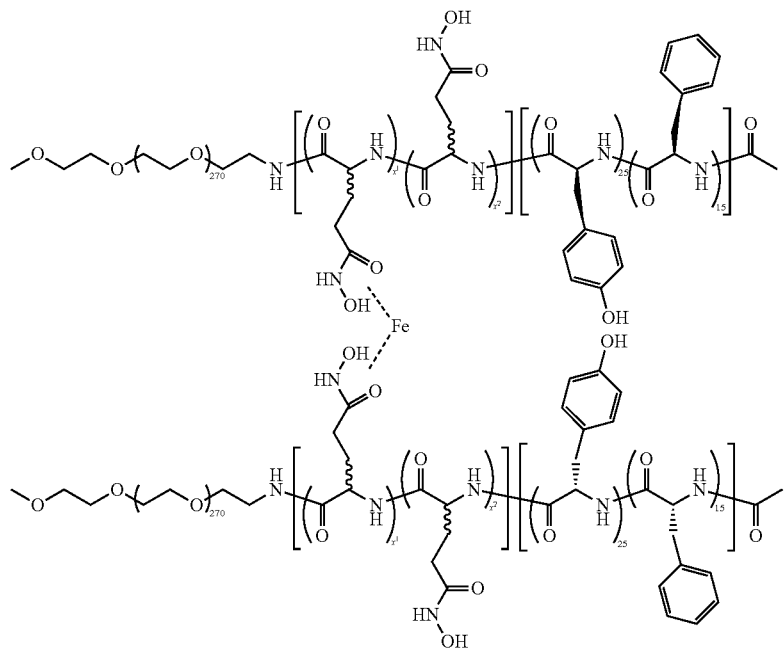

In certain embodiments, the present invention provides a crosslinked, drug-loaded micelle, as described herein, wherein the drug is a taxane.

In certain embodiments, the present invention provides a crosslinked, drug-loaded micelle, as described herein, wherein the drug is cabazitaxel.

In certain embodiments, the present invention provides a crosslinked, drug-loaded micelle, as described herein, wherein the drug is an epothilone.

In certain embodiments, the present invention provides a crosslinked, drug-loaded micelle, as described herein, wherein the drug is Epothilone B or Epothilone D.

In certain embodiments, the present invention provides a crosslinked, drug-loaded micelle, as described herein, wherein the drug is Epothilone A or Epothilone C.

In certain embodiments, the present invention provides a crosslinked, drug-loaded micelle, as described herein, wherein the drug is a vinca alkaloid.

In certain embodiments, the present invention provides a crosslinked, drug-loaded micelle, as described herein, wherein the drug is vinorelbine.

In certain embodiments, the present invention provides a crosslinked, drug-loaded micelle, as described herein, wherein the drug is berberine.

In certain embodiments, the present invention provides a crosslinked, drug-loaded micelle, as described herein, wherein the drug is berberrubine.

In certain embodiments, the present invention provides a crosslinked, drug-loaded micelle, as described herein, wherein the drug is a camptothecin.

In certain embodiments, the present invention provides a crosslinked, drug-loaded micelle, as described herein, wherein the drug is SN-38.

In certain embodiments, the present invention provides a crosslinked, drug-loaded micelle, as described herein, wherein the drug is S39625.

In certain embodiments, the present invention provides a crosslinked, drug-loaded micelle, as described herein, wherein the drug is an anthracycline.

In certain embodiments, the present invention provides a crosslinked, drug-loaded micelle, as described herein, wherein the drug is daunorubicin.

In certain embodiments, the present invention provides a crosslinked, drug-loaded micelle, as described herein, wherein the drug is doxorubicin.

In certain embodiments, the present invention provides a crosslinked, drug-loaded micelle, as described herein, wherein the drug is aminopterin.

In certain embodiments, the present invention provides a crosslinked, drug-loaded micelle, as described herein, wherein the drug is picoplatin.

In certain embodiments, the present invention provides a crosslinked, drug-loaded micelle, as described herein, wherein the drug is a platinum therapeutic.

In certain embodiments, the present invention provides a crosslinked, drug-loaded micelle, as described herein, wherein the drug is a tyrosine kinase inhibitor.

In certain embodiments, the present invention provides a crosslinked, drug-loaded micelle, as described herein, wherein the drug is a molecularly targeted therapeutic.

In certain embodiments, the present invention provides a crosslinked, drug-loaded micelle, as described herein, wherein the drug is LY2835219.

In certain embodiments, the present invention provides a crosslinked, drug-loaded micelle, as described herein, wherein the drug is palbociclib.

In certain embodiments, the present invention provides a crosslinked, drug-loaded micelle, as described herein, wherein the drug is selumetinib.

In certain embodiments, the present invention provides a crosslinked, drug-loaded micelle, as described herein, wherein the drug is MEK162.

In certain embodiments, the present invention provides a crosslinked, drug-loaded micelle, as described herein, wherein the drug is rametinib.

In certain embodiments, the present invention provides a crosslinked, drug-loaded micelle, as described herein, wherein the drug is alisertib.

In certain embodiments, the present invention provides a crosslinked, drug-loaded micelle, as described herein, wherein the drug is birinapant.

In certain embodiments, the present invention provides a crosslinked, drug-loaded micelle, as described herein, wherein the drug is LCL161.

In certain embodiments, the present invention provides a crosslinked, drug-loaded micelle, as described herein, wherein the drug is AT-406.

In certain embodiments, the present invention provides a crosslinked, drug-loaded micelle, as described herein, wherein the drug is BBI608.

In certain embodiments, the present invention provides a crosslinked, drug-loaded micelle, as described herein, wherein the drug is KP46 [tris(8-quinolinolato)gallium(III)].

In certain embodiments, the present invention provides a crosslinked, drug-loaded micelle, as described herein, wherein the drug is everolimus.

In certain embodiments, the present invention provides a crosslinked, drug-loaded micelle, as described herein, wherein the drug is XL 147.

In certain embodiments, the present invention provides a crosslinked, drug-loaded micelle, as described herein, wherein the drug is E7016.

In certain embodiments, the present invention provides a crosslinked, drug-loaded micelle, as described herein, wherein the drug is XL765.

In certain embodiments, the present invention provides a crosslinked, drug-loaded micelle, as described herein, wherein the drug is TG101348.

In certain embodiments, the present invention provides a crosslinked, drug-loaded micelle, as described herein, wherein the drug is E7820.

In certain embodiments, the present invention provides a crosslinked, drug-loaded micelle, as described herein, wherein the drug is eribulin.

In certain embodiments, the present invention provides a crosslinked, drug-loaded micelle, as described herein, wherein the drug is INK 128.

In certain embodiments, the present invention provides a crosslinked, drug-loaded micelle, as described herein, wherein the drug is TAK-385.

In certain embodiments, the present invention provides a crosslinked, drug-loaded micelle, as described herein, wherein the drug is MLN2480.

In certain embodiments, the present invention provides a crosslinked, drug-loaded micelle, as described herein, wherein the drug is TAK733.

In certain embodiments, the present invention provides a crosslinked, drug-loaded micelle, as described herein, wherein the drug is MLN-4924.

In certain embodiments, the present invention provides a crosslinked, drug-loaded micelle, as described herein, wherein the drug is motesanib.

In certain embodiments, the present invention provides a crosslinked, drug-loaded micelle, as described herein, wherein the drug is ixazomib.

In certain embodiments, the present invention provides a crosslinked, drug-loaded micelle, as described herein, wherein the drug is TAK-700.

In certain embodiments, the present invention provides a crosslinked, drug-loaded micelle, as described herein, wherein the drug is dacomitinib.

In certain embodiments, the present invention provides a crosslinked, drug-loaded micelle, as described herein, wherein the drug is sunitinib.

In certain embodiments, the present invention provides a crosslinked, drug-loaded micelle, as described herein, wherein the drug is crizotinib.

In certain embodiments, the present invention provides a crosslinked, drug-loaded micelle, as described herein, wherein the drug is axitnib.

In certain embodiments, the present invention provides a crosslinked, drug-loaded micelle, as described herein, wherein the drug is PF 03084014.

In certain embodiments, the present invention provides a crosslinked, drug-loaded micelle, as described herein, wherein the drug is PD 0325901.

In certain embodiments, the present invention provides a crosslinked, drug-loaded micelle, as described herein, wherein the drug is PF05212384.

In certain embodiments, the present invention provides a crosslinked, drug-loaded micelle, as described herein, wherein the drug is PF 04449913.

In certain embodiments, the present invention provides a crosslinked, drug-loaded micelle, as described herein, wherein the drug is ridaforlimus.

In certain embodiments, the present invention provides a crosslinked, drug-loaded micelle, as described herein, wherein the drug is MK-1775.

In certain embodiments, the present invention provides a crosslinked, drug-loaded micelle, as described herein, wherein the drug is MK-2206.

In certain embodiments, the present invention provides a crosslinked, drug-loaded micelle, as described herein, wherein the drug is GSK2636771.

In certain embodiments, the present invention provides a crosslinked, drug-loaded micelle, as described herein, wherein the drug is GSK525762.

In certain embodiments, the present invention provides a crosslinked, drug-loaded micelle, as described herein, wherein the drug is eltrombopag.

In certain embodiments, the present invention provides a crosslinked, drug-loaded micelle, as described herein, wherein the drug is dabrefenib.

In certain embodiments, the present invention provides a crosslinked, drug-loaded micelle, as described herein, wherein the drug is foretinib.

In certain embodiments, the present invention provides a crosslinked, drug-loaded micelle, as described herein, wherein the drug is lapatinib.

In certain embodiments, the present invention provides a crosslinked, drug-loaded micelle, as described herein, wherein the drug is pazopanib.

In certain embodiments, the present invention provides a crosslinked, drug-loaded micelle, as described herein, wherein the drug is CH5132799.

In certain embodiments, the present invention provides a crosslinked, drug-loaded micelle, as described herein, wherein the drug is RO4987655.

In certain embodiments, the present invention provides a crosslinked, drug-loaded micelle, as described herein, wherein the drug is RG7338.

In certain embodiments, the present invention provides a crosslinked, drug-loaded micelle, as described herein, wherein the drug is A0379.

In certain embodiments, the present invention provides a crosslinked, drug-loaded micelle, as described herein, wherein the drug is erlotinib.

In certain embodiments, the present invention provides a crosslinked, drug-loaded micelle, as described herein, wherein the drug is pictilisib.

In certain embodiments, the present invention provides a crosslinked, drug-loaded micelle, as described herein, wherein the drug is GDC-0032.

In certain embodiments, the present invention provides a crosslinked, drug-loaded micelle, as described herein, wherein the drug is venurafenib.

In certain embodiments, the present invention provides a crosslinked, drug-loaded micelle, as described herein, wherein the drug is GDC-0980.

In certain embodiments, the present invention provides a crosslinked, drug-loaded micelle, as described herein, wherein the drug is GDC-0068.

In certain embodiments, the present invention provides a crosslinked, drug-loaded micelle, as described herein, wherein the drug is arry-520.

In certain embodiments, the present invention provides a crosslinked, drug-loaded micelle, as described herein, wherein the drug is pasireotide.

In certain embodiments, the present invention provides a crosslinked, drug-loaded micelle, as described herein, wherein the drug is dovitinib.

In certain embodiments, the present invention provides a crosslinked, drug-loaded micelle, as described herein, wherein the drug is cobmetinib.

In certain embodiments, the present invention provides a crosslinked, drug-loaded micelle, as described herein, wherein the drug is buparlisib.

In certain embodiments, the present invention provides a crosslinked, drug-loaded micelle, as described herein, wherein the drug is AVL-292.

In certain embodiments, the present invention provides a crosslinked, drug-loaded micelle, as described herein, wherein the drug is romidepsin.

In certain embodiments, the present invention provides a crosslinked, drug-loaded micelle, as described herein, wherein the drug is arry-797.

In certain embodiments, the present invention provides a crosslinked, drug-loaded micelle, as described herein, wherein the drug is lenalidomide.

In certain embodiments, the present invention provides a crosslinked, drug-loaded micelle, as described herein, wherein the drug is thalidomide.

In certain embodiments, the present invention provides a crosslinked, drug-loaded micelle, as described herein, wherein the drug is apremilast.

In certain embodiments, the present invention provides a crosslinked, drug-loaded micelle, as described herein, wherein the drug is AMG-900.

In certain embodiments, the present invention provides a crosslinked, drug-loaded micelle, as described herein, wherein the drug is AMG208.

In certain embodiments, the present invention provides a crosslinked, drug-loaded micelle, as described herein, wherein the drug is rucaparib.

In certain embodiments, the present invention provides a crosslinked, drug-loaded micelle, as described herein, wherein the drug is NVP-BEZ 235.

In certain embodiments, the present invention provides a crosslinked, drug-loaded micelle, as described herein, wherein the drug is AUY922.

In certain embodiments, the present invention provides a crosslinked, drug-loaded micelle, as described herein, wherein the drug is LDE225.

In certain embodiments, the present invention provides a crosslinked, drug-loaded micelle, as described herein, wherein the drug is midostaurin.

4. General Methods for Providing Compounds of the Present Invention

Multiblock copolymers of the present invention are prepared by methods known to one of ordinary skill in the art. Generally, such multiblock copolymers are prepared by sequentially polymerizing one or more cyclic amino acid monomers onto a hydrophilic polymer having a terminal amine wherein said polymerization is initiated by said amine. In certain embodiments, said polymerization occurs by ring-opening polymerization of the cyclic amino acid monomers. In other embodiments, the cyclic amino acid monomer is an amino acid NCA, lactam, or imide.

One step in the preparation of a compound of formula I comprises terminating the living polymer chain-end of the compound of formula C with a polymerization terminator to afford a compound of formula I. One of ordinary skill in the art would recognize that the polymerization terminator provides the $R^2$ group of formula I. Accordingly, embodiments directed to the $R^2$ group of formula I as set forth above and herein, are also directed to the polymerization terminator itself, and similarly, embodiments directed to the polymerization terminator, as set forth above and herein, are also directed to the $R^2$ group of formula I.

As described above, compounds of formula I are prepared from compounds of formula C by treatment with a terminating agent. One of ordinary skill in the art would recognize that compounds of formula I are also readily prepared directly from compounds of formula C. One of ordinary skill in the art would also recognize that the above method for preparing a compound of formula I may be performed as a "one-pot" synthesis of compounds of formula I that utilizes

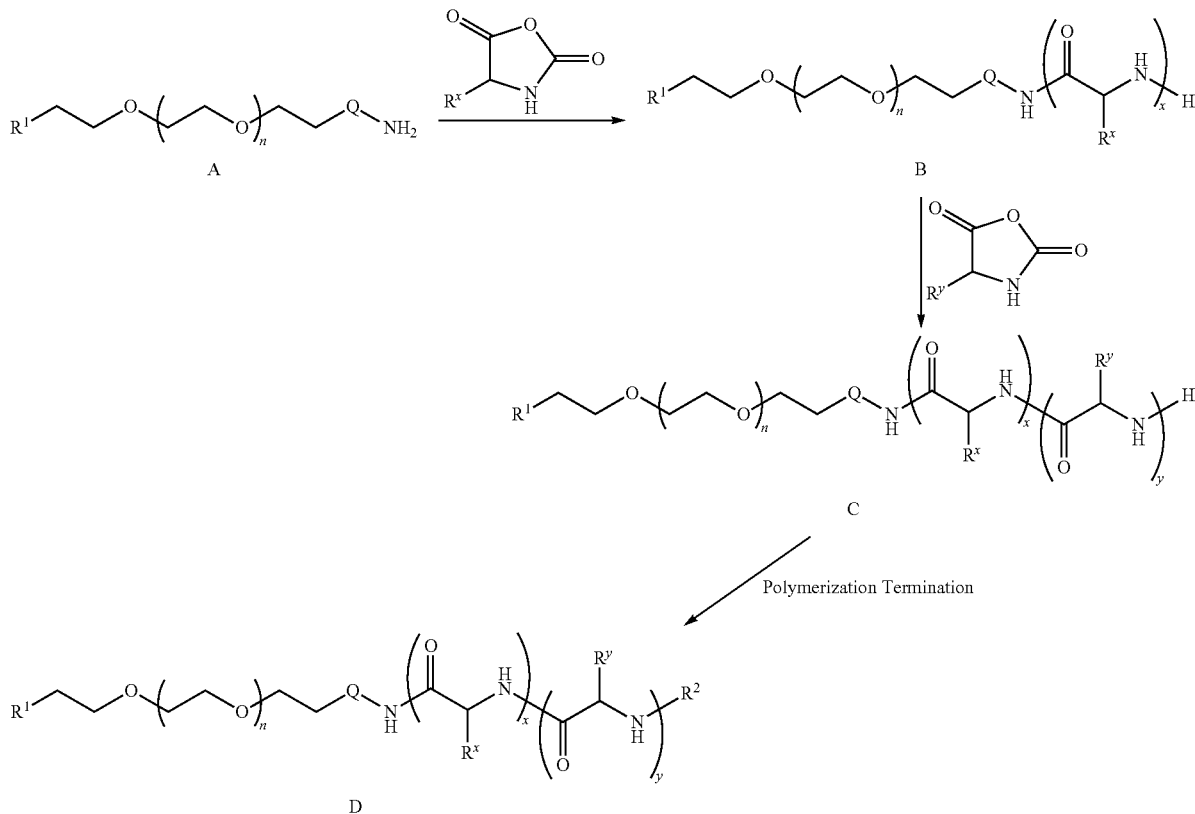

Scheme 3

Scheme 3 above depicts a general method for preparing multiblock polymers of the present invention. A macroinitiator of formula A is treated with a first amino acid NCA to form a compound of formula B having a first amino acid block. The second amino acid NCA is added to the living polymer of formula B to give a triblock copolymer of Formula C having two different amino acid blocks. Each of the $R^1$, $R^2$, n, Q, $R^x$, $R^y$, x, and y groups depicted in Scheme 3 are as defined and described in classes and subclasses, singly and in combination, herein.

the living polymer chain-end to incorporate the $R^2$ group of formula I. Alternatively, compounds of formula I may also be prepared in a multi-step fashion. For example, the living polymer chain-end of a compound of formula C may be quenched to afford an amino group which may then be further derivatized, according to known methods, to afford a compound of formula I.

One of ordinary skill in the art will recognize that a variety of polymerization terminating agents are for the present invention. Such polymerization terminating agents include any $R^2$-containing group capable of reacting with the living polymer chain-end of a compound of formula C, or the free-based amino group of formula C, to afford a compound of formula I. Thus, polymerization terminating agents include anhydrides, and other acylating agents, and groups that contain a leaving group LG that is subject to nucleophilic displacement.

Alternatively, compounds of formula C may be coupled to carboxylic acid-containing groups to form an amide thereof. Thus, it is contemplated that the amine group of formula C may be coupled with a carboxylic acid moiety to afford compounds of formula I wherein $R^2$ is —NHC(O)$R^4$. Such coupling reactions are well known in the art. In certain embodiments, the coupling is achieved with a coupling reagent. Such reagents are well known in the art and include, for example, DCC and EDC, among others. In other embodiments, the carboxylic acid moiety is activated for use in the coupling reaction. Such activation includes formation of an acyl halide, use of a Mukaiyama reagent, and the like. These methods, and others, are known to one of ordinary skill in the art, e.g., see, "Advanced Organic Chemistry," Jerry March, $5^{th}$ Ed., pp. 351-357, John Wiley and Sons, N.Y.

A "suitable leaving group that is subject to nucleophilic displacement" is a chemical group that is readily displaced by a desired incoming chemical moiety. Suitable leaving groups are well known in the art, e.g., see, March. Such leaving groups include, but are not limited to, halogen, alkoxy, sulphonyloxy, optionally substituted alkylsulphonyloxy, optionally substituted alkenylsulfonyloxy, optionally substituted arylsulfonyloxy, and diazonium moieties. Examples of suitable leaving groups include chloro, iodo, bromo, fluoro, methanesulfonyloxy (mesyloxy), tosyloxy, triflyloxy, nitro-phenylsulfonyloxy (nosyloxy), and bromo-phenylsulfonyloxy (brosyloxy).

According to an alternate embodiment, the leaving group may be generated in situ within the reaction medium. For example, a leaving group may be generated in situ from a precursor of that compound wherein said precursor contains a group readily replaced by said leaving group in situ.

Alternatively, when the $R^2$ group of formula I is a mono- or di-protected amine, the protecting group(s) is removed and that functional group may be derivatized or protected with a different protecting group. It will be appreciated that the removal of any protecting group of the $R^2$ group of formula I is performed by methods for that protecting group. Such methods are described in detail in Green.

In other embodiments, the $R^2$ group of formula I is incorporated by derivatization of the amino group of formula C via anhydride coupling, optionally in the presence of base as appropriate. One of ordinary skill in the art would recognize that anhydride polymerization terminating agents containing an azide, an aldehyde, a hydroxyl, an alkyne, and other groups, or protected forms thereof, may be used to incorporate said azide, said aldehyde, said protected hydroxyl, said alkyne, and other groups into the $R^2$ group of compounds of formula I. It will also be appreciated that such anhydride polymerization terminating agents are also suitable for terminating the living polymer chain-end of a compound of formula C, or freebase thereof. Such anhydride polymerization terminating agents include, but are not limited to, those set forth in Table 3 below.

TABLE 3

Representative Anhydride Polymerization Terminating Agents

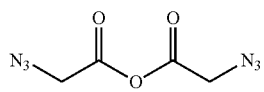 [SMILES: [N-]=[N+]=NCC(=O)OC(=O)CN=[N+]=[N-]]
A-1

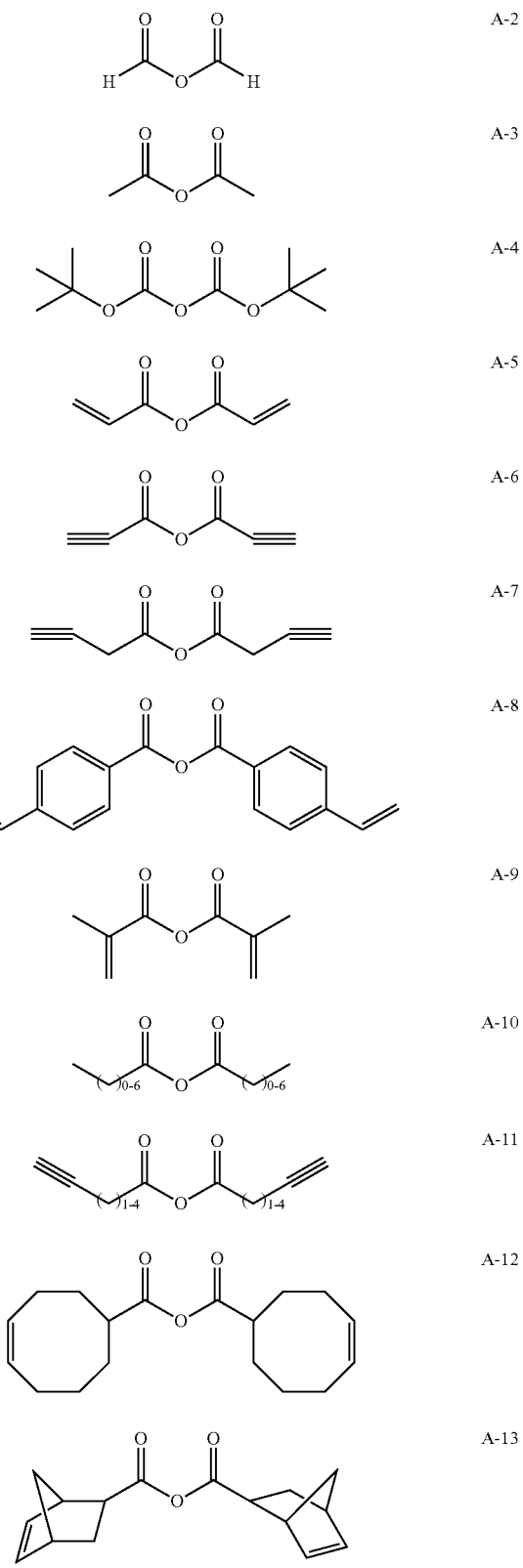

TABLE 3-continued

Representative Anhydride Polymerization Terminating Agents

A-14

A-15

A-16

In certain embodiments, the hydrophilic polymer block is poly(ethylene glycol) (PEG) having a terminal amine ("PEG macroinitiator"). This PEG macroinitiator initiates the polymerization of NCAs to provide the multiblock copolymers of the present invention. Such synthetic polymers having a terminal amine group are known in the art and include PEG-amines. PEG-amines may be obtained by the deprotection of a suitably protected PEG-amine. Preparation of such suitably protected PEG-amines, and methods of deprotecting the same, is described in detail in U.S. patent application Ser. No. 11/256,735, filed Oct. 24, 2005 and published as US 20060142506 on Jun. 29, 2006, the entirety of which is hereby incorporated herein by reference.

As described in US 20060142506, suitably protected PEG-amines may be formed by terminating the living polymer chain end of a PEG with a terminating agent that contains a suitably protected amine. Accordingly, in other embodiments, the terminating agent has suitably protected amino group wherein the protecting group is acid-labile.

Alternatively, synthetic polymers having a terminal amine may be prepared from synthetic polymers that contain terminal functional groups that may be converted to amines by known synthetic routes. In certain embodiments, the conversion of the terminal functional groups to the amine is conducted in a single synthetic step. In other embodiments, the conversion of the terminal functional groups to the amine is achieved by way of a multi-step sequence. In yet another embodiment, a protected amine initiator can be used to polymerize ethylene oxide then terminated with an appropriate functional group to form the $R^1$ group of Formula I. The protected amine initiator can then be deprotected to afford the free amine for subsequent polymerization. Functional group transformations that afford amines or protected amines are well known in the art and include those described in Larock, R. C., "Comprehensive Organic Transformations," John Wiley & Sons, New York, 1999.

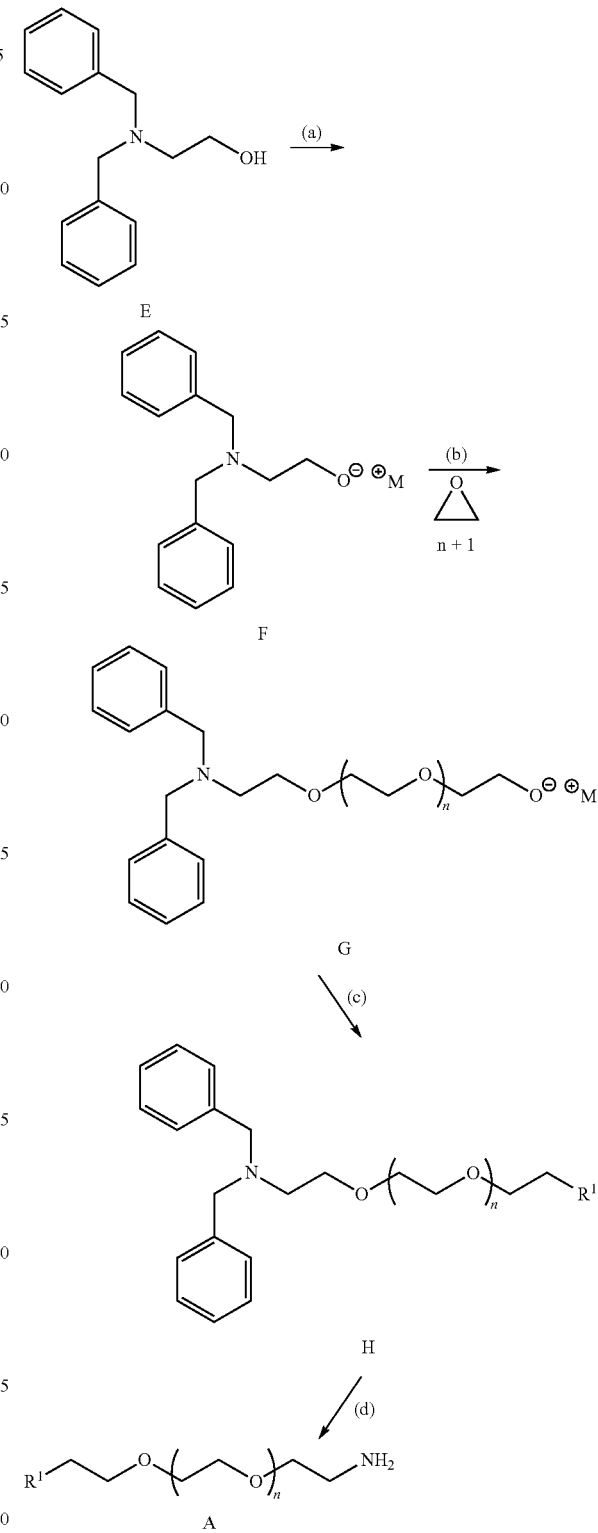

Scheme 4 above shows one exemplary method for preparing the bifunctional PEGs used to prepare the multiblock copolymers of the present invention. At step (a), the polymerization initiator E is treated with a base to form F. A variety of bases are suitable for the reaction at step (a). Such bases include, but are not limited to, potassium naphthalenide, diphenylmethyl potassium, triphenylmethyl potassium, and potassium hydride. At step (b), the resulting anion is treated with ethylene oxide to form the polymer G. Polymer G is then quenched with a termination agent in step (c) to form the $R^1$ group of polymer H. Exemplary termination agents for Polymer G can be found in Table 4. Polymer H can be transformed at step (d) to a compound of formula A by deprotecting the dibenzyl amine group by hydrogenation.

TABLE 4

Exemplary PEG Termination Agents

 D-1

 D-2

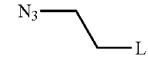 D-3

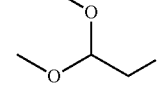 D-4

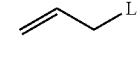 D-5

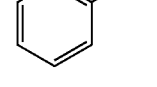 D-6

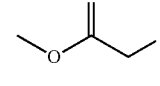 D-7

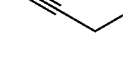 D-8

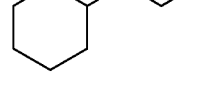 D-9

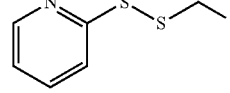 D-10

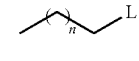 D-11

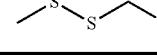 D-12

In some embodiments of the present invention, a polymer of formula I is prepared first by providing a triblock copolymer with chemical protecting groups, removing said protecting groups, then performing a chemical reaction to provide the hydroxamic acid functionality. Accordingly, it would be highly desirable to combine both the deprotection step with the conversion to hydroxamic acid in a tandem reaction. Such tandem reaction would require careful selection of the protecting group such that it would be removed with reagents used for the conversion to hydroxamic acid functionality. In certain embodiments, a glutamic ester moiety is treated with hydroxyl amine to provide the glutamate-hydoxamic acid. The acetyl group is a non-standard protecting group for tyrosine phenol in peptide chemistry, presumptively due to the potential instability of an acetyl ester in the presence of the amine functionality on amino acid. We have surprising found that the both the O-acetyl tyrosine amino acid [H-Tyr(OAc)—OH] is stable to storage and is readily converted to the acetyl tyrosine NCA following treatment with diphosgene. Furthermore, it was also found that the acetyl tyrosine NCA can be readily polymerized or copolymerized utilizing a PEG-amine macroinitiator using methods described above. It was also found that treatment of a polymer containing both a glutamic ester and acetyl tyrosine with hydroxyl amine will simultaneously deprotect the tyrosine by aminolysis of the acetyl ester group and will convert the glutamic ester to the glutamate-hydroxamic acid functionality.

In one embodiment, the present invention provides a method for preparing a multiblock copolymer of formula II comprising the steps of:

(a) providing a PEG macroinitiator of formula A:

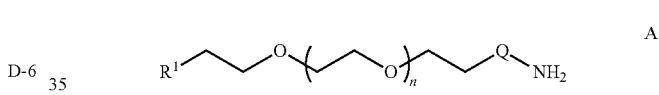

A wherein each of the $R^1$, Q, and n groups of formula A are as described in various classes and subclasses, both singly and in combination, herein;

(b) polymerizing a mixture of D and L benzyl glutamate N-carboxy anhydride monomers to provide a polymer of formula B-1:

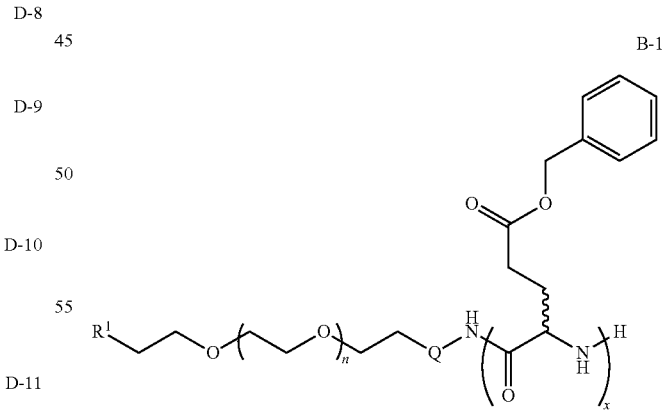

B-1 wherein each of the $R^1$, Q, x, and n groups of formula B-1 are as described in various classes and subclasses, both singly and in combination, herein;

(c) polymerizing a mixture consisting of L acetyl tyrosine N-carboxy anhydride monomer and D phenylalanine or D leucine N-carboxy anhydride monomer to provide a polymer of formula C-1:

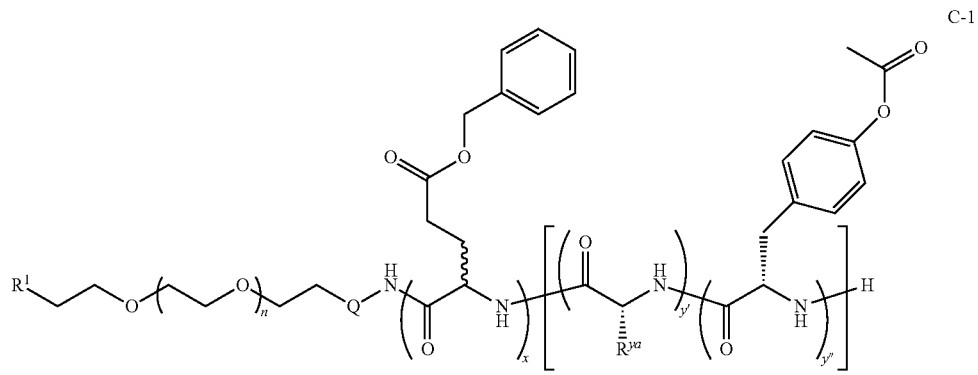

C-1 wherein each of the $R^1$, Q, x, $R^{ya}$, y', y" and n groups of formula C-1 are as described in various classes and subclasses, both singly and in combination, herein;
(d) terminating the polymerization by the addition of acetic anhydride, N-methylmorpholine, and N,N-dimethylaminopyridine to provide a polymer of formula D-1:

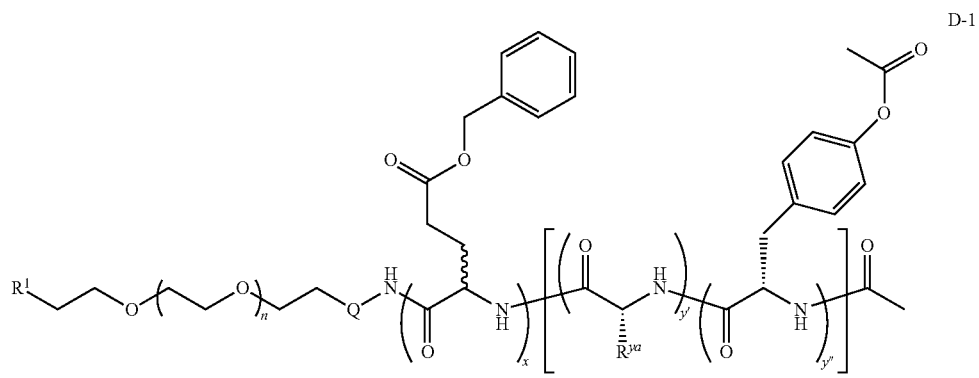

D-1 wherein each of the $R^1$, Q, x, $R^{ya}$, y', y" and n groups of formula D-1 are as described in various classes and subclasses, both singly and in combination, herein; and
(e) treating the polymer of formula D-1 with hydroxylamine to provide the multiblock copolymer of formula II:

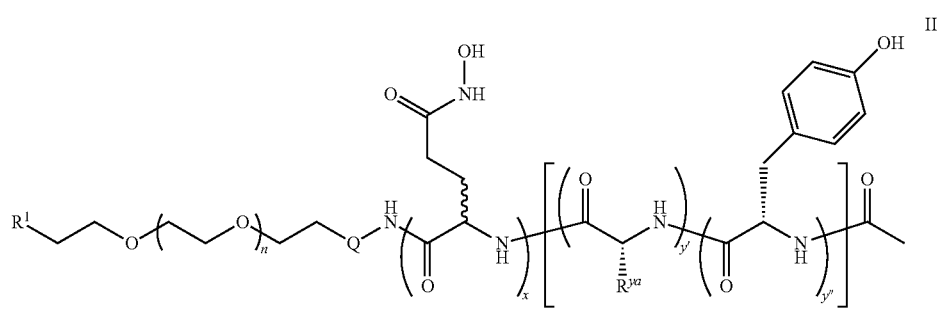

II wherein each of the $R^1$, Q, x, $R^{ya}$, y', y" and n groups of formula II are as described in various classes and subclasses, both singly and in combination, herein.

According to another embodiment, the present invention provides a method for preparing a micelle comprising a multiblock copolymer which comprises a polymeric hydrophilic block, optionally a crosslinkable or crosslinked poly(amino acid block), and a hydrophobic poly(amino acid) block, characterized in that said micelle has an inner core, an optionally crosslinkable or crosslinked outer core, and a hydrophilic shell, said method comprising the steps of:

(a) providing a multiblock copolymer of formula I:

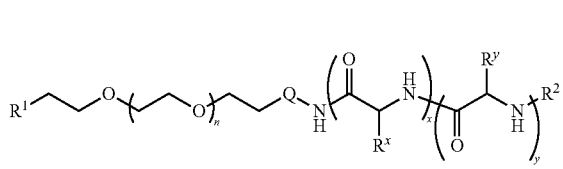

wherein each of the $R^1$, $R^2$, Q, $R^x$, $R^y$, n, x, and y groups of formula I, are as described in various classes and subclasses, both singly and in combination, herein,
(b) combining said compound of formula I with a therapeutic agent; and
(c) treating the resulting micelle with a crosslinking reagent to crosslink $R^x$.

According to yet another embodiment, the present invention provides a method for preparing a crosslinked, drug loaded micelle, said method comprising the steps of:
(a) providing a multiblock copolymer of formula I:

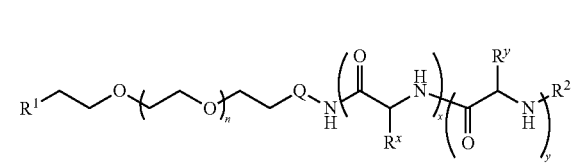

wherein each of the $R^1$, $R^2$, Q, $R^x$, $R^y$, n, x, and y groups of formula I, are as described in various classes and subclasses, both singly and in combination, herein,
(b) combining said compound of formula I with a drug;
(c) treating the resulting micelle with iron to crosslink $R^x$;
(d) aseptically filtering the resulting crosslinked, drug loaded micelle;
(e) adding trehalose, mannitol, or sucrose to the filtered solution; and
(f) lyophilizing the filtered solution to provide the crosslinked, drug loaded micelle as a dry powder.

In one embodiment, drugs are loaded into the micelle inner core by adding an aliquot of a copolymer solution in water to the drug to be incorporated. For example, a stock solution of the drug in a polar organic solvent is made and allowed to evaporate, and then the copolymer/water solution is added. In another embodiment, the drug is incorporated using an oil in water emulsion technique. In this case, the drug is dissolved in an organic solvent and added dropwise to the micelle solution in water, and the drug is incorporated into the micelle during solvent evaporation. In another embodiment, the drug is dissolved with the copolymer in a common polar organic solvent and dialyzed against water or another aqueous medium. See Allen, C.; Maysinger, D.; Eisenberg A. *Colloid Surface B* 1999, 16, 3-27.

5. Uses, Methods, and Compositions

As described herein, micelles of the present invention can encapsulate a wide variety of therapeutic agents useful for treating a wide variety of diseases. In certain embodiments, the present invention provides a drug-loaded micelle, as described herein, wherein said micelle is useful for treating the disorder for which the drug is known to treat. According to one embodiment, the present invention provides a method for treating one or more disorders selected from pain, inflammation, arrhythmia, arthritis (rheumatoid or osteoarthritis), atherosclerosis, restenosis, bacterial infection, viral infection, depression, diabetes, epilepsy, fungal infection, gout, hypertension, malaria, migraine, cancer or other proliferative disorder, erectile dysfunction, a thyroid disorder, neurological disorders and hormone-related diseases, Parkinson's disease, Huntington's disease, Alzheimer's disease, a gastro-intestinal disorder, allergy, an autoimmune disorder, such as asthma or psoriasis, osteoporosis, obesity and comorbidities, a cognitive disorder, stroke, AIDS-associated dementia, amyotrophic lateral sclerosis (ALS, Lou Gehrig's disease), multiple sclerosis (MS), schizophrenia, anxiety, bipolar disorder, tauopothy, a spinal cord or peripheral nerve injury, myocardial infarction, cardiomyocyte hypertrophy, glaucoma, an attention deficit disorder (ADD or ADHD), a sleep disorder, reperfusion/ischemia, an angiogenic disorder, or urinary incontinence, comprising administering to a patient a micelle comprising a multiblock copolymer which comprises a polymeric hydrophilic block, optionally a crosslinkable or crosslinked poly(amino acid block), and a hydrophobic D,L-mixed poly(amino acid block), characterized in that said micelle has a drug-loaded inner core, optionally a crosslinkable or crosslinked outer core, and a hydrophilic shell, wherein said micelle encapsulates a therapeutic agent suitable for treating said disorder.

In other embodiments, the present invention provides a method for treating one or more disorders selected from autoimmune disease, an inflammatory disease, a metabolic disorder, a psychiatric disorder, diabetes, an angiogenic disorder, tauopothy, a neurological or neurodegenerative disorder, a spinal cord injury, glaucoma, baldness, or a cardiovascular disease, comprising administering to a patient a multiblock copolymer which comprises a polymeric hydrophilic block, optionally a crosslinkable or crosslinked poly(amino acid block), and a hydrophobic D,L-mixed poly(amino acid block), characterized in that said micelle has a drug-loaded inner core, optionally a crosslinkable or crosslinked outer core, and a hydrophilic shell, wherein said micelle encapsulates a therapeutic agent suitable for treating said disorder.

In certain embodiments, drug-loaded micelles of the present invention are useful for treating cancer. Accordingly, another aspect of the present invention provides a method for treating cancer in a patient comprising administering to a patient a multiblock copolymer which comprises a polymeric hydrophilic block, optionally a crosslinkable or crosslinked poly(amino acid block), and a hydrophobic D,L-mixed poly(amino acid block), characterized in that said micelle has a drug-loaded inner core, optionally a crosslinkable or crosslinked outer core, and a hydrophilic shell, wherein said micelle encapsulates a chemotherapeutic agent. According to another embodiment, the present invention relates to a method of treating a cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, myeloid disorders, lymphoid disorders, Hodgkin's, hairy cells, buccal cavity and pharynx (oral), lip, tongue, mouth, pharynx, small intestine, colon-rectum, large intestine, rectum, brain and central nervous system, and leukemia, comprising administering a micelle in accordance with the present invention wherein said micelle encapsulates a chemotherapeutic agent suitable for treating said cancer.

P-glycoprotein (Pgp, also called multidrug resistance protein) is found in the plasma membrane of higher eukaryotes where it is responsible for ATP hydrolysis-driven export of hydrophobic molecules. In animals, Pgp plays an important role in excretion of and protection from environmental toxins, when expressed in the plasma membrane of cancer cells, it can lead to failure of chemotherapy by preventing the hydrophobic chemotherapeutic drugs from reaching their targets inside cells. Indeed, Pgp is known to transport hydrophobic chemotherapeutic drugs out of tumor cells. According to one aspect, the present invention provides a method for delivering a hydrophobic chemotherapeutic drug to a cancer cell while preventing, or lessening, Pgp excretion of that chemotherapeutic drug, comprising administering a drug-loaded micelle comprising a multiblock polymer of the present invention loaded with a hydrophobic chemotherapeutic drug. Such hydrophobic chemotherapeutic drugs are well known in the art and include those described herein.

Compositions

According to another embodiment, the invention provides a composition comprising a micelle of this invention or a pharmaceutically acceptable derivative thereof and a pharmaceutically acceptable carrier, adjuvant, or vehicle. In certain embodiments, the composition of this invention is formulated for administration to a patient in need of such composition. In other embodiments, the composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Pharmaceutically acceptable salts of the compounds of this invention include those derived from pharmaceutically acceptable inorganic and organic acids and bases. Examples of acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Salts derived from appropriate bases include alkali metal (e.g., sodium and potassium), alkaline earth metal (e.g., magnesium), ammonium and N+(C1-4 alkyl)4 salts. This invention also envisions the quaternization of any basic nitrogen-containing groups of the compounds disclosed herein. Water or oil-soluble or dispersible products may be obtained by such quaternization.

The compositions of the present invention may be administered orally, parenterally, by inhalation spray, topically, rectally, nasally, buccally, vaginally or via an implanted reservoir.

The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added. In certain embodiments, pharmaceutically acceptable compositions of the present invention are enterically coated.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a enema formulation. Topically-transdermal patches may also be used.

For topical applications, the pharmaceutically acceptable compositions may be formulated in an ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other preservatives, absorption promoters to enhance bioavailability, fluorocarbons, and/or other conventional solubilizing or dispersing agents.

In certain embodiments, the pharmaceutically acceptable compositions of this invention are formulated for oral administration.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the drug can be administered to a patient receiving these compositions.

It will be appreciated that dosages typically employed for the encapsulated drug are contemplated by the present invention. In certain embodiments, a patient is administered a drug-loaded micelle of the present invention wherein the dosage of the drug is equivalent to what is typically administered for that drug. In other embodiments, a patient is administered a drug-loaded micelle of the present invention wherein the dosage of the drug is lower than is typically administered for that drug.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

In order that the invention described herein may be more fully understood, the following examples are set forth. It will be understood that these examples are for illustrative purposes only and are not to be construed as limiting this invention in any manner.

EXEMPLIFICATION

As described generally above, multiblock copolymers of the present invention are prepared using the heterobifunctional PEGs described herein and in U.S. patent application Ser. No. 11/256,735, filed Oct. 24, 2005, published as WO2006/047419 on May 4, 2006 and published as US 20060142506 on Jun. 29, 2006, the entirety of which is hereby incorporated herein by reference. The preparation of multiblock polymers in accordance with the present invention is accomplished by methods known in the art, including those described in detail in U.S. patent application Ser. No. 11/325,020, filed Jan. 4, 2006, published as WO2006/74202 on Jul. 13, 2006 and published as US 20060172914 on Aug. 3, 2006, the entirety of which is hereby incorporated herein by reference.

In each of the Examples below, where an amino acid, or corresponding NCA, is designated "D", then that amino acid, or corresponding NCA, is of the D-configuration. Where no such designation is recited, then that amino acid, or corresponding NCA, is of the L-configuration.

General Methods:

Particle Size Analysis

Dynamic light scattering with a Wyatt Dynapro plate reader was used to determine the particle sizes of the uncrosslinked and crosslinked formulations. Solutions of the formulations were made at 1 mg/mL in 150 mM NaCl. The samples were centrifuged at 2000 RPM for 5 minutes, and then 300 µL each was added to a well of a 96-well plate in triplicate for analysis. 10 acquisitions per well with 30-second acquisition times and laser auto-attenuation were used to collect the data.

Encapsulation Verification Dialysis

The uncrosslinked formulation was dissolved in 3.5 mL of 10 mM phosphate buffer pH 8 at 20 mg/mL, and at 0.2 mg/mL. 3 mL of the samples was added to 3500 molecular weight-cutoff dialysis bags, and the remaining 0.5 mL was added to HPLC vials for the pre dialysis samples. The dialysis bags were placed in 300 mL of 10 mM PB pH 8 and stirred for 6 hours. Aliquots were then taken from inside the dialysis bags and HPLC analysis was used to determine the peak areas of drug from the pre dialysis and post dialysis samples. The areas were then used to calculate the % drug remaining post dialysis.

Iron-Dependent Crosslinking and Analysis

The uncrosslinked formulation was reconstituted in water at 20 mg/mL with either 0.1, 0.25, 0.5, 0.75, 1, 2.5, 5, 7.5 or 10 mM iron (III) chloride and allowed to stir over night at room temperature. The samples were then diluted to 0.2 mg mL in 10 mM phosphate buffer pH 8, with a final volume of 5 mL. Aliquots of 1.5 mL were taken as pre-dialysis samples for HPLC analysis, then 3 mL of each sample was added to a 3500 MWC cut-off dialysis bag and dialyzed against 10 mM phosphate buffer pH 8 for 6 hours. After 6 hours the samples were removed from inside the dialysis bags and analyzed by HPLC. The post-dialysis peak area for each sample was divided by the pre-dialysis peak areas and multiplied by 100 to converted to percent remaining.

Time-Dependent Crosslinking and Analysis

The uncrosslinked formulation was reconstituted in water at 20 mg/mL, and 50 µL was diluted into 4.95 mL for the uncrosslinked sample. A 500 mM stock solution of iron (III) chloride was then added to the uncrosslinked solution for a final concentration of 10 mM iron (III) chloride. This was used as the stock crosslinked solution, where 50 µL aliquots were taken at 5 minutes, 30 minutes, 1 hour, 2 hours, 4 hours and 16 hours and diluted to 0.2 mg mL in 10 mM phosphate buffer pH 8, with a final volume of 5 mL. Aliquots of 1.5 mL were taken as pre-dialysis samples for HPLC analysis, then 3 mL of each sample was added to a 3500 MWC cut-off dialysis bag and dialyzed against 10 mM phosphate buffer pH 8 for 6 hours. After 6 hours the samples were removed from inside the dialysis bags and analyzed by HPLC. The post-dialysis peak area for each sample was divided by the pre-dialysis peak areas and multiplied by 100 to converted to percent remaining.

pH-Dependent Crosslinking and Analysis

The uncrosslinked formulation was reconstituted in water at 20 mg/mL with 10 mM iron (III) chloride at pH 3, 4, 5, 6, 7, 7.4 and 8. The samples were allowed to incubate for 10 minutes following reconstitution and pH adjustment, and then diluted to 0.2 mg mL in 10 mM phosphate buffer pH 8, with a final volume of 5 mL. Aliquots of 1.5 mL were taken as pre-dialysis samples for HPLC analysis, then 3 mL of each sample was added to a 3500 MWC cut-off dialysis bag and dialyzed against 10 mM phosphate buffer pH 8 for 6 hours. After 6 hours the samples were removed from inside the dialysis bags and analyzed by HPLC. The post-dialysis peak area for each sample was divided by the pre-dialysis peak areas and multiplied by 100 to converted to percent remaining.

pH-Dependent Release of Crosslinked Formulations

The uncrosslinked formulation was reconstituted in water at 20 mg/mL with 10 mM iron (III) chloride, pH adjusted to 8.0 with NaOH and allowed to stir over night at room temperature. The next day the sample was diluted to 0.2 mg/mL in 10 mM phosphate buffer at pH 3, 4, 5, 6, 7, 7.4 and 8, with a final volume of 5 mL per sample. Aliquots of 1.5 mL were taken as pre-dialysis samples for HPLC analysis, then 3 mL of each sample was added to a 3500 MWC cut-off dialysis bag and dialyzed against 10 mM phosphate buffer pH 8 for 6 hours. After 6 hours the samples were removed from inside the dialysis bags and analyzed by HPLC. The post-dialysis peak area for each sample was divided by the pre-dialysis peak areas and multiplied by 100 to converted to percent remaining.

pH-Dependent Release of Uncrosslinked Formulations

The uncrosslinked formulation was reconstituted in water at 20 mg/mL, pH adjusted to 8.0 with NaOH and allowed to stir over night at room temperature. The next day the sample was diluted to 0.2 mg/mL in 10 mM phosphate buffer at pH 3, 4, 5, 6, 7, 7.4 and 8, with a final volume of 5 mL per sample. Aliquots of 1.5 mL were taken as pre-dialysis samples for HPLC analysis, then 3 mL of each sample was added to a 3500 MWC cut-off dialysis bag and dialyzed against 10 mM phosphate buffer pH 8 for 6 hours. After 6 hours the samples were removed from inside the dialysis bags and analyzed by HPLC. The post-dialysis peak area for each sample was divided by the pre-dialysis peak areas and multiplied by 100 to converted to percent remaining.

Salt-Dependent Release of Crosslinked Formulations

The uncrosslinked formulation was reconstituted in water at 20 mg/mL with 10 mM iron (III) chloride, pH adjusted to 8.0 with NaOH and allowed to stir for 10 minutes. The sample was then diluted to 0.2 mg/mL in 10 mM phosphate buffer pH 8 with increasing NaCl concentration from 0 to 10, 50, 100, 200, 300, 400 and 500 mM with a final volume of 5 mL per sample. Aliquots of 1.5 mL were taken as pre-dialysis samples for HPLC analysis, then 3 mL of each sample was added to a 3500 MWC cut-off dialysis bag and dialyzed against 10 mM phosphate buffer pH 8 with the corresponding salt concentration for 6 hours. After 6 hours the samples were removed from inside the dialysis bags and analyzed by HPLC. The post-dialysis peak area for each sample was divided by the pre-dialysis peak areas and multiplied by 100 to converted to percent remaining.

In-Vitro Cytotoxicity of Aminopterin Formulations

Cells originally purchased from ATCC (A549, Panc-1, OVCAR3, and BXPC-3) were seeded in 96 well tissue culture plates to be 50% confluent by 24 hours. Cells were incubated at 37° C. with 5.0% $CO_2$. Cells were treated with escalating doses of free aminopterin, crosslinked aminopterin formulation, uncrosslinked aminopterin formulation, and non drug-loaded micelle formulations 24 hours after plate seeding. Free aminopterin was dissolved in DMSO and administered to cells with a total volume of DMSO equal to or less than 0.0025%. Micelle formulations were re-suspended in biology grade water. Dilutions were done in deep well plates with cell media and water or DMSO (for free aminopterin only) equalizing displaced volume. Incubation media was aspirated from the 96 well plates and 100 µl of each dilution was added to the wells in triplicate and incubated over 72 hours at 37° C. with 5.0% $CO_2$. Crosslinked and uncrosslinked non drug-loaded micelle formulations were administered at the four highest doses and were calculated at comparative mg/ml concentrations to drug-loaded micelle concentrations of delivery vehicle. After 72-hour incubation, plates were allowed to cool to room temperature and 25 µl of cell titer-glo was added to each well. Plates were briefly shaken to mix and luminescence readings were read on a plate reader. Luminescence reading for triplicate doses are averaged and divided by average luminescence readings from untreated cells on the same plate to calculate the % of viable cells per dose.

Formulation Method A

Polymer was dissolved in water at a concentration of 5 mg/mL by stirring and heating to 40 degrees Celsius for approximately 30 minutes. Sucrose was then added to the polymer solution at 5 mg/mL and stirred at room temperature until homogenous. The solution was then allowed to cool to room temperature while stirring. The active pharmaceutical ingredient (API) was dissolved in organic solvent just below the limit of solubility. The API/organic solution was then added to the polymer/sucrose solution while shear mixing at 10,000 RPM for approximately 30 seconds, or until a homogenous emulsion resulted. The solution was then processed with a single pass through a microfluidizer with an operating pressure of approximately 23,000 PSI with the outlet stream cooled by an ice water bath. The solution was then passed through a 0.22 micron dead-end filter, and then processed by ultrafiltration using tangential flow filtration until a total of 4-times the original volume of sucrose buffer was exchanged and the final concentration of polymer in solution was approximately 20 mg/mL. Iron (III) Chloride was then added to the formulation for a final concentration of 10 mM. The pH of the solution was then adjusted to 6.0 with NaOH and stirred at room temperature for 4 hours. One volume of buffer containing a cryopreservative agent at 20 mg/mL was then added to the solution, and then concentrated back down to approximately 20 mg/mL polymer concentration. The solution was then frozen at −40 degrees Celsius and lyophilized.

Formulation Method B

Polymer was dissolved in water at a concentration of 2 mg/mL by stirring and heating to 40 degrees Celsius for approximately 30 minutes. The solution was then allowed to cool to room temperature while stirring. The active pharmaceutical ingredient (API) was dissolved in organic solvent just below the limit of solubility. The API/organic solution was then added to the polymer/sucrose solution while shear mixing at 10,000 RPM for approximately 30 seconds, or until a homogenous emulsion resulted. The solution was then stirred over night in a fume hood to allow the organic solution to evaporate. The next day the solution was passed through a 0.22 micron dead-end filter, and then processed by ultrafiltration using tangential flow filtration to concentrate the sample from 2 mg/mL to approximately 20 mg/mL. Iron (III) Chloride was then added to the formulation for a final concentration of 10 mM. The pH of the solution was then adjusted to 6.0 with NaOH and stirred at room temperature for 4 hours. The solution was then frozen at −40 degrees Celsius and lyophilized.

SN-38 Formulation Weight Loading Analysis

Weight loading was determined by comparing a standard curve of SN38 to a known concentration of formulation by HPLC analysis. SN38 was dissolved in methanol in a range from 30 μg/mL to 150 μg/mL, and the formulation was dissolved at 5 mg/mL in methanol. The amount of SN-38 in the formulation is then converted to % based on the known quantity of formulation used (i.e. 5 mg/mL).

Daunorubicin Formulation Weight Loading Analysis

Weight loading was determined by comparing a standard curve of daunorubicin to a known concentration of formulation by HPLC analysis. Daunorubicin was dissolved in methanol in a range from 40 g/mL to 200 μg/mL, and the formulation was dissolved at 2 mg/mL in methanol. The amount of daunorubicin in the formulation is then converted to % based on the known quantity of formulation used (i.e. 2 mg/mL).

Aminopterin Formulation Weight Loading Analysis

Weight loading was determined by comparing a standard curve of aminopterin to a known concentration of formulation by HPLC analysis. Aminopterin was dissolved in HPLC mobile phase (60% acetonitrile, 40% 10 mM phosphate buffer pH 8) in a range from 40 ⌠g/mL to 200 ⌠g/mL, and the formulation was dissolved at 5 mg/mL in HPLC mobile phase. The amount of aminopterin in the formulation is then converted to % based on the known quantity of formulation used (i.e. 5 mg/mL).

Berberine Formulation Weight Loading Analysis

Weight loading was determined by comparing a standard curve of berberine to a known concentration of formulation by HPLC analysis. Berberine was dissolved in methanol in a range from 40 μg/mL to 200 μg/mL, and the formulation was dissolved at 5 mg/mL in methanol. The amount of berberine in the formulation was then converted to % based on the known quantity of formulation used (i.e. 5 mg/mL).

Cabazitaxel Formulation Weight Loading Analysis

Weight loading was determined by comparing a standard curve of cabazitaxel to a known concentration of formulation by HPLC analysis. Cabazitaxel was dissolved in methanol in a range from 40 μg/mL to 200 μg/mL, and the formulation was dissolved at 10 mg/mL in methanol. The amount of cabazitaxel in the formulation was then converted to % based on the known quantity of formulation used (i.e. 10 mg/mL).

Epothilone D Formulation Weight Loading Analysis

Weight loading was determined by comparing a standard curve of epothilone D to a known concentration of formulation by HPLC analysis. Epothilone D was dissolved in methanol in a range from 40 μg/mL to 200 μg/mL, and the formulation was dissolved at 10 mg/mL in methanol. The amount of epothilone D in the formulation was then converted to % based on the known quantity of formulation used (i.e. 10 mg/mL).

General Rat Pharmacokinetic Experiments

Sprague-Dawly rats surgically modified with jugular vein catheters were purchased from Harlan Laboratories, Dublin, Va. Formulations were dissolved in water with 150 mM NaCl for a final concentration of typically 10 mg API per kg animal body weight for 1 mL bolus injection via JVC over approximately 1 minute, followed by a flush of approximately 250 ⌠L heparinized saline. Time points for blood collection following test article administration were as followed: 1, 5, 15 minutes, 1, 4, 8 and 24 hours. Approximately 250 μL of blood per time point was collected by JVC into K3-EDTA blood collection tubes followed by a flush of approximately 250 μL heparinized saline. Blood was then centrifuged at 2000 RPM for 5 minutes to isolate plasma. Plasma was then collected and snap frozen until processed for HPLC analysis. Samples were prepared for analysis by first thawing the plasma samples at room temperature. 50 μL plasma was added to a 2 mL eppendorf tube 150 μL of extraction solution (0.1% phosphoric acid in methanol, 5 μg/mL internal standard). Samples were then vortexed for 10 minutes and centrifuged for 10 minutes at 13,000 RPM. Supernatant was then transferred into HPLC vials then analyzed by HPLC. Quantitation of API was determined using a standard curve of API formulation in rat plasma compared to samples collected from rats at each time point.

Example 1

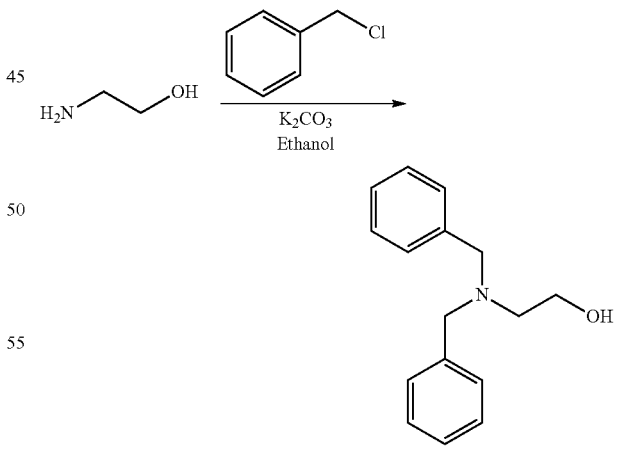

Dibenzylamino Ethanol

Benzyl chloride (278.5 g, 2.2 mol), ethanol amine (60 mL, 1 mol), potassium carbonate (283.1 g, 2.05 mol) and ethanol (2 L) were mixed together in a 3 L 3-neck flask, fitted with an overhead stirrer, a condenser and a glass plug. The apparatus was heated up to reflux for 36 hr, after which the insoluble solid was filtered through a medium frit. The filtrate was recovered and ethanol was removed by rotary evaporation. The viscous liquid was redissolved in ether, the solid suspension removed by filtration and extracted twice against water. The ether solution was kept and the aqueous layer was extracted twice with dichloromethane (2×400 mL). The fraction were recombined, dried over MgSO$_4$, stirred over carbon black for 15 min and filtered through a celite pad. Dichloromethane was removed and the solid was redissolved into a minimal amount of ether (combined volume of 300 mL with the first ether fraction, 300 mL). Hexanes (1700 mL) was added and the solution was heated up gently till complete dissolution of the product. The solution was then cooled down gently, placed in the fridge (+4° C.) overnight and white crystals were obtained. The recrystallization was done a second time. 166.63 g, 69% yield. $^1$H NMR (d$_6$-DMSO) δ 7.39-7.24 (10H), 4.42 (1H), 3.60 (4H), 3.52 (2H), 2.52 (2H).

Example 2

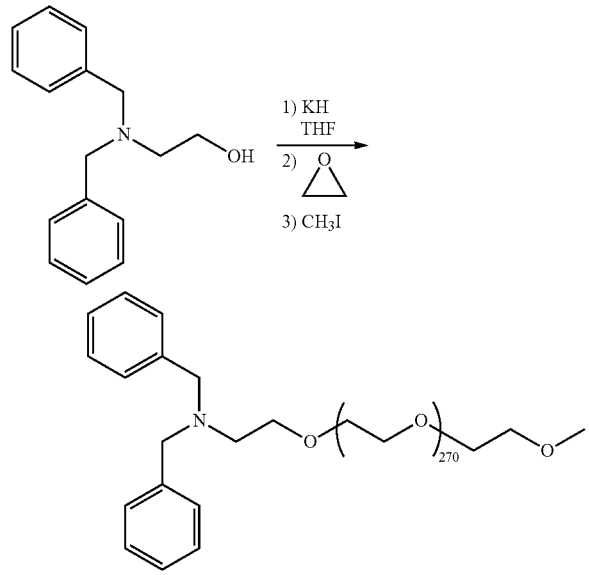

Dibenzylamino-PEG-Methoxy

An apparatus consisting of a 4 L jacketed 3-necked polymerization flask equipped with a glass magnetic stirring bar and thermally-insulated jacketed addition funnel was evacuated down to 10 mTorr then backfilled with argon. The reaction flask was loaded with N,N-dibenzylaminoethanol (4.28 g, 17.7 mmol) and 50% KH solid in paraffin wax (1.70 g, 21.2 mmol) under a gentle stream of argon gas. Anhydrous THF, approximately 2 L, was introduced into the reaction flask and the mixture was stirred under Argon at ambient temperature for 16 h. The resulting slurry was cooled to 10° C., and the addition funnel under vacuum was chilled to −30° C. Ethylene oxide gas was condensed into the chilled evacuated funnel until 225 mL (4.8 mol) of liquid EO was collected. The liquid ethylene oxide in the condensation funnel was added in one portion into the reaction mixture. The reaction mixture was stirred in a closed flask at 10° C. for 6 hours, then 20° C. for 16 hours. The polymerization was completed by raising the temperature to 30° C. for 16 hours, then to 40° C. for 2 days. The reaction mixture was cooled to 25° C., then methyl iodide (1.6 mL) was added at once and the mixture was stirred at 25° C. for 10 hours. The excess of unreacted potassium hydride was then destroyed by addition of ethanol (99%, 100 mL). After 30 min, the quenched reaction mixture was transferred into a large beaker and the polymer product was precipitated by addition of ethyl ether (8 L). The precipitated product was collected by filtration on a large Buchner funnel and then dried in vacuo. The yield was 215.1 g of a white solid. Aqueous GPC showed $M_n$ of 12.0 kDa and a PDI of 1.01. $^1$H-NMR (d$_6$-DMSO, 400 MHz): 7.344 (m, 8H), 7.225 (m, 4H), 3.681 (m, 8H), 3.507 (m, approx. 1000H), 3.320 (m, 6H+water signal), 3.237 (s, 3H), 2.551 (t, 6.0 Hz, 2H).

Example 3

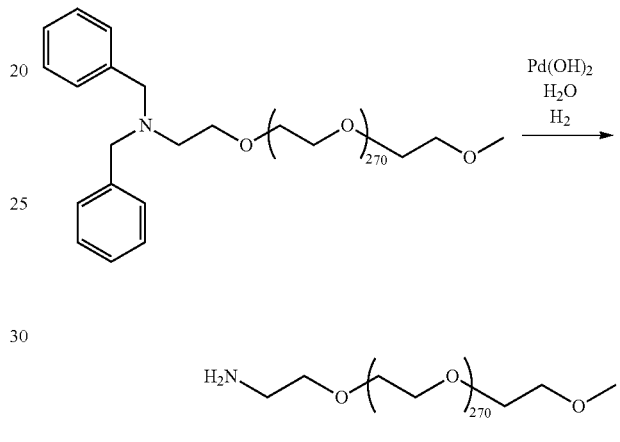

mPEG-Amine

The mPEG-dibenzylamine product Example 3 (214.0 g) was dissolved in deionized water (1 L). Pearlman's catalyst 13.2 g (20% Pd hydroxide on carbon, Aldrich) slurry in deionized water (150 mL) was activated by stirring under hydrogen balloon at ambient temperature. The hydrogen in the flask was replaced with nitrogen, the solution of dibenzylamino mPEG starting material was added to the catalyst slurry and the flask was evacuated, then back-filled with hydrogen (repeated 3 times). The hydrogenation was then continued at ambient temperature under hydrogen balloon for 2½ days at which point $^1$H-NMR indicated a complete disappearance of benzyl signals. Sodium chloride (350 g) solid was added to the reaction mixture and the mixture was stirred for half a day under nitrogen, the spent catalyst was removed by filtration and rinsed thoroughly with brine. The combined filtrates were made alkaline (to approx pH 11) by addition of a small volume of 1 M NaOH and extracted with dichloromethane (4×0.7 L). The combined extracts were dried with anhydrous sodium carbonate, filtered and concentrated on rotovap down to about 0.75 μL total volume, then precipitated without a delay by adding excess of ether (8 L). The precipitated product was collected by filtration and dried in vacuo to provide 202.5 g of a voluminous snow-white solid. $^1$H-NMR (d$_6$-DMSO, 400 MHz): 3.681 (m, 8H), 3.507 (m, approx. 1000H), 3.341 (m, 4H+water signal), 3.238 (s, 3H), 2.634 (t, 5.7 Hz, 2H).

Example 4

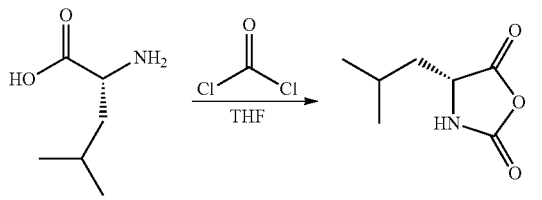

D-Leucine NCA

H-D-Leu-OH (100 g, 0.76 mol) was suspended in 1 L of anhydrous THF and heated to 50° C. while stirring heavily. Phosgene (20% in toluene) (500 mL, 1 mol) was added to the amino acid suspension. After 1 h 20 min, the amino acid dissolved, forming a clear solution. The solution was concentrated on the rotovap, transferred to a beaker, and hexane was added to precipitate the product. The white solid was isolated by filtration and dissolved in toluene (~700 mL) with a small amount of THF (~60 mL). The solution was filtered over a bed of Celite to remove any insoluble material. An excess of hexane (~4 L) was added to the filtrate to precipitate the product. The NCA was isolated by filtration and dried in vacuo. (91 g, 79% yield) D-Leu NCA was isolated as a white, crystalline solid. $^1$H NMR (d$_6$-DMSO) δ 9.13 (1H), 4.44 (1H), 1.74 (1H), 1.55 (2H), 0.90 (6H) ppm.

Example 5

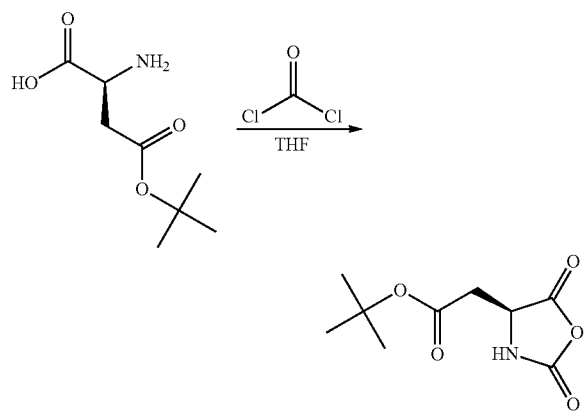

Tert-Butyl Aspartate NCA

H-Asp(OBu)—OH (120 g, 0.63 mol) was suspended in 1.2 L of anhydrous THF and heated to 50° C. while stirring heavily. Phosgene (20% in toluene) (500 mL, 1 mol) was added to the amino acid suspension. After 1 h 30 min, the amino acid dissolved, forming a clear solution. The solution was concentrated on the rotovap, transferred to a beaker, and hexane was added to precipitate the product. The white solid was isolated by filtration and dissolved in anhydrous THF. The solution was filtered over a bed of Celite to remove any insoluble material. An excess of hexane was added to precipitate the product. The NCA was isolated by filtration and dried in vacuo. 93 g (68%) of Asp(OBu) NCA was isolated as a white, crystalline solid. $^1$H NMR (d$_6$-DMSO) δ 8.99 (1H), 4.61 (1H), 2.93 (1H), 2.69 (1H), 1.38 (9H) ppm.

Example 6

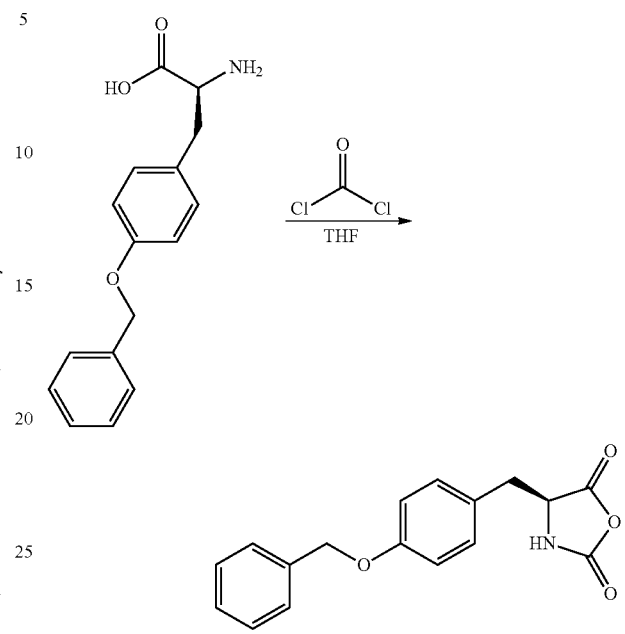

Benzyl Tyrosine NCA

H-Tyr(OBzl)-OH (140 g, 0.52 mol) was suspended in 1.5 L of anhydrous THF and heated to 50° C. while stirring heavily. Phosgene (20% in toluene) (500 mL, 1 mol) was added to the amino acid suspension via cannulation. The amino acid dissolved over the course of approx. 1 h30, forming a pale yellow solution. The solution was first filtered through a Buchner fitted with a Whatman paper #1 to remove any particles still in suspension. Then, the solution was concentrated by rotary evaporation, transferred to a beaker, and hexane was added to precipitate the product. The off-white solid was isolated by filtration and dissolved in anhydrous THF (~600 mL). The solution was filtered over a bed of Celite to remove any insoluble material. An excess of hexane (~6 L) was added to the filtrate to precipitate the product. The NCA was isolated by filtration and dried in vacuo. 114.05 g, 74.3% of Tyr(OBzl) NCA was isolated as an off-white powder. $^1$H NMR (d$_6$-DMSO) δ 9.07 (1H), 7.49-7.29 (5H), 7.12-7.07 (2H), 6.98-6.94 (2H), 5.06 (2H), 4.74 (1H), 3.05-2.88 (2H) ppm.

Example 7

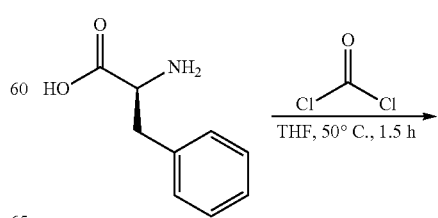

-continued

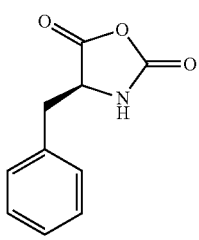

Phenylalanine NCA

H-L-Phe-OH (20.0 g, 132 mmol) was suspended in 300 mL of anhydrous THF and heated to 50° C. Phosgene (20% in toluene) (90 mL, 182 mmol) was added to the amino acid suspension, and the amino acid dissolved over the course of approx. 1 hr, forming a cloudy solution. The solution was filtered through a paper filter (Whatman #1), concentrated on by rotary evaporation, transferred to a beaker, and hexane was added to precipitate the product. The white solid was isolated by filtration and dissolved in anhydrous THF. The solution was filtered over a bed of Celite to remove any insoluble material. An excess of hexanes were added on the filtrate while stirring with a spatula. The NCA was isolated by filtration and dried in vacuo. 20.0 g (86% yield) of D-PheNCA was isolated as a white, crystalline solid. $^1$H NMR (d$_6$-DMSO) δ 9.09 (1H), 7.40-7.08 (5H), 4.788 (1H), 3.036 (2H) ppm.

Example 8

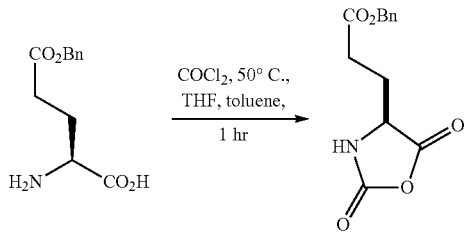 [SMILES: N[C@@H](CCC(=O)OCc1ccccc1)C(=O)O ; O=C(CC[C@@H]1NC(=O)OC1=O)OCc1ccccc1]

L-Benzylglutamate NCA

Vacuum-dried H-Glu(OBn)-OH (71.2 g, 300.0 mmol) was suspended in 900 mL of anhydrous THF. Phosgene (20% in toluene) (210 mL, 420 mmol) was added to the amino acid suspension at room temperature and after ten minutes, the mixture was heated to 50° C. The amino acid dissolved over the course of approx. 1 hr, forming a clear solution. The solution was slightly cooled and concentrated on the rotovap. Fresh anhydrous THF (400 mL) was added to the residue and the solution was re-evaporated on the rotovap to give a colorless solid, which was dissolved in 300 mL anhydrous THF, transferred to a 4 L beaker and precipitated by the slow addition of 1.5 L of anhydrous heptane. The pure NCA was isolated by suction filtration and dried in vacuo. 75.31 g (95.4% yield) of Glu(OBn) NCA was isolated as a colorless, crystalline solid. $^1$H NMR (CDCl$_3$) δ 7.36 (5H), 6.40 (1H), 5.14 (2H), 4.40 (1H), 2.60 (2H), 2.22 (2H).

Example 9

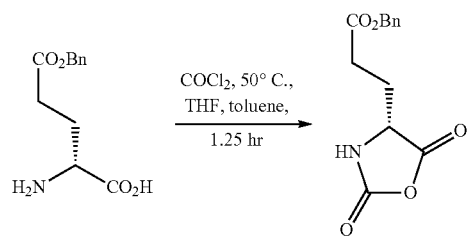 [SMILES: N[C@H](CCC(=O)OCc1ccccc1)C(=O)O ; O=C(CC[C@H]1NC(=O)OC1=O)OCc1ccccc1]

D-Benzylglutamate NCA

By using the same method and reaction scale of Example 8 and substituting H-d-Glu(OBn)-OH as starting material, reaction with phosgene for 1.25 hours at 50° C. afforded 75.53 g (Yield=95.6%) of d-Glu(OBn) NCA as a colorless, crystalline solid. $^1$H NMR (CDCl$_3$): identical to Example 8.

Example 10

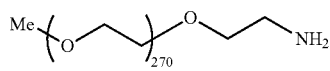

1. Toluene, 60° C.,
   azeotrope in vacuo
2. Glu(OBn)NCA,
   d-Glu(OBn)NCA,
   NMP, RT, 18 hr
3. d-PheNCA, Tyr(OBn)NCA,
   RT → 35° C., 48 hr
4. Ac$_2$O, NMM,
   DMAP, RT

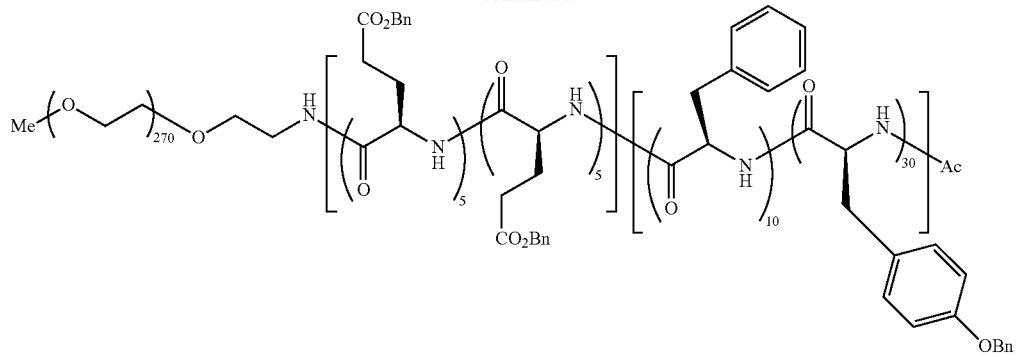

mPEG12K-b-Poly-(d-Glu(OBn)$_5$-Co-Glu(OBn)$_5$)-b-Poly (Tyr(OBn)$_{30}$-Co-d-Phe$_{10}$)-Ac m-PEG12k-NH$_2$, (119.7 g, 10.0 mmol) was weighed into an oven-dried, 2 L-round-bottom flask, dissolved in toluene (1 L), and dried by azeotropic distillation. After distillation to dryness, the polymer was left under vacuum for three hours. The flask was subsequently backfilled with N$_2$, re-evacuated under reduced pressure, and dry N-methylpyrrolidone (NMP) (1100 mL) was introduced by cannula. The mixture was briefly heated to 40° C. to expedite dissolution and then recooled to 25° C. Glu(OBn) NCA (13.16 g, 50.0 mmol) and d-Glu(OBn) NCA (13.16 g, 50.0 mmol) were added to the flask, and the reaction mixture was allowed to stir for 16 hours at ambient room temperature under nitrogen gas. Then, d-Phe NCA (19.12 g, 100 mmol) and Tyr (OBn) NCA (89.19 g, 300 mmol) were added and the solution was allowed to stir at 35° C. for 48 hours at which point the reaction was complete (GPC, DMF/0.1% LiBr). The solution was cooled to room temperature and acetic anhydride (10.21 g, 100 mmol, 9.45 mL), N-methylmorpholine (NMM) (11.13 g, 110 mmol, 12.1 mL) and dimethylaminopyridine (DMAP) (1.22 g, 10.0 mmole) were added. Stirring was continued for 1 day at room temperature. The polymer was precipitated into diethyl ether (14 L) and isolated by filtration, washed with fresh 500 mL portions of diethyl ether, and dried in vacuo to give the block copolymer as a fine, nearly colorless powder (214.7 g, Yield=92.3%). $^1$H NMR (d$_6$-DMSO) δ 8.42-7.70 (theo. 50H, obs'd. 47H), 7.30 (theo. 250H, obs'd. 253H), 6.95 (theo. 120H, obs'd. 122H), 5.10-4.85 (theo. 80H, obs'd. 80H), 4.65-4.20 ((theo. 50H, obs'd. 56H), 3.72-3.25 (theo. 1087H, obs'd. 1593H), 3.05-2.45 (theo. 80H, obs'd. 83H), 2.44-1.60 (theo. 40H, obs'd. 42H).

Example 11

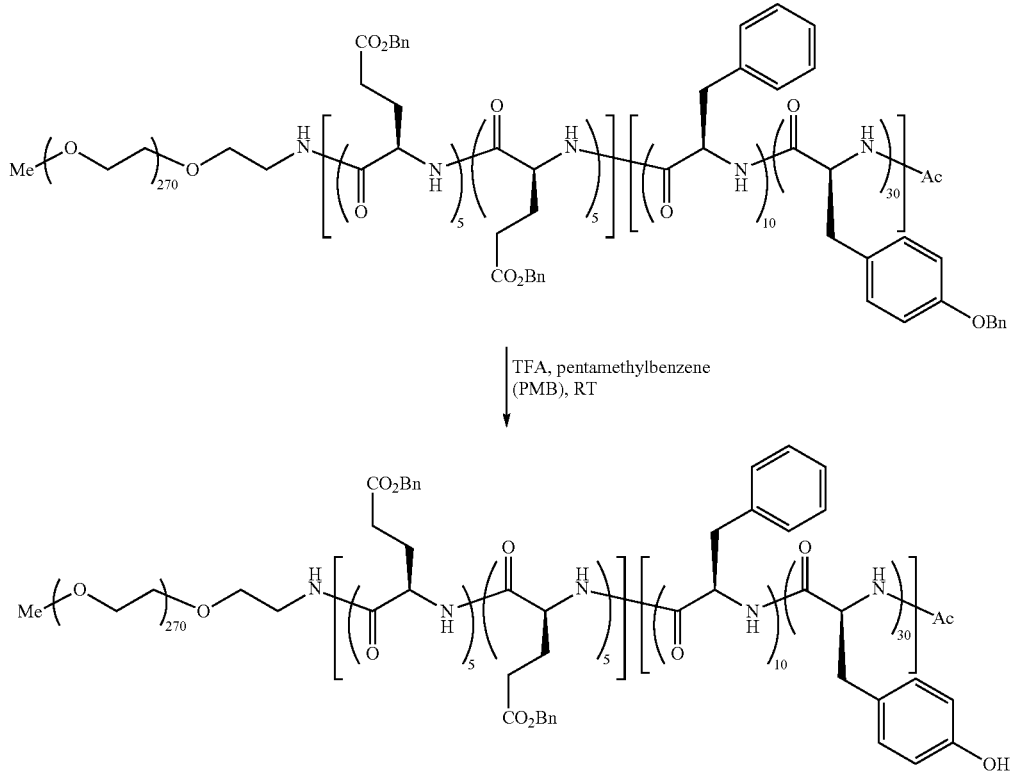

mPEG12K-b-Poly-[d-Glu(OBn)₅-Co-Glu(OBn)₅]-b-Poly(Tyr(OH)₃₀-Co-d-Phe₁₀)-Ac mPEG12K-b-Poly-(d-Glu(OBn)₅-co-d-Phe₁₀)-Ac from Example 10 (151.3 g, 6.5 mmol) and pentamethylbenzene (86.1 g, 0.58 mole) were dissolved into 1400 mL of trifluoroacetic acid (TFA). The reaction was rapidly stirred for six hours at room temperature. The TFA was removed on a rotary evaporator with the water bath temperature not exceeding 35° C. The resultant stiff paste was dissolved in 800 mL of dry THF and the crude product was precipitated into 12 L diethyl ether while cooling to −30° C. The resultant solid was collected by filtration, redissolved in 500 mL of dry THF and reprecipitated into 3 μL diethyl ether. A nearly colorless, odorless, fluffy polymer was obtained after drying the product overnight in vacuo (126.0 g, Yield=94.2%). ¹H NMR (d₆-DMSO) δ 9.09 (theo. 30H, obs'd. 29.4H), 8.50-7.75 (theo. 50H, obs'd. 52.7H), 7.40-6.45 (theo. 220H, obs'd. 220H), 5.04 (theo. 20H, obs'd. 17.5H), 4.70-4.20 (theo. 50H, obs'd. 54.5H), 3.91-3.05 (theo. 1087H, obs'd. 1391H), 3.03-2.10 (theo. 80H, obs'd. 91H), 2.09-1.50 (theo. 40H, obs'd. 46H).

Example 12 mPEG12K-b-Poly-[d-Glu(NHOH)₅-Co-Glu(NHOH)₅]-b-Poly(Tyr(OH)₃₀-Co-d-Phe₁₀)-Ac mPEG12K-b-Poly-[d-Glu(OBn)₅-co-Glu(OBn)₅]-b-Poly(Tyr(OH)₃₀-co-d-Phe₁₀)-Ac (113.3 g, 5.5 mmol) was dissolved in 1130 mL of dry THF and treated with hydroxylamine solution (50% aqueous, 2.20 mole, 146 mL) and 1,5,7-triazabicyclo [4.4.0]dec-5-ene (TBD, 2.30 g, 16.5 mmol). The resultant slightly turbid solution was stirred at 50° C. for 19 hours under N₂, cooled to room temperature and diluted with 1130 mL MeOH. The crude product was precipitated from 8 L diethyl ether while cooling to −30° C. The resultant solid was collected by filtration, redissolved in a mixture of 250 mL of dry THF and 125 mL acetone, treated with acetic acid (4.72 g, 79 mmol, 4.5 mL), heated to reflux for five minutes, and then allowed to stir at ambient temperature for 1.5 hours. The product was precipitated by addition of 2 L diethyl ether, collected by suction filtration, washed with fresh portions of diethyl ether, and dried overnight in vacuo to afford 106.3 g (Yield=97.5%) of nearly colorless, fluffy polymer. ¹H NMR (d₆-DMSO δ 9.12 (theo. 30H, obs'd. 30H), 8.80-7.75 (theo. 50H, obs'd. 38.4H), 7.15 (theo. 50H, obs'd. 50H), 6.80 (theo. 120H, obs'd. 120H), 4.65-4.05 (theo. 50H, obs'd. 50.4H), 3.80-3.15 (theo. 1087H, obs'd. 1360H), 3.00-2.20 (theo. 80H, obs'd. 79H), 2.15-1.60 (theo. 40H, obs'd. 40H).

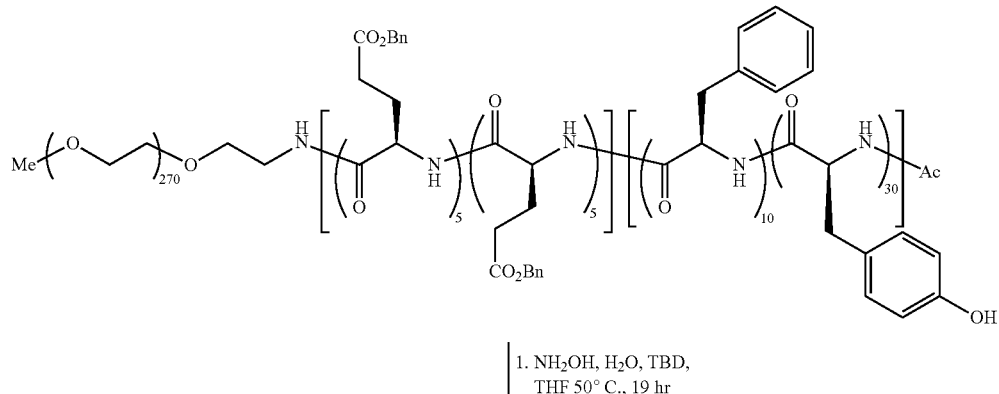

1. NH₂OH, H₂O, TBD, THF 50° C., 19 hr
2. THF, acetone (2, 1), HOAc (cat), 1.5 hr

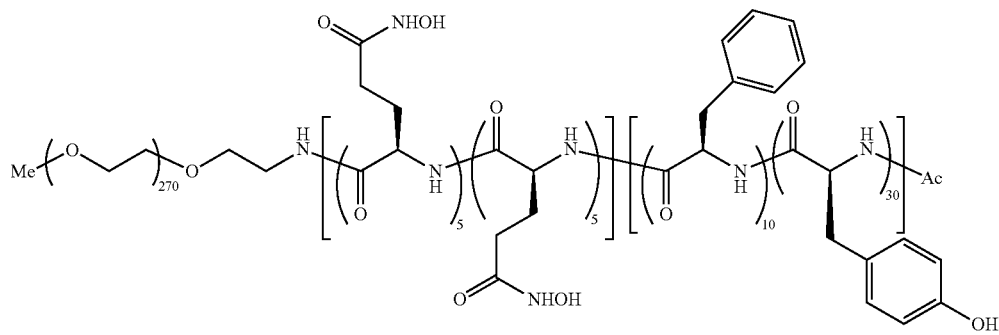

Example 13

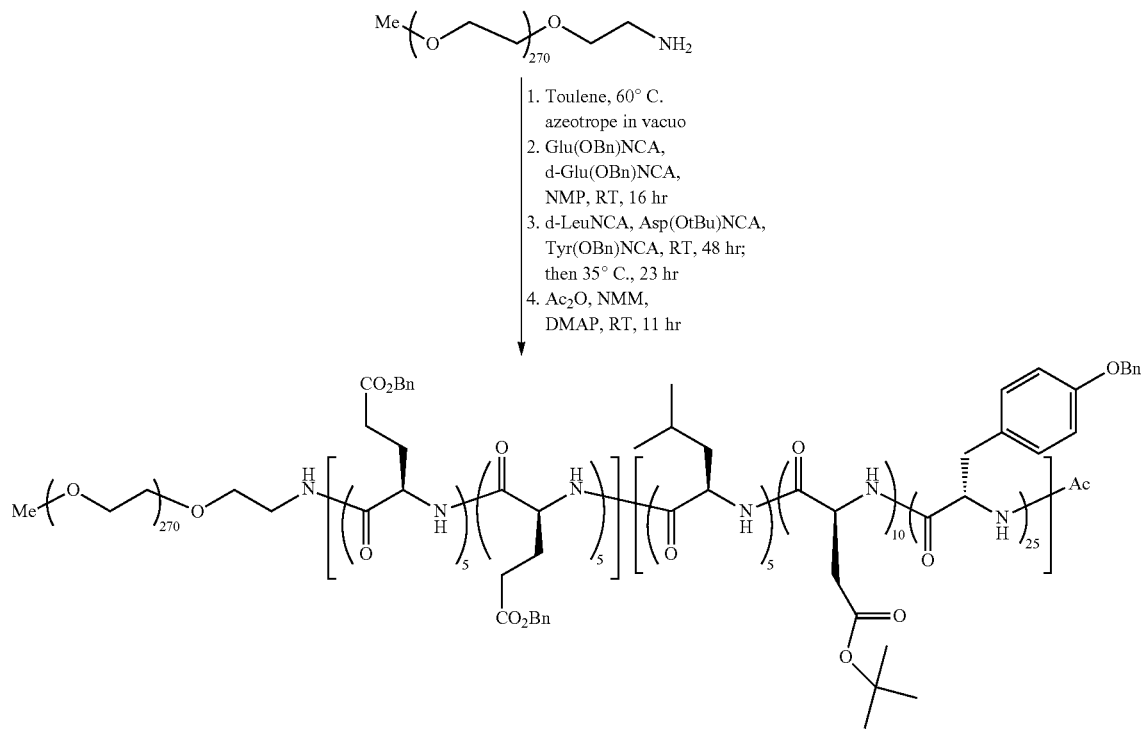

mPEG12K-b-Poly-(d-Glu(OBn)$_5$-Co-Glu(OBn)$_5$)-b-Poly (d-Leu$_5$-Co-Asp(OtBu)$_{10}$-Co-Tyr(OBn)$_{25}$)-Ac Using the general protocol detailed in Example 10 and substituting the appropriate NCA starting materials afforded a crude polymer that was precipitated with 12 volumes of diethyl ether, then reprecipitated from dichloromethane/diethyl ether: 1,12. After filtration and drying in vacuo, the title compound (Yield=93.9%) was obtained as a fine, colorless, odorless solid.

Example 14

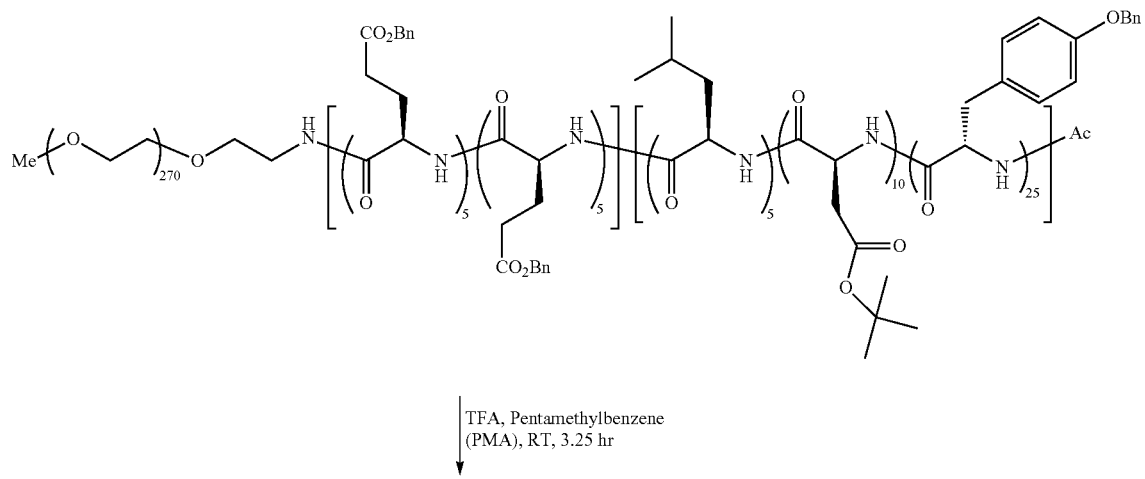

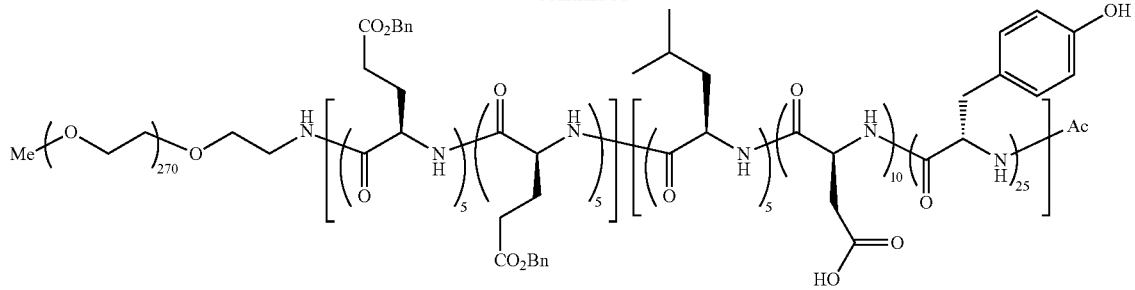

mPEG12K-b-Poly-(d-Glu(OBn)$_5$-Co-Glu(OBn)$_5$)-b-Poly(d-Leu$_5$-Co-Asp(OH)$_{10}$-Co-Tyr(OH)$_{25}$)-Ac By using the method of Example 11 and substituting mPEG12K-b-Poly-(d-Glu(OBn)$_5$-co-Glu(OBn)$_5$)-b-Poly(d-Leu$_5$-co-Asp(OtBu)$_{10}$-co-Tyr(OBn)$_{25}$)-Ac as starting material, reaction for three hours, 15 minutes at room temperature afforded the title product (Yield=97.0%) as a fluffy, colorless, odorless polymer.

Example 15

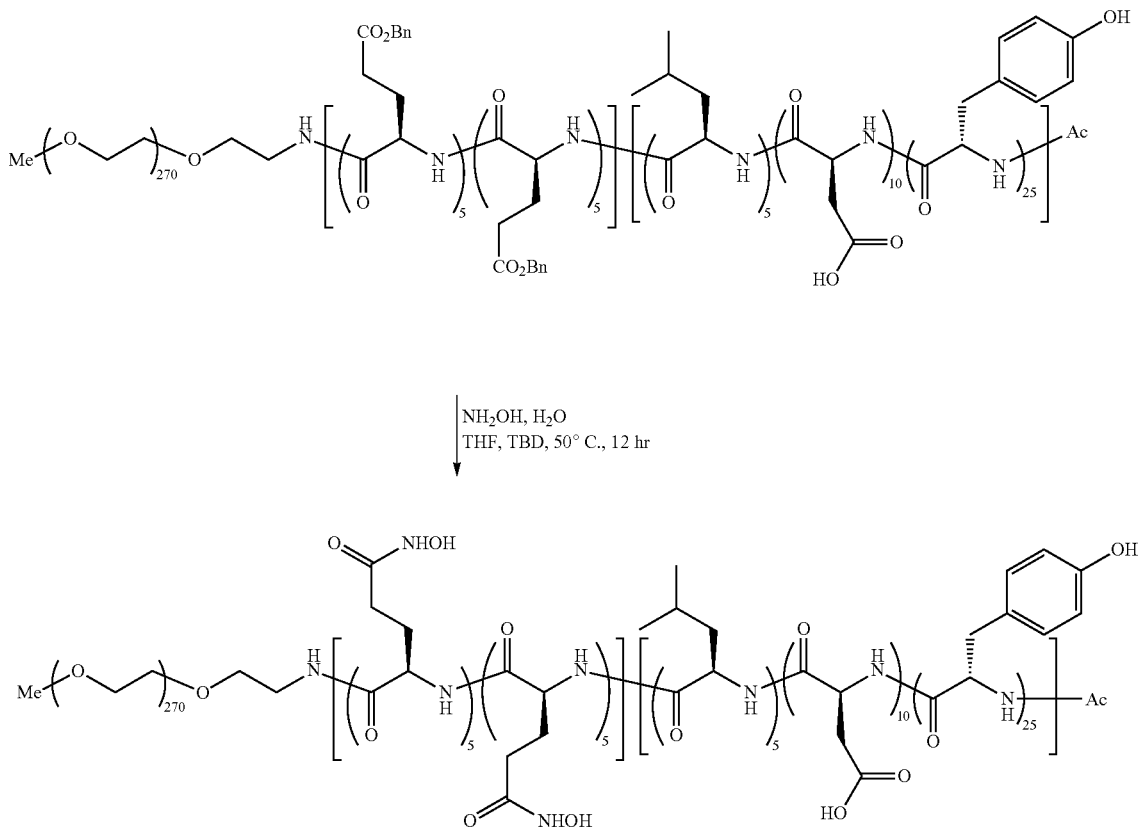

mPEG12K-b-Poly-(d-Glu(NHOH)$_5$-Co-Glu(NHOH)$_5$)-b-Poly(d-Leu$_5$-Co-Asp(OH)$_{10}$-Co-Tyr(OH)$_{25}$)-Ac mPEG12K-b-Poly-(d-Glu(OBn)$_5$-co-Glu(OBn)$_5$)-b-Poly(d-Leu$_{15}$-co-Asp(OH)$_{10}$-co-Tyr(OH)$_{25}$)-Ac (20.81 g, 1.0 mmol) was dissolved in 210 mL of THF and treated with hydroxylamine solution (50% aqueous, 0.80 mole, 53.0 mL) and 1,5,7-triazabicyclo[4.4.0]dec-5-ene (TBD, 0.84 g, 6.0 mmol). The resultant slightly turbid solution was stirred at 50° C. for 17 hours under N$_2$, cooled to room temperature and diluted with 210 mL of MeOH. The crude product was precipitated with 1 L diethyl ether, filtered, washed with fresh portions of diethyl ether, and dried overnight in vacuo (Yield=93.3%, hydroxylamine salt) as a fine, colorless polymer.

Example 16

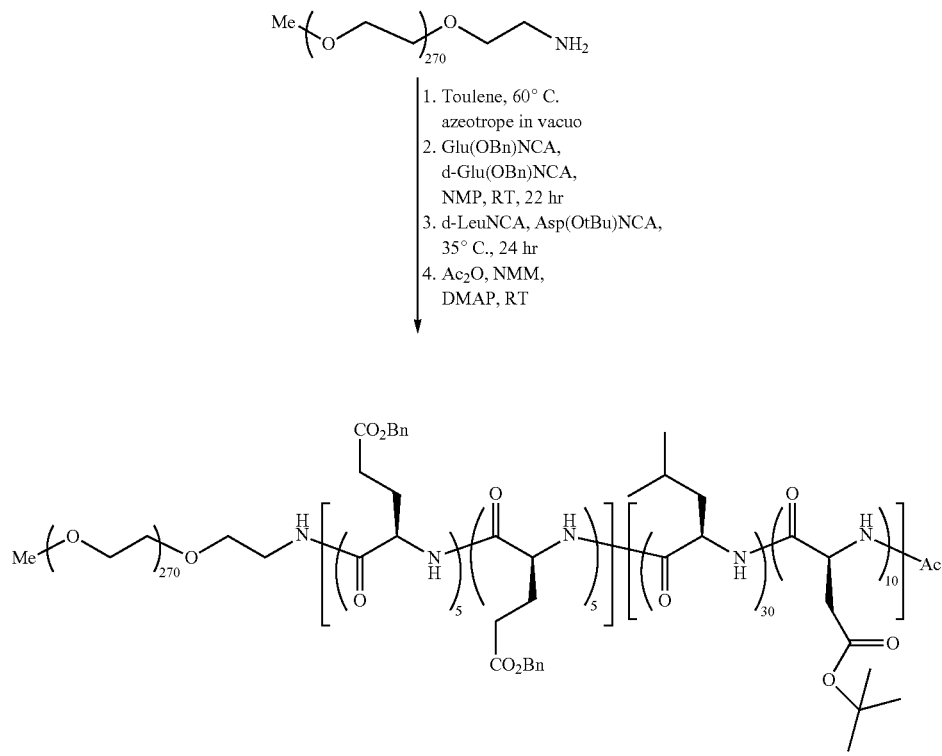

mPEG12K-b-Poly-(d-Glu(OBn)$_5$-Co-Glu(OBn)$_5$)-b-Poly(d-Leu$_{30}$-Co-Asp(OtBu)$_{10}$)-Ac Using the general protocol detailed in Example 10 and substituting the appropriate NCA starting materials afforded a crude polymer that was precipitated with 30 volumes of diethyl ether/heptane: 6,1, then reprecipitated from dichloromethane/diethyl ether: 1,20. After filtration and drying in vacuo, the title compound (Yield=90.7%) was obtained as a cream colored, odorless solid.

Example 17

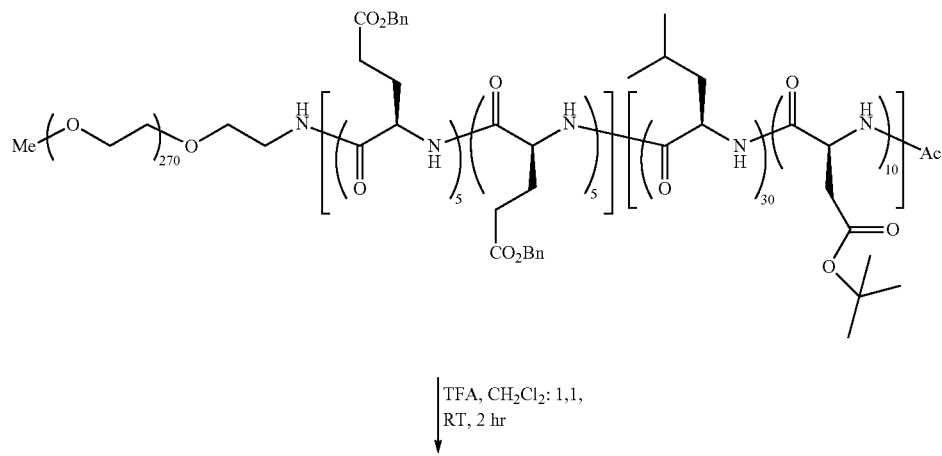

-continued

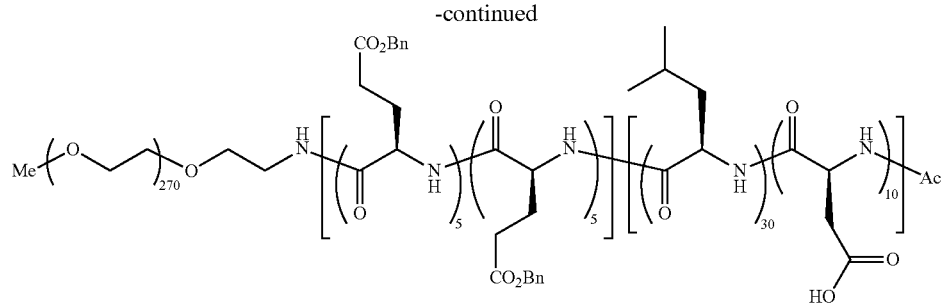

mPEG12K-b-Poly-(d-Glu(OBn)$_5$-Co-Glu(OBn)$_5$)-b-Poly(d-Leu$_{30}$-Co-Asp(OH)$_{10}$)-Ac By using the method of Example 11, substituting mPEG12K-b-Poly-(d-Glu(OBn)$_5$-co-Glu(OBn)$_5$)-b-Poly(d-Leu$_{30}$-co-Asp(OtBu)$_{10}$)-Ac as starting material and omitting PMB, reaction for two hours at room temperature afforded the title product (Yield=97.4%) as a fluffy, colorless polymer.

Example 18

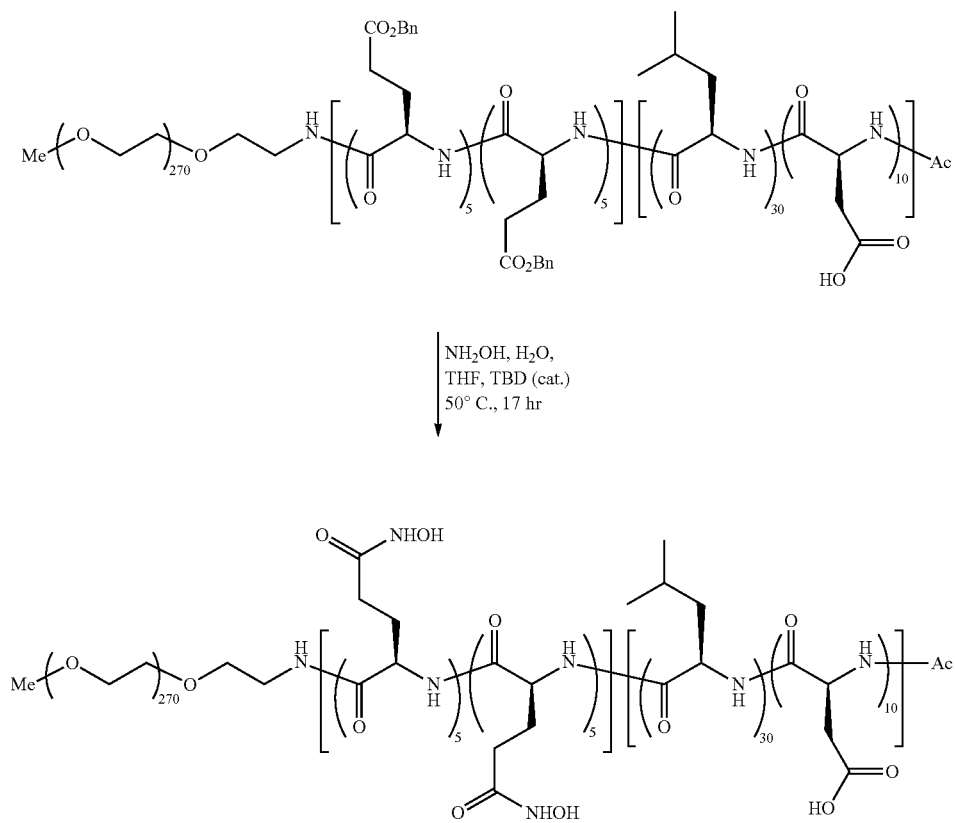

mPEG12K-b-Poly-(d-Glu(NHOH)$_5$-Co-Glu(NHOH)$_5$)-b-Poly(d-Leu$_{30}$-Co-Asp(OH)$_{10}$)-Ac By using the method of Example 12 and substituting mPEG12K-b-Poly-(d-Glu(OBn)$_5$-co-Glu(OBn)$_5$)-b-Poly(d-Leu$_{30}$-co-Asp(OH)$_{10}$)-Ac as starting material, reaction for 17 hours at 50° C. afforded the title product (Yield=96.4%, hydroxylamine salt) as a fine, colorless polymer.

Example 19

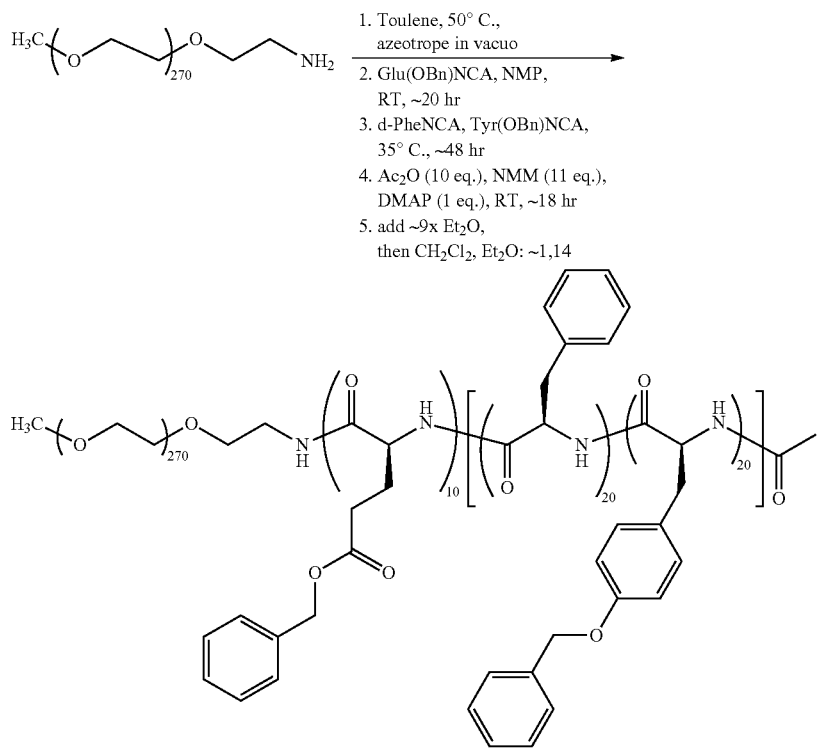

mPEG12K-b-Poly-(Glu(OBn)$_{10}$)-b-Poly(d-Phe$_{20}$-Co-Tyr(OBn)$_{20}$)-Ac

Using the general protocol detailed in Example 10 and substituting the appropriate NCA starting materials afforded a crude polymer that was precipitated with 9 volumes of diethyl ether, then reprecipitated from dichloromethane/diethyl ether: 1,14. After filtration and drying in vacuo, the title compound (Yield=89%) was obtained as a cream colored, odorless solid.

Example 20

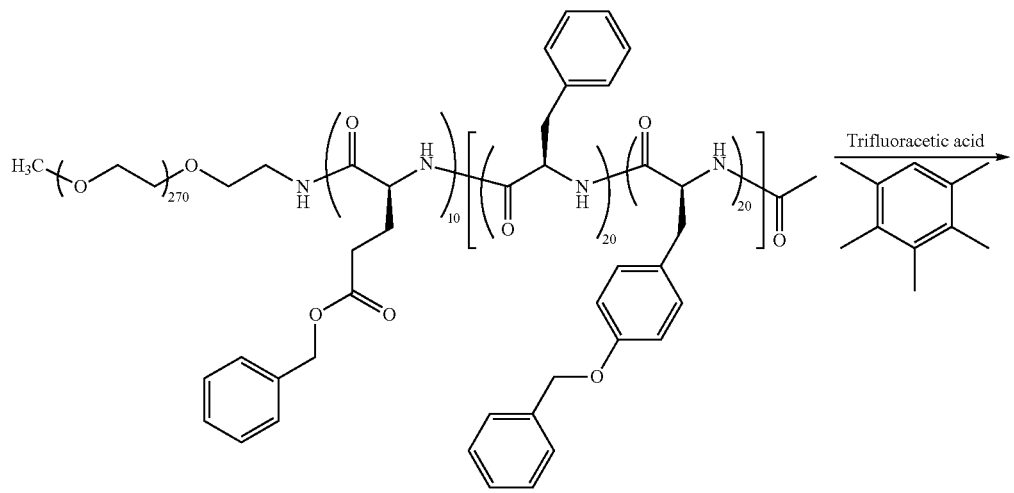

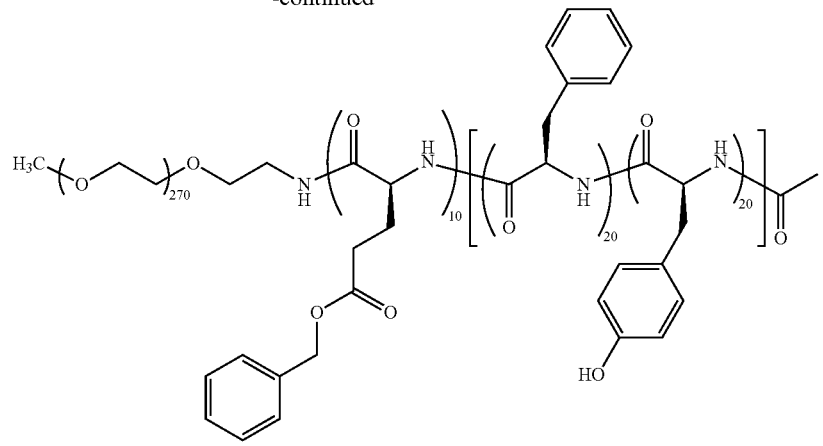

mPEG12K-b-Poly-(Glu(OBn)$_{10}$)-b-Poly(d-Phe$_{20}$-Co-Tyr$_{20}$)-Ac

By using the method of Example 11, substituting mPEG12K-b-Poly-(Glu(OBn)$_{10}$)-b-Poly(d-Phe$_{20}$-co-Tyr(OBz)$_{20}$)-Ac as starting material and reacting for four hours at room temperature afforded the title product (Yield=87%) as a fluffy, colorless polymer.

Example 21

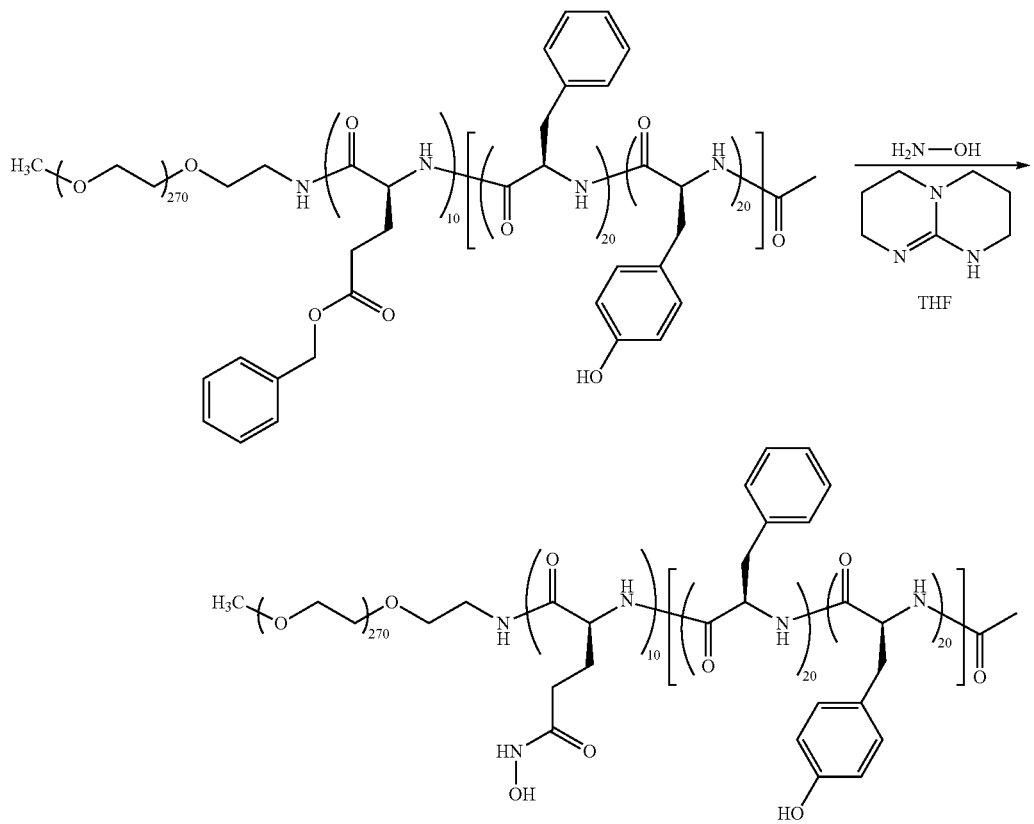

mPEG12K-b-Poly-(Glu(NHOH)$_{10}$)-b-Poly(d-Phe$_{20}$-Co-Tyr$_{20}$)-Ac

By using the Tyr$_{20}$)-Ac as starting material, reaction for 17 hours at 50° C. afforded the title product (Yield=94%, hydroxylamine salt) as a fine, colorless polymer.

Example 22

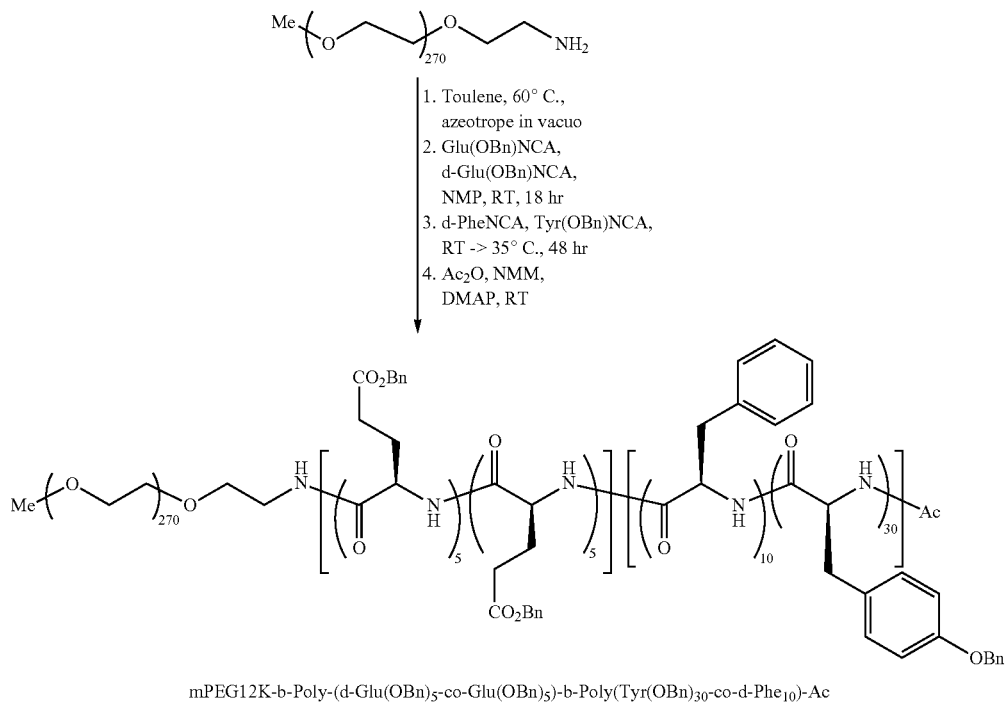

mPEG12K-b-Poly-(d-Glu(OBn)₅-co-Glu(OBn)₅)-b-Poly(Tyr(OBn)₃₀-co-d-Phe₁₀)-Ac

Synthesis of mPEG12K-b-Poly-(d-Glu(OBn)₅-Co-Glu(OBn)₅)-b-Poly (Tyr(OBn)₃₀-Co-d-Phe₁₀)-Ac m-PEG10k-NH₂ (119.7 g, 10.0 mmol, Example 3) was weighed into an oven-dried, 2 L-round-bottom flask, dissolved in toluene (1 L), and dried by azeotropic distillation. After distillation to dryness, the polymer was left under vacuum for three hours. The flask was subsequently backfilled with N₂, re-evacuated under reduced pressure, and dry N-methylpyrrolidone (NMP) (1100 mL) was introduced by cannula. The mixture was briefly heated to 40° C. to expedite dissolution and then recooled to 25° C. Glu(OBn) NCA (13.16 g, 50.0 mmol) and d-Glu(OBn) NCA (13.16 g, 50.0 mmol) were added to the flask, and the reaction mixture was allowed to stir for 16 hours at ambient room temperature under nitrogen gas. Then, d-Phe NCA (19.12 g, 100 mmol) and Tyr (OBn) NCA (89.19 g, 300 mmol) were added and the solution was allowed to stir at 35° C. for 48 hours at which point the reaction was complete (GPC, DMF/0.1% LiBr). The solution was cooled to room temperature and acetic anhydride (10.21 g, 100 mmol, 9.45 mL), N-methylmorpholine (NMM) (11.13 g, 110 mmol, 12.1 mL) and dimethylaminopyridine (DMAP) (1.22 g, 10.0 mmole) were added. Stirring was continued for 1 day at room temperature. The polymer was precipitated into diethyl ether (14 L) and isolated by filtration, washed with fresh 500 mL portions of diethyl ether, and dried in vacuo to give the block copolymer as a fine, nearly colorless powder (214.7 g, Yield=92.3%). $^1$H NMR (d₆-DMSO) δ 8.42-7.70 (theo. 50H, obs'd. 47H), 7.30 (theo. 250H, obs'd. 253H), 6.95 (theo. 120H, obs'd. 122H), 5.10-4.85 (theo. 80H, obs'd. 80H), 4.65-4.20 ((theo. 50H, obs'd. 56H), 3.72-3.25 (theo. 1087H, obs'd. 1593H), 3.05-2.45 (theo. 80H, obs'd. 83H), 2.44-1.60 (theo. 40H, obs'd. 42H).

Example 23

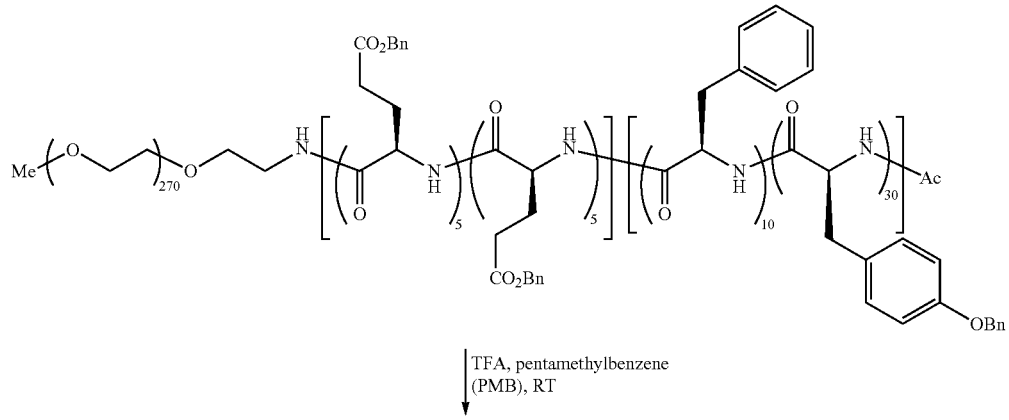

TFA, pentamethylbenzene (PMB), RT

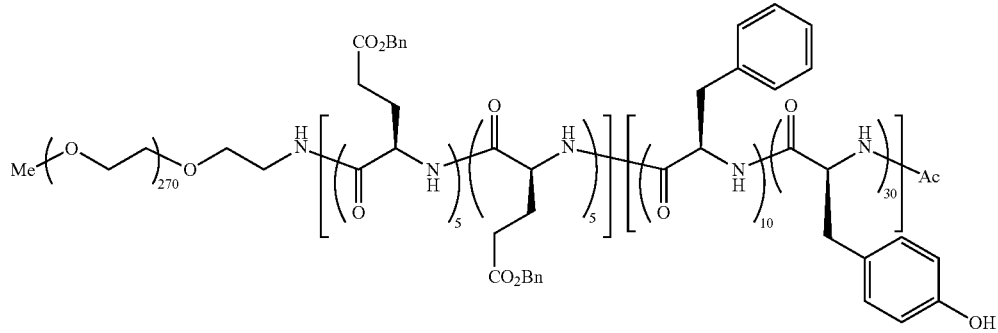

mPEG12K-b-Poly-[d-Glu(OBn)$_5$-co-Glu(OBn)$_5$]-b-Poly-(Tyr(OH)$_{30}$-co-d-Phe$_{10}$)-Ac Synthesis of mPEG12K-b-Poly-[d-Glu(OBn)$_5$-Co-Glu(OBn)]-b-Poly-(Tyr(OH)$_{30}$-Co-d-Phe$_{10}$)-Ac mPEG12K-b-Poly-[d-Glu(OBn)S-co-Glu(OBn)$_5$]-b-Poly-(Tyr(OBn)$_{30}$-co-d-Phe$_{10}$)-Ac (151.3 g, 6.5 mmol) and pentamethylbenzene (86.1 g, 0.58 mole) were dissolved into 1400 mL of trifluoroacetic acid (TFA). The reaction was rapidly stirred for six hours at room temperature. The TFA was removed on a rotary evaporator with the water bath temperature not exceeding 35° C. The resultant stiff paste was dissolved in 800 mL of dry THF and the crude product was precipitated into 12 μL diethyl ether while cooling to −30° C. The resultant solid was collected by filtration, redissolved in 500 mL of dry THF and reprecipitated into 3 L diethyl ether. A nearly colorless, odorless, fluffy polymer was obtained after drying the product overnight in vacuo (126.0 g, Yield=94.2%). $^1$H NMR (d$_6$-DMSO) δ 9.09 (theo. 30H, obs'd. 29.4H), 8.50-7.75 (theo. 50H, obs'd. 52.7H), 7.40-6.45 (theo. 220H, obs'd. 220H), 5.04 (theo. 20H, obs'd. 17.5H), 4.70-4.20 (theo. 50H, obs'd. 54.5H), 3.91-3.05 (theo. 1087H, obs'd. 1391H), 3.03-2.10 (theo. 80H, obs'd. 91H), 2.09-1.50 (theo. 40H, obs'd. 46H).

Example 24

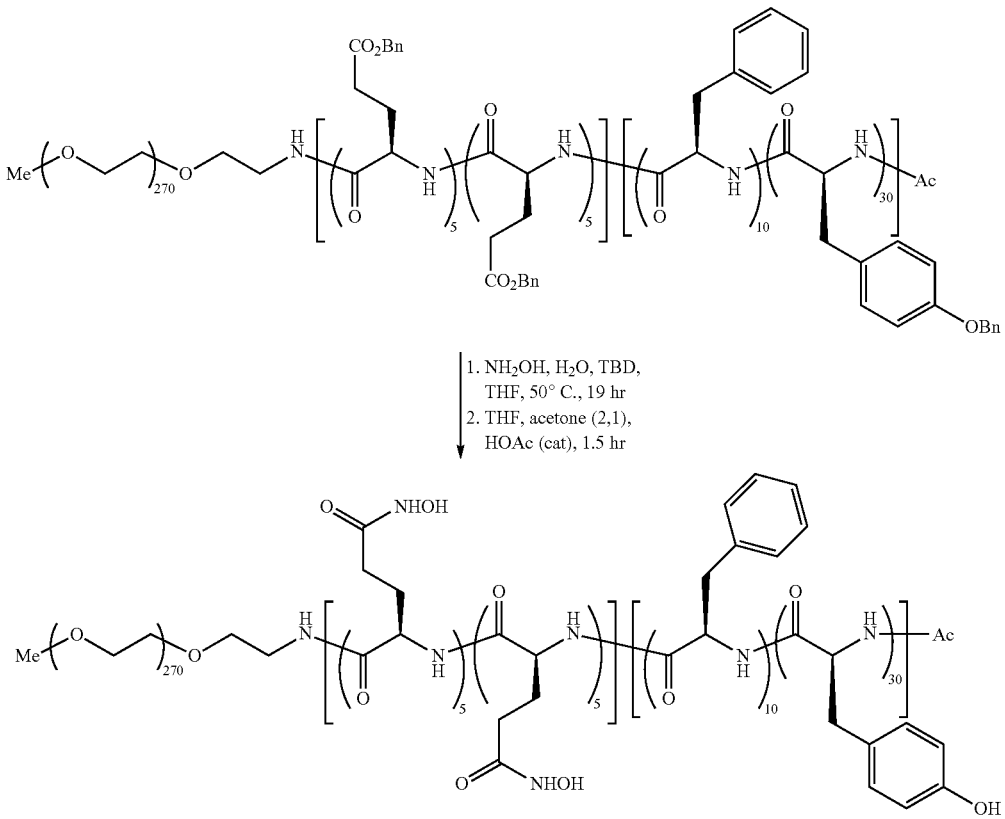

mPEG12K-b-Poly-[d-Glu(NHOH)$_5$-co-Glu(NHOH)$_5$]-b-Poly-(Tyr(OH)$_{30}$-co-d-Phe$_{10}$)-Ac

Synthesis of mPEG12K-b-Poly-[d-Glu(NHOH)$_5$-Co-Glu(NHOH)$_5$]-b-Poly-(Tyr(OH)$_{30}$-Co-d-Phe$_{10}$)-Ac mPEG12K-b-Poly-[d-Glu(OBn)$_5$-co-Glu(OBn)$_5$]-b-Poly-(Tyr(OH)$_{30}$-co-d-Phe$_{10}$)-Ac (113.3 g, 5.5 mmol) was dissolved in 1130 mL of dry THF and treated with hydroxylamine solution (50% aqueous, 2.20 mole, 146 mL) and 1,5,7-triazabicyclo [4.4.0]dec-5-ene (TBD, 2.30 g, 16.5 mmol). The resultant slightly turbid solution was stirred at 50° C. for 19 hours under N$_2$, cooled to room temperature and diluted with 1130 mL MeOH. The crude product was precipitated from 8 L diethyl ether while cooling to −30° C. The resultant solid was collected by filtration, redissolved in a mixture of 250 mL of dry THF and 125 mL acetone, treated with acetic acid (4.72 g, 79 mmol, 4.5 mL), heated to reflux for five minutes, and then allowed to stir at ambient temperature for 1.5 hours. The product was precipitated by addition of 2 L diethyl ether, collected by suction filtration, washed with fresh portions of diethyl ether, and dried overnight in vacuo to afford 106.3 g (Yield=97.5%) of nearly colorless, fluffy polymer. $^1$H NMR (d$_6$-DMSO δ 9.12 (theo. 30H, obs'd. 30H), 8.80-7.75 (theo. 50H, obs'd. 38.4H), 7.15 (theo. 50H, obs'd. 50H), 6.80 (theo. 120H, obs'd. 120H), 4.65-4.05 (theo. 50H, obs'd. 50.4H), 3.80-3.15 (theo. 1087H, obs'd. 1360H), 3.00-2.20 (theo. 80H, obs'd. 79H), 2.15-1.60 (theo. 40H, obs'd. 40H).

Example 25

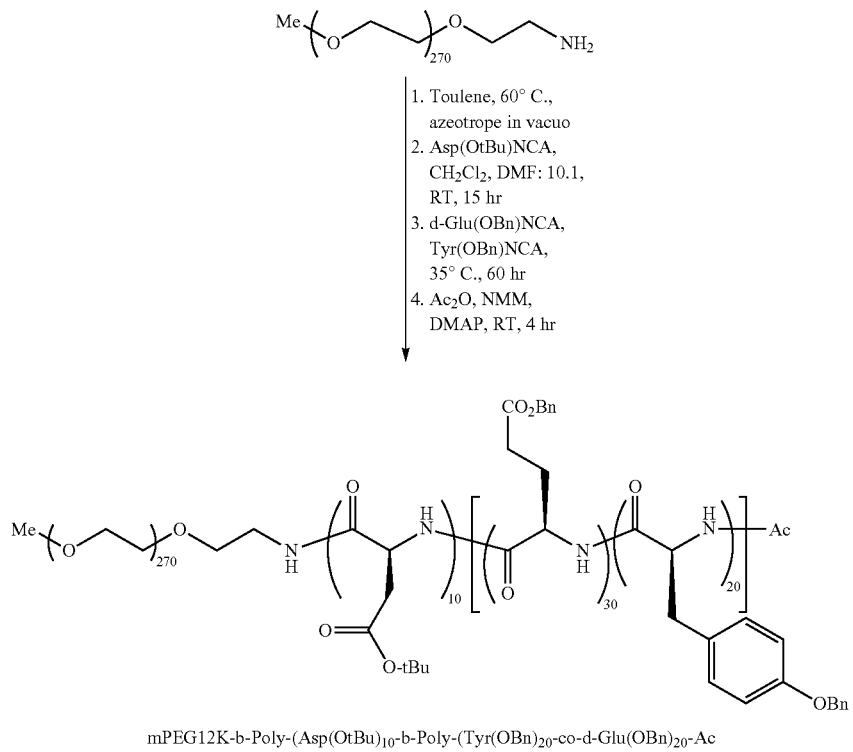

mPEG12K-b-Poly-(Asp(OtBu))$_{10}$-b-Poly-(Tyr(OBn))$_{20}$-co-d-Glu(OBn)$_{20}$-Ac

Synthesis of mPEG12K-b-Poly-(Asp(OtBu)$_{10}$-b-Poly-(Tyr(OBn)$_{20}$-Co-d-Glu(OBn)$_{20}$-Ac Using the protocol detailed in Example 22, replacing the NMP solvent with dichloromethane:DMF: 10,1, and substituting the appropriate NCA starting materials, the title compound (Yield=93.9%) was prepared as a fine, colorless, odorless solid. $^1$H NMR (d$_6$-DMSO) δ 8.42-7.85 (theo. 50H, obs'd. 51H), 7.30 (theo. 200H, obs'd. 198H), 6.98 (theo. 80H, obs'd. 72H), 5.15-4.85 (theo. 80H, obs'd. 80H), 4.68-4.20 (theo. 50H, obs'd. 46H), 3.72-3.25 (theo. 1087H, obs'd. 1415H), 3.05-1.50 (theo. 120H, obs'd. 114H), 1.35 (theo. 90H, obs'd. 76H).

Example 26

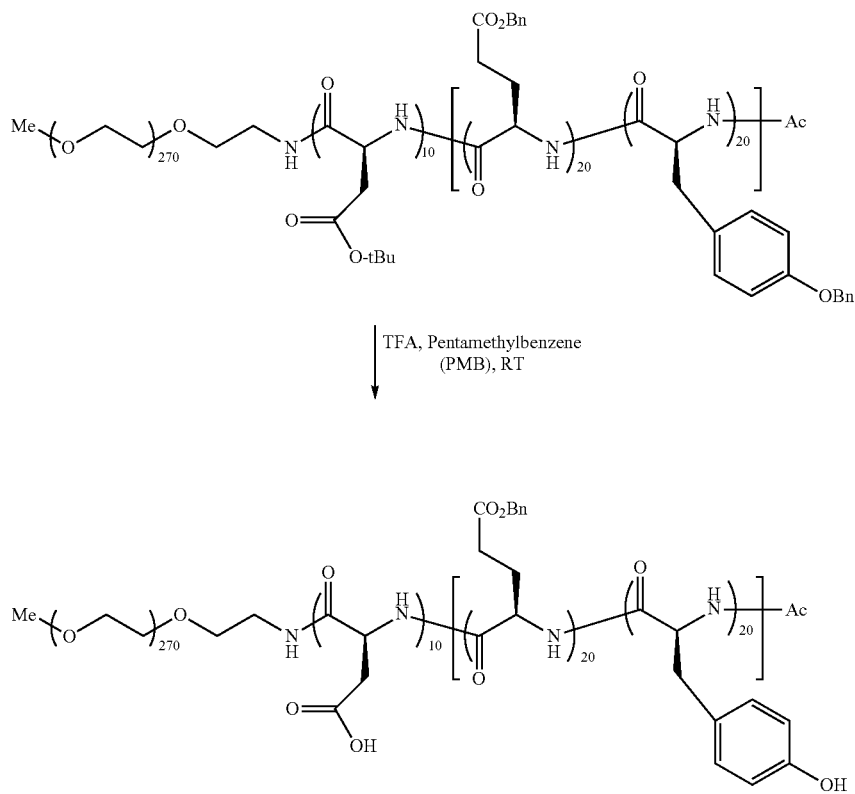

mPEG12K-b-Poly-(Asp(OH)₁₀-b-Poly-(Tyr(OH)₂₀-co-d-Glu(OBn)₂₀-Ac

Synthesis of mPEG12K-b-Poly-(Asp(OH)₁₀-b-Poly-(Tyr(OH)₂₀-Co-d-Glu(OBn)₂₀-Ac

By using the method of Example 23 and substituting mPEG12K-b-Poly-(Asp(OtBu)₁₀-b-Poly-(Tyr(OBn)₂₀-co-d-Glu(OBn)₂₀-Ac as starting material, reaction for three hours, 15 minutes at room temperature and precipitation from a mixture of dichloromethane, diethyl ether: 1,8.5 afforded the title product (Yield=98.9%) as a fine, colorless, odorless polymer. $^1$H NMR ($d_6$-DMSO) δ 12.38 (theo. 10H, obs'd. 9H), 9.13 (theo. 20H, obs'd. 17H), 8.40-7.80 (theo. 50H, obs'd. 43H), 7.32 (theo. 100H, obs'd. 82H), 6.80 (theo. 80H, obs'd. 83H), 5.04 (theo. 40H, obs'd. 34.2H), 4.60-4.20 (theo. 50H, obs'd. 55H), 3.80-3.20 (theo. 1087H, obs'd. 1100H), 2.95-1.45 (theo. 140H, obs'd. 154.6H)

Example 27

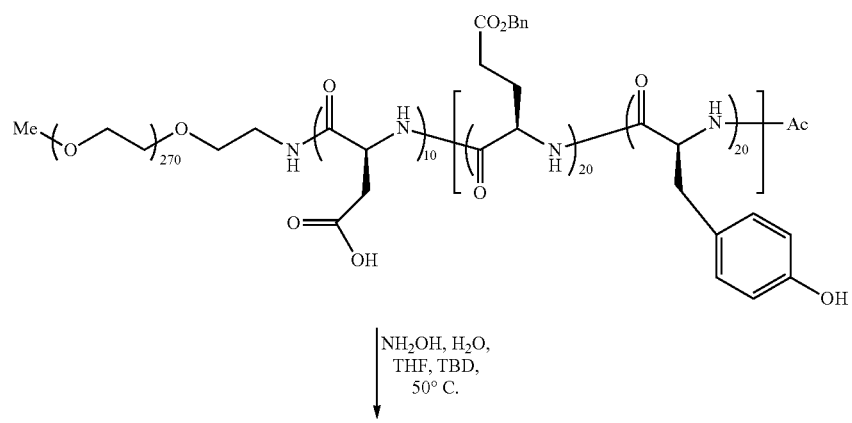

-continued

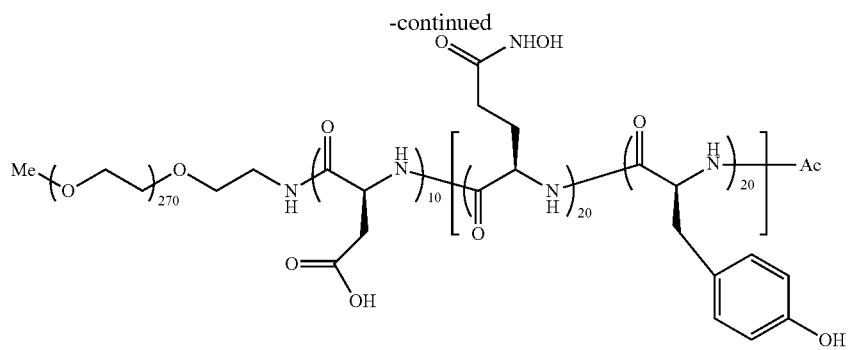

mPEG12K-b-Poly-(Asp(OH))$_{10}$-b-Poly-(Tyr(OH))$_{20}$-co-d-Glu(NHOH)$_{20}$-Ac Synthesis of mPEG12K-b-Poly-(Asp(OH))$_{10}$-b-Poly-(Tyr(OH))$_{20}$-Co-d-Glu(NHOH)$_{20}$-Ac mPEG12K-b-Poly-(Asp(OH))$_{10}$-b-Poly-(Tyr(OH))$_{20}$-co-d-Glu(OBn)$_{20}$-Ac (20.81 g, 1.0 mmol) was dissolved in 210 mL of THF and treated with hydroxylamine solution (50% aqueous, 0.80 mole, 53.0 mL) and 1,5,7-triazabicyclo[4.4.0]dec-5-ene (TBD, 0.84 g, 6.0 mmol). The resultant slightly turbid solution was stirred at 50° C. for 17 hours under N$_2$, cooled to room temperature and diluted with 210 mL of MeOH. The crude product was precipitated with 1 L diethyl ether, filtered, washed with fresh portions of diethyl ether, and dried overnight in vacuo to afford 19.68 g (Yield=98.5%) of colorless, fluffy polymer as the hydroxylamine salt. A portion of the hydroxylamine salt (10.0 g) was dissolved in 1 L of 30% tert-butyl alcohol/water, treated with ammonium carbonate (3.33 g), and lyophilized to afford the native carboxylic acid salt form (quantitative yield) as a colorless, odorless, fluffy solid. $^1$H NMR (d$_6$-DMSO, hydroxylamine salt) δ 9.08 (theo. 20H, obs'd. 10H), 6.80 (theo. 80H, obs'd. 80H), 4.60-4.02 (theo. 50H, obs'd. 54.7H), 3.80-3.15 (theo. 1087H, obs'd. 1211H), 2.90 (theo. 40H, obs'd. 45H), 2.80-1.50 (theo. 100H, obs'd. 120H). Spectrum showed traces of solvent that affected integration in the upfield region.

Example 28

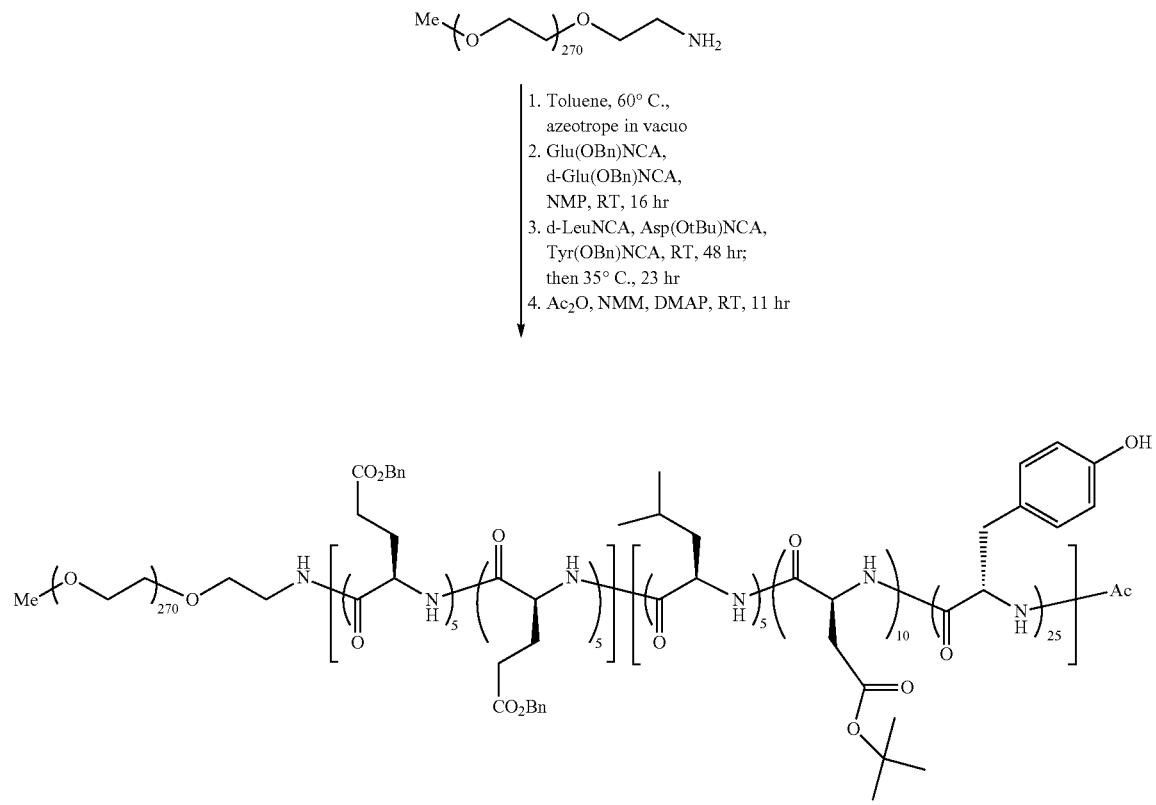

mPEG12K-b-Poly-(d-Glu(OBN)$_5$-co-Glu(OBn)$_5$)-b-Poly(d-Leu$_5$-co-Asp(OtBu)$_{10}$-co-Tyr(OBn)$_{25}$)-Ac

Synthesis of mPEG12K-b-Poly-(d-Glu(OBn)₅-Co-Glu(OBn)₅)-b-Poly(d-Leu₅-Co-Asp(OtBu)₁₀-Co-Tyr(OBn)₂₅)-Ac Using the general protocol detailed in Example 22 and substituting the appropriate NCA starting materials afforded a crude polymer that was precipitated with 12 volumes of diethyl ether, then reprecipitated from dichloromethane/diethyl ether: 1,12. After filtration and drying in vacuo, the title compound (Yield=89.2%) was obtained as a fine, colorless, odorless solid. $^1$H NMR ($d_6$-DMSO) δ 8.52-7.75 (theo. 50H, obs'd. 49H), 7.35 (theo. 175H, obs'd. 198H), 7.11 (theo. 50H, obs'd. 49H), 6.80 (theo. 50H, obs'd. 50H), 5.10-4.75 (theo. 70H, obs'd. 75H), 4.70-4.15 (theo. 50H, obs'd. 56H), 3.72-3.25 (theo. 1087H, obs'd. 1580H), 3.05-1.65 (theo. 110H, obs'd. 144H), 1.58-0.55 (theo. 135H, obs'd. 155H).

Example 29

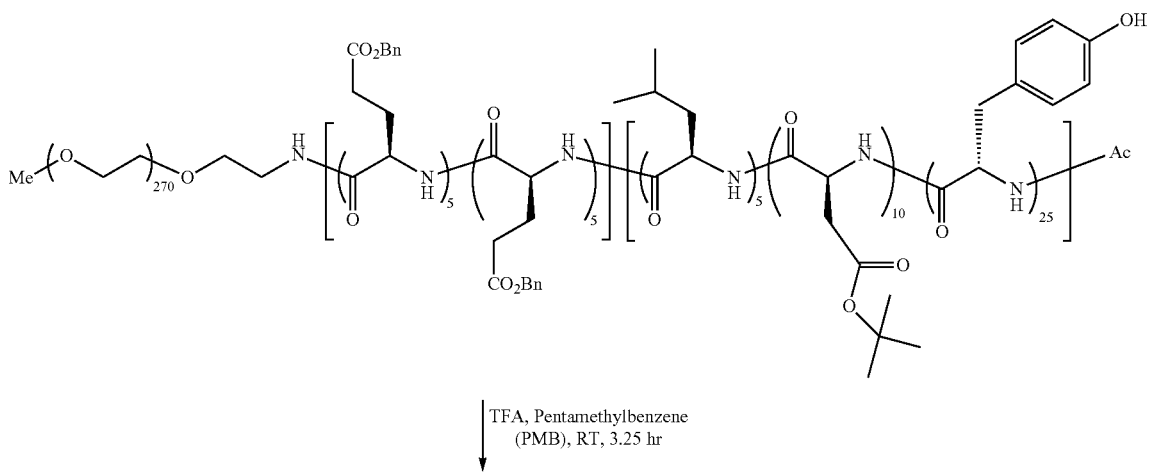

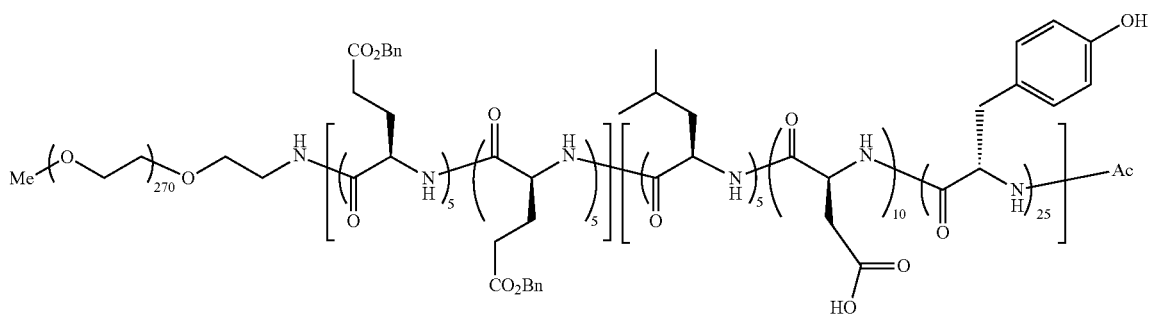

mPEG12K-b-Poly-(d-Glu(OBn)₅-co-Glu(OBn)₅)-b-Poly-(d-Leu₅-co-Asp(OH)₁₀-co-Tyr(OH)₂₅)-Ac

Synthesis of mPEG12K-b-Poly-(d-Glu(OBn)₅-Co-Glu(OBn)₅)-b-Poly(d-Leu₅-Co-Asp(OH)₁₀-Co-Tyr(OH)₂₅)-Ac By using the method of Example 23 and substituting mPEG12K-b-Poly-(d-Glu(OBn)₅-co-Glu(OBn)₅)-b-Poly(d-Leu₅-co-Asp(OtBu)₁₀-co-Tyr(OBn)₂₅)-Ac as starting material, reaction for three hours, 15 minutes at room temperature and precipitations from a mixture of dichloromethane, diethyl ether: 1,24 followed by dichloromethane, diethyl ether: 1,12 afforded the title product (Yield=97.0%) as a fluffy, colorless, odorless polymer. $^1$H NMR ($d_6$-DMSO) δ 9.4-8.5 (theo. 35H, obs'd. 34H), 8.40-7.75 (theo. 50H, obs'd. 61H), 7.35-7.15 (theo. 50H, obs'd. 43H), 6.98 (theo. 50H, obs'd. 49H), 6.60 (theo. 50H, obs'd. 50H), 5.04 (theo. 20H, obs'd. 18H), 4.65-4.10 (theo. 50H, obs'd. 58H), 3.80-3.20 (theo. 1087H, obs'd. 1367H, contains masked H₂O peak), 3.00-2.15 (theo. 90H, obs'd. 95H), 2.05-1.70 (theo. 20H, obs'd. 26H), 1.63-0.57 (theo. 45H, obs'd. 45H).

Example 30

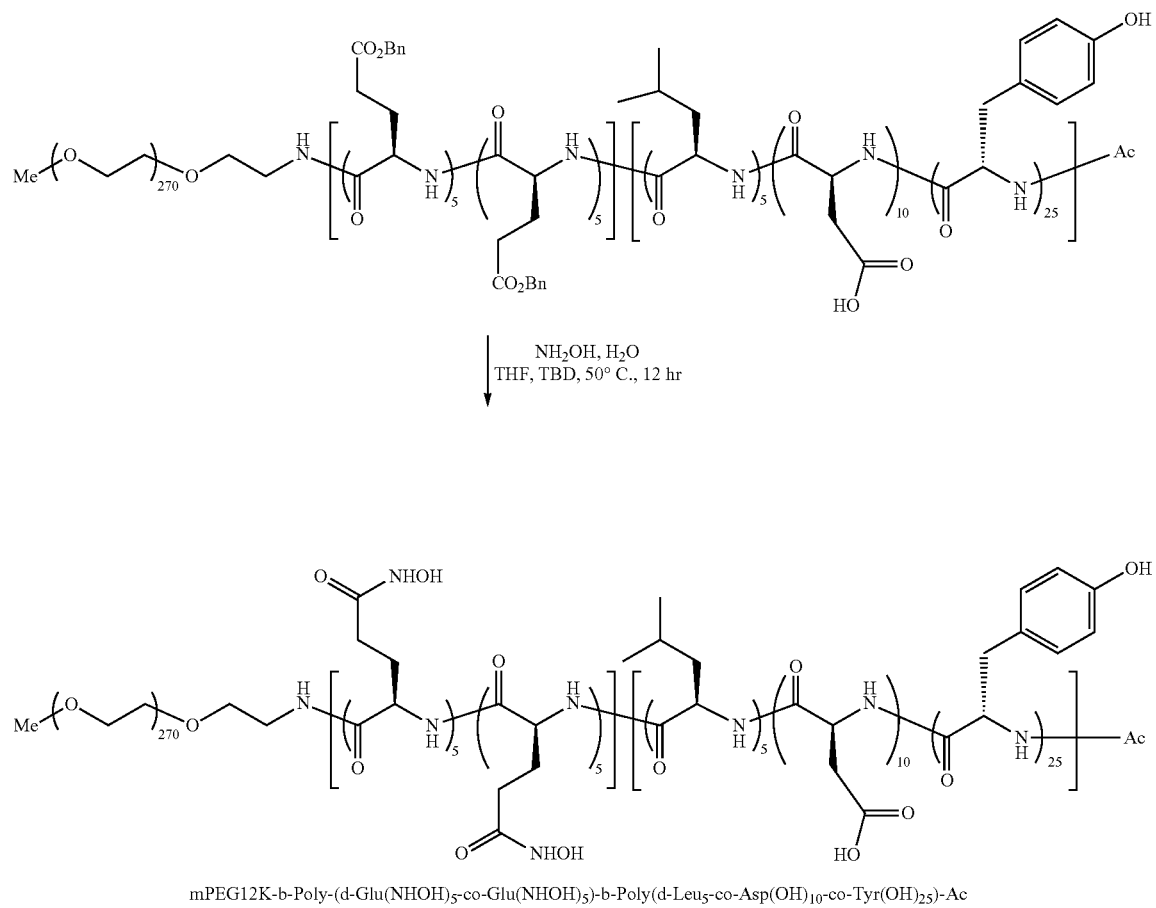

mPEG12K-b-Poly-(d-Glu(NHOH)₅-co-Glu(NHOH)₅)-b-Poly(d-Leu₅-co-Asp(OH)₁₀-co-Tyr(OH)₂₅)-Ac Synthesis of mPEG12K-b-Poly-(d-Glu(OBn)₅-Co-Glu(OBn)₅)-b-Poly(d-Leu₁₅-Co-Asp(OH)₁₀-Co-Tyr(OH)₂₅)-Ac By using the method of Example 27 and substituting mPEG12K-b-Poly-(d-Glu(OBn)₅-co-Glu(OBn)₅)-b-Poly(d-Leu₅-co-Asp(OH)₁₀-co-Tyr(OH)₂₅)-Ac as starting material, reaction for 12 hours at 50° C. afforded the title product (Yield=93.3%, hydroxylamine salt) as a fine, colorless polymer. $^1$H NMR (d$_6$-DMSO) δ 9.4-8.5 (theo. 35H, obs'd. 34H), 8.60-7.75 (theo. 50H, obs'd. 43H), 7.2-6.85 (theo. 50H, obs'd. 55H), 6.60 (theo. 50 H, obs'd. 50H), 4.60-4.00 (theo. 50H, obs'd. 41H), 3.80-3.00 (theo. 1087H, obs'd. 1174H, contains masked H₂O peak), 3.00-1.65 (theo. 110H, obs'd. 124H), 1.63-0.57 (theo. 45H, obs'd. 40H).

Example 31

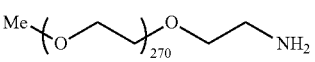

1. Toluene, 60° C., azeotrope in vacuo
2. Glu(OBn)NCA, d-Glu(OBn)NCA, NMP, RT, 22 hr
3. d-LeuNCA, Asp(OtBu)NCA, 35° C. 24 hr
4. Ac₂O, NMM, DMAP, RT

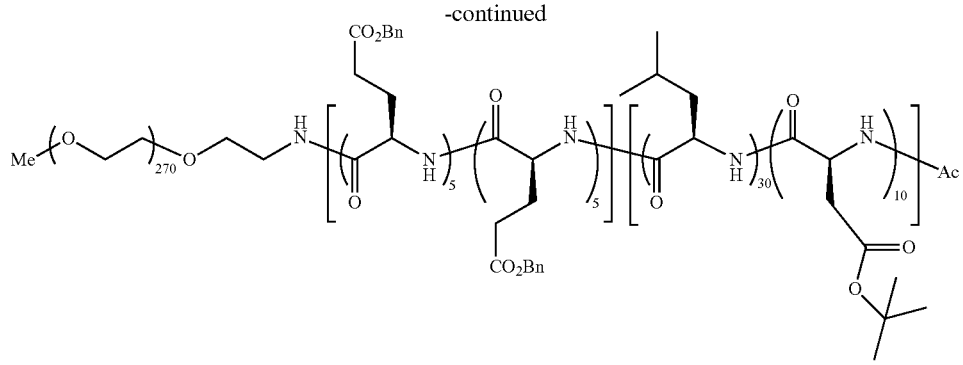

mPEG12K-b-Poly-(d-Glu(OBN)$_5$-co-Glu(OBn)$_5$)-b-Poly(d-Leu$_{30}$-co-Asp(OtBu)$_{10}$)-Ac Synthesis of mPEG12K-b-Poly-(d-Glu(OBn)$_5$-Co-Glu(OBn)$_5$)-b-Poly(d-Leu$_{30}$-Co-Asp(OtBu)$_{10}$)-Ac Using the general protocol detailed in Example 22 and substituting the appropriate NCA starting materials afforded a crude polymer that was precipitated with 30 volumes of diethyl ether/heptane: 6,1, then reprecipitated from dichloromethane/diethyl ether: 1,20. After filtration and drying in vacuo, the title compound (Yield=90.7%) was obtained as a cream colored, odorless solid. $^1$H NMR (d$_4$-MeOH) δ 7.31 (theo. 50H, obs'd. 66H), 5.04 (theo. 20H, obs'd. 20H), 4.45-3.97 (theo. 50H, obs'd. 37H), 3.95-3.25 (theo. 1087H, obs'd. 1876H), 3.05-0.80 (theo. 420H, obs'd. 313H).

Example 32

Synthesis of mPEG12K-b-Poly-(d-Glu(NHOH)$_5$-Co-Glu(NHOH)$_5$)-b-Poly(d-Leu$_5$-Co-Asp(OH)$_{10}$-Co-Tyr(OH)$_{25}$)-Ac By using the method of Example 27 and substituting mPEG12K-b-Poly-(d-Glu(OBn)$_5$-co-Glu(OBn)$_5$)-b-Poly(d-Leu-co-Asp(OH)$_{10}$-co-Tyr(OH)$_{25}$)-Ac as starting material, reaction for 12 hours at 50° C. afforded the title product (Yield=93.3%, hydroxylamine salt) as a fine, colorless polymer. $^1$H NMR (d$_6$-DMSO) δ 9.4-8.5 (theo. 35H, obs'd. 34H), 8.60-7.75 (theo. 50H, obs'd. 43H), 7.2-6.85 (theo. 50H, obs'd. 55H), 6.60 (theo. 50H, obs'd. 50H), 4.60-4.00 (theo. 50H, obs'd. 41H), 3.80-3.00 (theo. 1087H, obs'd. 1174H, contains masked H$_2$O peak), 3.00-1.65 (theo. 110H, obs'd. 124H), 1.63-0.57 (theo. 45H, obs'd. 40H).

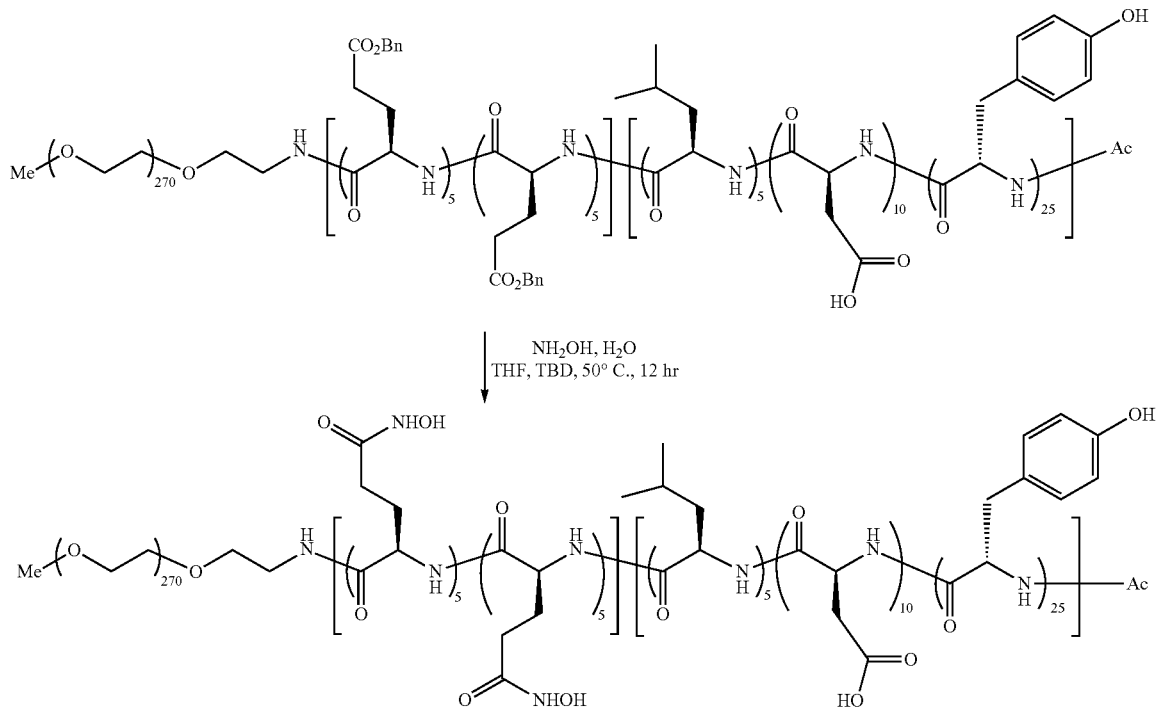

mPEG12K-b-Poly-(d-Glu(NHOH)$_5$-co-Glu(NHOH)$_5$)-b-Poly(d-Leu$_5$-co-Asp(OH)$_{10}$-co-Tyr(OH)$_{25}$)-Ac

Example 33

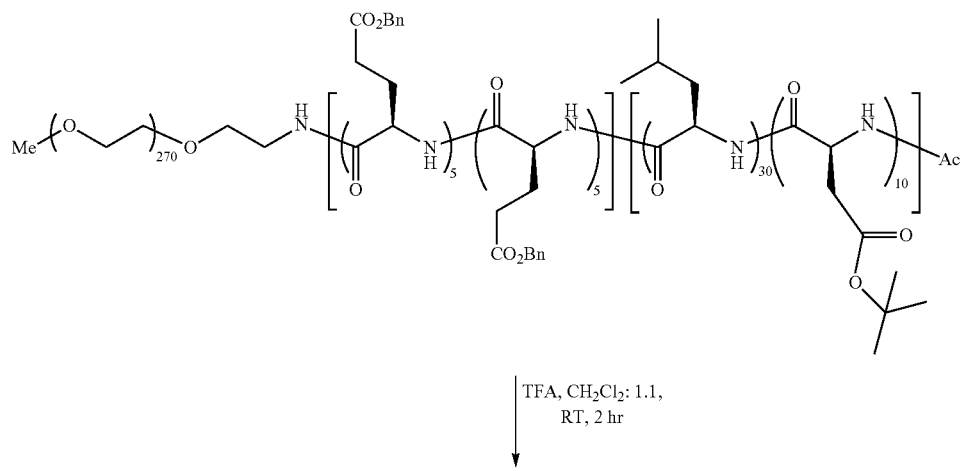

mPEG12K-b-Poly-(d-Glu(OBn)₅-co-Glu(OBn)₅)-b-Poly-(d-Leu₃₀-co-Asp(OH)₁₀)-Ac

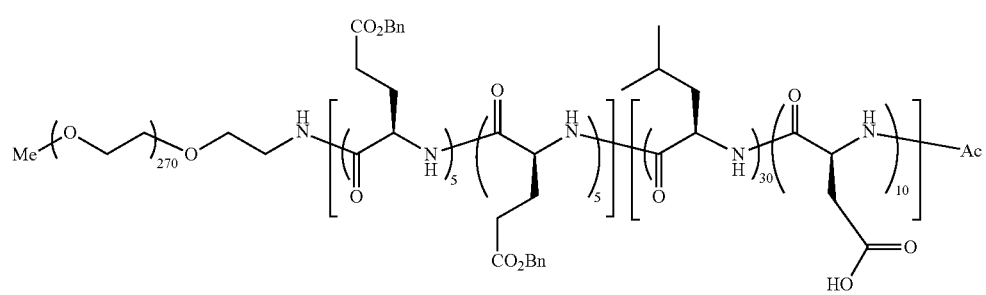

mPEG12K-b-Poly-(d-Glu(OBn)₅-co-Glu(OBn)₅)-b-Poly-(d-Leu₃₀-co-Asp(OH)₁₀)-Ac

Synthesis of mPEG12K-b-Poly-(d-Glu(OBn)₅-Co-Glu(OBn)₅)-b-Poly(d-Leu₃₀-Co-Asp(OH)₁₀)-Ac By Using the Method of Example 23, Substituting mPEG12K-b-Poly-(d-Glu(OBn)₅-co-Glu(OBn)₅)-b-Poly(d-Leu₃₀-co-Asp(OtBu)₁₀)-Ac as starting material and omitting PMB, reaction for two hours at room temperature and precipitation from dichloromethane, diethyl ether: 1, 13 afforded the title product (Yield=97.4%) as a fluffy, colorless polymer. $^1$H NMR (d₄-MeOH) δ 7.31 (theo. 50H, obs'd. 61H), 5.04 (theo. 20H, obs'd. 20H), 4.45-3.97 (theo. 50H, obs'd. 29H), 3.95-3.25 (theo. 1087H, obs'd. 1542H), 3.05-0.80 (theo. 330H, obs'd. 258H).

Example 34

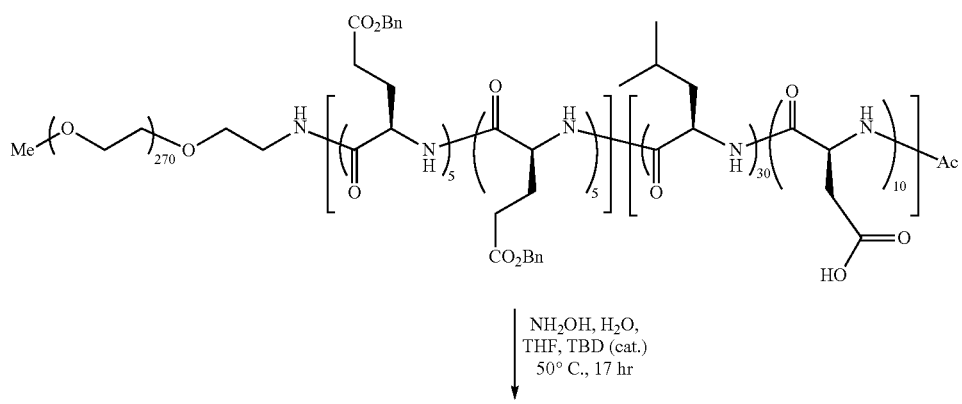

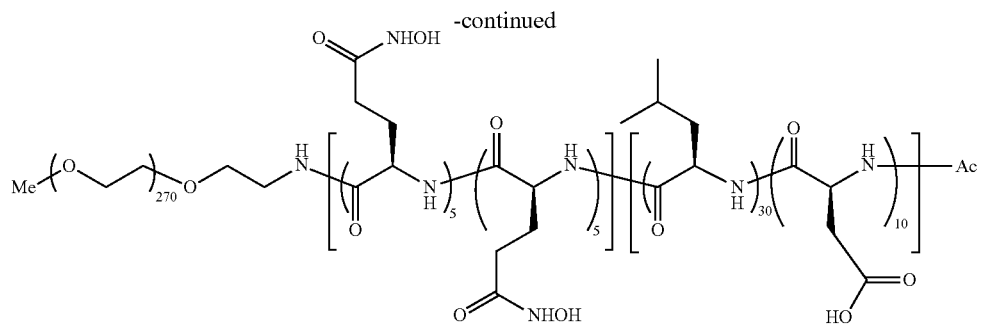

mPEG12K-b-Poly-(d-Glu(NHOH)$_5$-co-Glu(NHOH)$_5$)-b-Poly-(d-Leu$_{30}$-co-Asp(OH)$_{10}$)-Ac

Synthesis of mPEG12K-b-Poly-(d-Glu(NHOH)$_5$-Co-Glu(NHOH))-b-Poly(d-Leu$_{30}$-Co-Asp(OH)$_{10}$)-Ac By using the method of Example 27 and substituting mPEG12K-b-Poly-(d-Glu(OBn)$_5$-co-Glu(OBn)$_5$)-b-Poly-(d-Leu$_{30}$-co-Asp(OH)$_{10}$)-Ac as starting material, reaction for 17 hours at 50° C. afforded the title product (Yield=96.4%, hydroxylamine salt) as a fine, colorless polymer. $^1$H NMR (d$_6$-DMSO) δ 8.8-7.2 (theo. 70H, obs'd. 67H), 4.55-3.85 (theo. 50H, obs'd. 50H), 3.80-3.30 (theo. 1087H, obs'd. 1520H), 3.29-2.60 (theo. 60H, obs'd. 80H), 2.42-0.70 (theo. 270H, obs'd. 278H).

Example 35

Synthesis of mPEG12K-b-Poly-[d-Glu(NHOH)$_5$-co-Glu(NHOH)$_5$]-b-Poly-(Tyr(OH)$_{30}$-co-d-Phe$_{10}$)-Ac mPEG12K-b-Poly-[d-Glu(OBn)$_5$-co-Glu(OBn)$_5$]-b-Poly-(Tyr(OH)$_{30}$-co-d-Phe$_{10}$)-Ac (30.86 g, 1.50 mmol) was dissolved in 310 mL of dry THF and treated with hydroxylamine solution (50% aqueous, 0.60 mole, 39.7 mL) and 1,5,7-triazabicyclo [4.4.0]dec-5-ene (TBD, 626.4 mg, 4.5 mmol). The resultant slightly turbid solution was stirred at room temperature for 69 hours under N$_2$ and diluted with 310 mL MeOH. The crude product was precipitated from 3 L diethyl ether while cooling to −30° C. The resultant solid was collected by filtration, redissolved in a mixture of 150 mL of dry THF and 100 mL acetone, treated with acetic acid (1.26 g, 21.0 mmol, 1.2 mL) and then allowed to stir at ambient temperature for 2 hours. The product was precipi-

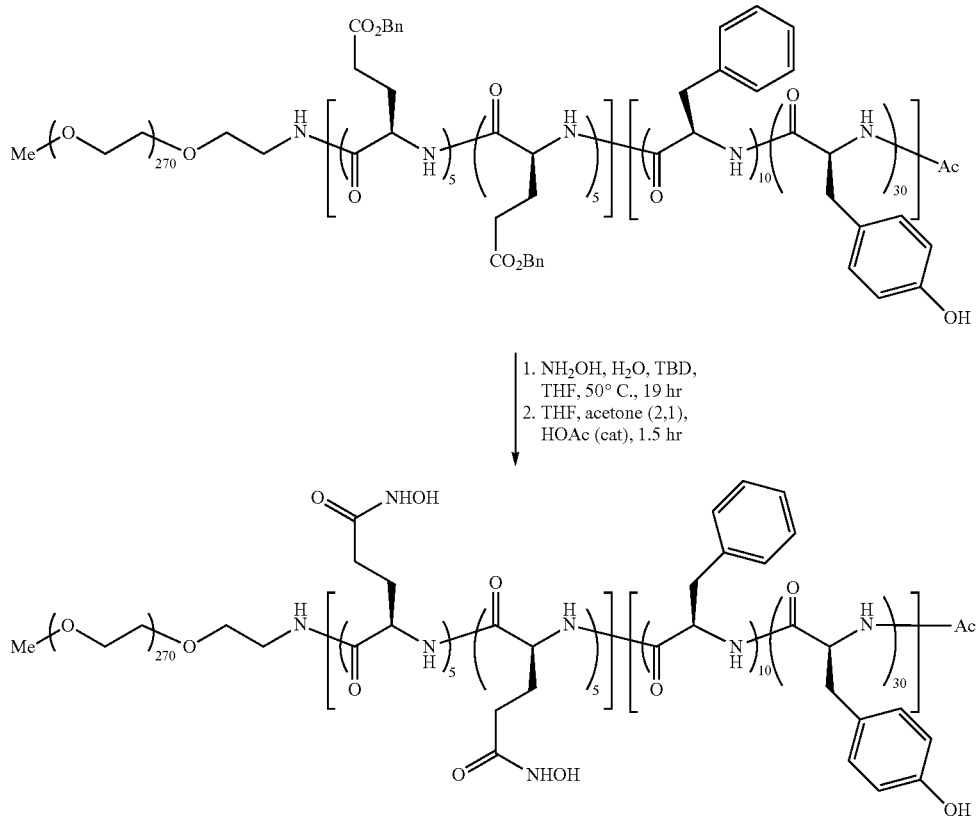

mPEG12K-b-Poly-[d-Glu(NHOH)$_5$-co-Glu(NHOH)$_5$]-b-Poly-(Tyr(OH)$_{30}$-co-d-Phe$_{10}$)-Ac tated by addition of 1.5 L diethyl ether, collected by suction filtration, washed with fresh portions of diethyl ether, and dried overnight in vacuo to afford 29.41 g (Yield=98.9%) of nearly colorless, fluffy polymer. $^1$H NMR (d$_6$-DMSO): identical to Example 24.

Example 36

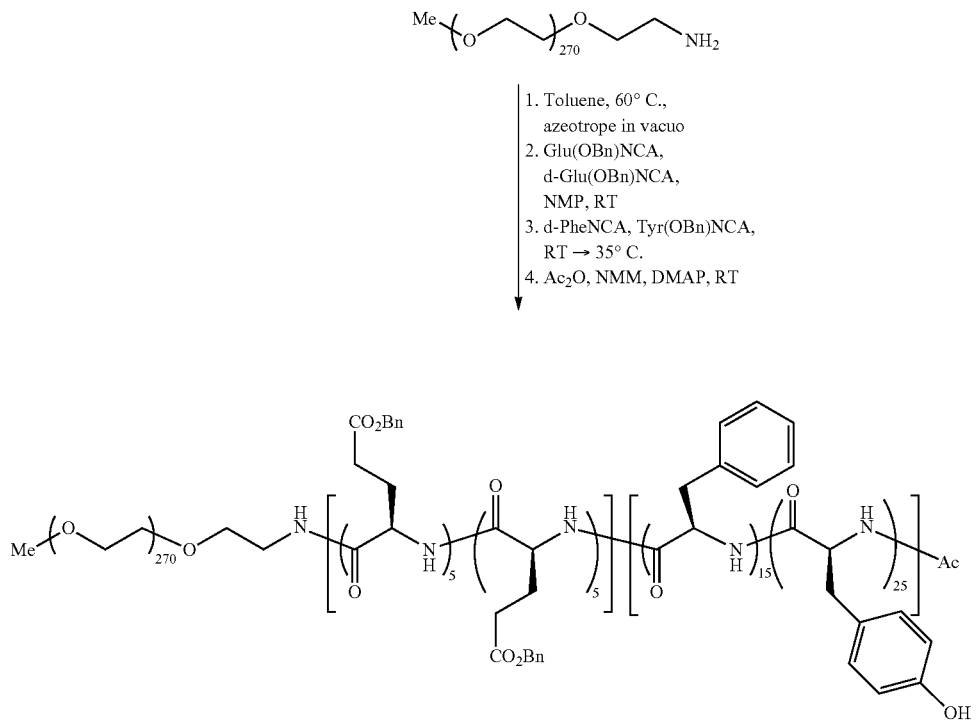

mPEG12K-b-Poly-(d-Glu(OBn)$_5$-co-Glu(OBn)$_5$)-b-Poly-(Tyr(OBn)$_{25}$-co-d-Phe$_{15}$)-Ac Synthesis of mPEG12K-b-Poly-(d-Glu(OBn)$_5$-Co-Glu(OBn)$_5$)-b-Poly-(Tyr(OBn)$_{25}$-Co-d-Phe$_{15}$)-Ac Using the protocol detailed in Example 24 and substituting the appropriate NCA starting materials afforded a crude polymer that was precipitated with 10 volumes of diethyl ether. After filtration and drying in vacuo, the title compound (Yield=83.6%) was obtained as a fine, colorless, odorless solid. $^1$H NMR (d$_6$-DMSO) δ 8.42-7.80 (theo. 50H, obs'd. 43H), 7.42-6.68 (theo. 350H, obs'd. 350H), 5.10-4.80 (theo. 70H, obs'd. 73H), 4.65-4.20 (theo. 50H, obs'd. 50H), 3.75-3.25 (theo. 1087H, obs'd. 1755H), 3.01-2.30 (theo. 80H, obs'd. 85H), 2.02-1.60 (theo. 40H, obs'd. 38H).

Example 37

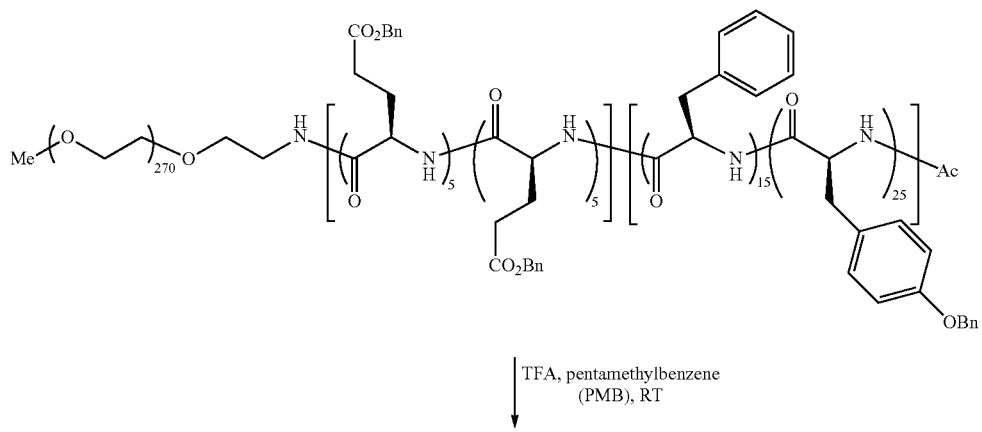

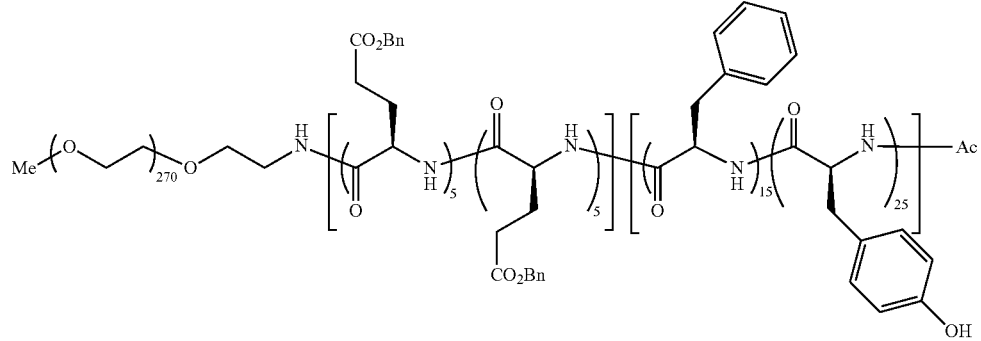

mPEG12K-b-Poly-[d-Glu(OBn)5-co-Glu(OBn)5]-b-Poly-(Tyr(OH)25-co-d-Phe15)-Ac

Synthesis of mPEG12K-b-Poly-[d-Glu(OBn)5-Co-Glu(OBn)5]-b-Poly-(Tyr(OH)25-Co-d-Phe15)-Ac By using the method of Example 23 and substituting mPEG2K-b-Poly-[d-Glu(OBn)5-co-Glu(OBn)5]-b-Poly-(Tyr(OBn)25-co-d-Phe15)-Ac as starting material, reaction for 5.25 hours at room temperature afforded the title product (Yield=99.3%) as a fine, colorless, odorless polymer. $^1$H NMR (d$_6$-DMSO) δ 9.09 (theo. 25H, obs'd. 22H), 8.40-7.75 (theo. 50H, obs'd. 49H), 7.40-6.50 (theo. 225H, obs'd. 225H), 5.04 (theo. 20H, obs'd. 21H), 4.65-4.20 (theo. 50H, obs'd. 54H), 3.81-3.20 (theo. 1087H, obs'd. 1613H), 3.05-2.10 (theo. 80H, obs'd. 90H), 2.05-1.63 (theo. 40H, obs'd. 38H).

Example 38

Synthesis of mPEG12K-b-Poly-[d-Glu(NHOH)5-Co-Glu(NHOH)5]-b-Poly-(Tyr(OH)25-Co-d-Phe15)-Ac mPEG12K-b-Poly-[d-Glu(OBn)5-co-Glu(OBn)5]-b-Poly-(Tyr(OH)25-co-d-Phe15)-Ac (51.23 g, 2.50 mmol) was dissolved in 515 mL of dry THF and treated with hydroxylamine solution (50% aqueous, 1.00 mole, 66.3 mL, 40 equiv./Bn ester moiety) and 1,5,7-triazabicyclo [4.4.0]dec-5-ene (TBD, 1.044 g, 7.5 mmol, 0.3 equiv.). The resultant slightly turbid solution was stirred at room temperature for 108 hours under $N_2$ and diluted with 515 mL of IPA. The crude product was precipitated from 6 L of diethyl ether. The resultant solid was collected by filtration, redissolved in a mixture of 300 mL of dry THF and 200 mL acetone, treated with acetic acid (2.25 g, 37.5 mmol, 2.15 mL), and then

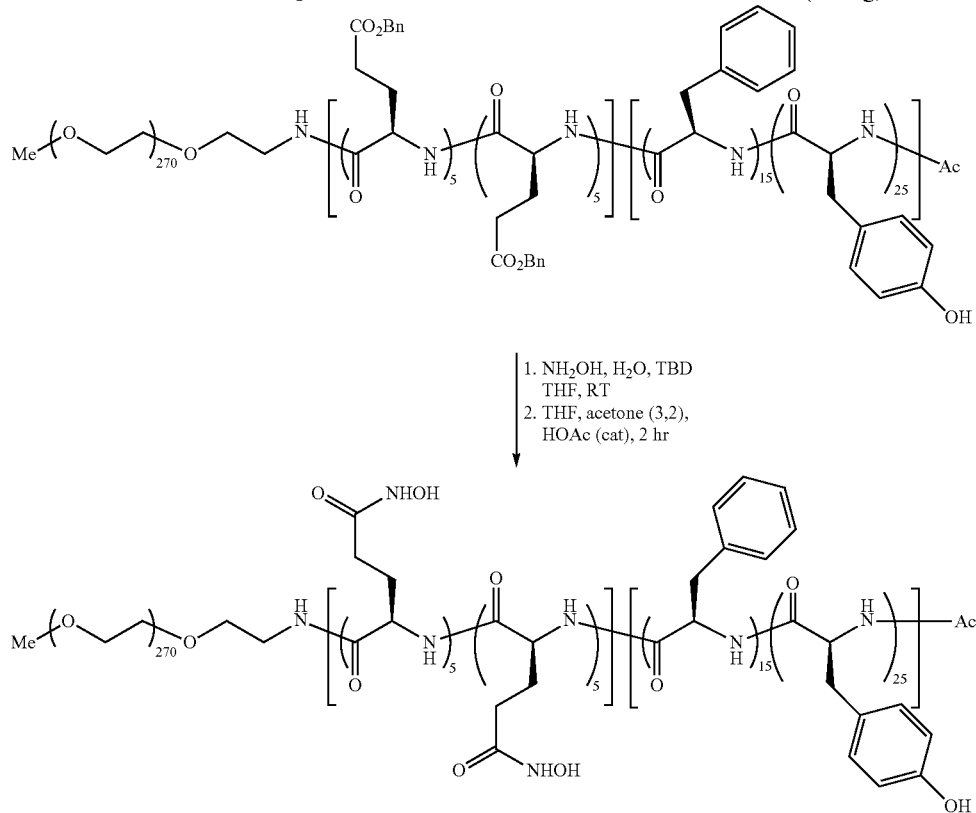

mPEG12K-b-Poly-[d-Glu(NHOH)5-co-Glu(NHOH)5]-b-Poly-(Tyr(OH)25-co-d-Phe15)-Ac allowed to stir at ambient temperature for 2.5 hours. The product was precipitated by addition of 3 L of diethyl ether, collected by suction filtration, washed with fresh portions of diethyl ether, and dried overnight in vacuo to afford 45.16 g (Yield=91.5%) of the title compound as a nearly colorless, fluffy polymer with a slight odor of acetic acid. $^1$H NMR ($d_6$-DMSO) δ 9.35-8.85 (theo. 45H, obs'd. 28H), 8.42-7.75 (theo. 50H, obs'd. 37H), 7.37-6.46 (theo. 175H, obs'd. 164H), 4.65-4.00 (theo. 50H, obs'd. 50H), 3.82-3.07 (theo. 1087H, obs'd. 1708H, contains masked $H_2O$ peak), 3.05-2.20 (theo. 80H, obs'd. 84H), 2.18-1.63 (theo. 40H, obs'd. 68H, contains trace of HOAc).

Example 39

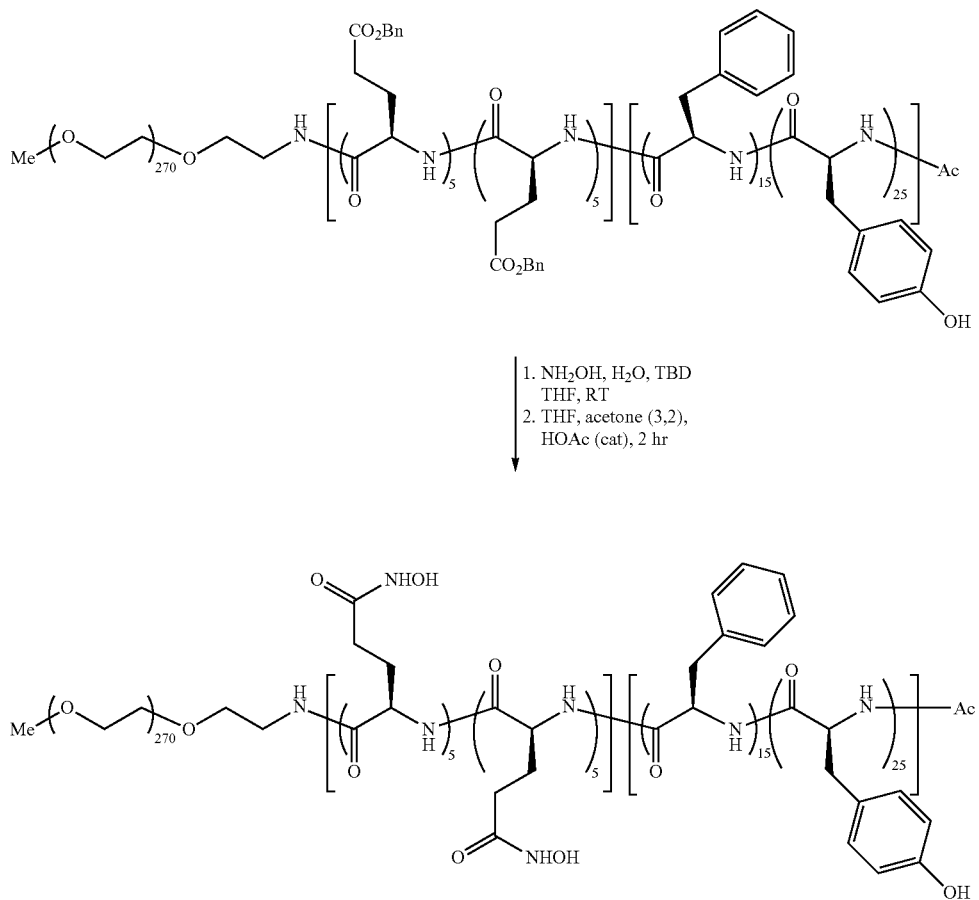

Synthesis of mPEG12K-b-Poly-[d-Glu(NHOH)$_5$-Co-Glu(NHOH)$_5$]-b-Poly-(Tyr(OH)$_{25}$-Co-d-Phe$_{15}$)-Ac By using the method of Example 38 and increasing the hydroxylamine concentration (80 equiv./Bn ester), reaction for 65 hours at room temperature and work-up as above afforded the title product (Yield=87.8%) as a fine, colorless polymer with a slight odor of acetic acid. $^1$H NMR ($d_6$-DMSO): identical to Example 38.

Example 40

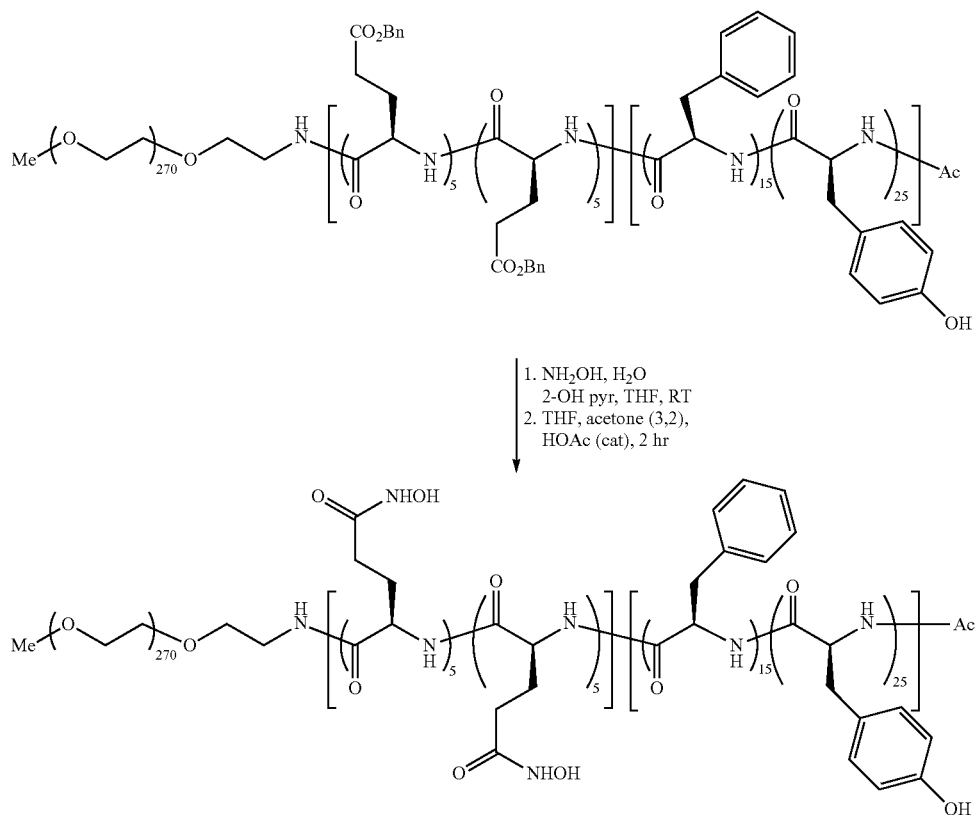

mPEG12K-b-Poly-[d-Glu(NHOH)$_5$-co-Glu(NHOH)$_5$]-b-Poly-(Tyr(OH)$_{25}$-co-d-Phe$_{15}$)-Ac Synthesis of mPEG12K-b-Poly-[d-Glu(NHOH)$_5$-Co-Glu(NHOH)$_5$]-b-Poly-(Tyr(OH)$_{25}$-Co-d-Phe$_{15}$)-Ac By using the method of Example 39 and substitution of TBD with 2-hydroxypyridine (0.3 equiv.), reaction for 137 hours at room temperature and work-up as above afforded the title product (Yield=91.2%) as a fine, colorless polymer with a slight odor of acetic acid. $^1$H NMR (d$_6$-DMSO): identical to Example 38.

Example 41

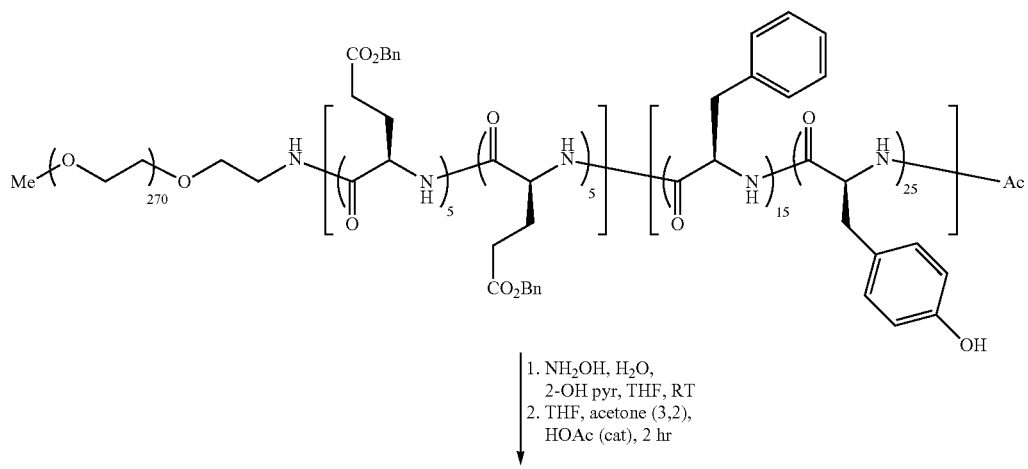

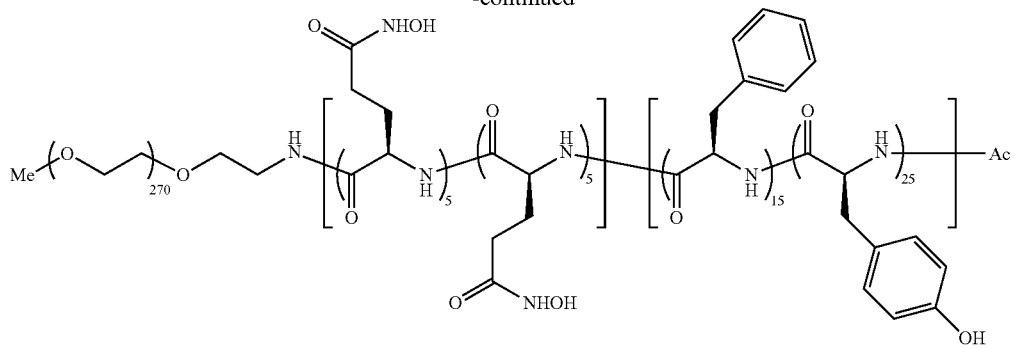

mPEG12K-b-Poly-[d-Glu(NHOH)$_5$-co-Glu(NHOH)$_5$]-b-Poly-(Tyr(OH)$_{25}$-co-d-Phe$_{15}$)-Ac Synthesis of mPEG12K-b-Poly-[d-Glu(NHOH)$_5$-Co-Glu(NHOH)$_5$]-b-Poly-(Tyr(OH)$_{25}$-Co-d-Phe$_{15}$)-Ac By using the method of Example 38 and substitution of TBD with 2-hydroxypyridine (0.3 equiv.), reaction at 50° C. for 24.5 hours and work-up as above afforded the title product (Yield=91.2%) as a fine, colorless polymer with a slight odor of acetic acid. $^1$H NMR (d$_6$-DMSO): identical to Example 38.

Example 42

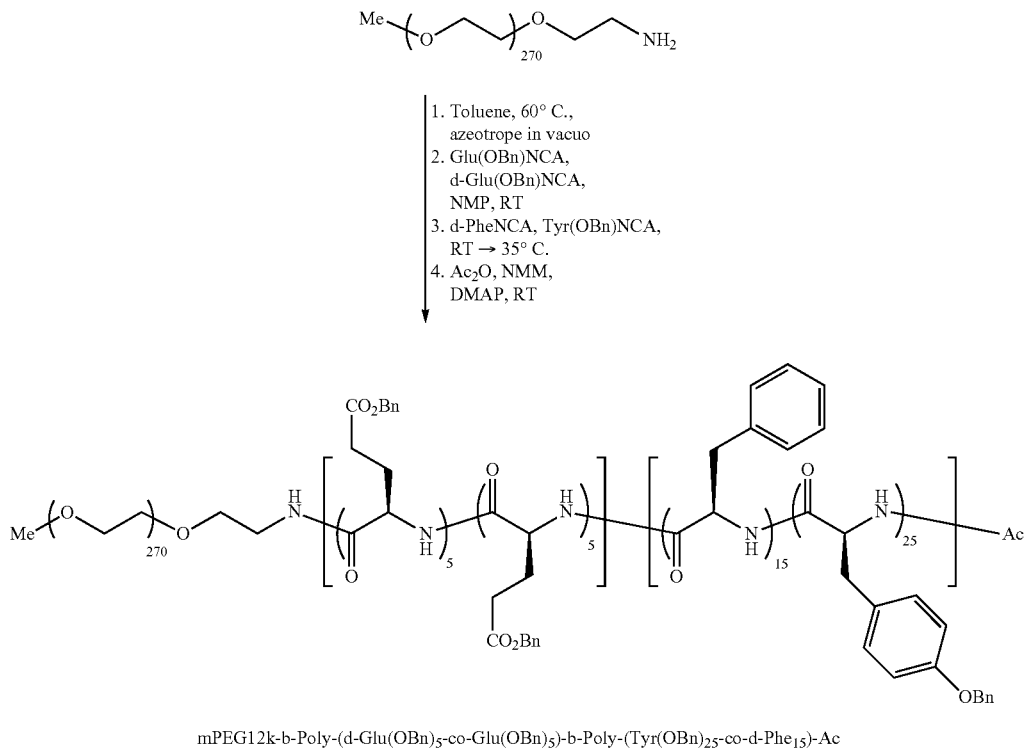

mPEG12k-b-Poly-(d-Glu(OBn)$_5$-co-Glu(OBn)$_5$)-b-Poly-(Tyr(OBn)$_{25}$-co-d-Phe$_{15}$)-Ac Synthesis of mPEG12K-b-Poly-(d-Glu(OBn)$_5$-Co-Glu(OBn)$_5$)-b-Poly-(Tyr(OBn)$_{25}$-Co-d-Phe$_{15}$)-Ac Using the protocol detailed in Example 36 and substituting the appropriate NCA starting materials afforded a crude polymer that was precipitated with 5 volumes of isopropanol. After filtration and drying in vacuo, the title compound (Yield=84.2%) was obtained as a fine, colorless, odorless solid. $^1$H NMR (d$_6$-DMSO): identical to Example 36.

Example 43

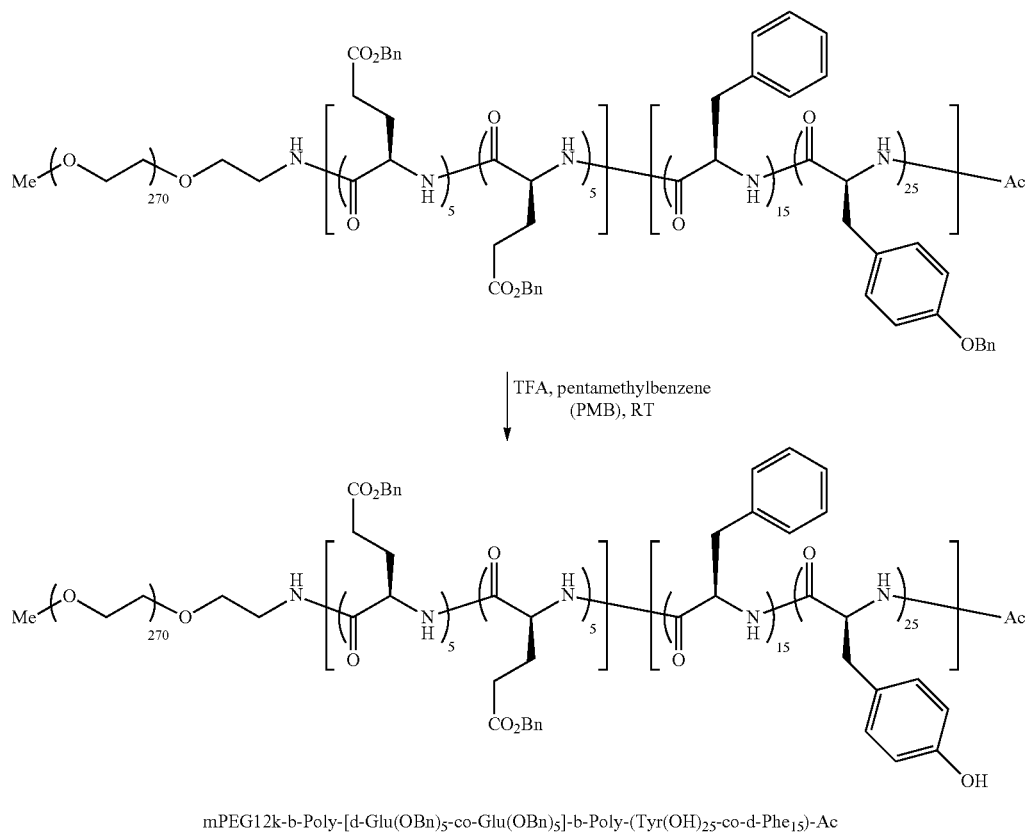

mPEG12k-b-Poly-[d-Glu(OBn)₅-co-Glu(OBn)₅]-b-Poly-(Tyr(OH)₂₅-co-d-Phe₁₅)-Ac

Synthesis of mPEG12K-b-Poly-[d-Glu(OBn)₅-Co-Glu(OBn)₅]-b-Poly-(Tyr(OH)₂₅-Co-d-Phe₁₅)-Ac By using the method of Example 37, reaction of mPEG12K-b-Poly-[d-Glu(OBn)₅-co-Glu(OBn)₅]-b-Poly-(Tyr(OBn)₂₅-co-d-Phe₁₅)-Ac with PMB in TFA for four hours at room temperature and precipitation from a mixture of chlorobutane, TBME: 1,3 afforded the title product (Yield=93.1%) as a fine, colorless, odorless polymer. $^1$H NMR (d$_6$-DMSO): identical to Example 37.

Example 44

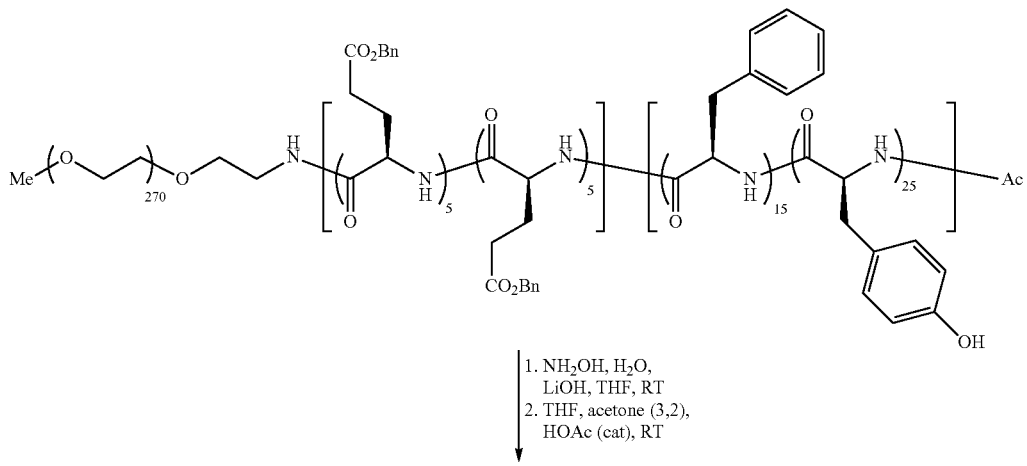

-continued

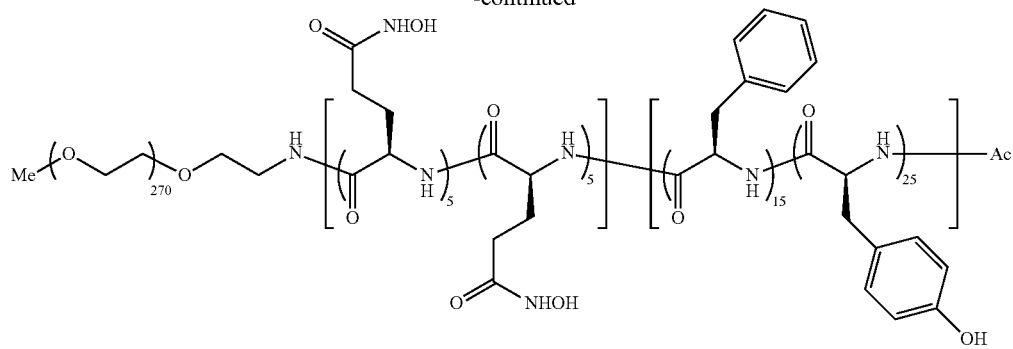

mPEG12K-b-Poly-[d-Glu(NHOH)$_5$-co-Glu(NHOH)$_5$]-b-Poly-(Tyr(OH)$_{25}$-co-d-Phe$_{15}$)-Ac

Synthesis of mPEG12K-b-Poly-[d-Glu(NHOH)$_5$-Co-Glu(NHOH)$_5$]-b-Poly-(Tyr(OH)$_{25}$-Co-d-Phe$_{15}$)-Ac mPEG12K-b-Poly-[d-Glu(OBn)$_5$-co-Glu(OBn)$_5$]-b-Poly-(Tyr(OH)$_{25}$-co-d-Phe$_{15}$)-Ac (4.10 g, 0.20 mmol) was dissolved in 41 mL of dry THF and treated with hydroxylamine solution (50% aqueous, 40.0 mmol, 2.65 mL, 20 equiv./Bn ester moiety) and lithium hydroxide monohydrate (84.0 mg, 2.0 mmol, 1.0 equiv./Bn ester moiety). The resultant clear pale yellow solution was stirred at room temperature for 22 hours under N$_2$ and diluted with 41 mL of IPA. The crude product was precipitated from 160 mL of TBME with rapid stirring. The resultant solid was collected by filtration, dried in vacuo, and redissolved in a mixture of 24 mL dry THF and 16 mL acetone. The solution was treated with acetic acid (0.18 g, 3.00 mmol, 0.17 mL), briefly heated to reflux, and allowed to stir at ambient temperature for 15 hours. The product was precipitated by addition of volumes of TBME, collected by suction filtration, washed with fresh portions of TBME, and dried overnight in vacuo to afford 3.62 g (Yield=91.7%) of the title compound as a nearly colorless, fluffy polymer. $^1$H NMR (d$_6$-DMSO): identical to Example 38.

Example 45

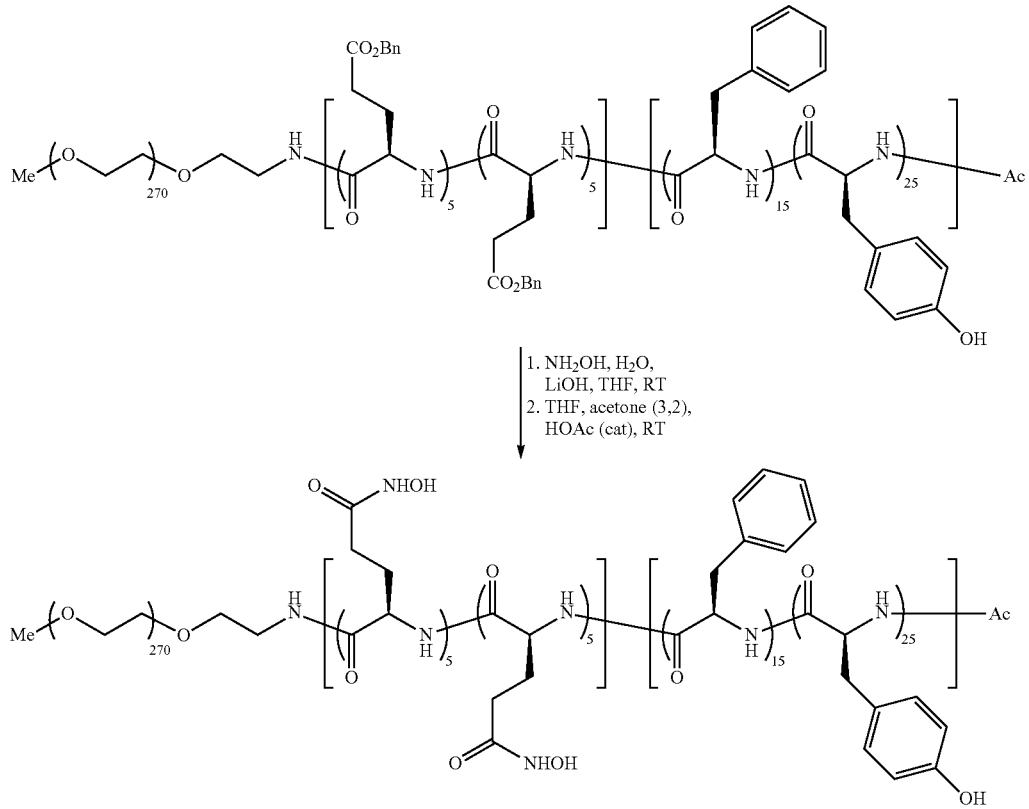

mPEG12K-b-Poly-[d-Glu(NHOH)$_5$-co-Glu(NHOH)$_5$]-b-Poly-(Tyr(OH)$_{25}$-co-d-Phe$_{15}$)-Ac Synthesis of mPEG12K-b-Poly-[d-Glu(NHOH)$_5$-Co-Glu(NHOH)$_5$]-b-Poly-(Tyr(OH)$_{25}$-Co-d-Phe$_{15}$)-Ac Using the method described above in Example 44, mPEG12K-b-Poly-[d-Glu(OBn)$_5$-co-Glu(OBn)$_5$]-b-Poly-(Tyr(OH)$_{25}$-co-d-Phe$_{15}$)-Ac was converted to the title compound using lithium hydroxide monohydrate (2.0 equiv./Bn ester moiety). Reaction time was 18 hours. The crude product was precipitated from 16 volumes of IPA and the resultant solid was treated with THF, acetone, and acetic acid as detailed in Example 44. After precipitation from two volumes of TBME, filtration, and drying in vacuo, the title compound (Yield=96.2%) was obtained as a fine, colorless solid. $^1$H NMR (d$_6$-DMSO): identical to Example 38.

Example 46

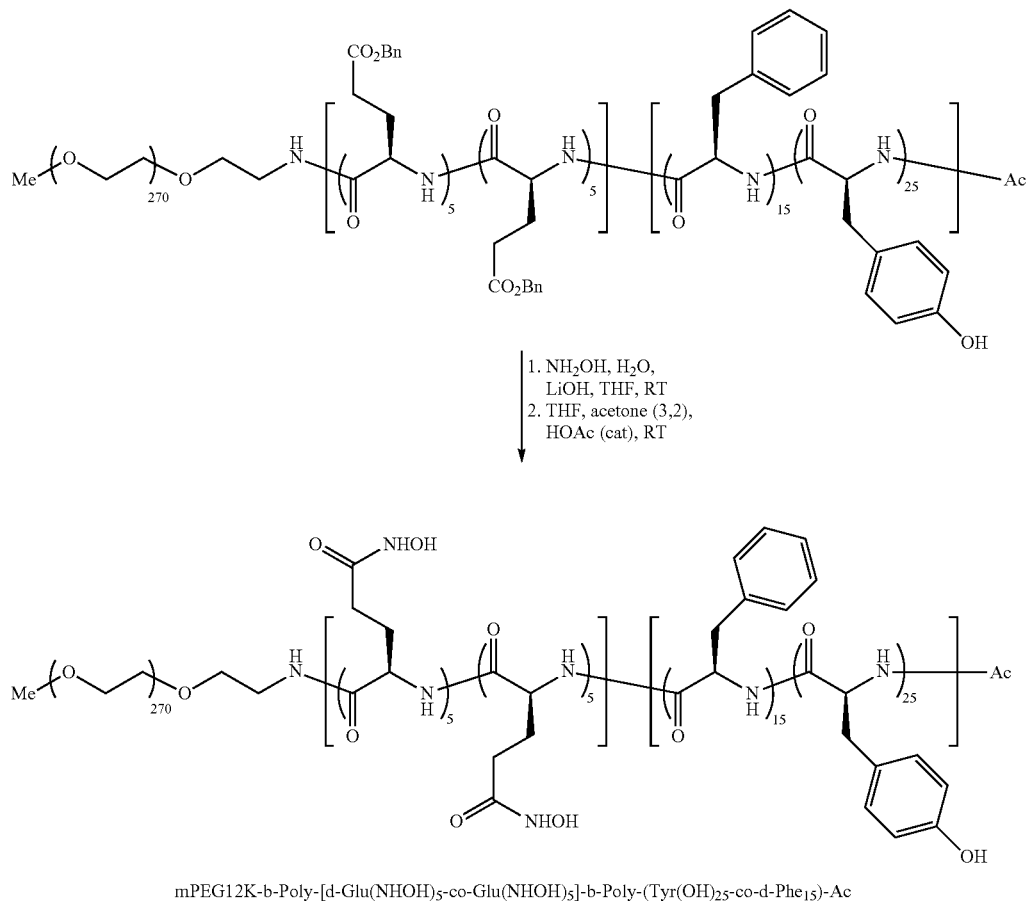

mPEG12K-b-Poly-[d-Glu(NHOH)$_5$-co-Glu(NHOH)$_5$]-b-Poly-(Tyr(OH)$_{25}$-co-d-Phe$_{15}$)-Ac Synthesis of mPEG12K-b-Poly-[d-Glu(NHOH)$_5$-Co-Glu(NHOH)$_5$]-b-Poly-(Tyr(OH)$_{25}$-Co-d-Phe$_{15}$)-Ac mPEG12K-b-Poly-[d-Glu(OBn)$_5$-co-Glu(OBn)$_5$]-b-Poly-(Tyr(OH)$_{25}$-co-d-Phe$_{15}$)-Ac (2.05 g, 0.10 mmol) was dissolved in 21 mL of methanol and treated with hydroxylamine solution (50% aqueous, 20.0 mmol, 1.32 mL, 20 equiv./Bn ester moiety) and 1M lithium hydroxide solution (1.0 mL, 1.0 mmol, 1.0 equiv./Bn ester moiety). The resultant pale yellow solution was stirred at room temperature for 22 hours under N$_2$ and then an additional portion of 1M lithium hydroxide solution (1.0 mL, 1.0 mmol, 1.0 equiv./Bn ester moiety) was added. After an additional 24 hours, the crude product was precipitated from 160 mL of TBME. The resultant solid was collected by filtration, dried in vacuo, and redissolved in a mixture of 12 mL dry THF and 8 mL acetone. The solution was treated with acetic acid (0.21 g, 3.50 mmol, 0.20 mL), briefly heated to reflux, and allowed to stir at ambient temperature for 16 hours. The product was precipitated by addition of 40 mL TBME, collected by suction filtration, washed with fresh portions of TBME, and dried overnight in vacuo to afford 1.87 g (Yield=94.9%) of the title compound as a nearly colorless, fluffy polymer. $^1$H NMR (d$_6$-DMSO): identical to Example 38.

Example 47

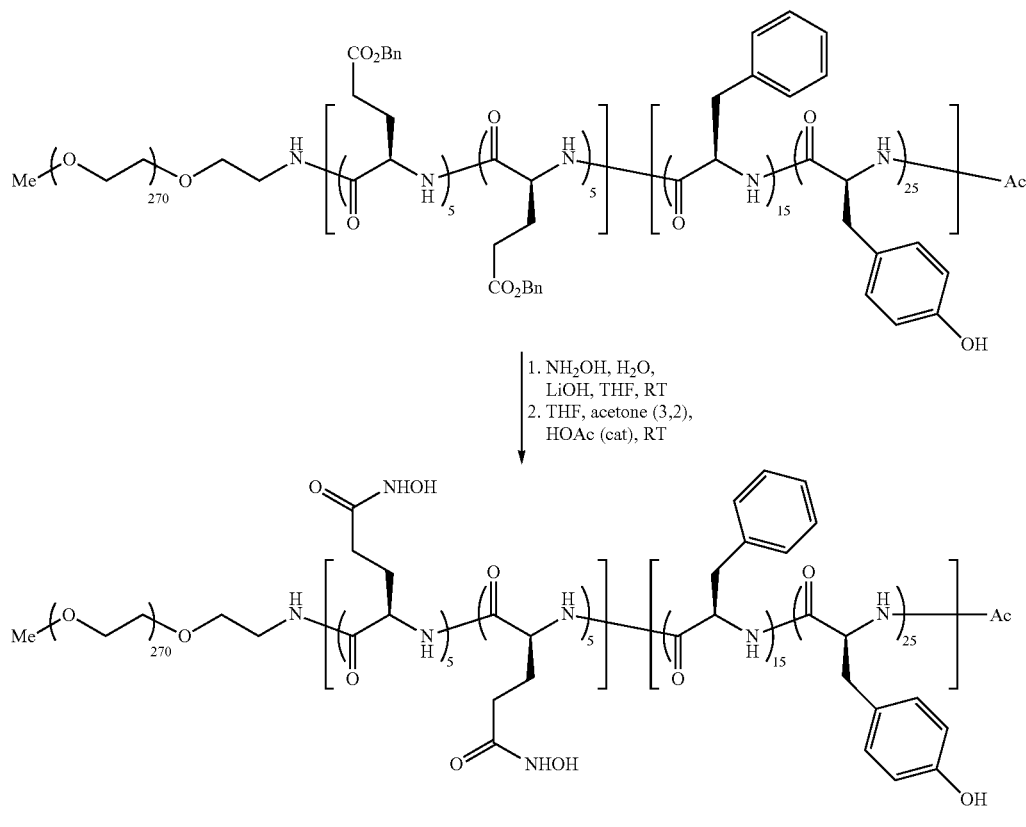

mPEG12K-b-Poly-[d-Glu(NHOH)₅-co-Glu(NHOH)₅]-b-Poly-(Tyr(OH)₂₅-co-d-Phe₁₅)-Ac

Synthesis of mPEG12K-b-Poly-[d-Glu(NHOH)₅-Co-Glu(NHOH)₅]-b-Poly-(Tyr(OH)₂₅-Co-d-Phe₁₅)-Ac Using the method described above in Example 44, mPEG12K-b-Poly-[d-Glu(OBn)₅-co-Glu(OBn)₅]-b-Poly-(Tyr(OH)₂₅-co-d-Phe₁₅)-Ac was converted to the title compound using lithium hydroxide solution (0.5 equiv./Bn ester moiety). Reaction time was 72 hours. The solution was diluted with one volume of IPA, and crude product was precipitated from two volumes of TBME. The resultant solid was treated with THF, acetone, and acetic acid as detailed in Example 44. After precipitation from two volumes of TBME, filtration, and drying in vacuo, the title compound (Yield=91.1%) was obtained as a fine, colorless solid. $^1$H NMR (d₆-DMSO): identical to Example 38.

Example 48

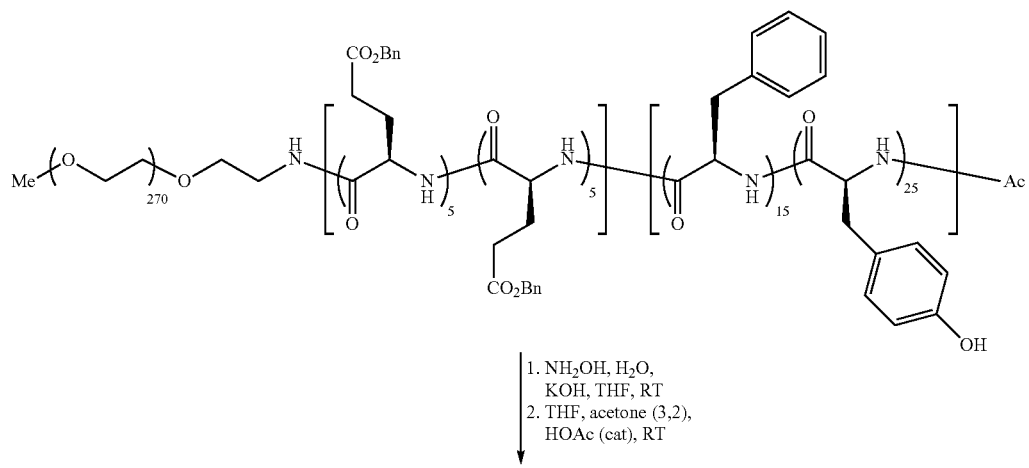

-continued

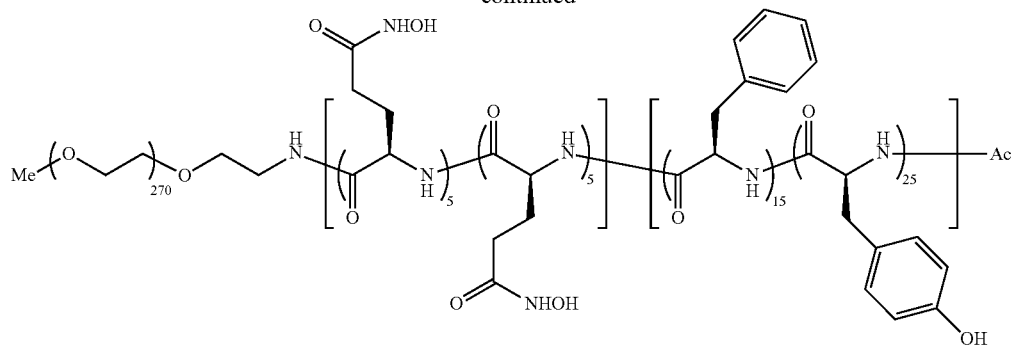

mPEG12K-b-Poly-[d-Glu(NHOH)$_5$-co-Glu(NHOH)$_5$]-b-Poly-(Tyr(OH)$_{25}$-co-d-Phe$_{15}$)-Ac Synthesis of mPEG12K-b-Poly-[d-Glu(NHOH)$_5$-Co-Glu(NHOH)$_5$]-b-Poly-(Tyr(OH)$_{25}$-Co-d-Phe$_{15}$)-Ac Using the method described above in Example 47, mPEG12K-b-Poly-[d-Glu(OBn)$_5$-co-Glu(OBn)$_5$]-b-Poly-(Tyr(OH)$_{25}$-co-d-Phe$_{15}$)-Ac was converted to the title compound using 1M potassium hydroxide solution (2.0 equiv./Bn ester moiety). Reaction time was 6 hours. Workup afforded the title compound (Yield=92.4%) as a fine, colorless solid. $^1$H NMR (d$_6$-DMSO): identical to Example 38.

Example 49

(450 mL), and dried by azeotropic distillation. After distillation to dryness, the polymer was left under vacuum for 16 hours. The flask was subsequently backfilled with N$_2$, re-evacuated under reduced pressure, and dry N-methylpyrrolidone (NMP, 250 mL) and then dichloromethane (250 mL) were introduced by cannula. The mixture was briefly heated to 40° C. to expedite dissolution and then recooled to 25° C. Glu(OBn) NCA (4.61 g, 17.5 mmol) and d-Glu(OBn) NCA (4.61 g, 17.5 mmol) were added to the flask, and the reaction mixture was allowed to stir for 24 hours at ambient room temperature under nitrogen gas. Then, d-Phe NCA (14.34 g, 75.0 mmol) and Tyr (OBn) NCA (37.16 g, 125.0 mmol) were added and the solution was allowed to stir at room temperature for three days and then heated 35° C. for 7 hours

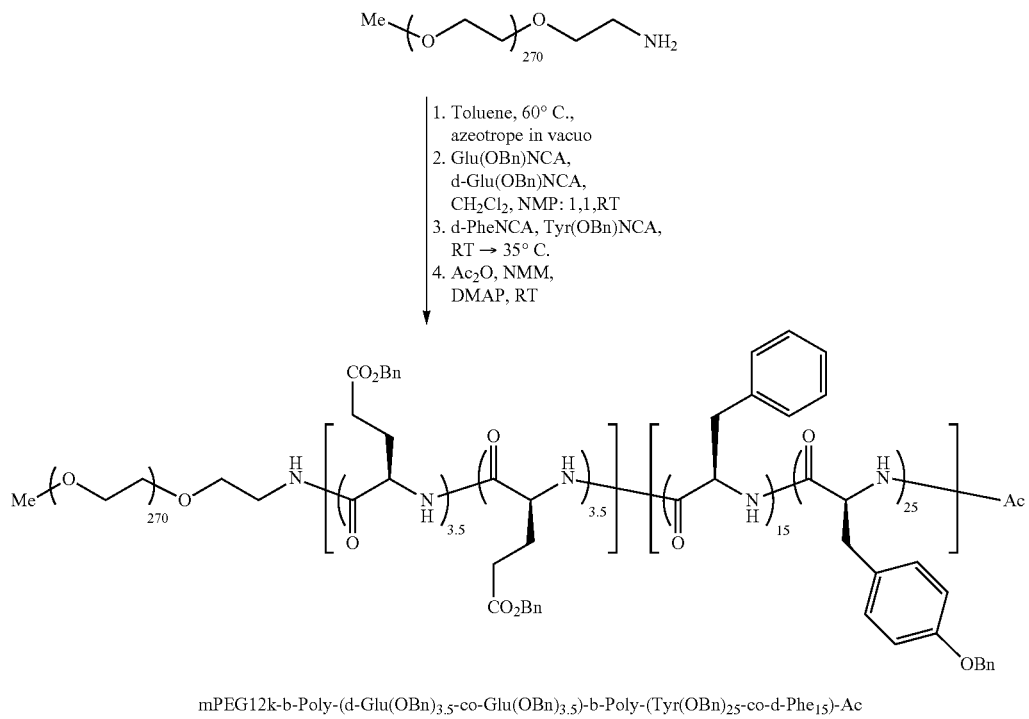

mPEG12k-b-Poly-(d-Glu(OBn)$_{3.5}$-co-Glu(OBn)$_{3.5}$)-b-Poly-(Tyr(OBn)$_{25}$-co-d-Phe$_{15}$)-Ac Synthesis of mPEG12K-b-Poly-(d-Glu(OBn)$_{3.5}$-Co-Glu(OBn)$_{3.5}$)-b-Poly (Tyr(OBn)$_{25}$-Co-d-Phe$_{15}$)-Ac m-PEG10k-NH$_2$, (59.86 g, 5.0 mmol) was weighed into an oven-dried, 1 L-round-bottom flask, dissolved in toluene at which point the reaction was complete (GPC, DMF/0.1% LiBr). The solution was cooled to room temperature and acetic anhydride (5.11 g, 50.0 mmol, 4.80 mL), N-methylmorpholine (NMM) (5.56 g, 55.0 mmol, 6.1 mL) and dimethylaminopyridine (DMAP) (0.61 g, 5.0 mmole) were added. Stirring was continued for 18 hours at room temperature and the dichloromethane was removed on the rotary evaporator. The polymer was precipitated into isopropanol (2.6 L) and isolated by filtration, washed with fresh 500 mL portions of isopropanol, and dried in vacuo to give the block copolymer as a fine, nearly colorless powder (102.40 g, Yield=92.6%). $^1$H NMR ($d_6$-DMSO) δ 8.42-7.80 (theo. 47H, obs'd. 44H), 7.35 (theo. 75H, obs'd. 75H), 7.28-6.65 (theo. 125H, obs'd. 125H), 5.10-4.84 (theo. 64H, obs'd. 59H), 4.64-4.20 (theo. 47H, obs'd. 39H), 3.72-3.25 (theo. 1087H, obs'd. 16713H), 3.00-2.20 (theo. 80H, obs'd. 88H), 2.03-1.60 (theo. 28H, obs'd. 27H).

Example 50

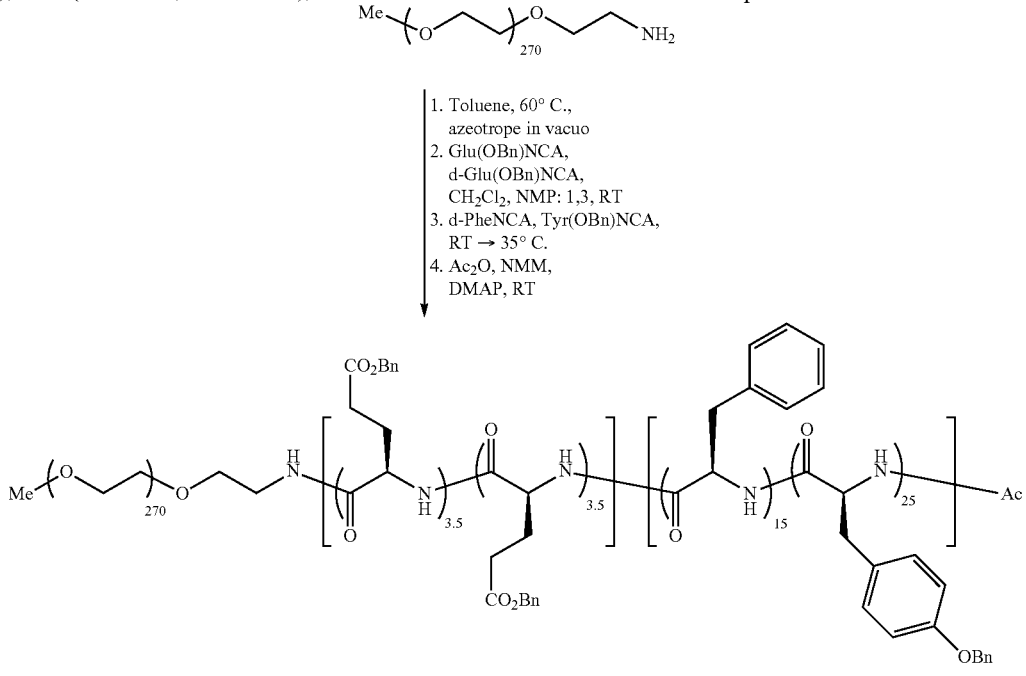

mPEG12k-b-Poly-(d-Glu(OBn)$_{3.5}$-co-Glu(OBn)$_{3.5}$)-b-Poly (Tyr(OBn)$_{25}$-co-d-Phe$_{15}$)-Ac Synthesis of mPEG12K-b-Poly-(d-Glu(OBn)$_{3.5}$-Co-Glu(OBn)$_{3.5}$)-b-Poly (Tyr(OBn)$_{25}$-Co-d-Phe$_{15}$)-Ac Using the protocol detailed in Example 49 with dry N-methylpyrrolidone (NMP, 125 mL) and dichloromethane (375 mL) as solvents afforded a crude polymer that was precipitated with 5 volumes of isopropanol. After filtration and drying in vacuo, the title compound (Yield=96.5%) was obtained as a fine, colorless, odorless solid. $^1$H NMR ($d_6$-DMSO): identical to Example 49.

Example 51

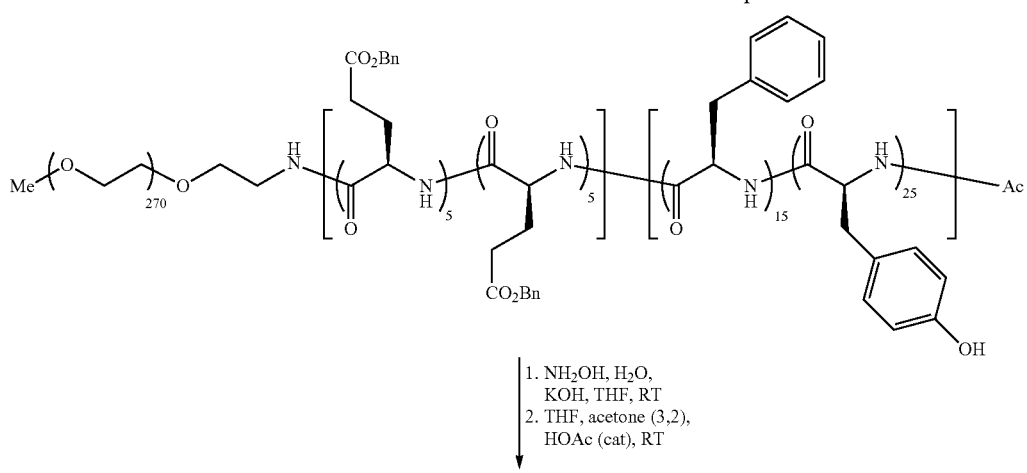

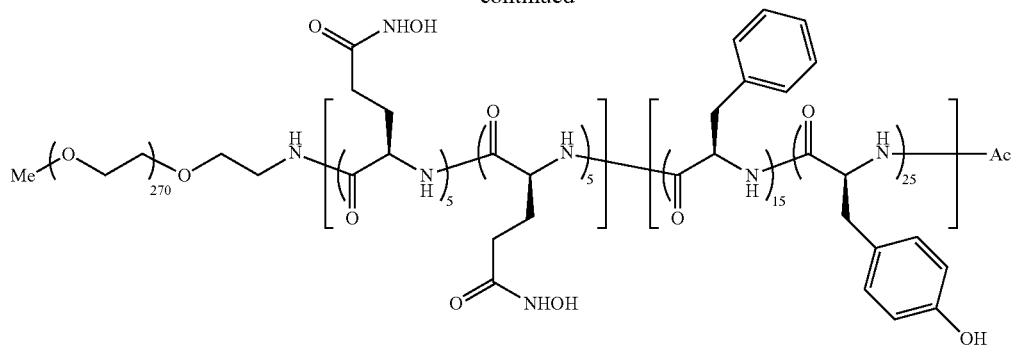

mPEG12K-b-Poly-[d-Glu(NHOH)₅-co-Glu(NHOH)₅]-b-Poly-(Tyr(OH)₂₅-co-d-Phe₁₅)-Ac

Synthesis of mPEG12K-b-Poly-[d-Glu(NHOH)₅-Co-Glu(NHOH)₅]-b-Poly-(Tyr(OH)₂₅-Co-d-Phe₁₅)-Ac mPEG12K-b-Poly-[d-Glu(OBn)₅-co-Glu(OBn)₅]-b-Poly-(Tyr(OH)₂₅-co-d-Phe₁₅)-Ac (4.10 g, 0.20 mmol) was dissolved in 41 mL of THF and treated with hydroxylamine solution (2.65 mL, 40.0 mmol) and 1M potassium hydroxide (2.0 mL, 2.0 mmol, 1.0 equiv./Bn ester moiety). The resultant slightly hazy pink solution was stirred at room temperature for 42 hours under $N_2$ and then diluted with acetone (58.1 g, 1.0 mol, 74 mL). Acetic acid (2.40 g, 40.0 mmol, 2.3 mL) was added, the solution was briefly heated to reflux, and then was stirred at room temperature for four hours. The product was precipitated with TBME (300 mL) using vigorous stirring. After stirring an additional 30 minutes, filtration and drying in vacuo afforded the title compound (Yield=92.9%) as a fine, colorless solid. ¹H NMR (d₆-DMSO): identical to Example 38.

Example 52

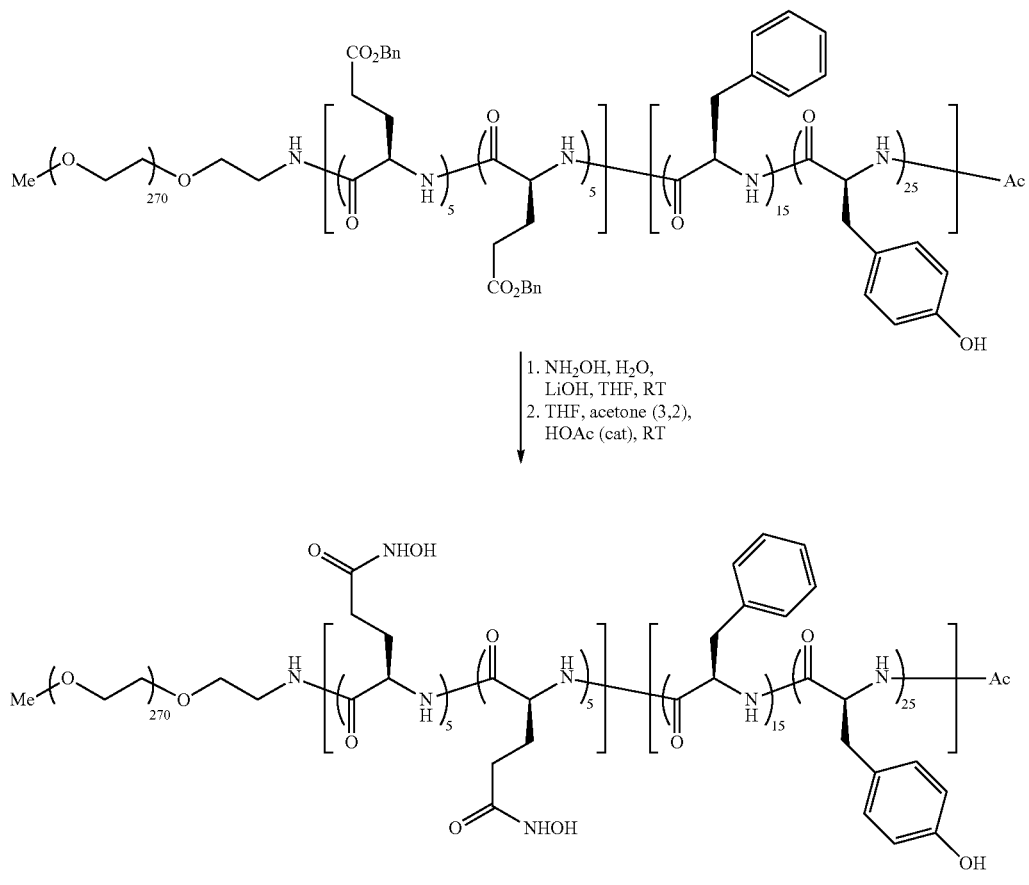

mPEG12K-b-Poly-[d-Glu(NHOH)₅-co-Glu(NHOH)₅]-b-Poly-(Tyr(OH)₂₅-co-d-Phe₁₅)-Ac

Synthesis of mPEG12K-b-Poly-[d-Glu(NHOH)5-Co-Glu(NHOH)5]-b-Poly-(Tyr(OH)25-Co-d-Phe15)-Ac Using the method described above in Example 51, mPEG12K-b-Poly-[d-Glu(OBn)5-co-Glu(OBn)5]-b-Poly-(Tyr(OH)25-co-d-Phe15)-Ac was converted to the title compound using 1M lithium hydroxide solution (2.0 equiv./Bn ester moiety). Reaction time was 6 hours. Workup as above and dilution with IPA (1 volume) followed by precipitation with TBME (3 volumes) afforded the title compound (Yield=90.6%) as a fine, colorless solid. $^1$H NMR (d$_6$-DMSO): identical to Example 38.

Example 53

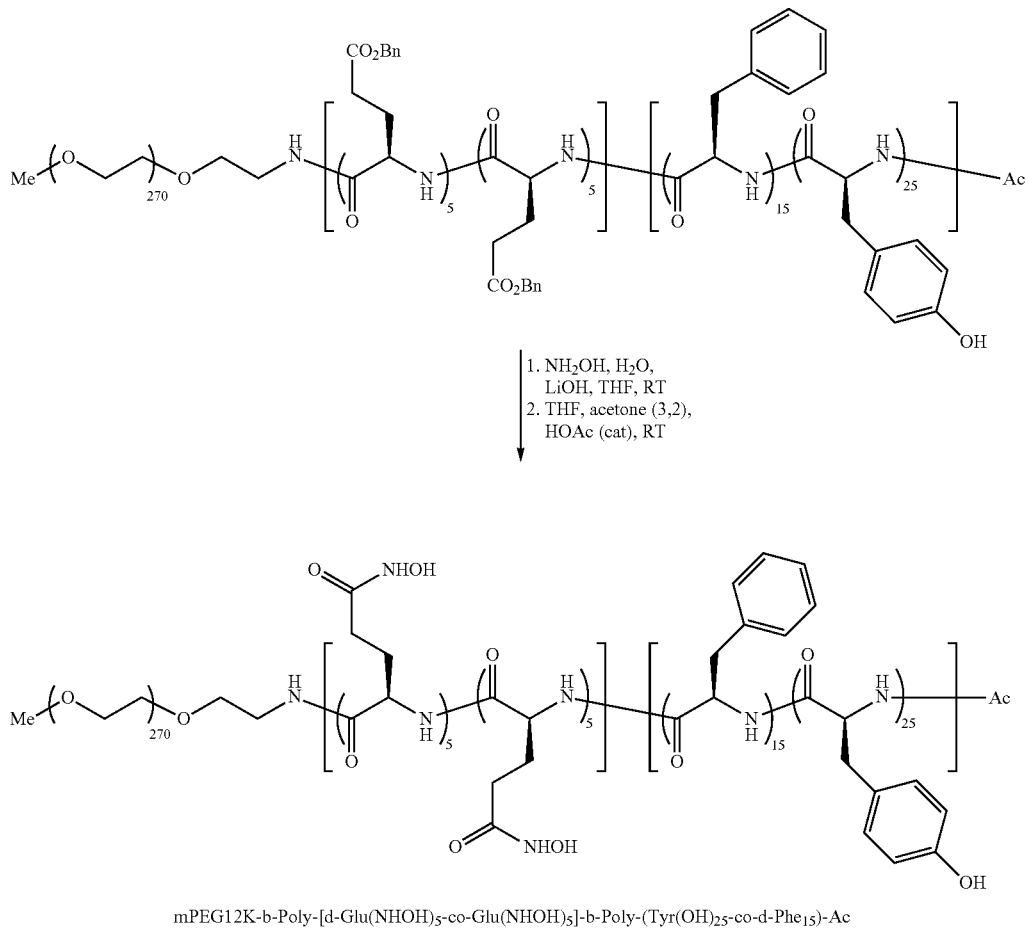

mPEG12K-b-Poly-[d-Glu(NHOH)5-co-Glu(NHOH)5]-b-Poly-(Tyr(OH)25-co-d-Phe15)-Ac

Synthesis of mPEG12K-b-Poly-[d-Glu(NHOH)5-Co-Glu(NHOH)5]-b-Poly-(Tyr(OH)25-Co-d-Phe15)-Ac Using the method described above in Example 52, mPEG12K-b-Poly-[d-Glu(OBn)5-co-Glu(OBn)5]-b-Poly-(Tyr(OH)25-co-d-Phe15)-Ac was converted to the title compound using solid lithium hydroxide monohydrate (2.0 equiv./Bn ester moiety). Reaction time was 6 hours. Workup afforded the title compound (Yield=99.2%) as a fine, colorless solid. $^1$H NMR (d$_6$-DMSO): identical to Example 38.

Example 54

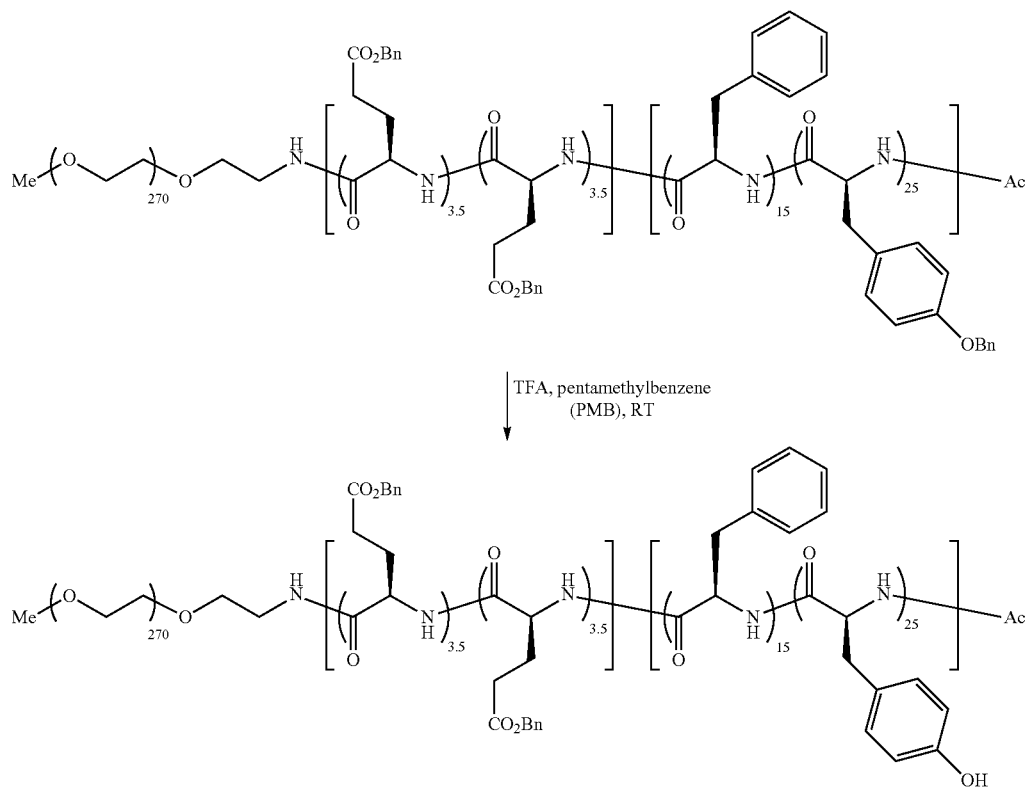

mPEG12k-b-Poly-[d-Glu(OBn)$_{3.5}$-co-Glu(OBn)$_{3.5}$]-b-Poly-(Tyr(OH)$_{25}$-co-d-Phe$_{15}$)-Ac Synthesis of mPEG12K-b-Poly-[d-Glu(OBn)$_{3.5}$-Co-Glu(OBn)$_{3.5}$]-b-Poly-(Tyr(OH)$_{25}$-Co-d-Phe$_{15}$)-Ac By using the method of Example 37, reaction of mPEG12K-b-Poly-[d-Glu(OBn)$_{3.5}$-co-Glu(OBn)$_{3.5}$]-b-Poly-(Tyr(OBn)$_{25}$-co-d-Phe$_{15}$)-Ac with PMB in TFA for 3.5 hours at room temperature and precipitation from a mixture of dichloromethane, TBME: 1,7 afforded the title product (Yield=96.1%) as a fine, colorless, odorless polymer. $^1$H NMR (d$_6$-DMSO) δ 9.09 (theo. 25H, obs'd. 22H), 8.46-7.79 (theo. 47H, obs'd. 48H), 7.40-6.45 (theo. 210H, obs'd. 229H), 5.04 (theo. 14H, obs'd. 13H), 4.65-4.20 (theo. 47H, obs'd. 47H), 3.81-3.15 (theo. 1087H, obs'd. 1308H), 3.03-2.10 (theo. 80H, obs'd. 78H), 2.06-1.62 (theo. 40H, obs'd. 27H).

Example 55

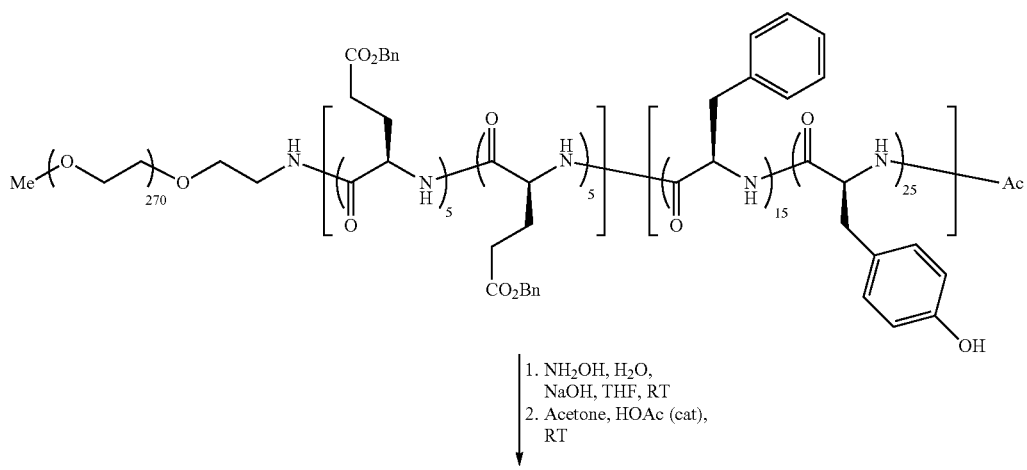

1. NH$_2$OH, H$_2$O, NaOH, THF, RT
2. Acetone, HOAc (cat), RT

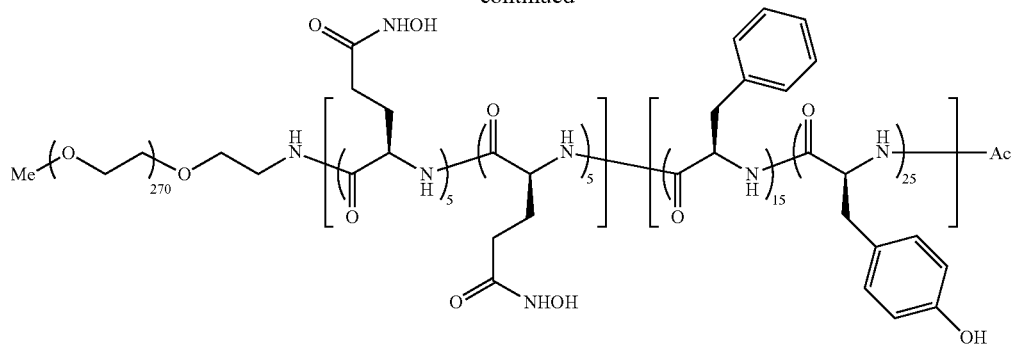

mPEG12K-b-Poly-[d-Glu(NHOH)$_5$-co-Glu(NHOH)$_5$]-b-Poly-(Tyr(OH)$_{25}$-co-d-Phe$_{15}$)-Ac Synthesis of mPEG12K-b-Poly-[d-Glu(NHOH)$_5$-Co-Glu(NHOH)$_5$]-b-Poly-(Tyr(OH)$_{25}$-Co-d-Phe$_{15}$)-Ac Using the method described above in Example 51, mPEG12K-b-Poly-[d-Glu(OBn)$_5$-co-Glu(OBn)$_5$]-b-Poly-(Tyr(OH)$_{25}$-co-d-Phe$_{15}$)-Ac was converted to the title compound using 4M sodium hydroxide solution (2.0 equiv./Bn ester moiety). Reaction time was 4 hours. The solution was diluted with acetone (0.30 volumes based on total reaction mixture volume) and acetic acid (1.0 equiv./hydroxylamine) was added. After 14 hours, the crude product was precipitated from three volumes of TBME, stirred for three days, and filtered. The filter cake was washed with TBME (50 mL), TBME, IPA: 20,1 (50 mL) and dried in vacuo to afford the title compound (Yield=93.5%) as a fine, colorless solid with a slight odor of acetic acid. $^1$H NMR (d$_6$-DMSO): identical to Example 38.

Example 56

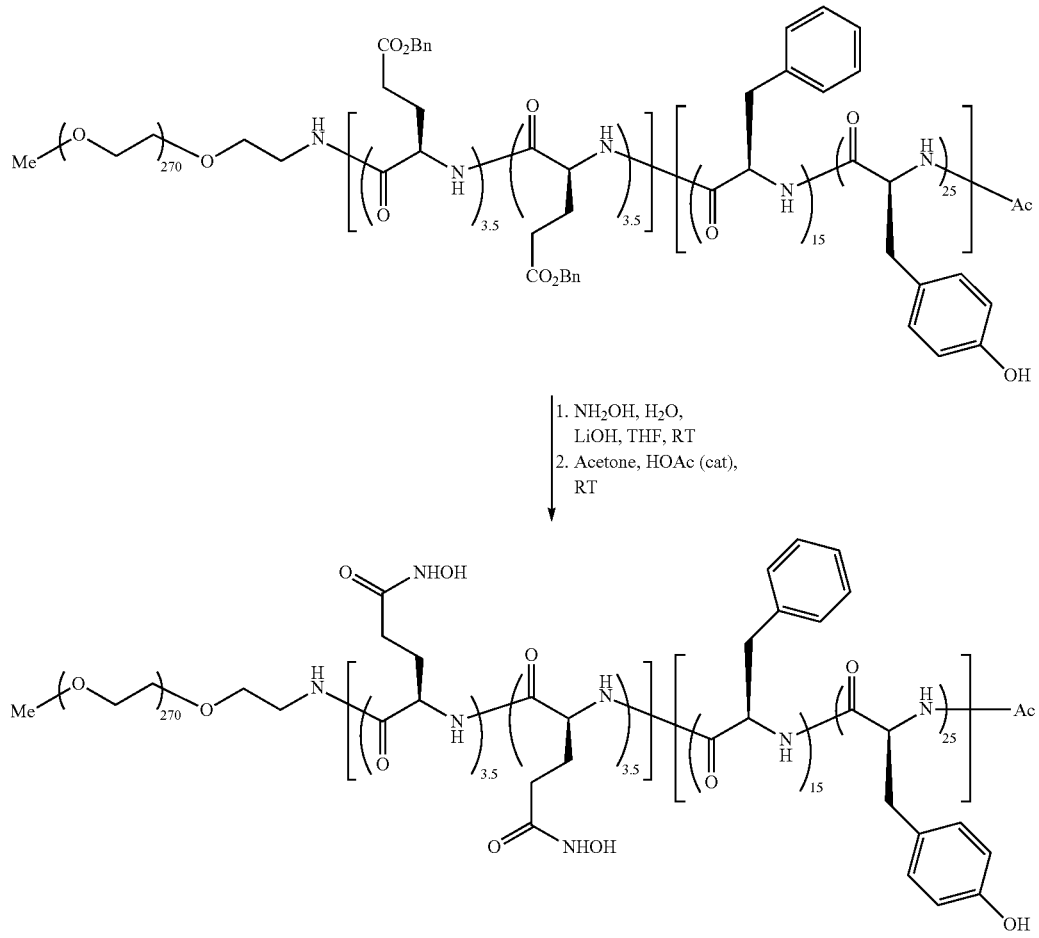

mPEG12K-b-Poly-[d-Glu(NHOH)$_{3.5}$-co-Glu(NHOH)$_{3.5}$]-b-Poly-(Tyr(OH)$_{25}$-co-d-Phe$_{15}$)-Ac Synthesis of mPEG12K-b-Poly-[d-Glu(NHOH)$_{3.5}$-Co-Glu(NHOH)$_{3.5}$]-b-Poly-(Tyr(OH)$_{25}$-Co-d-Phe$_{15}$)-Ac Using the method described above in Example 52, mPEG12K-b-Poly-[d-Glu(OBn)$_{3.5}$-co-Glu(OBn)$_{3.5}$]-b-Poly-(Tyr(OH)$_{25}$-co-d-Phe$_{15}$)-Ac was converted to the title compound using solid lithium hydroxide monohydrate (2.0 equiv./Bn ester moiety). Reaction time was 6 hours. Workup afforded the title compound (Yield=94.9%) as a fine, colorless solid with a slight odor of acetic acid. $^1$H NMR (d$_6$-DMSO) δ 10.2-9.2 (theo. 25H, obs'd. 19H), 8.52-7.90 (theo. 47H, obs'd. 38H), 7.40-6.49 (theo. 175H, obs'd. 175H), 4.63-4.00 (theo. 47H, obs'd. 42H), 3.84-3.11 (theo. 1087H, obs'd. 1496H, contains masked H$_2$O peak), 3.00-2.20 (theo. 80H, obs'd. 78H), 2.16-1.60 (theo. 28H, obs'd.~26H, contains overlapping HOAc peak at δ 1.69).

Example 57

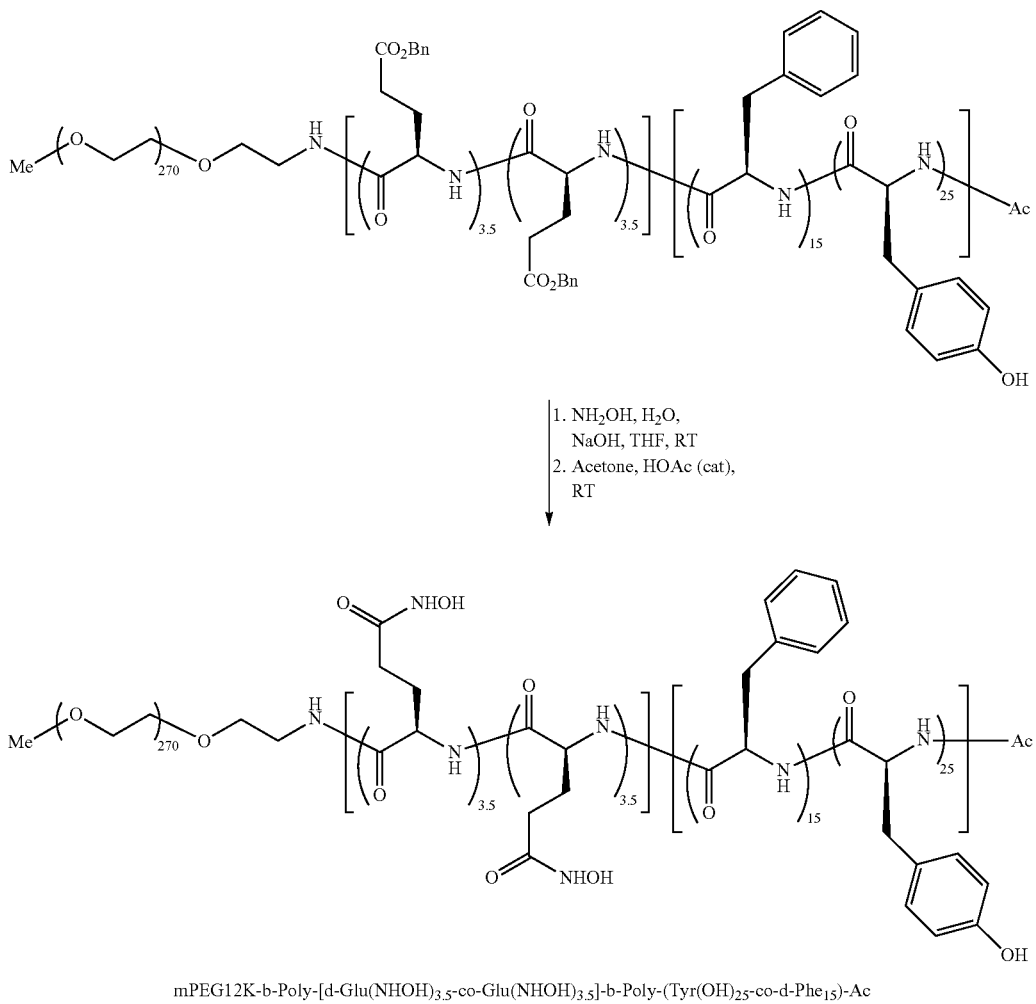

mPEG12K-b-Poly-[d-Glu(NHOH)$_{3.5}$-co-Glu(NHOH)$_{3.5}$]-b-Poly-(Tyr(OH)$_{25}$-co-d-Phe$_{15}$)-Ac Synthesis of mPEG12K-b-Poly-[d-Glu(NHOH)$_{3.5}$-Co-Glu(NHOH)$_{3.5}$]-b-Poly-(Tyr(OH)$_{25}$-Co-d-Phe$_{15}$)-Ac Using the method described above in Example 52, mPEG12K-b-Poly-[d-Glu(OBn)$_{3.5}$-co-Glu(OBn)$_{3.5}$]-b-Poly-(Tyr(OH)$_{25}$-co-d-Phe$_{15}$)-Ac was converted to the title compound using 10M sodium hydroxide solution (2.0 equiv./Bn ester moiety). Reaction time was 3 hours. Workup afforded the title compound (Yield=85.8%) as a fine, colorless solid with a slight odor of acetic acid. $^1$H NMR (d$_6$-DMSO): identical to Example 56.

Example 58

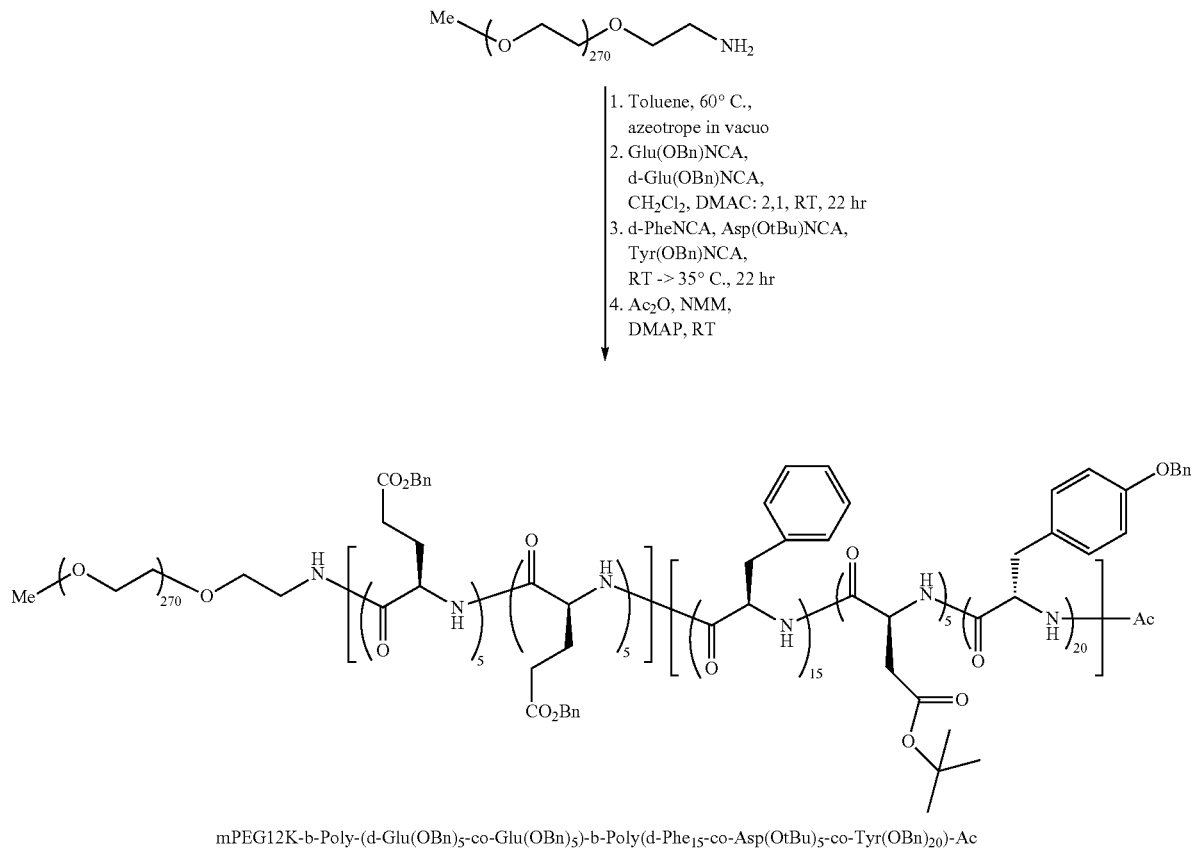

mPEG12K-b-Poly-(d-Glu(OBn)₅-co-Glu(OBn)₅)-b-Poly(d-Phe₁₅-co-Asp(OtBu)₅-co-Tyr(OBn)₂₀)-Ac Synthesis of mPEG12K-b-Poly-(d-Glu(OBn)$_5$-Co-Glu(OBn)$_5$)-b-Poly(d-Phe$_{15}$-Co-Asp(OtBu)$_5$-Co-Tyr(OBn)$_{20}$)-Ac Using the method detailed in Example 49 with anhydrous dichloromethane (2 parts) and N,N-dimethylacetamide (DMAC, 1 part) as solvents and substituting the appropriate NCA building blocks afforded a crude polymer that was precipitated with 5 volumes of isopropanol. After filtration and drying in vacuo, the title compound (Yield=95.4%) was obtained as a fine, colorless, odorless solid. $^1$H NMR (d$_6$-DMSO) δ 8.57-7.75 (theo. 50H, obs'd. 47H), 7.41-6.67 (theo. 305H, obs'd. 305H), 5.10-4.85 (theo. 60H, obs'd. 59H), 4.70-4.18 (theo. 50H, obs'd. 49H), 3.72-3.25 (theo. 1087H, obs'd. 1131H), 3.05-2.20 (theo. 80H, obs'd. 100H), 2.05-1.58 (theo. 40H, obs'd. 25H), 1.38-1.20 (theo. 45H, obs'd. 40H).

Example 59

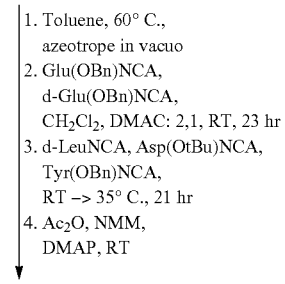

1. Toluene, 60° C., azeotrope in vacuo
2. Glu(OBn)NCA, d-Glu(OBn)NCA, CH₂Cl₂, DMAC: 2,1, RT, 23 hr
3. d-LeuNCA, Asp(OtBu)NCA, Tyr(OBn)NCA, RT -> 35° C., 21 hr
4. Ac₂O, NMM, DMAP, RT

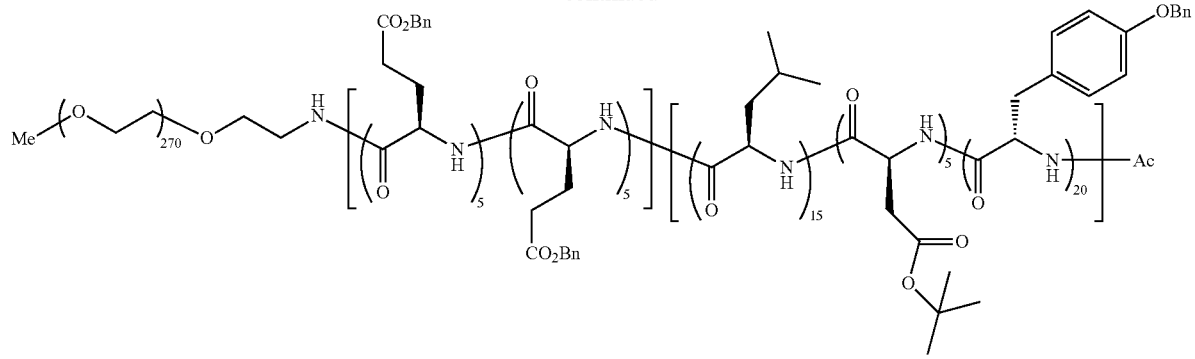

mPEG12K-b-Poly-(d-Glu(OBn)$_5$-co-Glu(OBn)$_5$)-b-Poly(d-Leu$_{15}$-co-Asp(OtBu)$_5$-co-Tyr(OBn)$_{20}$)-Ac mPEG12K-b-Poly-(d-Glu(OBn)$_5$-Co-Glu(OBn)$_5$)-b-Poly-(d-Leu$_{15}$-Co-Asp(OtBu)$_5$-Co-Tyr(OBn)$_{20}$)-Ac Using the method detailed in Example 58 and substituting the appropriate NCA building blocks afforded a crude polymer that was precipitated with 5 volumes of isopropanol. After filtration and drying in vacuo, the title compound (Yield=95.5%) was obtained as a fine, colorless, odorless solid. $^1$H NMR (d$_6$-DMSO) δ 8.45-7.78 (theo. 50H, obs'd. 47H), 7.45-6.67 (theo. 230H, obs'd. 230H), 5.10-4.80 (theo. 60H, obs'd. 59H), 4.65-4.00 (theo. 50H, obs'd. 52H), 3.70-3.25 (theo. 1087H, obs'd. 1196H), 3.05-2.55 (theo. 40H, obs'd. 41H), 2.48-2.30 (theo. 40H, obs'd. 33H), 2.05-1.71 (theo. 40H, obs'd. 25H), 1.69-1.02 (theo. 60H, obs'd. 65H), 0.95-0.55 (theo. 90H, obs'd. 83H).

Example 60

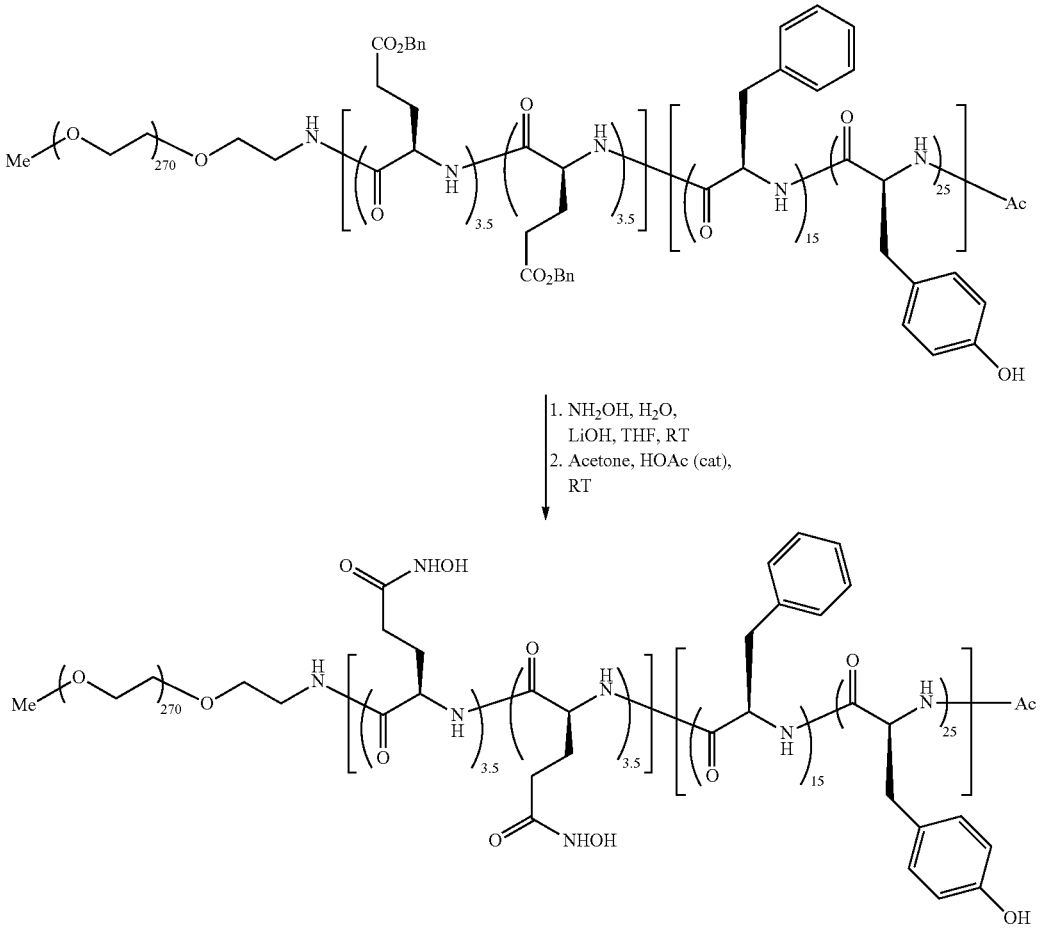

mPEG12K-b-Poly-[d-Glu(NHOH)$_{3.5}$-co-Glu(NHOH)$_{3.5}$]-b-Poly-(Tyr(OH)$_{25}$-co-d-Phe$_{15}$)-Ac Synthesis of mPEG12K-b-Poly-[d-Glu(NHOH)$_{3.5}$-Co-Glu(NHOH)$_{3.5}$]-b-Poly-(Tyr(OH)$_{25}$-Co-d-Phe$_{3.5}$)-Ac Using the method described above in Example 57, mPEG12K-b-Poly-[d-Glu(OBn)$_{3.5}$-co-Glu(OBn)$_{3.5}$]-b-Poly-(Tyr(OH)$_{25}$-co-d-Phe$_{15}$)-Ac was converted to the title compound using 4M sodium hydroxide solution (2.0 equiv./Bn ester moiety). Reaction time was 16 hours. Workup with three times the normal volume of IPA followed by precipitation with TBME afforded the title compound (Yield=92.7%) as a fine, pale cream-colored, solid with a slight odor of acetic acid.

Example 61

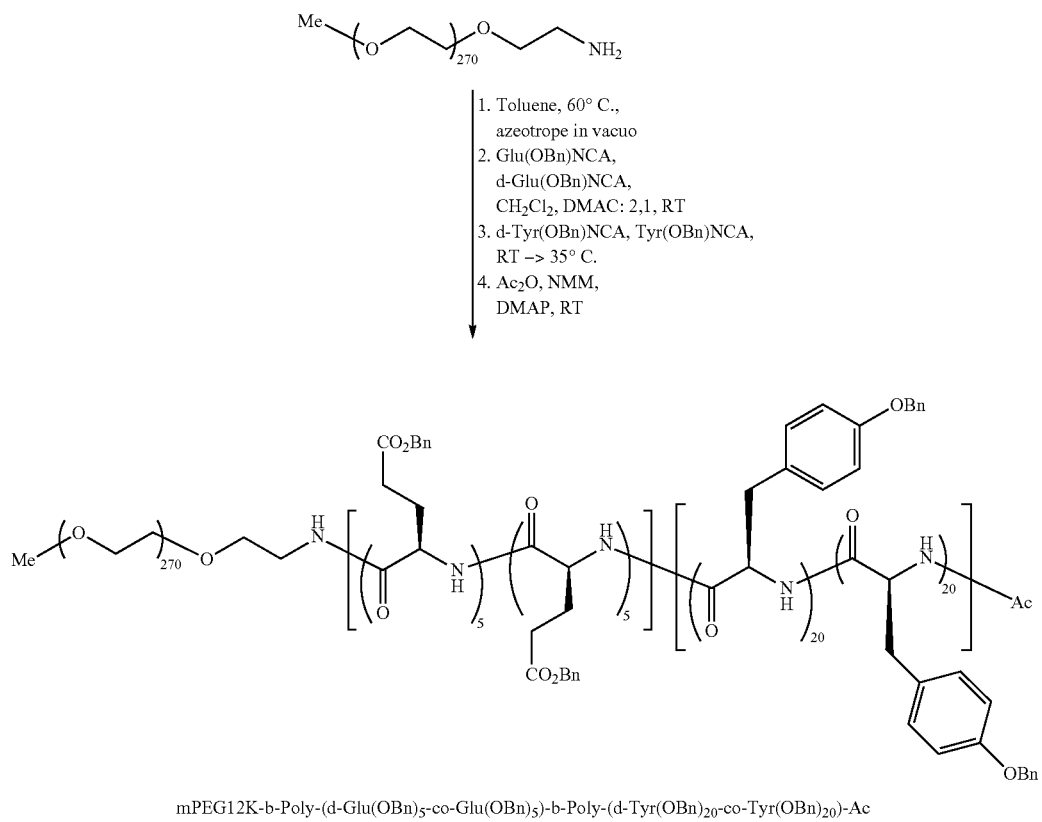

mPEG12K-b-Poly-(d-Glu(OBn)$_5$-co-Glu(OBn)$_5$)-b-Poly-(d-Tyr(OBn)$_{20}$-co-Tyr(OBn)$_{20}$)-Ac Synthesis of mPEG12K-b-Poly-(d-Glu(OBn)$_5$-Co-Glu(OBn)$_5$)-b-Poly-(d-Tyr(OBn)$_{20}$-Co-Tyr(OBn)$_{20}$)-Ac Using the mixed reaction solvent method detailed in Example 58 and substituting the appropriate NCA building blocks afforded a crude polymer that was precipitated with 9 volumes of isopropanol. After filtration and drying in vacuo, the title compound (Yield=96.6%) was obtained as a fine, colorless, odorless solid. $^1$H NMR (d$_6$-DMSO) δ 8.44-7.80 (theo. 50H, obs'd. 47H), 7.40-6.75 (theo. 410H, obs'd. 410H), 5.11-4.84 (theo. 100H, obs'd. 94H), 4.60-4.20 (theo. 50H, obs'd. 52H), 3.70-3.25 (theo. 1087H, obs'd. 1605H), 3.00-2.28 (theo. 80H, obs'd. 95H), 2.03-1.60 (theo. 40H, obs'd. 31H).

Example 62

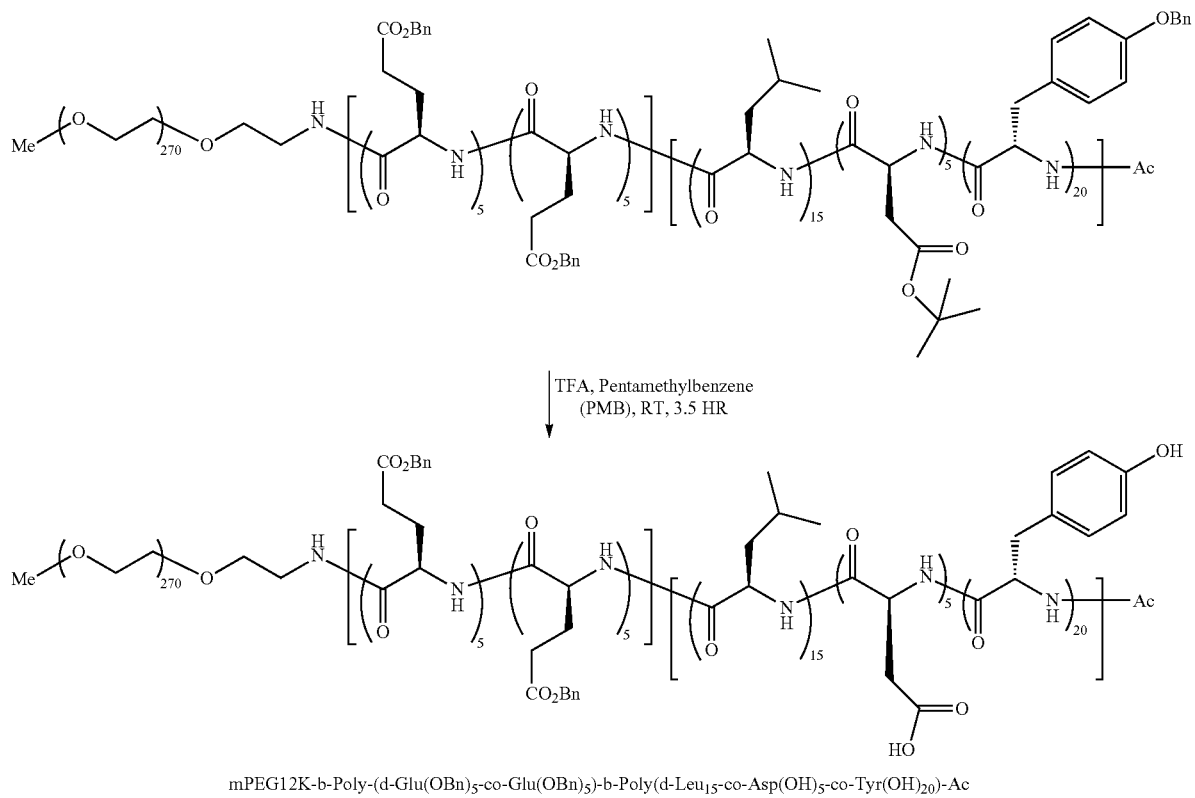

mPEG12K-b-Poly-(d-Glu(OBn)$_5$-co-Glu(OBn)$_5$)-b-Poly(d-Leu$_{15}$-co-Asp(OH)$_5$-co-Tyr(OH)$_{20}$)-Ac

Synthesis of mPEG12K-b-Poly-(d-Glu(OBn)-Co-Glu(OBn)$_5$)-b-Poly-(d-Leu$_{15}$-Co-Asp(OH)$_5$-Co-Tyr(OH)$_{20}$)-Ac By using the method of Example 54, reaction of mPEG12K-b-Poly-(d-Glu(OBn)$_5$-co-Glu(OBn)$_5$)-b-Poly-(d-Leu$_{15}$-co-Asp(OtBu)$_5$-co-Tyr(OBn)$_{20}$)-Ac with PMB in TFA for 3.5 hours at room temperature and precipitation from a mixture of dichloromethane, TBVE: 1,6 afforded the title product (Yield=95.5%) as a fine, colorless, odorless polymer. 1H NMR (d$_6$-DMSO) δ 9.15 (theo. 20H, obs'd. 18H), 8.43-7.60 (theo. 50H, obs'd. 47H), 7.40-6.45 (theo. 130H, obs'd. 130H), 5.04 (theo. 20H, obs'd. 13H), 4.65-4.00 (theo. 50H, obs'd. 48H), 3.85-3.15 (theo. 1087H, obs'd. 1334H), 3.01-2.10 (theo. 80H, obs'd. 80H), 2.05-1.65 (theo. 40H, obs'd. 42H), 1.63-0.55 (theo. 90H, obs'd. 75H).

Example 63

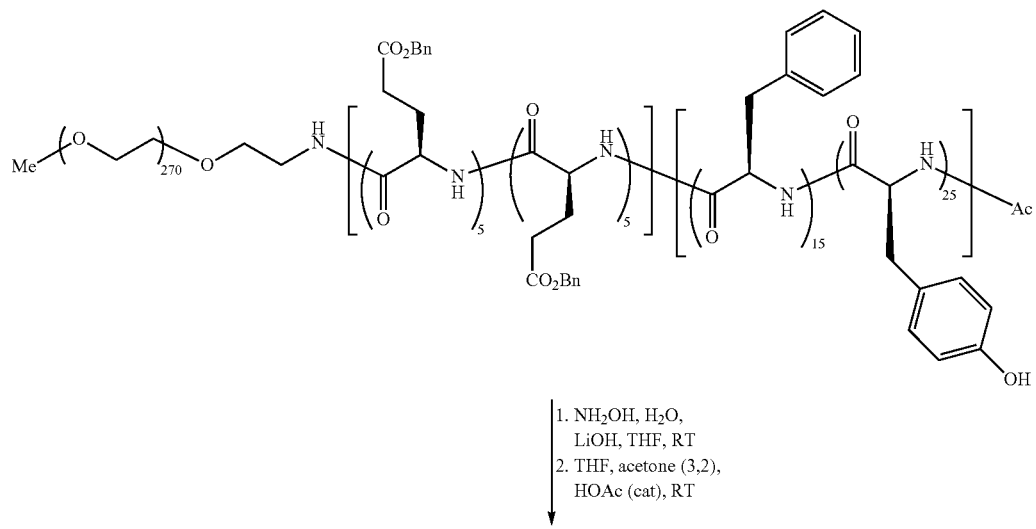

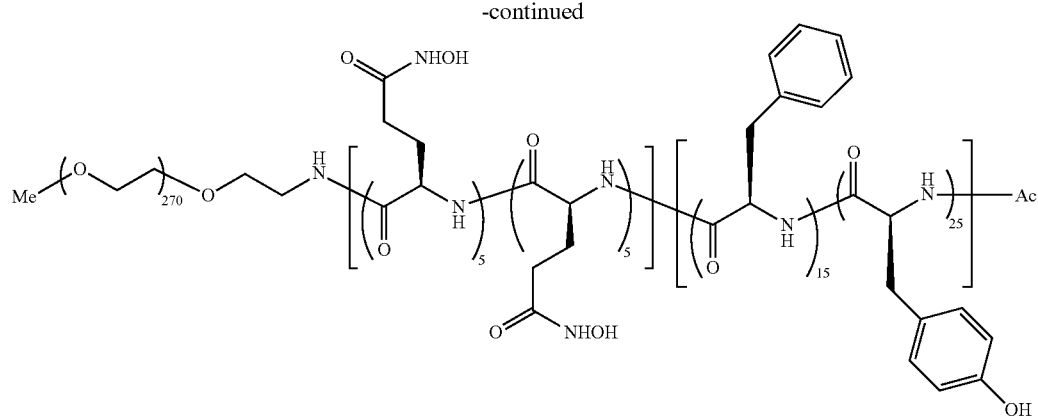

mPEG12K-b-Poly-[d-Glu(NHOH)$_5$-co-Glu(NHOH)$_5$]-b-Poly-(Tyr(OH)$_{25}$-co-d-Phe$_{15}$)-Ac Synthesis of mPEG12K-b-Poly-[d-Glu(NHOH)$_5$-Co-Glu(NHOH)$_5$]-b-Poly-(Tyr(OH)$_{25}$-Co-d-Phe$_{15}$)-Ac Using the method described above in Example 47, mPEG12K-b-Poly-[d-Glu(OBn)$_5$-co-Glu(OBn)$_5$]-b-Poly-(Tyr(OH)$_{25}$-co-d-Phe$_{15}$)-Ac was converted to the title compound using solid potassium hydroxide (2.0 equiv./Bn ester moiety) pre-dissolved in the hydroxylamine solution. Reaction time was 5.5 hours. Workup afforded the title compound (Yield=74.0%) as a fine, colorless solid with a slight odor of acetic acid. $^1$H NMR (d$_6$-DMSO): identical to Example 38.

Example 64

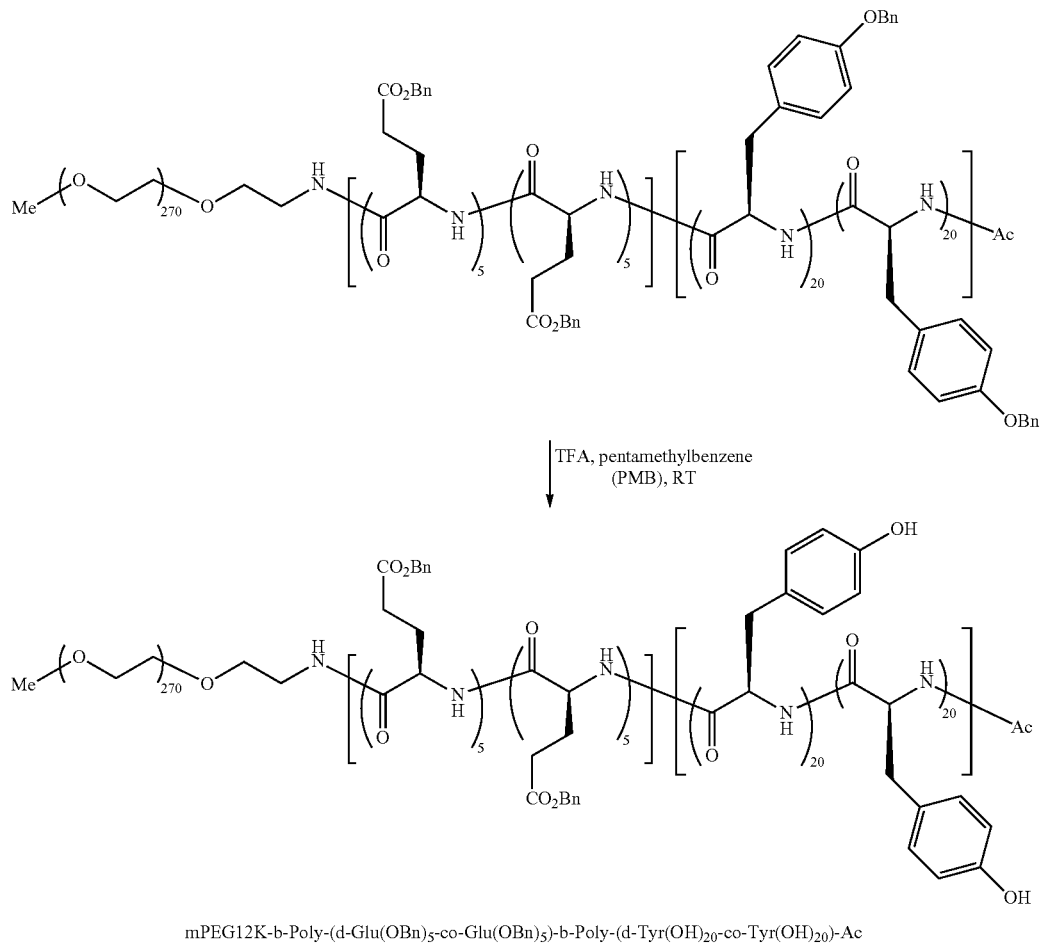

mPEG12K-b-Poly-(d-Glu(OBn)$_5$-co-Glu(OBn)$_5$)-b-Poly-(d-Tyr(OH)$_{20}$-co-Tyr(OH)$_{20}$)-Ac Synthesis of mPEG12K-b-Poly-(d-Glu(OBn)$_5$-Co-Glu(OBn)$_5$)-b-Poly-(d-Tyr(OH)$_{20}$-Co-Tyr(OH)$_{20}$)-Ac By using the method of Example 54, reaction of mPEG12K-b-Poly-(d-Glu(OBn)$_5$-co-Glu(OBn)$_5$)-b-Poly-(d-Tyr(OBn)$_2$-co-Tyr(OBn)$_{20}$)-Ac with PMB in TFA for 4.5 hours at room temperature and precipitation from a mixture of dichloromethane, TBME: 1,5 afforded the title product (Yield=97.7%) as a fine, colorless, odorless solid. $^1$H NMR (d$_6$-DMSO) δ 9.1 (theo. 40H, obs'd. 33H), 8.36-7.77 (theo. 50H, obs'd. 52H), 7.40-6.45 (theo. 210H, obs'd. 234H), 5.04 (theo. 20H, obs'd. 17H), 4.60-4.20 (theo. 50H, obs'd. 50H), 4.02-3.15 (theo. 1087H, obs'd. 1384H, contains obscured water peak), 3.00-2.10 (theo. 80H, obs'd. 78H), 2.06-1.62 (theo. 40H, obs'd. 39H).

Example 65

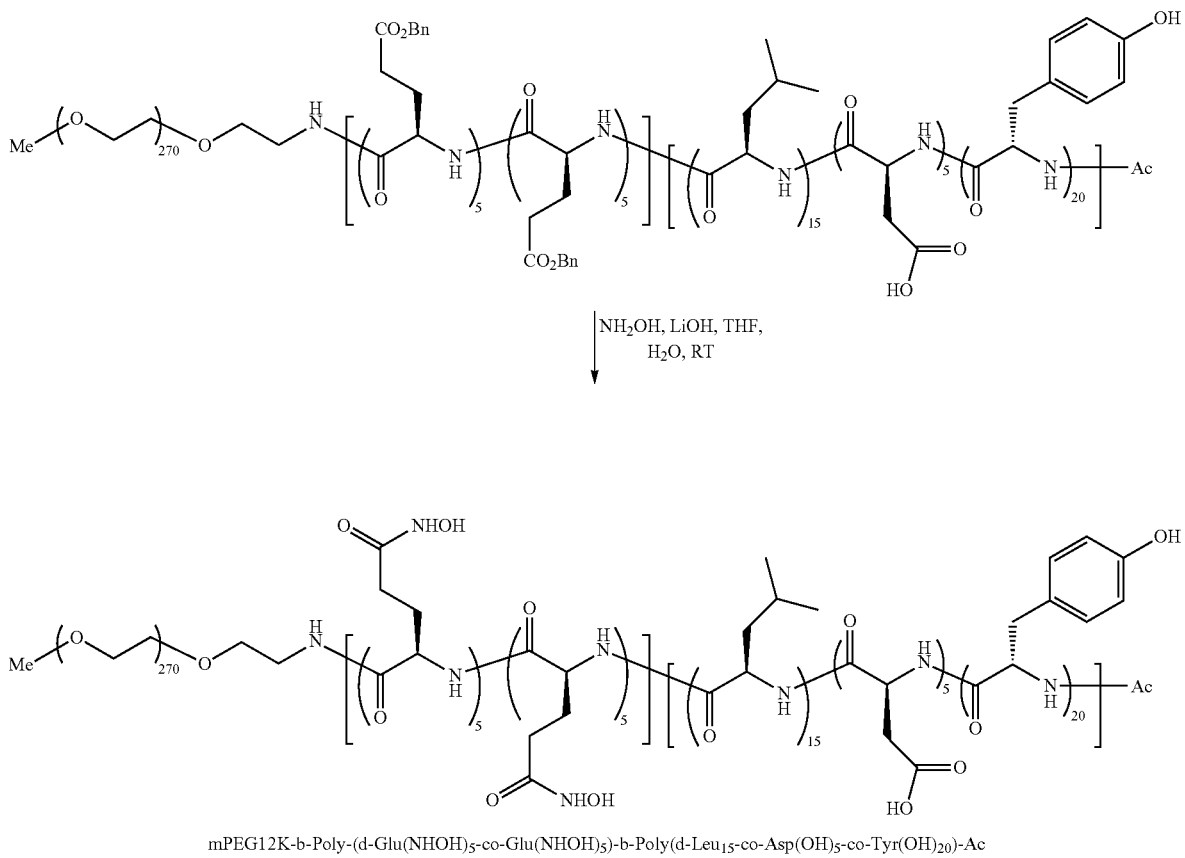

mPEG12K-b-Poly-(d-Glu(NHOH)$_5$-co-Glu(NHOH)$_5$)-b-Poly(d-Leu$_{15}$-co-Asp(OH)$_5$-co-Tyr(OH)$_{20}$)-Ac Synthesis of mPEG12K-b-Poly-(d-Glu(NHOH)$_5$-Co-Glu(NHOH)$_5$)-b-Poly-(d-Leu$_{15}$-Co-Asp(OH)$_5$-Co-Tyr(OH)$_{20}$)-Ac Using the method described above in Example 52, mPEG12K-b-Poly-(d-Glu(OBn)$_5$-co-Glu(OBn)$_5$)-b-Poly-(d-Leu$_{15}$-co-Asp(OH)$_5$-co-Tyr(OH)$_{20}$)-Ac was converted to the title compound using lithium hydroxide monohydrate (2.0 equiv./Bn ester moiety). Reaction time was 15 hours. Workup followed by precipitation with IPA, TBME afforded the title compound (Yield=quantitative) as a fine, colorless solid with a slight odor of acetic acid. $^1$H NMR (d$_6$-DMSO) δ 10.2-9.0 (theo. 40H, obs'd. 31H), 8.65-7.75 (theo. 50H, obs'd. 37H), 7.27-6.50 (theo. 80H, obs'd. 80H), 4.61-4.00 (theo. 50H, obs'd. 58H), 3.90-3.15 (theo. 1087H, obs'd. 1356H), 3.02-2.20 (theo. 80H, obs'd. 100H), 2.40-1.70 (theo. 40H, obs'd.~47H, contains overlapping HOAc peak at δ 1.69), 1.63-0.55 (theo. 105H, obs'd. 96H).

Example 66

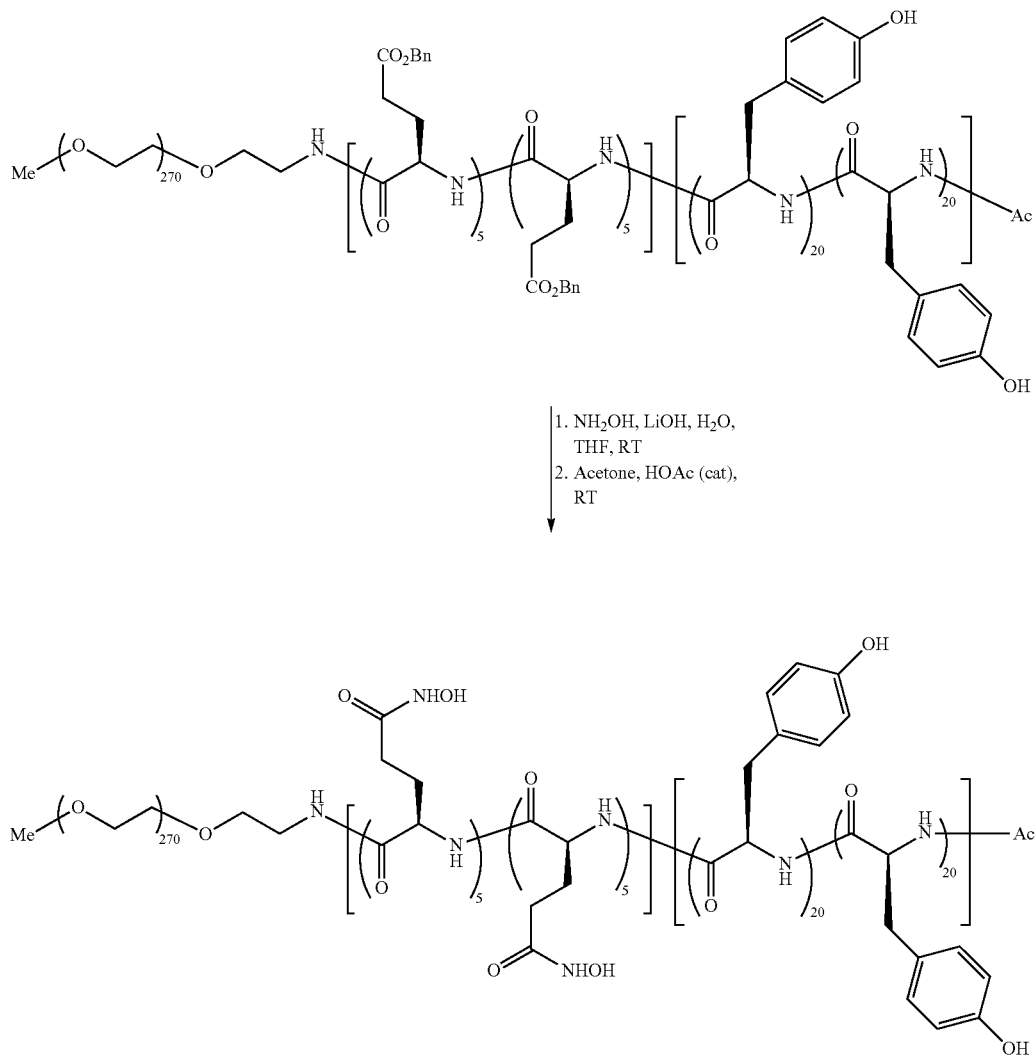

mPEG12K-b-Poly-(d-Glu(NHOH)₅-co-Glu(NHOH)₅)-b-Poly-(d-Tyr(OH)₂₀-co-Tyr(OH)₂₀)-Ac

Synthesis of mPEG12K-b-Poly-(d-Glu(NHOH)$_5$-Co-Glu(NHOH)$_5$)-b-Poly-(d-Tyr(OH)$_{20}$-Co-Tyr(OH)$_{20}$)-Ac Using the method described above in Example 52, mPEG12K-b-Poly-(d-Glu(OBn)$_5$-co-Glu(OBn)$_5$)-b-Poly-(d-Tyr(OH)$_2$-co-Tyr(OH)$_{20}$)-Ac was converted to the title compound using lithium hydroxide monohydrate (2.0 equiv./Bn ester moiety). Reaction time was 5.5 hours. Workup followed by precipitation with IPA, TBME afforded the title compound (Yield=93.2%) as a fine, colorless solid with a slight odor of acetic acid. $^1$H NMR (d$_6$-DMSO) δ 9.55 (theo. 40H, obs'd. 26H), 8.45-7.90 (theo. 50H, obs'd. 34H), 7.37-6.51 (theo. 160H, obs'd. 166H), 4.55-4.10 (theo. 50H, obs'd. 50H), 3.80-3.20 (theo. 1087H, obs'd. 1269H, contains obscured water peak), 3.00-2.20 (theo. 80H, obs'd. 108H), 2.18-1.60 (theo. 40H, obs'd. 39H, contains overlapping HOAc peak at δ 1.69).

Example 67

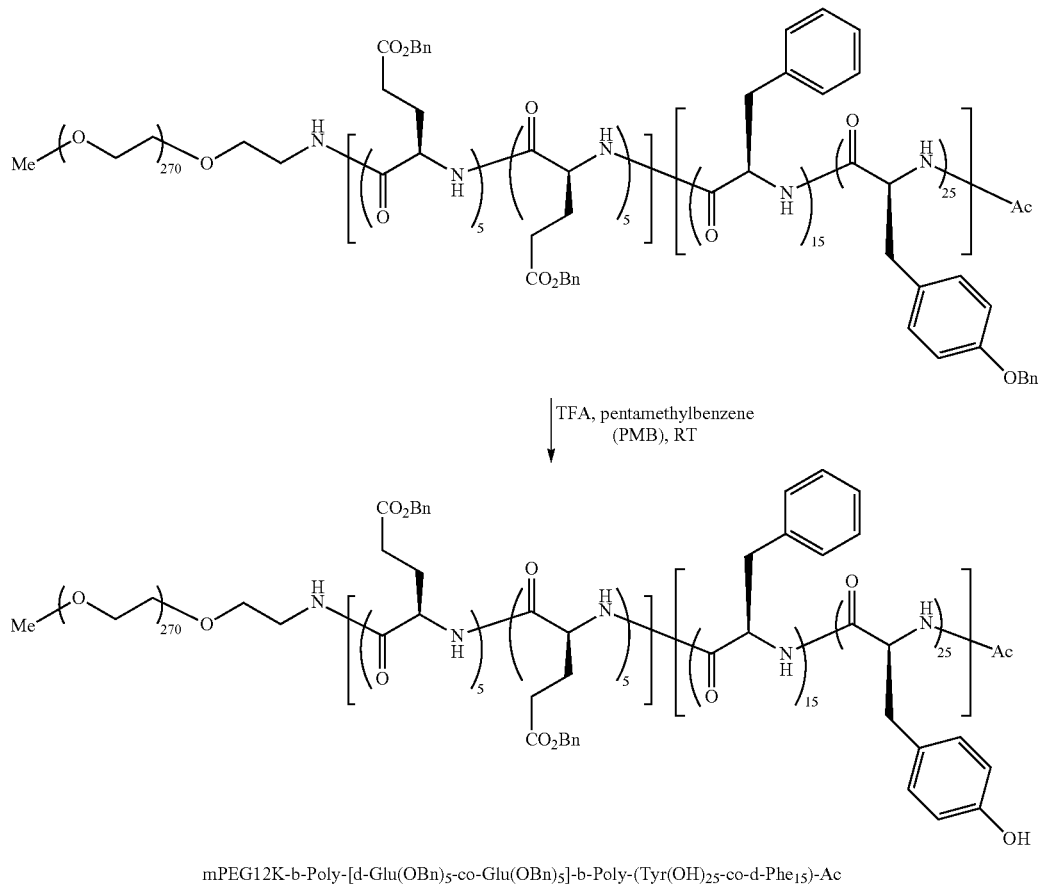

mPEG12K-b-Poly-[d-Glu(OBn)₅-co-Glu(OBn)₅]-b-Poly-(Tyr(OH)₂₅-co-d-Phe₁₅)-Ac

Synthesis of mPEG12K-b-Poly-[d-Glu(OBn)₅-Co-Glu(OBn)₅]-b-Poly-(Tyr(OH)₂₅-Co-d-Phe₁₅)-Ac By using the method of Example 43, reaction of mPEG12K-b-Poly-[d-Glu(OBn)₅-co-Glu(OBn)₅]-b-Poly-(Tyr(OBn)₂₅-co-d-Phe₁₅)-Ac with PMB in TFA for 3.5 hours at room temperature gave a crude product, which was dissolved in dichloromethane (2 volumes) and then precipitated from TBME (5 volumes). Filtration and drying in vacuo afforded the title product (Yield=93.1%) as a fine, colorless, odorless solid. $^1$H NMR (d₆-DMSO): identical to Example 37.

Example 68

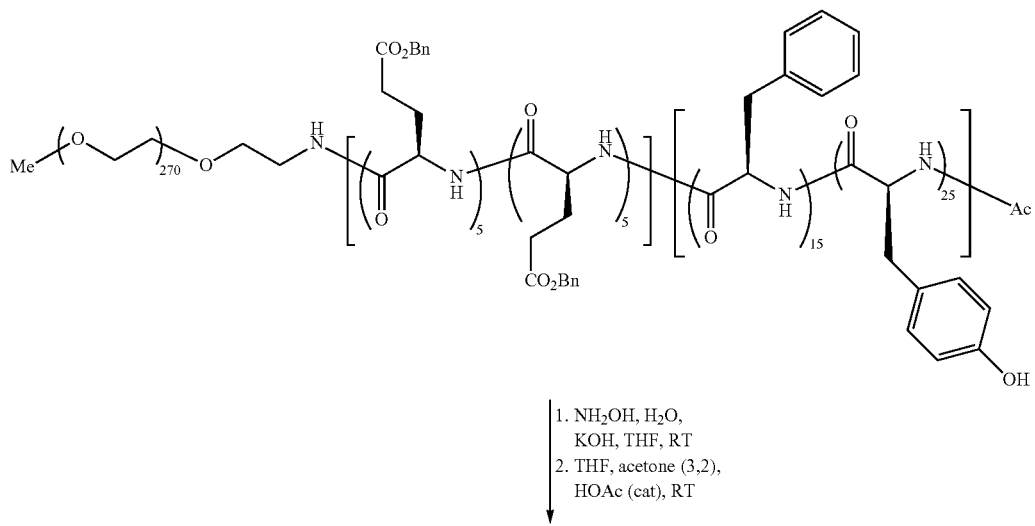

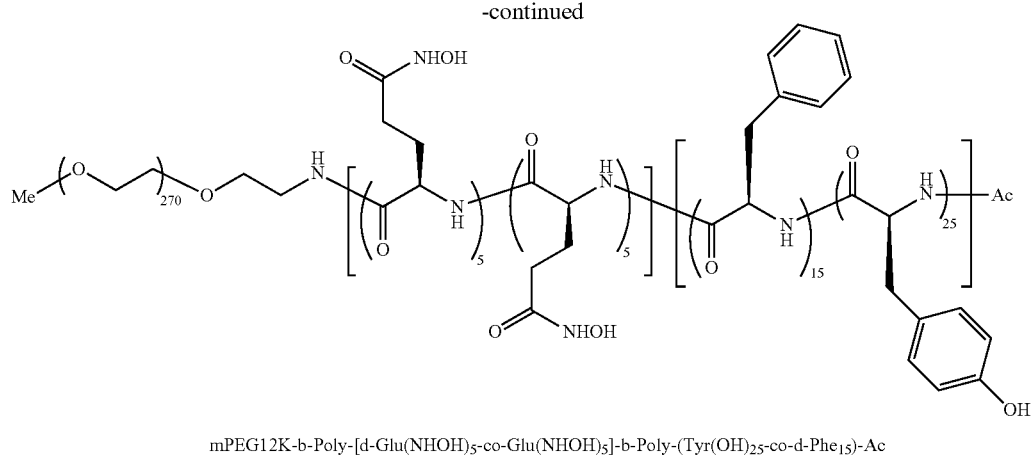

mPEG12K-b-Poly-[d-Glu(NHOH)5-co-Glu(NHOH)5]-b-Poly-(Tyr(OH)25-co-d-Phe15)-Ac

Synthesis of mPEG12K-b-Poly-[d-Glu(NHOH)5-Co-Glu(NHOH)5]-b-Poly-(Tyr(OH)25-Co-d-Phe15)-Ac mPEG12K-b-Poly-[d-Glu(OBn)5-co-Glu(OBn)5]-b-Poly-(Tyr(OH)25-co-d-Phe15)-Ac (38.94 g, 1.90 mmol) was dissolved in 390 mL of THF and treated with hydroxylamine solution (25.2 mL, 380.0 mmol) and 4M potassium hydroxide solution (9.5 mL, 38.0 mmol, 2.0 equiv./Bn ester moiety). The resultant slightly hazy pale yellow solution was stirred at room temperature for 5.5 hours under $N_2$ and then diluted with acetone (220.7 g, 3.8 mol, 280 mL). Acetic acid (22.82 g, 380.0 mmol, 21.7 mL) was added, the solution was briefly heated to reflux, and then was stirred at room temperature for 18 hours. The solution was diluted with 280 mL of acetone and the product was precipitated by addition of TBME (5 L) and diethyl ether (1 L) using vigorous mechanical stirring. After cooling to −25° C. and stirring an additional 30 minutes, filtration and drying in vacuo afforded the title compound (35.98 g, Yield=87.3%) as a fine, colorless solid with a slight odor of acetic acid. $^1$H NMR ($d_6$-DMSO): identical to Example 38.

Example 69

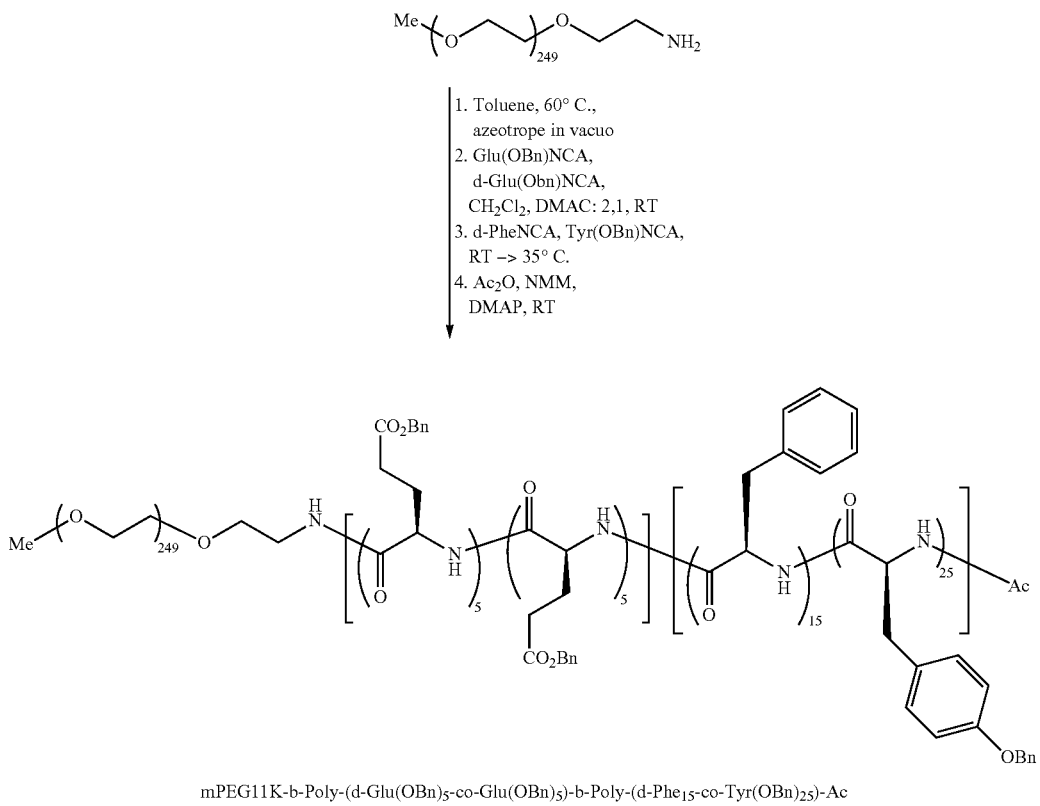

mPEG11K-b-Poly-(d-Glu(OBn)5-co-Glu(OBn)5)-b-Poly-(d-Phe15-co-Tyr(OBn)25)-Ac

Synthesis of mPEG11K-b-Poly-(d-Glu(OBn)$_5$-Co-Glu(OBn)$_5$)-b-Poly-(d-Phe$_{15}$-Co-Tyr(OBn)$_{25}$)-Ac Utilizing the dichloromethane, DMAC co-solvent method detailed in Example 58 with m-PEG11k-NH$_2$ (1.10 kg, 100.0 mmol) and the appropriate NCA building blocks afforded a crude polymer solution in DMAC that was precipitated with 8 volumes of isopropanol. After filtration, the crude product was slurried in 5 volumes of isopropanol for two hours. The resultant solid was filtered, washed with fresh IPA/Et$_2$O, Et$_2$O and then vacuum oven dried overnight to afford 2130 g (97.8% yield) of product as a nearly colorless, odorless solid. $^1$H-NMR (d$_6$-DMSO) δ 8.45-7.85 (theo. 50H, obs'd. 50H), 7.45-6.60 (theo. 350H, obs'd. 350H), 5.10-4.84 (theo. 70H, obs'd. 68H), 4.65-4.20 (theo. 50H, obs'd. 48H), 3.72-3.25 (theo. 1000H, obs'd. 1120H), 3.05-2.55 (theo. 50H, obs'd. 49H), 2.44-1.60 (theo. 70H, obs'd. 68H).

Example 70

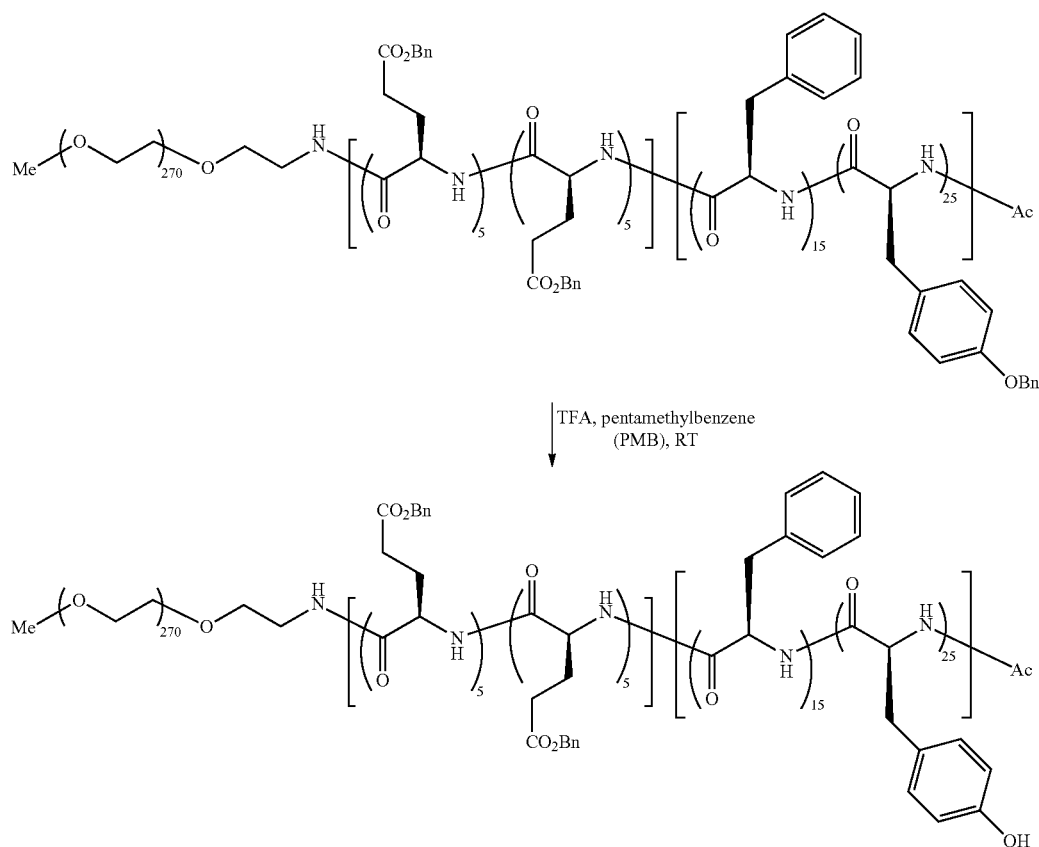

mPEG12K-b-Poly-[d-Glu(OBn)$_5$-co-Glu(OBn)$_5$]-b-Poly-(Tyr(OH)$_{25}$-co-d-Phe$_{15}$)-Ac Synthesis of mPEG12K-b-Poly-[d-Glu(OBn)$_5$-Co-Glu(OBn)$_5$]-b-Poly-(Tyr(OH)$_{25}$-Co-d-Phe$_{15}$)-Ac By using the method of Example 37, reaction of mPEG12K-b-Poly-[d-Glu(OBn)$_5$-co-Glu(OBn)$_5$]-b-Poly-(Tyr(OBn)$_{25}$-co-d-Phe$_{15}$)-Ac with PMB in TFA for three hours at room temperature and precipitation from a mixture of dichloromethane, TBME: 1, 5 afforded the title product (Yield=92.7%) as a fine, colorless, odorless polymer. $^1$H NMR (d$_6$-DMSO) identical to Example 37.

Example 71

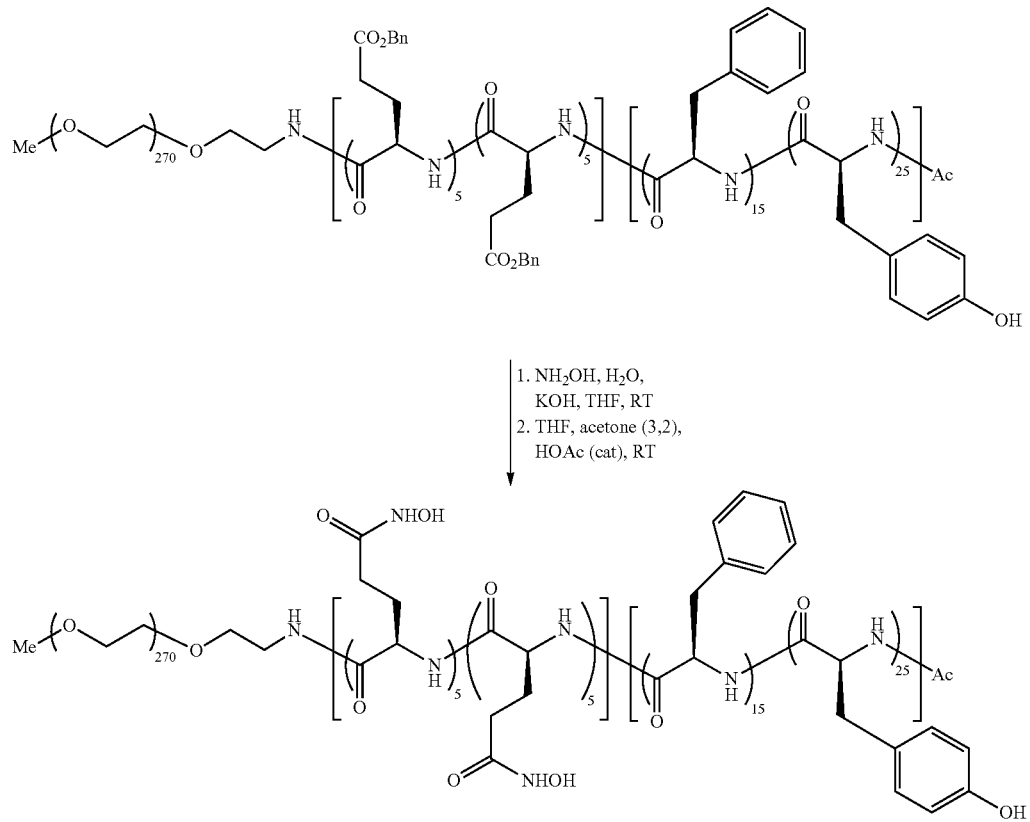

mPEG12K-b-Poly-[d-Glu(NHOH)5-co-Glu(NHOH)5]-b-Poly-(Tyr(OH)25-co-d-Phe15)-Ac

Synthesis of mPEG12K-b-Poly-[d-Glu(NHOH)5-Co-Glu(NHOH)5]-b-Poly-(Tyr(OH)25-Co-d-Phe15)-Ac Using the method described in Example 52, mPEG12K-b-Poly-[d-Glu(OBn)5-co-Glu(OBn)5]-b-Poly-(Tyr(OH)25-co-d-Phe15)-Ac was converted to the title compound using hydroxylamine solution (5 equiv./ester moiety) and 4M potassium hydroxide solution (2.0 equiv./Bn ester moiety). Reaction time was 5.25 hours. Acetone/acetic acid workup, precipitation with IPA, TBME: 1, 2 and further trituration of the filter cake with IPA, TBME: 1, 2 and vacuum drying afforded the title compound (Yield=89.9%) as a cream-colored solid with a slight odor of acetic acid. $^1$H NMR ($d_6$-DMSO): identical to Example 38.

Example 72

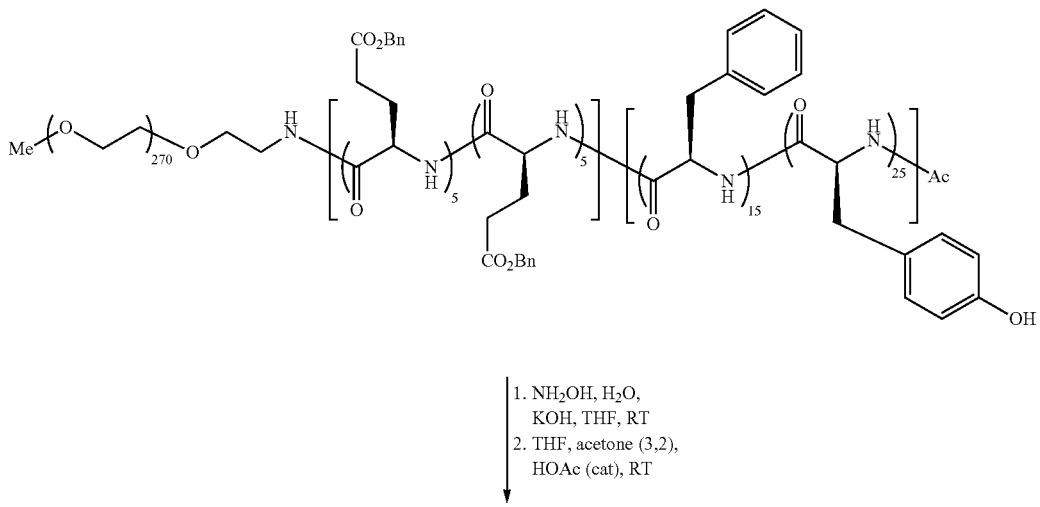

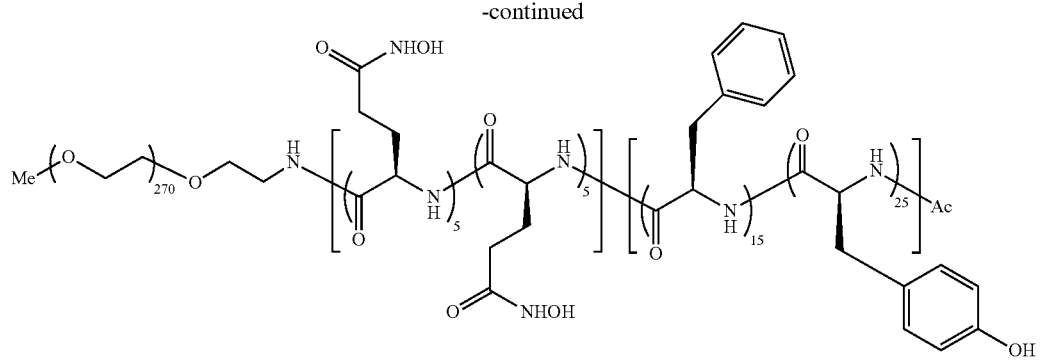

mPEG12K-b-Poly-[d-Glu(NHOH)$_5$-co-Glu(NHOH)$_5$]-b-Poly-(Tyr(OH)$_{25}$-co-d-Phe$_{15}$)-Ac Synthesis of mPEG12K-b-Poly-[d-Glu(NHOH)$_5$-Co-Glu(NHOH)$_5$]-b-Poly-(Tyr(OH)$_{25}$-Co-d-Phe$_{15}$)-Ac Using the method described in Example 71, mPEG12K-b-Poly-[d-Glu(OBn)$_5$-co-Glu(OBn)$_5$]-b-Poly-(Tyr(OH)$_{25}$-co-d-Phe$_{15}$)-Ac was converted to the title compound using hydroxylamine solution (10 equiv./ester moiety) and 4M potassium hydroxide solution (2.0 equiv./Bn ester moiety). Reaction time was 5.5 hours. Acetone/acetic acid workup, precipitation with IPA, TBME: 1, 4 and vacuum drying afforded the title compound (Yield=82.9%) as a fine, colorless solid with a slight odor of acetic acid. $^1$H NMR (d$_6$-DMSO): identical to Example 38.

Example 73

Synthesis of mPEG12K-b-Poly-(d-Glu(OBn)$_5$-Co-Glu(OBn)$_5$)-b-Poly (Tyr(OBn)$_{10}$-Co-d-Phe$_{20}$-Co-Asp(oTbu)$_{10}$-Ac mPEG12K-NH2 prepared in the same manner as Example 3, was weighed (30 g, 2.5 mmol) into a clean 500 mL round bottom flask and dissolved completely in toluene and dried by azeotropic distillation. Toluene was collected into a second 500 mL round bottom flask chilled with nitrogen, via a simple glass bridge. Resultant solid was allowed to dry completely for three hours. To the dry solid freshly distilled N-methylpyrrolidine was added via cannula and vacuum transfer. This mixture was allowed to dissolve completely before the addition NCA. The NCA as prepared from example 8 and example 9 accordingly, was weighed out into a clean two neck round bottom flask Glu(oBn) NCA (2.87 g) d-Glu(oBn) NCA (2.87 g) and evacuated for one hour before

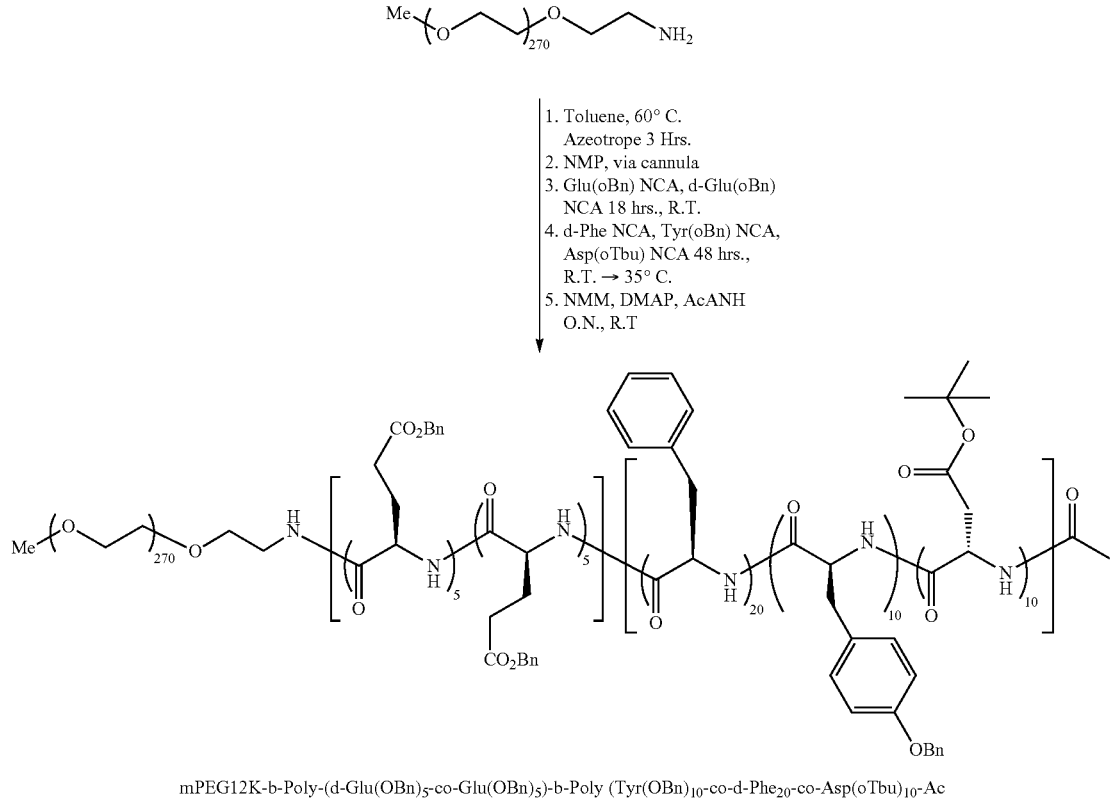

mPEG12K-b-Poly-(d-Glu(OBn)$_5$-co-Glu(OBn)$_5$)-b-Poly (Tyr(OBn)$_{10}$-co-d-Phe$_{20}$-co-Asp(oTbu)$_{10}$-Ac this solid was dissolved completely in NMP, and then cannulated into the flask containing the PEG. This polymerization was stirred at room temperature and monitored by GPC (DMF, 0.1% LiBr) to ensure completion (about 16 hrs). Upon completion of polymerization of this first block of NCA, the second addition of NCA was done in the same manner as the first, and consisted of d-Phe (9.5 g) from example 7, Tyr(oBn) (7.4 g) from example 6, and Asp(otBu) (5.38 g) from example 5. This was allowed to polymerize at room temperature for two hours and then heated to 35° C. until completion (about 24 hrs). Once confirmed by GPC, N-Methyl-Morpholine (2.5 g, 2.7 mL, 25 mmol), DMAP (0.3 g, 2.5 mmol), and Acetic Anhydride (2.5 g, 2.36 mL, 25 mmol), was added to the reaction solution was stirred overnight. This reaction mixture was poured into a two liter beaker with a magnetic stir-bar, and diethyl ether was slowly added until a white precipitate was observed. This solid was filtered and washed on a medium porosity sintered glass frit. This solid was dried in vacuo, characterized with $^1$H NMR and GPC. (yield=74.8%, 40 grams). $^1$H NMR (d$_6$-DMSO) δ 8.42-7.70, 7.30, 6.95, 5.10-4.9, 4.65-4.20, 3.77-3.25, 3.05-2.45, 2.44-1.60, 1.38-1.22.

Example 74

Synthesis of mPEG12K-b-Poly-(d-Glu(OBn)$_5$-co-Glu(OBn)$_5$)-b-Poly (Tyr$_{10}$-co-d-Phe$_{20}$-co-Asp$_{10}$-Ac The Protected Triblock co-polymer (Example 73) was weighed (30 g, 1.4 mmol) into a clean 500 mL beaker and dissolved in triflouroacetic acid. Pentamentylbenzene (4 g, 26.98 mmol) was added and stirred with a magnetic stir-bar. The reaction mixture was stirred for two hours and monitored by NMR for complete removal of benzylic protecting groups on tyrosine and t-Butyl group on aspartate. After completion of this deprotection the solution was precipitated in cold diethyl ether. This solid was then filtered on a medium sintered glass frit and re-dissolved in methylene chloride and again precipitated in cold ether and filtered. This solid (24.7 g, Yield=88.4%) was dried in vacuo and characterized. $^1$H NMR (d6-DMSO) δ 9.09, 8.50-7.75, 7.40-6.45, 5.03, 4.70-4.20, 3.91-3.05, 3.03-2.10, 2.09-1.50.

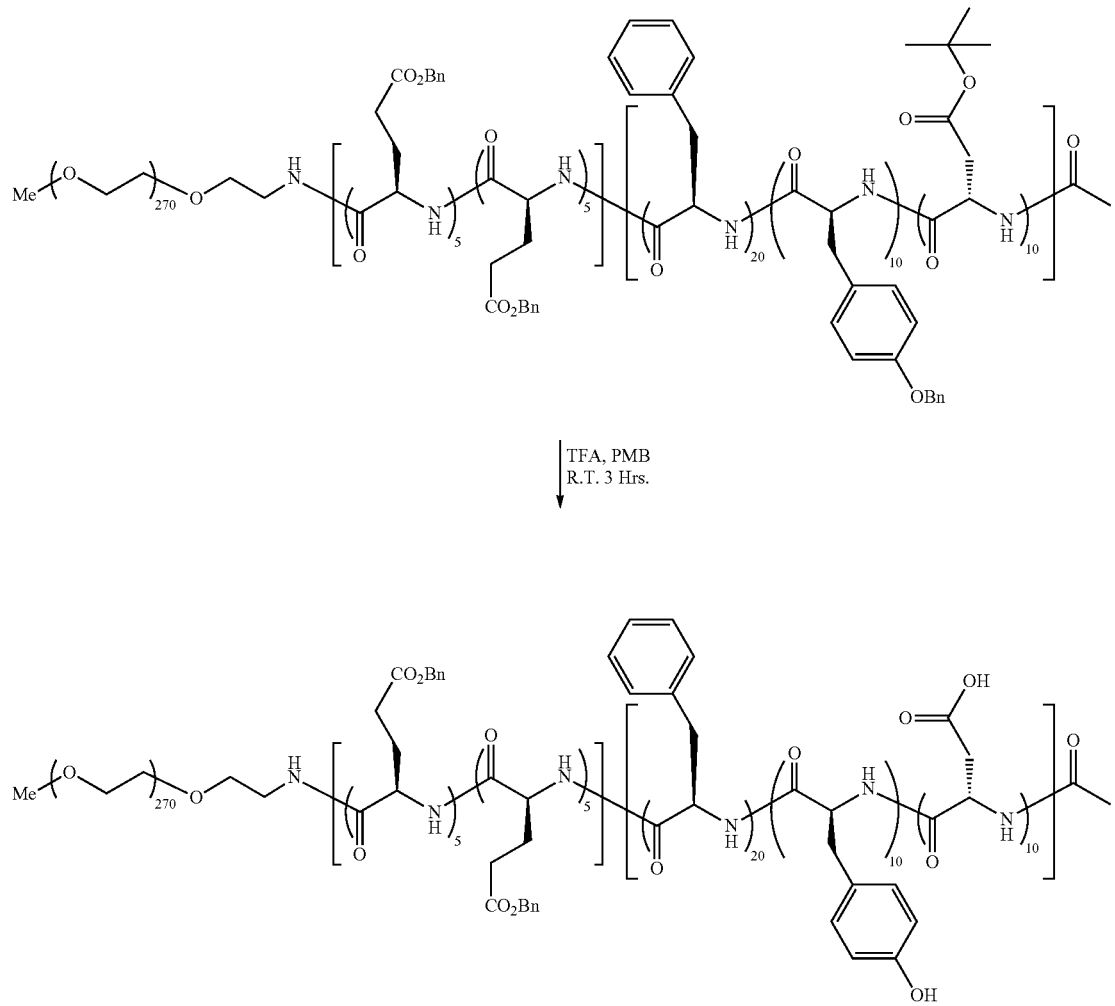

Example 75

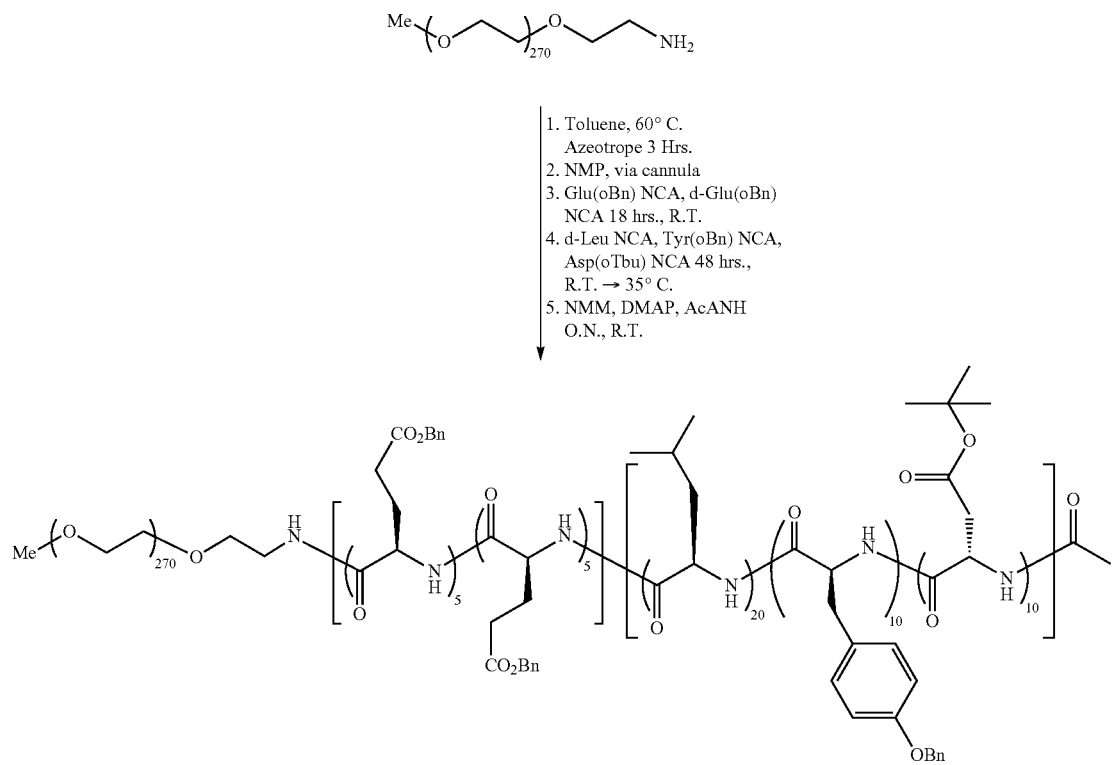

Synthesis of mPEG12K-b-Poly-(d-Glu(oBn)$_5$-Co-Glu(oBn)$_5$)-b-Poly (Tyr(OBn)$_{10}$-Co-d-Leu$_{20}$-Co-Asp(oTbu)$_{10}$-Ac Using the general protocol from Example 73 and substituting appropriate NCA starting materials resulted in the crude polymer, this was precipitated with diethyl ether about 10 volumes. After filtration and drying the title compound (Yield=80.2%) was collected as a colorless solid. $^1$H NMR (d6-DMSO) δ 8.50-7.75, 7.40-6.6, 5.03, 4.70-4.20, 3.69-3.09, 3.03-2.10, 2.09-1.50, 1.43-1.25, 0.85-0.62.

Example 76

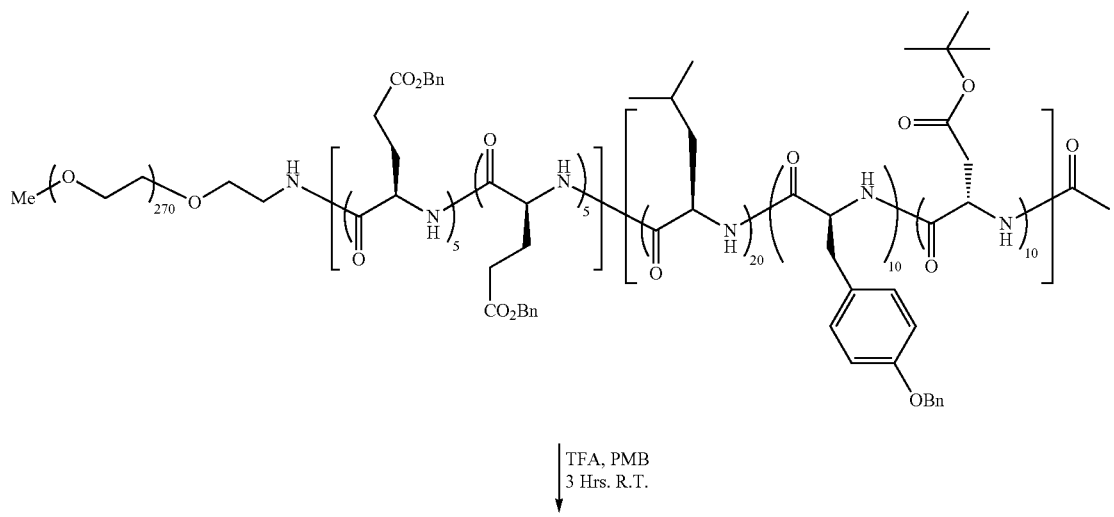

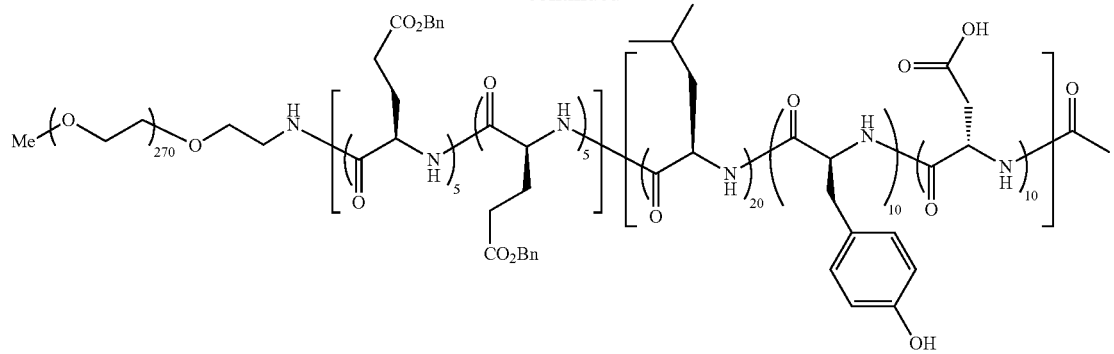

Synthesis of mPEG12K-b-Poly-(d-Glu(oBn)₅-Co-Glu(oBn)₅-b-Poly (Tyr(OH)₅-Co-d-Leu₂₀-Co-Asp₁₀)-Ac Thirty four grams of the protected triblock polymer (Example 75) was weighed into a clean 500 mL beaker and dissolved in triflouroacetic acid (500 mL). To this solution (4 g, 27 mmol) pentamentyl-benzene was added and stirred with a magnetic stir-bar. At thirty mins post addition of pentamethyl-benzene a precipitate was observed in solution. The reaction mixture was stirred for 2.5 hours and monitored by NMR for complete removal of benzylic protecting groups on tyrosine and t-Butyl group on aspartate. After completion of this deprotection the solution was rotovapped to a thick paste, redissolved in methylene chloride and then precipitated in cold diethyl ether. This solid was then filtered on a medium sintered glass frit and re-dissolved in methylene chloride and again precipitated in cold ether and filtered. This solid was dried under vacuum and characterized. $^1$H NMR (d6-DMSO) δ 9.09, 8.50-7.75, 7.45-6.55, 5.03, 4.65-4.00, 3.69-3.09, 3.03-2.10, 2.09-1.50, 0.85-0.55.

Example 77

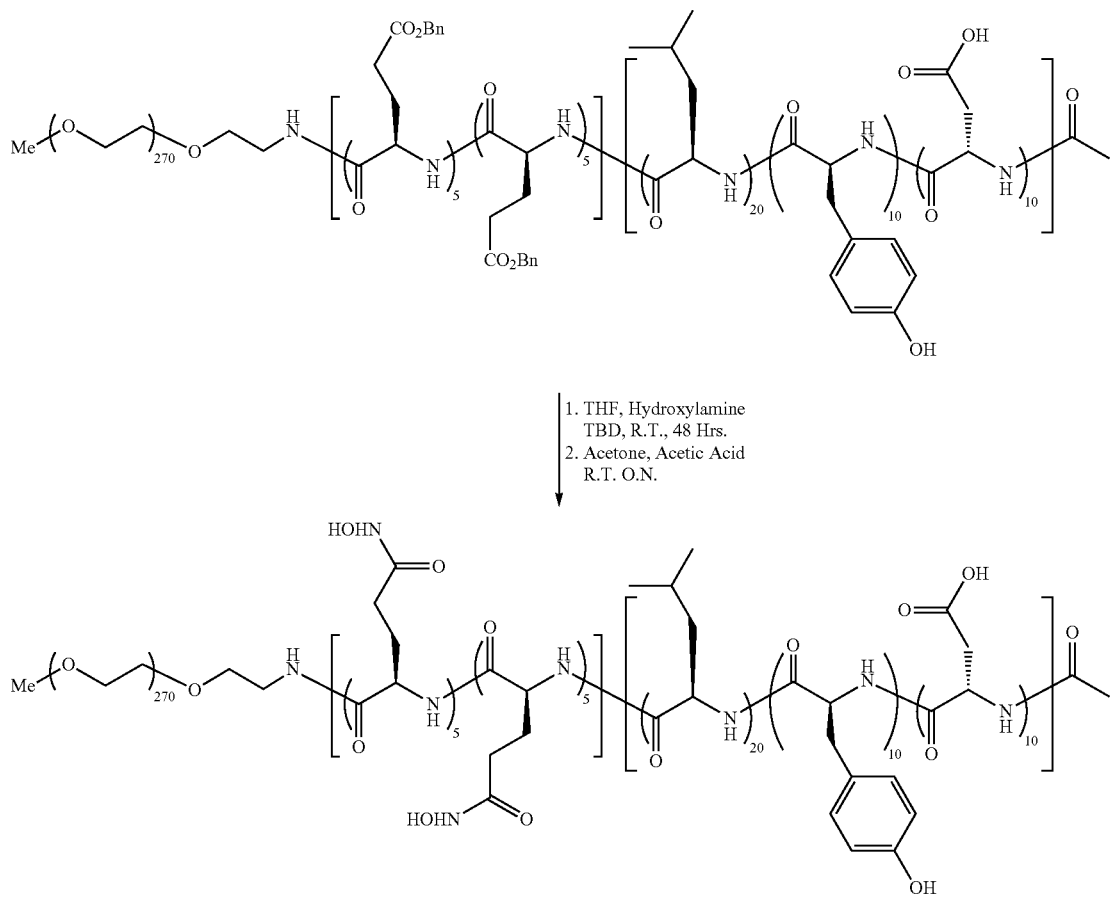

Synthesis of mPEG12K-b-(d-Glu(NHOH)$_5$-Co-Glu(NHOH)-b-Poly (Tyr(OH)$_{10}$-Co-d-Leu$_{20}$-Co-Asp$_{10}$)-Ac Triblock ester (Example 76) was weighed (20 g, 0.96 mmol) into a clean 500 mL round bottom flask and 200 mL of tetrahydrofuran was added and dissolved completely. To this solution thirty equivalents of hydroxylamine (1.9 mL, 28 mmol) and 0.5 g of TBD catalyst was stirred under nitrogen at 50° C. overnight. Completion was verified by $^1$H NMR. This solution was mixed with 100 mL methanol and precipitated with diethyl ether (about 7 volumes). This white solid was collected by filtration and washed with fresh diethyl ether. The collected solid was then dissolved in acetone and a catalytic amount of acetic acid was allowed to stir overnight. The solution was poured into a clean two liter beaker and diethyl ether was slowly added to the solution with stirring. $^1$H NMR (d6-DMSO) δ 9.4-8.6, 8.51-7.77, 7.44-7.57, 6.96, 6.56, 4.52-4.00, 3.75-3.29, 3.03-2.45, 2.08-1.21, 0.95-0.57.

Example 78

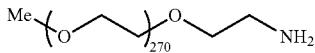

1. Toluene, 60° C. Azeotrope 3 Hrs.
2. NMP, via cannula
3. Glu(oBn) NCA, d-Glu(oBn) NCA 18 hrs., R.T.
4. d-Phe NCA, Tyr(oBn) NCA, 48 hrs., R.T. → 35° C.
5. NMM, DMAP, AcANH O.N., R.T

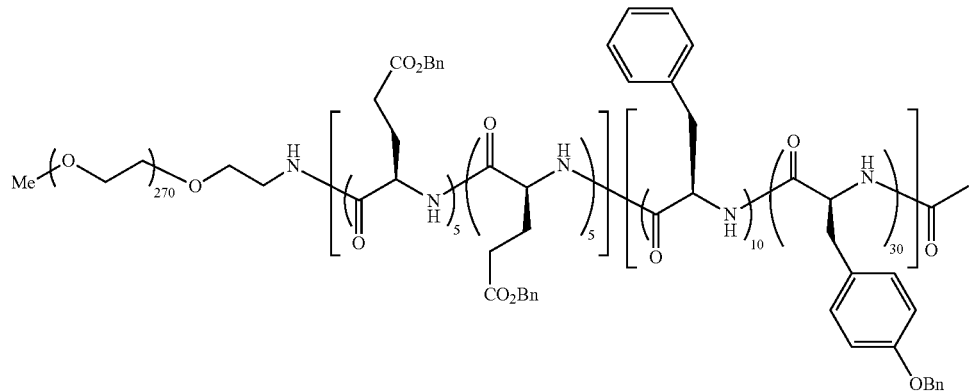

Synthesis of mPEG12K-b-(d-Glu(OBn)$_5$-Co-Glu(OBn)$_5$)-b-Poly (Tyr(OBn)$_{30}$-Co-d-Phe$_{10}$)-Ac The first block of the copolymer was prepared using the same scale and procedure as example 73. Upon completion of this first block of NCA a second addition of NCA of d-Phe NCA (4.78 g, 25 mmol) prepared in the same manner as example 7, and of Tyr(oBn) NCA (22.29 g, 75 mmol) from the procedure in example 6. This solution was allowed to polymerize at room temperature for two hours and then heated to 35° C. until completion (about 48 hrs). Once confirmed by GPC, N-Methyl-Morpholine (2.5 g, 2.7 mL, 25 mmol), DMAP (0.3 g, 2.5 mmol), and Acetic Anhydride (2.5 g, 2.36 mL, 25 mmol), was added to the reaction solution was stirred overnight. This capped polymer was worked up in the same manner as in Example 73. (yield=79.6%) about 40 grams. $^1$H NMR (d6-DMSO) δ 8.46-7.72, 7.44-6.57, 5.10-4.80, 4.62-4.13, 3.74-3.23, 3.03-2.77, 2.62-2.21, 2.02-1.56 (solvent impurities).

Example 79

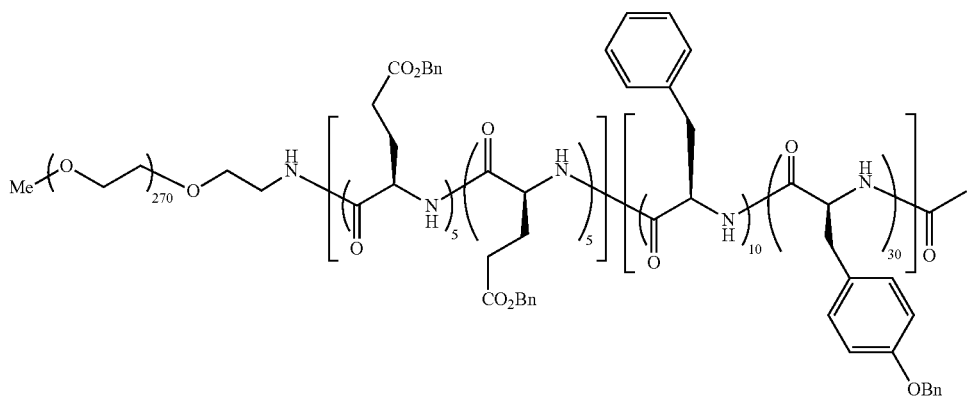

1. PMB, TFA
R.T. 3 Hrs

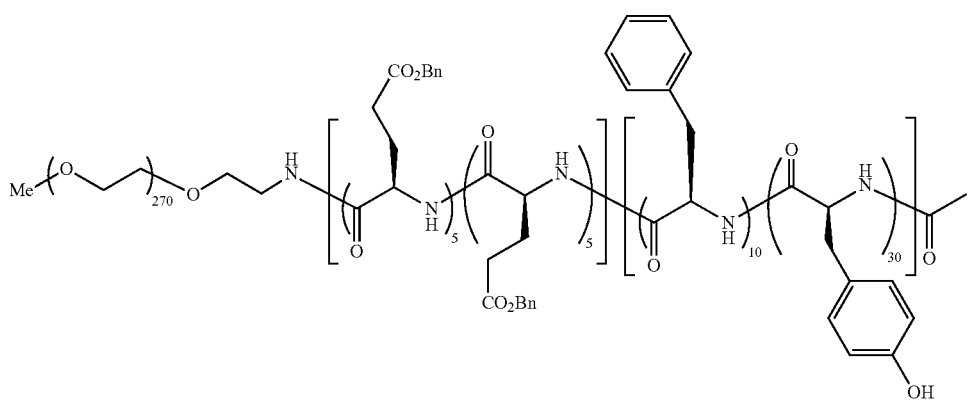

Synthesis of mPEG12K-b-Poly-(d-Glu(oBn)$_5$-Co-Glu(oBn)$_5$-b-Poly (Tyr(OH)$_{30}$-Co-d-Phe$_{10}$)-Ac The protected triblock co-polymer (from Example 78) was weighed (34 g, 1.46 mmol) into a clean 500 mL beaker and dissolved in triflouroacetic acid (500 mL). To this solution (4 g, 27 mmol) pentamentyl-benzene was added and stirred with a magnetic stir-bar. At thirty minutes post addition of pentamethyl-benzene a precipitate was observed in solution. The reaction mixture was stirred for 2.5 hours and monitored by NMR for complete removal of benzylic protecting groups on tyrosine. After completion of this deprotection (3 hrs) the solution was rotovapped to a thick paste, redissolved in methylene chloride and then precipitated in cold diethyl ether. This solid was then filtered on a medium sintered glass frit and re-dissolved in methylene chloride and again precipitated in cold ether and filtered. This solid was dried in vacuo and characterized. $^1$H NMR (d6-DMSO) δ 9.10, 8.38-7.77, 7.39-6.73, 6.59, 5.03, 4.64-3.79, 3.71-3.30, 2.98-2.56, 2.02-1.62.

Example 80

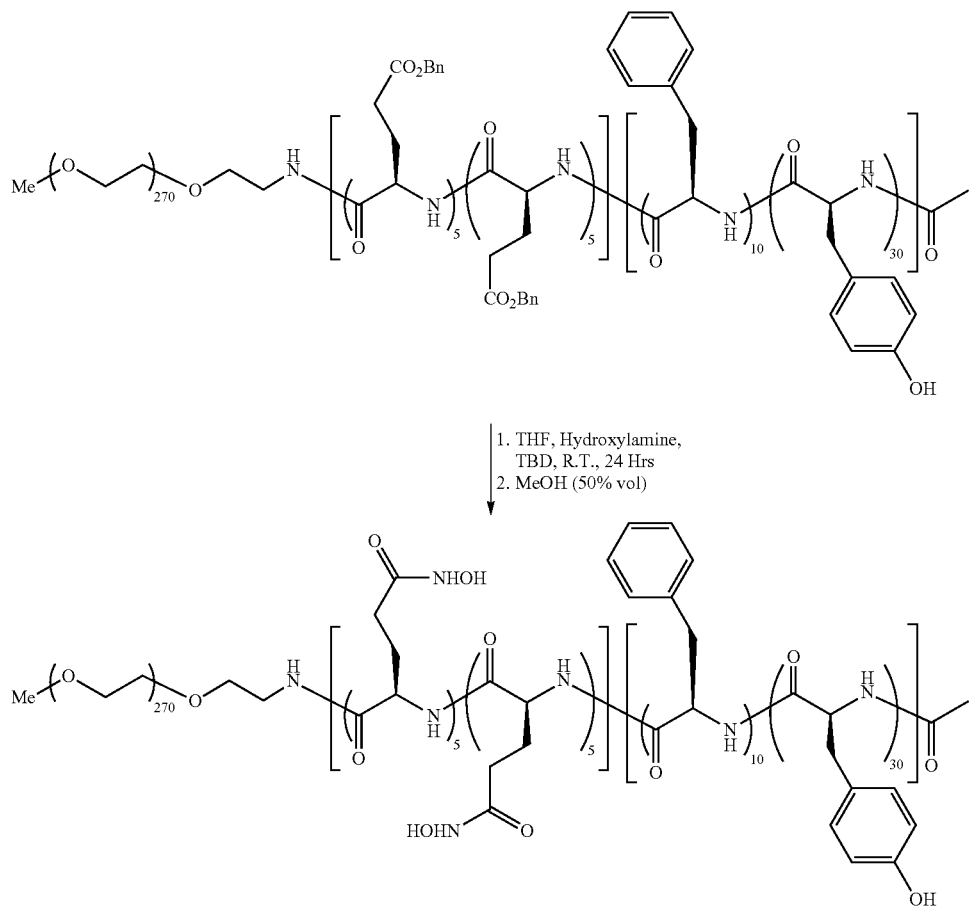

Synthesis of mPEG12K-b-Poly-(d-Glu(NHOH)₅-Co-Glu(NHOH)₅)-b-Poly (Tyr(OH)₃₀-Co-d-Phe₁₀)-Ac 20 g of Triblock ester (From Example 79) was weighed into a clean 500 mL round bottom flask and 200 mL of tetrahydrofuran was added and dissolved completely. To this solution ten equivalents of hydroxylamine, and 1,5,7-triazabicyclo [4.4.0]dec-5-ene (TBD, 0.5 g, 3.5 mmol) was stirred under nitrogen at room temperature. Completion was verified by $^1$H NMR (48 Hrs). This solution was mixed with 100 mL methanol and this solution was poured into a clean two liter beaker. Methyltertbutyl ether (about 5 volumes) was slowly added to the solution with stirring. The resultant white solid was then collected on a medium frit and dried in vacuo. (17.34 g, Yield=90%). $^1$H NMR (d₆-DMSO) δ 9.10-8.65, 8.39-7.78, 7.28-6.75, 6.80, 6.59, 4.59-4.31, 3.75-3.13, 3.00-2.57, 2.16-1.57.

Example 81

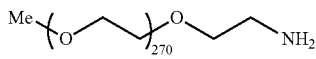

1. Toluene, 60° C. Azeotrope 3 Hrs.
2. NMP, via cannula
3. Glu(oBn) NCA, d-Glu(oBn) NCA 18 hrs., R.T.
4. d-Phe NCA, Tyr(oBn) NCA, 48 hrs., R.T. → 35° C.
5. NMM, DMAP, AcANH O.N., R.T.

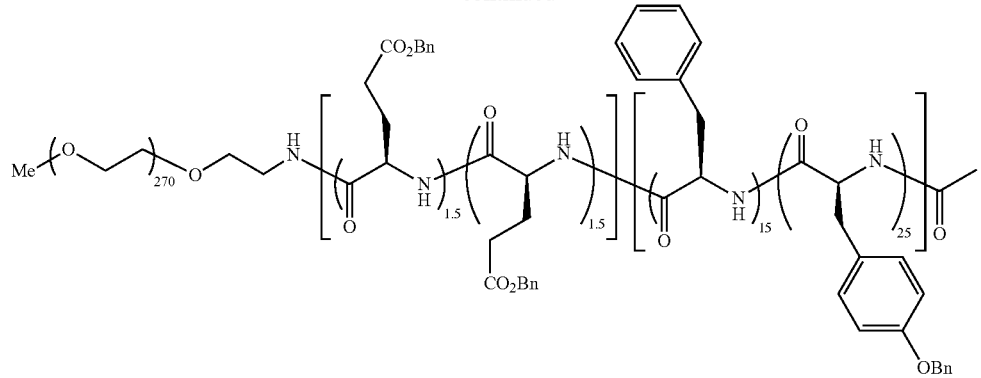

Synthesis of mPEG12K-b-Poly-(d-Glu(OBn)$_{1.5}$-Co-Glu(OBn)$_{1.5}$)-b-Poly (Tyr(OBn)$_{25}$-Co-d-Phe$_{15}$)-Ac mPEG12KNH$_2$ prepared in the same manner as example 3 (25 g, 2.08 mm) was weighed into a clean, oven dried, 1000 mL, two neck, round bottom flask and dissolved in toluene (300 mL) with heating and dried by azeotropic distillation. After distillation to dryness, the polymer was left under vacuum for three hours. The flask was subsequently backfilled with N$_2$, re-evacuated under reduced pressure, and dry N-methylpyrrolidone (NMP) (250 mL) was introduced by cannula. The mixture was briefly heated to 40° C. to expedite dissolution and then cooled to 25° C. Glu(OBn) NCA (0.82 g, 3.1 mmol) made in the same manner as example 8, and d-Glu(OBn) NCA (0.82 g, 3.1 mmol) from example 9, were added to the flask directly, and the reaction mixture was allowed to stir for 18 hours at room temperature under nitrogen gas. Then, d-Phe NCA (5.97 g, 31.25 mmol) from example 7, and Tyr(OBn) NCA (15.49 g, 52.08 mmol) prepared from example 6, and were then added to the solution and stirred for 2 hours then heated to 35° C. for 48 hours at which point the reaction was complete (GPC, DMF/0.1% LiBr). The solution was cooled to room temperature and acetic anhydride (2.04 g, 20 mmol, 1.88 mL), N-methylmorpholine (NMM) (2.23 g, 22 mmol, 2.47 mL) and dimethylaminopyridine (DMAP) (0.24 g, 2.0 mmole) were added. Stirring was continued for 1 day at room temperature. The polymer was precipitated into diethyl ether:heptane 10:1 (2.5 L) and isolated by filtration, washed with fresh 100 mL portions of diethyl ether, and dried in vacuo to give the block copolymer as a fine, off white powder (39.81 g, Yield=90.3%). $^1$H NMR (d$_6$-DMSO) δ 9.26-9.04, 8.36-7.75, 7.41-7.25, 6.97, 6.60, 5.04, 4.59-4.13, 3.81-3.13, 2.96-2.76, 2.75-2.57, 2.43-2.12, 2.00-1.45.

Example 82

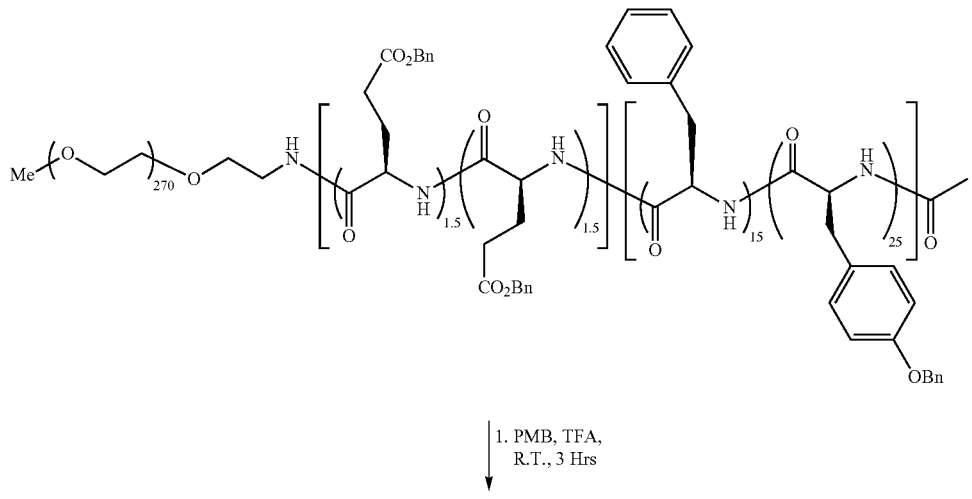

1. PMB, TFA, R.T., 3 Hrs

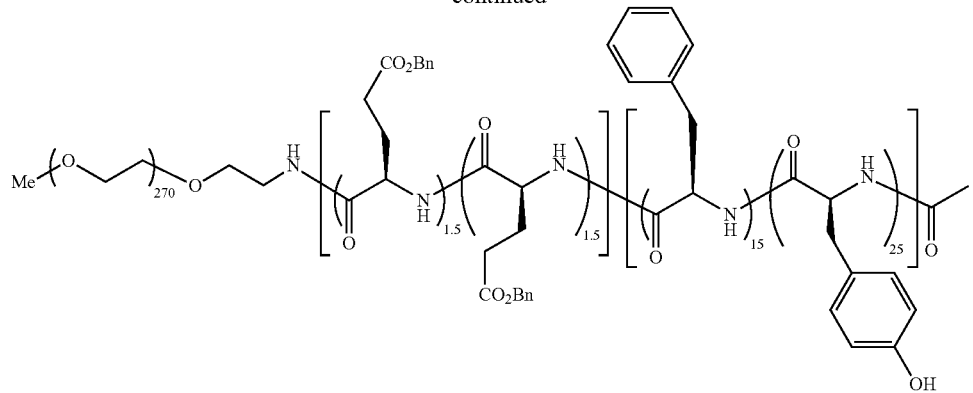

Synthesis of mPEG12K-b-Poly-(d-Glu(OBn)$_{1.5}$-Co-Glu(OBn)$_{1.5}$)-b-Poly (Tyr(OH)$_{25}$-Co-d-Phe$_{15}$)-Ac The polymer from Example 81 was deprotected using the general method from example 74 only adjusting stoichometry. Once complete (3 hrs) the solution was rotovapped to a thick paste and then redissolved in dicholomethane and precipitated in cold Diethyl ether, collected by filtration and dried in vacuo. This reaction yielded 22 g of dry material (Yield=76.92%). $^1$H NMR (d6-DMSO) δ 9.09, 8.50-7.75, 7.35-6.45, 5.04, 4.70-4.20, 3.91-3.05, 3.03-2.10, 2.09-1.50.

Example 83

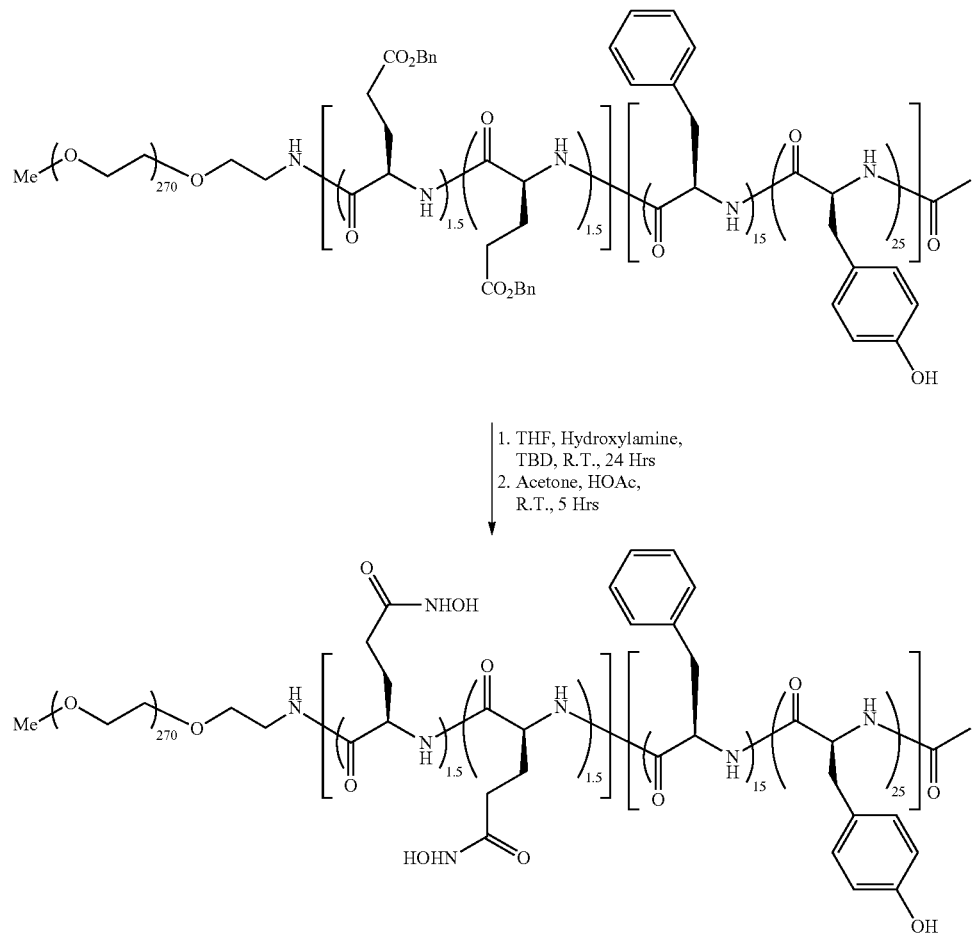

mPEG12K-b-Poly-(d-Glu(NHOH)$_{1.5}$-co-Glu(NHOH)$_{1.5}$)-b-Poly (Tyr(OH)$_{25}$-co-d-Phe$_{15}$)-Ac Synthesis of mPEG12K-b-Poly-(d-Glu(NHOH)$_{1.5}$-Co-Glu(NHOH)$_{1.5}$)-b-Poly (Tyr(OH)$_{25}$-Co-d-Phe$_{15}$)-Ac The polymer from Example 82 (13.2 g, 0.705 mmol) was dissolved completely in 160 mL of THF with heating, this solution was allowed to cool to room temp before 1,5,7-triazabicyclo [4.4.0]dec-5-ene (TBD, 0.3 g, 2.2 mmol) was added followed by Hydroxylamine (50% water solution, 25 mL, 378 mmol) this solution was stirred at room temperature for 24 hours. Methanol (80 mL) was added and then precipitated with methyltertbutyl ether, collected by filtration, and dissolved in acetone. Acetic acid was added to this acetone solution and stirred for 5 hours. The solution was evaporated until nearly dry, redissolved in methylene chloride and precipitated in MTBE, collected by filtration and dried in vacuo (12.1 g, Yield=92.8%). $^1$H NMR (d$_6$-DMSO) δ 9.11, 8.34-7.75, 7.37-7.05, 6.92, 6.58 4.60-4.32, 3.81-3.12, 2.99-2.57, 2.49-2.32, 2.10-1.73.

Example 84

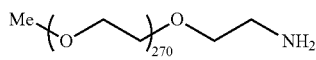

1. Toluene, 60° C. Azeotrope 3 Hrs.
2. NMP, via cannula
3. Glu(oBn) NCA, d-Glu(oBn) NCA 18 hrs., R.T.
4. d-Phe NCA, Tyr(oBn) NCA, 48 hrs., R.T. → 35° C.
5. NMM, DMAP, AcANH O.N., R.T.

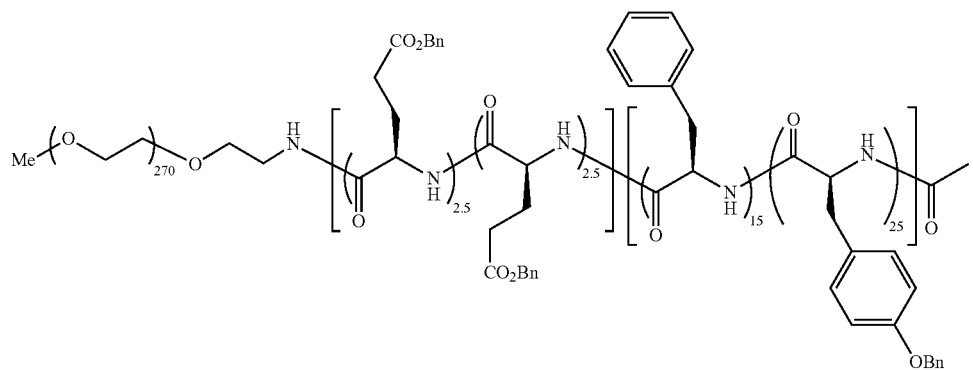

mPEG12K-b-Poly-(d-Glu(OBn)$_{2.5}$-co-Glu(OBn)$_{2.5}$)-b-Poly (Tyr(OBn)$_{25}$-co-d-Phe$_{15}$)-Ac Synthesis of mPEG12K-b-Poly-(d-Glu(OBn)$_{2.5}$-Co-Glu(OBn)$_{2.5}$)-b-Poly (Tyr(OBn)$_{25}$-Co-d-Phe$_{15}$)-Ac mPEG12KNH$_2$ prepared from the same method as Example 3, (25 g, 2.08 mm) was weighed into a clean, oven dried, 1000 mL, two neck, round bottom flask and dissolved in toluene (300 mL) with heating and dried by azeotropic distillation. After distillation to dryness, the polymer was left under vacuum for three hours. The flask was subsequently backfilled with N$_2$, re-evacuated under reduced pressure, and dry N-methylpyrrolidone (NMP) (250 mL) was introduced by cannula. The mixture was briefly heated to 40° C. to expedite dissolution and then cooled to 25° C. Glu(OBn) NCA (1.37 g, 5.2 mmol) and d-Glu(OBn) NCA (1.37 g, 5.2 mmol) were added to the flask, and the reaction mixture was allowed to stir for 18 hours at room temperature under nitrogen gas. After completion of the first block of NCA, d-Phe NCA (5.97 g, 31.25 mmol) prepared in the same manner as Example 79, and Tyr (OBn) NCA (15.49 g, 52.08 mmol) from example 6, were added and the solution was allowed to stir at room temperature for two hours at 35° C. for 48 hours at which point the reaction was complete (GPC, DMF/0.1% LiBr). The solution was cooled to room temperature and acetic anhydride (2.04 g, 20 mmol, 1.88 mL), N-methylmorpholine (NMM) (2.23 g, 22 mmol, 2.47 mL) and dimethylaminopyridine (DMAP) (0.24 g, 2.0 mmole) were added. Stirring was continued for 1 day at room temperature. The polymer was precipitated into diethyl ether:heptane 10:1 (2.5 L) and isolated by filtration, washed with fresh 100 mL portions of diethyl ether, and dried in vacuo to give the block copolymer as a fine, off white powder (36 g, Yield=80%). $^1$H NMR (d$_6$-DMSO) δ 9.10 8.37-7.83, 7.39-7.21, 6.95, 6.56, 5.02, 4.61-4.34, 4.32-4.20, 3.71-3.25, 2.94-2.59, 2.40-2.10, 1.96-1.45.

Example 85

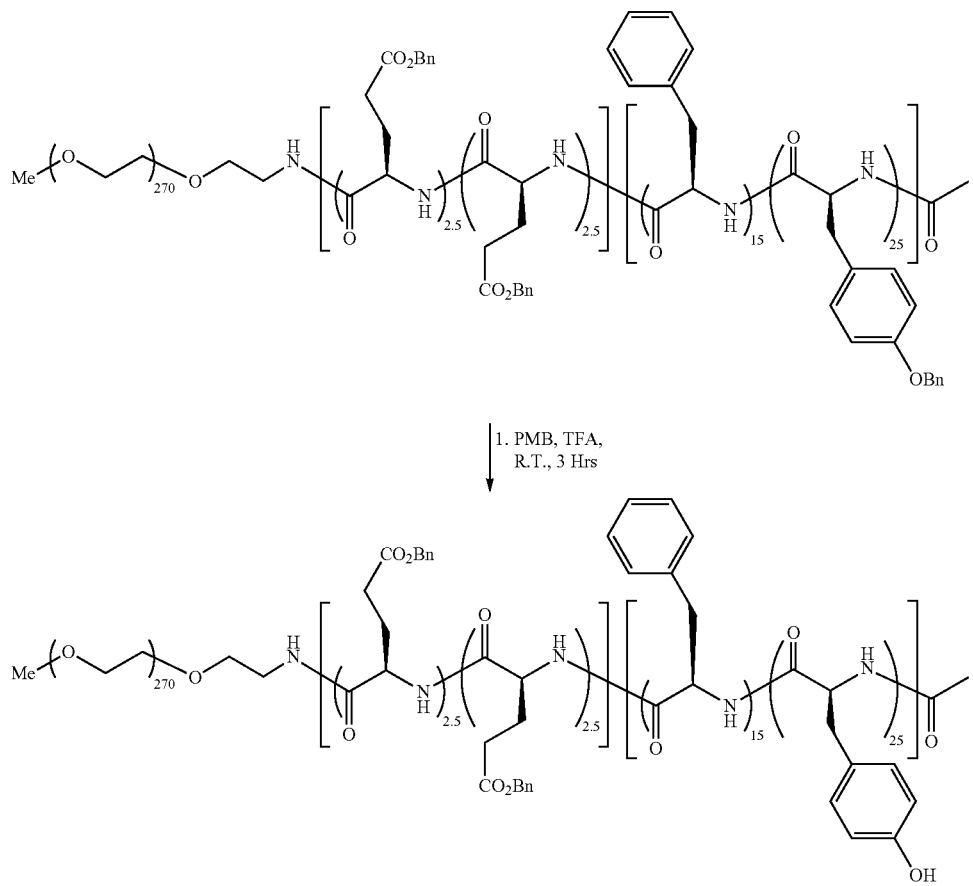

Synthesis of mPEG12K-b-Poly-(d-Glu(OBn)$_{2.5}$-Co-Glu(OBn)$_{2.5}$)-b-Poly (Tyr(OH)$_{25}$-Co-d-Phe$_{15}$)-Ac Using the general method from Example 74 and adjusting stoichiometry, the polymer from Example 84 was deprotected (32 g, 1.65 mmol). Once complete (3 Hrs.) the solution was rotovapped to a thick paste and then redissolved in DCM and precipitated in cold Diethyl ether, collected by filtration and dried in vacuo. This reaction yielded 27 g of dry material (94.2%). $^1$H NMR (d6-DMSO) δ 9.09, 8.50-7.75, 7.35-6.45, 5.04, 4.70-4.20, 3.91-3.05, 3.03-2.10, 2.09-1.50.

Example 86

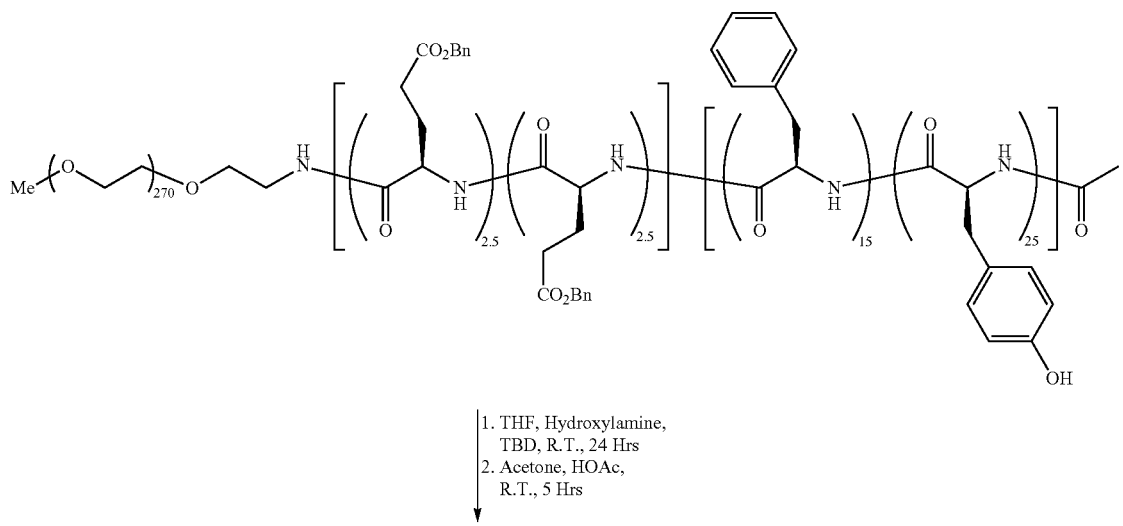

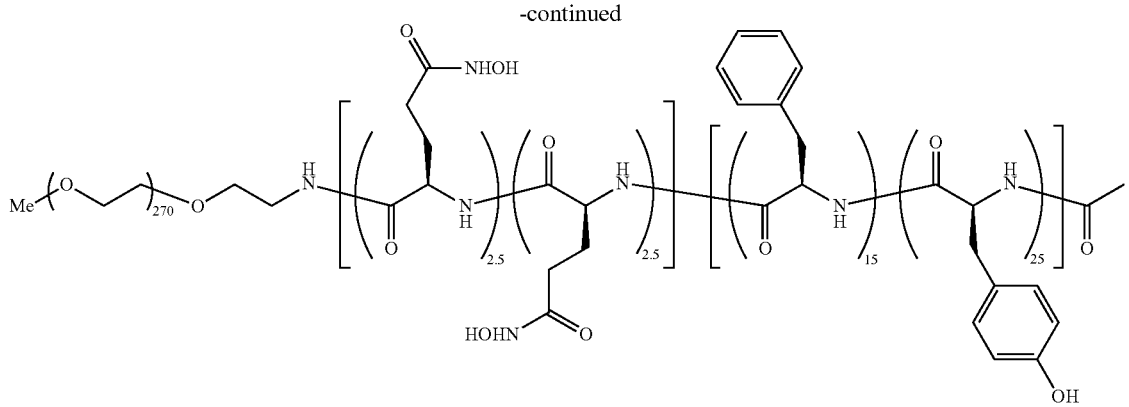

Synthesis of mPEG12K-b-Poly-(d-Glu(NHOH)$_{2.5}$-Co-Glu(NHOH)$_{2.5}$)-b-Poly (Tyr(OH)$_{25}$-Co-d-Phe$_{15}$)-Ac Polymer from Example 85 (20 g, 1 mmol) dissolved completely in 160 mL of THF with heating, this solution was allowed to cool to room temp before 1,5,7-triazabicyclo[4.4.0]dec-5-ene (TBD, 0.5 g, 3.6 mmol) was added, followed by Hydroxylamine (50% water solution, 30 mL, 545 mmol) this solution was stirred at room temperature for 24 hours. Methanol (80 mL) was added and then precipitated with methyltertbutyl ether, collected by filtration, and dissolved in acetone. Acetic acid was added to this acetone solution and stirred for 5 hours, then this solution was rotovapped until nearly dry, redissolved in methylenechloride and precipitated in MTBE, collected by filtration and dried in vacuo (18 g, Yield=91.7%). $^1$H NMR (d$_6$-DMSO) δ 9.11, 8.34-7.75, 7.15, 6.80, 4.60-4.32, 3.81-3.12, 2.99-2.32, 1.93-1.83).

Example 87

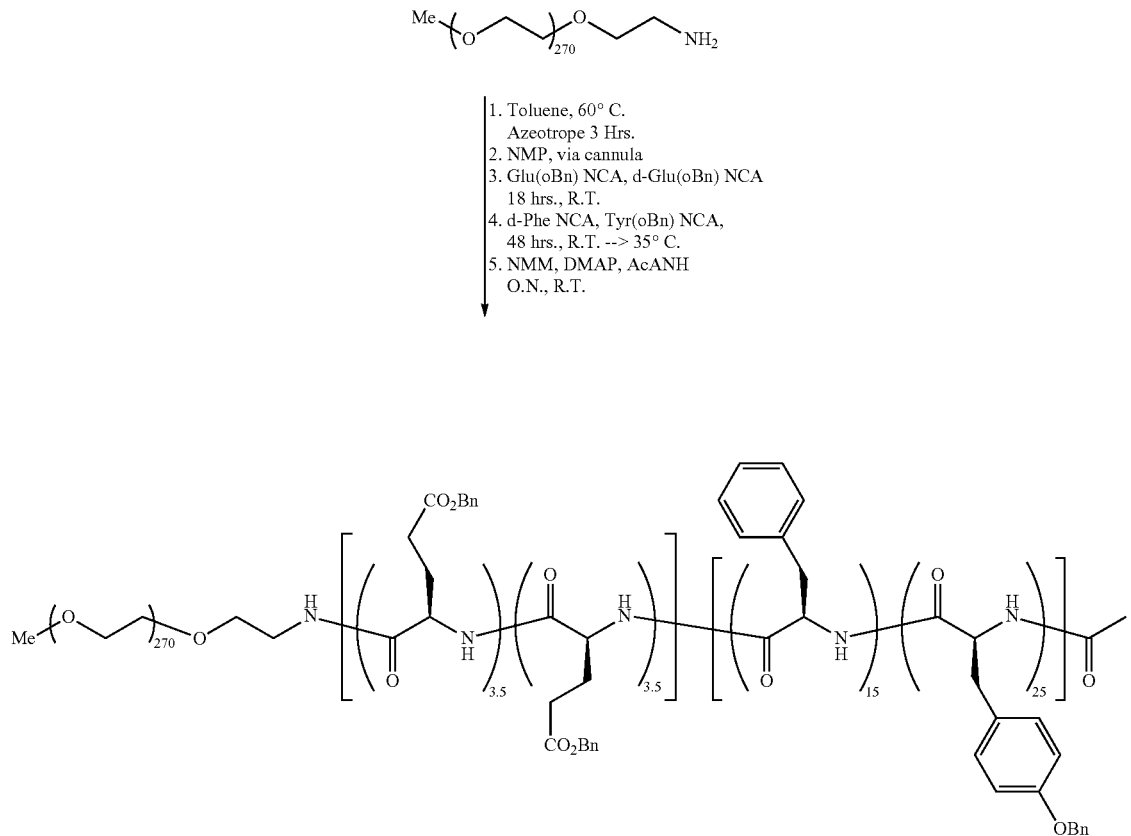

Synthesis of mPEG12K-b-Poly-(d-Glu(OBn)$_{3.5}$-Co-Glu(OBn)$_{3.5}$)-b-Poly (Tyr(OBn)$_{25}$-Co-d-Phe$_{15}$)-Ac mPEG12KNH$_2$ prepared in the same manner as example 3 (25 g, 2.08 mm) was weighed into a clean, oven dried, 1000 mL, two neck, round bottom flask and dissolved in toluene (300 mL). This polymer was prepared in the same manner as example 1. Glu(OBn) NCA (1.92 g, 7.3 mmol) from Example 8 and d-Glu(OBn) NCA (1.92 g, 7.3 mmol) from Example 9, were added to the flask, and the reaction mixture was allowed to stir for 18 hours at ambient room temperature under nitrogen gas. Then, d-Phe NCA (5.97 g, 31.25 mmol) from Example 7 and Tyr (OBn) NCA (15.49 g, 52.08 mmol) prepared in the same way as example 6, were added and the solution was allowed to stir at room temp for 2 hours and then heated to 35° C. for 48 hours at which point the reaction was complete (GPC, DMF/0.1% LiBr). The solution was cooled to room temperature and acetic anhydride (2.04 g, 20 mmol, 1.88 mL), N-methylmorpholine (NMM) (2.23 g, 22 mmol, 2.47 mL) and dimethylaminopyridine (DMAP) (0.24 g, 2.0 mmole) were added. Stirring was continued for 1 day at room temperature. The polymer was precipitated into diethyl ether:heptane 10:1 (2.5 L) and isolated by filtration, washed with fresh 100 mL portions of diethyl ether, and dried in vacuo to give the block copolymer as a fine, nearly colorless powder (37.0 g, Yield=80.6%). $^1$H NMR (d$_6$-DMSO) δ 9.08 8.42-7.70, 7.29, 6.96, 6.58, 5.10-4.85, 4.65-4.20, 3.71-3.25, 2.94-2.59, 2.40-2.10, 1.97-1.50.

Example 88

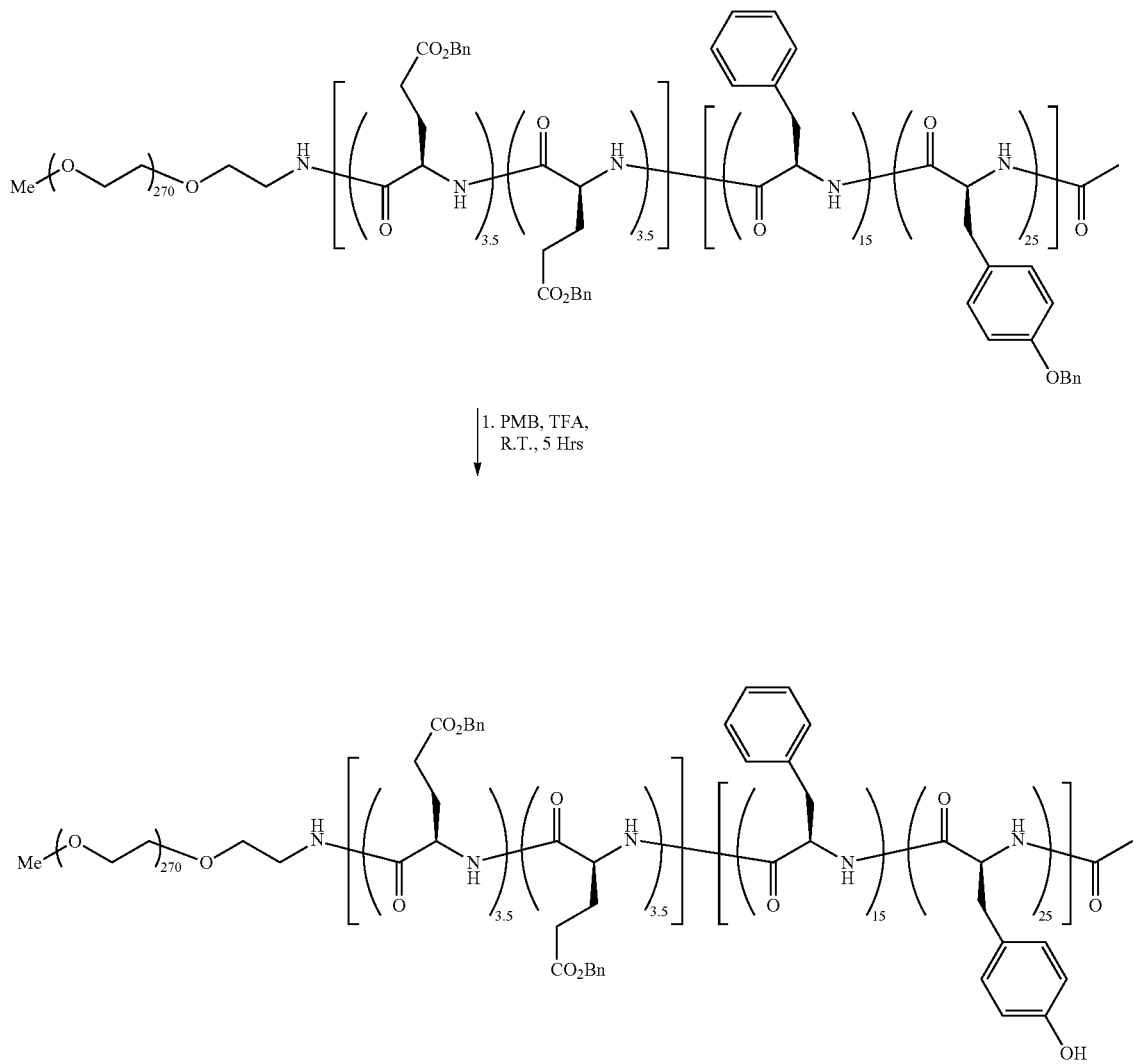

Synthesis of mPEG12K-b-Poly-(d-Glu(OBn)$_{3.5}$-Co-Glu(OBn)$_{3.5}$)-b-Poly (Tyr(OH)$_{25}$-Co-d-Phe$_{15}$)-Ac The polymer from Example 87 was deprotected using the general method from Example 74 only adjusting stoichometry (32 g, 1.61 mmol). Once complete (3 Hrs.) the solution was rotovapped to a thick paste and then redissolved in DCM and precipitated in cold Diethyl ether, collected by filtration and dried in vacuo. This reaction yielded 23 g of dry material (80%). $^1$H NMR (d6-DMSO) δ 9.09, 8.50-7.75, 7.35-6.45, 5.04, 4.70-4.20, 3.91-3.05, 3.03-2.10, 2.09-1.50.

Example 89

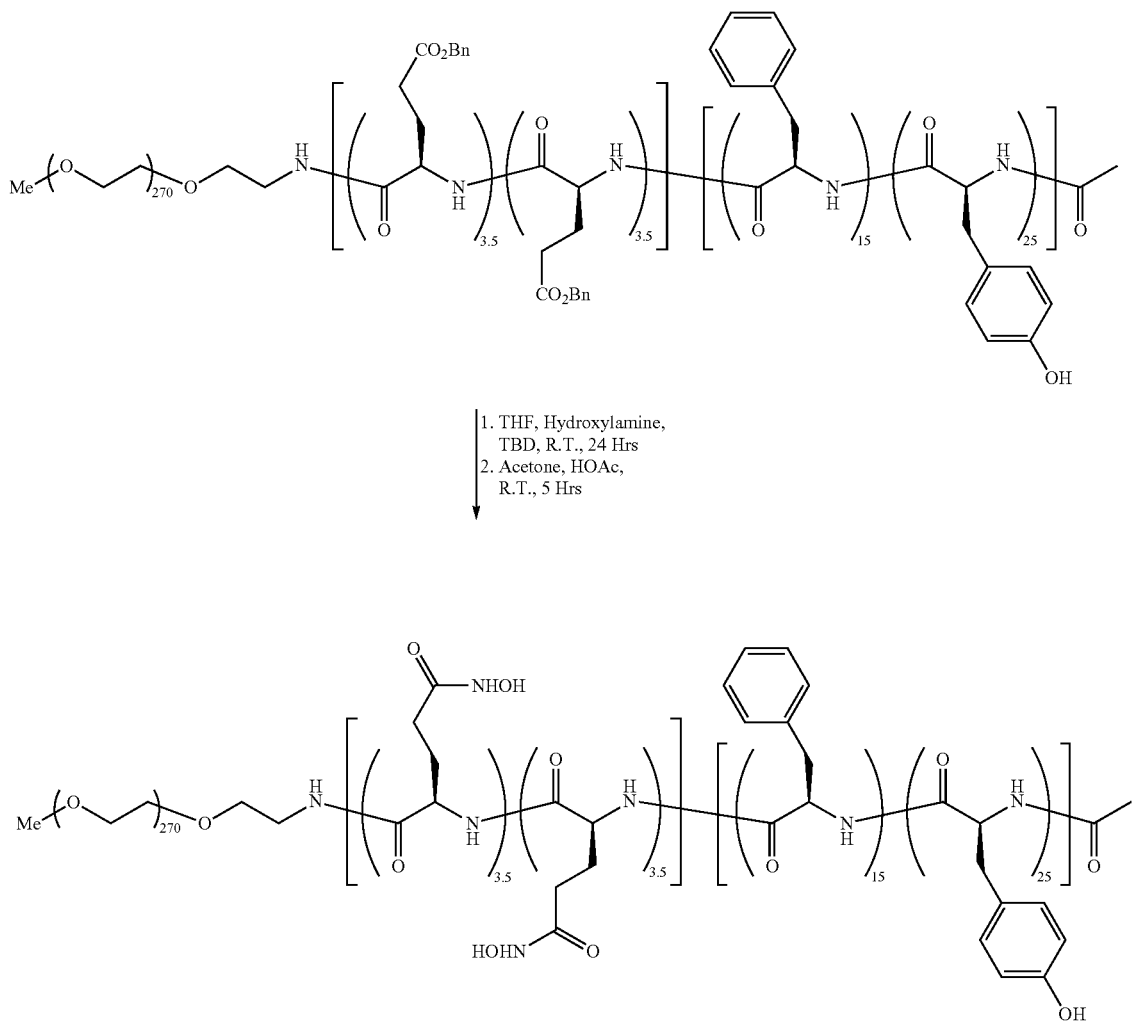

Synthesis of mPEG12K-b-Poly-(d-Glu(NHOH)$_{3.5}$-Co-Glu(NHOH)$_{3.5}$)-b-Poly (Tyr(OH)$_{25}$-Co-d-Phe$_{15}$)-Ac The polymer (20 g, 1 mmol) from Example 88 was dissolved completely in 160 mL of THF with heating, this solution was allowed to cool to room temp before 1,5,7-triazabicyclo [4.4.0]dec-5-ene (TBD, 0.5 g, 3.6 mmol) was added, followed by Hydroxylamine (50% water solution, 30 mL, 545 mmol) this solution was stirred at room temperature for 24 hours. Methanol (80 mL) was added and then precipitated with methyltertbutyl ether, collected by filtration, and dissolved in acetone. Acetic acid was added to this acetone solution and stirred overnight. The solution was rotovapped until nearly dry, redissolved in methylene chloride and precipitated in MTBE, collected by filtration and dried in vacuo (18.1 g, Yield=92.9%). $^1$H NMR (d$_6$-DMSO) δ 9.11, 8.34-7.75, 7.15, 6.80, 4.60-4.32, 3.81-3.12, 2.99-2.32, 1.93-1.83.

Example 90

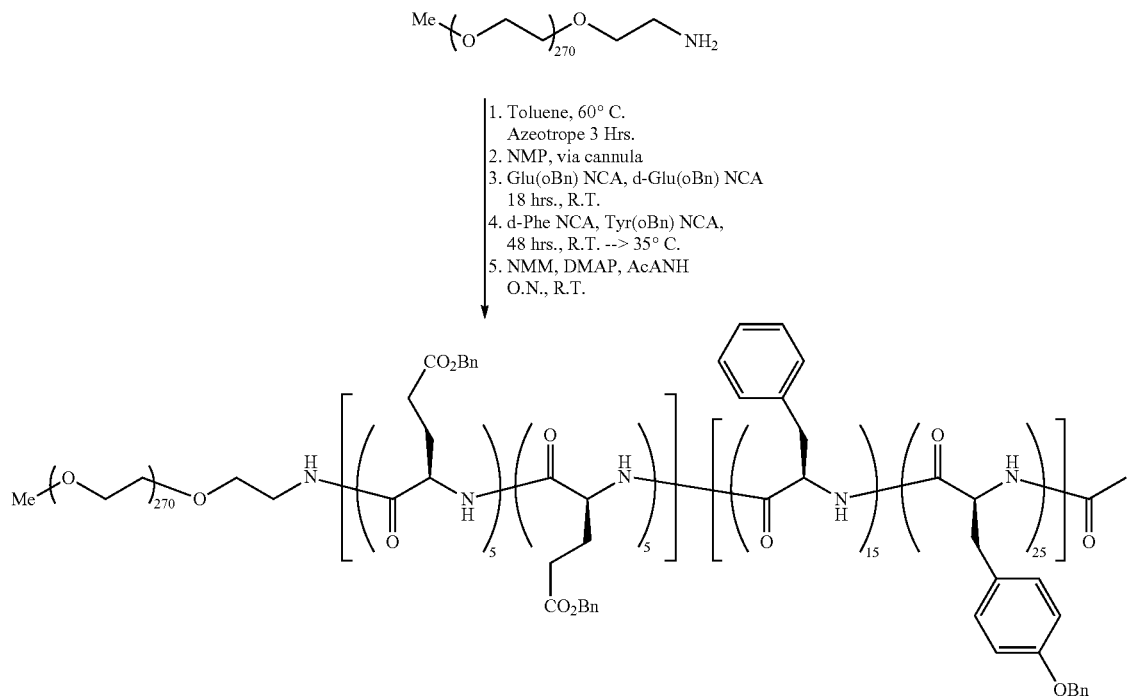

Synthesis of mPEG12K-b-Poly-(d-Glu(OBn)$_5$-Co-Glu(OBn)$_5$)-b-Poly (Tyr(OBn)$_{25}$-Co-d-Phe$_{15}$)-Ac mPEG12KNH$_2$ prepared by the same method as Example 3, was weighed (25 g, 2.08 mm) into a clean, oven dried, 1000 mL, two neck, round bottom flask and dissolved in toluene (300 mL) This polymer was prepared in the same manner as Example 73. Then Glu(OBn) NCA (2.74 g, 10.4 mmol) prepared in the same manner as Example 8, and d-Glu(OBn) NCA (2.74 g, 10.4 mmol) prepared in the same manner as Example 9, were added to the flask, and the reaction mixture was allowed to stir for 18 hours at ambient room temperature under nitrogen gas. Then, d-Phe NCA (5.97 g, 31.25 mmol) from Example 7 and Tyr (OBn) NCA (15.49 g, 52.08 mmol) prepared from the method in Example 6, were added and the solution was allowed to stir at room temp for 2 hours and then heated to 35° C. for 48 hours at which point the reaction was complete (GPC, DMF/0.1% LiBr). The solution was cooled to room temperature and acetic anhydride (2.04 g, 20 mmol, 1.88 mL), N-methylmorpholine (NMM) (2.23 g, 22 mmol, 2.47 mL) and dimethylaminopyridine (DMAP) (0.24 g, 2.0 mmole) were added. Stirring was continued for 1 day at room temperature. The polymer was precipitated into diethyl ether:heptane 10:1 (2.5 L) and isolated by filtration, washed with fresh 100 mL portions of diethyl ether, and dried in vacuo to give the block copolymer as a fine, nearly colorless powder (38.48 g, Yield=81.4%). $^1$H NMR (d$_6$-DMSO) δ 9.08 8.42-7.70, 7.29, 6.97, 5.11-4.84, 4.65-4.20, 3.72-3.25, 3.05-2.45, 2.44-1.59.

Example 91

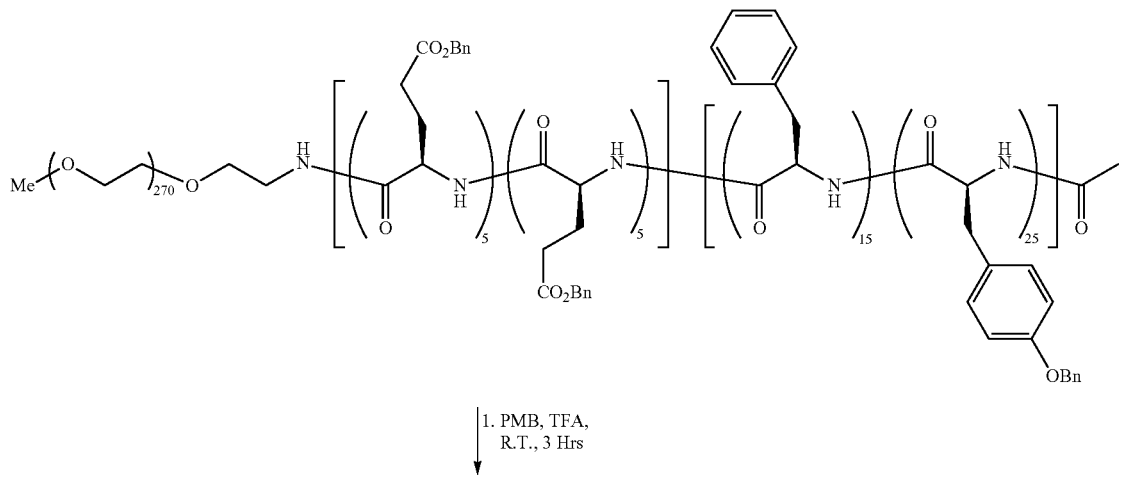

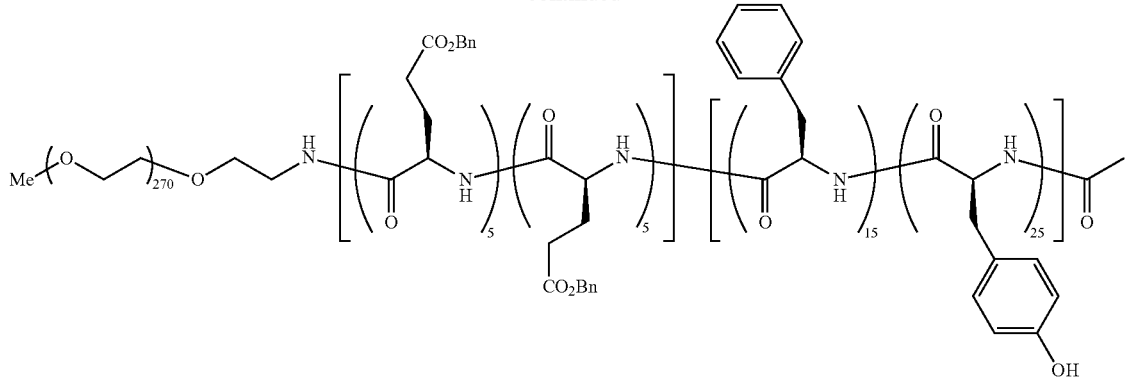

Synthesis of mPEG12K-b-Poly-(d-Glu(OBn)$_5$-Co-Glu(OBn)$_5$)-b-Poly (Tyr(OH)$_{25}$-Co-d-Phe$_{15}$)-Ac Using the general method from example 74 only adjusting stoichometry this polymer was deprotected (32 g, 1.56 mmol). Once complete (3 Hrs.) the solution was rotovapped to a thick paste and then redissolved in DCM and precipitated in cold Diethyl ether, collected by filtration and dried in vacuo. This reaction yielded 27 g of dry material (93.6%). $^1$H NMR (d6-DMSO) δ 9.09, 8.50-7.75, 7.35-6.45, 5.04, 4.70-4.20, 3.91-3.05, 3.03-2.10, 2.09-1.50.

Synthesis of mPEG12K-b-Poly-(d-Glu(NHOH)$_5$-Co-Glu(NHOH)$_5$)-b-Poly (Tyr(OH)$_{25}$-Co-d-Phe$_{15}$)-Ac The polymer (18 g, 0.88 mmol) from Example 91 was dissolved completely in 160 mL of THF with heating, this solution was allowed to cool to room temp before 1,5,7-triazabicyclo [4.4.0]dec-5-ene (TBD, 0.5 g, 3.6 mmol) was added, followed by Hydroxylamine (50% water solution, 30 mL, 545 mmol) this solution was stirred at room temperature for 24 hours. Methanol (80 mL) was added and then precipitated with methyltertbutyl ether, collected by filtration, and dissolved in acetone. Acetic acid was added to this Example 92

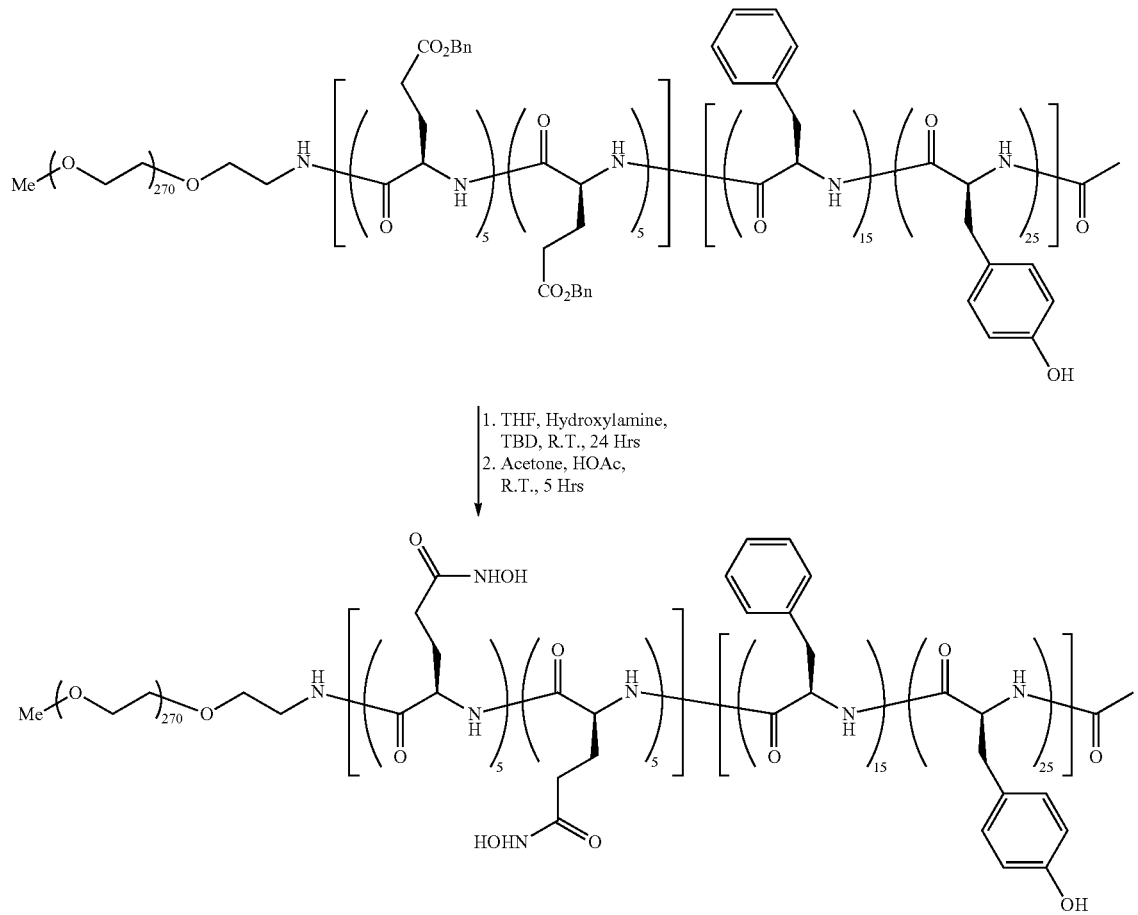

acetone solution and stirred for 5 hours and then worked up. The solution was rotovapped until nearly dry, redissolved in methylene chloride and precipitated in MTBE, collected by filtration and dried in vacuo (16.7 g, Yield=96.3%).

Example 93

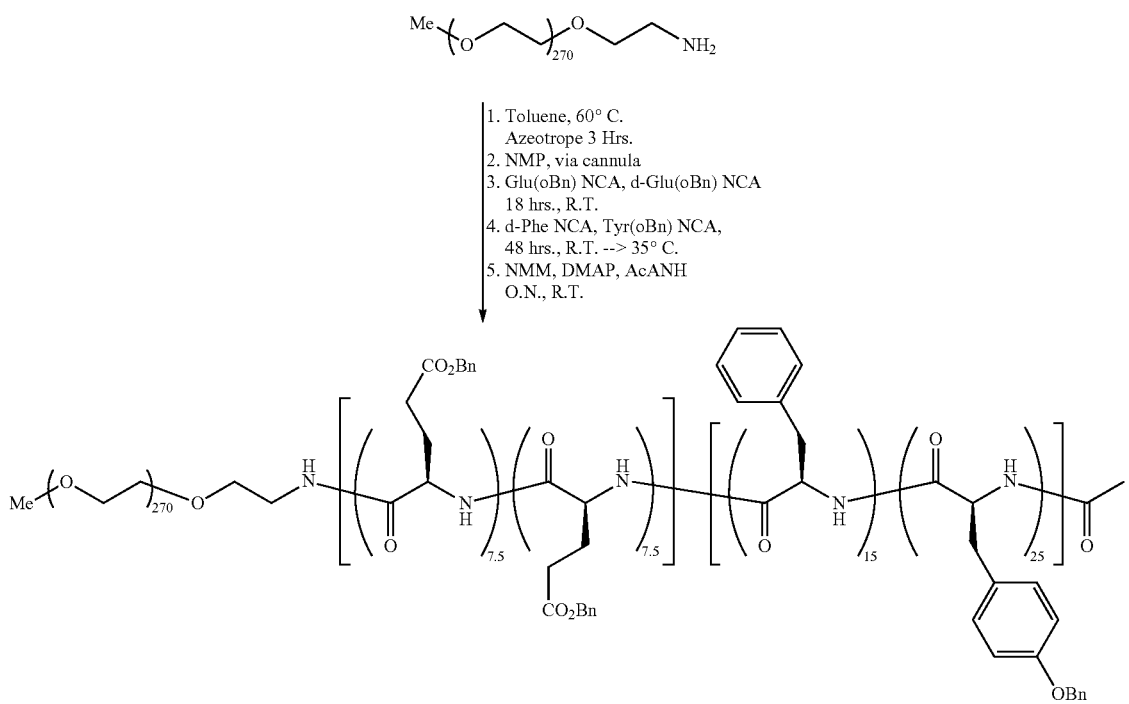

Synthesis of mPEG12K-b-Poly-(d-Glu(OBn)$_{7.5}$-Co-Glu(OBn)$_{7.5}$)-b-Poly (Tyr(OBn)$_{25}$-Co-d-Phe$_{15}$)-Ac mPEG12KNH$_2$ (25 g, 2.08 mm) prepared in the same manner as Example 3, was weighed into a clean, oven dried, 1000 mL, two neck, round bottom flask and dissolved in toluene (300 mL) This polymer was prepared in the same manner as example 1. Glu(OBn) NCA (2.74 g, 10.4 mmol) prepared in the same way as example 8 and d-Glu(OBn) NCA (2.74 g, 10.4 mmol) from Example 9, were added to the flask, and the reaction mixture was allowed to stir for 18 hours at room temperature under nitrogen gas. Then, d-Phe NCA (5.97 g, 31.25 mmol) from Example 7 and Tyr (OBn) NCA (15.49 g, 52.08 mmol) from Example 6, were added and the solution was allowed to stir at room temp for 2 hours and then heated to 35° C. for 48 hours at which point the reaction was complete (GPC, DMF/0.1% LiBr). The solution was cooled to room temperature and acetic anhydride (2.04 g, 20 mmol, 1.88 mL), N-methylmorpholine (NMM) (2.23 g, 22 mmol, 2.47 mL) and dimethylaminopyridine (DMAP) (0.24 g, 2.0 mmole) were added. Stirring was continued overnight at room temperature. The polymer was precipitated into diethyl ether:heptane 10:1 (2.5 L) and isolated by filtration, washed with fresh 100 mL portions of diethyl ether, and dried in vacuo to give the block copolymer as a nearly colorless powder (37.0 g, Yield=74.66%). $^1$H NMR (d$_6$-DMSO) δ 9.10 8.42-7.71, 7.27, 6.97, 5.11-4.85, 4.65-4.20, 3.72-3.25, 3.05-2.45, 2.45-1.60.

Example 94

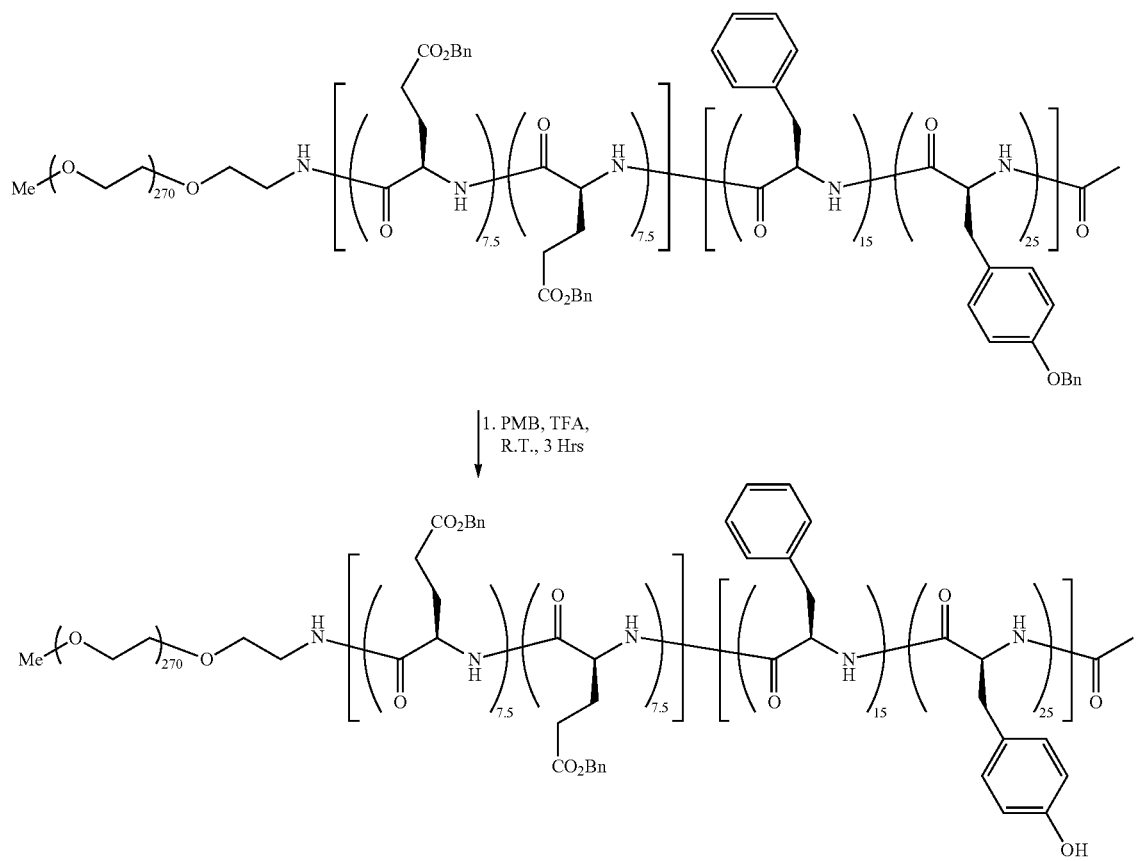

Synthesis of mPEG12K-b-Poly-(d-Glu(OBn)$_{7.5}$-Co-Glu(OBn)$_{7.5}$)-b-Poly (Tyr(OH)$_{25}$-Co-d-Phe$_{15}$)-Ac Using the general method from Example 74 only adjusting stoichometry this polymer was deprotected (32 g, 1.48 mmol). Once complete (3 Hrs.) the solution was rotovapped to a thick paste and then redissolved in DCM and precipitated in cold Diethyl ether, collected by filtration and dried in vacuo. This reaction yielded 24 g of dry material (82.8%). $^1$H NMR (d6-DMSO) δ 9.09, 8.50-7.75, 7.35-6.45, 5.04, 4.70-4.20, 3.91-3.05, 3.03-2.10, 2.09-1.50.

Example 95

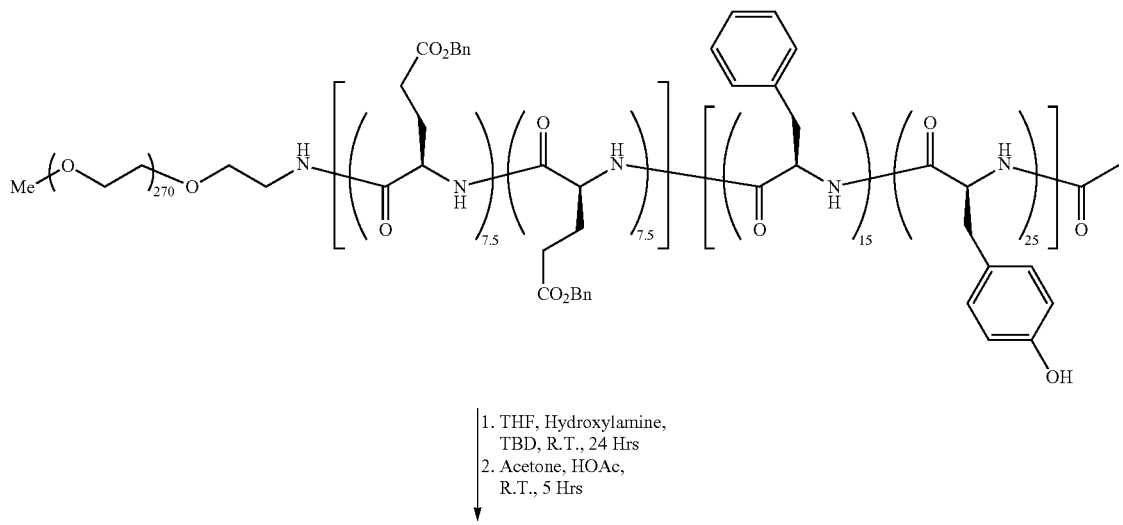

-continued

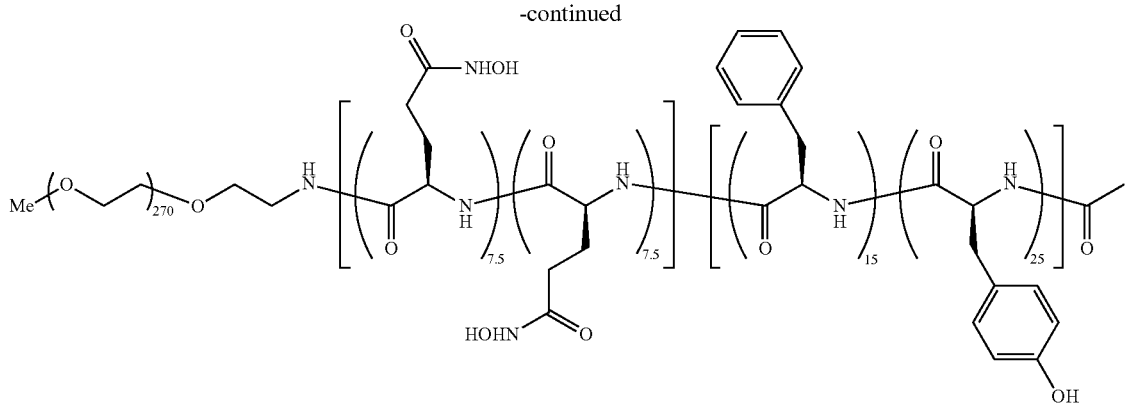

Synthesis of mPEG12K-b-Poly-(d-Glu(NHOH)$_{7.5}$-Co-Glu(NHOH)$_{7.5}$)-b-Poly (Tyr(OH)$_{25}$-Co-d-Phe$_{15}$)-Ac The polymer (19 g, 0.88 mmol) prepared in Example 94 was dissolved completely in 160 mL of THF with heating, this solution was allowed to cool to room temp before 1,5,7-triazabicyclo [4.4.0]dec-5-ene (TBD, 0.5 g, 3.6 mmol) was added, followed by Hydroxylamine (50% water solution, 30 mL, 545 mmol) this solution was stirred at room temperature for 24 hours. Methanol (80 mL) was added and then precipitated with methyltertbutyl ether, collected by filtration, and dissolved in acetone. Acetic acid was added to this acetone solution and stirred for 5 hours. The solution was rotovapped until nearly dry, redissolved in methylene chloride and precipitated in MTBE, collected by filtration and dried in vacuo (16.4 g, Yield=91.1%). $^1$H NMR (d$_6$-DMSO) δ 9.11, 8.34-7.75, 7.15, 6.80, 4.60-4.32, 3.81-3.12, 2.99-2.32, 1.93-1.83.

Example 96

Synthesis of mPEG12K-b-Poly-(d-Glu(OBn)$_{10}$-Co-Glu(OBn)$_{10}$)-b-Poly (Tyr(OBn)$_{25}$-Co-d-Phe$_{15}$)-Ac mPEG12KNH$_2$ (25 g, 2.08 mm) prepared in the same was as Example 3, was weighed into a clean, oven dried, 1 L, two neck, round bottom flask and dissolved in toluene (300 mL) This polymer was prepared in the same manner as example 1. Glu(OBn) NCA (5.48 g, 20.8 mmol) prepared in the same manner as Example 8, and d-Glu(OBn) NCA (5.48 g, 20.8 mmol) prepared by the method in Example 9, were added to the flask directly, and the reaction mixture was allowed to stir for 16 hours at ambient room temperature under nitrogen gas. Then, d-Phe NCA (5.97 g, 31.25 mmol) from Example 7 and Tyr (OBn) NCA (15.49 g, 52.08 mmol) from Example 6, were added and the solution and allowed to stir at room temp for 2 hours and then heated to 35° C. for 48 hours at which point the reaction was complete (GPC, DMF/0.1% LiBr). The solution was cooled to room temperature and acetic anhydride (2.04 g, 20 mmol, 1.88 mL), N-methylmorpholine (NMM) (2.23 g, 22 mmol, 2.47 mL) and dimethylaminopyridine (DMAP) (0.24 g, 2.0 mmole) were added. Stirring was continued for 1 day at room temperature. The polymer was precipitated into diethyl ether:heptane

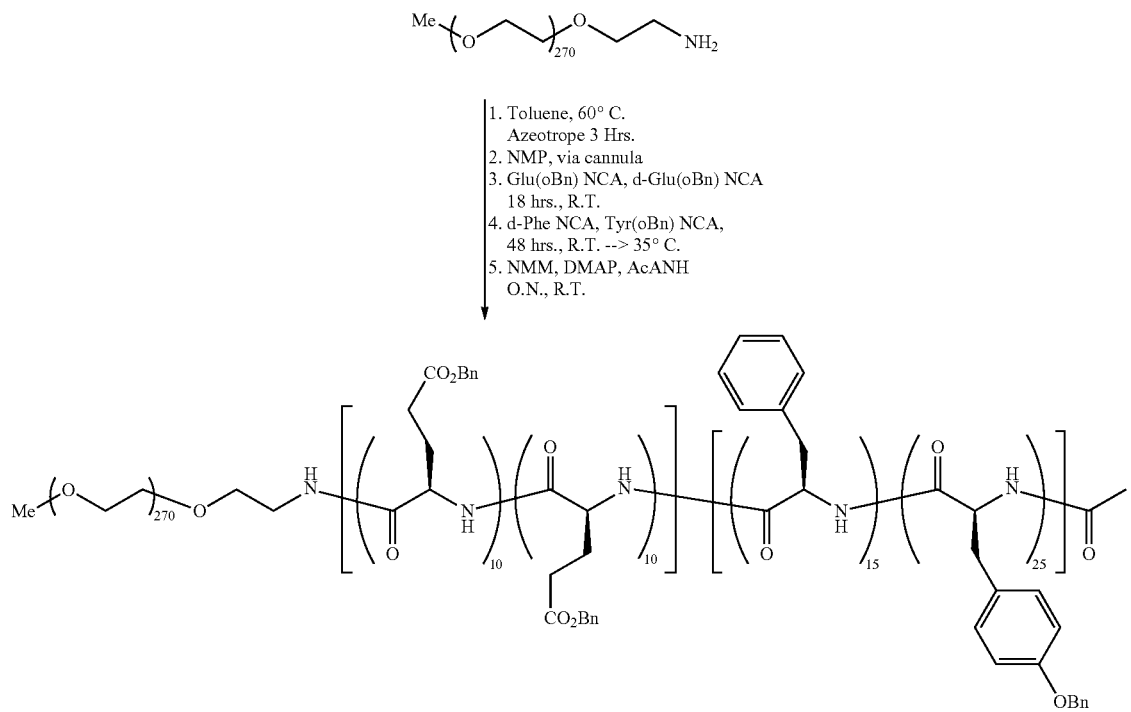

10:1 (2.5 L) and isolated by filtration, washed with fresh 100 mL portions of diethyl ether, and dried in vacuo to give the block copolymer as a fine, nearly colorless powder (38.9 g, Yield=75.23%). $^1$H NMR (d$_6$-DMSO) δ 9.08, 8.40-7.65, 7.35-7.25, 6.99, 6.76, 5.10-4.85, 4.65-4.20, 3.72-3.25, 3.06-2.45, 2.34-1.59.

Example 97

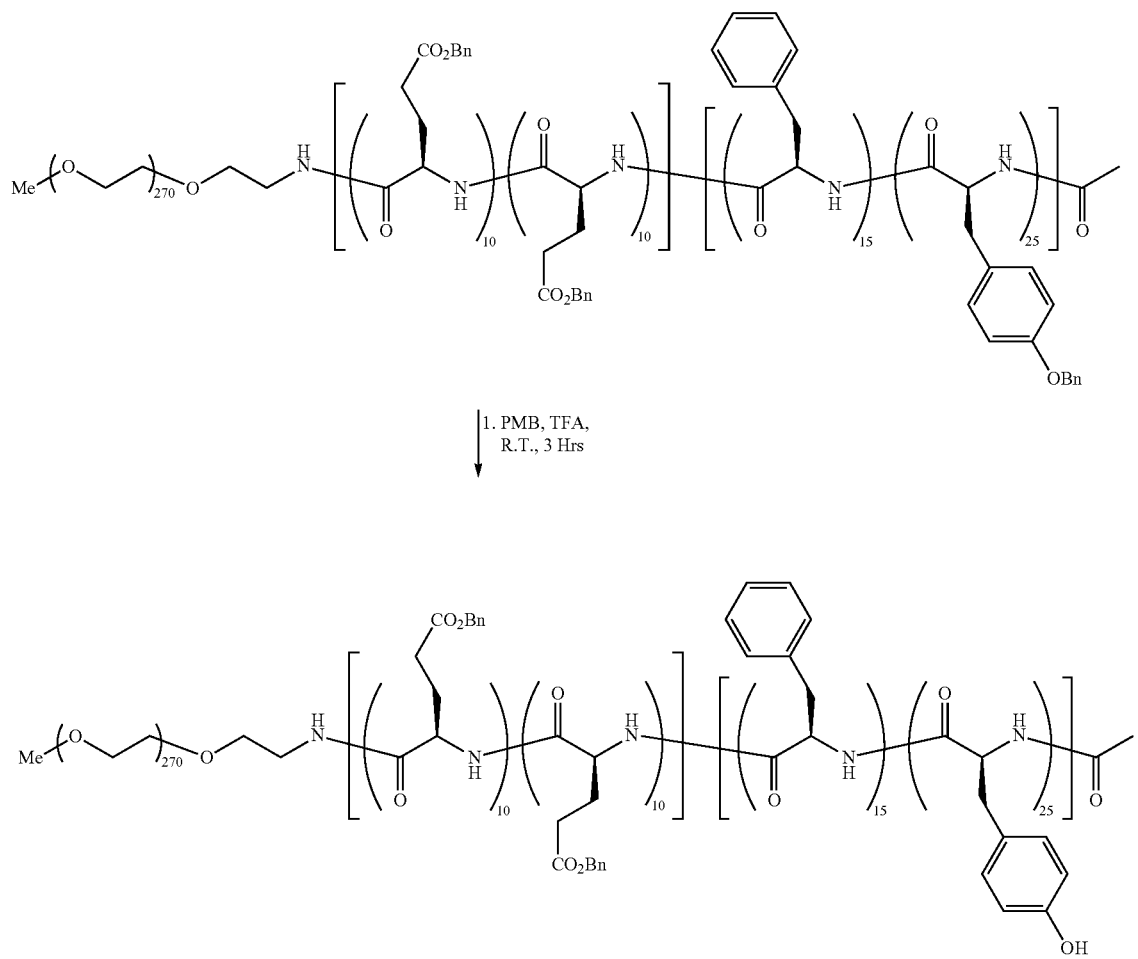

Synthesis of mPEG12K-b-Poly-(d-Glu(OBn)$_{10}$-Co-Glu(OBn)$_{10}$)-b-Poly (Tyr(OH)$_{25}$-Co-d-Phe$_{15}$)-Ac Using the general method from Example 74 only adjusting stoichometry this polymer was deprotected (32 g, 1.41 mmol). Once complete (3 Hrs.) the solution was rotovapped to a thick paste and then redissolved in DCM and precipitated in cold Diethyl ether, collected by filtration and dried in vacuo. This reaction yielded 27 g of dry material (92.8%). $^1$H NMR (d6-DMSO) δ 9.09, 8.50-7.75, 7.35-6.45, 5.04, 4.70-4.20, 3.91-3.05, 3.03-2.10, 2.09-1.50.

Example 98

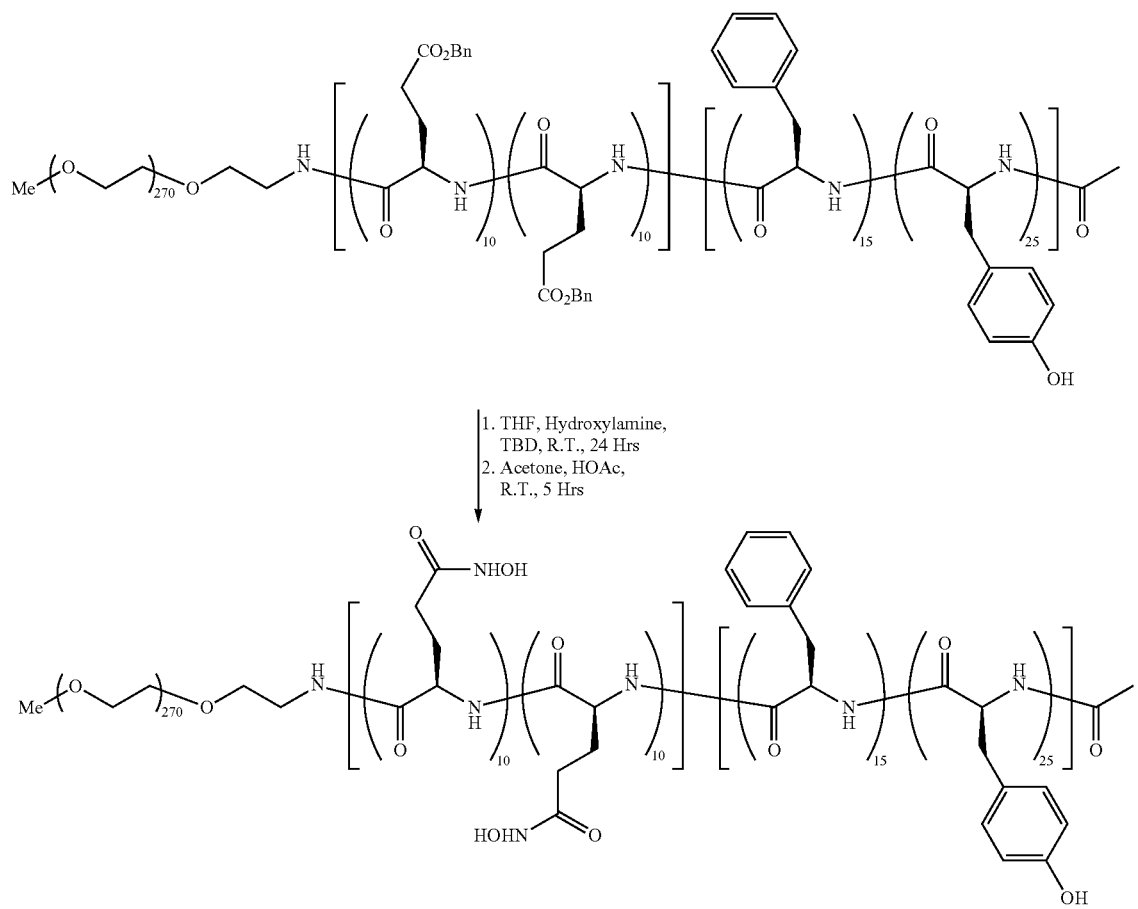

Synthesis of mPEG12K-b-Poly-(d-Glu(NHOH)$_{10}$-Co-Glu(NHOH)$_{10}$)-b-Poly (Tyr(OH)$_{25}$-Co-d-Phe$_{15}$)-Ac The polymer (20 g, 0.88 mmol) from Example 98 was dissolved completely in 160 mL of THF with heating, this solution was allowed to cool to room temp before 1,5,7-triazabicyclo [4.4.0]dec-5-ene (TBD, 0.5 g, 3.6 mmol) was added, followed by Hydroxylamine (50% water solution, 30 mL, 545 mmol) this solution was stirred at room temperature for 24 hours. Methanol (80 mL) was added and then precipitated with methyltertbutyl ether, collected by filtration, and dissolved in acetone. Acetic acid was added to this acetone solution and stirred for 5 hours and then worked up. The solution was rotovapped until nearly dry, redissolved in methylenechloride and precipitated in MTBE, collected by filtration and dried in vacuo (17.2 g, Yield=92.1%). $^1$H NMR (d$_6$-DMSO) δ 9.11, 8.33-7.69, 7.15, 6.98, 6.79, 5.06-4.85, 4.60-4.32, 3.81-3.19, 2.99-2.32, 2.03-1.59.

Example 99

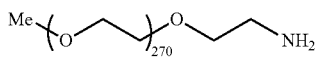

1. Toluene Azeotrope, 60° C. 3 Hrs
2. Glu(oBn) NCA, d-Glu(oBn) NCA R.T., 16 Hrs, NMP
3. d-Phe NCA, Tyr(oBn) NCA R.T. -> 35° C. 48 Hrs
4. NMM, AcAnh, DMAP R.T., 16 Hrs

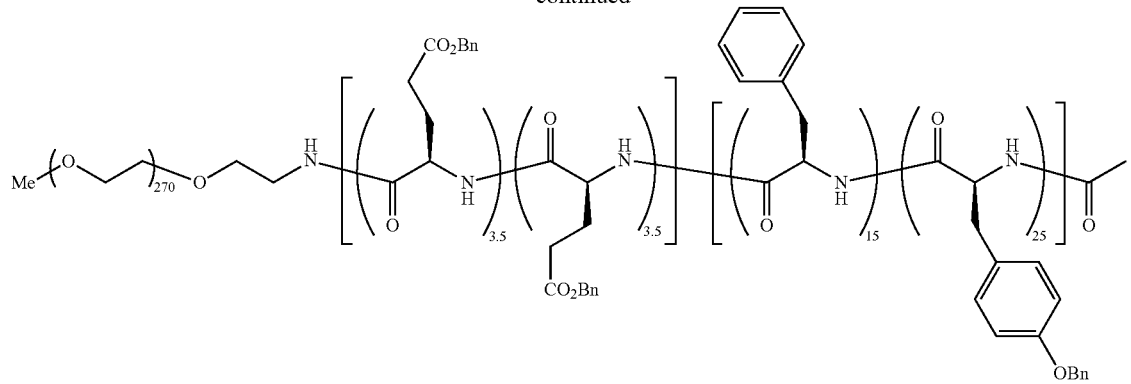

Synthesis of mPEG12K-b-Poly-(d-Glu(OBn)$_{3.5}$-Co-Glu(OBn)$_{3.5}$)-b-Poly (Tyr(OBn)$_{25}$-Co-d-Phe$_{15}$)-Ac mPEG12KNH$_2$ (45.34 g, 3.78 mmol) prepared by the same method detailed in Example 3, was weighed into a clean, oven dried, 1000 mL, two neck, round bottom flask and dissolved in toluene (300 mL) This polymer was prepared in the same manner as Example 73. Glu(OBn) NCA (3.5 g, 13.29 mmol) from the method detailed in Example 8, and d-Glu(OBn) NCA (3.5 g, 13.29 mmol) from the method detailed in Example 9, were added to the flask, and the reaction mixture was allowed to stir for 16 hours at ambient room temperature under nitrogen gas. Then, d-Phe NCA (10.89 g, 56.9 mmol) from the method detailed in Example 7, and Tyr (OBn) NCA (28.24 g, 94.98 mmol) from the method detailed in Example 6, were added and the solution was allowed to stir at 35° C. for 48 hours at which point the reaction was complete (GPC, DMF/0.1% LiBr). The solution was cooled to room temperature and acetic anhydride (3.88 g, 37.8 mmol, 3.58 mL), N-methylmorpholine (NMM) (3.76 g, 37.8 mmol, 4.16 mL) and dimethylaminopyridine (DMAP) (0.47 g, 3.8 mmole) were added. Stirring was continued for 1 day at room temperature. The polymer was precipitated into diethyl ether:heptane 10:1 (2.5 L) and isolated by filtration, washed with fresh 100 mL portions of diethyl ether, and dried in vacuo to give the block copolymer as a fine, nearly colorless powder (68.22 g, Yield=82.2%).
$^1$H NMR (d$_6$-DMSO) δ 8.43-7.84, 7.30, 6.98, 6.97-6.65, 5.04, 4.98-4.80, 4.66-4.16, 3.72-3.21, 3.01-2.76, 2.74-2.56, 2.41-2.26, 2.23-2.10, 2.01-1.58.

Example 100

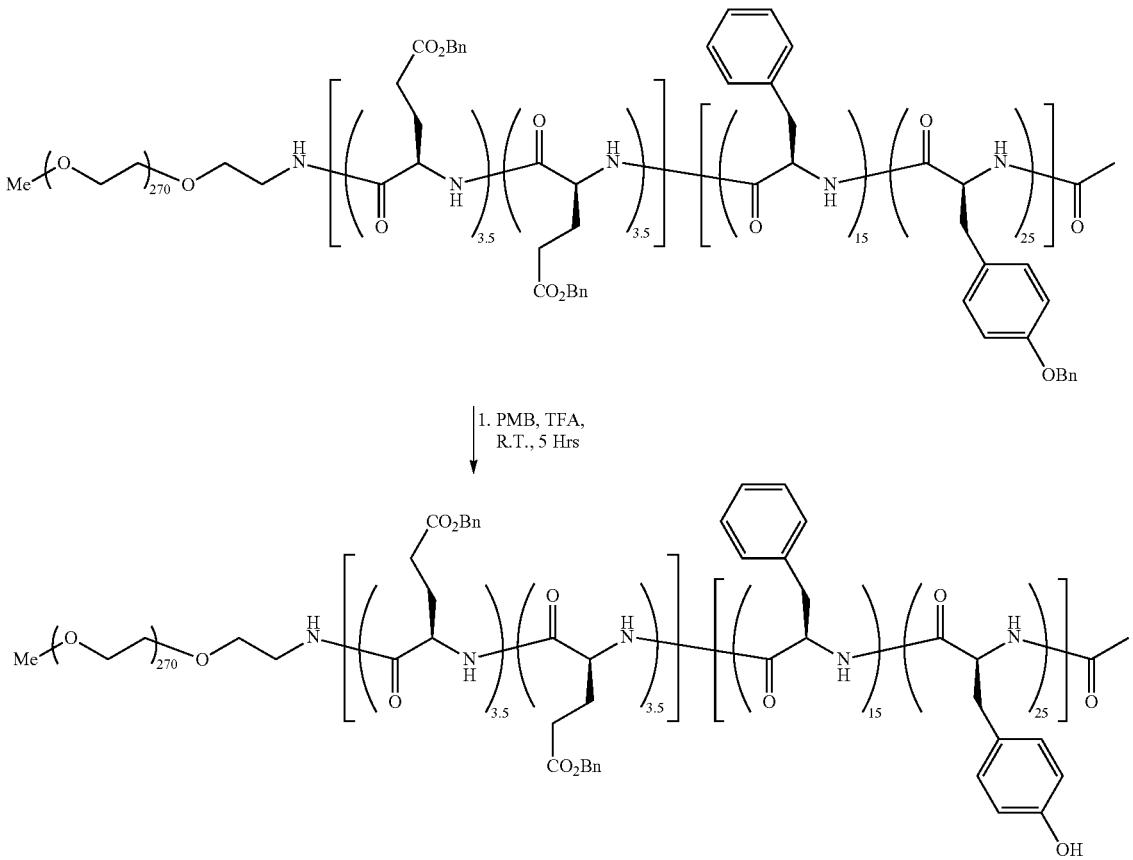

Synthesis of mPEG12K-b-Poly-(d-Glu(OBn)$_{3.5}$-Co-Glu(OBn)$_{3.5}$)-b-Poly (Tyr(OH)$_{25}$-Co-d-Phe$_{15}$)-Ac Using the general method from Example 74 only adjusting stoichometry this polymer was deprotected (60 g, 2.73 mmol). Once complete (5 Hrs.) the solution was rotovapped to a thick paste and then redissolved in DCM and precipitated in cold Diethyl ether, collected by filtration, washed several times with fresh 200 mL portions of cold diethyl ether and dried in vacuo. This reaction yielded 43.8 g of dry material (81.4%). $^1$H NMR (d6-DMSO) δ 9.04, 8.38-7.73, 7.38-6.73, 5.04, 4.62-4.19, 3.82-3.27, 3.02-2.76, 2.75-2.56, 2.42-2.26, 2.20-1.61, 1.08 (solvent, ether).

Example 101

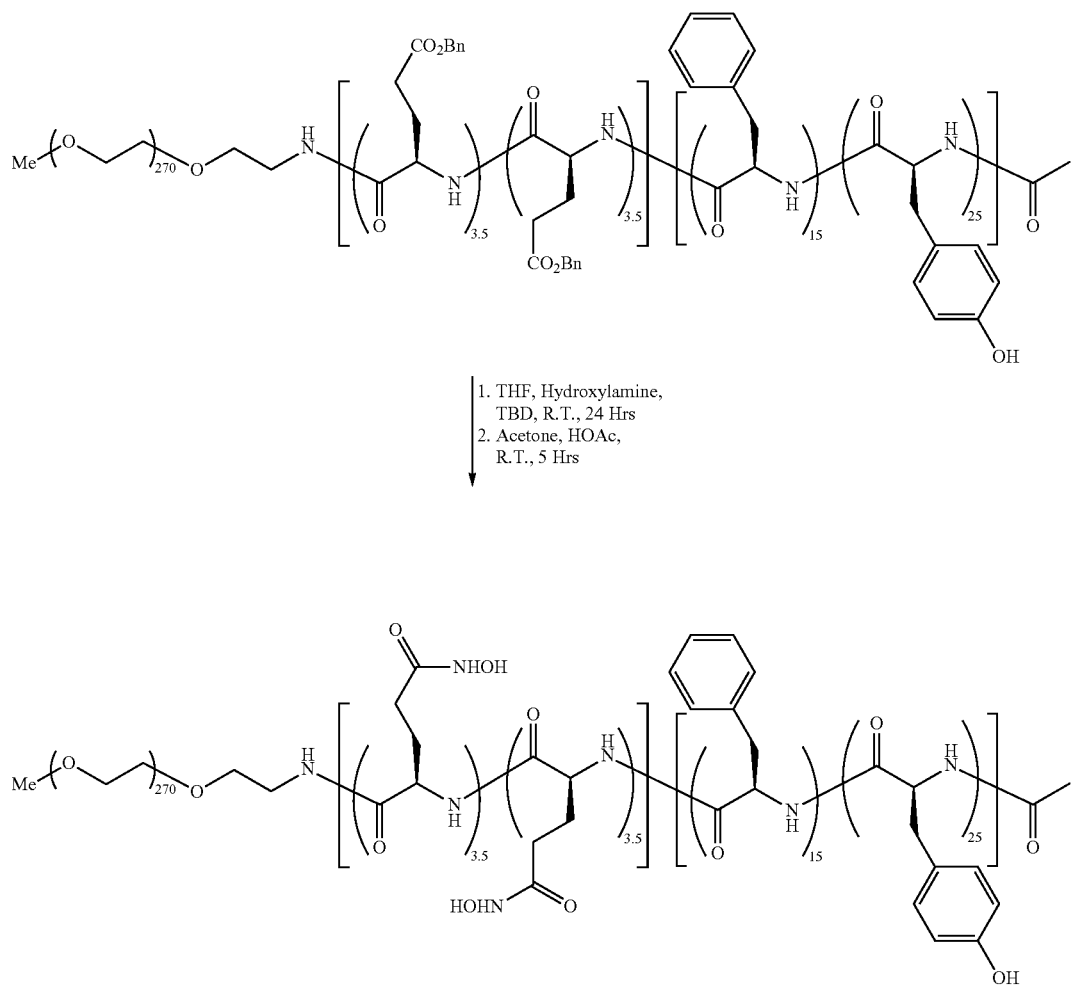

Synthesis of mPEG12K-b-Poly-(d-Glu(NHOH)$_{3.5}$-Co-Glu(NHOH)$_{3.5}$)-b-Poly (Tyr(OH)$_{25}$-Co-d-Phe$_{15}$)-Ac The polymer (40 g, 1 mmol) from Example 100, was dissolved completely in 700 mL of THF with heating, this solution was allowed to cool to room temp before 1,5,7-triazabicyclo [4.4.0]dec-5-ene (TBD, 1.5 g, 10.8 mmol) was added, followed by Hydroxylamine (50% water solution, 45 mL, 817.5 mmol) this solution was stirred at room temperature for 24 hours. Isopropanol (200 mL) was added and then precipitated with methyltertbutyl ether, collected by filtration, and dissolved in acetone (500 mL). Acetic acid (5 mL) was added to this acetone solution and stirred overnight. The solution was rotovapped until nearly dry, redissolved in methylenechloride and precipitated in MTBE, collected by filtration and dried in vacuo (33.5 g, Yield=86%). $^1$H NMR (d$_6$-DMSO) δ 9.03, 8.37-7.70, 7.36-6.72, 6.68-6.42, 4.64-4.14, 3.73-3.10, 3.00-2.76, 2.71-2.56, 2.42-2.27, 2.21-1.61.

Example 102

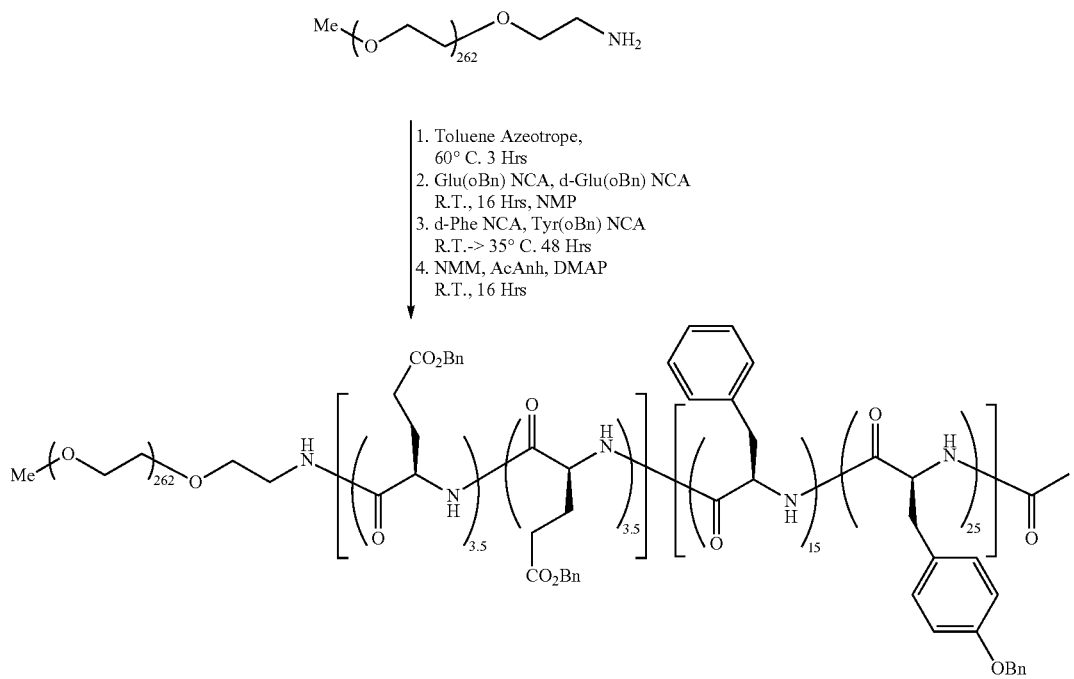

Synthesis of mPEG11.5K-b-Poly-(d-Glu(OBn)$_{3.5}$-Co-Glu(OBn)$_{3.5}$)-b-Poly (Tyr(OBn)$_{25}$-Co-d-Phe$_{15}$)-Ac mPEG11.5KNH$_2$ (15 g, 1.3 mmol) prepared with the same method as Example 3 with the exception of molecular weight, was weighed into a clean, oven dried, 1000 mL, two neck, round bottom flask and dissolved in toluene (300 mL) This polymer was prepared in the same manner as Example 73. Glu(OBn) NCA (1.2 g, 4.56 mmol) prepared with the same method as Example 8, and d-Glu(OBn) NCA (1.2 g, 4.56 mmol) prepared with the same method as Example 9, were added to the flask, and the reaction mixture was allowed to stir for 16 hours at ambient room temperature under nitrogen gas. Then, d-Phe NCA (2.88 g, 19.56 mmol) prepared with the same method as Example 7, and Tyr(OBn) NCA (8.26 g, 32.60 mmol) prepared with the same method as Example 6, were added and the solution directly, and allowed to stir at room temp for 2 hours and then heated to 35° C. for 48 hours at which point the reaction was complete (GPC, DMF/0.1% LiBr). The solution was cooled to room temperature and acetic anhydride (1.34 g, 13 mmol, 1.23 mL), N-methylmorpholine (NMM) (1.3 g, 13 mmol, 1.43 mL) and dimethylaminopyridine (DMAP) (0.16 g, 1.3 mmole) were added. Stirring was continued for 16 hours at room temperature. The polymer was precipitated into diethyl ether:heptane 10:1 (2.5 L) and isolated by filtration, washed with fresh 100 mL portions of diethyl ether, and dried in vacuo to give the block copolymer as a fine, nearly colorless powder (26 g, Yield=82.2%). $^1$H NMR (d$_6$-DMSO) δ 8.40-7.83, 7.27, 7.16-6.98, 6.83-6.64, 5.06-4.79, 4.62-4.18, 3.71-3.21, 2.98-2.78, 2.75-2.58, 2.42-2.25, 2.22-2.13, 1.99-1.70.

Example 103

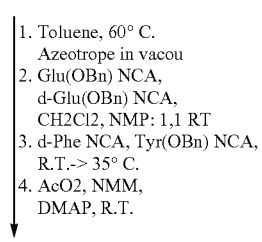

1. Toluene, 60° C.
   Azeotrope in vacou
2. Glu(OBn) NCA,
   d-Glu(OBn) NCA,
   CH2Cl2, NMP: 1,1 RT
3. d-Phe NCA, Tyr(OBn) NCA,
   R.T.-> 35° C.
4. AcO2, NMM,
   DMAP, R.T.

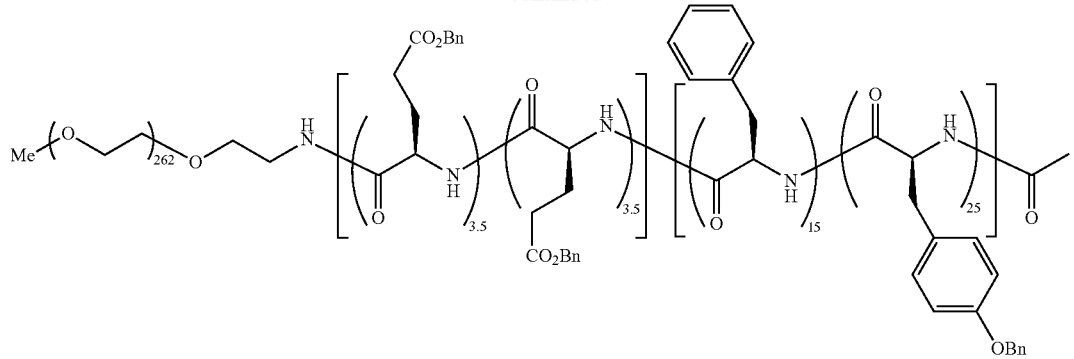

Synthesis of mPEG11.5K-b-Poly-(d-Glu(OBn)$_{3.5}$-Co-Glu(OBn)$_{3.5}$)-b-Poly (Tyr(OBn)$_{25}$-Co-d-Phe$_{15}$)-Ac mPEG11.5KNH$_2$ (15 g, 1.3 mmol) prepared with the same method in Example 3 with the exception of molecular weight, was weighed into a clean, oven dried, 1000 mL, two neck, round bottom flask and dissolved in toluene (300 mL) with heating and dried by azeotropic distillation. After distillation to dryness, the polymer was left under vacuum for three hours. The flask was subsequently backfilled with N$_2$, re-evacuated under reduced pressure, and dry NMP:DCM (1:1) (450 mL) was introduced by cannula. Glu(OBn) NCA (1.2 g, 4.56 mmol) prepared with the same method as Example 8, and d-Glu(OBn) NCA (1.2 g, 4.56 mmol) prepared with the same method as Example 9, were added to the flask, and the reaction mixture was allowed to stir for 48 hours at ambient room temperature under nitrogen gas. Then, d-Phe NCA (2.88 g, 19.56 mmol) prepared with the same method as Example 7 and Tyr (OBn) NCA (8.26 g, 32.60 mmol) prepared with the same method as Example 6, were added and the solution was allowed to stir at room temp for two hours and then heated to 35° C. for 48 hours at which point the reaction was complete (GPC, DMF/0.1% LiBr). The solution was cooled to room temperature and acetic anhydride (1.34 g, 13 mmol, 1.23 mL), N-methylmorpholine (NMM) (1.3 g, 13 mmol, 1.43 mL) and dimethylaminopyridine (DMAP) (0.16 g, 1.3 mmole) were added. Stirring was continued for 16 hours at room temperature. The polymer was precipitated into diethyl ether: heptane 10:1 (2.5 L) and isolated by filtration, washed with fresh 100 mL portions of diethyl ether, and dried in vacuo to give the block copolymer as a fine, nearly colorless powder (25 g, Yield=82.2%). $^1$H NMR (d$_6$-DMSO) δ 8.38-7.80, 7.42-7.18, 6.75, 5.02, 4.97-4.80, 4.66-4.16, 3.75-3.20, 3.02-2.80, 2.76-2.56, 2.44-2.25, 2.00-1.59.

Example 104

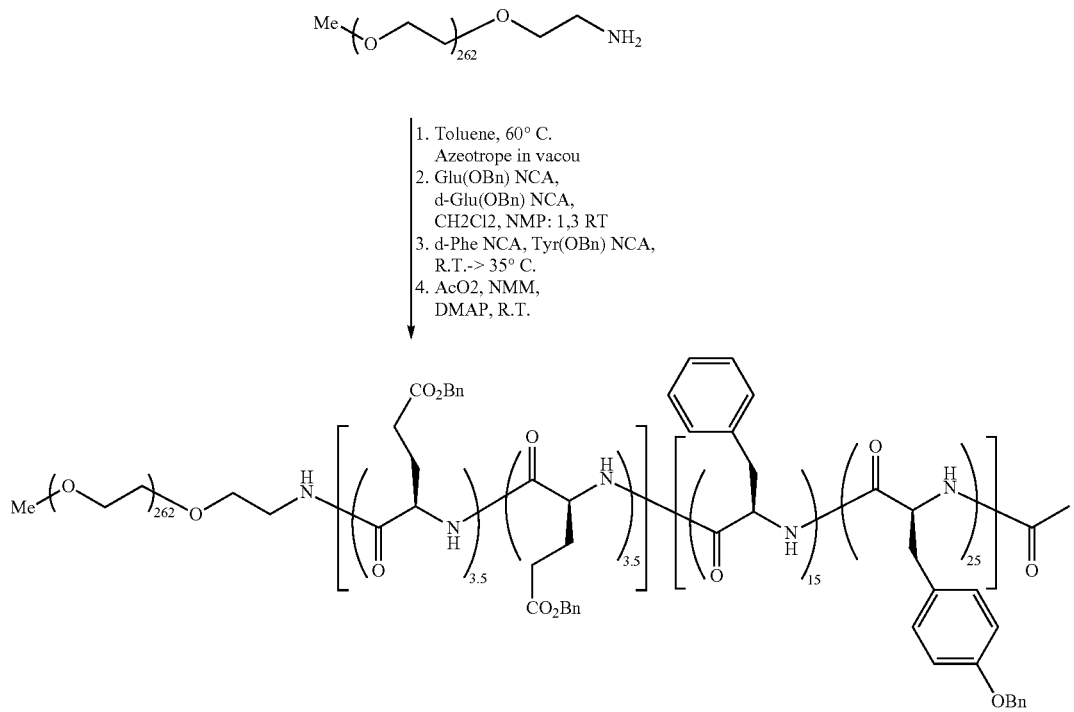

Synthesis of mPEG11.5K-b-Poly-(d-Glu(OBn)$_{3.5}$-Co-Glu(OBn)$_{3.5}$)-b-Poly (Tyr(OBn)$_{25}$-Co-d-Phe$_{15}$)-Ac mPEG11.5KNH$_2$ (15 g, 1.3 mmol) prepared with the same method as Example 3 with the exception of molecular weight, was weighed into a clean, oven dried, 1000 mL, two neck, round bottom flask and dissolved in toluene (300 mL) with heating and dried by azeotropic distillation. After distillation to dryness, the polymer was left under vacuum for three hours. The flask was subsequently backfilled with N$_2$, re-evacuated under reduced pressure, and dry (NMP) and DCM (1:3 ratio) (450 mL) was introduced by cannula. Glu(OBn) NCA (1.2 g, 4.56 mmol) prepared with the same method as Example 8, and d-Glu(OBn) NCA (1.2 g, 4.56 mmol) prepared with the same method as Example 9, were added to the flask, and the reaction mixture was allowed to stir for 48 hours at ambient room temperature under nitrogen gas. Then, d-Phe NCA (2.88 g, 19.56 mmol) prepared with the same method as Example 7, and Tyr (OBn) NCA (8.26 g, 32.60 mmol) prepared with the same method as Example 6, were added and the solution directly and allowed to stir at room temperature for 2 hours and then heated to 35° C. for 48 hours, at which point the reaction was complete (GPC, DMF/0.1% LiBr). The solution was cooled to room temperature and acetic anhydride (1.34 g, 13 mmol, 1.23 mL), N-methylmorpholine (NMM) (1.3 g, 13 mmol, 1.43 mL) and dimethylaminopyridine (DMAP) (0.16 g, 1.3 mmole) were added. Stirring was continued for 16 hours at room temperature. The polymer was precipitated into diethyl ether:heptane 10:1 (2.5 L) and isolated by filtration, washed with fresh 100 mL portions of diethyl ether, and dried in vacuo to give the block copolymer as a fine, nearly colorless powder (26 g, Yield=82.2%). $^1$H NMR (d$_6$-DMSO) δ 8.46-7.85, 7.48-6.95, 6.84-6.61, 5.02, 4.97-4.79, 4.66-4.16, 3.75-3.21, 3.00-2.79, 2.76-2.56, 2.43-2.25, 2.00-1.57.

Example 105

1. Toluene, 60° C.
   Azeotrope 3 Hrs.
2. NMP:DCM 1:1, via cannula
3. Glu(oBn) NCA, d-Glu(oBn) NCA
   18 hrs., R.T.
4. d-Leu NCA, Tyr(oBn) NCA, Asp(oTbu) NCA
   48 hrs., R.T.--> 35° C.
5. NMM, DMAP, AcANH
   O.N., R.T.

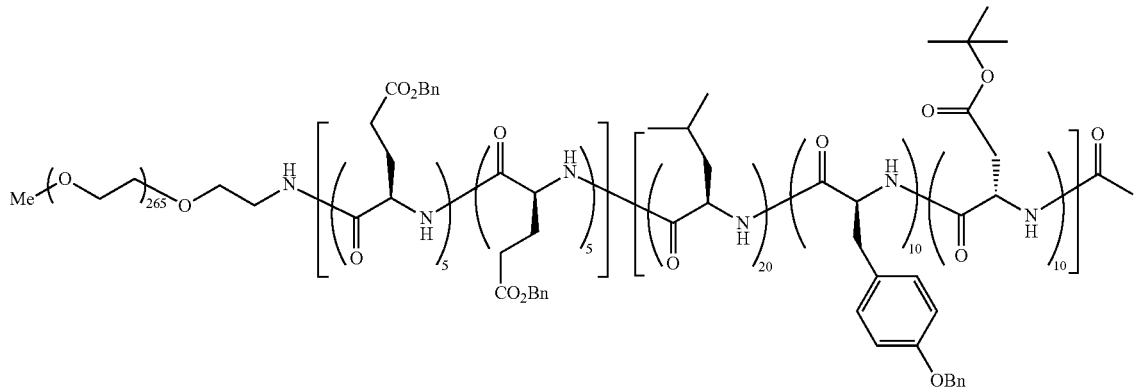

Synthesis of mPEG11.6K-b-Poly-(d-Glu(oBn)$_5$-Co-Glu(oBn)$_5$)-b-Poly (Tyr(OBn)$_{10}$-Co-d-Leu$_{20}$-Co-Asp(oTbu)$_{10}$-Ac Using the general protocol from Example 73 and substituting appropriate NCA starting materials and using a 1:1 ratio of NMP:DCM resulted in the crude polymer, this was precipitated with diethyl ether about 10 volumes. After filtration and drying the title compound was collected as a colorless solid (30.5 g, Yield=87.1%). $^1$H NMR (d6-DMSO) δ 8.39-7.94, 7.41-7.17, 7.15-7.02, 6.82, 5.01, 4.60-4.16, 3.72-3.30, 2.70, 2.42-2.26 2.02-1.71, 1.33, 0.9-0.55.

Example 106

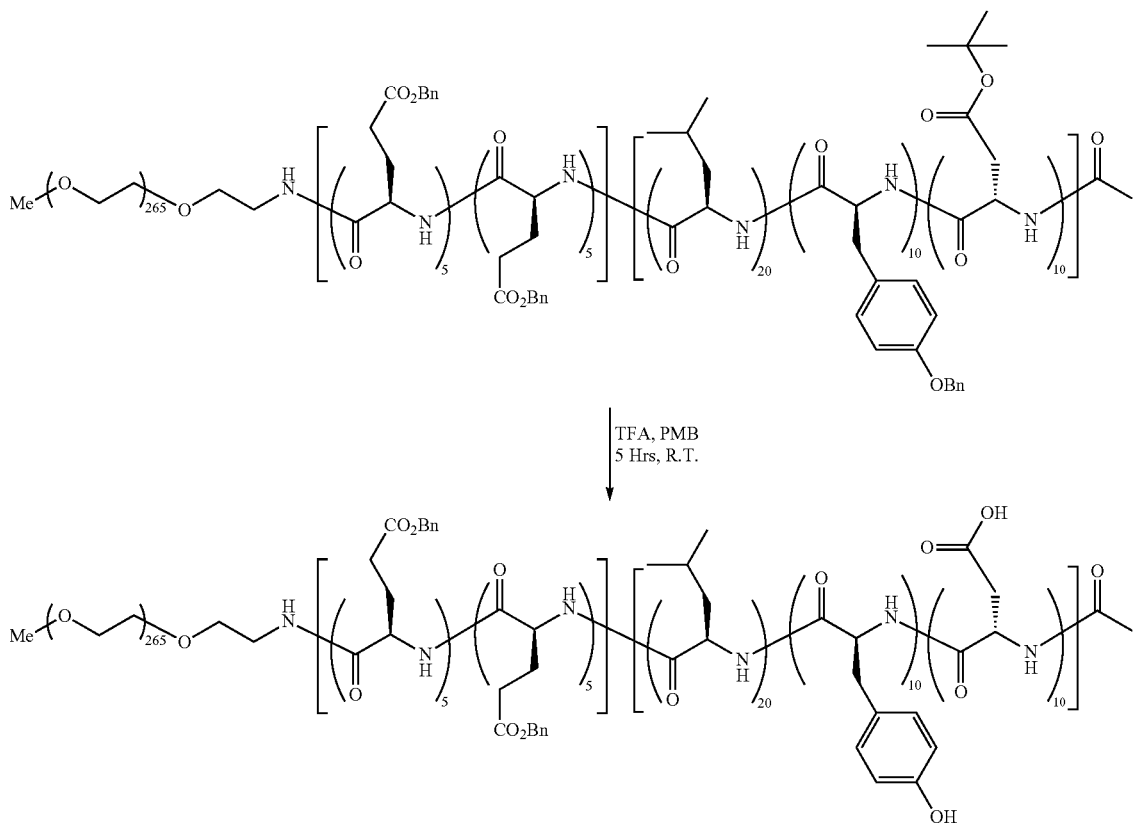

Synthesis of mPEG11.6K-b-Poly-(d-Glu(oBn)$_5$-Co-Glu(oBn$_5$)-b-Poly (Tyr(OH)$_{10}$-Co-d-Leu$_{20}$-Co-Asp$_{10}$)-Ac The triblock co-polymer from Example 105 was weighed (29 g, 1.38 mmol) into a clean 500 mL beaker and dissolved in triflouroacetic acid. To this solution pentamentyl-benzene (6.14 g, 41.4 mmol) was added and stirred with a magnetic stir-bar. At thirty mins post addition of pentamethyl-benzene a precipitate was observed in solution. The reaction mixture was stirred for two hours and monitored by NMR for complete removal of benzylic protecting groups on tyrosine and t-Butyl group on aspartate. After completion of this deprotection (5 Hrs) the solution was rotovapped to a thick paste, redissolved in methylene chloride and then precipitated in cold diethyl ether and collected by filtration. This solid was washed three times with 100 mL portions of cold ether and dried in vacuo and characterized. (26 g, Yield=96.6%)$^1$H NMR (d6-DMSO) δ 9.09, 8.44-7.58, 7.35-6.89, 6.96, 6.58, 5.03, 4.62-4.16, 3.71-3.22, 2.75-2.64, 2.40-2.26, 2.23-2.04, 0.92-0.54.

Example 107

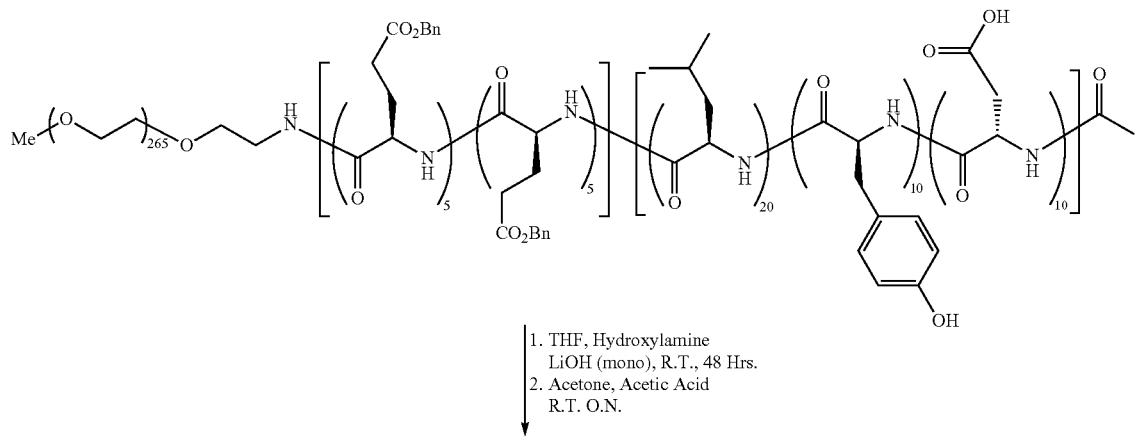

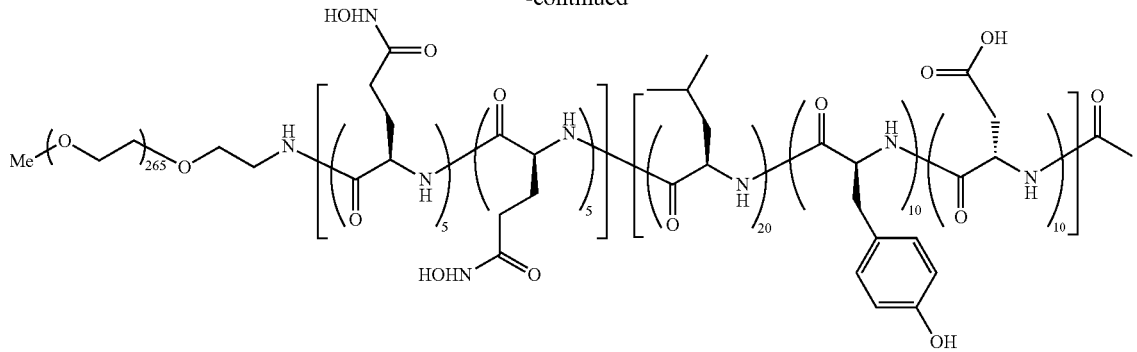

Synthesis of mPEG11.6K-b-Poly-(d-Glu(NHOH)$_5$-Co-Glu(NHOH)-b-Poly (Tyr(OH)$_{10}$-Co-d-Leu$_{20}$-Co-Asp$_{10}$)-Ac Triblock ester from Example 106 was weighed (25 g, 1.38 mmol) into a clean 500 mL round bottom flask and the polymer was dissolved completely in 200 mL of tetrahydrofuran. To this solution thirty equivalents of hydroxylamine (1.9 mL, 0.028 mmol) and lithium hydroxide monohydrate (1.16 g, 27.6 mmol) was stirred under nitrogen at room temp over night. Completion of the reaction was verified by $^1$H NMR. This solution was mixed with 100 mL methanol and precipitated with diethyl ether (about 7 volumes). This white solid was collected by filtration and washed with fresh diethyl ether. The collected solid was then dissolved in acetone and a catalytic amount of acetic acid was allowed to stir overnight. the solution was poured into a clean two liter beaker and diethyl ether was slowly added to the solution with stirring. This white solid was collected by filtration and then dried in vacuo. Yielded 22 g (92%). $^1$H NMR (d6-DMSO) δ 9.4-8.5, 8.40-7.71, 7.40-7.11, 6.93, 6.57, 5.10, 4.53-3.99, 3.86-3.02, 2.99-2.87, 2.09-1.19, 1.6-1.2, 1.01-0.5.

Example 108

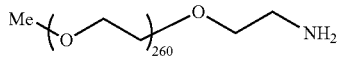

1. Toluene, 60° C.
   Azeotrope 3 Hrs.
2. DMAC:DCM 1:2, via cannula
3. Glu(oBn) NCA, d-Glu(oBn) NCA
   14 hrs., R.T.
4. d-Phe NCA, Tyr(oBn) NCA, Asp(oTbu) NCA
   26 hrs., R.T.--> 35° C.
5. NMM, DMAP, AcANH
   O.N., R.T.

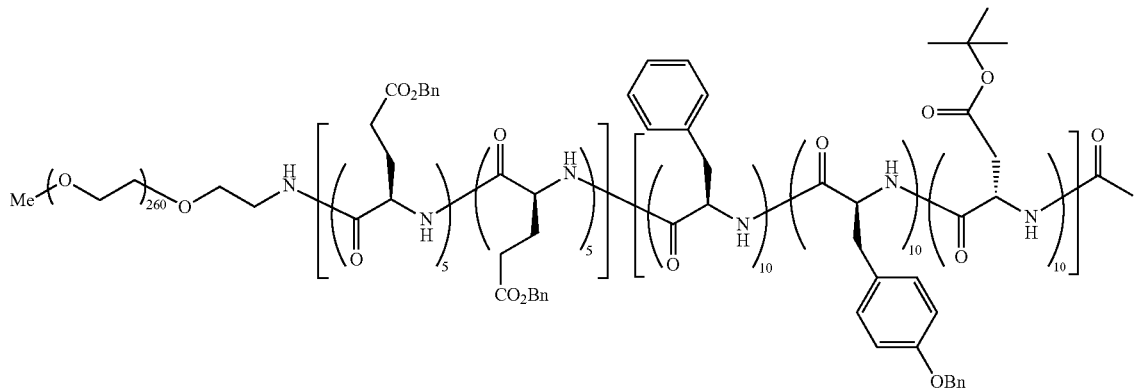

Synthesis of mPEG11.5K-b-Poly-(d-Glu(oBn)$_5$-Co-Glu(oBn$_5$)-b-Poly (Tyr(OBn)$_{10}$-Co-d-Phe$_{10}$-Co-Asp (otBu)$_{10}$)-Ac mPEG11.5KNH$_2$ (31 g, 2.7 mmol) prepared by the same method as Example 3 except for the molecular weight, was weighed into a clean, oven dried, 1000 mL, two neck, round bottom flask and dissolved in toluene (400 mL) with heating and dried by azeotropic distillation. After distillation to dryness, the polymer was left under vacuum for three hours. The flask was subsequently backfilled with N$_2$, re-evacuated under reduced pressure, and a 1:2 ratio of Dimethylacetamide:methylene chloride was introduced by cannula and dissolved completely. Glu(OBn) NCA (3.4 g, 12.9 mmol) prepared by the same method in Example 8, and d-Glu(OBn) NCA (3.4 g, 12.9 mmol) prepared by the same method as Example 9, were weighed into a clean 500 mL round bottom flask and evacuated for 2 hours backfilled with N$_2$ and then dissolved in DMAC and cannulated into the flask containing PEG. This reaction mixture was allowed to stir for 14 hours at ambient room temperature under nitrogen gas. Then, d-Phe NCA (5.15 g, 26.9 mmol) prepared by the same method as Example 7 and Tyr (OBn) NCA (7.99 g, 26.9 mmol) prepared by the same method as Example 6, were added in the same manner as mentioned above and the solution was allowed to stir at room temp for two hours and then heated to 35° C. for 26 hours at which point the reaction was complete (GPC, DMF/0.1% LiBr). The solution was cooled to room temperature and acetic anhydride (2.77 g, 269 mmol, 2.46 mL), N-methylmorpholine (NMM) (2.69 g, 269 mmol, 1.43 mL) and dimethylaminopyridine (DMAP) (0.33 g, 2.7 mmole) were added. Stirring was continued for 1 day at room temperature. The reaction solution was rotovapped to remove the methylene chloride and then the polymer was precipitated into isopropanol (3.5 L) and isolated by filtration, washed with fresh 100 mL portions of isopropanol, and dried in vacuo to give the block copolymer as a nearly colorless powder (44.5 g, Yield=83.1%). $^1$H NMR (d$_6$-DMSO) δ 8.59-7.86, 7.45-7.25, 7.10, 6.79, 5.12-4.79, 4.69-4.17, 3.84-3.23, 3.02-2.58, 2.40-2.23, 2.04-1.71, 1.33.

Example 109

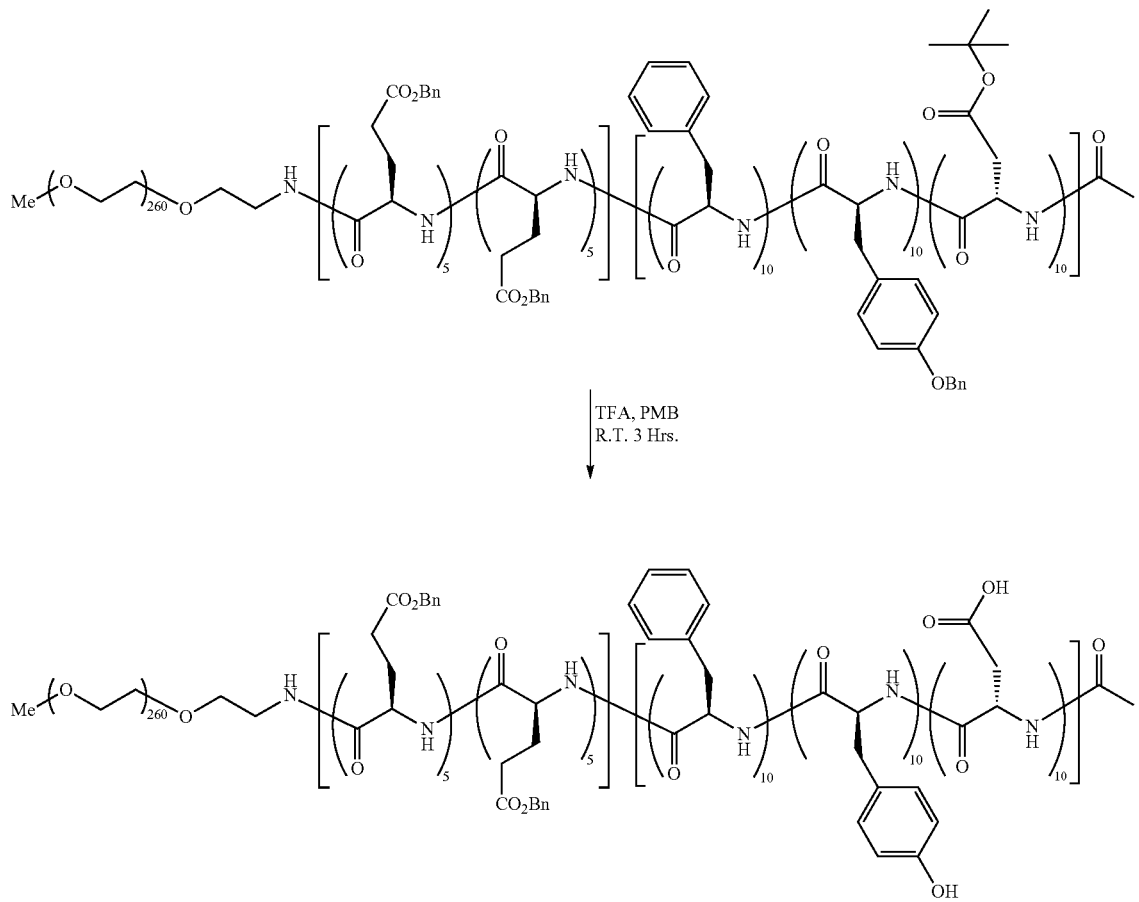

Synthesis of mPEG11.5K-b-Poly-(d-Glu(oBn)$_5$-Co-Glu(oBn$_5$)-b-Poly-(Tyr(OH)$_{10}$-Co-d-Phe$_{10}$-Co-Asp (OH)$_{10}$)-Ac Using the general method from Example 74 only adjusting scale, this polymer was deprotected (30 g, 1.54 mmol). Once complete (3 Hrs.) the solution was rotovapped to a thick paste and then redissolved in DCM and precipitated in MTBE, collected by filtration, washed several times with fresh 100 mL portions of MTBE and dried in vacuo. This reaction yielded 24 g of dry material (86.9%). $^1$H NMR (d6-DMSO) δ 9.07, 8.50-7.80, 7.40-7.28, 6.98, 6.62, 5.04, 4.69-4.17, 3.72-3.23, 3.02-2.76, 2.73-2.57, 2.42-2.27, 2.23-1.59.

Example 110

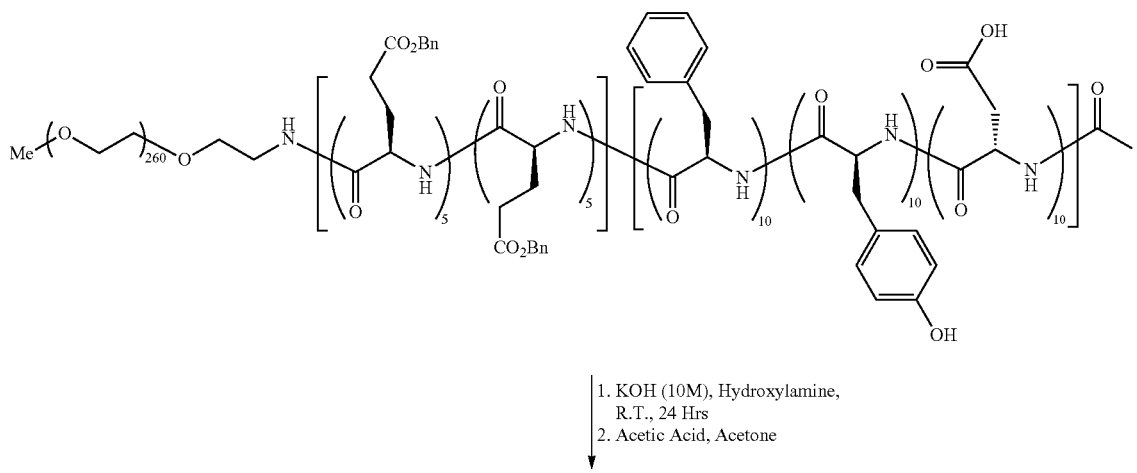

1. KOH (10M), Hydroxylamine, R.T., 24 Hrs
2. Acetic Acid, Acetone

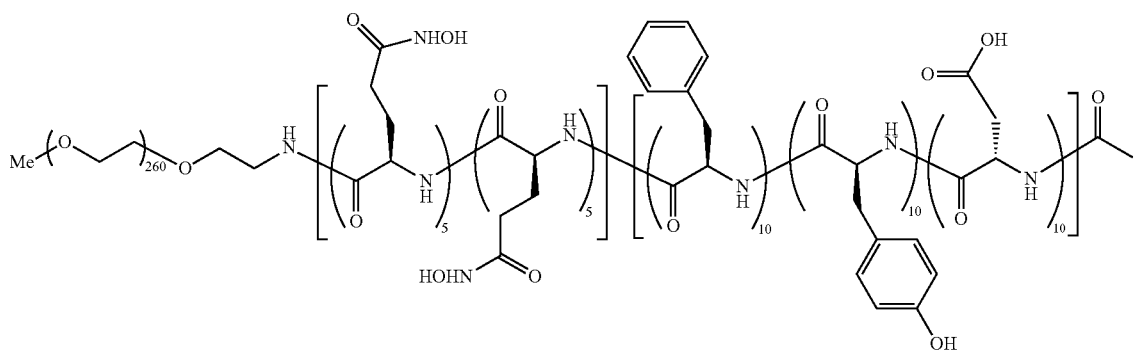

Synthesis of mPEG11.5K-b-Poly-(d-Glu(NHOH)$_5$-Co-Glu(NHOH)$_5$-b-Poly (Tyr(OH)$_{10}$-Co-d-Phe$_{10}$-Co-Asp(OH)$_{10}$)-Ac The polymer from Example 109 (22 g, 1.2 mmol) was dissolved completely in 200 mL of THF with heating. This solution was allowed to cool to room temp before 10M KOH solution was added (2 mL, 1.5 g, 10.8 mmol), followed by Hydroxyl amine (50% water solution, 6 mL, 3.6 g, 108 mmol) this solution was stirred at room temperature for 24 hours. Acetone 20 mL and Acetic acid (2 mL) was added to this reaction solution and stirred 4 hours. The solution was rotovapped until nearly dry, redissolved in methylene chloride and precipitated in MTBE, collected by filtration and dried in vacuo (20 g, Yield=94.9%). $^1$H NMR (d$_6$-DMSO) δ 8.61-7.90, 7.50-6.29, 5.38-5.01, 4.63-4.12, 3.78-3.22, 2.17, 2.11, 1.81-1.63.

Example 111

Me—(O—)$_{270}$O—NH$_2$

1. Difluoracetic acid, Toluene, 55-60° C., azeotrope in vacuo
2. Asp(tOBu)NCA, NMP, RT
3. d-LeuNCA, Tyr(OBn)NCA, RT-> 35° C.
4. Ac$_2$O, Pyridine, DMAP, RT

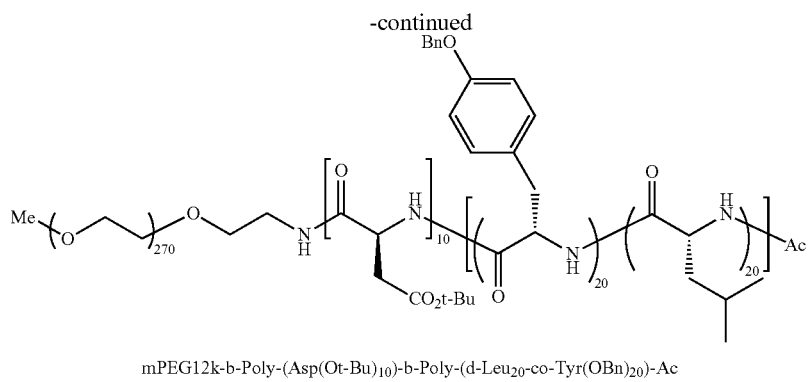

mPEG12k-b-Poly-(Asp(Ot-Bu)₁₀)-b-Poly-(d-Leu₂₀-co-Tyr(OBn)₂₀)-Ac

Synthesis of mPEG12K-b-Poly-(Asp(Ot-Bu)₁₀)-b-Poly-(d-Leu₂₀-Co-Tyr(OBn)₂₀)-Ac mPEG12KNH₂ from Example 3 (360 g, 30.0 mmol) was weighed into a clean, oven dried, 5000 mL, three neck, round bottom jacketed flask and dissolved in toluene (3000 mL) with heating in an oil bath at 55–60° C. and dried by azeotropic vacuum distillation. After about 30% of the toluene was removed the distillation was stopped and Diflouroacetic acid (DFA) was added by syringe (2.26 mL, 0.036 mmol) to form the DFA salt. The solution was stirred for 30 minutes and then the azeotrope was started again and dried completely. The polymer salt was left under vacuum overnight. The flask was subsequently backfilled with N₂, re-evacuated under reduced pressure, and dry N-methylpyrrolidone (NMP) (3500 mL) was introduced by cannula. The mixture was briefly heated to 40° C. to expedite dissolution and then cooled to 25° C. Asp(OtBu) NCA (64.56 g, 300 mmol) was weighed into a clean 1 L, 2 neck RBF and evacuated for an hour before freshly distilled NMP was cannulated into the flask and completely dissolved the NCA. This solution was then cannulated into the PEG flask and allowed to stir at room temperature for 48 hours under nitrogen gas. Then, d-Leu NCA (94.30 g, 600 mmol) and Tyr (OBn) NCA (178.39 g, 600 mmol) were added to the solution by the same method as described above and the resultant solution was allowed to stir at 35° C. for 48 hours at which point the reaction was deemed complete (GPC, DMF/0.1% LiBr). The solution was cooled to room temperature and acetic anhydride (45.9 g, 0.45 mol, 42.5 mL), pyridine (59.3 g, 0.75 mol, 60.7 mL) and dimethylaminopyridine (DMAP) (0.37 g, 3.0 mmole) were added. Stirring was continued for 1 day at room temperature. The polymer was precipitated into 5 volumes of diethyl ether (15 L) and isolated by filtration, washed with fresh 300 mL portions of diethyl ether, and dried in vacuo to give the block copolymer as a fine, off white powder (434.9 g, Yield=69.0%). ¹H NMR (d₆-DMSO) δ 8.50-7.90, 7.60-7.30, 7.25-6.77, 5.10-4.85, 4.65-4.10, 3.72-3.25, 3.05-2.45, 2.44-1.60, 1.40-1.25, 0.90-0.50.

Example 112

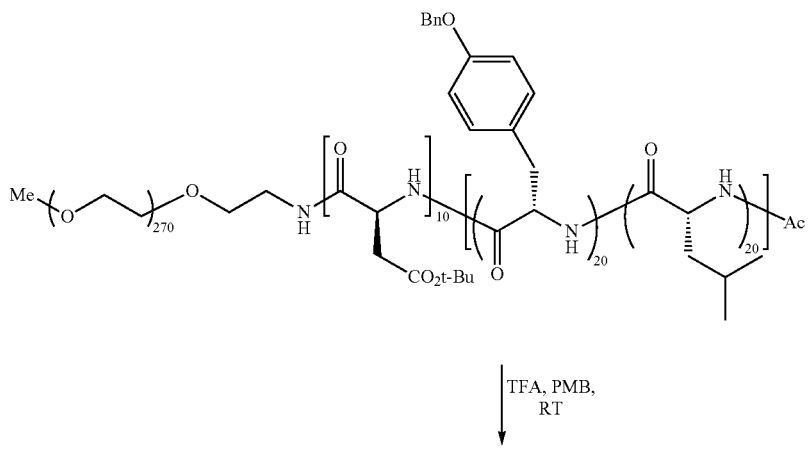

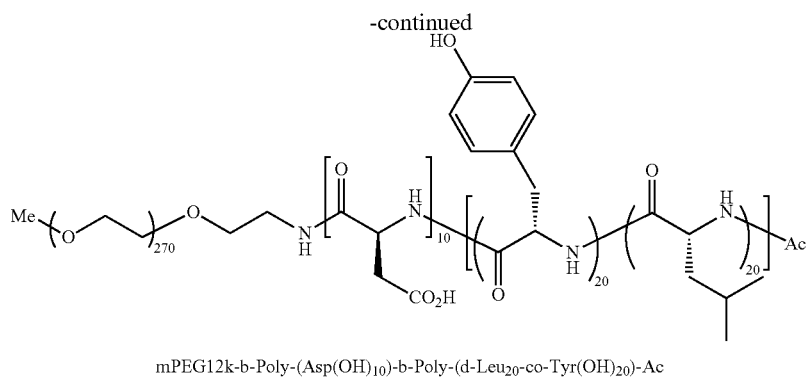

mPEG12k-b-Poly-(Asp(OH)$_{10}$)-b-Poly-(d-Leu$_{20}$-co-Tyr(OH)$_{20}$)-Ac

Synthesis of mPEG12K-b-Poly-(Asp(OH)$_{10}$)-b-Poly-(d-Leu$_{20}$-Co-Tyr(OH)$_{20}$)-Ac mPEG12K-b-Poly-(Asp(Ot-Bu)$_{10}$)-b-Poly-(d-Leu$_{20}$-co-Tyr(OBn)$_{20}$)-Ac from Example 111 (314.5 g, 14.9 mmol) and pentamethylbenzene (141.4 g, 0.954 mole) were dissolved into 2.2 L of trifluoroacetic acid (TFA). The reaction was rapidly stirred for 14 hours at ambient room temperature. The TFA was removed on a rotary evaporator with the water bath temperature not exceeding 35° C. The resultant putty-like solid was dissolved in 1.4 L of dichloromethane, transferred to a 12 L tub, and precipitated by slow addition of 5.6 L of diethyl ether using rapid mechanical stirring. The resultant slurry was stirred for 30 minutes, solids were collected by filtration, washed with 2×1 L portions of fresh diethyl ether, and vacuum dried. The solid was redissolved in 900 mL of dichloromethane and precipitated by addition of 10 L of diethyl ether. Filtration and vacuum drying afforded the product as a colorless, fluffy solid (254.4 g, Yield=91.3%). $^1$H NMR (d$_6$-DMSO) δ 12.4, 9.09, 8.50-7.80, 7.05-6.45, 4.65-4.0, 3.85-3.1, 3.03-2.45, 2.44-1.63, 1.58-0.95, 0.90-0.50.

Example 113

Formulation of Daunorubicin—

Triblock copolymer from Example 18 (330 mg) was dissolved in water at 1.65 mg/mL by stirring at ~50° C. for 10 minutes. The solution was allowed to cool and the pH was adjusted to 7.0 with 0.1 N NaOH. Daunorubicin feed rate for the formulation was 10% of the polymer weight. An organic solution (20% methanol, 80% dichloromethane) was used to dissolve 33 mg daunorubicin at 8.25 mg/mL by placing the solution in a sonicating water bath followed by heating and vortexing, and repeating until a clear, red solution persisted. The organic solution was allowed to cool to room temperature then 17 L of triethylamine was added. The organic solution was then added to the polymer solution while shear mixing at 10,000 RPM for ~1 minute. The resulting emulsion, which was a turbid, red solution, was allowed to stir in a fume hood over night. As the organic solvent evaporated the solution became less turbid and more red in color. The next day the solution was filtered through a 0.22 micron, dead end filter. A tangential flow filtration apparatus equipped with a 10 kD cutoff filter was used to concentrate the sample from 200 mL to approximately 50 mL. The formulation was then frozen at −70° C. and lyophilized. Formulation of daunorubicin resulted in an 88% yield. Weight loading was determined by comparing a standard curve of daunorubicin to a known concentration of formulation by HPLC analysis. Daunorubicin was dissolved in methanol in a range from 40 µg/mL to 200 µg/mL, and the formulation was dissolved at 2 mg/mL in methanol. The amount of daunorubicin in the formulation is then converted to % based on the known quantity of formulation used (i.e. 2 mg/mL). This formulation demonstrated a weight loading of 7.8% from a 10% feed; representing a 69% efficient process. Particle size analysis of the uncrosslinked formulation by dynamic light scattering resulted in average diameter of 75 nm. Encapsulation of daunorubicin was verified by dialysis of the uncrosslinked formulation above the critical micelle concentration (CMC) at 20 mg/mL, and below the CMC at 0.2 mg/mL. As shown in FIG. 5, the formulation dialyzed above the CMC resulted in approximately 88% retention of daunorubicin while dialysis below the CMC resulted in approximately 15% retention of daunorubicin. This result shows that the daunorubicin is effectively encapsulated in the micelle at high concentrations (above the CMC) and that the micelle falls apart when diluted below the CMC.

Example 114

Crosslinking of Daunorubicin Loaded Micelles—

Figure 6:
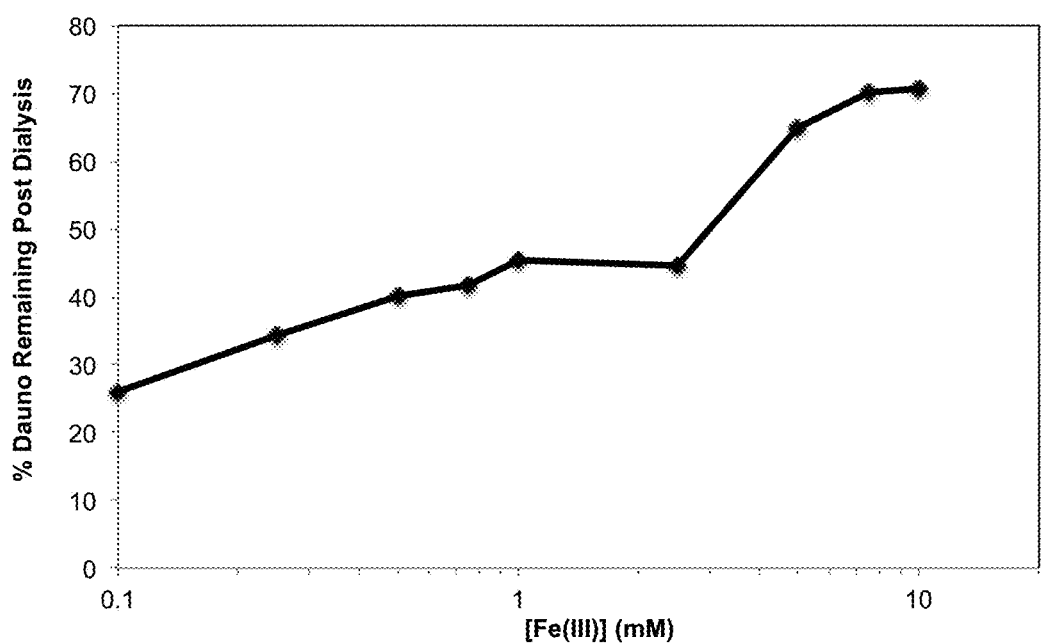
FIG. 6. Iron-dependent crosslinking verification by dialysis at 0.2 mg/mL in phosphate buffer pH 8 for 6 hours.

The daunorubicin loaded micelles of Example 113 were in water at 20 mg/mL with 0.1, 0.25, 0.5, 0.75, 1, 2.5, 5, 7.5 or 10 mM iron (III) chloride for approximately 16 hours. Each of the nine separate samples was diluted to 0.2 mg/mL and dialyzed for 6 hours against phosphate buffer pH 8 to determine the extent of crosslinking. The result of this experiment is shown in FIG. 6. This result demonstrates that daunorubicin loaded micelles are stable to dilution (crosslinked) when treated with iron (III) chloride, with the best results obtained with concentrations above 5 mM of iron (III) chloride.

Example 115

Optimization of Crosslinking Time—

Figure 7:
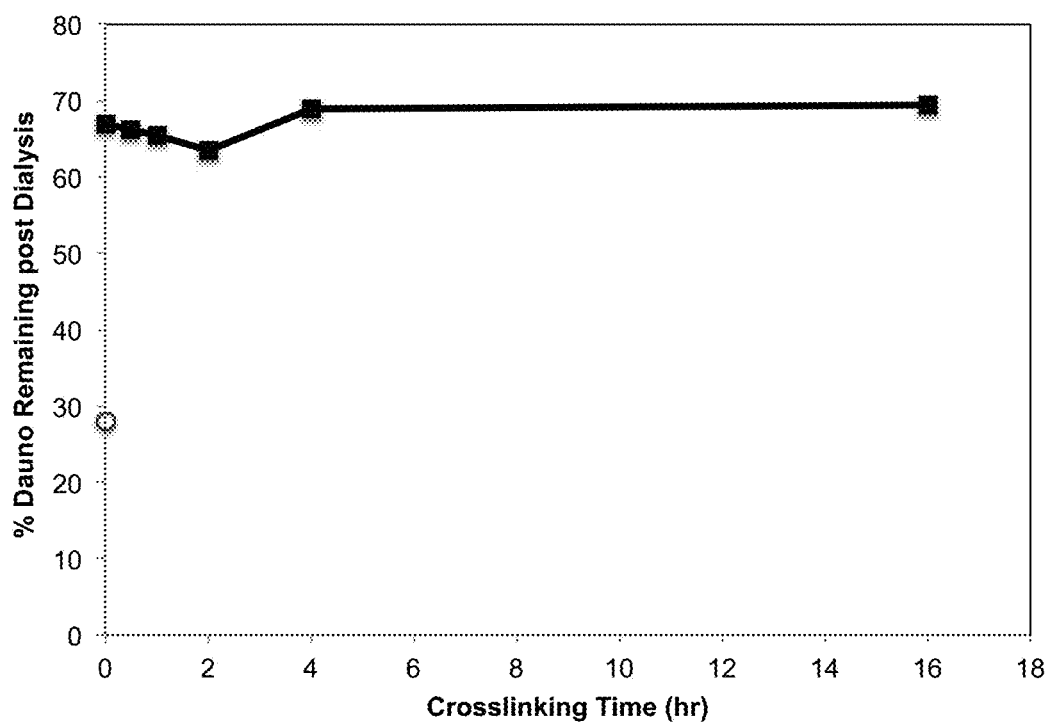
FIG. 7. Verification of time-dependency on iron-mediated crosslinking by dialysis at 0.2 mg/mL in phosphate buffer pH 8 for 6 hours.

The daunorubicin loaded micelles of Example 113 were in 10 mM iron (III) chloride at 20 mg/mL. Aliquots of the sample were taken at 5 minutes, 30 minutes, 1 hour, 2 hours, 4 hours and 16 hours, along with an uncrosslinked sample with no iron at 5 minutes, diluted to 0.2 mg/mL and dialyzed against 10 mM phosphate buffer pH 8 for 6 hours. The % daunorubicin remaining post dialysis for the time-dependent crosslinking is shown in FIG. 7. Based on FIG. 3 the crosslinking of the sample occurred rapidly, with nearly 70% retention of the daunorubicin remaining after just 5 minutes incubation of the sample with the iron (III) chloride solution prior to dilution below the CMC.

Example 116

Figure 8:
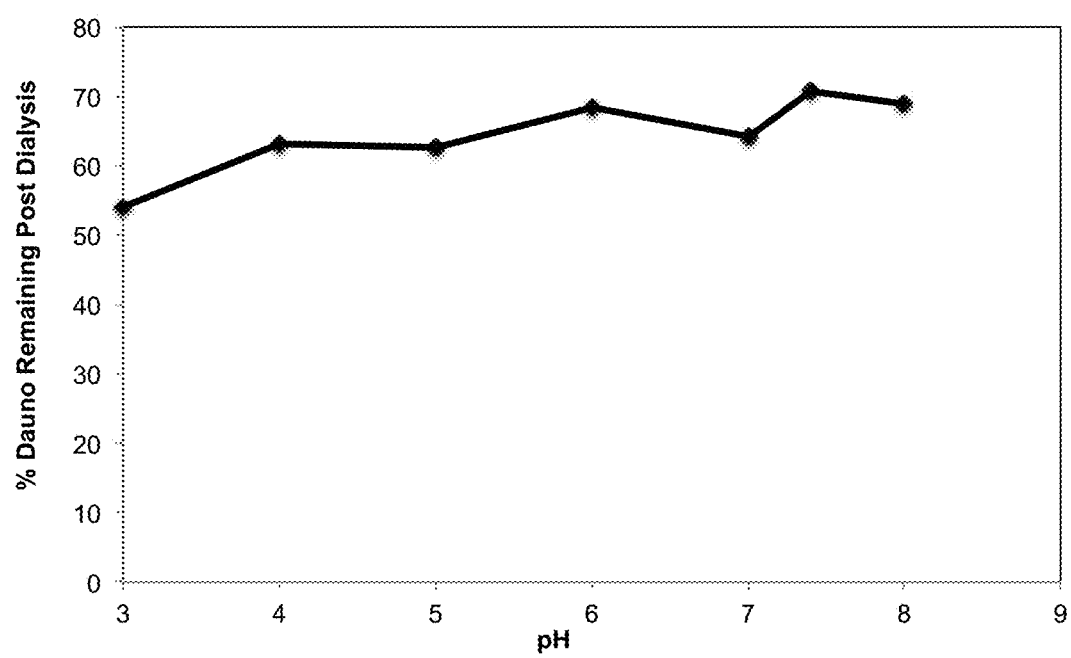
FIG. 8. The uncrosslinked sample was reconstituted at 20 mg/ml and pH adjusted to 3, 4, 5, 6, 7, 7.4 and 8 to determine the pH dependency of iron-mediated crosslinking. The samples were diluted to 0.2 mg/mL and dialyzed against 10 mM phosphate buffer pH 8 for 6 hours.

Optimization of Crosslinking pH—
The daunorubicin loaded micelles of Example 113 were in 10 mM iron (III) chloride at 20 mg/mL then aliquots of this solution adjusted to pH 3, 4, 5, 6, 7, 7.4 and 8 with dilute sodium hydroxide and stirred for 10 minutes. Each sample was then diluted to 0.2 mg/mL and dialyzed against 10 mM phosphate buffer pH 8 for 6 hours. The % daunorubicin remaining post dialysis against 10 mM phosphate buffer pH 8 is shown in FIG. 8. This result demonstrated that the optimal pH for crosslinking is 7.4.

Figure 9:
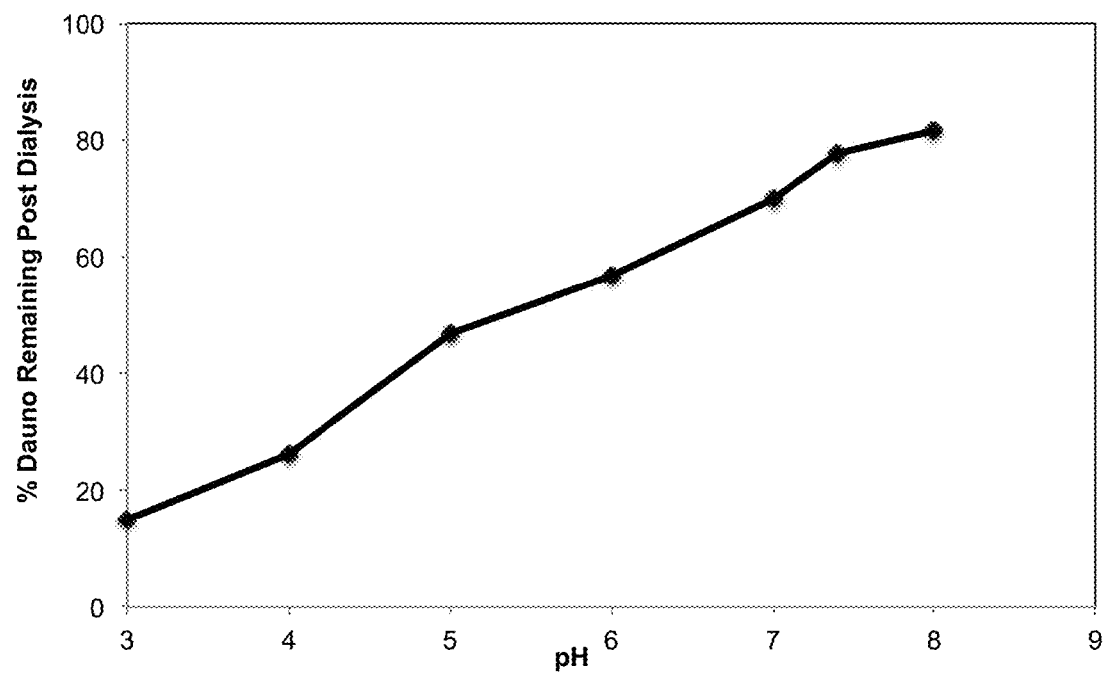
FIG. 9. pH-dependent release of crosslinked daunorubicin formulation dialyzed against 10 mM phosphate buffer pH adjusted to 3, 4, 5, 6, 7, 7.4 and 8 for 6 hours.

Example 117 pH Dependent Release of Daunorubicin from Crosslinked Micelles—
The daunorubicin loaded micelles of Example 113 were in 10 mM iron (III) chloride at 20 mg/mL then adjusted to pH 7.4 with dilute sodium hydroxide and stirred for 10 minutes. This sample was then diluted to 0.2 mg/mL and dialyzed against 10 mM phosphate buffer at pH 3, 4, 5, 6, 7, 7.4 and 8 for 6 hours. The % daunorubicin remaining post dialysis against 10 mM phosphate buffer as a function of pH is shown in FIG. 9. This result demonstrates a pH dependent release of drug from a crosslinked micelle.

Example 118

Figure 10:
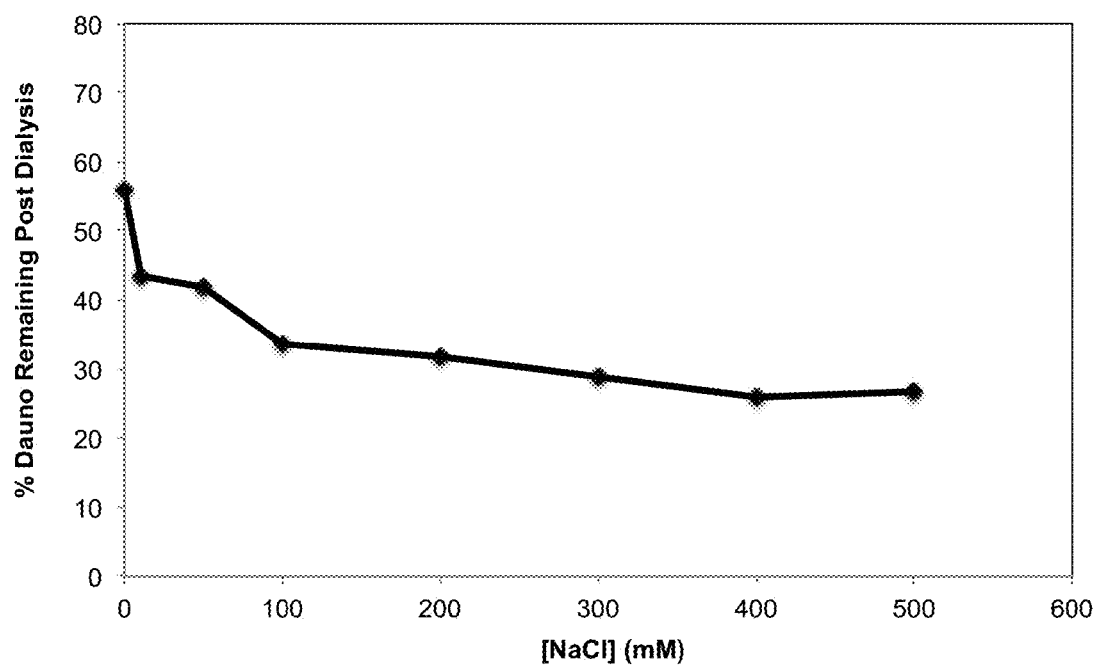
FIG. 10. Salt-dependent release of the crosslinked daunorubicin formulation at 0.2 mg/mL dialyzed against 10 mM phosphate buffer with NaCl concentrations of 0, 10, 50, 100, 200, 300, 400 or 500 mM.

Salt Dependent Release of Daunorubicin from Crosslinked Micelles—
The daunorubicin loaded micelles of Example 113 were in 10 mM iron (III) chloride at 20 mg/mL then adjusted to pH 7.4 with dilute sodium hydroxide and stirred for 10 minutes. Each sample was then diluted to 0.2 mg/mL and dialyzed against 10 mM phosphate buffer at pH 8 with concentrations ranging from 0 to 500 mM NaCl for 6 hours. The % daunorubicin remaining post dialysis against 10 mM phosphate buffer as a function of salt concentration is shown in FIG. 10. This result demonstrates a salt dependent release of drug from a crosslinked micelle.

Example 119

Figure 11:
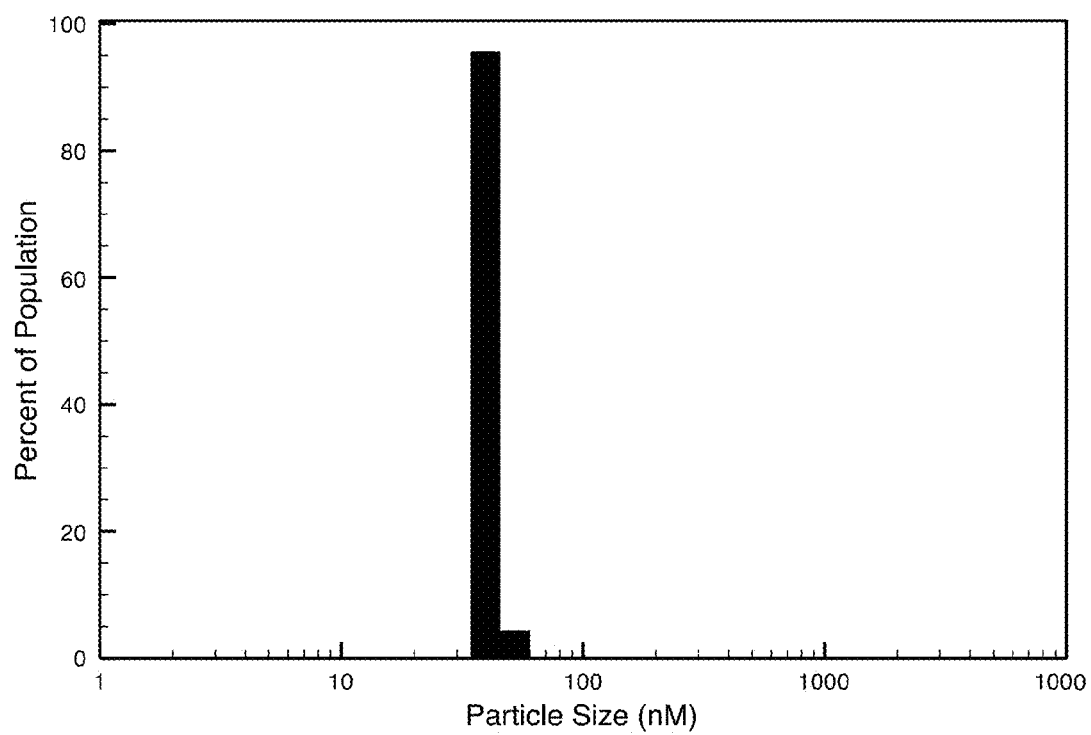
FIG. 11. DLS histogram demonstrating particle size distribution for crosslinked aminopterin formulation.

Encapsulation of Aminopterin—
Triblock copolymer from Example 18 (800 mg) was dissolved in water at 2 mg/mL by stirring at ~50° C. for 30 minutes. The solution was allowed to cool and the pH was adjusted to 7.0 with 0.1 N NaOH. Aminopterin feed for the formulation was 4% of the polymer weight. An organic solution (20% methanol, 80% dichloromethane, 15 mg/mL para-toluenesufonic acid) was used to dissolve 32 mg aminopterin at 3.2 mg/mL by placing the solution in a sonicating water bath followed by heating and vortexing, and repeating until a clear, yellow solution persisted. Once the organic solution cooled it was added to the polymer solution while shear mixing at 10,000 RPM for ~1 minute. The resulting emulsion, which was a turbid, yellow solution, was allowed to stir in a fume hood over night. As the organic solvent evaporated the solution became less turbid and more yellow in color. The next day the solution was pH adjusted to 7.0 with NaOH and filtered through a 0.22 micron, dead end filter. A tangential flow filtration apparatus equipped with a 10 kD cutoff filter was used for diafiltration with a three-fold buffer exchange to remove unencapsulated aminopterin and trace solvents. The formulation was then frozen at −70° C. and lyophilized. Formulation of aminopterin with the triblock copolymer resulted in an 85% yield of product. Weight loading was determined by comparing a standard curve of aminopterin to a known concentration of formulation by HPLC analysis. Aminopterin was dissolved in HPLC mobile phase (60% acetonitrile, 40% 10 mM phosphate buffer pH 8) in a range from 40 µg/mL to 200 g/mL, and the formulation was dissolved at 5 mg/mL in HPLC mobile phase. The amount of aminopterin in the formulation is then converted to % based on the known quantity of formulation used (i.e. 5 mg/mL). The aminopterin-loaded micelle was found to have a loading of 2.5% weight loading from a 4% feed, resulting in a 53% efficient process. Particle size of the uncrosslinked formulation demonstrated a single distribution average particle size of approximately 70 nm, as shown in FIG. 11.

Example 120

Figure 12:
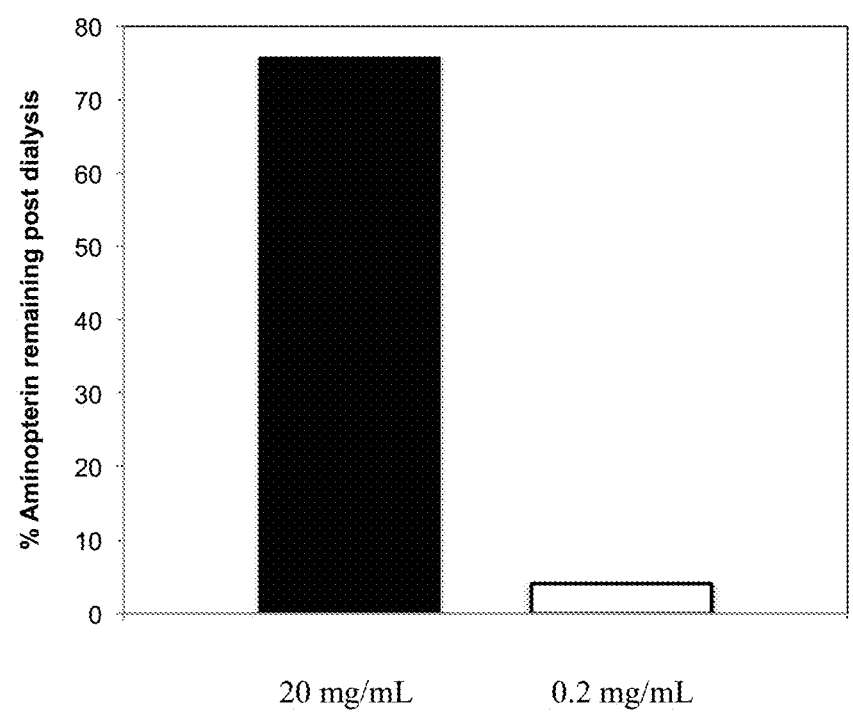
FIG. 12. Verification of encapsulation by dialysis of the formulation above (20 mg/mL, black bar) and below (0.2 mg/mL, white bar) the CMC.

Verification of Aminopterin Encapsulation—
The aminopterin loaded micelles from Example 119 was dissolved at 20 mg/mL in 10 mM phosphate buffer pH 8. The uncrosslinked formulation was also diluted below the CMC (0.2 mg/mL) and dialyzed against 10 mM phosphate buffer pH 8 for six hours. The histogram shown in FIG. 12 demonstrates the stability of the uncrosslinked formulation at 20 mg/mL, with greater than 75% of the aminopterin remaining inside the dialysis bag over 6 hours. However, when diluted to 0.2 mg/mL, less than 10% of the aminopterin was left in the dialysis bag after 6 hours. This result shows that the aminopterin is effectively encapsulated in the micelle at high concentrations (above the CMC) and that the micelle falls apart when diluted below the CMC.

Figure 13:
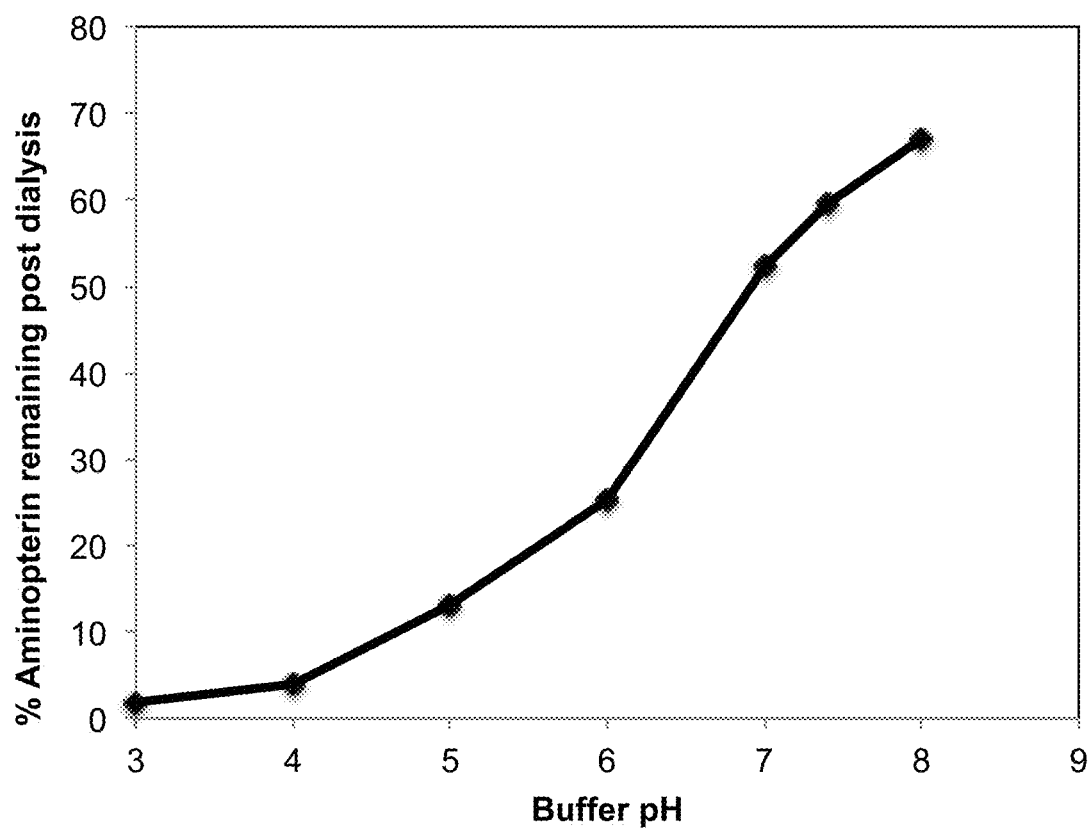
FIG. 13. Verification of crosslinking and pH-dependent release of aminopterin formulation at 0.2 mg/mL by dialysis in 10 mM phosphate buffer over 6 hours.

Example 121 pH Dependent Release of Aminopterin from Crosslinked Micelles—
The aminopterin loaded micelles from Example 119 was dissolved at 20 mg/mL in 10 mM iron (III) chloride and stirred for 10 minutes. This sample was then diluted to 0.2 mg/mL and dialyzed against 10 mM phosphate buffer at pH 3, 4, 5, 6, 7, 7.4 and 8 for 6 hours. The % aminopterin remaining post dialysis against 10 mM phosphate buffer as a function of pH is shown in FIG. 13. This result demonstrates a pH dependent release of aminopterin from a crosslinked micelle.

Example 122

Figure 14:
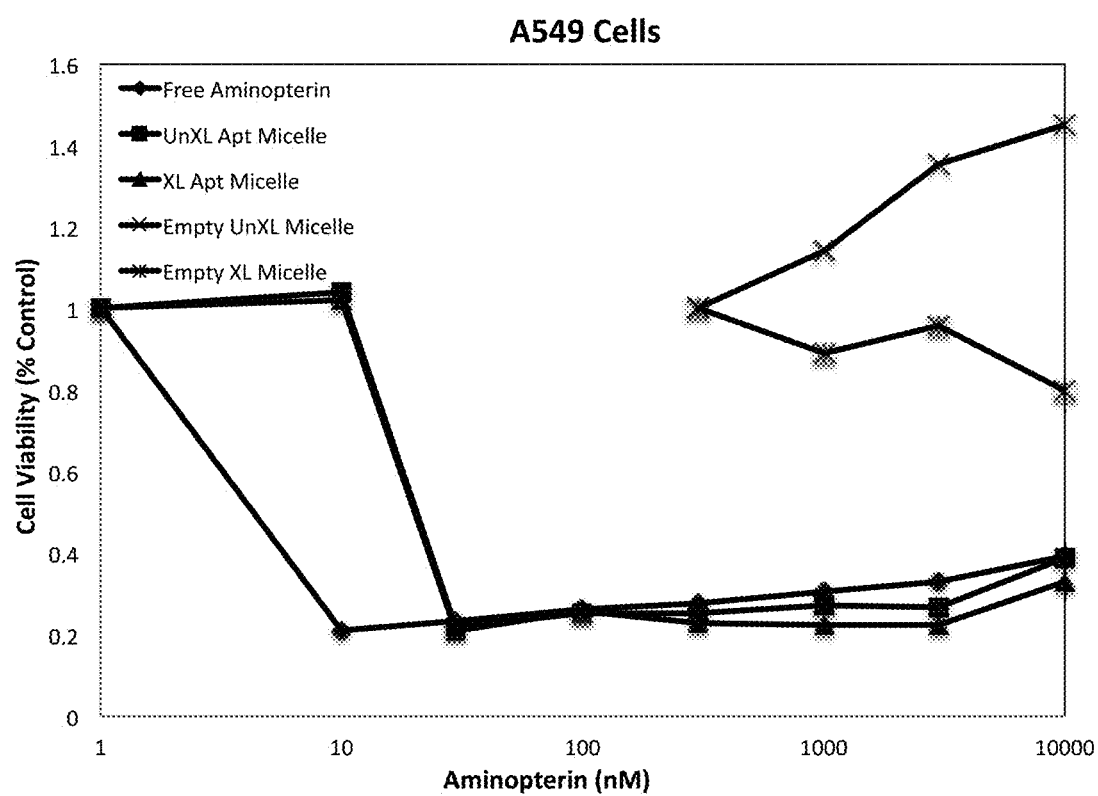
FIG. 14. Cell viability for A549 lung cancer cells treated with free aminopterin, uncrosslinked aminopterin formulation, crosslinked aminopterin formulation, uncrosslinked empty micelle vehicle and crosslinked empty micelle vehicle.
Figure 15:
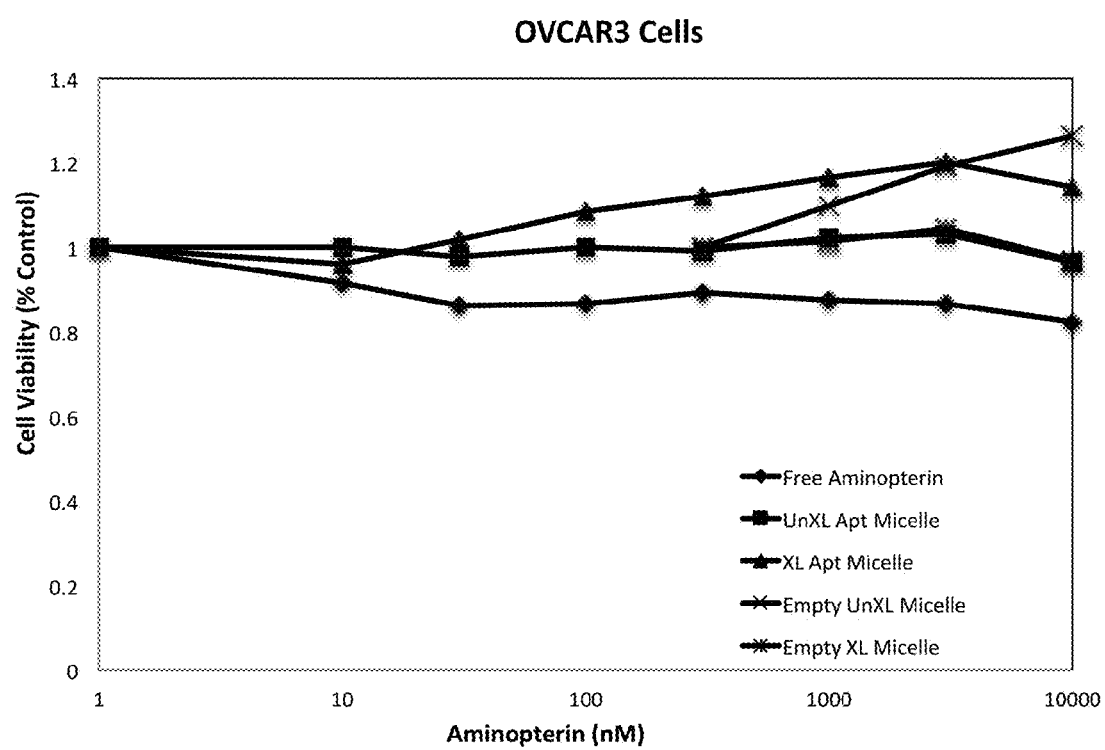
FIG. 15. Cell viability for OVCAR3 ovarian cancer cells treated with free aminopterin, uncrosslinked aminopterin formulation, crosslinked aminopterin formulation, uncrosslinked empty micelle vehicle and crosslinked empty micelle vehicle.
Figure 16:
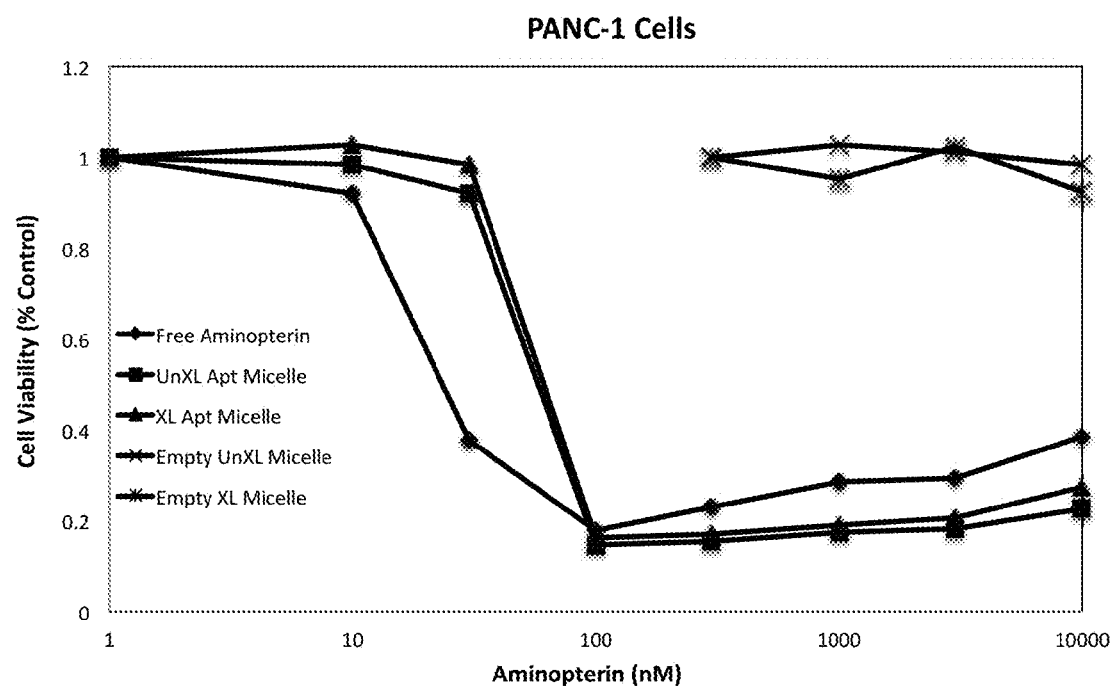
FIG. 16. Cell viability for PANC-1 pancreatic (folate receptor +) cancer cells treated with free aminopterin, uncrosslinked aminopterin formulation, crosslinked aminopterin formulation, uncrosslinked empty micelle vehicle and crosslinked empty micelle vehicle.
Figure 17:
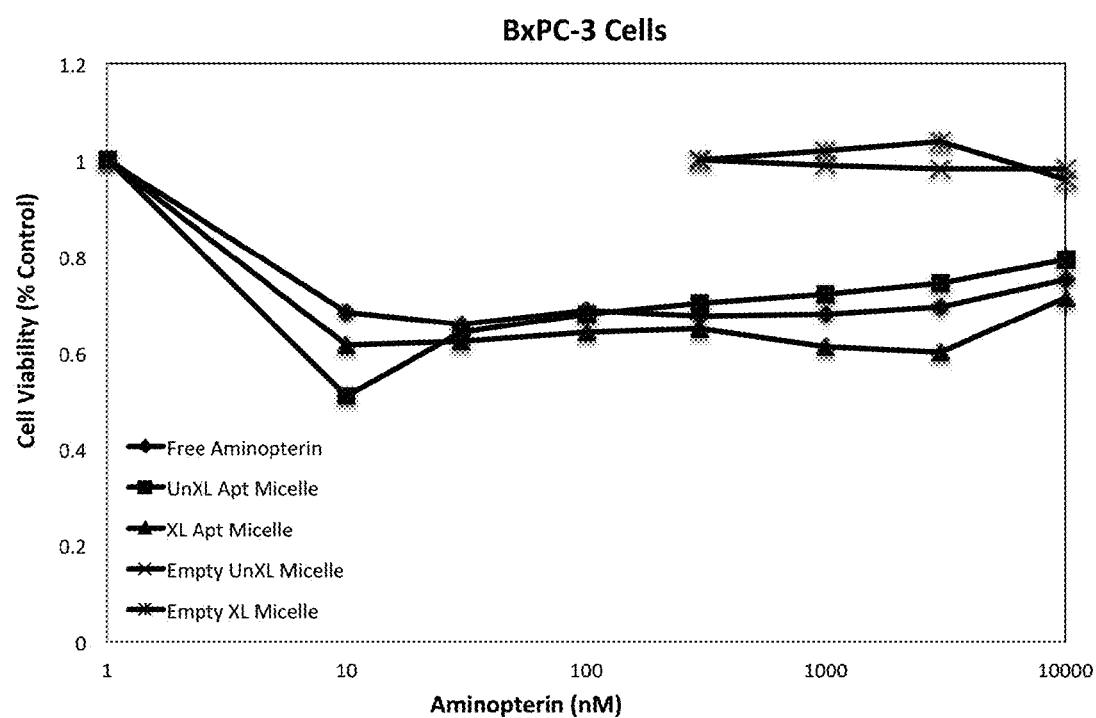
FIG. 17. Cell viability for BxPC3 pancreatic (folate receptor −) cancer cells treated with free aminopterin, uncrosslinked aminopterin formulation, crosslinked aminopterin formulation, uncrosslinked empty micelle vehicle and crosslinked empty micelle vehicle.

Cytotoxicity of Aminopterin Loaded Crosslinked Micelles—
The aminopterin loaded micelles from Example 119 and Example 121 were tested for cytotoxicity compared to free aminopterin and the crosslinked and uncrosslinked non drug-loaded micelle formulations (from polymer of Example 18) against A549 lung, OVCAR3 ovarian, PANC-1 (folate receptor +) pancreatic and BxPC3 (folate receptor −) pancreatic cancer cell lines. The cytotoxicity profiles for each treatment for each cell line in FIG. 14 (A549 Lung), FIG. 15 (OVCAR3 Ovarian), FIG. 16 (PANC-1 Pancreatic), and FIG. 17 (BxPC3 pancreatic). Aminopterin inhibited cell viability by 50% ($IC_{50}$) in the low nanomolar range (~7-25 nM) in A549 and PANC-1 cells, however no $IC_{50}$ was obtained for OVCAR3 or BxPC3 cells. Likewise, the uncrosslinked and crosslinked formulations demonstrated $IC_{50}$ values in the low nanomolar range (~20-70 nM) for A549 and PANC-1 cells without reaching 50% inhibition in OVCAR3 or BxPC3 cells. Treatment with both uncrosslinked and crosslinked non drug-loaded micelles was well tolerated, with greater than 80% viability for all cells tested.

Example 123

Encapsulation of Berberine—

Triblock copolymer from Example 18 (300 mg) was dissolved in water at 2 mg/mL by stirring at ~50° C. for 10 minutes. The solution was allowed to cool and the pH was adjusted to 7.0 with 0.1 N NaOH. Berberine feed rate for the formulation was 5% of the polymer weight. An organic solution (20% methanol, 80% dichloromethane) was used to dissolve 15 mg berberine at 6 mg/mL by vortexing until a clear, yellow solution persisted. The organic solution was then added to the polymer solution while shear mixing at 10,000 RPM for ~1 minute. The resulting emulsion, which was a turbid, yellow solution, was allowed to stir in a fume hood over night. As the organic solvent evaporated the solution became less turbid and more yellow in color. The next day the solution was filtered through a 0.22 micron, dead end filter. A tangential flow filtration apparatus equipped with a 10 kD cutoff filter was used to concentrate the sample from 200 mL to approximately 50 mL. The formulation was then frozen at −70° C. and lyophilized. Weight loading was determined by comparing a standard curve of berberine to a known concentration of formulation by HPLC analysis. Berberine was dissolved in methanol in a range from 40 µg/mL to 200 µg/mL, and the formulation was dissolved at 5 mg/mL in methanol. The amount of berberine in the formulation was then converted to % based on the known quantity of formulation used (i.e. 5 mg/mL). Weight loading of the berberine formulation was 4% from a 5% feed, as determined by HPLC analysis of the formulation compared to a standard curve of the free drug. Encapsulation efficiency of the formulation was 72%. Particle size analysis by dynamic light scattering resulted in an average particle size of 72.5 nm for the uncrosslinked sample. Encapsulation dialysis resulted in 53% retention, demonstrating that berberine is effectively encapsulated in the micelle.

Example 124

Crosslinking of the Berberine Loaded Micelle—

The lyophilized uncrosslinked powder from Example 123 was reconstituted in water at 20 mg/mL. Iron (III) chloride was added to the solution for a final concentration of 5 mM, and stirred for ~30 minutes. The formulation was then frozen at −70° C. and lyophilized. To verify crosslinking the uncrosslinked and crosslinked samples were diluted to 0.2 mg/mL and dialyzed for 6 hours. The uncrosslinked micelle showed 5% of the berberine retained, while the crosslinked sample showed 43% berberine remaining. This result demonstrates that the berberine micelle is stabilized by the addition of iron.

Example 125

Encapsulation of Paclitaxel—

Triblock copolymer from Example 18 (300 mg) was dissolved in water at 2 mg/mL by stirring at ~50° C. for 10 minutes. The solution was allowed to cool and the pH was adjusted to 7.0 with 0.1 N NaOH. Paclitaxel feed rate for the formulation was 1% of the polymer weight. An organic solution (20% methanol, 80% dichloromethane) was used to dissolve 3 mg paclitaxel at 3 mg/mL by vortexing until a clear, colorless solution persisted. The organic solution was then added to the polymer solution while shear mixing at 10,000 RPM for ~1 minute. The resulting emulsion was allowed to stir in a fume hood over night. The next day the solution was filtered through a 0.22 micron, dead end filter. The formulation was then frozen at −70° C. and lyophilized. Weight loading of the paclitaxel formulation was 0.78% from a 1% feed, as determined by HPLC analysis of the formulation compared to a standard curve of the free drug. Particle size analysis by dynamic light scattering resulted in an average particle size of 45.7 nm for the uncrosslinked sample. Encapsulation verification dialysis above the critical micelle concentration (20 mg/mL) resulted in 52% retention of the paclitaxel post dialysis.

Example 126

Encapsulation of SN-38—

Triblock copolymer from Example 18 (1 g) was dissolved at 5 mg/mL in water by stirring at ~50° C. for 10 minutes. Sucrose (1 g) was then added to the polymer solution and stirred until fully dissolved. The solution was allowed to cool to room temperature and pH adjusted to 6.0 with 0.1 N NaOH. SN-38 feed for the formulation was 3% of the polymer weight. DMSO was used to dissolve 30 mg SN-38 at 80 mg/mL by heating, vortexing and placing the solution in a sonicating water bath until a clear, yellow solution persisted. The organic solution was allowed to cool to room temperature and was then added to the polymer solution while shear mixing at 10,000 RPM for ~1 minute. The resulting emulsion, which was a turbid, light yellow solution, was then transferred to the feed chamber of a microfluidizer. The solution was processed with a single pass through a Microfluidics M110Y microfluidizer. The microfluidizer outlet stream was cooled with an ice water bath. The solution was then filtered through a 0.22 micron deadend filter, and the resulting solution was then subjected to ultrafiltration with a Spectrum Labs KrosFlo tangential flow filtration system and a 10 kDa diafiltration membrane. The solution was concentrated from 200 mL to ~50 mL, then 150 mL of water with 3 mg/mL sucrose was added and concentrated back down to ~50 mL. The ultrafiltration was repeated until a total of 4-times the original volume of buffer was exchanged (800 mL). The resulting solution was then frozen at −70° C. and lyophilized.

Example 127

Crosslinking of SN-38 Micelle—

SN-38 micelles from Example 126 were dissolved at 20 mg/mL in aqueous 10 mM $FeCl_3$. The pH was then adjusted to 6.8 with dilute NaOH. The solution was stirred for 1 h at room temperature then lyophilized. This crosslinked, SN-38 loaded micelle was isolated as brownish powder with a weight loading of 1.75%, representing a 81.4% efficient process. Particle size analysis by dynamic light scattering resulted in an average diameter of 70 nm.

Example 128

Preparation and Crosslinking SN-38 Micelles—

Formulations were done with the following polymers: 128A=mPEG12k-b-p[Glu(NHOH)$_2$]-b-p[Phe$_{15}$-co-Tyr$_{25}$]-Ac (SEQ ID NO: 4), from Example 81; 128B=mPEG12k-b-p[Glu(NHOH)$_7$]-b-p[Phe$_{15}$-co-Tyr$_{25}$]-Ac (SEQ ID NO: 5)

from Example 56; 128C=mPEG12k-b-p[Glu(NHOH)$_{10}$]-b-p[Phe$_{15}$-co-Tyr$_{25}$]-Ac (SEQ ID NO: 6), from Example 38; 128D=mPEG12k-b-p[Glu(NHOH)$_{20}$]-b-p[Phe$_{15}$-co-Tyr$_{25}$]-Ac (SEQ ID NO: 7) from Example 98; and 128E=mPEG12k-b-p[Asp$_{10}$]-b-p[Leu$_{20}$-co-Tyr$_{20}$]-Ac (SEQ ID NO: 8) from Example 112. Triblock copolymer (1 g) was dissolved at 5 mg/mL in water by stirring at ~40° C. for 30 minutes. 1 g of sucrose was then added to the polymer solution and stirred until fully dissolved. The solution was allowed to cool to room temperature and pH adjusted to 6.0 with NaOH. SN38 feed rate for the formulation was 5% of the polymer weight. DMSO was used to dissolve 50 mg SN-38 at 80 mg/mL by heating, vortexing and placing the solution in a sonicating water bath until a clear, yellow solution persisted. The organic solution was allowed to cool to room temperature and was then added to the polymer solution while shear mixing at 10,000 RPM for ~1 minute. The resulting emulsion, which was a turbid, light yellow solution, was then transferred to the feed chamber of a microfluidizer. The solution was processed with a single pass through the microfluidizer. The microfluidizer outlet stream was cooled with an ice water bath. The solution was then filtered through a 0.22 micron dead-end filter, and the resulting solution was then subjected to ultrafiltration with a Spectrum Labs KrosFlo tangential flow filtration system and a 10 kDa diafiltration membrane. The solution was concentrated from 200 mL to ~50 mL, then 150 mL of water with 5 mg/mL sucrose was added and concentrated back down to ~50 mL. The ultrafiltration was repeated until a total of 4-times the original volume of buffer was exchanged (800 mL). Iron (III) Chloride was then added to the formulation for a final concentration of 10 mM. The pH of the solution was then adjusted to 6.0 with NaOH and stirred at room temperature for 4 hours. One volume of buffer containing sucrose at 20 mg/mL was then added to the solution, and then concentrated back down to approximately 20 mg/mL polymer concentration. The solution was then frozen at −40 degrees Celsius and lyophilized. Formulations of SN-38 with triblock copolymers resulted in an average yield of 85% of product with a weight loading of 3.5%. Actual weight loadings: A=3.4%, B=3.2%, C=3.6%, D=3.6%, E=3.2%. Particle size analysis by dynamic light scattering resulted in an average diameter of 90 nm. Actual particle sizes: A=84 nm B=88 nm, C=89 nm, D=110 nm, E=91 nm.

Example 129

Parmacokinetics of Crosslinked SN-38 Micelles—

Figure 18:
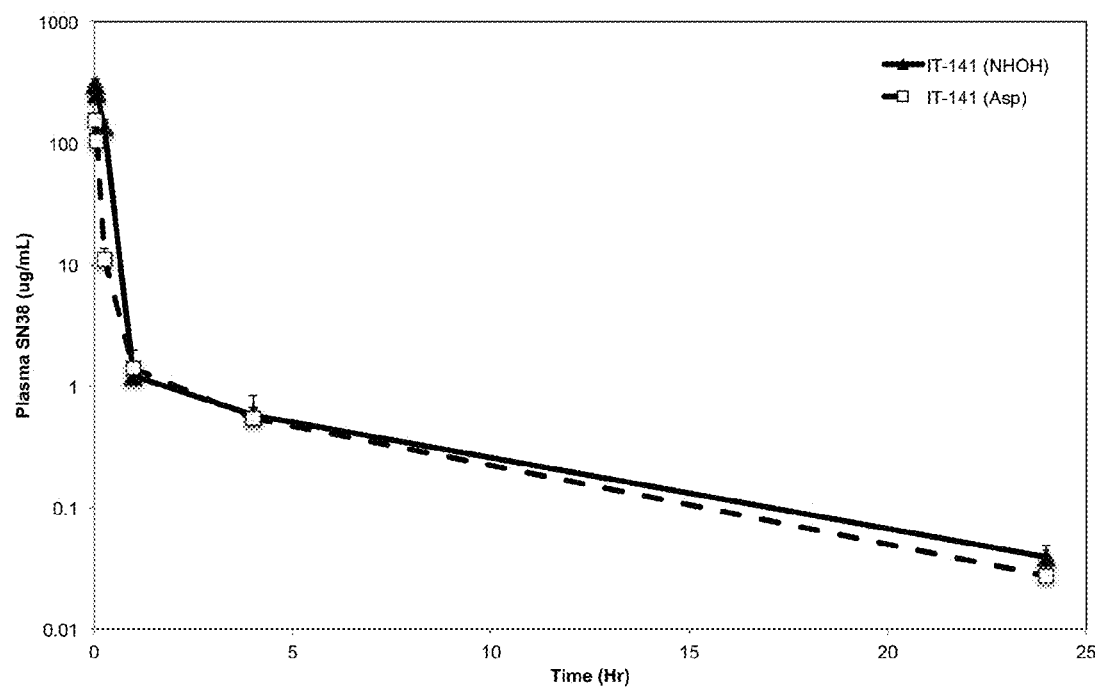
FIG. 18. Concentration of SN-38 in the plasma compartment of rats from IT-141 (NHOH; 127C) formulation compared to IT-141 (Asp; 127E) formulation at 10 mg/kg.

Sprague-Dawly rats surgically modified with jugular vein catheters were purchased from Harlan Laboratories, Dublin, Va. SN-38 crosslinked formulations (From Example 128C and 128E) were dissolved in water with 150 mM NaCl for a final concentration of 10 mg SN-38 per kg animal body weight for 2 mL bolus injection via JVC over approximately 1 minute, followed by a flush of approximately 250 µL heparinized saline. Time points for blood collection following test article administration were as followed: 1, 5, 15 minutes, 1, 4, and 24 hours. Approximately 250 µL of blood per time point was collected by JVC into K3-EDTA blood collection tubes followed by a flush of approximately 200 µL heparinized saline. Blood was then centrifuged at 2000 RPM for 5 minutes to isolate plasma. Plasma was then collected and snap frozen until processed for HPLC analysis. Samples were prepared for analysis by first thawing the plasma samples at room temperature. 50 µL plasma was added to a 2 mL eppendorf tube 150 µL of extraction solution (0.1% phosphoric acid in methanol, 5 µg/mL camp-tothecin internal standard). Samples were then vortexed for 10 minutes and centrifuged for 10 minutes at 13,000 RPM. Supernatant was then transferred into HPLC vials then analyzed by HPLC. Quantitation of SN-38 was determined using a standard curve of SN-38 formulation in rat plasma compared to samples collected from rats at each time point. The results of this experiment are shown in FIG. 18. The CMax of SN-38 in the plasma from IT-141 (NHOH; 128C) was 304.5 µg/mL, determined 1 minute post administration. The exposure of SN-38 to the plasma compartment delivered by the hyrdoxyamic acid formulation was 111.5 µg*h/mL. The exposure of SN-38 to the plasma compartment from IT-141 (Asp; 127E) was 31.6 µg*h/mL, with a CMax of 156.0 µg/mL.

Example 130

Figure 19:
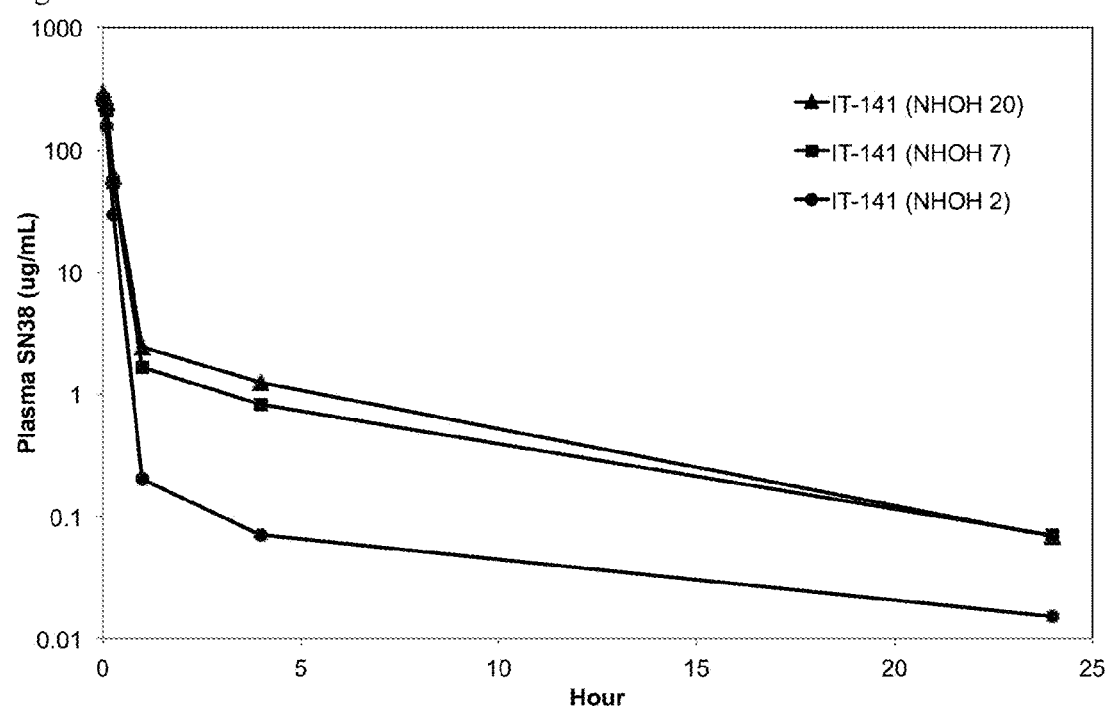
FIG. 19. Rat pharmacokinetics of SN-38 formulations.

Determination of Optimal Crosslinking Block Length Determined by Rat Pharmacokinetics Using the procedure of Example 129, Formulations of Examples 128A, 128B, and 128D were administered to rats at 10 mg/kg. The CMax of SN-38 in the plasma from Example 128D (NHOH-20) was 292.9 µg/mL, determined 1 minute post administration. The exposure of SN-38 to the plasma compartment as determined by the area under the concentration versus time curve delivered by the formulation was 85.7 µg*h/mL. The exposure of SN-38 to the plasma compartment from Example 128B(NHOH-7) was 71.3 µg*h/mL, with a CMax of 256.9 µg/mL determined at 1 minute post administration. The CMax of SN-38 in the plasma from Example 128A (NHOH-2) was 267.7 µg/mL, determined 1 minute post administration. The exposure of SN38 to the plasma compartment as determined by the area under the concentration versus time curve delivered by the formulation was 41.8 µg*h/mL. The results are shown in FIG. 19. It was determined that Example 128C demonstrated the optimal crosslinking results.

Example 131

Preparation of Daunorubicin Loaded Micelles

Triblock copolymer from Example 112 (Aspartic acid core block) and water (2 L) was added to a 4 L beaker and stirred until a homogeneous solution was present. Daunorubicin hydrochloride (301 mg) was suspended in 4:1 dichloromethane:methanol (60 mL), followed by the addition of triethylamine (82 uL). The resulting daunorubicin suspension was added dropwise to the rapidly stirring aqueous solution. The resulting solution was covered with foil and allowed to stir for an additional eight hours. The solution was filtered through a 0.22 µm filter and then lyophilized to give 2.95 g (89% yield) as a red powder. A portion of this material was dissolved at 25 mg/mL polymer concentration in 20 mM Tris, pH 7.5 supplemented with 5 mM FeCl$_3$. Once a homogeneous solution was present, the pH was adjusted to 8.0 with 1 N NaOH, then stirred overnight. The solution was frozen and lyophilized to give a dark red powder.

Example 132

Preparation of Aminopterin Micelles

Triblock copolymer from Example 30 mPEG12k-b-p[Glu(NHOH)10]-b-p[Asp5-co-Leu15-co-Tyr20]-Ac (SEQ ID NO: 9) (800 mg) was dissolved in water at 2 mg/mL by stirring at ~40° C. for 30 minutes. The solution was allowed to cool and the pH was adjusted to 7.0 with NaOH. Aminopterin feed rate for the formulation was 4% of the polymer weight. An organic solution (20% methanol, 80% dichloromethane, 25 mg/mL para-toluenesufonic acid) was used to dissolve 32 mg aminopterin at 3.2 mg/mL by placing the solution in a sonicating water bath followed by heating and vortexing, and repeating until a clear, yellow solution persisted. Once the organic solution cooled it was added to the polymer solution while shear mixing at 10,000 RPM for ~1 minute. The resulting emulsion, which was a turbid, yellow solution, was allowed to stir in a fume hood over night. As the organic solvent evaporated the solution became less turbid and more yellow in color. The next day the solution was pH adjusted to 7.0 with NaOH and filtered through a 0.22 micron dead-end filter, and the resulting solution was then subjected to ultrafiltration with a Spectrum Labs Kros-Flo tangential flow filtration system and a 10 kDa diafiltration membrane. The solution was concentrated from 2 mg/mL polymer concentration to approximately 20 mg/mL polymer concentration, and Iron (III) Chloride was added to the formulation for a final concentration of 10 mM. The pH of the solution was then adjusted to 7.0 with NaOH and stirred at room temperature for 4 hours. The solution was then adjusted to 5 mg/mL polymer concentration with water, and concentrated to approximately 20 mg/mL by ultrafiltration. The solution was then frozen at −40 degrees Celsius and lyophilized. Formulation of aminopterin with the triblock copolymer resulted in an 85% yield of product with a 2.5% weight loading from a 4% feed, resulting in a 53% efficient process. Particle size of the uncrosslinked and crosslinked formulations demonstrated a single distribution average particle size of approximately 70 nm.

Example 133

Preparation of Cabizataxel Micelles

Figure 20:
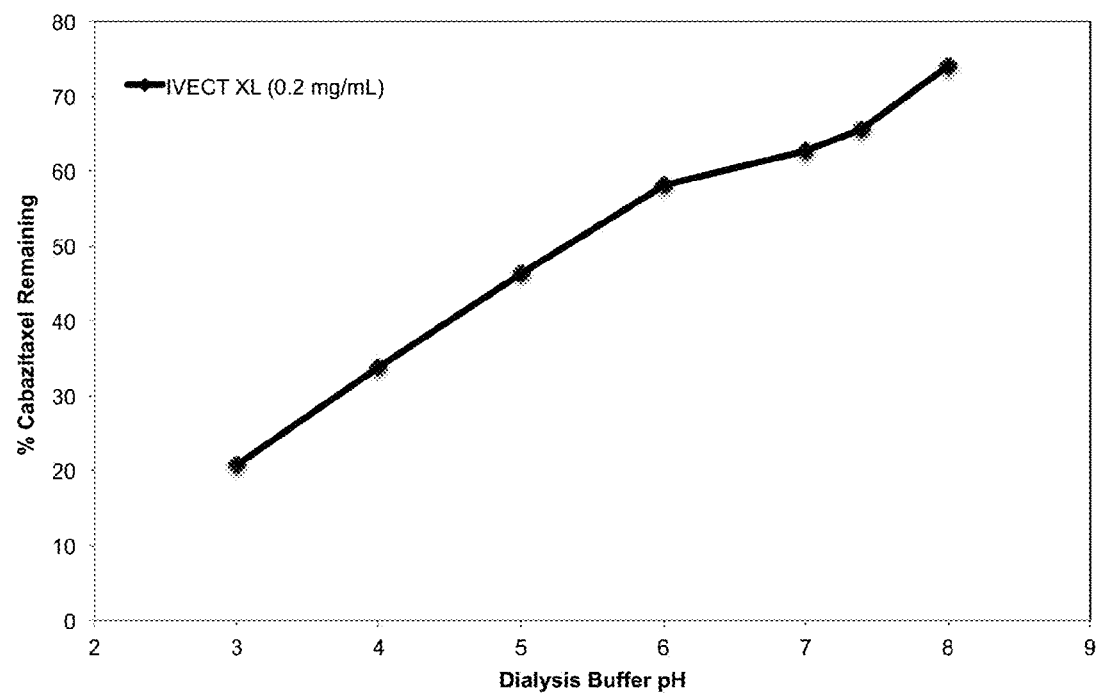
FIG. 20. pH-dependent release of crosslinked cabizataxel formulation dialyzed against 10 mM phosphate buffer pH adjusted to 3, 4, 5, 6, 7, 7.4 and 8 for 6 hours.

Triblock copolymer from Example 38 mPEG12k-b-p[Glu(NHOH)10]-b-p[Phe15-co-Tyr25]-Ac (SEQ ID NO: 6) (300 mg) was dissolved in water at 2 mg/mL by stirring at ~40 degrees Celsius for 30 minutes. The solution was allowed to cool and the pH was adjusted to 7.0 with NaOH. Cabazitaxel feed rate for the formulation was 1.5% of the polymer weight. An organic solution (20% methanol, 80% dichloromethane) was used to dissolve 4.5 mg cabazitaxel at 2 mg/mL by vortexing until a clear, colorless solution persisted. The organic solution was then added to the polymer solution while shear mixing at 10,000 RPM for ~1 minute. The resulting emulsion was allowed to stir in a fume hood over night. The next day the solution was filtered through a 0.22 micron dead end filter, and the resulting solution was then subjected to ultrafiltration with a Spectrum Labs Kros-Flo tangential flow filtration system and a 10 kDa diafiltration membrane. The solution was concentrated from 2 mg/mL polymer concentration to approximately 20 mg/mL polymer concentration, and Iron (III) Chloride was added to the formulation for a final concentration of 10 mM. The pH of the solution was then adjusted to 7.0 with NaOH and stirred at room temperature for 4 hours. The solution was then adjusted to 5 mg/mL polymer concentration with water, and concentrated to approximately 20 mg/mL by ultrafiltration. The solution was then frozen at ~40 degrees Celsius and lyophilized. Weight loading for the cabazitaxel formulation was 1% from a 1.5% feed. Particle size of the formulation was 62 nm in diameter. Encapsulation dialysis of the uncrosslinked formulation resulted 68% retention above the CMC at 20 mg/mL, and 72% retention when the crosslinked formulation was diluted to 0.2 mg/mL. FIG. 20 shows the results of the pH dependent crosslinking dialysis for crosslinked Cabizataxel micelles.

Example 134

Preparation of Epothilone D Micelles

Triblock copolymer from Example 98 mPEG12k-b-p[Glu(NHOH)20]-b-p[Phe15-co-Tyr25]-Ac (SEQ ID NO: 7) (300 mg) was dissolved in water at 2 mg/mL by stirring at ~40 degrees Celsius for 30 minutes. The solution was allowed to cool and the pH was adjusted to 7.0 with NaOH. Epothilone D feed rate for the formulation was 2% of the polymer weight. An organic solution (20% methanol, 80% dichloromethane) was used to dissolve 6 mg epothilone D at 2 mg/mL by vortexing until a clear, colorless solution persisted. The organic solution was then added to the polymer solution while shear mixing at 10,000 RPM for ~1 minute. The resulting emulsion was allowed to stir in a fume hood over night. The next day the solution was filtered through a 0.22 micron dead end filter, and the resulting solution was then subjected to ultrafiltration with a Spectrum Labs Kros-Flo tangential flow filtration system and a 10 kDa diafiltration membrane. The solution was concentrated from 2 mg/mL polymer concentration to approximately 20 mg/mL polymer concentration, and Iron (III) Chloride was added to the formulation for a final concentration of 10 mM. The pH of the solution was then adjusted to 6.0 with NaOH and stirred at room temperature for 4 hours. The solution was then adjusted to 5 mg/mL polymer concentration with water, and concentrated to approximately 20 mg/mL by ultrafiltration. The solution was then frozen at −40 degrees Celsius and lyophilized. This process resulted in a 71% efficient process with a weight loading of 1.5% from a 2% feed and an overall yield of 94%. The particle size of the formulation was 82 nm in diameter. Encapsulation dialysis of the uncrosslinked formulation resulted in 88% retention of epothilone D over 6 hours at 20 mg/mL, while dilution to 0.2 mg/mL resulted in 10% retention of the drug over 6 hours.

Example 135

Preparation of Berberine Micelles

Triblock copolymer from Example 98 mPEG12k-b-p[Glu(NHOH)10]-b-p[Asp5-co-Leu15-co-Tyr20]-Ac (SEQ ID NO: 9) (300 mg) was dissolved in water at 2 mg/mL by stirring at ~40 degrees Celsius for 30 minutes. The solution was allowed to cool and the pH was adjusted to 7.0 with 0.1 N NaOH. Berberine feed rate for the formulation was 5% of the polymer weight. An organic solution (20% methanol, 80% dichloromethane) was used to dissolve 15 mg berberine at 6 mg/mL by vortexing until a clear, yellow solution persisted. The organic solution was then added to the polymer solution while shear mixing at 10,000 RPM for ~1 minute. The resulting emulsion, which was a turbid, yellow solution, was allowed to stir in a fume hood over night. As the organic solvent evaporated the solution became less turbid and more yellow in color. The next day the solution was filtered through a 0.22 micron dead-end filter, and the resulting solution was then subjected to ultrafiltration with a Spectrum Labs KrosFlo tangential flow filtration system and a 10 kDa diafiltration membrane. The solution was concentrated from 2 mg/mL polymer concentration to approximately 20 mg/mL polymer concentration, and Iron (III) Chloride was added to the formulation for a final concentration of 10 mM. The pH of the solution was then adjusted to 7.0 with NaOH and stirred at room temperature for 4 hours. The solution was then adjusted to 5 mg/mL polymer concentration with water, and concentrated to approximately 20 mg/mL by ultrafiltration. The solution was then frozen at ~40 degrees Celsius and lyophilized. Weight loading of the berberine formulation was 4% from a 5% feed, as determined by HPLC analysis of the formulation compared to a standard curve of the free drug. Encapsulation efficiency of the formulation was 72%. Particle size analysis by dynamic light scattering resulted in an average particle size of 66.7 nm in diameter for the crosslinked sample, and 72.5 nm for the uncrosslinked sample.

Example 136

Preparation of Vinorelbine Micelles

Triblock copolymer from Example 38 (300 mg) was dissolved in water at 2 mg/mL by stirring at ~40 degrees Celsius for 30 minutes. The solution was allowed to cool and the pH was adjusted to 7.0 with 0.1 N NaOH. Vinorelbine feed rate for the formulation was 5% of the polymer weight. An organic solution (20% methanol, 80% dichloromethane) was used to dissolve 15 mg vinorelbine at 6 mg/mL by vortexing until a clear, colorless solution persisted. The organic solution was then added to the polymer solution while shear mixing at 10,000 RPM for ~1 minute. The resulting emulsion, which was a turbid solution, was allowed to stir in a fume hood over night. As the organic solvent evaporated the solution became less turbid and colorless. The next day the solution was filtered through a 0.22 micron dead-end filter, and the resulting solution was then subjected to ultrafiltration with a Spectrum Labs Kros-Flo tangential flow filtration system and a 10 kDa diafiltration membrane. The solution was concentrated from 2 mg/mL polymer concentration to approximately 20 mg/mL polymer concentration, and Iron (III) Chloride was added to the formulation for a final concentration of 10 mM. The pH of the solution was then adjusted to 7.0 with NaOH and stirred at room temperature for 4 hours. The solution was then adjusted to 5 mg/mL polymer concentration with water, and concentrated to approximately 20 mg/mL by ultrafiltration. The solution was then frozen at −40 degrees Celsius and lyophilized.

Example 137

Preparation of Everolimus Micelles

Triblock copolymer from Example 38 (300 mg) was dissolved in water at 2 mg/mL by stirring at ~40 degrees Celsius for 30 minutes. The solution was allowed to cool and the pH was adjusted to 7.0 with 0.1 N NaOH. Everolimus feed rate for the formulation was 5% of the polymer weight. An organic solution (20% methanol, 80% dichloromethane) was used to dissolve 15 mg everolmus at 6 mg/mL by vortexing until a clear, colorless solution persisted. The organic solution was then added to the polymer solution while shear mixing at 10,000 RPM for ~1 minute. The resulting emulsion, which was a turbid solution, was allowed to stir in a fume hood over night. As the organic solvent evaporated the solution became less turbid and colorless. The next day the solution was filtered through a 0.22 micron dead-end filter, and the resulting solution was then subjected to ultrafiltration with a Spectrum Labs Kros-Flo tangential flow filtration system and a 10 kDa diafiltration membrane. The solution was concentrated from 2 mg/mL polymer concentration to approximately 20 mg/mL polymer concentration, and Iron (III) Chloride was added to the formulation for a final concentration of 10 mM. The pH of the solution was then adjusted to 7.0 with NaOH and stirred at room temperature for 4 hours. The solution was then adjusted to 5 mg/mL polymer concentration with water, and concentrated to approximately 20 mg/mL by ultrafiltration. The solution was then frozen at −40 degrees Celsius and lyophilized.

Example 138

Rat Pharmacokinetics of Daunorubicin Micelles Compared to Free Daunorubicin

Figure 21:
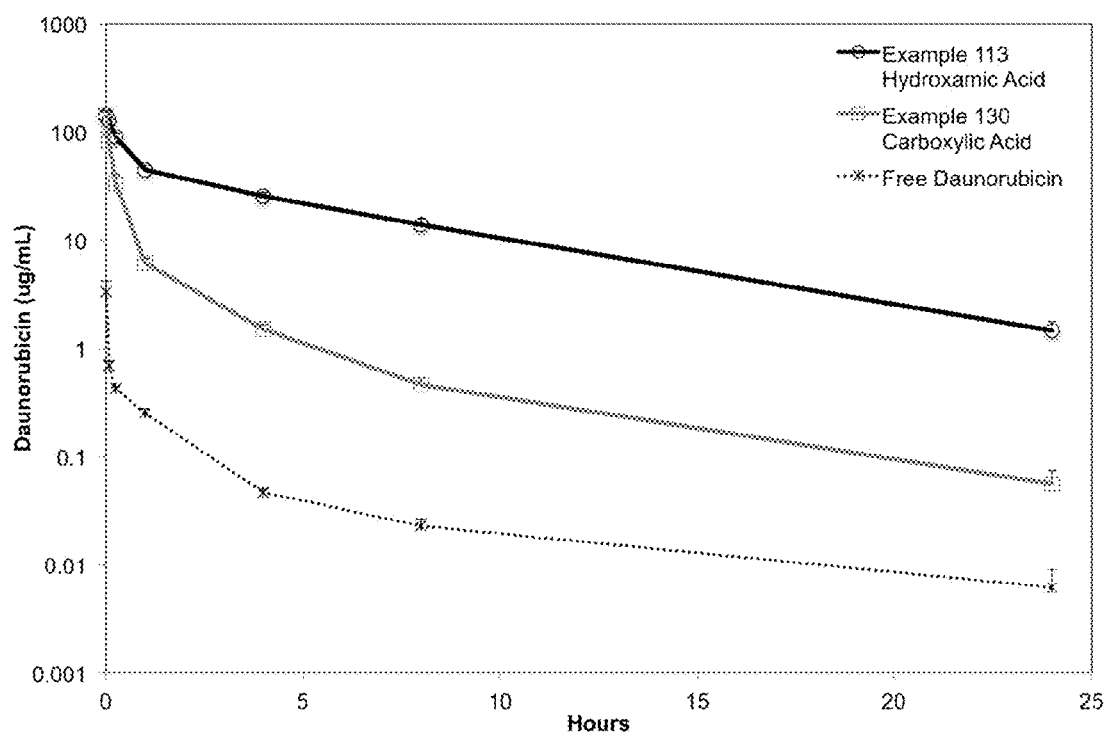
FIG. 21. Pharmacokinetics free daunorubicin and daunorubicin formulations in rats.

Fisher rats that possessed a jugular vein catheter were injected with 10 mg/kg of free daunorubicin, crosslinked (hydroxamic acid) daunorubicin micelle (prepared according to Example 113), and carboxylic acid crosslinked daunorubicin loaded micelles (prepared according to Example 130) by a fast IV bolus with an injection volume of 2 mL. The delivery vehicle for drug administration was isotonic saline. Rat blood was collected from the catheter into $K_2$-EDTA tubes by heart puncture at time points of 1, minute, 5 minutes, 15 minutes, 1 hour, 4 hours, 8 hours and 24 hours. Plasma was isolated by centrifugation at 1000 RPM for 5 minutes, and 150 uL of extraction solution (ice cold methanol/100 ng/mL daunorubicin internal standard) was added to 50 uL of each plasma sample. Samples were then vortexed for 10 minutes, centrifuged at 13,000 RPM for 10 minutes, and 150 uL of the supernatant is transferred to HPLC vials for analysis. Samples were analyzed on a Waters Alliance 2695 equipped with a 2475 fluorescence detector (Ex=470 nm; Em=580). A 5 μL sample injection was made onto a Waters 4 μm Nova Pak C18 (3.9×150 mm) at 30° C. with a flow rate of 0.750 mL per minute of 10 mM phosphate buffer (pH=1.4), methanol and acetonitrile (gradient from 70/10/20 to 40/10/50 for buffer/methanol/acetonitrile was made over eight minutes). Analyte eluted at 5.9 minutes under these conditions, was normalized to the internal standard, and quantitated using a standard curve comprised of seven standards. The pharmacokinetic parameters are summarized in the table below and the curves are shown in FIG. 21. The exposure of daunorubicin to the plasma compartment as determined by the area under the concentration versus time curve (AUC) delivered by the hydroxamic acid formulation was 383.6 g*h/mL. The terminal (elimination) half-life of daunorubicin delivered to the plasma by the formulation was 3.9 hours. This is compared to the free drug that showed an AUC of 1.3 g*h/mL and a half life of 3.4 hours as well as the carboxylic acid formulation that showed an AUC of 51.8 g*h/mL and a half life of 2.4 hours. Therefore, the carboxylic acid crosslinked formulations had an exposure of 40 times higher than free drug, and the hydroxamic acid formulation had an exposure of 295 times better than the free drug.

| Sample | AUC (μg*h/mL) | CMax (μg/mL) | Half-life (h) |
|---|---|---|---|
| Hydroxamic Acid Formulation from Example 113 | 383.6 | 144.0 | 3.9 |
| Carboxylic Acid Formulation from Example 130 | 51.8 | 143.5 | 2.4 |
| Free Daunorubicin | 1.3 | 3.3 | 3.3 |

Example 139

Rat Pharmacokinetics of Crosslinked Cabizataxel Micelles

Figure 22:
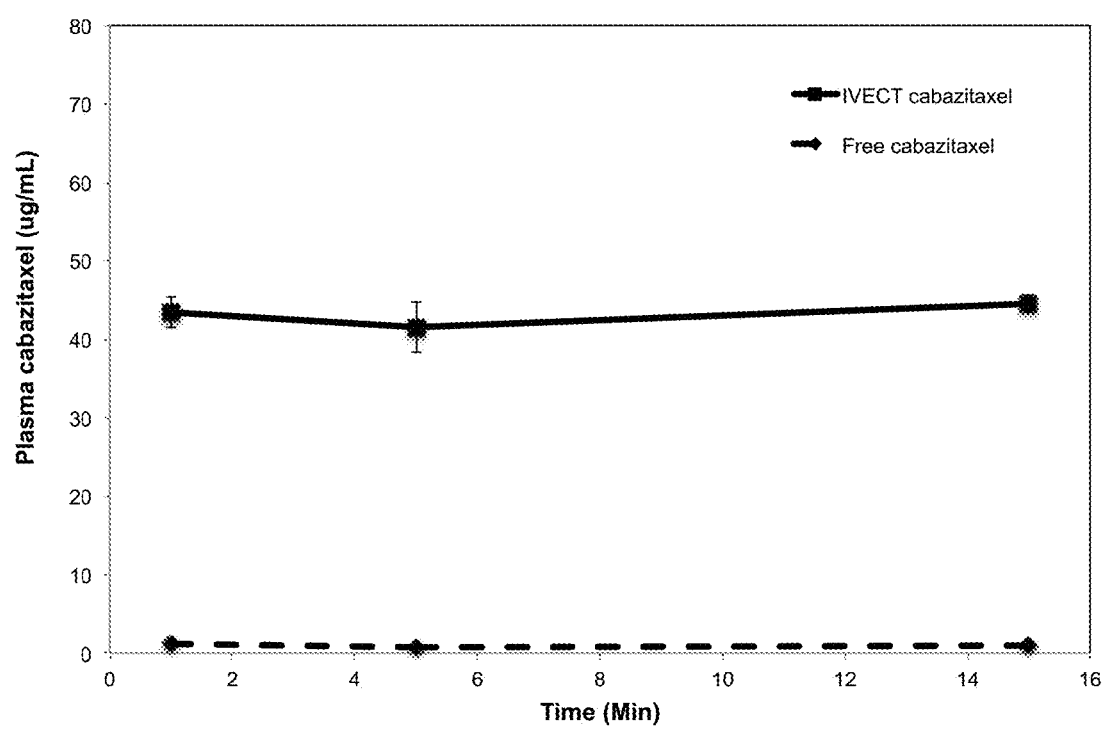
FIG. 22. Rat plasma levels of cabizataxel following administration of crosslinked cabizataxel formulation and free cabizataxel.

Fisher rats that possessed a jugular vein catheter were injected with 5 mg/kg of free cabizataxel or crosslinked cabizataxel micelle (prepared according to Example 132) by a fast IV bolus with an injection volume of 2 mL. The delivery vehicle for drug administration was isotonic saline. Rat blood was collected from the catheter into $K_2$-EDTA tubes by heart puncture at time points of 1, minute, 5 minutes, and 15 minutes. Plasma was isolated by centrifugation at 1000 RPM for 5 minutes, and 150 uL of extraction solution was added to 50 uL of each plasma sample. Samples were then vortexed for 10 minutes, centrifuged at 13,000 RPM for 10 minutes, and 150 uL of the supernatant is transferred to HPLC vials for analysis. FIG. 22 demonstrates the concentration of cabazitaxel in the rat plasma for the first 15 minutes after test article administration. The exposure of cabazitaxel to the plasma compartment over 15 minutes was 10 g*h/mL with a CMax of 44.5 μg/mL, compared to 0.2 g*h/mL exposure for the free drug with a CMax of 1.2 μg/mL.

Example 140

Anti-Tumor Efficacy of SN-38 Micelles

Figure 23:
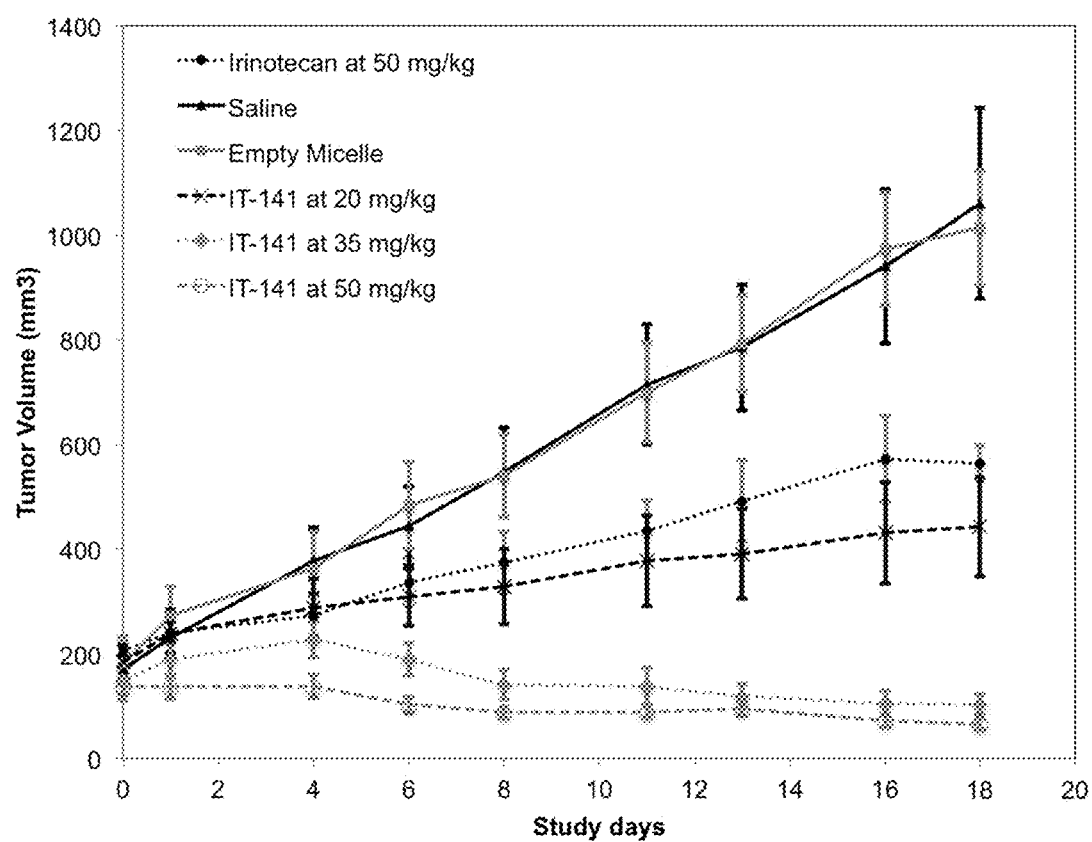
FIG. 23. Anti-tumor efficacy of crosslinked SN-38 formulations in an HCT-116 xenograft model.

HCT-116 colon cancer cells were cultured according to ATCC guidelines, harvested by trypsin incubation, and resuspended at a concentration of 2 million cells per 0.1 mL in saline for injection. Mice were inoculated by injecting 0.1 mL (i.e. 2 million cells) subcutaneously into the right flanks of the mice. When tumors reached approximately 100 mm$^3$ the mice were randomized into treatment groups. Each group consisted of 8 mice per group. Treatment groups included saline control; polymer control; free irinotecan at 35 mg/kg; and SN-38 formulation from Example 127C at 20, 35, and 50 mg/kg. Mice were dosed by a fast IV bolus into the tail vein; the injection volume was 0.2 mL. Tumors were measured by digital caliper, and volume (mm$^3$) was calculated using the formula $V=(W^2 \times L)/2$, where width (W) is the largest diameter measurement and length (L) is the diameter measurement perpendicular to the width. The dosing schedule was once a week for three weeks (3×QW). The vehicle for polymer delivery was isotonic saline. Clinical observations during the study included changes in mouse body weight, morphological observations of sick mouse syndrome (dehydration, spinal curvature, and opportunistic infections of the eyes, genitals, or skin rash), and gross pathological changes determined by necropsies upon termination of the experiment. The graph of the growth rate is shown in FIG. 23. The data showed a 6-fold increase in tumor volume for the saline control group, with a mean growth rate of 46.8 mm$^3$ per day. The polymer control group saw no statistical difference in tumor growth compared to the saline control group, with a 5.5-fold increase in volume and a mean growth rate of 43.7 mm$^3$ per day. The irinotecan at 50 mg/kg free drug control group saw a 40% reduction in tumor volume compared to saline, with a 2.7-fold increase in volume and a mean growth rate of 18.9 mm$^3$ per day. The 20 mg/kg SN-38 formulation group saw a 71% inhibition in tumor volume compared to saline control and a mean growth rate of 13.6 mm$^3$ per day. The 35 mg/kg SN-38 formulation group saw 30% regression in tumor volume with a 1.5 fold decrease in size and a mean tumor regression rate of −2.4 mm$^3$ per day. The 50 mg/kg SN-38 formulation group saw 47.6% regression in tumor volume with a 2.1 fold decrease in size and a mean tumor regression rate of −3.8 mm$^3$ per day.

Example 141

Pharmacokinetics and Biodistribution of Crosslinked Aminopterin Micelles

Figure 24:
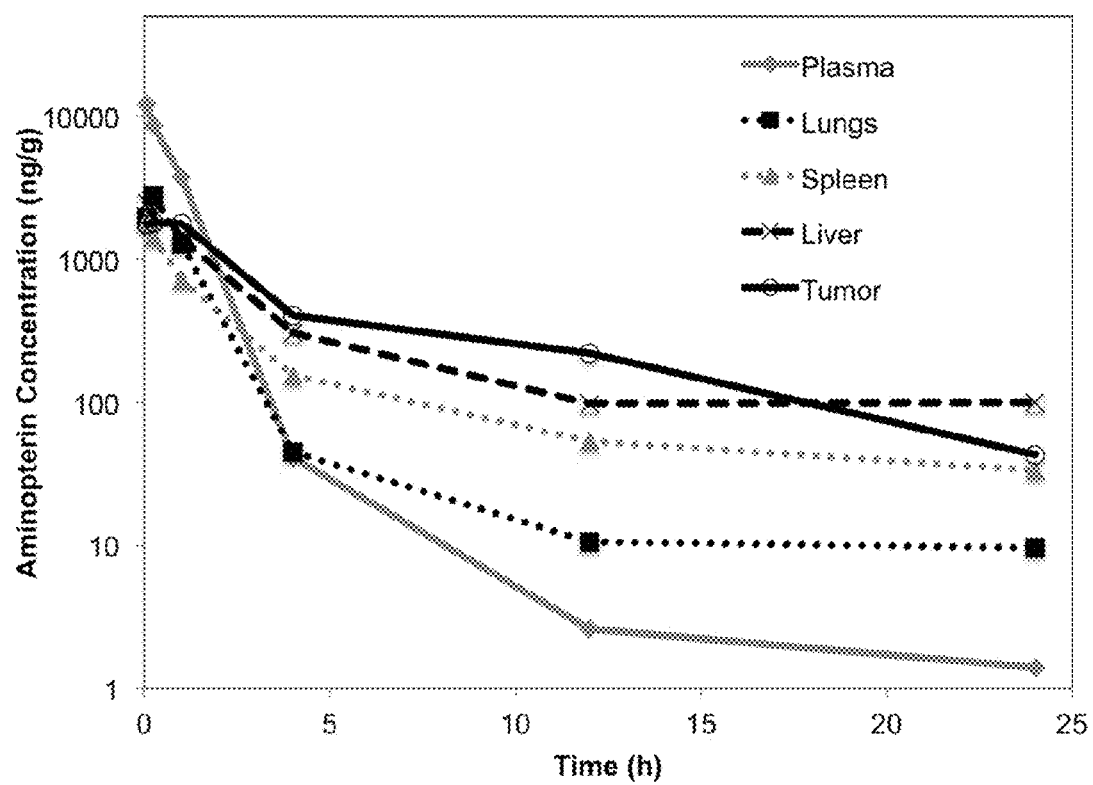
FIG. 24. Biodistribution of aminopterin from crosslinked aminopterin formulations in an OVCAR-3 xenograft model.

Female athymic nude mice were supplied by Harlan (Indianapolis, Ind.). Mice were received at 4-5 weeks of age, 12-15 g in weight. The mice were housed in microisolator and maintained under specific pathogen-free conditions. Study Female mice were inoculated subcutaneously in the right flank with 0.1 ml of a 50% RPMI/50% Matrigel™ (BD Biosciences, Bedford, Mass.) mixture containing a suspension of OVCAR-3 tumor cells (approximately 5.0×106 cells/mouse). Tumors were measured using calipers and tumor weight was calculated using the formula $V=(W^2 \times L)/2$, where width (W) is the largest diameter measurement and length (L) is the diameter measurement perpendicular to the width. Study start days were staggered by group due to varying growth patterns in the tumors. Animals were administered test material, aminopertin micelles from Example 131 at 20 mg/kg, once tumor volume reached 150-250 mm$^3$. Upon euthanization of each mouse at 5 and 15 minutes, 1, 4, 12, 24, and 48 hours after treatment (4 mice per timepoint), plasma, tumor, spleen, liver and lung specimens were collected. Heparinized mouse plasma and tissue samples (liver, lung, spleen and tumor) were analyzed using a high pressure liquid chromatography assay with tandem mass spectral detection (LC-MS/MS). Calibrator and quality control (QC) samples were prepared by spiking aminopterin into sodium heparinized human plasma. Tissue samples were homogenized in 50% methanol and stored frozen at −80° C. until analyzed. Each study matrix type was analyzed in a separate analytical batch along with duplicate calibration and QC samples. A 100 μl aliquot of the calibrator, QC, blank, or study sample (plasma or tissue homogenate) was mixed with 50.0 uL of dilution buffer (1.0 mM ammonium formate containing 0.1% formic acid) followed by 400 μL of acetonitrile containing the internal standard (IS; methotrexate 50.0 ng/ml) in a microcentrifuge tube to precipitate proteins. The tubes were capped, vortexed, allowed to digest for 5 minutes, and centrifuged at 14,000 rpm and 4° C. for 5 minutes. A 100 uL aliquot of the supernatant was diluted with 1.5 mL of dilution buffer, vortex mixed, and 20 uL injected into the LC-MS/MS system. The concentration of each sample was determined by comparison to a standard curve. Concentration-time curves for each compartment were constructed and pharmacokinetic data calculated for each compartment. The mean plasma and tissue PK profiles can be seen in FIG. 24. Plasma NCA determined the mean half-life of Aminopterin to be 37.65 hours. The mean AUC0-48 hr in plasma was found to be 12571 ng*hr/ml. The mean half-life of Aminopterin in tumor, lungs and spleen was determined to be 9.65, 11153 and 51.87 hours, respectively. The terminal slope of the liver concentrations did not allow for a half-life calculation since at 48 hours the concentration was higher than at 12 and 24 hours. The mean AUC0-48 hr of tumor, lungs, spleen and liver was found to be 9559, 4276, 4586, and 9909 ng*hr/g, respectively.

Example 142

Anti-Tumor Efficacy of Crosslinked Aminopterin Micelles

Figure 25:
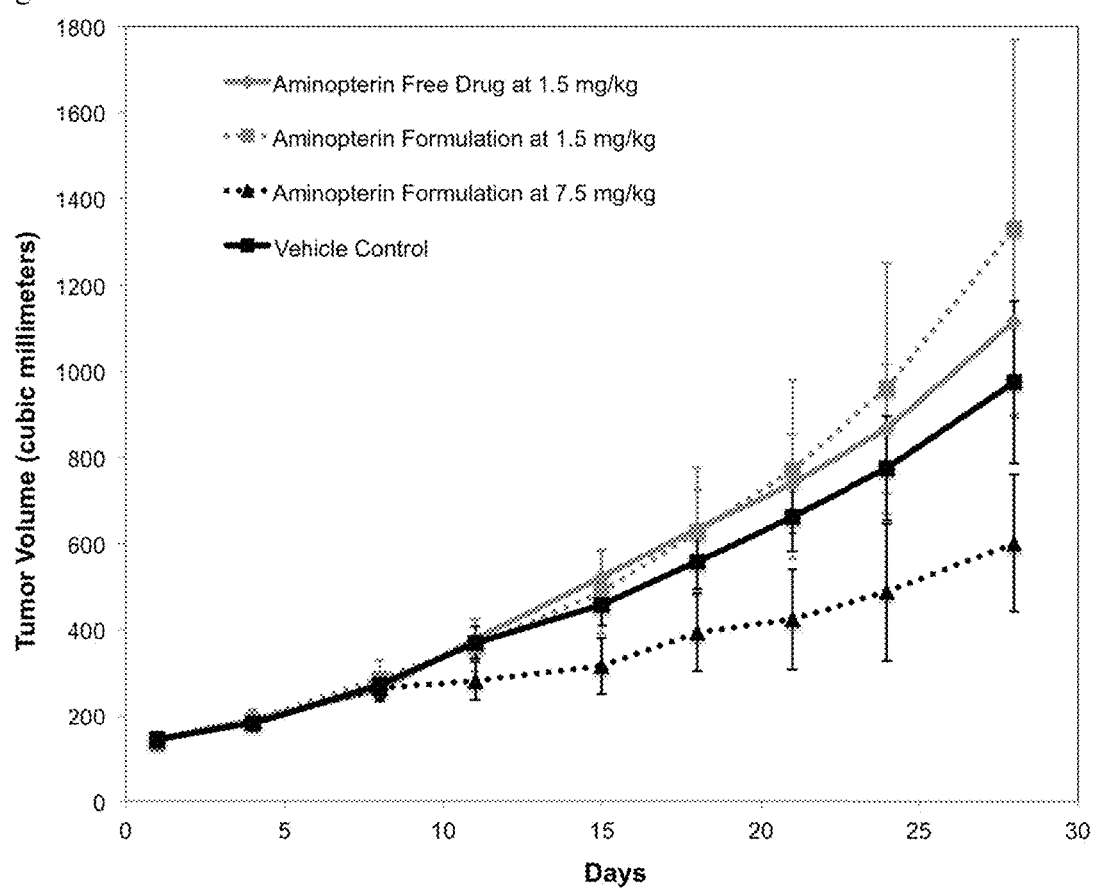
FIG. 25. Anti-tumor efficacy of crosslinked aminopterin formulations in an MFE-296 xenograft model.

The MFE-296 human endometrial tumor cell line was received from and cultured according to ATCC. Female athymic NCR nude mice (CrTac:NCr-Foxn1nu) were supplied by Taconic. Female athymic nude mice were inoculated subcutaneously in the right flank with 0.1 ml of a 50% RPMI 1640/50% Matrigel™ (BD Biosciences, Bedford, Mass.) mixture containing a suspension of MFE-296 tumor cells (approximately $1 \times 10^7$ cells/mouse). Twenty days following inoculation, tumors were measured using calipers and tumor weight was calculated using the formula $V=(W^2 \times L)/2$, where width (W) is the largest diameter measurement and length (L) is the diameter measurement perpendicular to the width. Fifty mice with tumor sizes of 80-257 mm³ were randomized into five groups of ten mice each with a mean of approximately 143 mm³ by random equilibration. Body weights were recorded when the mice were randomized and were taken twice per week thereafter in conjunction with tumor measurements. Treatment groups included polymer control, free aminopterin at 1.5 mg/kg, aminopterin micelles from Example 132 at 1.5 mg/kg and 7.5 mg/kg. Treatments were performed on Day 1, 8, and 15, or once a week for three weeks (3×QW) by tail vein intravenous administration. Injections were 0.2 mL and the vehicle was isotonic saline. The graph of the tumor growth for each group is shown in FIG. 25. The polymer control group reached a mean tumor weight of 973.9 mg by Day 28. This group experienced no appreciable body weight loss during the study. No adverse dosing reactions were observed. Treatment with aminopterin formulation at 1.5 mg/kg resulted in a mean tumor weight of 1330.4 mg by Day 28. This group produced no reportable inhibition when compared to the vehicle control on Day 28. This group experienced no appreciable body weight loss during the study. No adverse dosing reactions were observed. Treatment with aminopterin formulation 7.5 mg/kg resulted in a mean tumor weight of 599.7 mg by Day 28. This group produced an inhibition of 44.8% when compared to the vehicle control on Day 28. This group experienced mild body weight loss with a maximum of 4.3% on Day 4. Body weights were fully recovered by Day 15. No adverse dosing reactions were observed. Treatment with free aminopterin 1.5 mg/kg resulted in a mean tumor weight of 1115.1 mg by Day 28. This group produced no reportable inhibition when compared to the vehicle control on Day 28. No significant difference in tumor weight was observed when compared to the vehicle control on Day 28. This group experienced no appreciable body weight loss during the study.

Example 143

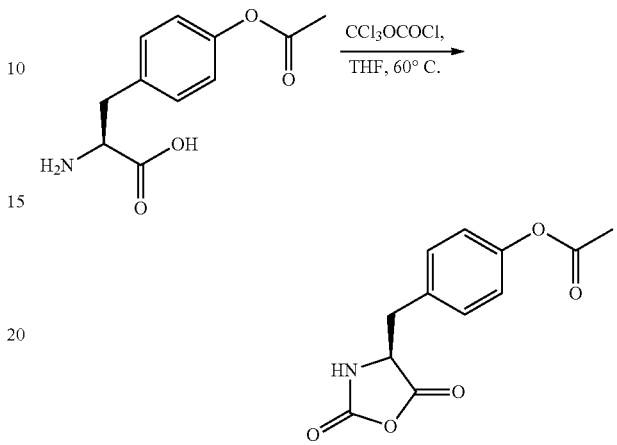

Synthesis of Acetyl Tyrosine NCA

H-Tyr(OAc)—OH (97.0 g, 0.435 mol) was suspended in 1320 mL of anhydrous THF. Diphosgene (86.06 g, 0.435 mol, 52.5 mL) was added to the amino acid suspension at room temperature and after ten minutes, the mixture was heated to 60° C. under a nitrogen blanket. The amino acid dissolved over the course of approx. 2 hr, forming a clear solution. The solution was slightly cooled and concentrated on the rotovap. Fresh anhydrous THF (700 mL) was added to the residue and the solution was re-evaporated on the rotovap to give a light tan solid, which was dissolved in 700 mL anhydrous THF, transferred to a 4 µL beaker, and precipitated by the slow addition of 2.0 µL of anhydrous heptane. The pure NCA was isolated by suction filtration, washed with two 500 mL portions of heptane, and dried in vacuo. 101.9 g (94.0% yield) of Tyr(OAc) NCA was isolated as a pale creamed-colored, fluffy solid. $^1$H NMR (CDCl$_3$) δ 7.25 (2H), 7.06 (2H), 6.34 (1H), 4.50 (1H), 3.27 (2H), 2.96 (2H), 2.30 (3H).

Example 144

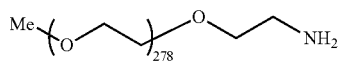

1. Toluene, 60° C., azeotrope in vacuo
2. Glu(OBn)NCA, d-Glu(OBn)NCA, CH$_2$Cl$_2$, DMAC, RT, 18 hr
3. d-PheNCA, Tyr(OAc)NCA, RT -> 35° C.
4. Ac$_2$O (10 eq.), NMM (11 eq.), DMAP (1 eq.), RT, ON
5. Evapn, ppt'n. from IPA (7x), then slurry in IPA (10x)

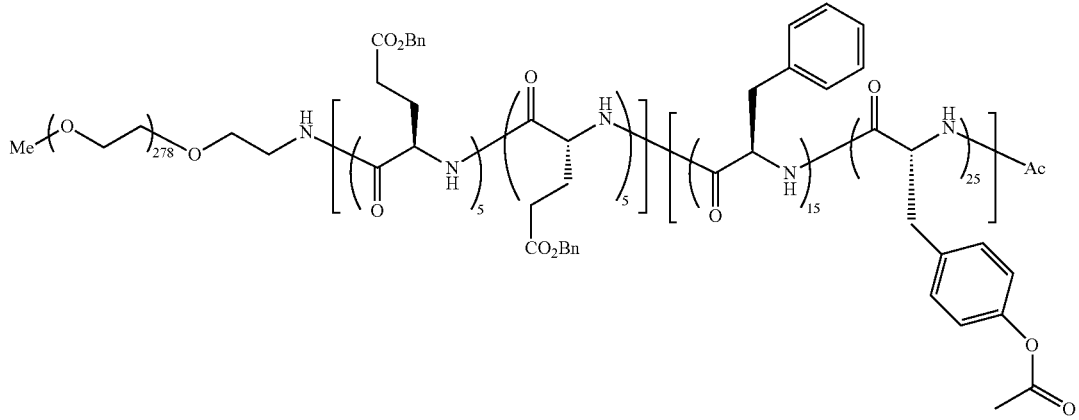

Synthesis of mPEG12.3K-b-Poly-(d-Glu(OBn)$_5$-Co-Glu(OBn)$_5$)-b-Poly-(d-Phe$_{15}$-Co-Tyr(OAc)$_{25}$)-Ac from mPEG12.3KNH$_2$ Free Base mPEG12.3k-NH$_2$, (61.36 g, 5.0 mmol) was weighed into an oven-dried, 500 mL-round-bottom flask, dissolved in toluene (500 mL), and dried by azeotropic distillation. After distillation to dryness, the polymer was left under high vacuum for three hours. The flask was subsequently back-filled with N$_2$, re-evacuated under reduced pressure, and dry dichloromethane (380 mL) and N,N-dimethylacetamide (DMAC, 190 mL) were introduced by cannula. Glu(OBn) NCA (6.58 g, 25.0 mmol) and d-Glu(OBn) NCA (6.58 g, 25.0 mmol) were added to the flask, and the reaction mixture was allowed to stir for 18 hours at ambient room temperature under a nitrogen blanket. GPC analysis (DMF/0.1% LiBr) of an aliquot indicated complete consumption of the NCAs. Then, d-Phe NCA (14.34 g, 75.0 mmol) and Tyr (OAc) NCA (31.15 g, 125.0 mmol) were added. The solution was stirred at room temperature for 2 hours and then heated to 35° C. over the weekend, at which point the reaction was deemed complete (GPC, DMF/0.1% LiBr). The solution was cooled to room temperature and acetic anhydride (5.11 g, 50.0 mmol, 4.73 mL), N-methylmorpholine (NMM, 5.56 g, 55.0 mmol, 6.05 mL) and N,N-dimethylaminopyridine (DMAP) (611 mg, 5.0 mmole) were added. Stirring was continued for 20 hours at room temperature. The dichloromethane was removed on the rotovap and the resultant viscous solution (343 gm) was transferred to a 4 L beaker. Isopropanol (IPA, 2 L) was added with vigorous mechanical stirring and the solid slurry was stirred for one hour. The product was collected by suction filtration, washed with IPA (300 mL), IPA, MTBE: 1,1 (300 mL) and partially dried. The product was transferred to a 2 L beaker and slurried with IPA (1.1 L) for two hours, filtered, and the solid was washed with IPA, MTBE: 1,1 (2×500 mL) and dried in vacuo to give the title compound as a fine, pale cream-colored solid (102.8 g, Yield=94.1%). $^1$H NMR (d$_6$-DMSO) δ 8.51-7.85 (theo. 50H, obs'd. 49H), 7.40-6.75 (theo. 225H, obs'd. 225H), 5.05 (theo. 20H, obs'd. 20H), 4.70-4.15 (theo. 50H, obs'd. 49H), 3.72-3.22 (theo. 1114H, obs'd. 1180H), 3.08-2.45 (theo. 80H, obs'd. 86H), 2.17 (theo. 75H, obs'd. 72H), 2.44-1.60 (theo. 40H, obs'd. 42H).

Example 145

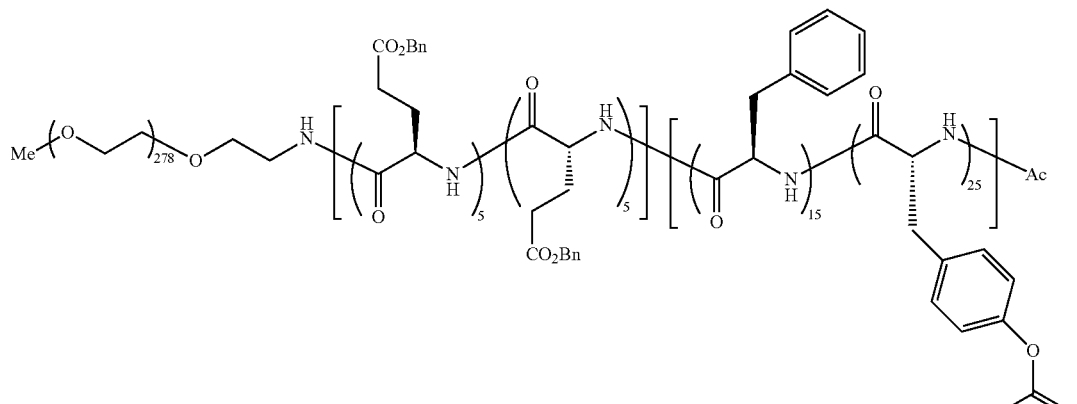

1. NH$_2$OH (5x), LiOH·H$_2$O (1x), THF, H$_2$O, RT, 26 hr
2. Acetone (10x), HOAc (1x), RT-> reflux -> RT
3. Pptn from IPA (4x)

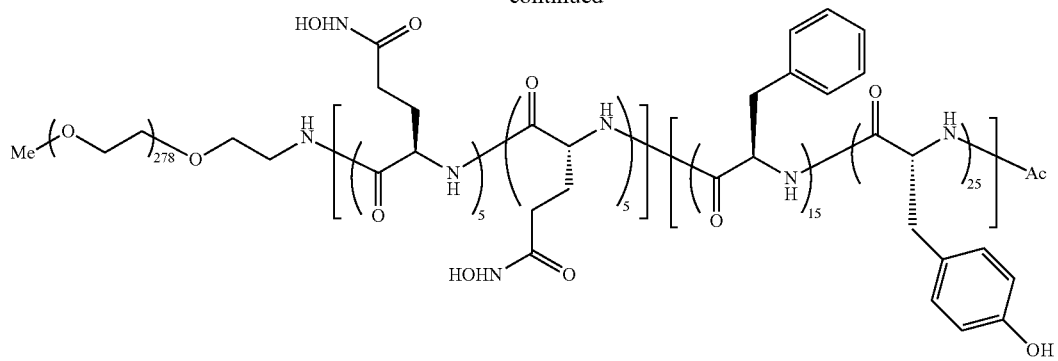

-continued

Tandem Deprotection and Hydroxylamination of mPEG12.3K-b-Poly-[d-Glu(OBn)$_5$-Co-Glu(OBn)$_5$]-b-Poly-(d-Phe$_{15}$-Co-Tyr(OAc)$_{25}$)-Ac with Hydroxylamine mPEG12.3K-b-Poly-[d-Glu(OBn)$_5$-co-Glu(OBn)$_5$]-b-Poly-(d-Phe$_{15}$-co-Tyr(OAc)$_{25}$)-Ac (21.84 g, 1.00 mmol, from Example 143) was dissolved in 220 mL of dry THF and treated with hydroxylamine solution (50% aqueous, 175.0 mmol, 11.6 mL) and solid lithium hydroxide monohydrate (1.47 g, 35.0 mmol). The resultant slightly turbid solution was stirred at room temperature under a nitrogen blanket. After one hour, NMR (DMSO-d$_6$) analysis of an aliquot indicated the complete cleavage of the Tyr(OAc) acetate moiety. After 26 hours at room temperature, NMR indicated complete loss of the benzyl ester signal. The reaction mixture was then treated with acetone (101.6 g, 1.75 mol, 129 mL) and acetic acid (10.50 g, 175.0 mmol, 10.0 mL), whereupon a clear pale yellow solution formed and an exotherm from 22 to 34° C. was observed. The solution was briefly heated to reflux, and then was stirred at room temperature for 22 hours. The solution was diluted with IPA (130 mL), transferred to a 4 L beaker, and the product was then precipitated with IPA (2.1 L) using vigorous mechanical stirring. After stirring an additional hour, the product was collected by filtration, washed with IPA (300 mL), IPA, MTBE: 1.1 (300 mL), and MTBE (300 mL). Drying in vacuo afforded 18.1 g of the title compound as a fine, colorless solid with a trace odor of acetic acid. The yield was 89.8%. $^1$H-NMR (d$_6$-DMSO) δ 10.5-8.8 (v. br, theo. 45H, obs'd. 44H), 8.60-7.80 (theo. 50H, obs'd. 51H), 7.30-6.45 (theo. 175H, obs'd. 178H), 4.65-4.10 (theo. 50H, obs'd. 50H), 3.70-3.15 (theo. 1114H, obs'd. 1361H), 3.00-1.60 (theo. 120H, obs'd. 140H), 1.75 (singlet, 5.1-5.9H).

We claim:
1. A micelle comprising a triblock copolymer, wherein said micelle has a drug-loaded inner core, a crosslinked outer core, and a hydrophilic shell, wherein the triblock copolymer is of formula VII:

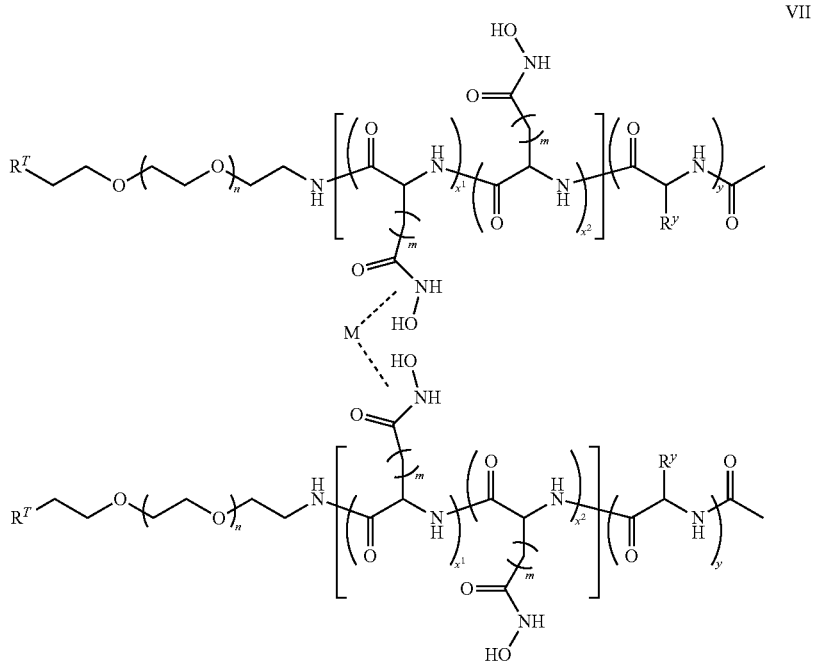

wherein:
n is 20-500;
m is 1 or 2;
$x^1$ is 1-20;
$x^2$ is 0-20;
y is 5 to 100;
$R^y$ is selected from one or more natural or unnatural amino acid side chain groups such that the overall block is hydrophobic;
M is a metal ion;
$R^T$ is $OCH_3$; and
wherein the drug is a molecularly targeted therapeutic.

2. The micelle according to claim 1, wherein the drug is a tyrosine kinase inhibitor.

3. The micelle according to claim 1, wherein the drug is:

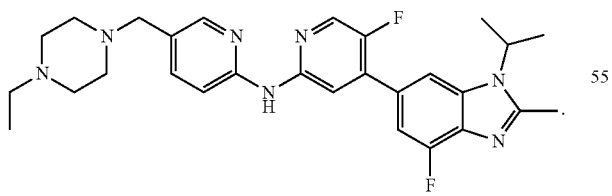

LY2835219

4. The micelle according to claim 1, wherein the drug is:

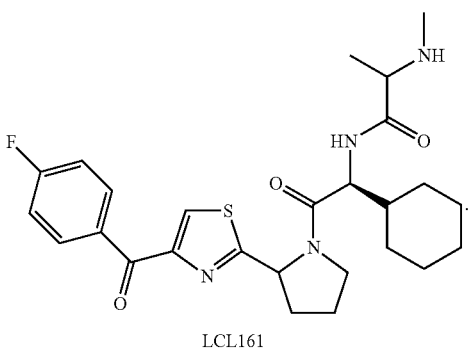 [SMILES: CNC(C)C(=O)N[C@H](C(=O)N1CCCC1c1nc(C(=O)c2ccc(F)cc2)cs1)C1CCCCC1]

LCL161

* * * * *